US008634072B2

(12) United States Patent
Trainer

(10) Patent No.: US 8,634,072 B2
(45) Date of Patent: Jan. 21, 2014

(54) METHODS AND APPARATUS FOR DETERMINING CHARACTERISTICS OF PARTICLES

(76) Inventor: Michael Trainer, Coopersburg, PA (US)

(*) Notice: Subject to any disclaimer, the term of this patent is extended or adjusted under 35 U.S.C. 154(b) by 636 days.

(21) Appl. No.: 12/784,719

(22) Filed: May 21, 2010

(65) Prior Publication Data

US 2010/0225913 A1 Sep. 9, 2010

Related U.S. Application Data

(63) Continuation-in-part of application No. 12/749,714, filed on Mar. 30, 2010, and a continuation-in-part of application No. 11/924,327, filed on Oct. 25, 2007, now abandoned, which is a continuation of application No. 11/538,669, filed on Oct. 4, 2006, now abandoned, which is a continuation-in-part of application No. 10/598,443, filed as application No. PCT/US2005/007308 on Mar. 7, 2005, now Pat. No. 7,471,393.

(60) Provisional application No. 60/723,639, filed on Oct. 25, 2007, provisional application No. 60/550,591, filed on Mar. 6, 2004.

(51) Int. Cl.
*G01N 15/02* (2006.01)
*G01N 21/00* (2006.01)

(52) U.S. Cl.
USPC ............................. 356/335; 356/336; 356/341

(58) Field of Classification Search
USPC .................................................. 356/450–458
See application file for complete search history.

(56) References Cited

U.S. PATENT DOCUMENTS

| 3,553,462 | A |   | 1/1971 | Johnson |         |
|-----------|---|---|--------|---------|---------|
| 3,750,136 | A |   | 7/1973 | Roess   |         |
| 3,788,742 | A |   | 1/1974 | Garbuny |         |
| 3,873,206 | A | * | 3/1975 | Wilcock | 356/338 |
| 4,015,135 | A |   | 3/1977 | Tipton, Jr. |     |
| 4,074,938 | A |   | 2/1978 | Taylor  |         |
| 4,211,487 | A |   | 7/1980 | Morrison et al. |  |
| 4,273,443 | A |   | 6/1981 | Hogg    |         |
| 4,765,737 | A | * | 8/1988 | Harris et al. | 356/336 |
| 4,850,707 | A | * | 7/1989 | Bowen et al. | 356/336 |
| 4,870,274 | A |   | 9/1989 | Hebert et al. |   |
| 4,953,978 | A | * | 9/1990 | Bott et al. | 356/336 |

(Continued)

FOREIGN PATENT DOCUMENTS

| EP | 0899548 A3 | 3/1999 |
|----|-----------|--------|
| EP | 1063512 A3 | 12/2000 |

(Continued)

*Primary Examiner* — Gregory J Toatley
*Assistant Examiner* — Jarreas C Underwood
(74) *Attorney, Agent, or Firm* — William H. Eilberg

(57) ABSTRACT

An instrument for measuring characteristics of a particle sample by counting and classifying particles into selected ranges of particle characteristics. The particle concentration is reduced to the level where the probability of measuring scattering from multiple particles of interest at one time is reduced to an acceptable level. A light beam is projected through a sample space, through which the particles flow. As each particle passes through the beam, it scatters, absorbs, and transmits different amounts of the light, depending upon the particle characteristics. So both the decrease in the beam intensity, due to light removal by the particle, and light scattered by the particle, may be used to determine the particle characteristics, to classify the particle and count it in a certain range of particle characteristics.

38 Claims, 130 Drawing Sheets

(56) References Cited

U.S. PATENT DOCUMENTS

| | | | |
|---|---|---|---|
| 4,975,278 | A | 12/1990 | Brown |
| 5,059,395 | A | 10/1991 | Brittenham et al. |
| 5,090,808 | A | 2/1992 | Ishikawa et al. |
| 5,094,526 | A | 3/1992 | Freud |
| 5,094,532 | A | 3/1992 | Trainer |
| 5,125,737 | A * | 6/1992 | Rodriguez et al. ............. 356/39 |
| 5,280,272 | A | 1/1994 | Nagashima et al. |
| 5,387,789 | A * | 2/1995 | Ota ............................ 250/201.7 |
| 5,428,443 | A | 6/1995 | Kitamura et al. |
| 5,610,712 | A | 3/1997 | Schmitz et al. |
| 5,760,900 | A | 6/1998 | Ito |
| 5,784,160 | A | 7/1998 | Naqwi |
| 6,067,157 | A | 5/2000 | Altendorf |
| 6,084,670 | A | 7/2000 | Yamazaki et al. |
| 6,094,266 | A | 7/2000 | Trainer |
| 6,104,490 | A | 8/2000 | Trainer |
| 6,104,491 | A | 8/2000 | Trainer |
| 6,118,531 | A * | 9/2000 | Hertel et al. ................ 356/336 |
| 6,177,983 | B1 | 1/2001 | Trainer |
| 6,177,994 | B1 * | 1/2001 | Watson et al. ............... 356/343 |
| 6,236,458 | B1 | 5/2001 | Igushi et al. |
| 6,281,973 | B1 | 8/2001 | Trainer |
| 6,396,979 | B1 | 5/2002 | Freud |
| 6,507,400 | B1 | 1/2003 | Pina |
| 6,538,730 | B2 | 3/2003 | Vaez-Iravani et al. |
| 6,738,144 | B1 | 5/2004 | Dogariu |
| 6,794,671 | B2 | 9/2004 | Nicoli et al. |
| 6,847,456 | B2 | 1/2005 | Yang et al. |
| 7,079,243 | B2 | 7/2006 | Sandberg et al. |
| 2001/0007496 | A1 | 7/2001 | Modlin et al. |
| 2002/0093641 | A1 | 7/2002 | Ortyn et al. |
| 2004/0011975 | A1 | 1/2004 | Nicoli |

FOREIGN PATENT DOCUMENTS

| | | |
|---|---|---|
| JP | 1018043 A | 7/1987 |
| JP | 2304333 A | 5/1989 |
| JP | 3221837 A | 1/1990 |
| JP | 2943343 B | 8/1999 |
| JP | 2002-048700 A | 2/2002 |
| JP | 2003-121338 A | 4/2003 |
| WO | 9946577 A1 | 9/1999 |
| WO | 0129538 A1 | 4/2001 |

* cited by examiner

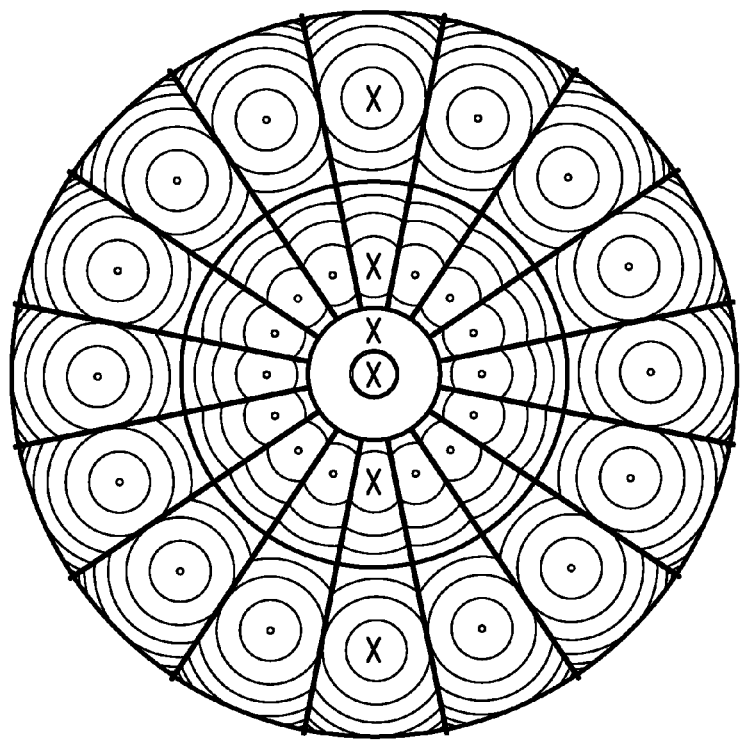 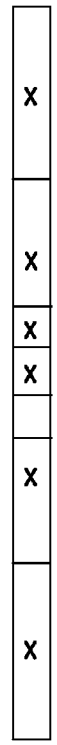
front view
side view on edge
FIG.81a
FIG.81b

US 8,634,072 B2

METHODS AND APPARATUS FOR DETERMINING CHARACTERISTICS OF PARTICLES

CROSS-REFERENCE TO PRIOR APPLICATIONS

This is a continuation-in-part of U.S. patent application Ser. No. 12/749,714, filed Mar. 30, 2010. This application is also a continuation-in-part of U.S. patent application Ser. No. 11/924,327, filed Oct. 25, 2007, which is a continuation of U.S. patent application Ser. No. 11/538,669, filed Oct. 4, 2006, now abandoned, which is a continuation-in-part of U.S. patent application Ser. No. 10/598,443, filed Aug. 30, 2006, now U.S. Pat. No. 7,471,393, which is a U.S. national phase of PCT/US2005/07308, which claims the priority of U.S. provisional application Ser. No. 60/550,591, filed Mar. 6, 2004. Priority is also claimed from U.S. provisional application Ser. No. 60/723,639, filed Oct. 5, 2005.

BACKGROUND OF THE INVENTION

This invention relates to systems and methods for analyzing particles in a sample using laser light diffraction. More particularly, the present invention relates to systems and methods that analyze laser light diffraction patterns to determine the size of particles in a sample.

SUMMARY OF THE INVENTION

The present invention comprises a method for enhancing the accuracy of a count of particles by rejecting events which do not have scatter signal parameters consistent with single-particle scatter, the method comprising a) creating a multidimensional space in which each dimension comprises a scatter signal parameter, such that any particle with specific values of particle parameters can be identified by a point in said space, b) determining a path through said multidimensional space according to expected or measured values of scatter signal parameters for various particles, c) rejecting counted events where said events have scatter signal parameters such that said events, when represented in said multidimensional space, are located beyond a predetermined distance from said path, and d) selecting counted events which have not been rejected in step (c) for further analysis. The invention also comprises apparatus for practicing the above-described method.

The invention also comprises a method for determining particle size and/or shape from scatter signal parameters of a counted event, comprising the steps of a) creating a set of simultaneous equations relating each scatter signal parameter to a function of particle parameters, and b) solving the set of equations for the particle parameters, using measured scatter signal parameters. The invention also comprises apparatus for practicing the above-described method.

The invention also comprises a method for determining particle size and/or shape from scatter signal parameters of a counted event, comprising the steps of a) measuring a two-dimensional scatter distribution of light scattered by a particle, b) calculating a two-dimensional inverse Fourier transform of said two-dimensional scatter distribution to produce a second two-dimensional distribution, and c) determining size and shape of said particle from a shape of said second two-dimensional distribution.

BRIEF DESCRIPTION OF THE DRAWINGS

FIG. 16 depicts various masks to be utilized in the optical systems of FIG. 15 and FIG. 15a.

FIG. 20 provides a diagram showing more detail of the light beam focus and the focus of each detector field of view, using the concepts depicted in FIG. 2 and FIG. 2a.

FIG. 81*a* provides a front view of the array of FIG. 80, utilizing diffractive optical elements.

FIG. 81*b* provides a side view of the array of FIG. 81*a*.

Figure 1:
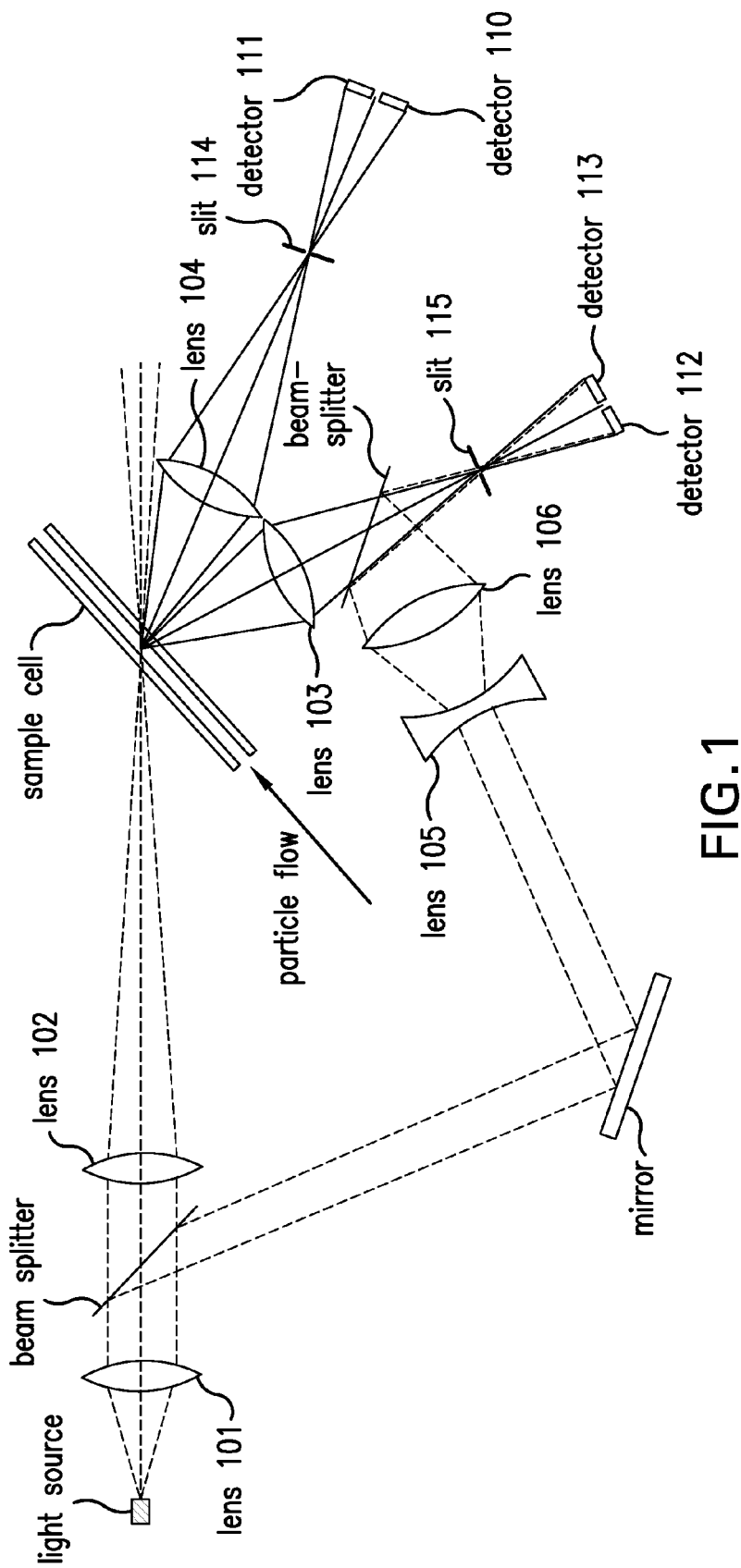
FIG. 1 provides a schematic diagram of a scattering plane view of a scattering detection system which detects scattered light from particles in a small volume, according to the present invention.
Figure 106:
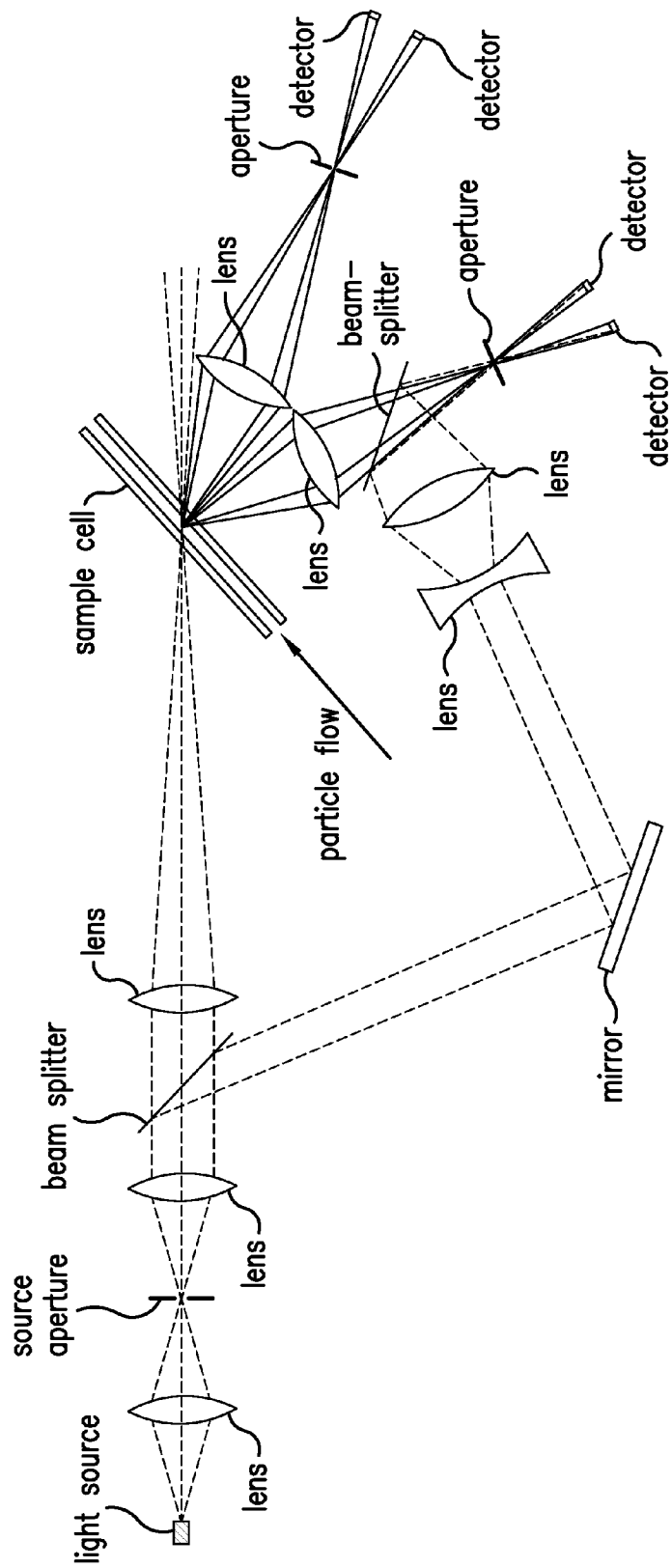

FIG. 106 provides a schematic diagram illustrating the use of detector size to define the angular range of each detector in FIG. 1.

Figure 107:
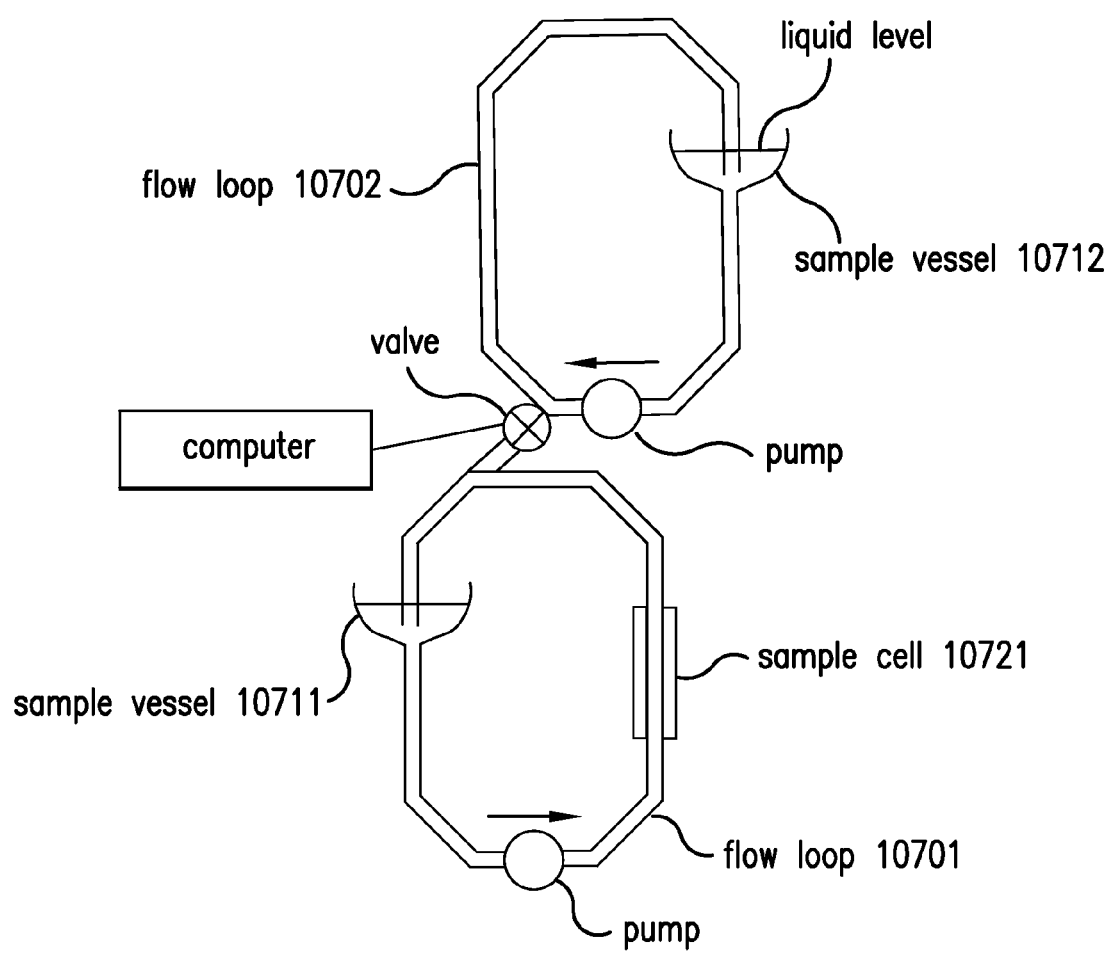

FIG. 107 provides a schematic diagram of a particle sample system which adjusts particle concentration to an optimum value, according to the present invention.

Figure 108:
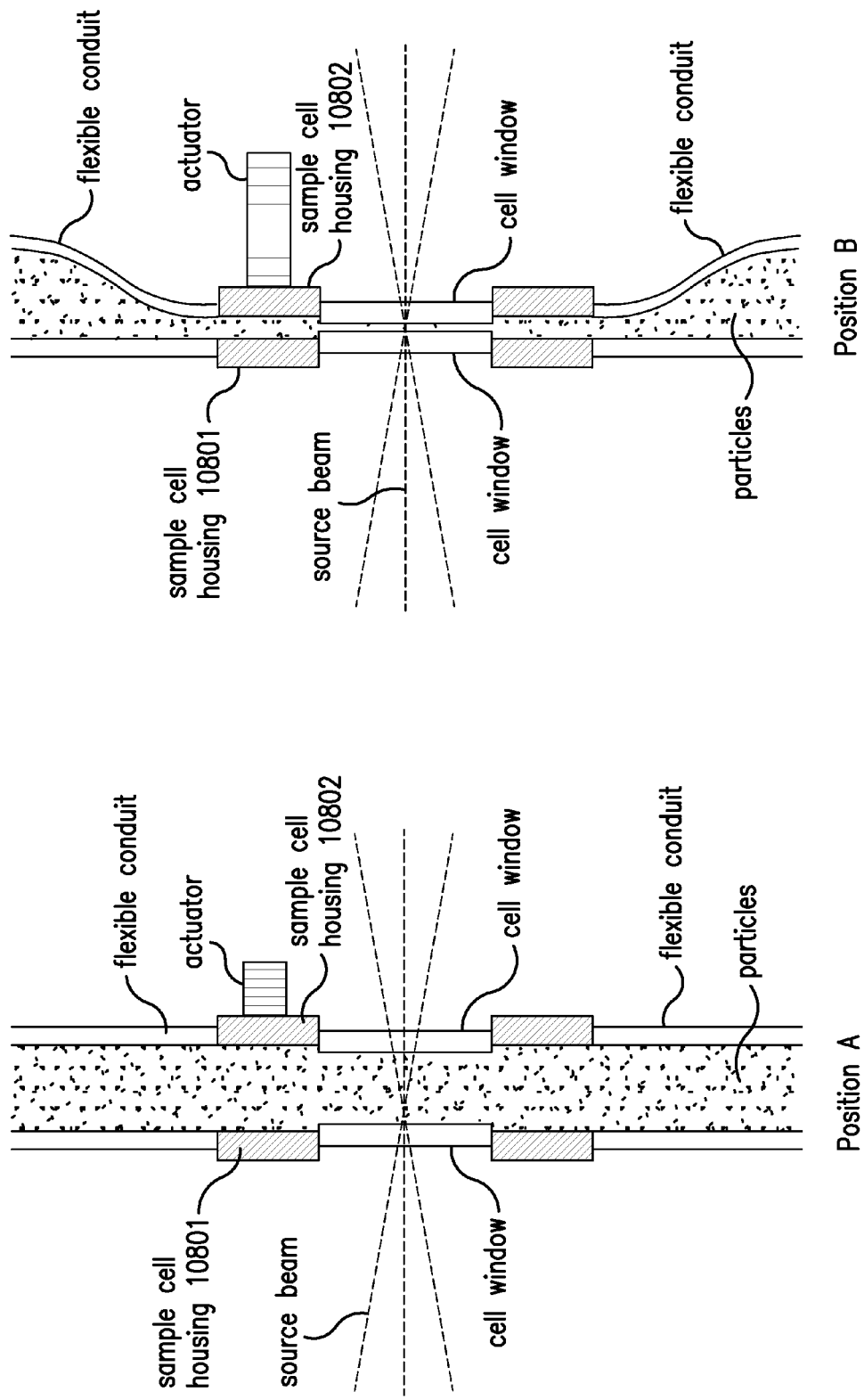

FIG. 108 provides diagrams showing two window positions for a particle dispersion sample cell with adjustable pathlength, according to the present invention.

Figure 109:
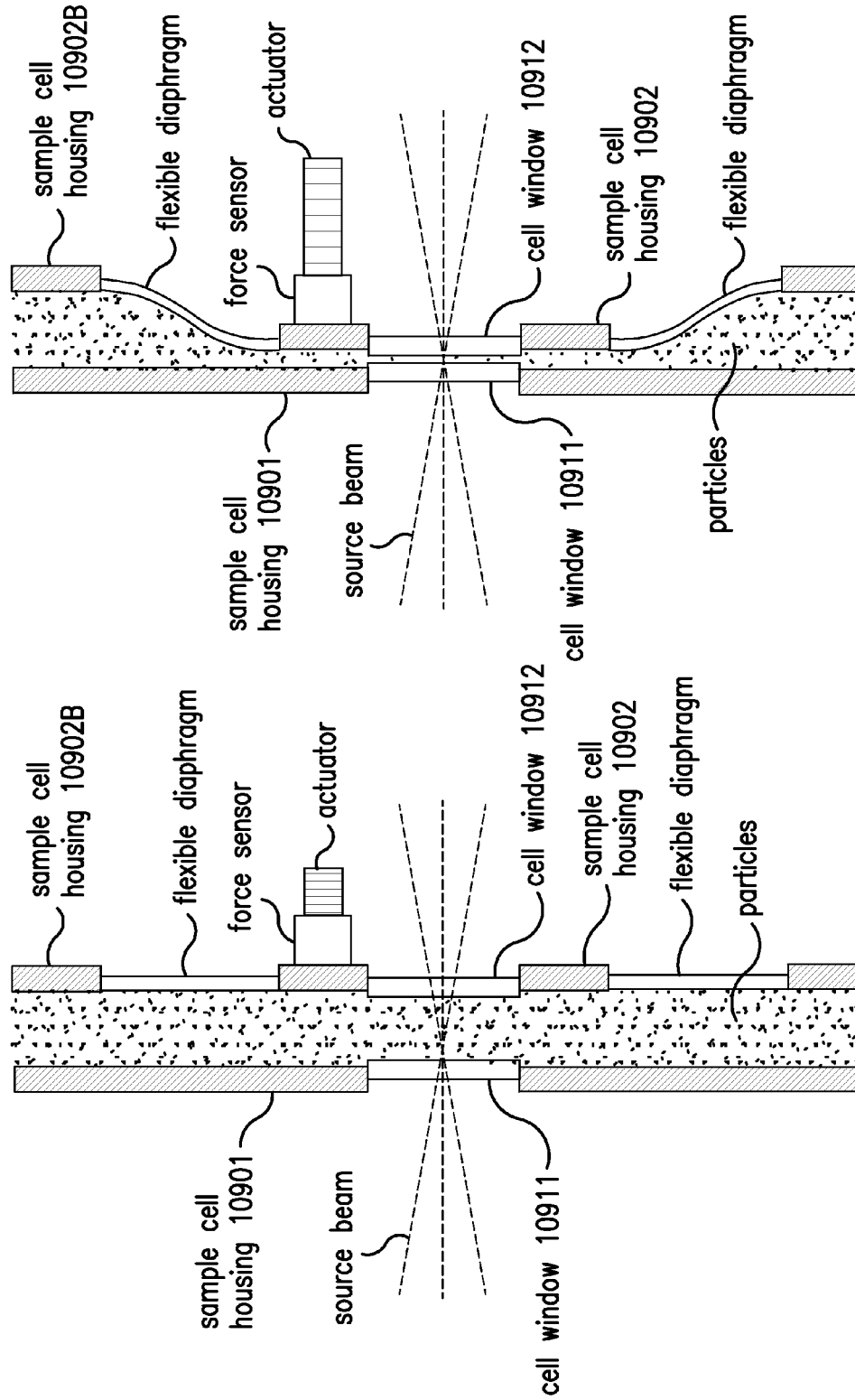

FIG. 109 provides diagrams showing two window positions for a particle dispersion sample cell, with adjustable pathlength, which utilizes a flexible diaphragm, according to the present invention.

Figure 110:
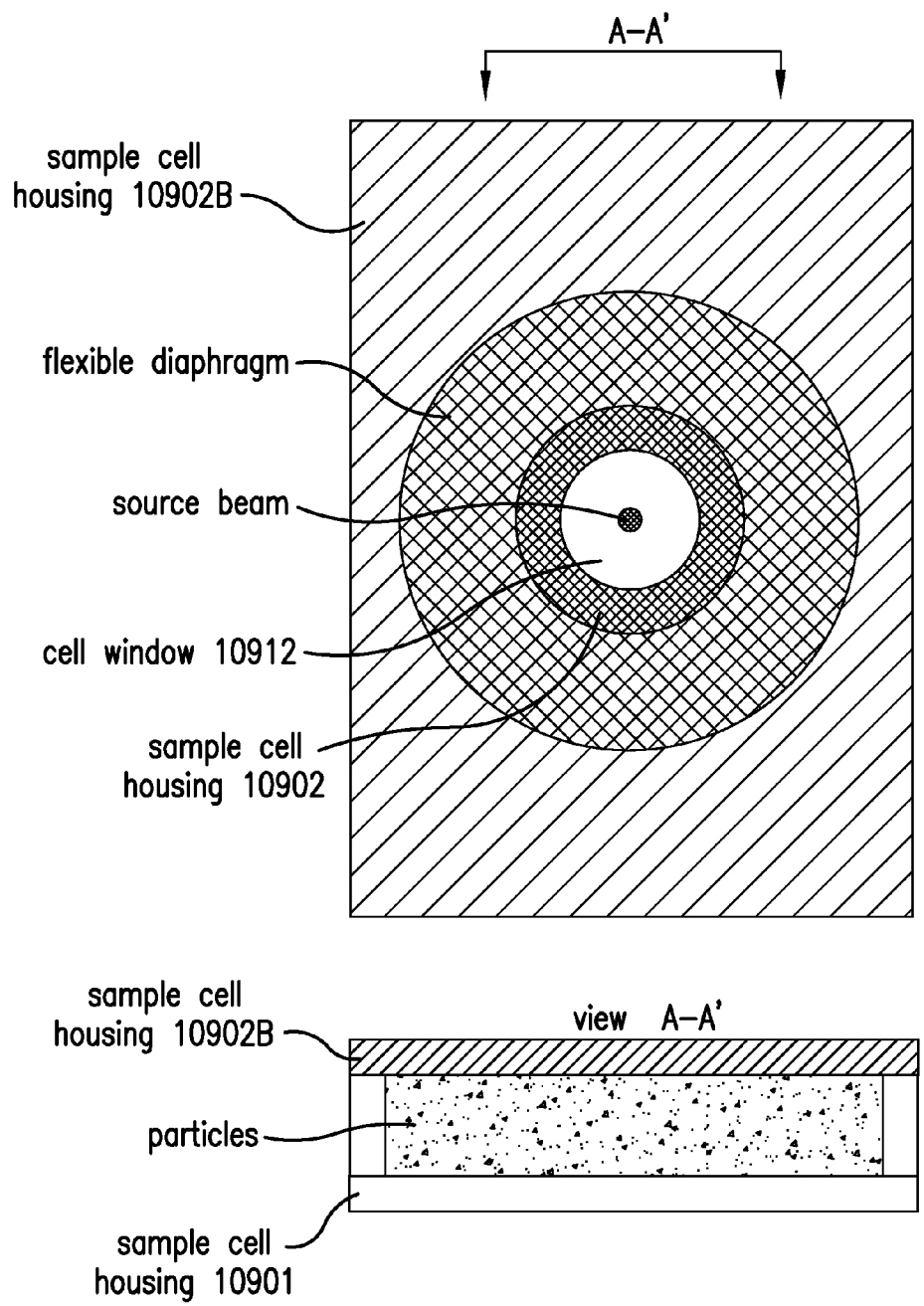

FIG. 110 provides diagrams showing front and top views of the device of FIG. 109.

Figure 111:
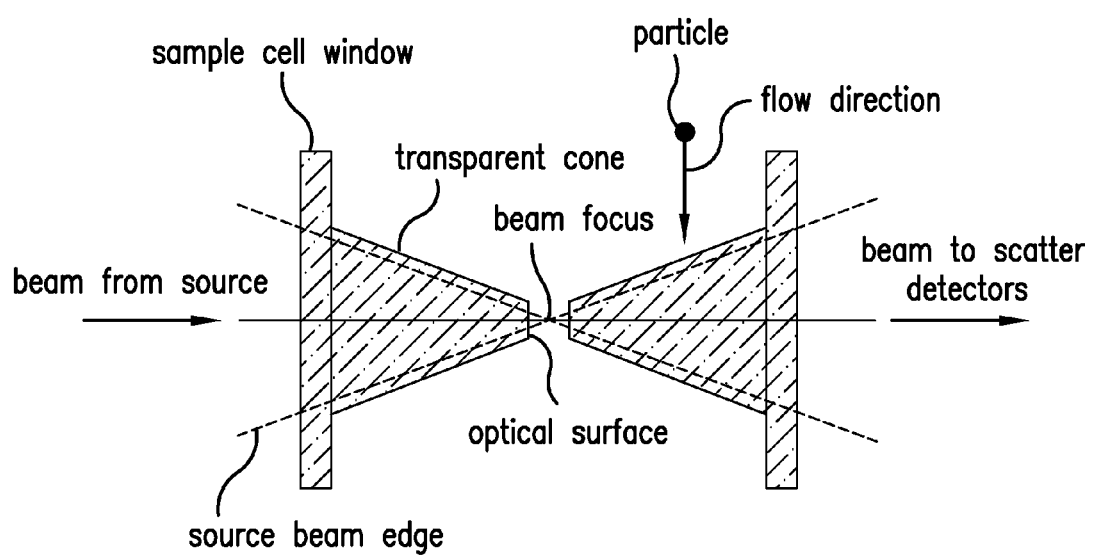

FIG. 111 provides a diagram showing modifications to sample cell windows to allow larger particles to pass around the interaction volume and to reduce unwanted light scattering from outside of the interaction volume, according to the present invention.

Figure 14:
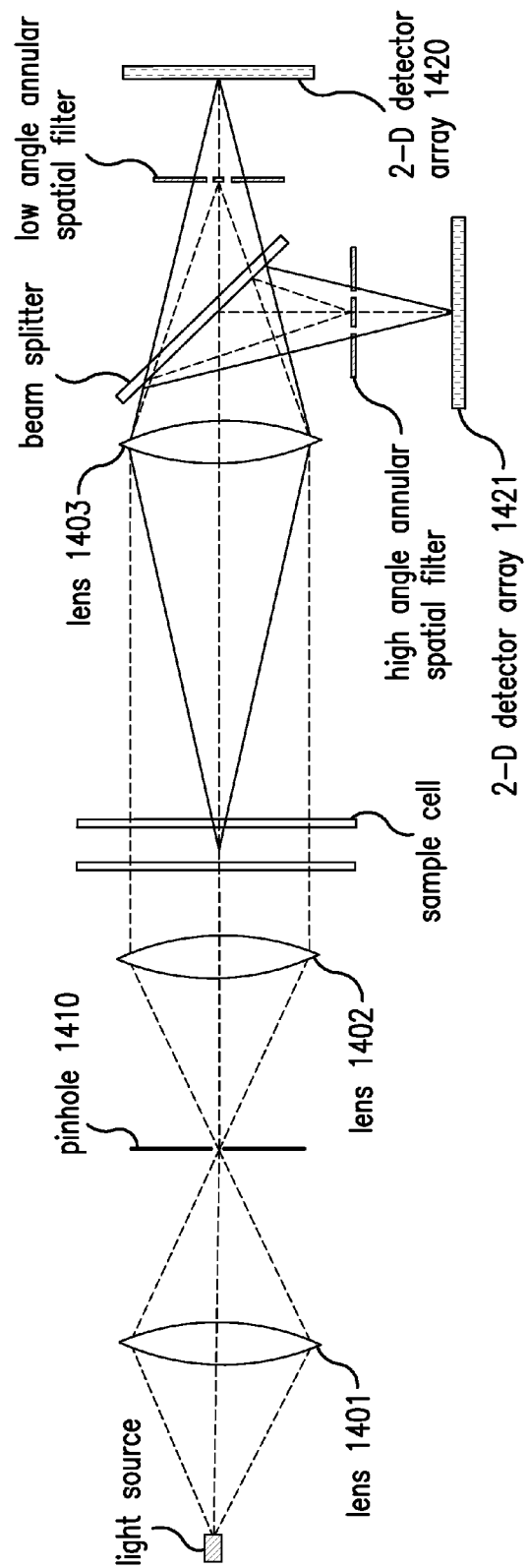
FIG. 14 provides a schematic drawing of an optical system which measures the light scattered, in multiple ranges of scattering angle, by each of many particles at the same time, according to the present invention.
Figure 112:
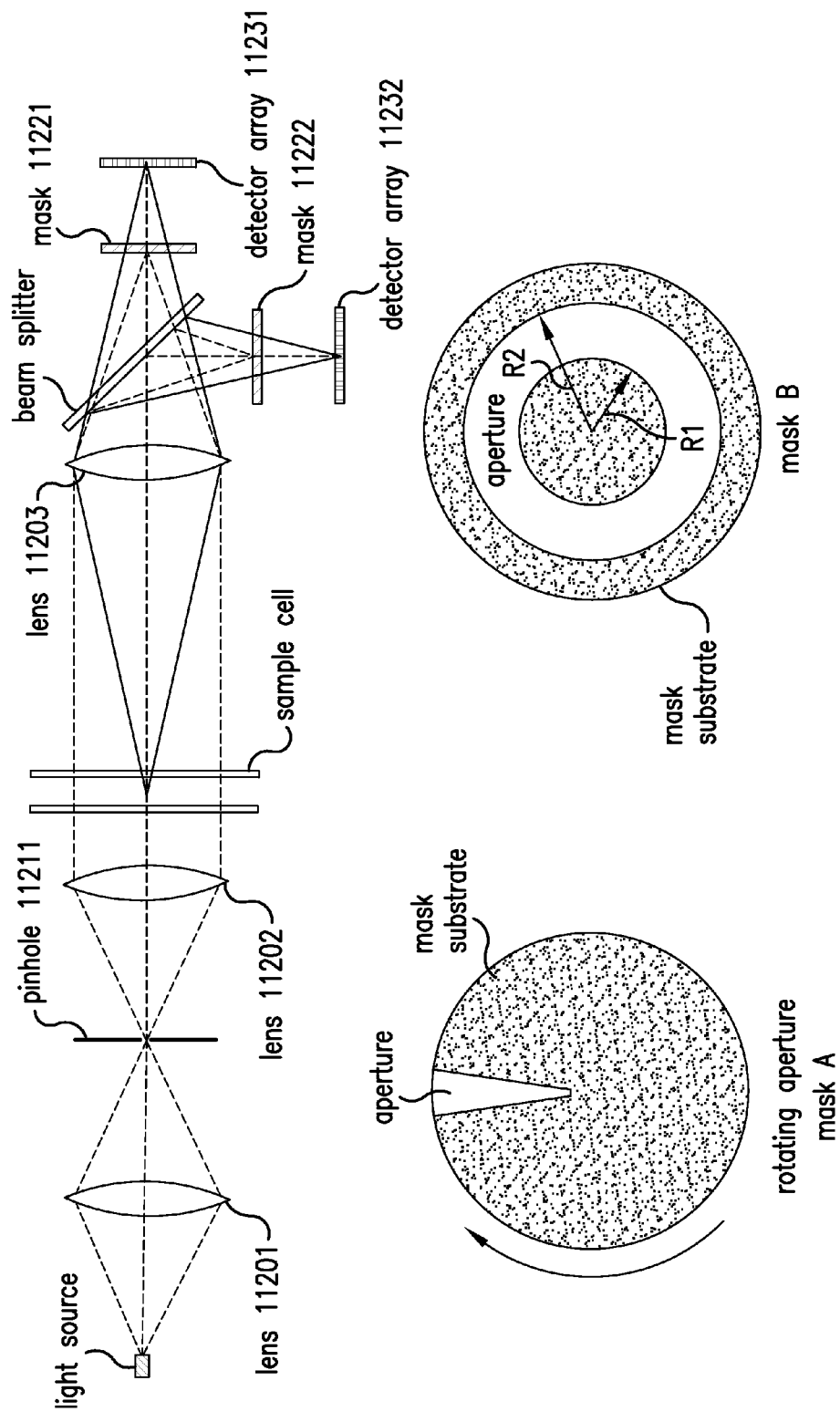

FIG. 112 provides a schematic diagram of a modification to FIG. 14, which provides measurement of scattered light from selected scatter planes by utilizing at least one scattering plane mask.

Figure 113:
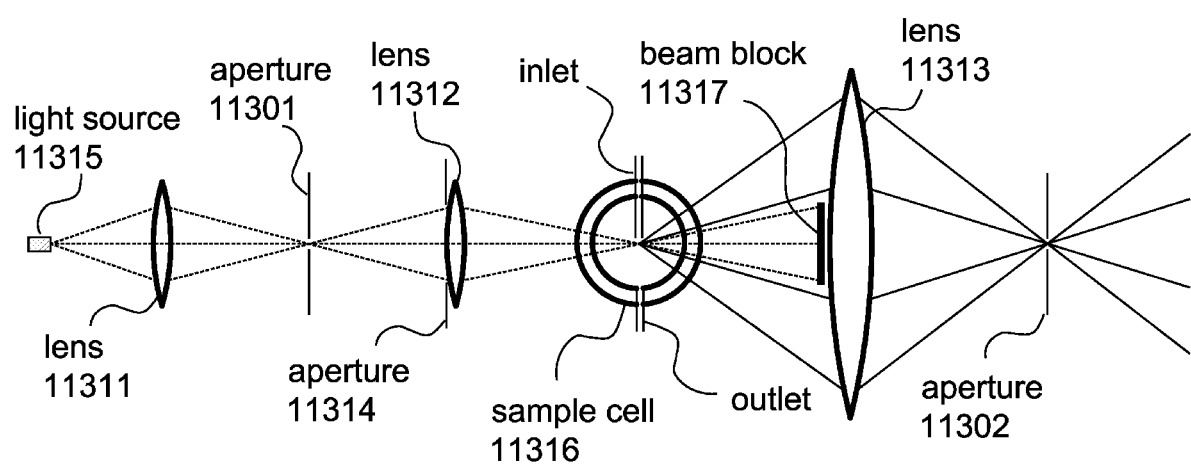

FIG. 113 provides a schematic diagram of an illumination system and scatter collection lens.

Figure 114:
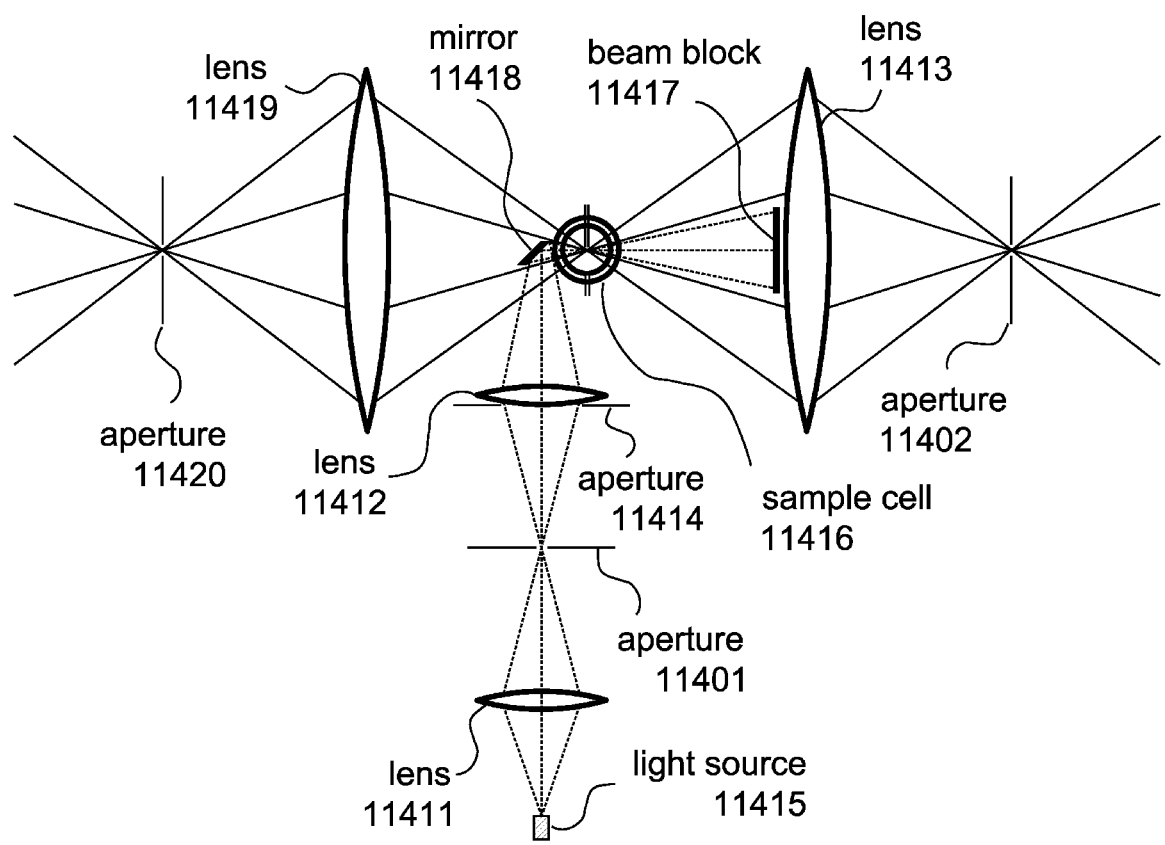

FIG. 114 provides a schematic diagram of the system shown in FIG. 113, adapted for measuring scattered light at low and high scattering angles.

Figure 115:
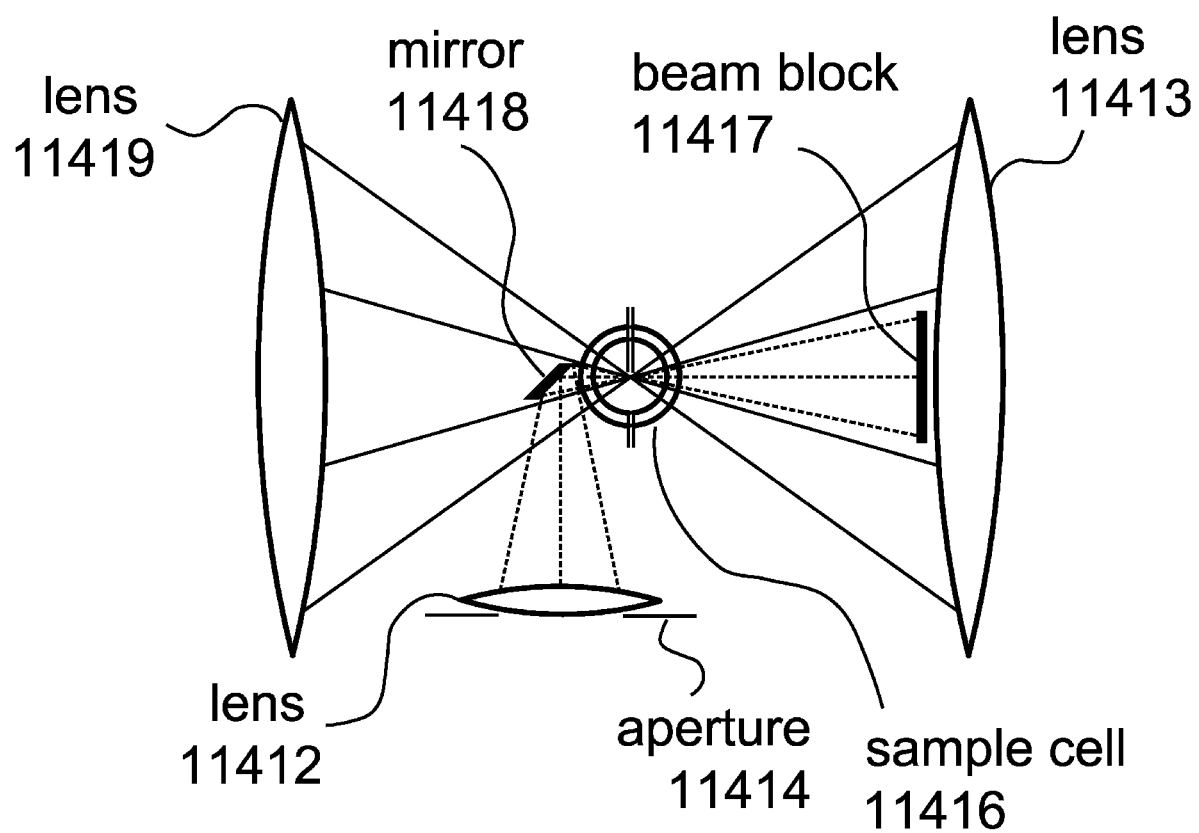

FIG. 115 shows details of FIG. 114 in the vicinity of the sample cell.

Figure 116:
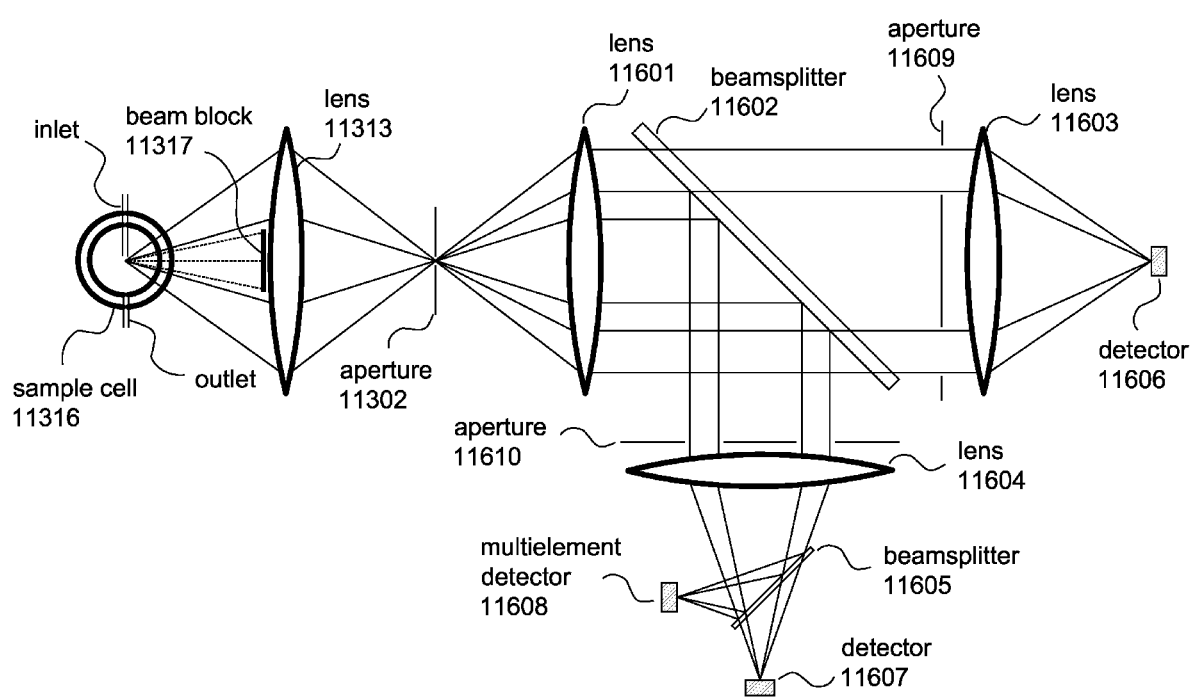

FIG. 116 shows a scatter detection module which is interfaced to the system shown in FIG. 113.

Figure 117:
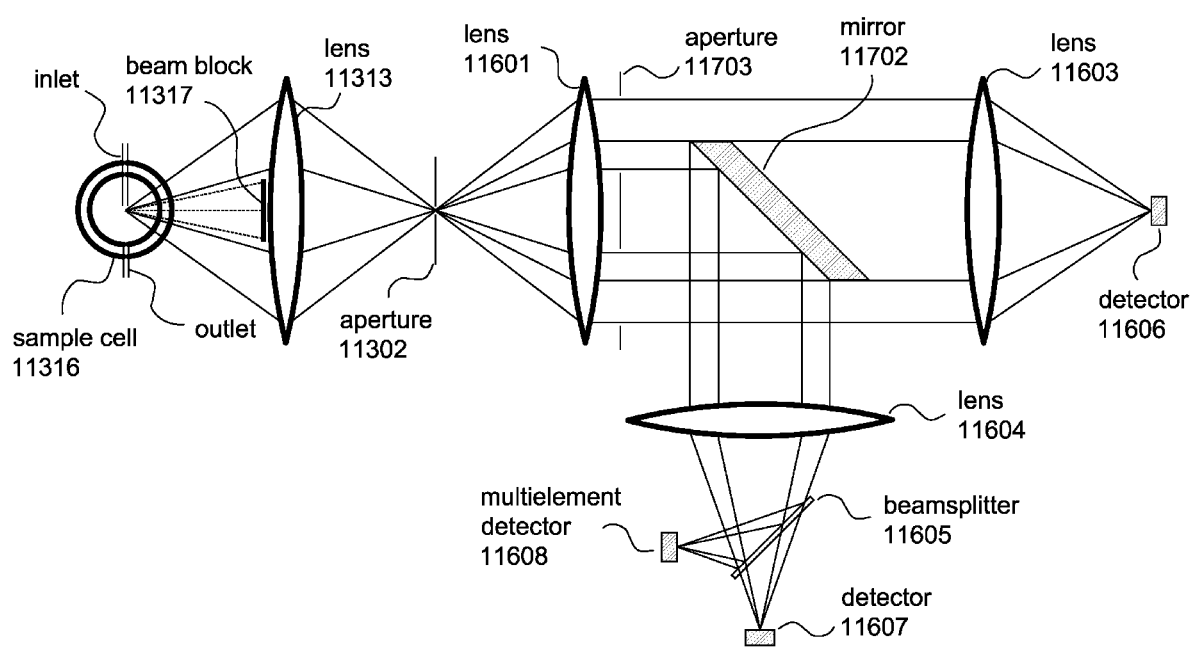

FIG. 117 provides a schematic diagram of the detection module of FIG. 116, with a modification which utilizes a mirror.

Figure 118:
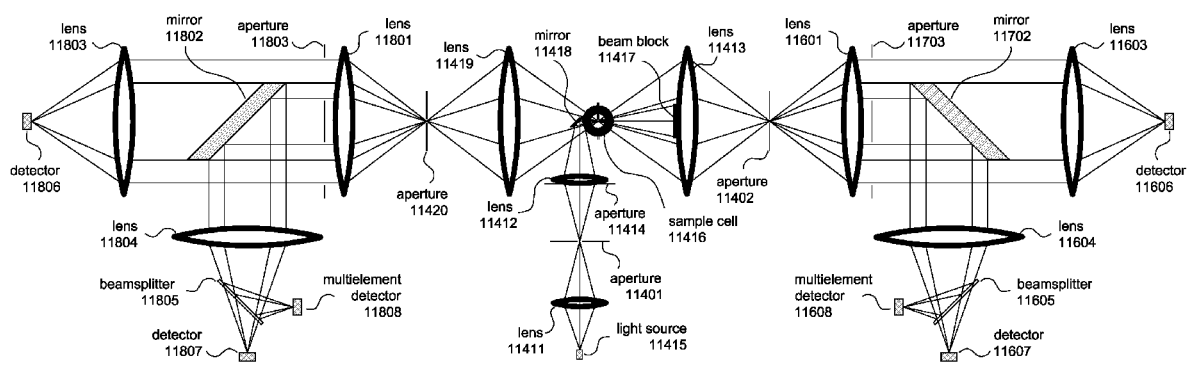

FIG. 118 provides a schematic diagram of an optical system which utilizes two detection modules to measure scattered light at low and high scattering angles.

Figure 119:
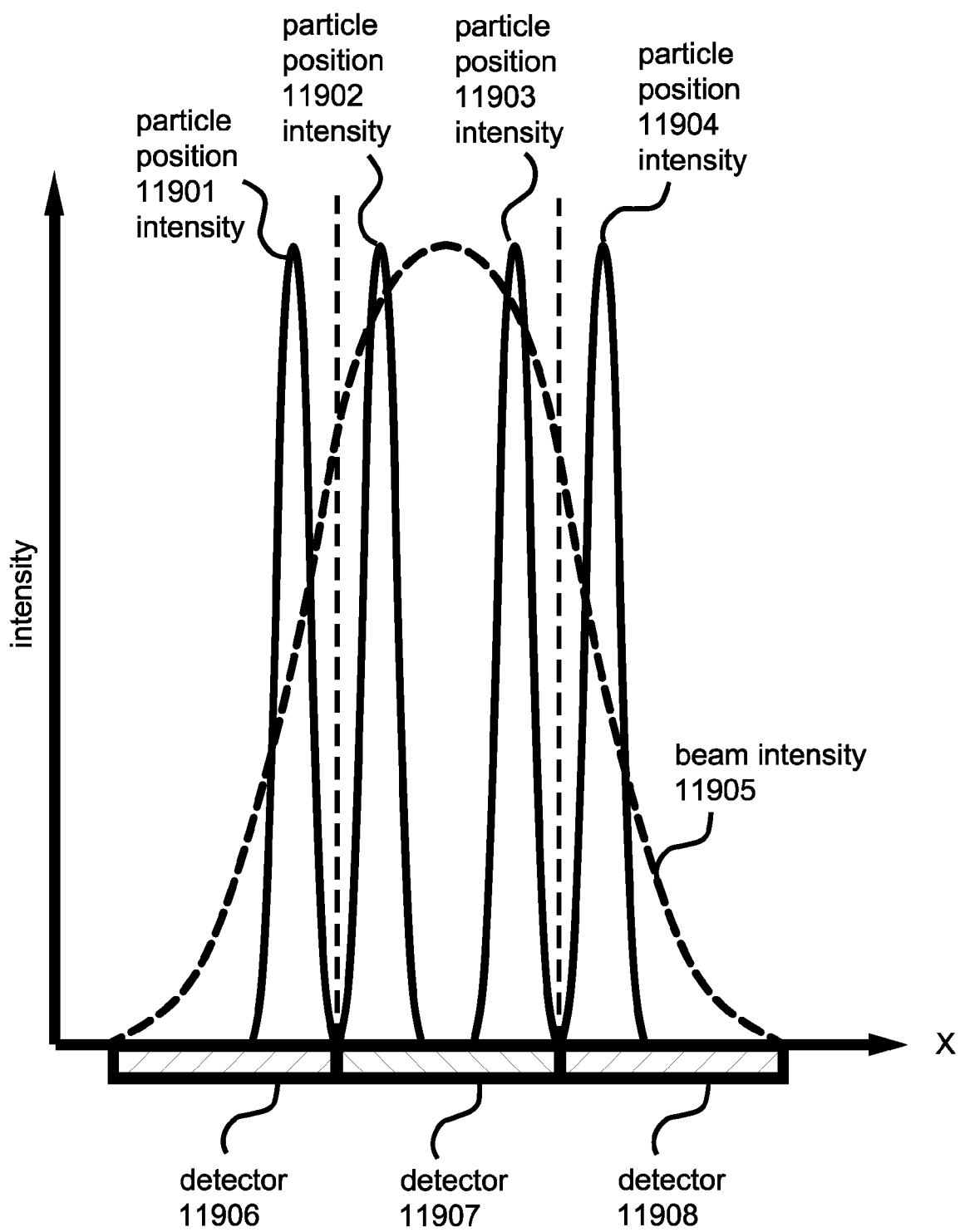

FIG. 119 provides a diagram of the intensity distributions from particles with four different positions on a particle position detector utilizing three detectors.

Figure 120:
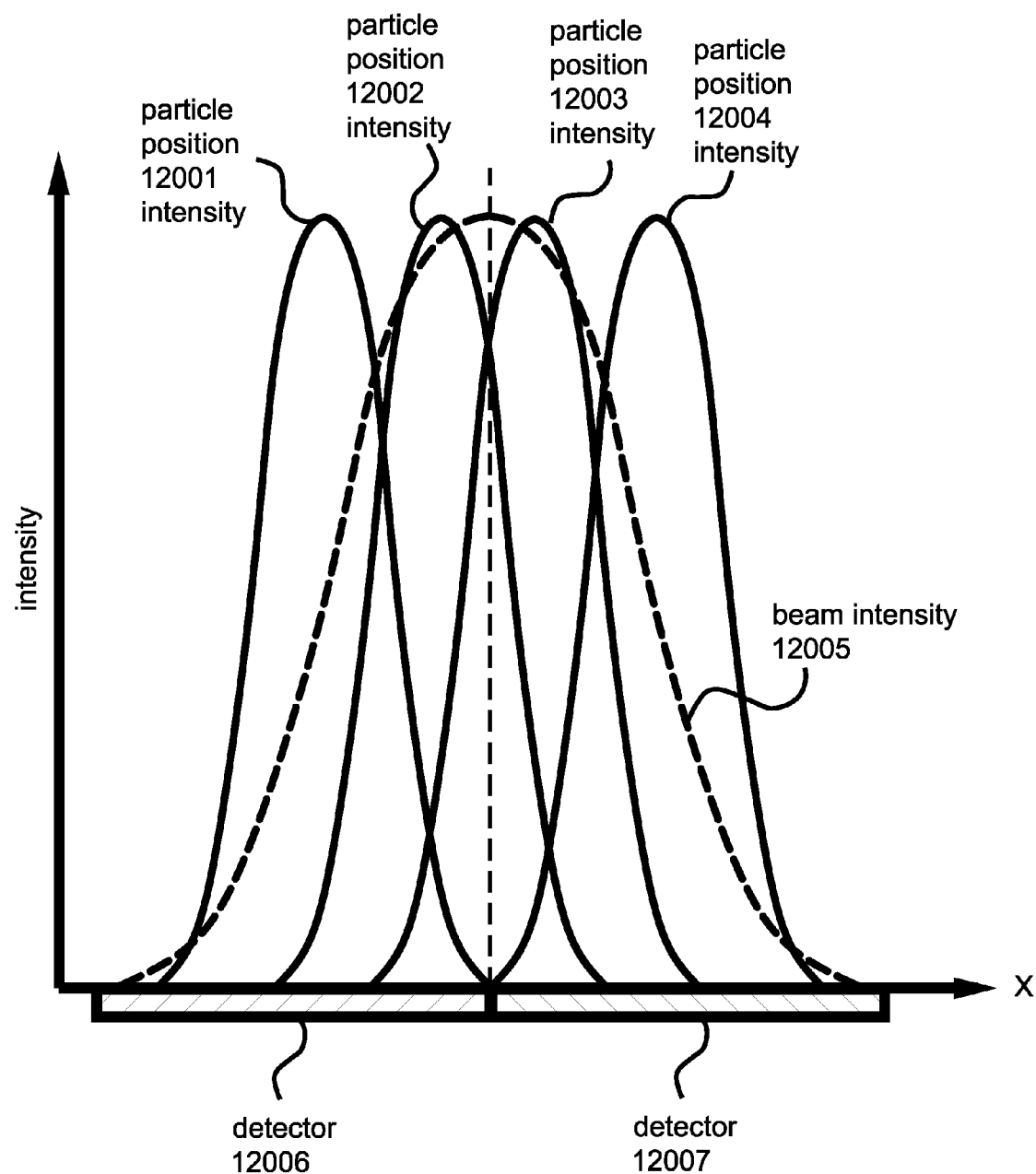

FIG. 120 provides a diagram of the intensity distributions from particles with four different positions on a particle position detector utilizing two detectors.

Figure 121:
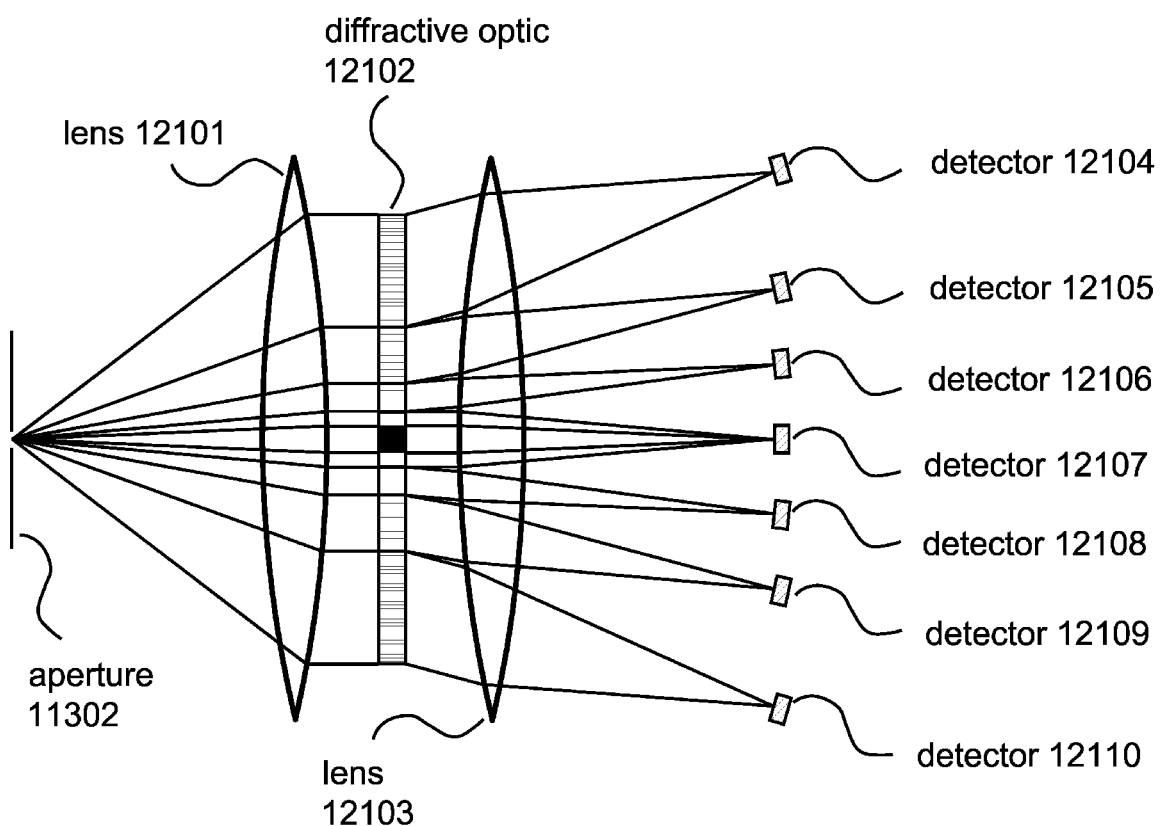

FIG. 121 provides a schematic diagram of a scatter detection module utilizing a diffractive optic.

Figure 122:
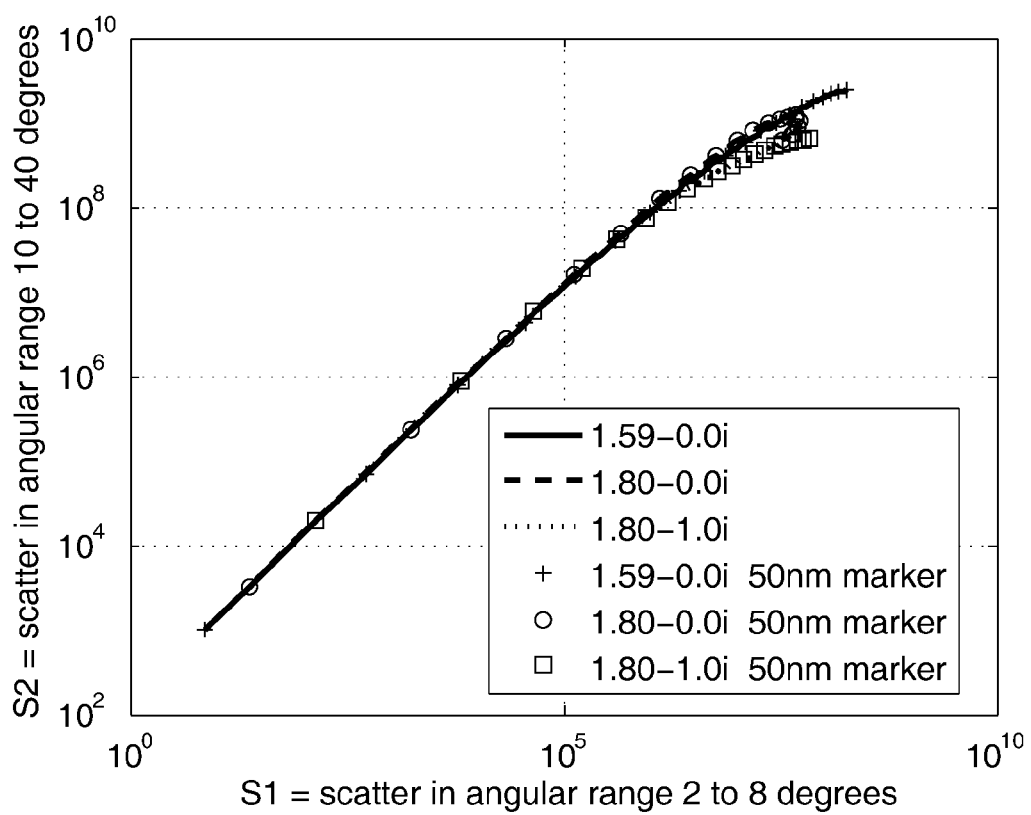

FIG. 122 provides a plot of scatter signal in angular range 10 to 40 degrees vs. scatter signal in angular range 2 to 8 degrees for particles of various diameters.

Figure 123:
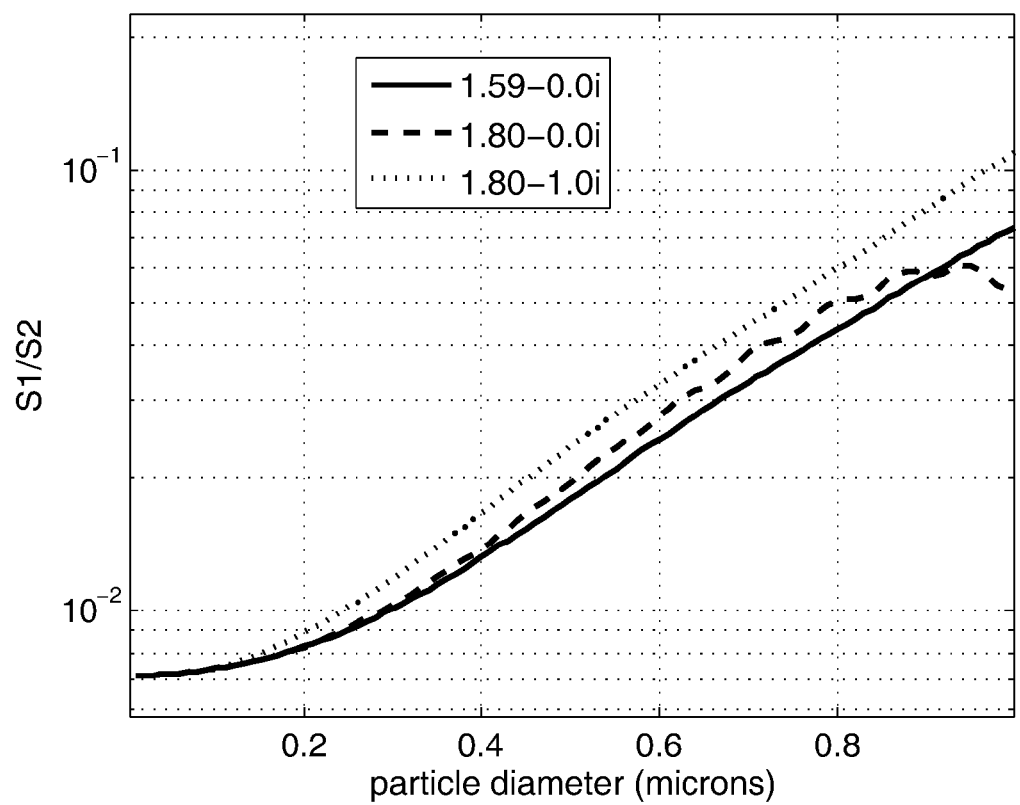

FIG. 123 provides a plot of the ratio of the scatter signals from FIG. 122 vs. particle diameter.

Figure 124:
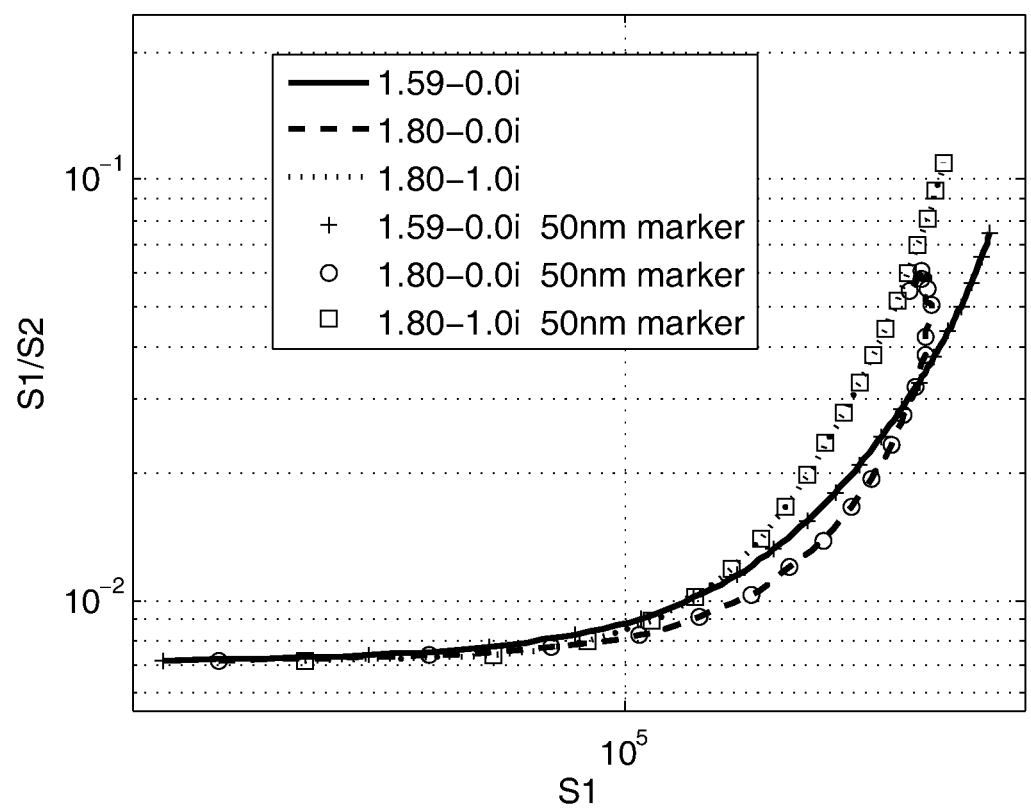

FIG. 124 provides a plot of scatter signal ratio of FIG. 123 vs. scatter signal in angular range 2 to 8 degrees for particles of various diameters.

Figure 125:
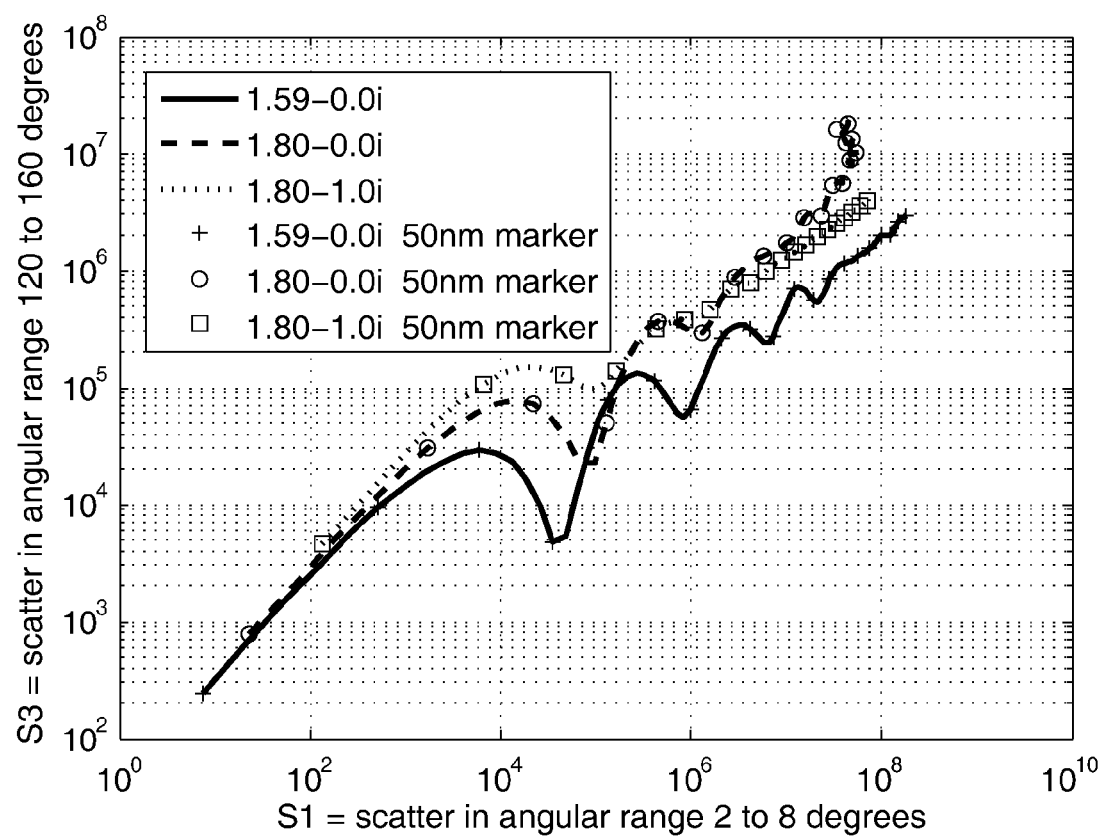

FIG. 125 provides a plot of scatter signal in angular range 120 to 160 degrees vs. scatter signal in angular range 2 to 8 degrees for particles of various diameters.

Figure 126:
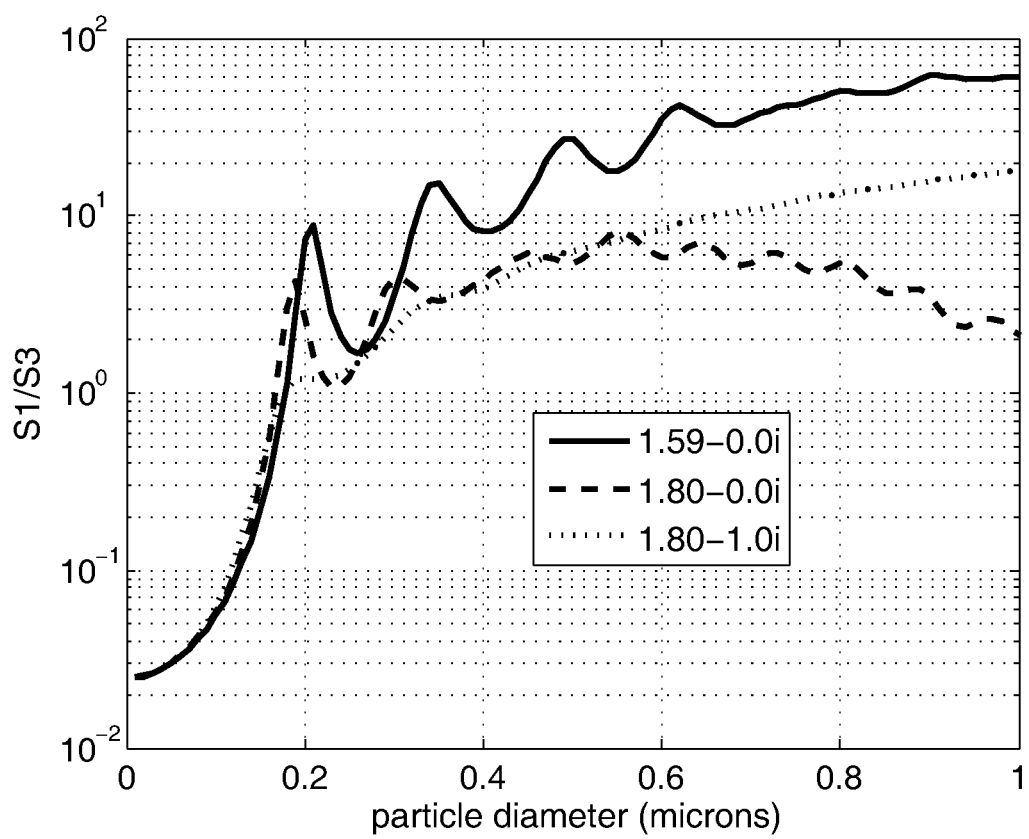

FIG. 126 provides a plot of the ratio of the scatter signals from FIG. 125 vs. particle diameter.

Figure 127:
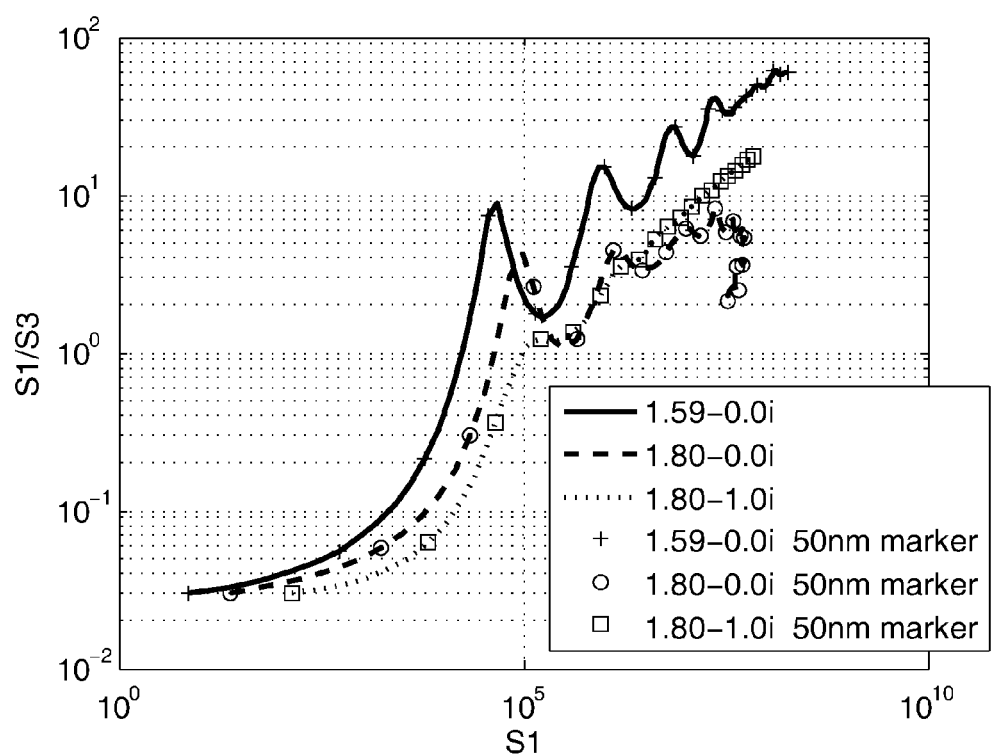

FIG. 127 provides a plot of scatter signal ratio of FIG. 126 vs. scatter signal in angular range 2 to 8 degrees for particles of various diameters.

Figure 128:
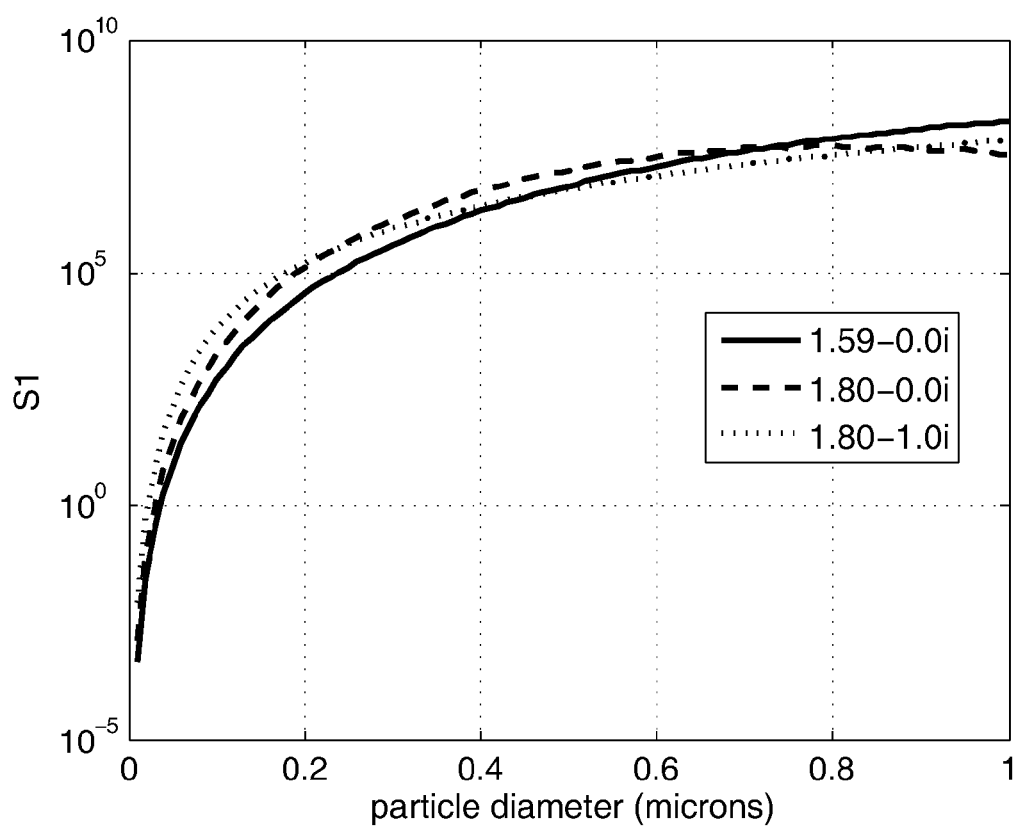

FIG. 128 provides a plot of scatter signal in angular range 2 to 8 degrees vs. particle diameter.

DETAILED DESCRIPTION OF THE INVENTION

This application describes an instrument for measuring the size distribution of a particle sample by counting and classifying particles into selected size ranges. The particle concentration is reduced to the level where the probability of measuring scattering from multiple particles at one time is reduced to an acceptable level. A light beam is focused or collimated through a sample cell, through which the particles flow. As each particle passes through the beam, it scatters, absorbs, and transmits different amounts of the light, depending upon the particle size. So both the decrease in the beam intensity, due to light removal by the particle, and increase of light, scattered by the particle, may be used to determine the particle size, to classify the particle and count it in a certain size range. If all of the particles pass through a single beam, then many small particles must be counted for each large one because typical distributions are uniform on a particle volume basis, and the number distribution is related to the volume distribution by the particle diameter cubed. This large range of counts and the Poisson statistics of the counting process limit the size dynamic range for a single measurement. For example, a uniform particle volume vs. size distribution between 1 and 10 microns requires that one thousand 1 micron particles be measured for each 10 micron particle. The Poisson counting statistics require 10000 particles to be counted to obtain 1% reproducibility in the count. Hence one needs to measure more than 10 million particles. At the typical rate of 10,000 particles per second, this would require more than 1000 seconds for the measurement. In order to reduce the statistical count uncertainties, large counts of small particles must be measured for each large particle. This problem may be eliminated by flowing portions of the sample flow through light beams of various diameters, so that larger beams can count large count levels of large particles while small diameter beams count smaller particles without the small particle coincidence counts of the large beam. Accurate particle size distributions are obtained by using multiple beams of ever decreasing spot size to improve the dynamic range of the count. The count vs. size distributions from each beam are scaled to each other using overlapping size ranges between different pairs of beams in the group, and the count distributions from all of the beams are then combined.

Light scattered from the large diameter beam should be measured at low scattering angles to sense large particles. The optical pathlength of this beam in the particle sample must be large enough to pass the largest particle of interest for that beam. For small particles, the interaction volume in the beam must be reduced along all three spatial directions. The beam crossection is reduced by an aperture or by focusing the beam into the interaction volume. The interaction volume is the intersection of the particle dispersion volume, the incident light beam, and viewing volume of the detector system. When the particle dispersion volume is much larger than the light beam and detector viewing volume, the interaction volume is the intersection of the incident light beam and the field of view for the detector which measures scattered light from the particle. However, for very small particles, reduction of the optical path along the beam propagation direction is limited by the gap thickness through which the sample must flow. This could be accomplished by using a cell with various pathlengths or a cell with a wedge shaped window spacing (see FIG. 9a) to provide a range of optical pathlengths. Smaller source beams would pass through the thinner portions of the cell, reducing the intersection of the incident beam and particle dispersant volume to avoid coincidence counts. The other alternative is to restrict the field of view of the scattering collection optics so as to only detect scatterers in a very small sample volume, which reduces the probability of multiple particles in the measurement volume. So particularly in the case of very small particles, a focused laser beam intersected with the limited field of view of collection optics must be used to insure single particle counting. However, this system would require correction of larger beams for coincidence counts based upon counts in smaller beams. To avoid these count errors, this disclosure proposes the use of a small interrogation volume for small particles, using multiple scattering angles, and a 2 dimensional detector array for counting large numbers of particles above approximately 1 micron at high speeds.

Three problems associated with measuring very small particles are scattering signal dynamic range, particle composition dependence, and Mie resonances. The low angle scattered intensity per particle changes by almost 6 orders of magnitude between 0.1 and 1 micron particle diameter. Below approximately 0.4 micron, photon multiplier tubes (PMT) are needed to measure the minute scattered light signals. Also the scattered intensity can change by a factor of 10 between particles of refractive index 1.5 to 1.7. However, the shape of the scattering function (as opposed to the amplitude) vs. scattering angle is a clear indicator of particle size, with very little refractive index sensitivity. This invention proposes measurement of multiple scattering angles to determine the size of each individual particle, with low sensitivity to particle composition and scattering intensity. Since multiple angle detection is difficult to accomplish with bulky PMT's, this invention also proposes the use of silicon photodiodes and heterodyne detection, in some cases, to measure low scattered signals from particles below 1 micron. However, the use of any type of detector and coherent or non-coherent detection are claimed.

Spherical particles with low absorption will produce a transmitted light component which interferes with light diffracted by the particle. This interference causes oscillations in the scattering intensity as a function of particle size. The best method of reducing these oscillations is to measure scattering from a white light or broad band source, such as an LED. The interference resonances at multiple wavelengths are out of phase with each other, washing out the resonance effects. But for small particles, one needs a high intensity source, eliminating broad band sources from consideration. The resonances primarily occur above 1.5 micron particle diameter, where the scattering crossection is sufficient for the lower intensity of broadband sources. So the overall concept may use laser sources and multiple scattering angles for particles below approximately 1 micron, and broad band sources with low angle scattering or total scattering for particle size from approximately 1 micron up to thousands of microns. We will start with the small particle detection system.

Figure 1A:
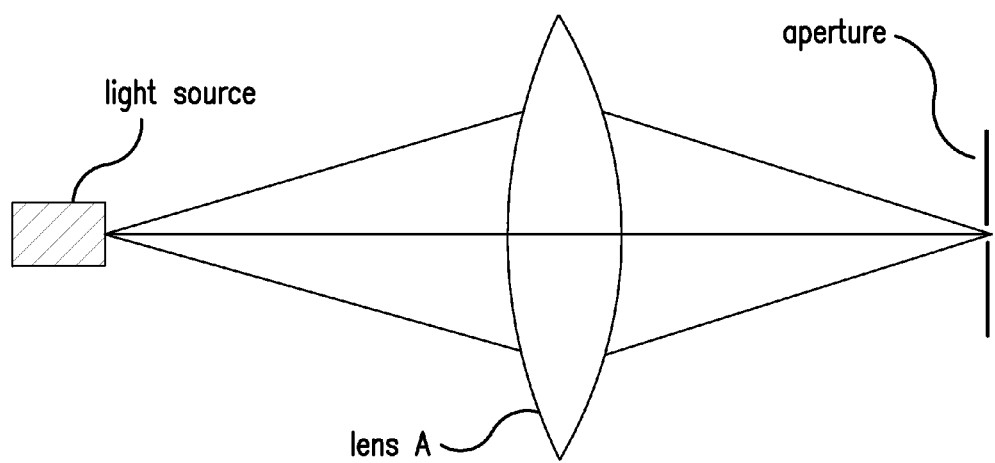
FIG. 1A provides a schematic diagram showing an aperture which controls the light intensity profile of a light source, according to the present invention.

FIG. 1 shows a configuration for measuring and counting smaller particles. A light source is projected into a sample cell, which consists of two optical windows for confining the flowing particle dispersion. The light source in FIG. 1 could also be replaced by an apertured light source as shown in FIG. 1A. This aperture, which is in an image plane of the light source, blocks unwanted stray light which surrounds the source spot and the aperture can control the spatial intensity distribution of the source in the sample cell by eliminating low intensity tails of the distribution. In the case of laser sources, this aperture may be used to select a section of uniform intensity from the center of the laser crossectional intensity profile. In all figures in this disclosure, either source configuration is assumed. The choice is determined by source properties and intensity uniformity requirements in the sample cell. So either the light source, or the apertured image of the light source, is collimated by lens 101 and a portion of this collimated beam is split off by a beam splitter to provide the local oscillator for heterodyne detection. While collimation between lenses 101 and 102 is not required (eliminating the need for lens 102), it provides for easy transport to the heterodyne detectors 112 and 113. Lens 102 focuses the beam into a two-window cell as a scattering light source for particles passing through the cell. The scattered light is collected by two optical systems, a high angle heterodyne system for particles below approximately 0.5 microns and a low angle non-coherent detector for 0.4 to 1.2 micron diameter particles. Each system has multiple detectors to measure scattering at multiple angles. FIG. 1 shows a representative system, where the representative approximate mean scattering angles for detectors 110, 111, 112, and 113 are 10, 20, 30, and 80 degrees, respectively. However, other angles and numbers of detectors could be used, including more than 2 detectors for each of lens 103 or lens 104. All four scattering intensity measurements are used for each particle passing through the intersection of the field of view of each of the two systems with the focused source beam. Detectors 110 and 111 use non-coherent detection because the signal levels for the larger particles measured by these two detectors are sufficiently large to avoid the complexity of a heterodyne system. Also the Doppler frequency for particles passing through the cell at meter per second speeds are too low to accumulate many cycles within the single particle pulse envelope at these low scattering angles. The Doppler frequencies may be much larger at larger scattering angles where the heterodyne detection is needed to measure the small scattering intensities from smaller particles.

Lens 104 collects scattered light from particles in the flowing dispersant. Slit 114 is imaged by lens 104 into the cell. The intersection of the rays passing through that image and the incident source beam define the interrogation volume where the particle must reside to be detected by detectors 110 and 111. Detectors 110 and 111 each intercept a different angular range of scattered light. Likewise for lens 103, slit 115 and detectors 112 and 113. The intersection of the rays by back-projection image of slit 115 and the source beam define an interrogation volume for the heterodyne system. The positions of slit 114 and slit 115 are adjusted so that their interrogation volumes coincide on the source beam. In order to define the smallest interaction volume, the images of the two slits should coincide with the minimum beam waist in the sample cell. These slits could also be replaced by other apertures such as pinholes or rectangular apertures. A portion the source beam, which was split off by a beamsplitter (the source beamsplitter), is reflected by a mirror to be expanded by a negative lens 105. This expanded beam is focused by lens 106 to match the wavefront of the scattered beam through lens 103. This matching beam is folded through slit 115 by a second beamsplitter (the detector beamsplitter) to mix with the scattered light on detectors 112 and 113. The total of the optical pathlengths from the source beamsplitter to the particle in the sample cell and from the particle to detectors 112 and 113, must match the total optical pathlength of the local oscillator beam from the source beamsplitter through the mirror, lenses 105 and 106, the detector beamsplitter, and slit 115 to detectors 112 and 113. The difference between these two total optical pathlengths must be less than the coherence length of the source to insure high interferometric visibility in the heterodyne signal. The scattered light is Doppler shifted by the flow velocity of the particles in the cell. By mixing this Doppler frequency shifted scattered light with unshifted light from the source on a quadratic detector (square of the combined E fields), a Doppler beat frequency is generated in the currents of detectors 112 and 113. The current oscillation amplitude is proportional to the square-root of the product of the source intensity and the scattered intensity. Hence, by increasing the amount of source light in the mixing, the detection will reach the Shot noise limit, allowing detection of particles below 0.1 micron diameter. By using a sawtooth drive function to vibrate the mirror with a vibrational component perpendicular to the mirror's surface, introducing optical phase modulation, the frequency of the heterodyne carrier can be increased to produce more signal oscillations per particle pulse. During each rise of the sawtooth function and corresponding motion of the mirror, the optical frequency of the light reflected from the mirror is shifted, providing a heterodyne beat signal on detectors 112 and 113 equal to that frequency shift. Then the mirror vibration signal could be used with a phase sensitive detection, at the frequency and phase of the beat frequency, to improve signal to noise. This could also be accomplished with other types of optical phase modulators (electro-optic and acousto-optic) or frequency shifters (acousto-optic). The reference signal for the phase sensitive detection could be provided by a separate detector which measures the mixture of light, which is reflected by the moving mirror (or frequency shifted by another device), with the unshifted light from the source.

For particles above approximately 0.4 microns, signals from all 4 detectors will have sufficient signal to noise to provide accurate particle size determination. The theoretical values for these 4 detectors vs. particle size may be placed in a lookup table. The 4 detector values from a measured unknown particle are compared against this table to find the two closest 4 detector signal groups, based upon the least squares minimization of the function:

$$(S1-S1T)^2+(S2-S2T)^2+(S3-S3T)^2+(S4-S4T)^2$$

where S1, S2, S3, S4 are signals from the 4 detectors, S1T, S2T, S3T, S4T are the theoretical values of the four signals for a particular particle size, and ^2 is the power of 2 or square of the quantity preceding the ^.

The true size is then determined by interpolation between these two best data sets based upon interpolation in 4 dimensional space. The size could also be determined by using search algorithms, which would find the particle size which minimizes the least square error while searching over the 4 dimensional space of the 4 detector signals. For particles of size below some empirically determined size (possibly around 0.4 micron), detector 110 and 111 signals could be rejected for insufficient signal to noise, and only the ratio of the signals (or other function of two signals) from shot noise limited heterodyne detectors 112 and 113 would be used to size each particle. If the low angle signals from detectors 110 and 111 are needed for small particles, they could be heterodyned with the source light using the same optical design as used for detectors 112 and 113. In any case, only signals with sufficient signal to noise should be used in the size determination, which may include only the use of detectors 110 and 111 when detector 112 and 113 signals are low. The look up table could also be replaced by an equation in all 4 detector signals, which would take the form of: particle size equals a function of the 4 detector signals. These techniques, least squares or function, could be extended to more than 4 detectors. For example, 3 detectors could be used for each system, discarding the low angle non-coherent detection when the signal to noise reaches unacceptable levels. In this case, a 6-dimensional space could be searched, interpolated, or parameterized as described above for the 4 detector system. This disclosure claims the use of any number of detectors to determine the particle size, with the angles and parameterization functions chosen to minimize size sensitivity to particle composition.

Figure 2:
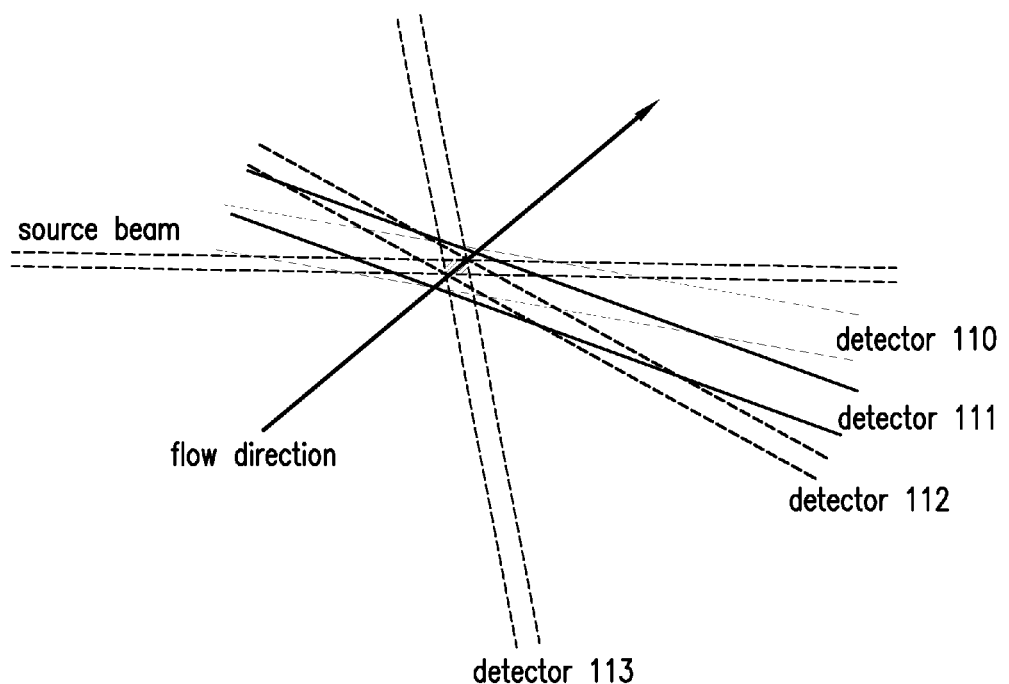
FIG. 2 provides a diagram showing the common volume between the light source and the viewing volumes of various detectors according to the present invention, the scatter volume common to all detectors being determined by detector 113.
Figure 2A:
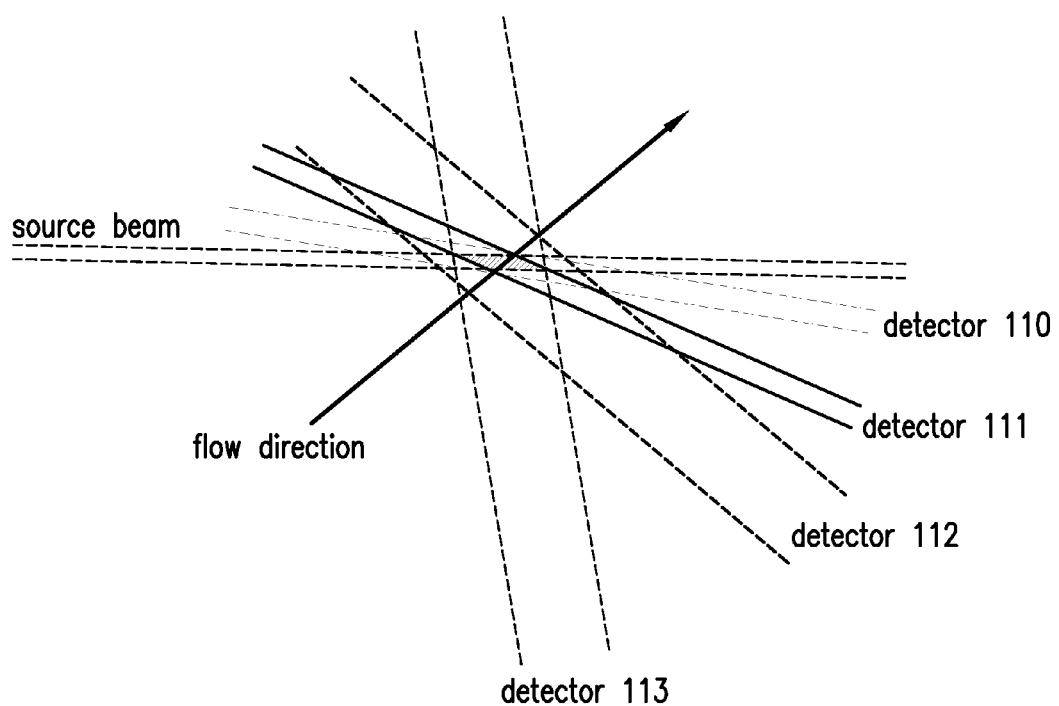
FIG. 2a provides a variation of FIG. 2, wherein the common scatter volume is determined by detector 111.

By tracing rays back from slits 114 and 115, the fields of view for two systems are determined, as shown in FIG. 2. The traced rays and source beam converge into the interrogation volume, where they all intersect. FIG. 2 shows these rays and beam in the vicinity of this intersection volume, without detailed description of the converging nature of the beams. The intersection volume is the intersection of the source beam and the field of view of the detector. In this case, the beam from slit 114 may be wider than that from slit 115, so that the source beam and slit 115 field of view fall well within the field of view of slit 114. And the source beam falls well within the field of view of slit 115. By accepting only particle signal pulses which show coincidence with pulses from detector 113 (which has the smallest intersection with the source beam, shown by the crosshatched area), the interrogation volume is matched for all 4 detectors. The source beam could also have a rectangular crossection, with major axis aligned with the long axis of the slits. This would reduce the edge effects for particles passing near to the edges of the beam. The slit images are designed to be much longer than the major axis of the source beam, so that both slits only need to be aligned in the direction perpendicular to the source major axis. This provides for very easy alignment to assure that the intersection of images from detectors 112 and 113 and the source beam fall within the intersection of images from detectors 110 and 111. The slit position could also be adjusted along the optical axis of the detection system to bring the crossover point of both detector fields of view to be coincident with the source beam. Another configuration is shown in FIG. 2a, where slit 115 is wider than slit 114. Here detector 111 defines the smallest common volume as indicated by the cross hatched area. And so only particles which are counted by detector 111 can be counted by the other detectors. All other particles detected by the other detectors, but not detected by detector 111, are rejected because they do not produce concurrent signals in every detector. This process can be extended to more than 4 detectors. In some cases three or more detectors per optical system may be required to obtain accurate size measurement. In this case, the size could be determined by use of a look up table or search algorithm.

The data for each particle would be compared to a group of theoretical data sets. Using some selection routine, such as total RMS difference, the two nearest size successive theoretical sets which bracket either side of the measured set would be chosen. Then the measured set would be used to interpolate the particle size between the two chosen theoretical sets to determine the size. The size determination is made very quickly (unlike an iterative algorithm) so as to keep up with the large number of data sets produced by thousands of particles passing through the sample cell. In this way each particle could be individually sized and counted according to its size to produce a number-vs.-size distribution which can be converted to any other distribution form. These theoretical data sets could be generated for various particle refractive indices and particle shapes.

In general, a set of design rules may be created for the intersection of fields of view from multiple scattering detectors at various angles. Let us define a coordinate system for the incident light beam with the z axis along the direction of propagation and the x axis and y axis are both perpendicular to the z axis, with the x axis in the scattering plane and the y axis perpendicular to the scattering plane. The scattering plane is the plane which includes the source beam axis and the axis of the scattered light ray. In most cases the detector slits are oriented parallel to the y direction. Many configurations are possible, including three different configurations which are listed below:

1) The incident beam is smaller than the high scattering angle detector field crossection, which is smaller than the low scattering angle detector field crossection. Only particle pulses that are coincident with the high angle detector pulses are accepted. The incident beam may be spatially filtered (FIG. 1A) in the y direction, with the filter aperture imaged into the interaction volume. This aperture will cut off the Gaussian wings of the intensity profile in the y direction, providing a more abrupt drop in intensity. Then fewer small particles, which pass through the tail of the intensity distribution, will be lost in the detection noise and both large and small particles will see the same effective interaction volume.

2) The incident beam is larger than the low scattering angle detector field crossection, which is larger than the high scattering angle detector field crossection. Only particle pulses that are coincident with the high angle detector pulses are accepted. The correlation coefficient of the pulses or the delay (determined by cross correlation) between pulses is used to insure that only pulses from particles seen by every detector are counted.

3) The incident beam width and all fields from individual detectors progress from small to large size. Then particles counted by the entity with the smallest interaction volume will be sensed by all of the rest of the detectors. Only particles sensed by the smallest interaction volume entity will be counted, because this smallest interaction volume will be contained in all of the interaction volumes for the other detectors, which will also see this particle. For example, if the progression from smallest to largest interaction volume is low angle to high angle, then only events with a low angle scattering pulse will be accepted.

4) In all cases, the slits could be replaced by rectangular apertures, which would remove spurious scattering and source light components which are far from the interaction volume.

When the beam is larger than the detector fields of view, good intensity uniformity is obtained in the interaction volume. However, then many signal pulses, which are not common to all detector fields of view, will be detected and must be eliminated from the count by the methods described in this application. When the beam is smaller than the fields of view, the intensity uniformity is poor, but fewer signal pulses are detected outside of the common volume of the detector fields.

Also the higher source intensity of the smaller beam provides higher signal to noise for the scattered light pulses. In this case, the detector intensity variation can be corrected for by deconvolution methods described later or reduced by aperture (FIG. 1A for example) of the light source to select a region of uniform intensity of the light source. Each slit (source and detector) could be replaced by a rectangular aperture which defines the interaction volume and laser spot in both x and y directions. This would provide the best discrimination against spurious scattered light and provide best truncation of the tails of the laser spot intensity distribution. However, this configuration may be more difficult to align. One side of the rectangle should be oriented parallel to the flow so that particles are either entirely in or out of the beam as they pass through the sample cell. This aperture orientation and elimination of intensity tails in the source intensity distribution (FIG. 1A) will produce signal pulses, on all detectors, which have similar shape for any position of passage through the beam. This uniformity of pulse shape is effective in detection of low level pulses in noise. Because the shape and position of largest signal pulse of the detector set can be used to find the pulse from the detectors with weaker signals, by solving for that shape and position with an arbitrary background. The pulse height and signal baseline are determined from the digitized signals using regression analysis which assumes the pulse shape of the other stronger signal. This method is also useful when the field of view A, of the smaller signal detector, is larger than the field of view B of the larger signal detector, and view B is contained inside of view A. Then the smaller signal pulse will have the same shape as the larger signal pulse, during the duration of the larger pulse. This larger signal can also be multiplied times the smaller signal. This signal product would accentuate the correlated portion of the smaller signal. Also the larger signal could be used as a matching filter for the smaller signal detection. Both of these methods are describe later in this application.

In most cases the divergence of the laser beam should be minimized in the scatter plane to allow detection of particle scatter at low scattering angles. Then the laser spot should be wider in the x direction, and the major axis of the source rectangular aperture (FIG. 1A) would be parallel to the x axis to minimize the beam divergence in that plane. The major axis of the detector rectangular apertures (same locations as slits 114 and 115 and slits 301 and 302 of FIG. 3 and slits 501 and 502 of FIG. 5) could be parallel to the x or y axis. The image of the detector aperture in the interaction volume should be larger than the beam in the y axis, to provide for easy alignment, but restrictive in the x axis to define a small interaction volume. The aperture could be smaller than the source beam in both x and y, but with more difficult alignment. If the beam is much larger than the image of the detector aperture, this alignment difficulty is removed and the intensity uniformity in the interaction volume is improved, but with lower source intensity and scattered signal. Pinholes or square apertures could also be used in place of slits 114 and 115. In all cases, the intersection of the images of both apertures (detector and source for each detector) defines the interaction volume where particle scatter can be detected by that detector.

The two detector pairs, 1+2 and 3+4, could also be used independently to measure count vs. size distributions. The lower angle pair could only measure down to the size where the ratio of their angles is no longer sensitive to size and the scattering crossections are too small to maintain signal to noise. Likewise for the high angle detectors, they can only measure up to sizes where their ratio is no longer monotonic with particle size. However, absolute scattered signal levels could be used to determine the particle size outside of this size region. Since extremes of these operational ranges overlap on the size scale, the two pairs could be aligned and operated independently. The small angle detectors would miss some small particles and the high angle detectors would miss some large particles. But the two independently acquired particle size distributions could be combined using their particle size distributions in the size region where they overlap. Scale one distribution to match the other in the overlap region and then use the distribution below the overlap from the high angle detectors for below the overlap region and the distribution from the low angle detectors for the distribution above the overlap region. In the overlap region, the distribution starts with the high angle result and blends towards the low angle result as you increase particle size. Detector triplets could also be used, where the largest angle of the low angle set and the lowest angle of the high angle set overlap so as to scale the scattering measurements to each other.

In some cases, the angular range of each of the heterodyne detectors must be limited by the considerations described later (see FIG. 91 and discussion of detector angular widths) to maintain heterodyne signal visibility.

The flat window surfaces could be replaced by spherical surfaces (see FIG. 75) with centers of curvature which coincide with the center of the interrogation volume. Then the focal positions of all of the beams would remain in the same location for dispersing liquids with various refractive indices. These systems can also be designed using fiber optics, by replacing beamsplitters with fiber optic couplers. Then the vibrating mirror could be replaced by a fiber optic phase modulator.

Figure 3:
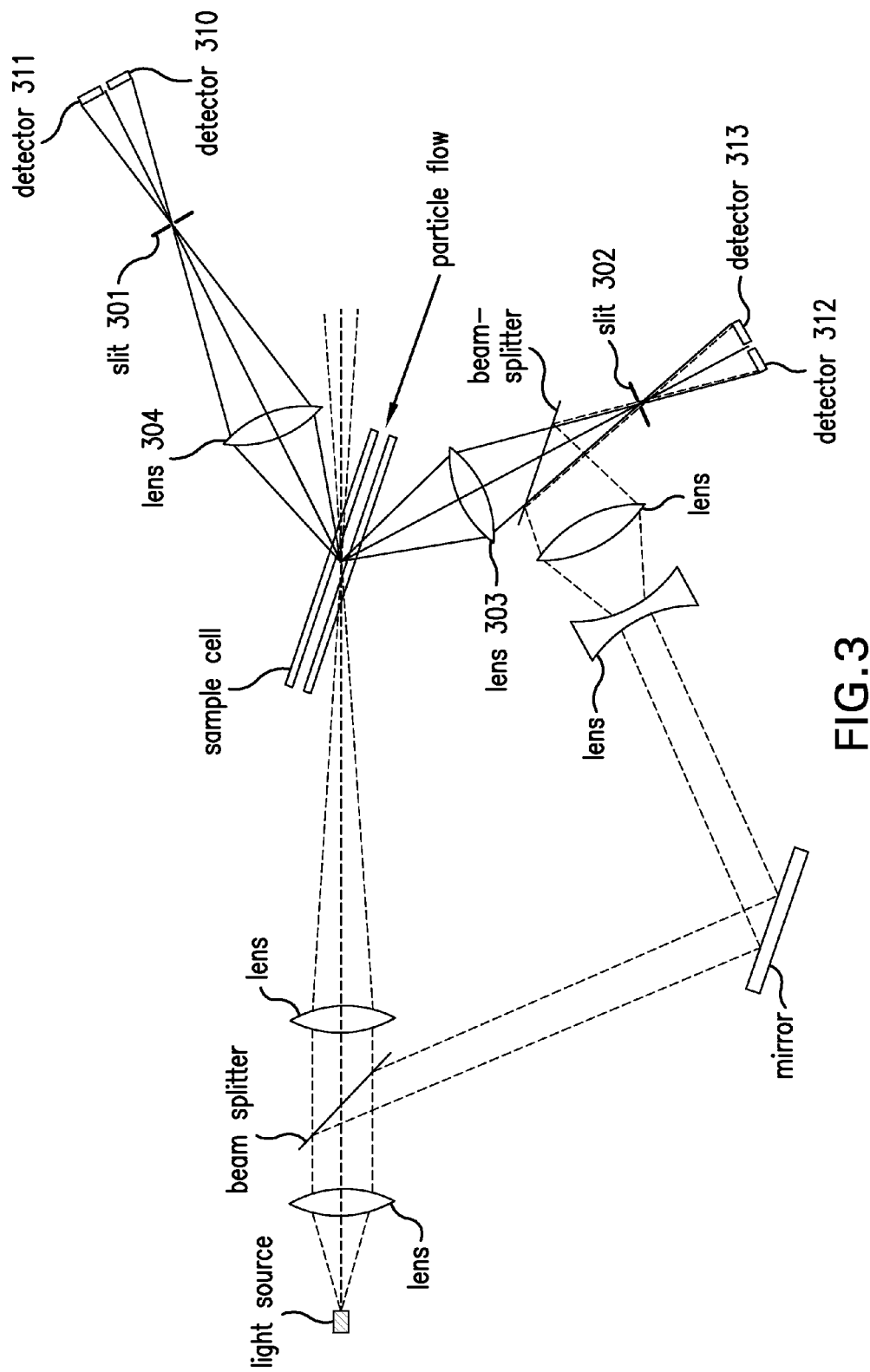
FIG. 3 provides a variation of FIG. 1, where lens 303 and lens 304 are on opposite sides of the light beam.

FIG. 3 shows an alternate optical configuration for FIG. 1, where the low angle scattering system is placed on the opposite side of the cell from the high angle system. In some cases, this configuration will facilitate the mechanical design of the support structure for the cell and optical systems.

Figure 101:
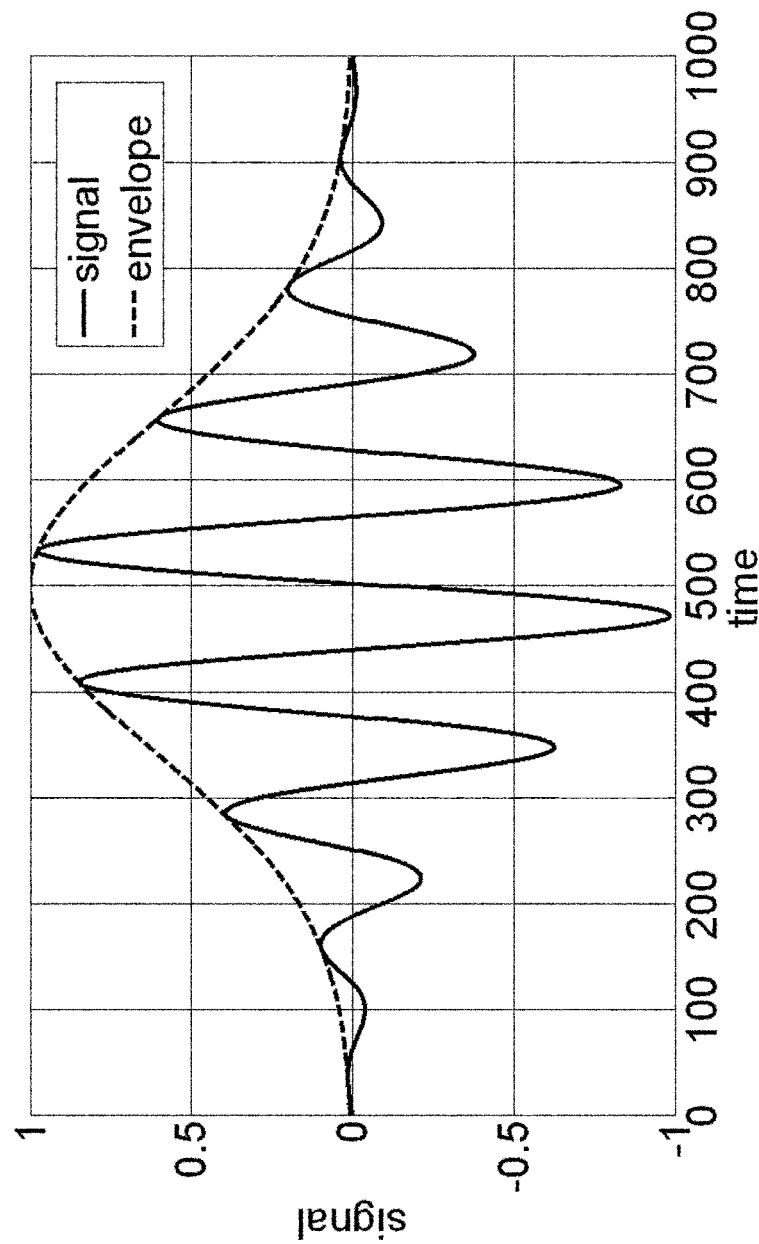
FIG. 101 provides a graph showing plots of an envelope function and heterodyne signal, which comprises a train of oscillations which are amplitude modulated by an envelope determined by the intensity profile of the incident light beam, according to the present invention.

The detector currents from the low angle system and the high angle system must be processed differently. Every particle passing through the interaction volume will produce a pulse in the detector current. Detectors 310 and 311 will show simple pulses, but detectors 312 and 313 will produce modulated pulses. The heterodyne detection measures the Doppler beat frequency as the particle passes through the beam. So each heterodyne pulse will consist of a train of oscillations which are amplitude modulated by an envelope determined by the intensity profile of the incident beam, as shown in FIG. 101 for a Gaussian beam profile. The heterodyne signal must pass through a high pass filter or bandpass filter (to remove the large local oscillator offset) and then an envelope detector (see FIG. 4) to remove the heterodyne oscillations, producing the signal envelope for further processing. This preprocessing envelope detection is used in the process steps below.

Figure 5:
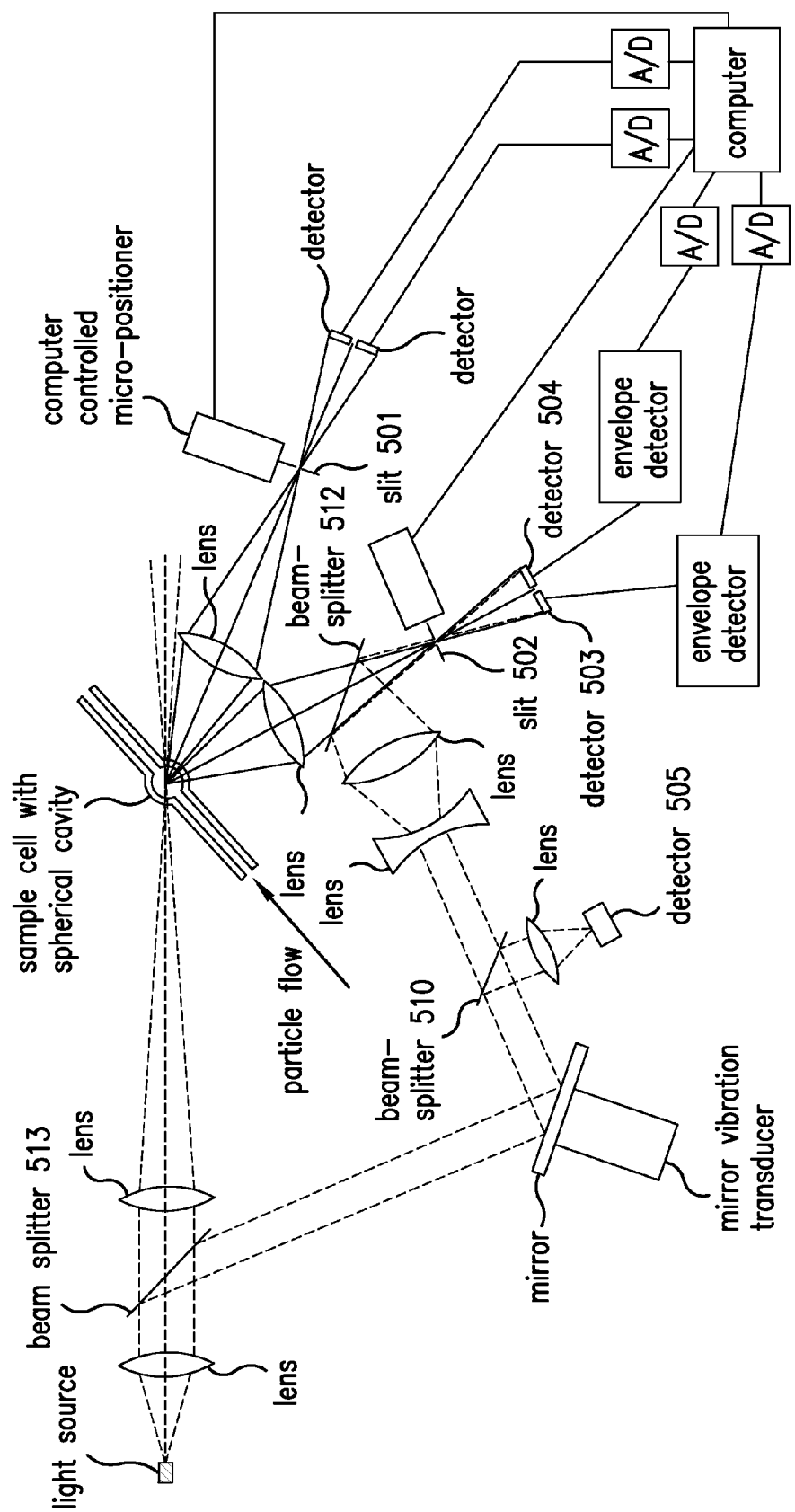
FIG. 5 provides a schematic diagram of an automated system for providing optical alignment of the system of FIG. 1.

For small particles the heterodyne signals will be buried in laser source noise. FIG. 5 shows an additional detector 505 which measures the intensity of the local oscillator laser noise. If we define a heterodyne detector current as I1 and the detector 505 laser monitor detector current as I2 we obtain the following equations which hold for each of the heterodyne detectors.

$$I1 = \text{sqrt}(R*Io(t)*COS(t))*COS(F*t+A)+R*Io$$

$$I1 = \text{sqrt}(R*Io(t)*S(1-R)Io)*COS(F*t+A)+R*Io$$

$$I2 = K*Io(t)$$

where:

$COS(x) = $ cosine of $x$

K is a constant which includes the product of the reflectivities of the beamsplitter 510 and beamsplitter 513

R and (1−R) are the effective reflectivity and transmission of the beam splitters, respectively $$R=R2*R3*(1-R1)$$

$$(1-R)=(1-R2)*(1-R3)$$

R2 is the reflectivity of beamsplitter 512
R3 is the reflectivity of beamsplitter 513
R1 is the reflectivity of beamsplitter 510
sqrt(x)=square root of x
Io(t) is the source beam intensity as function of time t
F is the heterodyne beat frequency at a heterodyne detector due to the motion of the scatterer in the sample cell. And A is an arbitrary phase angle for the particular particle. Is(t) is the scattered light intensity from the particle:
Is(t)=S*(1−R)*Io(t) where S is the scattering efficiency or scattering crossection for the particle The light source intensity will consist of a constant portion Ioc and noise n(t):

$$Io(t)=Ioc+n(t)$$

We may then rewrite equations for I1 and I2:

$$I1=\text{sqrt}(S*(1-R)*R)*(Ioc+n(t))*\text{COS}(F*t+A)+R*(Ioc+n(t))$$

$$I2=K*(Ioc+n(t))$$

The heterodyne beat from a particle traveling with nearly constant velocity down the sample cell will cover a very narrow spectral range with high frequency F. For example, at 1 meter per second flow rate, the beat frequency would be in the megahertz range. If we use narrow band filters to only accept the narrow range of beat frequencies we obtain the narrow band components for I1 and I2:

$$I1nb=\text{sqrt}(S*(1-R)*R)*Ioc*\text{COS}(F*t+A)+R*n(t)$$

$$I2nb=K*n(t)$$

where we have assumed that n(t) is much smaller than Ioc. And also n(t) is the portion of the laser noise that is within the electronic narrowband filter bandwidth (see below).

The laser noise can be removed to produce the pure heterodyne signal, Idiff, through the following relationship:

$$Idiff=I1nb-(R/K)*I2nb=\text{Sqrt}(R*(1-R)*S)*Ioc*\text{COS}(F*t+A)$$

This relationship is realized by narrowband filtering of each of the I1 and I2 detector currents. One or both of these filtered signals are amplified by programmable amplifiers, whose gains and phase shifts are adjustable. The difference of the two outputs of these amplifiers is generated by a difference circuit or differential amplifier. With no particles in the beam, the gain and phase shift of at least one of the programmable amplifiers is adjusted, under computer or manual control, to minimize the output of the difference circuit (i.e. (gain for I2)*R/K=1, assuming gain for I1=1) At this gain, the source intensity noise component in the detector 503 or detector 504 beat signal, with particles present, is eliminated in the difference signal, which is fed to an analog to digital converter (A/D), through a third narrowband filter, for analysis to sense the beat signal buried in noise. This filtered difference signal could also be detected by a phase locked loop, which would lock in on the beat frequency of current from the heterodyne detector.

The particle dispersion flow rate could also be adjusted to maximize the heterodyne signal, through the electronic narrowband filter, by matching the Doppler frequency from flowing particle scattered light with the center of the filter bandpass.

This entire correction could also be accomplished in the computer by using a separate A/D for each filtered signal and generating the difference signal by digital computation inside the computer. The phase and gain adjustments mentioned above, without particles in the beam, could be adjusted digitally. Also these gain adjustments could also be determined from measurement of the signal offsets I1dc and I2dc (the average value of the signal due to the local oscillator). If the scattering component of the heterodyne signal is negligible compared to the offset caused by the local oscillator, this adjustment could be determined from measurements taken with particles in the beam. In this case, the contribution from the source intensity noise should be proportional to the offset level because the noise is the same percentage of the average level of the intensity in both I1 and I2. Then the coefficient ratio R/K in the equation for Idiff can be calculated from:

$$R/K=I1dc/I2dc$$

Where I1dc and I2dc are the average of the unfiltered signals I1 and I2, respectively. And the gain (or digital multiplier) of I2 is then I2dc/I1dc (relative to a gain for signal I1=1).

If both signals were digitized separately, other correlation techniques could be used to reduce the effects of source intensity noise. Beamsplitter 512 and 513 reflections are adjusted to obtain shot noise limited heterodyne detection, with excess laser noise removed by the difference circuit.

The noise correction techniques described on the prior pages (and FIG. 5) can be applied to any heterodyning system by simply adjusting the filtering of currents I1 and I2 to pass the signal of interest, while blocking the low frequency component (Ioc) of Io(t). Excess laser noise and any other correlated noise component, which is present in both the heterodyne signal and the light source, can be removed from the signal of interest through this procedure. One application is dynamic light scattering, where the heterodyne signal is contaminated by laser source noise in the optical mixing process. The filters on I1 and I2 would be designed to pass the important portion of the Doppler broadened spectrum (using a lower frequency broad band filter or high pass filter instead of the high frequency narrow band filter) and to remove the large signal offset due to the local oscillator. Then by using the subtraction equation described below (where the narrow band filter is replaced by said broad band filter in all equations) the effects of laser noise can be removed from the Doppler spectrum, improving the particle size accuracy.

$$Idiff=I1nb-(R/K)*I2nb=\text{Sqrt}(R*(1-R)*S)*Ioc*\text{COS}(F*t+A)$$

In this case, the heterodyne signal is the sum of many COS functions with various frequencies and phases. The noise, common to both the heterodyne signal and incident light source intensity, will still be completely removed in Idiff. In the case of fiber optic heterodyning systems, the laser monitor current, I2, could be obtained at the exit of the unused output port of the fiber optic coupler which is used to transport the light to and from the particle sample, because this port carries light only from the optical source, without any scattered light. I2 can be measured with a light detector at any point in the optical system where the light source intensity vs. time is available. This subtraction shown in the equation above could be accomplished by the analog difference circuit or by digital subtraction after digitization of both the filtered contaminated signal and the filtered source monitor as outlined previously.

This procedure could also be accomplished using the unfiltered signals, but with much poorer accuracy due to the large signal offsets.

Figure 4:
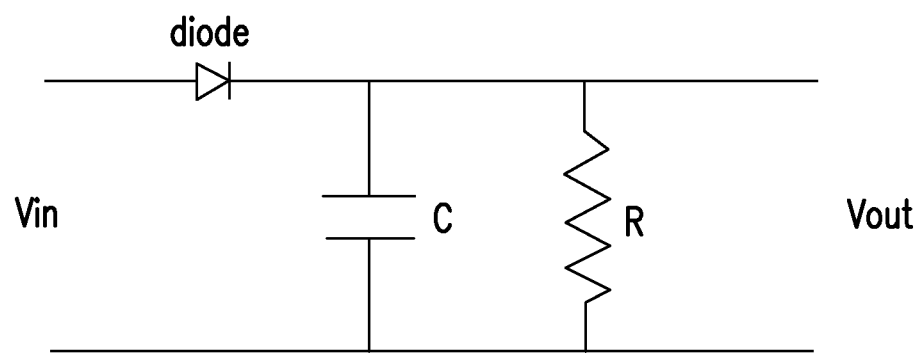
FIG. 4 provides a schematic diagram of a signal conditioning circuit which detects the envelope of a signal, as used in the present invention.
Figure 6:
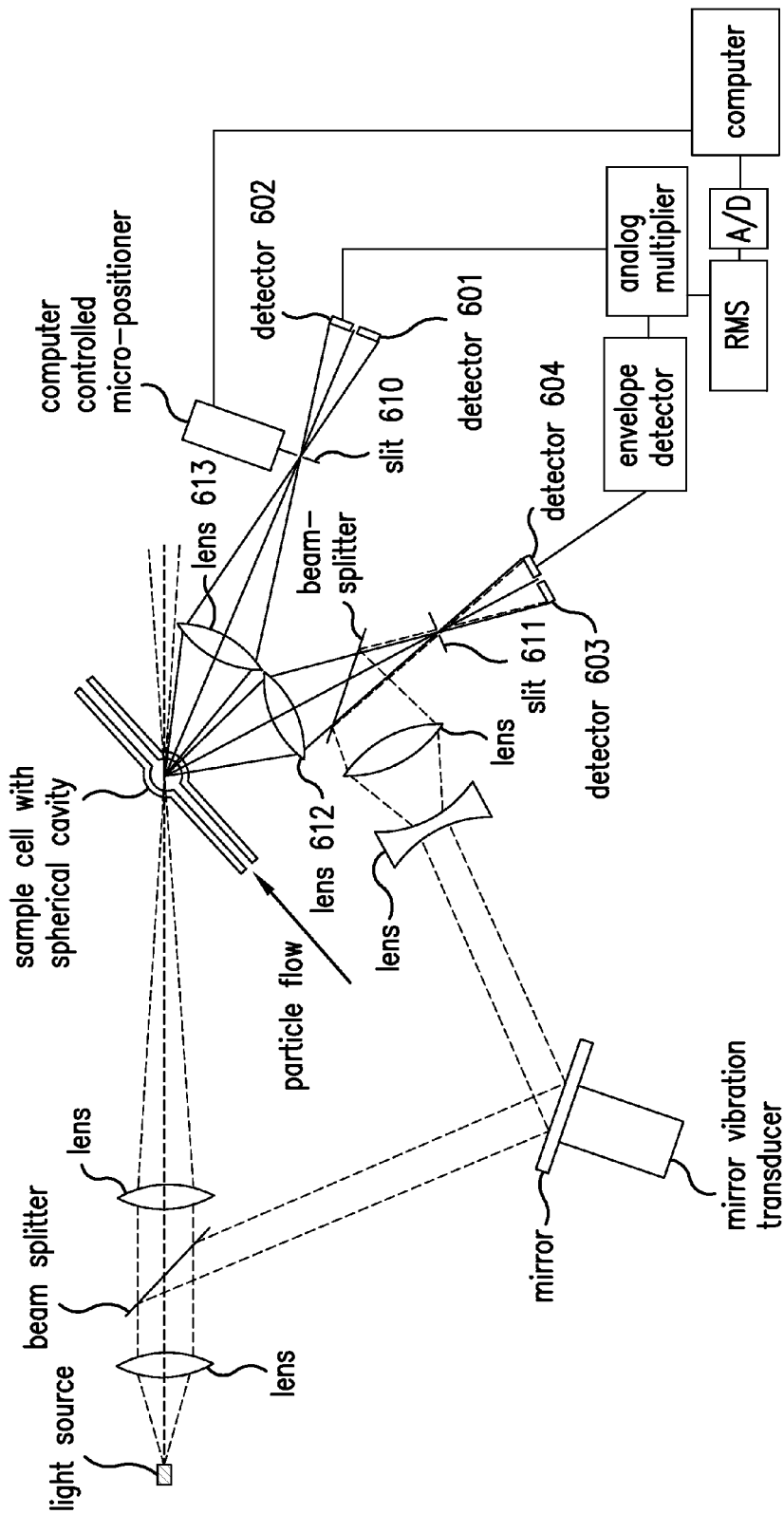
FIG. 6 provides a variation of FIG. 5, showing the use of an analog multiplier.

FIG. 6 shows the system with some additional features. The sample cell windows contain spherical surfaces with center of curvature at the interaction volume, similar to the concepts shown in FIG. 75. The light source beam and detector acceptance cones pass through these spherical surfaces in order to avoid focal shift of the source and detector beams when the refractive index of the dispersing fluid is changed. The heterodyne detector currents from detectors 603 and 604 are passed through a high pass filter to remove the large local oscillator current and then (after completing the noise removal described above) they are passed through an envelope detector to remove the heterodyne oscillation due to the Doppler shifted spectrum of the scattered light from the moving particles. As mentioned earlier, this Doppler frequency may be increased by vibrating the mirror so as to add phase modulation to the local oscillator. This will provide more signal oscillations per signal pulse. After the high pass or narrowband filter, the signal will consist of a sinusoid which is amplitude modulated by the scattering pulse due to the particle's transit through the source beam (see FIG. 101). The envelope of this modulated sinusoid is measured by an envelope detector as shown in FIG. 4. The resulting single pulse is digitized by an analog to digital converter (A/D) before analysis by a computer. This process is similar for each of detectors 603 and 604. Since lower angle scattering produces lower Doppler frequency, the lower scattering angle signals are usually measured without heterodyne detection when the signals are large. So for large signal levels, Detectors 601 and 602 do not require heterodyne detection; but a heterodyne optical system, as used for detectors 603 and 604, could be used for detectors 601 and 602 if the signal levels were small. Then the vibrating mirror phase modulator, shown in figure below, could be used to increase the heterodyning frequency. If the signals are large, the scattered light current pulses from detectors 601 and 602 can be digitized directly before computer analysis, without envelope detection. The analysis of these signals is described below.

One other aspect of this invention is a means for auto-alignment of the optics. Auto alignment is needed to correct for changes in beam direction and focus due to changes of dispersant refractive index and mechanical drift of optical components. Auto-alignment could be done periodically by the computer or whenever a new particle sample or new dispersing fluid is introduced to the system. These techniques can be used to auto-align any of the apertures, in this application, which are in an image plane of the particle, such as apertures 7802 and 7803 in FIG. 78. As shown in FIG. 2, the source beam and all four fields of view, from the four detectors, must intersect at the same point to all see scattering from the same particle. Images of slits 610 and 611 define the point where the view fields from each detector pair (1+2 or 3+4) intersect. The slit apertures usually only need alignment in one direction, perpendicular to the slit, but position adjustment may also be needed along the optical axis of the detector system to place the intersection between the fields of view from detectors 601 and 602 (or 603 and 604) on the source beam. Pinhole or rectangular apertures must be aligned in two orthogonal directions which are in the plane perpendicular to the optical axis of the scattering detection optical system. Either one or both slits may be adjusted to obtain alignment. FIG. 5 shows an example where both slit positions are optimized by a computer controlled micro-positioner. For example, the digitized signals from detector 602 and detector 603 could be digitally multiplied (after the envelope detector) and the resulting product integrated or low pass filtered to produce a correlation between the two detector signals. The position slit 610 is adjusted until this correlation signal is maximum with particles flowing through the interaction volume. If needed, both slits 610 and 611 may be moved to optimize this correlation signal. In general these should be small adjustments because the spherical window surfaces will prevent large beam refractions and focal shifts due to changing particle dispersant refractive index. In systems with large beam shifts, the slits may need to be moved perpendicular and parallel to the optical axis of each optical system to maximize the correlation between the detectors. This could be accomplished with dual axis micro-positioners, which could also be used when the slits are replaced by pinholes or rectangular apertures, which require alignment in two orthogonal axes perpendicular to the optical axis of the scattering detection optical system.

FIG. 2 shows larger fields of view for detectors 110 and 111 than for detectors 112 and 113. This is accomplished with slit 610 wider than slit 611 or by larger magnification for lens 613 than for lens 612 (image of the slit in the interaction volume). Hence the alignment of slit 610 is much less critical then slit 611 because image of slit 610 in the interaction volume is wider and has larger depth of focus than for slit 611. By placing computer controlled micro-positioners on slit 610 and slit 611, the system can be aligned by using the correlation between the signals. The micro-positioners move each slit perpendicular to the long axis of the slit opening and perpendicular to the optical axis of that lens. The alignment procedure is described below:

1) With low concentration of particles in the flow stream, adjust the position of slit 611 to maximize the correlation (using an analog multiplier and RMS circuit) between the signals from detectors 603 and 604. At this point the intersection of the fields of views of both detectors cross at the incident beam and the signals are maximum.
2) Then adjust the position of slit 610 until the correlation of detectors 601 and 602 with detectors 603 and 604 is a maximum. After this adjustment both detectors 601 and 602 view the intersection defined by step 1.

During particle counting and measurement, only particles seen by both detectors 603 and 604 are counted by all of the detectors, because they are a subset of the particles seen by detectors 601 and 602. By using different slit image sizes and using the smaller slit images to determine count acceptance, the system will accept only particles which are seen by all four detectors. If the slit images from detectors 603 and 604 are larger than the images from detectors 601 and 602, then detectors 601 and 602 would be adjusted before adjusting 603 and 604; and detectors 601 and 602 would select which particles are counted. The general rule is that the detector images which have the smallest intersection with the incident beam are adjusted first and they determine which particles will be counted. The slit widths are chosen to create one slit image with a small intersection volume and the other with a larger intersection volume so that when a particle is detected in the smaller volume, it is clearly within the larger volume. The smaller slit image only needs to cross the incident beam near to its image plane. Then the larger slit image only needs to cover the intersecting volume to insure that it sees all of the particles passing through the smaller slit image. Then by only counting particles detected by the smaller slit image, only particles which are seen by both detectors will be counted. If the slit images were comparable in size, very precise alignment of both slit images with each other would be required and the correlation between the detector signals would be needed to choose which particles to count. This comparable sized slit case is also claimed in this disclosure. Also the replacement of slits with rectangular apertures or pinholes is also claimed, but with the requirement for two axis alignment as indicated previously.

Figure 6A:
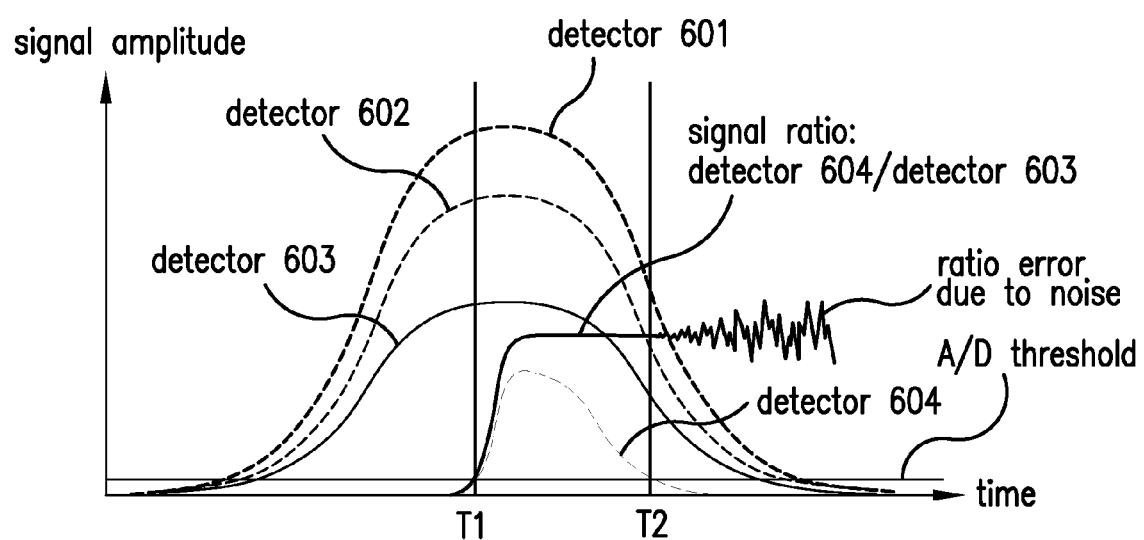
FIG. 6a provides a graph showing an example of scatter signals from a system as shown in FIG. 1.

FIG. 6a shows an example of scattered detection pulses from the four detectors. These signals are measured after a high pass filter for each of detectors 601 and 602, and after a high pass filter and envelope detector for each of detectors 603 and 604. The high pass filters could be replaced by narrow band filters. This data describes the case where the particle passes through a corner of the volume which is common to the source beam and the field of view from detector 604 (see FIG. 2). Detectors 601, 602, and 603 show similar profiles as a function of time as the particle passes through the interaction volume. However the signal from detector four is truncated at the leading edge due to the edge of the detector field of view. Over the region where the particle is well within the detector fields of view, each detector signal will maintain the same ratio with another detector signal as the detector signal amplitudes follow the particle passing through the source crossection intensity distribution. This region of stable signal ratio must be determined in order to eliminate the effects of the variation in source intensity by ratioing pairs of detector signals. Each of the four detector signals is digitized and the ratio of signal from the detector with the minimum interaction volume with one of the other detectors is calculated at each A/D (analog to digital conversion) sampling point. The A/D may be only turned on by a comparator during the period where all the detector signals are above a noise threshold, between times T1 and T2 in FIG. 6a. In this case the ratio between detectors 603 and 604 is used to determine the optimum portion the sampled data to use. The ratio of detector 604/detector 603 increases as the particle enters the field of view of detector 604. Once the particle is completely inside the field of view, the ratio between the two signals is nearly constant even though the individual signals are changing due to the source intensity distribution non-uniformity. Eventually, the signal levels drop and the signal ratio becomes very noisy. If we assume that there are 20 samples between T1 and T2, we could measure the variance of the ratio for samples 1 through 5 and then the variance of the ratio for samples 2 through 6, and so on up to samples 16 through 20. The 5 sample set with the lowest variance for the detector 603/detector 604 ratio would be chosen to determine the detector to detector ratios for all detector combinations for that particle, either by choosing the sample in the middle (sample 3) of that set or by averaging all 5 ratios to obtain an averaged ratio for the 5 samples in the set. The assumption of 20 samples and 5 samples per set is an example. This invention claims any appropriate data set size and segmentation.

The pulses shown in FIG. 6a are the result of some prior electronic filtering and envelope detection. The signals from detectors 601 and 602 will be simple pulses which may be cleaned up by a high pass filter before the A/D conversion. The signals from the heterodyne detectors 603 and 604 are the product of a pulse and a sinusoid. The pulse may consist of a megahertz sine wave, amplitude modulated by the intensity profile of the source beam over a period of about 100 microseconds, depending upon the size of the interaction volume and the particle flow velocity. This oscillatory signal sits on top of a large offset due to the local oscillator intensity. This offset and other source noise components may be removed from the heterodyne signal by high pass or narrow-band electronic filtering. The power spectrum of these pulses will reside in a 100 kilohertz band which is centered at 1 megahertz. Hence a narrow-band filter may provide optimal signal to noise for the heterodyne signals. After the filtering, the signals could be digitized directly for digital envelope detection or an analog envelope detector could be used to remove the 1 megahertz carrier, reducing the required sampling rate to only 10 to 20 samples per pulse instead of 400 samples per pulse. By using a dual phase lock-in amplifier with reference oscillator set to the heterodyne frequency (1 megahertz in this example), extremely high signal to noise could be obtained by measuring the filtered signal without the envelope detector. By using the zero degree and quadrature outputs of the dual phase lock-in amplifier, the phase sensitive signal would be recovered even though the reference and signal carriers are not necessarily in phase.

Figure 7:
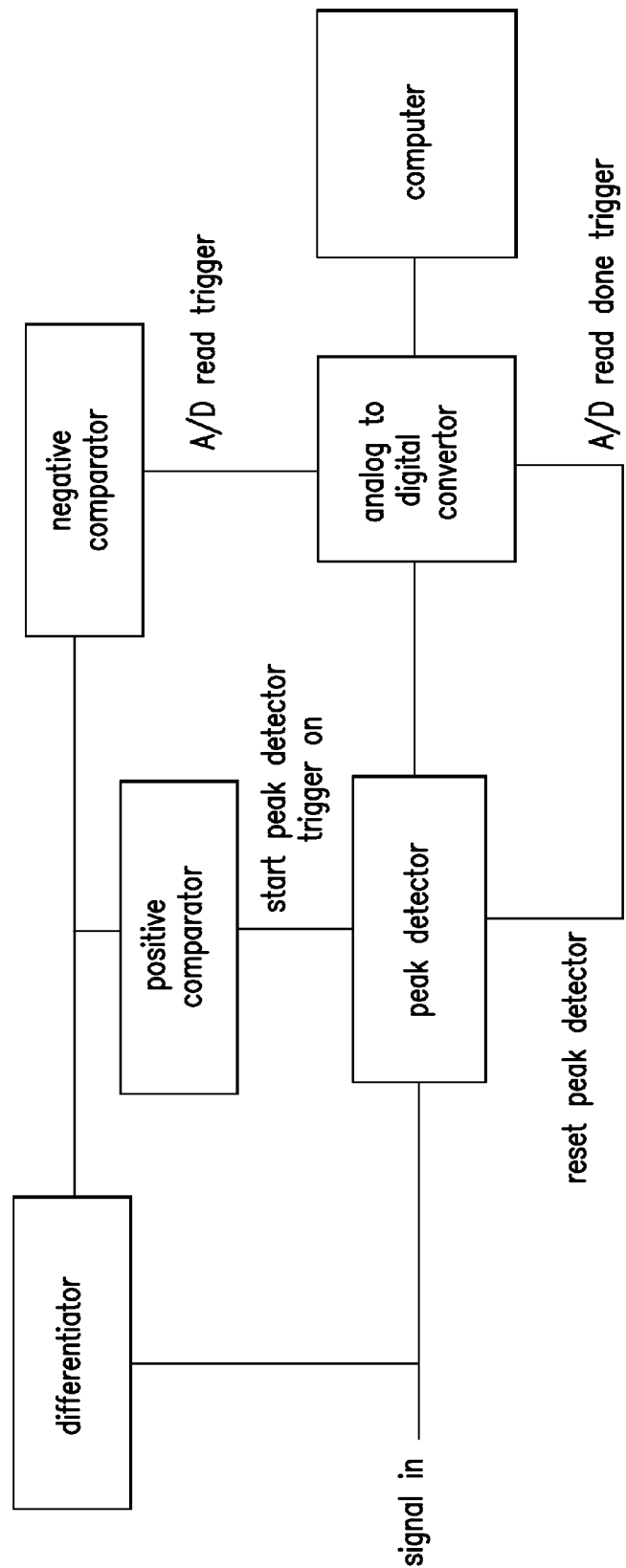
FIG. 7 provides a block diagram of a peak detection system which uses analog electronic devices to reduce the data rate requirements of the analog to digital converter, according to the present invention.

The particle counting rate can also be increased by digitizing the peak scattered signal (directly from detectors 601 and 602 and after the envelope detector from detectors 603 and 604) from each particle instead of digitizing many points across the scattering pulse and finding the peak digitally. This is accomplished by using an analog peak detector whose output is digitized in sync with the positive portion of the signal pulse derivative and reset by the negative portion of the derivative. Then only one digitization is needed for each particle, as shown in FIG. 7. The negative comparator switches on when the input signal drops below the reference setting and the positive comparator switches on when the signal is greater than the reference setting.

Figure 8:
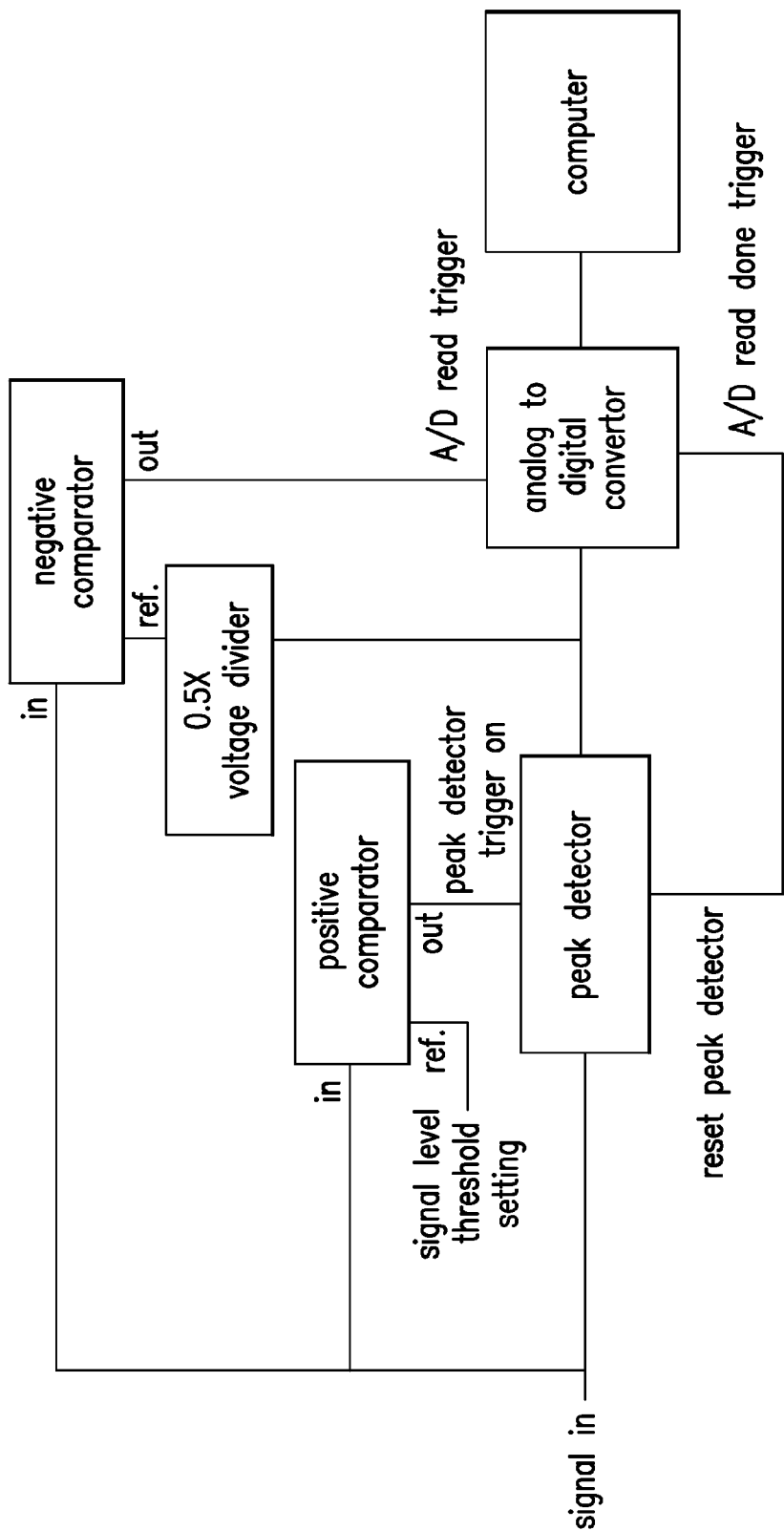
FIG. 8 provides a variation of the system shown in FIG. 7.
Figure 9:
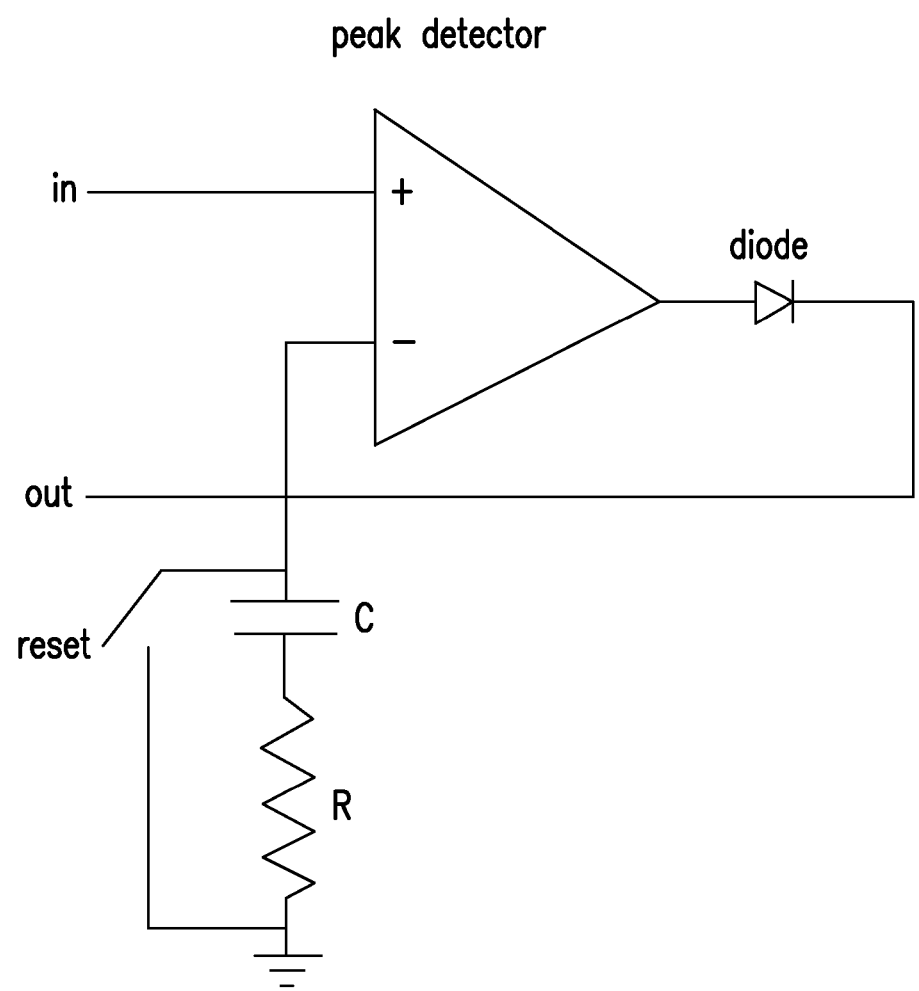
FIG. 9 provides a schematic diagram of the peak detector circuit used in the present invention.

Another variation of this concept triggers on the actual signal instead of the derivative, as shown in FIG. 8. When the signal rises above a preset threshold, the positive comparator takes the peak detector out of reset mode. As the signal rises, the output of the peak detector (see FIG. 9) follows the input signal until the signal reaches a peak. After this point, the peak detector holds the peak value with a time constant given by the RC of the peak detector circuit. The input signal drops below this as it falls down the backside of the peak. When the signal reaches some percentage of the peak value, the A/D is triggered to read and then reset the positive comparator. This percentage value is provided by a voltage divider (shown in the figure as 0.5× voltage divider, but other divider ratios would also be appropriate between approximately 0.2 to 0.8) which determines the reference level for the negative comparator. The A/D is only triggered once per signal pulse and measures the peak value of the pulse. Using this circuit, the detector with the smallest interaction volume generates the A/D trigger for all of the other detectors, so that only particles seen by all of the detectors are counted.

Figure 10:
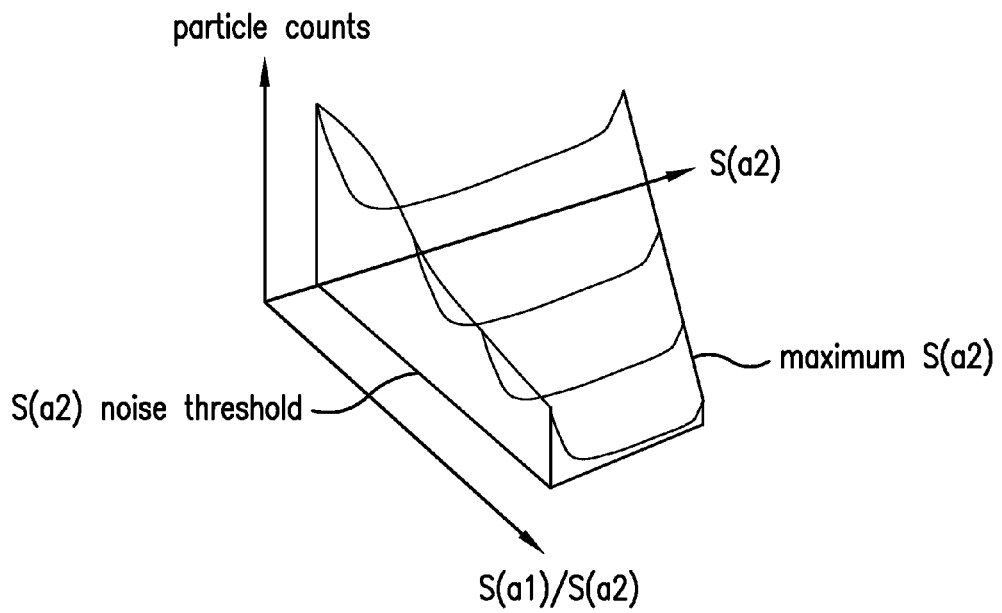
FIG. 10 provides a surface plot of a particle count distribution versus a scattering signal amplitude and a ratio of two scattering signals, according to the present invention.
Figure 10A:
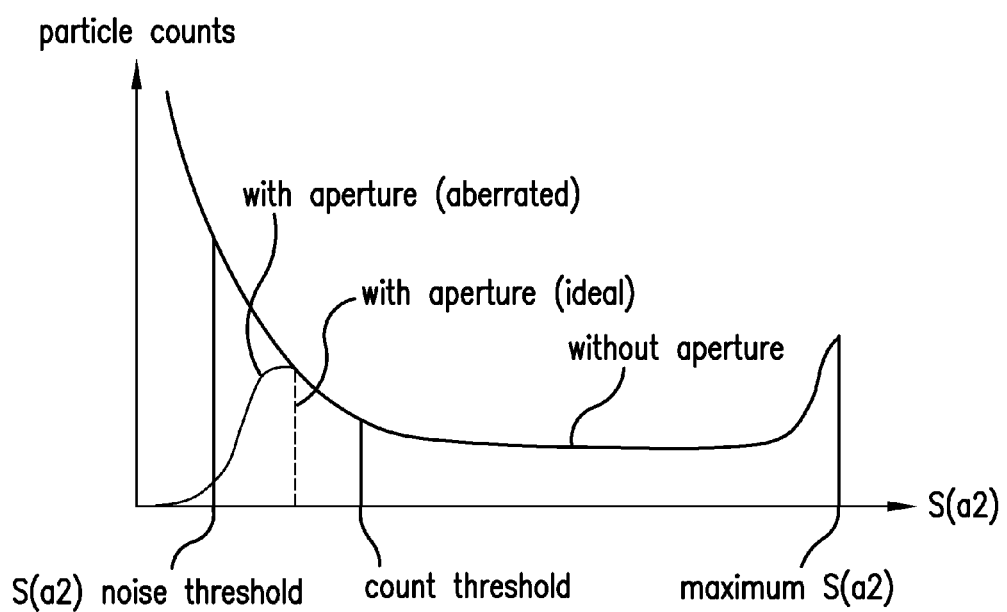
FIG. 10a shows a section of the surface plot of FIG. 10.

In most cases, the detector signals are either digitized directly, peak detected with the circuit in FIG. 7 or FIG. 8, or integrated and sampled at a lower rate. The signal can be continuously integrated (up to the saturation limit of the integrator). Then the integrated signal needs to be sampled only at points of zero slope in the integrated signal, between each pulse. By subtracting the integrated values on either side of the pulse, the integral of each pulse is sampled separately without having to sample the pulse at a high sampling rate. Also each pulse could be sampled at a lower rate and then a function could be fit to these samples to determine the peak value of the pulse. This should work particularly well using Gaussian functions which model the intensity profile of the laser beam. The parameters of the best fit Gaussian solution directly provides the peak, half width, or integral of the pulse. In any case, the final signal from each pulse will be analyzed and counted. One problem associated with particle counting is the incident beam intensity profile in the interaction volume. Identical particles passing through different portions of the beam will see different incident intensity and scatter light proportionally to that intensity. But the scattered intensity also depends upon the particle diameter, dropping as the sixth power of the diameter below 0.3 microns. So the effective interaction volume will depend upon particle diameter and detection noise, because particles will not be detected below this noise level. Therefore small particles will be lost in the noise when they pass through the tail of the intensity distribution. This means that larger particles have a larger effective interaction volume than smaller particles and therefore the number distribution is skewed in favor of large particles. This invention includes a method for creating a particle diameter-independent interaction volume, using signal analysis. The systems in FIGS. 1, 2, and 3 use at least 2 detectors per scatter collection system to remove the incident intensity dependence by using the ratio of two scattering angles to determine the particle size. Also for any number of detectors, ratios between any pair of detectors could be used to determine the size of particles in the size range covered by that pair. Instead of detector pairs, detector triplets or quadruplets, etc. could also be used with appropriate equations or lookup tables to determine the size of each particle independent of the incident intensity on the particle. In the case of detector pairs, both scattered signals, S(A1) and S(A2), are proportional to the scattering function, at that angle, times the incident light intensity:

$$S(a1) = K*I0*F(D,a1)$$

$$S(a2) = K*I0*F(D,a2)$$

where I0 is the incident intensity, K is an instrumental constant in this case, and F(D,A) is the scattering per particle per unit incident light intensity for a particle of diameter D, at scattering angle a. The variable "a" can refer to a single angle or a range of angles over which the signal is collected. Then a1 and a2 would refer to the a1 range of angles and a2 range of angles, respectively. For more than two detectors, there is a similar equation for each detector signal for angles a1, a2, a3, a4, etc. The scattering signals S(a) may be the pulse peak value or pulse integral of the envelope of the heterodyne signal (detectors 3 and 4) or of the direct non-coherent signals (detectors 1 and 2). So The ratio of the scattering at two angles is equal to F(D,a1)/F(D,a2), which is independent of incident intensity and relatively independent of position in the Gaussian beam profile of a laser. FIG. 10 shows a conceptual plot of number of particles vs. S(a1)/S(a2) and S(a2). A plot of number of particles vs. S(a1)/S(a2) and S(a1) could also be used. The scattering signal, for any diameter D, will show a very narrow range of S(a1)/S(a2) but a broad range of S(a2). Particles passing through the peak of the laser intensity profile will produce pulse peak amplitudes at the upper limit, maximum S(a2). The surface, describing this count distribution, is determined by fitting a surface function to, or by interpolation of, this count surface in FIG. 10. This surface function provides the parameters to determine an accurate particle count, because S(a1)/S(a2) is a strong function of particle size, but a very weak function of particle path through the beam. By setting an acceptance threshold for S(a2) at a certain percentage of this maximum value, separately at each value of S(a1)/S(a2), only particles passing through a certain volume (independent of particle size) of the beam will be accepted and counted. Because the particles, which are counted by these detectors, are all much smaller than the source beam crossection, they all have the same probability functions for describing the percentage of particles passing through each segment of the beam. Therefore, at any value of S(a1)/S(a2), the shape of the count vs. S(a2) function is nearly identical when you normalize the function to maximum S(a2). By setting a count-above threshold at a certain percentage of maximum S(a2) (but well above the noise level) at each value of S(a1)/S(a2), only particles passing through a certain portion of the interaction volume, with acceptable signal to noise, will be counted and sized, as shown in FIG. 10a. The noise threshold is chosen so that all particles with signals above that level will be accurately sized based upon the scattering signals.

This analysis is usually done for the detector with the smallest interaction volume, the heterodyne system in the case of FIG. 1. All four detectors are used to determine the particle diameter, but the acceptance criteria is determined by only detector 112 and 113 (S(a1)=detector 112 and S(a2) =detector 113). This analysis can also be performed, individually, on any pairs of signals, as long as the noise threshold is always the same percentage of the maximum value of signal used for the horizontal axis in FIG. 10a. These counts are accumulated into a set of size ranges, each range defines a different size channel. In many cases, each size range has a very narrow width in size and S(a1)/S(a2). The optimum channel size width is the minimum width which still contains sufficient particle counts in that channel to avoid statistical errors. Hence, the distribution of S(a2) for the range of S(a1)/S(a2) within a certain channel can determine the S(a2) acceptance limit for counts in that channel. This is accomplished by only counting particles with S(a2) above a certain percentage of the maximum S(a2) for that channel. If the theoretical scattering efficiency changes substantially across any channel, the S(a) for each count is divided by the theoretical scattering efficiency indicated by the size corresponding to the S(a1)/S(a2) for that particle. This may be especially important below 0.4 microns where the scattering efficiency drops as the inverse of the sixth power of the particle diameter.

The shape and width of the S(a2) profile is determined by how sharply the source crossectional intensity distribution drops off at the edges of the beam. If the beam profile was a step function, the effective interaction volume would be only weakly particle size dependent near the edges. This shape can be accomplished by spatially filtering the source, with the spatial filter aperture in a plane conjugate to the interaction volume. Then an image of the aperture, which is smeared by aberrations and diffraction limits, defines the sharpness of intensity drop at the edges of the beam. The intensity tails of the Gaussian beam are cut off by the aperture, which could be sized to cut off at any appropriate percentage of the peak intensity to limit the variation of scattering from a particle as it traverses the beam. The beam crossectional intensity distribution may also be shaped by use of appropriate apodization of the beam or by using diffractive beam shapers.

FIG. 10a describes this concept for data collected in one size channel. The pulse signal is collected and stored for each pulse above the count noise threshold. But only pulses which are within the range of S(a1)/S(a2) for that channel are collected into that channel. The frequency distribution of counts at each pulse level is plotted for a beam with a Gaussian intensity profile. The problem is that some particle pulses fall below the noise threshold and are not counted. The amount of missed particles depends upon the scattering efficiency of the particles. For smaller particles with lower scattering efficiency, a higher percentage of particles will be lost below the noise threshold. So the count error will be particle size dependent. The source beam can be spatially filtered to cut off the low intensity wings of the source intensity distribution. Then the count distribution would be as shown in the "with aperture (ideal)" curve and no particles would be lost in the noise. This could be accomplished by using a rectangular spatial filter that cut the wings off in the Y direction, because the particle flows in the XZ plane and the tails in this plane are actually measured in each pulse shape. However, the image of the spatial filter aperture in the interaction volume will be aberrated and diffraction limited as shown by the "with aperture (aberrated)" curve. In this case a few particles may still be lost in the noise and a count threshold must be set above this level to reject all questionable particle pulses. The maximum S(a2) value changes in each channel due to the change in scattering efficiency for the particles in that channel. As long as the count threshold is set to be the same percentage of that maximum S(a2) for each channel, all channels will lose the same percentage of particles and the distribution will be correct. Without this channel specific threshold, the smaller particle channels will lose a larger percentage of particles than the larger particle channels and the distribution will be skewed towards larger particles. This assumes that the sample is a homogeneous mixture of all the particle sizes and that the sufficient count exists in each channel to obtain an accurate estimate of the maximum S(a2).

The method described above handles the variations caused by the particle passing through various random paths in the interaction volume. This method can also correct for the variations due to random positions along the path where the digitization occurs. Therefore the peak detectors or integrators could be eliminated. The signal from the envelope detector (detectors 3+4) and direct signals from detectors 1+2 could be digitized directly at approximately 3 points per pulse. The maximum signal data point from each pulse would be added to the data list for input to the analysis described above. Any deviation from the peak value would not be a problem because the ratio of the signals determines the size and all four detectors will be low by the same percentage if they are not sampled at the peak intensity position in the interaction volume.

Also all the signals could be digitized directly after the high pass (or narrow band) filter on the detectors (detectors 112 and 113 are high pass filtered to remove local oscillator current and detectors 110 and 111 could also be high pass filtered to remove low frequency noise). Then all of the analog and digital operations (phase sensitive detection, envelope detection, etc.) could be done digitally but at the cost of reducing data collection rates. Also the source could be modulated for detectors 110 and 111 to use phase sensitive detection (lock-in amplifier) when their signals are low.

All of the optical design and algorithm techniques described in this disclosure may leave some residual size response broadening which may be particle size dependent. This instrument response broadening is determined by measuring a nearly mono-sized particle sample (such as polystyrene spheres). For example, due to noise or position dependence in the beam, a certain size particle will produce a range of S(a1)/S(a2) values as it repeatedly passes through different portions of the interaction volume. In any event, the broadening may be removed by solving the set of equations which describe the broadening phenomena. If the broadening is relatively the same for all size particles, the response broadening can be described by a convolution of the broadened number distribution response and the actual number vs. size distribution. Iterative deconvolution algorithms may be used to deconvolve the measured number vs. measured parameter distribution to obtain size resolution enhancement. This resolution enhancement will work for any ergodic stochastic process, where the broadening statistics are stable over time. This idea could be applied to (and is claimed for) any broadened counting phenomena with stable stochastic or deterministic broadening mechanisms. In particle counting measurements the amount of scatter from a particle may vary due to the random orientation and position of a particle as it passes through the exciting light beam, or by other structural and optical noise sources. The counting and classification of each of a group of identical particles will not produce a narrow peak when plotting count number vs. measured parameter. Here "measured parameter" refers to the parameter which is measured from each particle to determine its size. Examples of measured parameters are scattering optical flux amplitude, ratio of flux from two scattering angles, a function of fluxes from multiple scattering angles, or the decrease in intensity due to particle scattering and absorption, as will be described later in this disclosure. The peak of the number-vs.-measured parameter function from a group of monosized particles will be broadened in a predictable way. This broadening can be determined experimentally with a calibrated group of particles (by measuring the response from monosized particle samples) or it can be calculated theoretically based upon models for the random and deterministic broadening sources. Then the entire system can be modeled using a matrix equation, where each column in the matrix is the broadened measured parameter distribution from a certain sized particle. This broadening is reproducible as long as a large number of particles are counted for each trial. The matrix equation is described by the following relationship:

$$Nm = M*N$$

Where Nm is the vector of values of the measured (broadened) number-vs.-measured parameter distribution and N is the vector of values of the actual particle number-vs.-size distribution which would have been measured if the broadening mechanisms were not present. "*" is a matrix vector multiply. The number distribution is the number of particles counted with parameter amplitudes within certain ranges. It is a differential distribution which describes counts in different channels or bins, each bin with a different range of parameter, which may be size, scattering ratio, etc. M is a matrix of column vectors with values of the broadened number-vs.-measured parameter function for each particle size in N. For example, the nth column of M is a vector of values of the entire measured number-.vs.-measured parameter distribution obtained from a large ensemble of particles of the size which is represented by the nth element of vector N. This matrix equation can be solved for the particle number-vs.-size distribution, N, by matrix inversion of M or by iterative inversion of the matrix equation. This particle number-vs.-size distribution can be determined by using this matrix equation in many different forms. The term "measured parameter" in this paragraph can refer to many size dependent parameters including: scattering signal amplitude (pulse peak or integral, etc.), the ratio (or other appropriate mathematical relationship) between scattered signals at two or more different angles, or even particle diameter (a broadened particle size distribution determined directly from a broadened process can also be "unbroadened" by using broadened particle size distributions for each monosized sample column in matrix M). So we solve for N, given Nm and M.

If each column of M is simply a shifted version of the prior column, then the instrument response is shift invariant and the relationship is a convolution of N with the system impulse response IMP:

$$Nm = IMP**N$$

where ** is the convolution operator

For this case, deconvolution algorithms may be used to solve for N, given Nm and IMP.

Figure 9A:
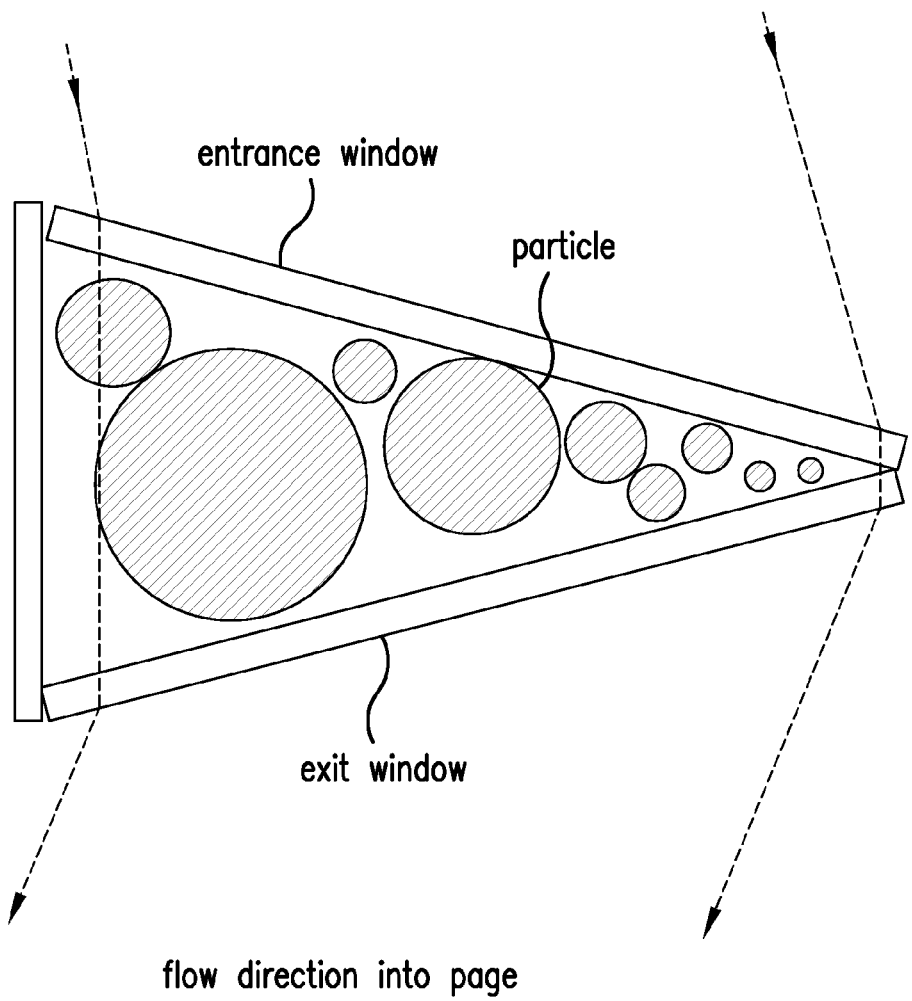
FIG. 9a provides a diagram of a wedge shaped particle dispersion sample cell, which provides a linearly increasing maximum particle size across the cell, according to the present invention.

The generalized matrix equation above may also include the effects of coincidence counting. As discussed earlier, over one million particles should be counted for a uniform volume distribution to be accurately determined in the large particle region. In order to insure low coincidence counts, the source spot size in the interaction region might be reduced to approximately 20 microns in width so that the particle concentration can be raised to count 1 million particles at flow rates of 1 meter per second in a reasonable time. For example, the worst case is slit 1 being the largest slit, because then the largest interaction volume might be approximately 20 micron×20 micron×200 micron, for example. If we require approximately 5 volumes per particle to avoid coincidence counts then the inter-particle spacing is 74 microns. 1 million particles spaced by 74 microns (on average) moving at 1 meter per second will take 74 seconds to measure. This spot size would provide good count reproducibility for the worst case of uniform volume distribution. However, a 20 micron spot and the corresponding detector fields of view may be difficult to align, requiring larger source spot size with a higher coincidence level. Even with a 20 micron spot, some coincidences will be seen at the 74 micron particle spacing. These coincidences can be corrected for by including their effects in the generalized matrix equation. If M were correcting for coincidences, a column in matrix M which corresponds to the large size end of vector N will have negative values in the region corresponding to the small size end of vector Nm, because the larger particles will block the scattered light from smaller particles which are ahead or behind that larger particle in the source beam. Also a column in matrix M which corresponds to the small size end of vector N will have a tail of positive values in the region corresponding to the large size end of vector Nm, because some smaller particles will be counted coincidentally with the larger particles and increase their measured size relative to their actual size. The effects of coincident counts can be mitigated by using a wedge shaped cell as shown in FIG. 9a. The cell consists of two windows at an angle so as to produce regions of different optical path along the cell. This cell could replace the cells in FIGS. 11 and 12. The dashed line rays define the edges of the source beam. Then at any point along the wedge direction, only particles smaller than a certain size may pass through that portion of the cell. The size distributions gathered at different points along the wedge, from the 2 dimensional detector array in FIGS. 11 and 12, may be combined by correcting the count in the larger particle areas for coincidentally counted smaller particles by using counts in the smaller particle regions of the wedge. This correction can be accomplished by solving a matrix equation of the form shown previously.

The correction for coincidences may also be accomplished by an iterative procedure, which solves for N, given Nm, and then corrects each scattered signal for coincidences. Each scattered signal, S1 and S2, consists of light scattered (or light lost due to absorption or scattering) from all the particles in the interaction volume. Ideally, the particle concentration is low and most of the time each scattering event is from a single particle. But for the general case, multiple coincident particles can be modeled by the following equation:

$$Ai = SUMj(G(Ni,Nj)Aj)$$

where SUMj means summation over the j index. Ai is the "particle signal" for a particle of the ith size bin in the particle size distribution. Particle signals can include S1, S2, or the log of attenuation or obscuration (described later in this disclosure) due scattering and absorption of a particle. G(Ni,Nj) is a function which describes the most probable total particle signal from a combination of particles of ith and jth sizes based upon their particle numbers (or concentrations), Ni (for the ith size) and Nj (for the jth size). Since the combination of particles in the interaction volume is a random process, G(Ni, Nj) represents the sum of all combinations (given Ni and Nj), weighted by their probability functions.

In the case of signals S(a1) and S(a2), the procedure for determining the number vs. size distribution is the following:
1) Use the surface plot of FIGS. 10 and 10a to determine the raw number distribution Nm.
2) Solve the matrix equation Nm=M*N for the true number distribution N.
3) Recalculate S(a1) and S(a2) using the equation above and the distribution N:

$$S(a1)i = SUMj(G1(Ni,Nj)S(a1)j)$$

$$S(a2)i = SUMj(G2(Ni,Nj)S(a2)j)$$

4) Do steps 1 through 3 again
5) repeat iteration loop of step 4 until the change in number distribution N between successive loops is below some threshold.

Figure 11:
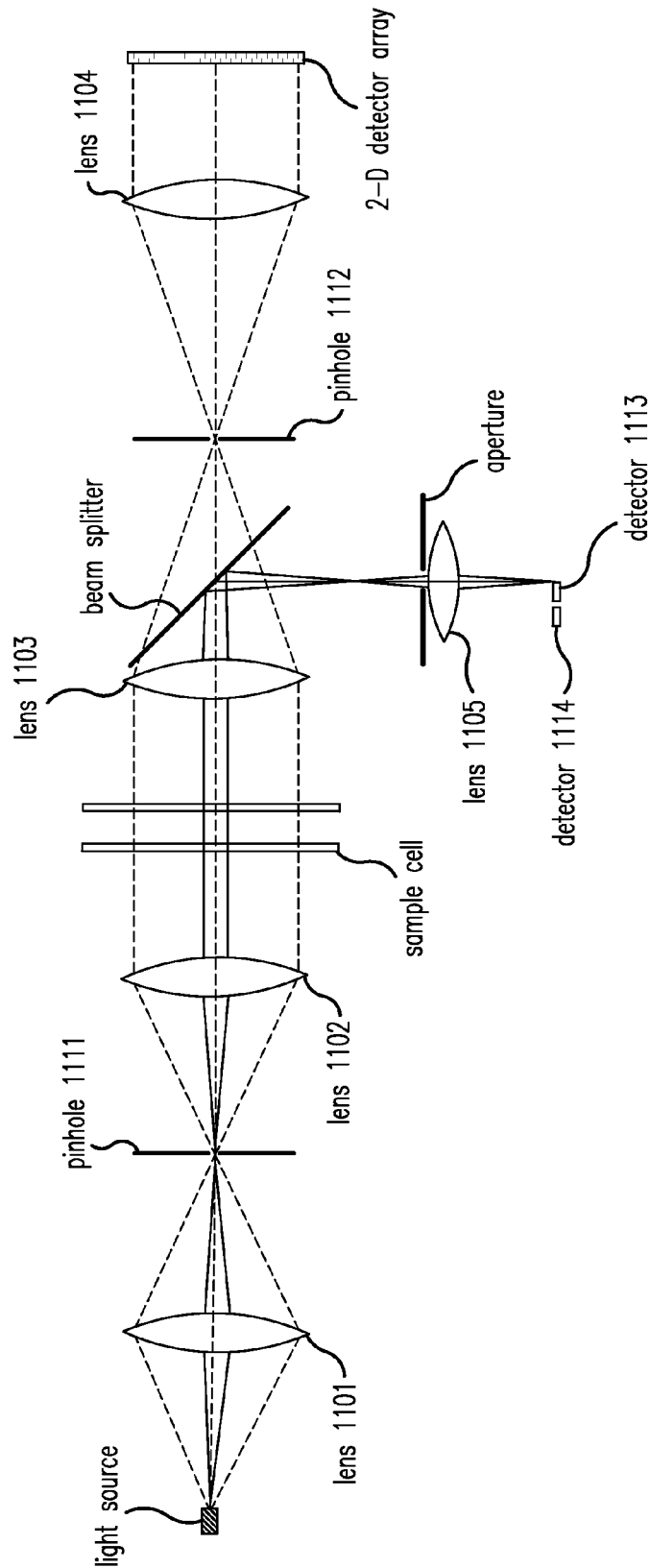
FIG. 11 provides a schematic diagram of an optical system which measures the amount of scattered light removed from the beam by each of many particles at the same time, according to the present invention.

For particles between approximately 1 and 10 microns, the ratio of scattered intensities at two angles below approximately 3 degrees scattering angle is optimal to provide highest size sensitivity and accuracy. A white light source or broad band LED should be used to reduce the Mie resonances for spherical particles. Above 10 microns, the measurement of total scatter from a white light source provides the best size sensitivity and depth of focus for a spatially filtered imaging system as shown in FIG. 11. A white light or broad band LED source is spatially filtered by lens 1101 and pinhole 1111 to provide a well collimated beam through lens 1102. If a well collimated source beam is required to measure scattering at very low scattering angles (for large particles), a laser source might also be used. This collimated beam passes through a cell consisting of two windows, which confine the flowing particle dispersion. Lens 1103 focuses this collimated beam through pinhole 1112, which removes most of the scattered light from the beam. This transmitted beam is transferred to a 2 dimensional detector array through lens 1104, which images the center of the sample cell onto the array. This array will see dark images of each particle on a bright background due to the light lost through scattering or absorption by the particle. A beamsplitter after lens 1103 diverts a portion of the light to an aperture and lens 1105. The aperture defines a narrow pencil of light through the cell and a small scattering volume, lowering the probability of coincidence counts for detectors 1113 and 1114, which are near to the focal plane of lens 1105. The aperture is optimally placed in the optical plane which is conjugate to the center of the sample cell, through lens 1103. Conjugate planes are a pair of image and object planes of an optical system. Detectors 1113 and 1114 are nominally placed in the optical plane which is conjugate to the optical source, through lenses 1101, 1102, 1103 and 1105. Detectors 1113 and 1114 measure scattered light at two angles, which are nominally below 3 degrees for larger particles but which can cover any angular range appropriate for the size range of the particle detector. Also more than two detectors could be used to increase the size range for this portion of the particle detection system. These detectors could also be annular ring detectors (similar configuration to mask 1250 in FIG. 12 and mask 8750 in FIG. 86) centered on the optical axis to reduce sensitivity to particle shape, by equally measuring all scattering planes. For example, detector 1113 could measure a scattering angular region around 1 degree; and detector 1114 could measure around 3 degrees. By combining the particle scattering pulse signals from these detectors, by ratio or polynomial, a relatively monotonic function of particle size is created without strong Mie resonances (due to the white light source and signal ratio). Detectors 1113 and 1114 count and size particles in much the same way as the system in FIG. 1. The concept is to use two angles to remove the variations in scattering intensity due to particles passing through different portions of the incident beam and to reduce calculated size sensitivity to particle and dispersant composition. Particles of size between approximately 1 and 10 microns could be handled by detectors 1113 and 1114 of FIG. 11; and particles above approximately 5 microns are handled by the 2-dimensional detector array. The two size distributions from these two measurements are combined with blending in the overlap region between 5 and 10 microns.

The 2-dimensional detector array is imaged into the center of the sample cell with magnification corresponding to approximately 10×10 micron per array pixel in the sample cell plane. A 10 micron particle will produce a single dark pixel if it is centered on one pixel or otherwise partially darkened adjacent pixels. By summing the total light lost in these adjacent pixels, the total light absorbed or scattered outside of pinhole 1112 for each single particle in the view of the array is determined. The particle concentration is limited to prevent coincidence counting in each separate 10×10 micron projection through the sample cell. At low concentrations, any group of contiguous pixels with reduced light levels will represent a single particle. And the total percentage light lost by these contiguous pixels determines the particle size. All pixels below a certain percentage of their non-obscured values are accepted as particle pixels. All contiguous particle pixels are then combined as representing one particle. This is accomplished by summing the pixel values of contiguous pixels and comparing that sum to the sum of those same pixels without the presence of a particle. This works well for smaller particles where the total scattered light is well outside of the pinhole 1112 aperture, because then the total percentage drop represents the scattering and absorption extinction of the particle. For larger particles, a larger portion of the scattered light will pass through pinhole 1112 and cause a deviation which will not agree with the total theoretical scattering extinction. This scatter leakage can be corrected for in the theoretical model by calculating the actual percentage loss for larger particles by integrating the actual scattered light outside of the pinhole. Alternatively, the particle can be sized directly by counting (and summing the total area of) contiguous pixels, because for the larger particles the detector array pixel size may be less than 0.1% of the total crossectional area of the particle and so the particle can be sized directly from image dimensions or the total image area. The accuracy of this calculation is improved by adding partial pixels at the edge of the particle image based upon their attenuation as a fraction of the attenuation of nearby interior pixels. Hence if a pixel in the interior of the image is attenuated by 10% and an edge pixel is attenuated by 4%, that edge pixel should count as 40% of its actual area when added to the sum of all contiguous attenuated pixels to determine the total crossectional area and size for that particle. Otherwise the theoretical loss per particle could be used.

This detector array system has an enormous particle size dynamic range. The particle will remove approximately the light captured by twice its crossectional area. So a 2 micron particle will reduce the total light flux on a 10×10 micron pixel by 8 percent. But the entire array of 1000×1000 pixels can cover a crossection of 10×10 millimeters. So the size range can cover 2 microns to 10000 microns. The size dynamic range is almost 4 orders of magnitude. The smallest particles are detected by their total light scattering and absorption. For very large particles, the angular extent of the scattering pattern may fall within the aperture of pinhole 1112. Then the summed light from all the contiguous pixels may not indicate accurate size. For the larger particles, the actual imaged size is determined by counting contiguous pixels. Pixels at the outer boundary are counted as partial pixels based upon the amount of light lost as a fraction of the amount lost from pixels in the interior of the contiguous set. The light loss in each pixel is determined by storing the light value for each pixel without particles in the sample cell and subtracting the particle present values these stored values. The source intensity can also be monitored to normalize each pixel measurement for light source intensity fluctuations.

In order to avoid smeared images, the detector array must integrate the current from each pixel over a short time to reduce the distance traveled by the particle dispersion flow during the exposure. This may also be accomplished by pulsing the light source to reduce the exposure time. Smearing in the image can be corrected for using deconvolution techniques. But the scattering extinction measurements will be accurate as long as each contiguous pixel group does not smear into another contiguous pixel group. Add up all of contiguous pixel signals (from the smeared image of the particle) after presence of the particle to determine the particle scattering attenuation and size. If the particle image is smaller than one pixel, then the attenuation of that pixel is the scattering extinction for that particle. Essentially, you are measuring nearly the total amount of light scattered or absorbed by the particle during the exposure. Using this total lost optical flux divided by the incident intensity provides the scattering crossection for the particle, even if the particle is not resolved by the optical system or if that loss is distributed over more pixels than expected from perfect imaging of the particle. This is the power of this technique. The size accuracy is not limited by the image resolution. A 10 mm by 10 mm detector array, with 10×10 micron pixels, can measure particle diameters from a few microns up to 10 mm, with thousands of particles in the source beam at one time. The 10 mm particles will be sized directly by adding up pixels and multiplying the interior pixels by 1 and the edge pixels by their fractional attenuation and adding all of the pixels up to get the total crossectional area and size. A 5 micron particle, centered on one 10×10 micron pixel, will attenuate that pixel by 50% (the total scattering extinction crossection is approximately twice the actual particle area, outside of the Mie resonance region). In both cases the particles are easily measured. You are adding up all of the signal differences (signal without particle—signal with particle) of contiguous changed pixels to get the total light lost due the particle. Pinhole 1112 blocks all of the light scattered outside of the angular range of the pinhole 1112, whose maximum scattering angle is equal to the inverse tangent of the pinhole 1112 radius divided by the focal length of lens 1103. So the signal difference (signal without particle—signal with particle) is the amount of light scattered by the particle at scattering angles above this maximum angle of the pinhole, including any light absorbed by the particle. The particle size is determined using scattering theory and the ratio of signal change (signal without particle—signal with particle) to the signal without a particle.

Image smearing could also be reduced by using pulsed flow. The particle sample flow would stop during the period when the light source is pulsed or when the detector array is integrating. Then a flow pulse would push the next slug of sample into the detector array field of view before the next signal collection period. The sample would be approximately stationary during the signal collection on the detector array. This pulsing could be accomplished by pressurizing the particle dispersion chamber and using a pulsed valve to leave short segments of the sample dispersion through the source beam interaction volume.

The nearly parallel window cell could also be replaced by a wedge shaped cell which would control the particle count in different size regions, as discussed above (see FIG. 9a).

Non-spherical particles present another problem for single particle sizing: non-symmetrical scattering patterns. Assume that the incident light beam is propagating along the Z direction and the XY plane is perpendicular to the Z direction, with origin at the particle. The XZ plane is the center scattering plane of the group of scattering planes which are intercepted by detectors 110, 111, 112, and 113. Each detector subtends a certain range of scattering angles, both parallel and perpendicular to the center scattering plane. For spherical particles, the scattering pattern is symmetrical about the Z axis and the scattering function could be described in cylindrical coordinates as a function of Z and of radius R from the Z axis, at some distance Z0 from the scattering particle. However, for non-spherical particles the scattering pattern is not symmetrical about the Z axis at Z0. The 2-dimensional array in FIG. 11 measures approximately the total light lost to scattering or absorption at all scattering angles, in all scattering planes. Hence it will produce particle size estimates which are related to the total crossectional area of the particle, for both spherical and non-spherical particles, without sensitivity to particle orientation. But detectors 110, 111, 112, and 113 in FIG. 1, and corresponding detectors in FIG. 3 or 11 measure the scattering only over scattering planes close to the XZ plane (or a limited range of scattering planes). If the pattern is not symmetrical, the particle size estimate will depend upon the orientation of the particle. So a group of particles with identical crossectional areas, but random orientations, would be reported over a wide range of particle crossectional area and size. This particle size distribution width could be corrected by deconvolution of the number vs. size distribution, as described by the matrix equation shown previously, where matrix M would describe the broadening of a count distribution from a group of particles, each with the same particle volume, but with all possible orientations. But the theoretical model would change with the particle shape. Another way to reduce spread is to use two sets of detector systems, one centered on the scattering plane which is +45 degrees with respect to the XZ plane and the other at −45 degrees from that plane, to sample two perpendicular particle orientations and maintain the optimum orientation for heterodyne detection. The average of the size distributions from these two systems would reduce the spread of the distribution. Another more effective method is to collect all of the scattered planes at a certain scattering angle, using the system shown in FIG. 12. A light source is focused into the sample dispersion. This focused spot is imaged onto a pinhole which removes unwanted background light. The light passed by the pinhole contains the incident light beam and the scattered light from the particles. This light is collected by lens 1203 which projects the light onto two masks, using a beamsplitter. Each mask contains an annular aperture which defines the range of scattering angle accepted by the collection optics. Lens 1204 collects high angle scattered light passing through mask 1250 and focuses it onto detector 1210. Likewise the low angle scatter is measured by mask 1251, lens 1205 and detector 1211.

Figure 12:
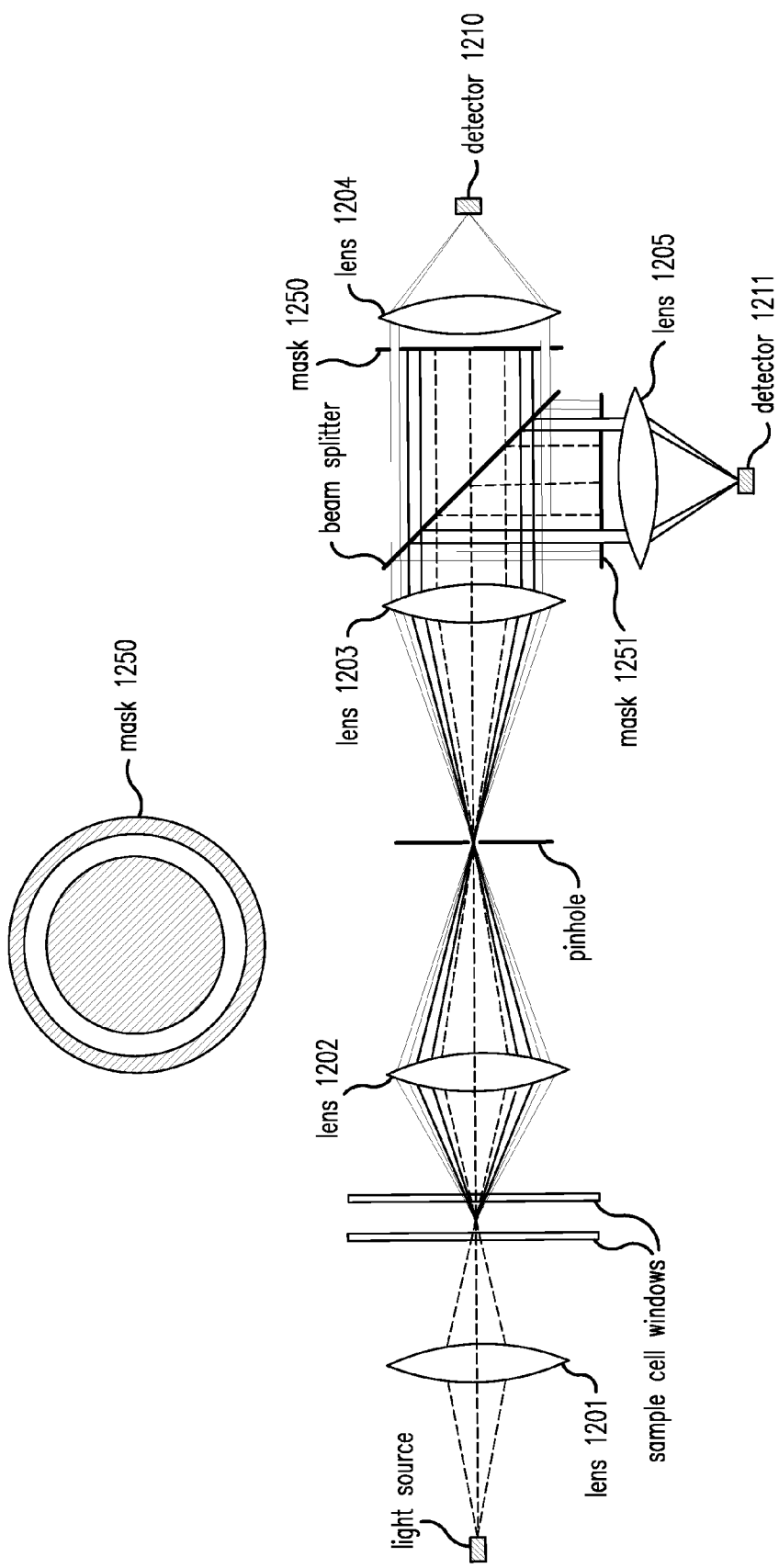
FIG. 12 provides a schematic diagram of an optical system which measures scattered light from different ranges of scattering angle, from a small volume in the particle dispersion sample cell, according to the present invention.

FIG. 12 shows the annular aperture for mask 1250, defining equal scattering collection in all the scattering planes. The ratio of signals from detector 1210 and 1211 would precisely determine the average radius of a non-spherical particle, without size broadening of the system response due to random particle orientation. The beam splitter and dual mask concept could also be applied to the system in FIG. 11. Lens 1105 and detectors 1113 and 1114 (all of FIG. 11) would be replaced by lens 1203, the beam splitter, the dual mask system, and detectors 1210 and 1211 (all of FIG. 12), with the masks in the same optical plane as detectors 1210 and 1211. Alternatively, lens 1105 and detectors 1113 and 1114 (all of FIG. 11) would be replaced by the pinhole, lens 1203, the beam splitter, the dual mask system, and detectors 1210 and 1211 (all of FIG. 12), with the pinhole in the image plane of the particles through lens 1103 of FIG. 11. Masks 1250 and 1251 act as angular filters which only pass scattered light in a certain range of scattering angles. The 2-dimensional array in FIG. 11 is already insensitive to particle orientation and needs no modification.

Figure 13:
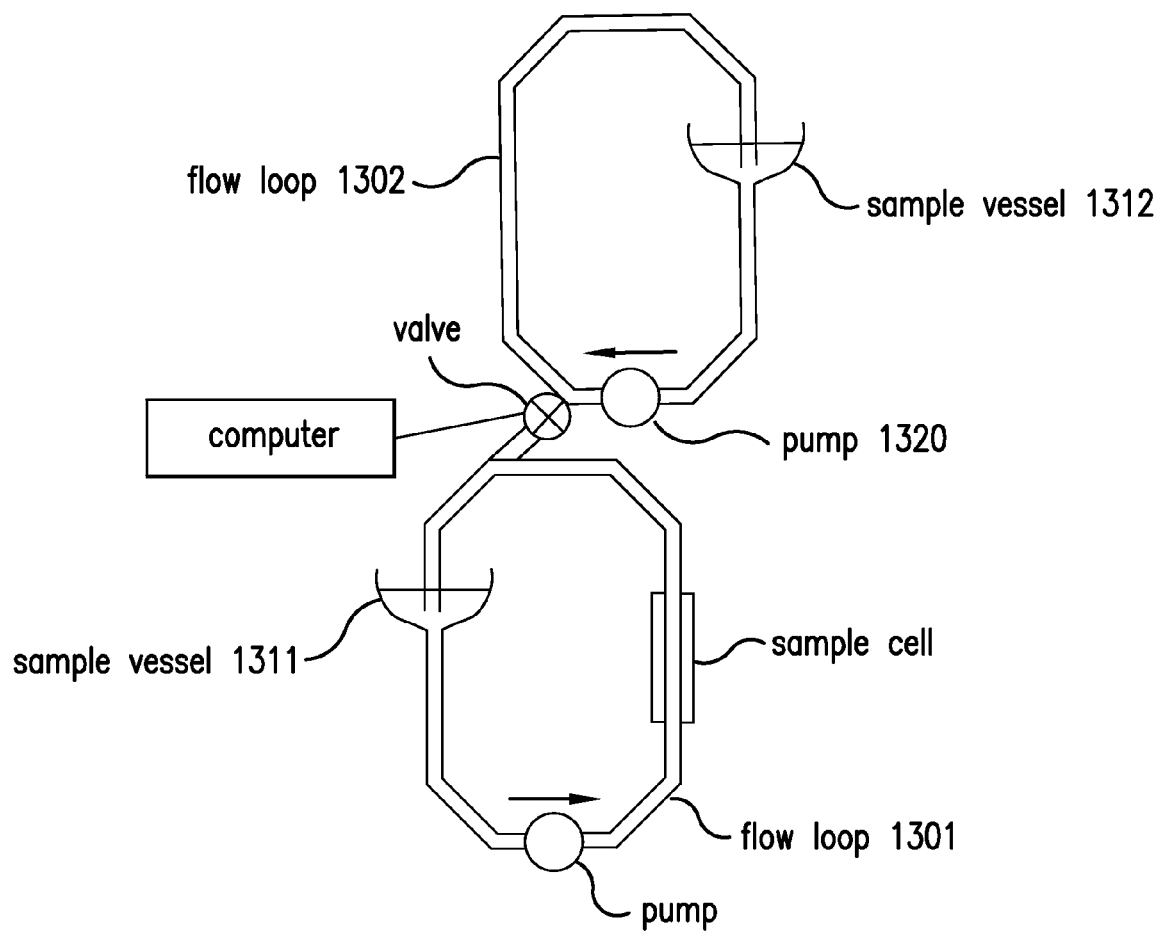
FIG. 13 provides a schematic diagram of a particle sample system which adjusts particle concentration to an optimum value, according to the present invention.

The particle concentration must be optimized to provide the largest count levels while still insuring single particle counting. The concentration may be optimized by computer control of particle injection into the flow loop which contains the sample cell, as shown in FIG. 13. Concentrated sample is introduced into flow loop 1302 through sample vessel 1312. The sample vessel may also contain a stirring means for maintaining a homogenous dispersion in the vessel. Pump 1320 pumps the dispersion around the loop to provide a homogenous dispersion in the loop and to prevent loss of larger particles through settling. A second flow system, flow loop 1301, is attached to flow loop 1302 through a computer controlled valve with minimal dead space. The computer opens the valve for a predetermined period to inject a small volume of concentrated dispersion into loop 1301. The optical system counts the particles and determines the probability of coincidence counting based upon Poisson statistics of the counting process. The computer then calculates the amount of additional particles needed to optimize the concentration and meters out another injection of concentrated sample into loop 1301, through the valve. Actually, both the concentration and pump speed for loop 1301 may be controlled by computer to optimize counting statistics. When the particle concentration is low, higher pump speed will maintain a sufficient particle count rate for good count statistics. The optimum concentration may be different for different detectors and detection systems. Therefore the computer valve may adjust the concentration to various levels in succession. At each concentration level, data is taken with the appropriate detector(s) for that concentration level or detector array for a sufficient period and flow rate to accumulate enough counts to reduce the count uncertainty (due to Poisson statistics) to an acceptable level.

Another consideration for FIG. 6a is the determination of signal baseline. The baseline for the scattered signals must be determined for each detector. Digitized values, measured before and after the scattered signal pulse, determine the signal baseline to be subtracted from the pulse signal, by interpolation of those values through the pulse region. These regions before and after each detector pulse should be chosen to be before and after the widest pulse of the group (in some rare cases, the pulse with the largest amplitude should be used if the signals are lost in noise). Then the baseline will certainly be determined from values in a region where no particle scattering has occurred in each of the detectors.

The system shown in FIG. 11 can also be modified to look at only scattered light over a certain angular region, instead of the total light removed from the beam by absorption and/or scattering. FIG. 14 shows such an optical system where the light source is spatially filtered by lens 1401 and pinhole 1410. Lens 1402 collimates and projects the source beam through the particle sample, which is imaged onto the 2 dimensional detector array by lens 1403. An annular spatial mask (or spatial filter) is placed in the back focal plane of lens 1403 to only pass scattered light over a certain range of scatter angle as defined by the inner and outer radii of the annular spatial mask, which is similar to mask 1250 shown in FIG. 12. The very low angle scattering and incident beam are blocked by central stop of the annular aperture in the back focal plane of lens 1403. FIG. 14 shows two such annular mask systems which are accessed through a beamsplitter. The detector arrays are in the image plane of the particles. Hence the detector array 1420 sees an image of the particles, and the sum of the contiguous pixels associated with each particle's image is equal to the scattered light from that particle over the angular range defined by the aperture (or spatial mask) in the back focal plane of lens 1403. A beam splitter splits off a portion of the light to a second annular spatial mask (in the back focal plane of lens 1403) and detector array 1421. The angular ranges of the two annular spatial filters are chosen to produce scattered values which are combined by an algorithm to determine the size of each particle. The sum of signals from contiguous pixels which view the same particle are analyzed to produce the particle size. One such algorithm would be a ratio of the corresponding sums (the sum of contiguous pixels from the image of each particle) from the same particle detected by both arrays. The key advantage is that when the particle size is too small to size accurately by dimensional measurements on the image (resolution is limited by pixel size) then the total scattered light from each particle may be used to determine the size. And if the total scattered light is sensitive to particle composition, then the ratio of the two scattering signals can be used to determine the particle size more accurately. In FIG. 14, scattered light is only present when a particle is present. In FIG. 11 the particle image creates a decrease in light, from a bright background level, on the 2-Dimensional array in the corresponding pixels, while in the system of FIG. 14 the particle image creates an increase from a dark background level. If the particle is smaller than a single pixel, then the amount of scattered light measured by that pixel will indicate the total light scattered from that particle in the angular range defined by the focal plane aperture, providing that particle's size. If more than one pixel is associated with a particle, those pixel values are summed together to obtain the scattered signal from that particle in a similar fashion as described before for FIG. 11. The only difference is that the increase in pixel signals, relative to the signal without particles, are summed to produce the total light scattered from that particle in the angular range of the annular aperture in FIG. 14. In FIG. 11, the decrease in pixel signals, relative to the signal without particles, are summed to produce the light lost due to scattering outside of pinhole 1112 or absorption by that particle. Signal to background should be better for FIG. 14, but with higher sensitivity to particle composition and position in the sample cell. The depth of focus and signal to noise should be better for FIG. 11 than for FIG. 14, because the pixel values drop by the total light scattered and absorbed by the particle in FIG. 14 as opposed to the light increasing by only the amount scattered through a narrow range of scattering angles defined by the aperture. As with all other systems described in this disclosure, these ideas can be extended to more than two detector arrays or more than two scattering angles, simply by adding more annular spatial masks and detectors by using beamsplitters. Also the 2-dimensional array optics in FIG. 11 could be combined, by beamsplitters, with those in FIG. 14 to provide total scatter information (both angular scatter and total light loss due to scatter and absorption) for determining size and to provide the unscattered intensity for each pixel to normalize the pixel scatter data of FIG. 14 detectors for the incident light intensity which may vary across the beam. In this way, each pixel in the detector array creates a small independent interaction volume, providing individual detection of a very small particle contained in that interaction volume, with low coincidence probability. But yet contiguous pixels can be combined to measure particles of sizes approaching the dimensions of the entire detector array's image in the sample cell. The size dynamic range is enormous. FIG. 14 could also be used with a source beam which is focused into the sample cell to reduce the interaction volume and increase the beam intensity and scattered signal. In this case the center portion of the annular mask must be increased in size to block the diverging light from the source so that each detector array only sees scattered light.

The optical source used with the detector arrays in FIGS. 11 and 14 could be a pulsed broad band source such as a xenon flash lamp which produces broadband light to wash out the Mie resonances, and which produces a short light pulse to freeze the motion of particles flowing through the cell.

Figure 15:
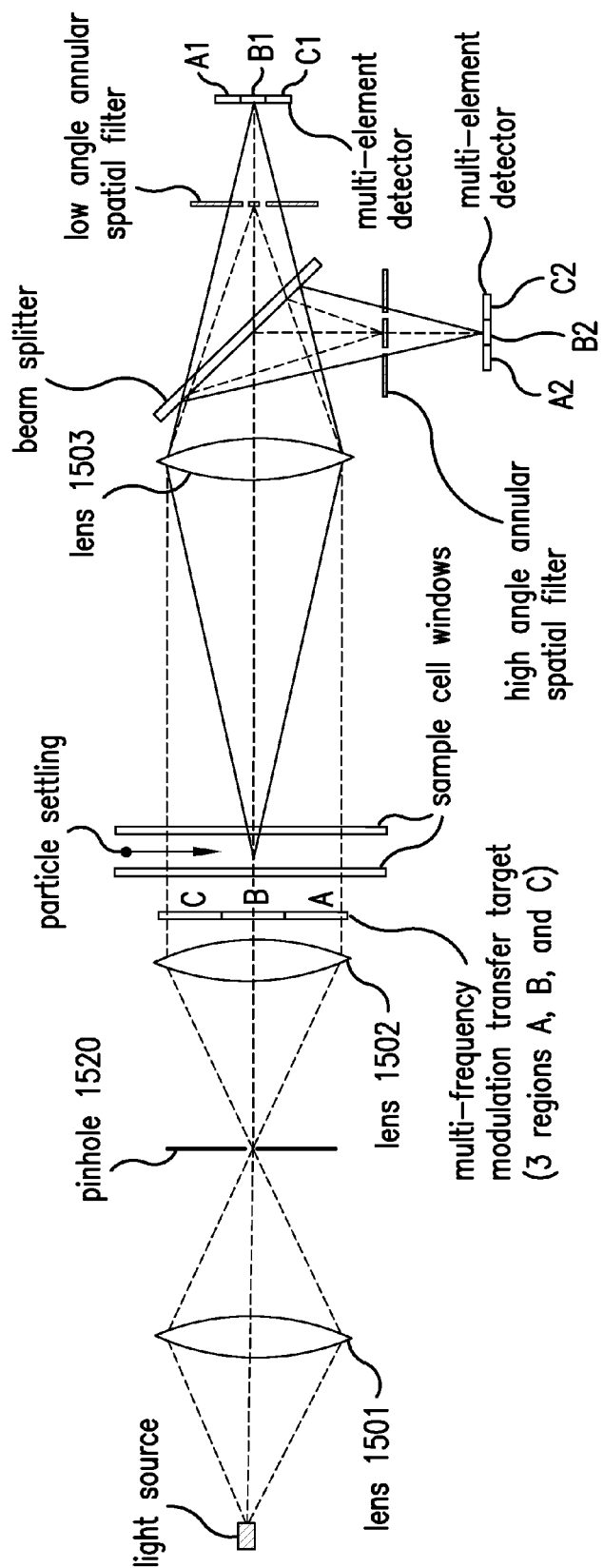
FIG. 15 provides a schematic drawing of an optical system which separates particle scatter signals based upon signal frequency and scattering angle, with a periodic mask for providing modulation of the scattering signal for particles passing through the sample cell, according to the present invention.
Figure 15A:
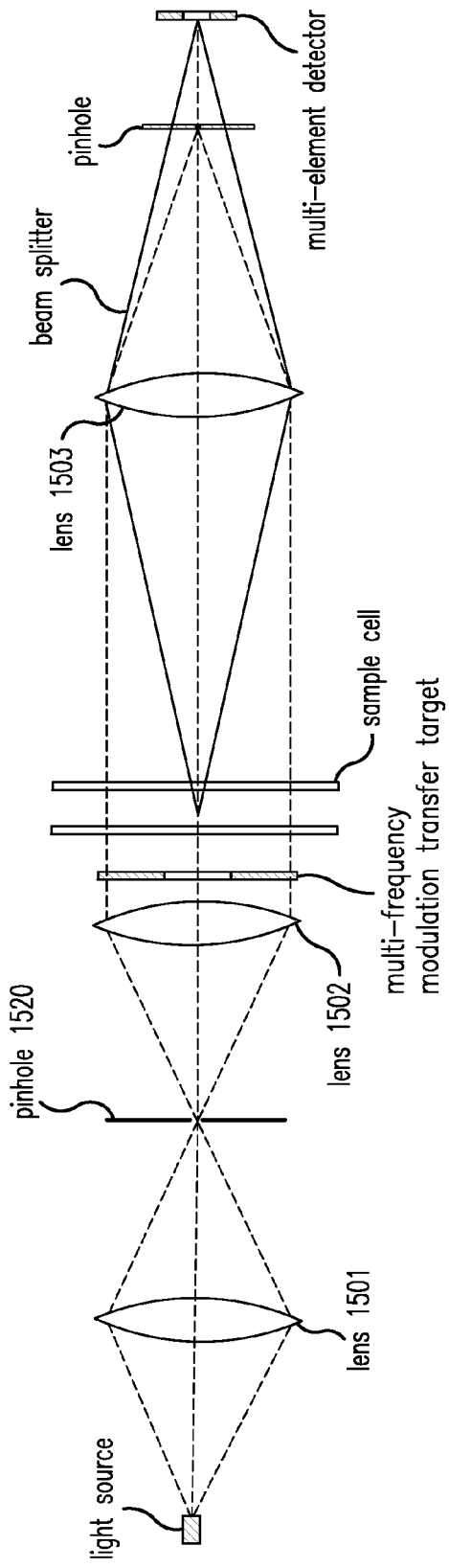
FIG. 15a provides a schematic diagram of an optical system which separates the amounts of scattered light, removed from the light beam, based upon signal frequency, according to the present invention.
Figure 16:
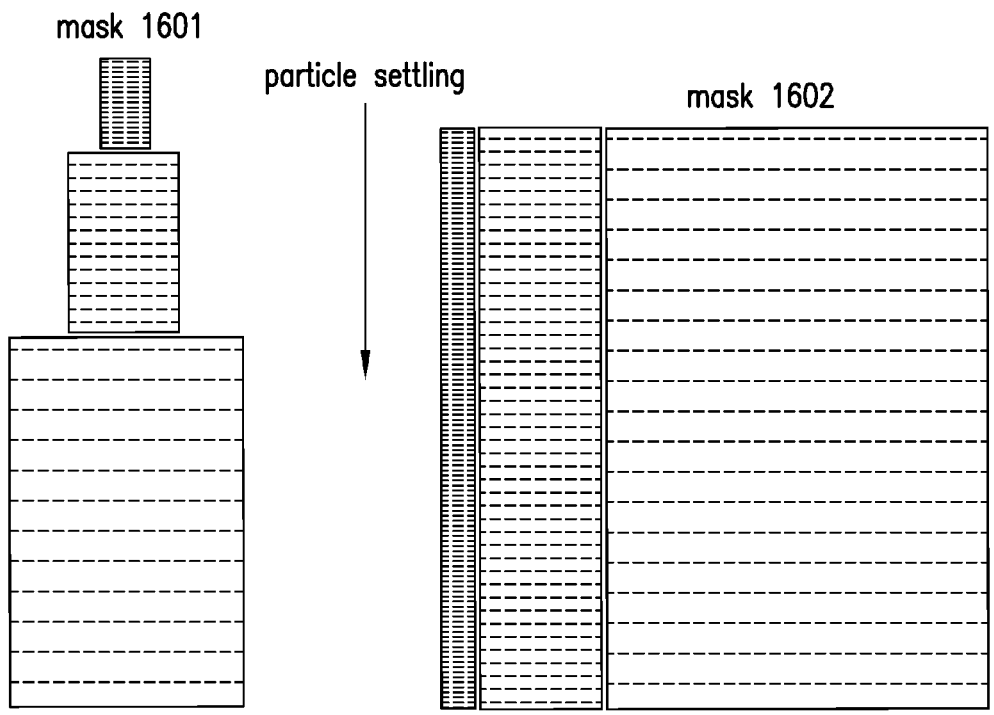
Figure 17:
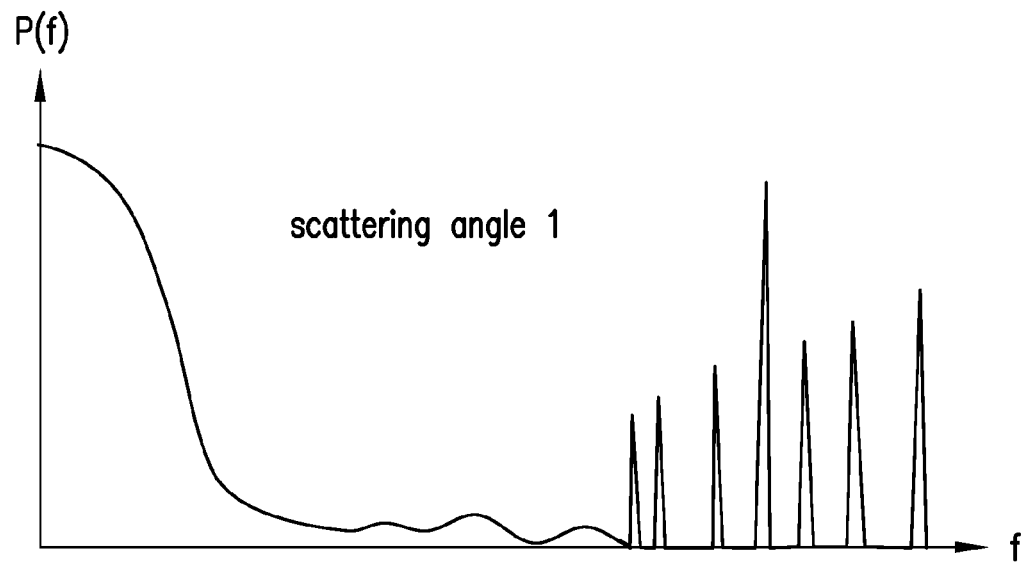
FIG. 17 provides graphs showing power spectra of signals measured at two scattering angles for the apparatus depicted in FIG. 15.
Figure 17:
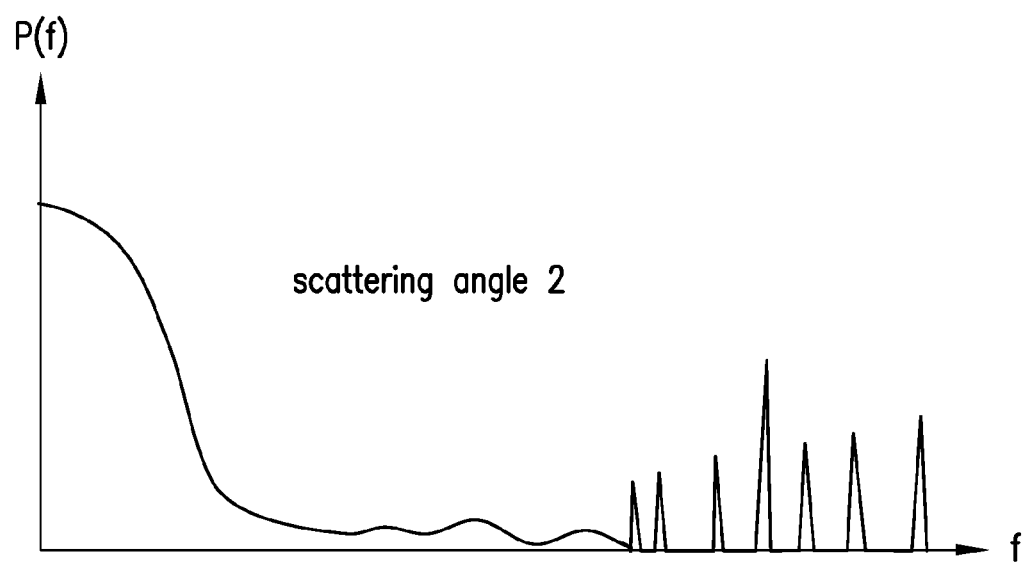

One problem with the techniques described above is coincidence counting. The cell path must be large to pass the largest anticipated particle (except for the wedge cell shown in FIG. 9a, where the pathlength changes across the cell). Hence for these collimated systems, many small particles may be in any sample volume seen by a single pixel. These coincidences could possibly be eliminated by measuring at various particle concentrations, but in order to count sufficient large particles to obtain reasonable count accuracy, the concentration must be raised to a level where more than one small particle is present in the sample cell volume, seen by each pixel. The scattered signals from these multiple particles can be separated, to be counted individually, by measuring their settling velocities. This is accomplished by the optical system shown in FIG. 15. A light source is collimated and spatially filtered by lenses 1501 and 1502 and pinhole 1520. A modulation transfer target or mask with a spatially periodic transmission function is placed in the collimated beam to create a sinusoidal (or other periodic function) intensity pattern in the collimated beam. This mask could also be placed in any plane which is conjugate to the particles, including the location shown in FIG. 64. The mask could also be placed in a plane, between lens 1502 and the light source, which is conjugate to the particles. The mask could also be placed in a plane, between the scatter collection lens (lens 1503 in FIG. 15) and the multi-element detector, which is conjugate to the particles. Examples of the sinusoidal (or other periodic) patterns are shown in FIG. 16. Each line in the patterns represents the peak of the sinusoidal transmission function which oscillates along the particle settling direction but is constant along the direction perpendicular to the settling. The mask consists of multiple regions with different spatial modulation frequencies. The projection of each region into the sample cell is imaged onto a separate detector by lens 1503. The light from lens 1503 is split into one or more directions, each having a different annular spatial mask which defines a different range of scattering angles. Each image plane for each spatial mask has multiple detectors, each of which intercept light from only one of mask regions in the sample cell. As a particle settles through the sinusoidal intensity pattern, the scattered light on the detector is modulated because the scattered light is proportional to the light intensity incident on the particle and the mask provides a spatially modulated illumination field. When a particle passes through a region where the spatial modulation wavelength is greater than the particle size, the scattered light from that particle will attain a large modulation visibility (the ratio of peak to trough values will be large). The scattered signal from the largest particles will have lowest modulation visibility in the high spatial frequency region because the particle will span over multiple cycles of the spatial modulation. Larger particles settle faster and produce higher frequency detector signals, because they have a higher terminal velocity. Therefore, a lower spatial modulation frequency can be used with larger particles to increase modulation visibility while still maintaining high signal oscillation frequency, because the scattering signal frequency is equal to the product of settling velocity and the mask spatial frequency. The size range is increased by using multiple regions with different spatial modulation frequencies, with higher frequencies for smaller slower settling particles. The area of the higher frequency portions of the mask are smaller to reduce the number of particles measured at one time by each detector, because typically there are much higher small particle counts per unit volume than for larger particles. FIG. 15a shows a similar system with a single pinhole filter. Detector signals will show the same oscillation characteristics as FIG. 15, but with a large offset due to the light transmitted by the pinhole. The power spectrum of the detector currents for the systems shown in both FIGS. 15 and 15a will be similar except that FIG. 15a will contain a large component at (and near to) zero frequency. FIG. 17 shows the power spectra from the low and high angle detector signals in FIG. 15, for the two detector elements, B1 and B2, which view the same portion, B, of the mask, but pass through different annular filters. Since each particle settles at a different velocity, each particle will produce a separate narrow peak at the same frequency in both of the power spectra of detectors B1 and B2 (from signals for scattering angle 1 and scattering angle 2, respectively). This is due to the fact that the detector signal power at any certain frequency, measured by each of the corresponding low and high angle detectors, will originate from the same particle or group of particles. Since the smaller particles will create a continuum at lower frequencies, they can be removed from the spectrum of the larger particles. The corresponding single peak values from power spectrum of current from detector B1 at frequency f1 and the power spectrum from current of detector B2 at frequency f1 for example (from each scattering angle) can be ratioed (or analyzed by other algorithms) to determine the size of the particle which created that peak in each spectra. In this way, multiple particles in the sampling volume can be counted individually. When particle size is close to the line spacing of the modulation target, the modulation of the scattered light will decrease because the signal is the convolution of the particle with the modulation target. However, the amplitude of the scattered signals at both angles will both decrease by the same percentage so that their ratio will still accurately indicate the size. Any peaks with amplitudes that are higher than that which would be expected from one particle are expected to originate from more than one particle. The expected amplitude for a single particle can be determined from the minimum value of other peaks in that frequency region for prior digitization sets. These multiple particle peaks can be either corrected for the second particle's contribution or eliminated from the particle count. If the particle density, liquid density and viscosity, are known, each individual particle size can also be determined by the frequency of the corresponding peak, by calculating the corresponding settling velocity and using the Stokes equation for settling to solve for the particle size.

The signal frequency for each particle signal pulse could also be determined individually by either the timing of zero crossings or by using a phase locked loop, avoiding the power spectrum calculation. Each particle pulse will consist of a train of oscillations which are modulated by the intensity profile through that particular mask region. The oscillation amplitude and frequency provide the scattering amplitude and settling velocity, respectively, for that particle. The size can be determined from the settling velocity, if the particle density and fluid viscosity are known, or the size can be determined from the ratio of amplitudes from two different scattering angles (or angular ranges), or the amplitude at one scattering angle (or angular range) (but with possible higher sensitivity to particle composition).

The particle density or fluid viscosity can be determined by combination of the scattering amplitudes and the signal oscillation frequency.

Figure 16A:
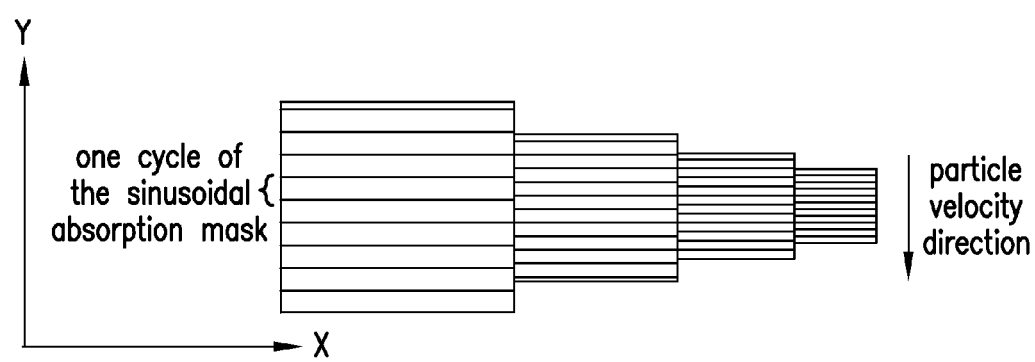
FIG. 16a depicts a mask, to be utilized in FIG. 15 and FIG. 15a, which reduces the detection volume and increases the signal frequency for smaller particles.
Figure 16B:
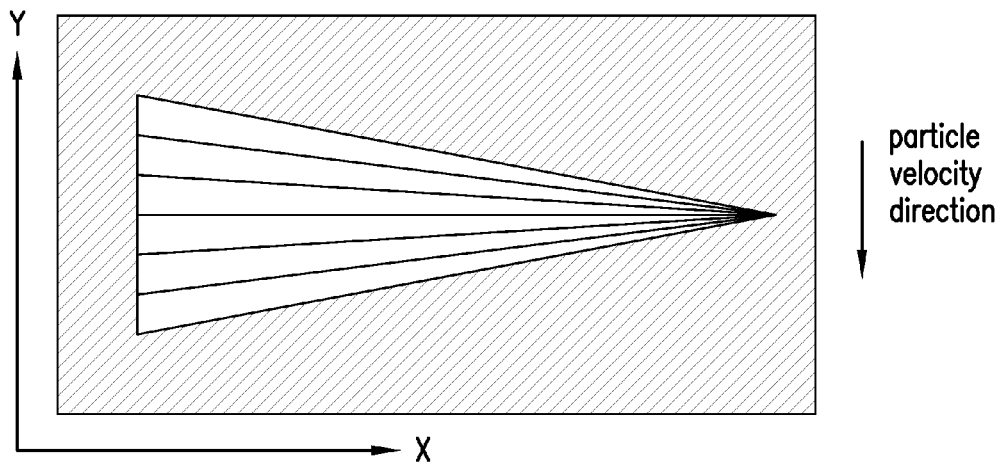
FIG. 16b depicts a variation of FIG. 16a, where the detection volume and signal frequency changes continuously across the mask.
Figure 16C:
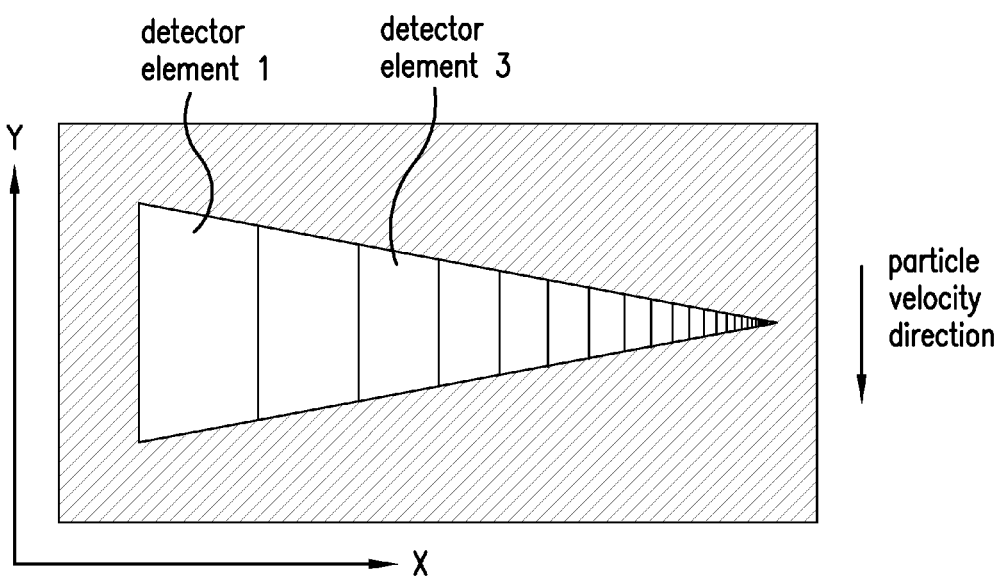
FIG. 16c depicts a scatter detector array which defines particle interaction volumes of varying size across the array, according to the present invention.
Figure 64:
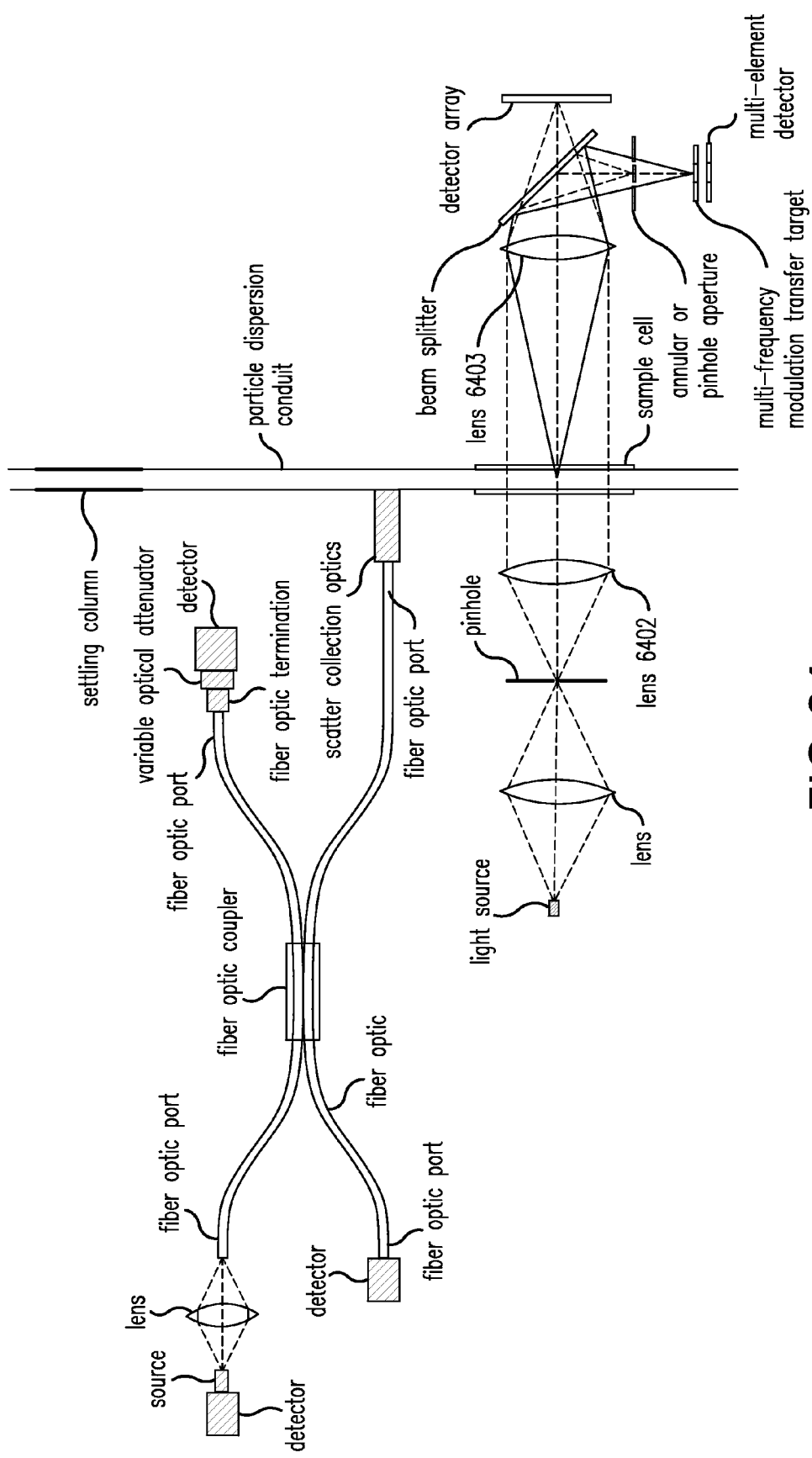
FIG. 64 provides a schematic diagram of an optical system which combines particle settling, ensemble angular scattering, and dynamic light scattering, according to the present invention.

Mask 1602 could be modified to provide different length sections as shown in FIG. 16a. In this case, each mask section would have a separate matching detector as shown in FIG. 15, 15a, or 64, but the detectors and mask sections are spaced in the plane perpendicular to the flow. This mask could be used with the wedged sample cell in FIG. 9a (where the y direction is out of the page) to provide definition of differing sized interaction volumes. The mask determines x and y dimensions and the pathlength of the cell provides the z dimension for each interaction volume. The cell pathlengths could also be defined by stepped regions instead of a continuous decrease in pathlength across the cell. The signals from different portions of the cell can be separated by using multiple detectors or based upon signal frequency as described previously for FIG. 16, in either settling or flowing modes. Also the mask in FIG. 16b provides a continuously variable spatial frequency across the sample cell, so that particles in each portion of the wedged sample cell will produce signals of differing frequency, in either the flow or settling case. This separation of interaction volumes in the wedged cell could also be provided by the detector array, shown in FIG. 16c, which defines ever decreasing interaction volumes for each detector element. Using the wedged sample cell in FIG. 14, each of the two detector arrays in FIG. 14 could be replaced by detector arrays, as shown in FIG. 16c, to measure two scattering angles for each interaction volume defined in the wedged cell. In all cases, the thin end of the wedge or the smallest mask opening is oriented to line up with the thin portion of the sample cell wedge so as to define ever decreasing interaction volumes in x, y, and z dimensions.

Figure 18:
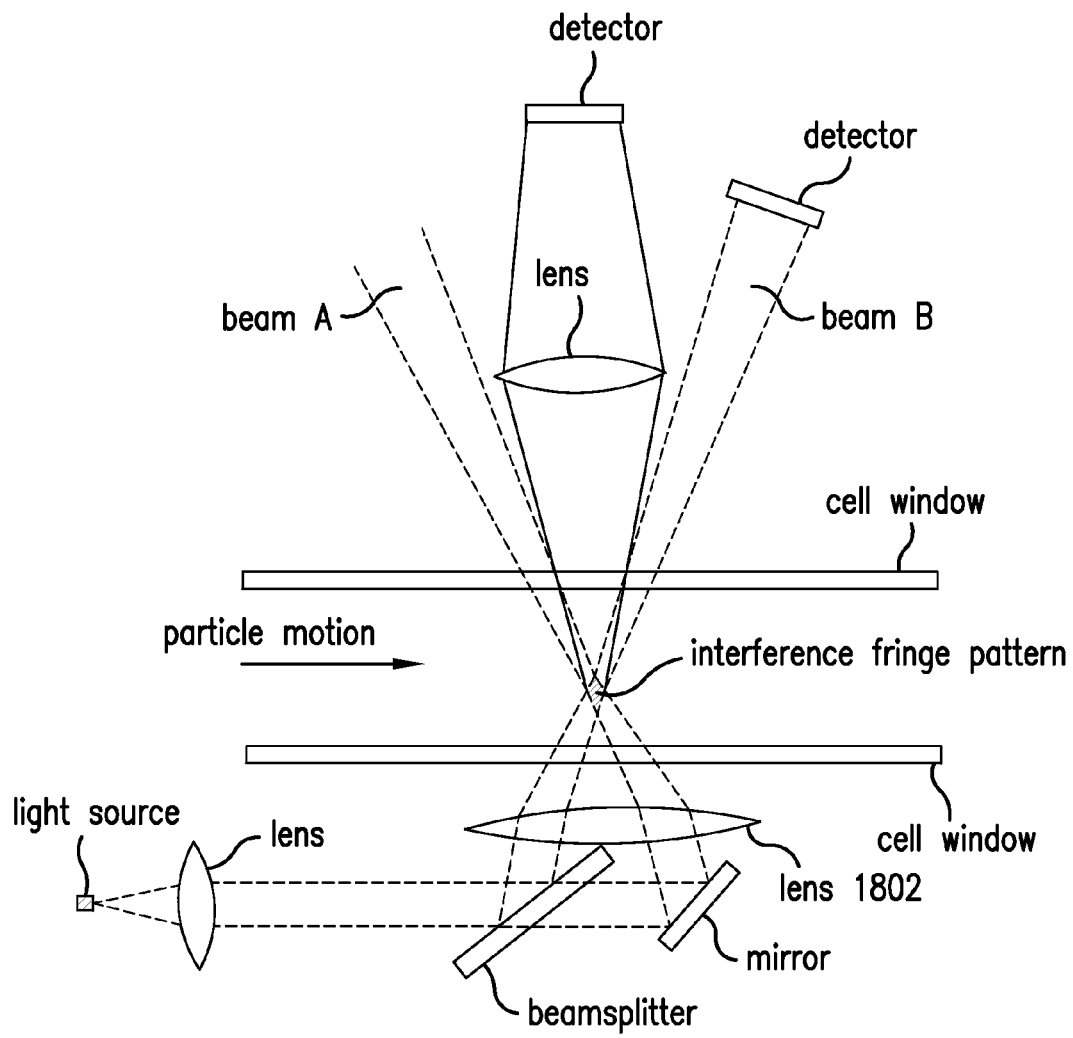
FIG. 18 provides a schematic diagram of an optical system which produces a modulated intensity profile by interference of two light beams, instead of imaging a periodic mask, according to the present invention.

FIG. 18 shows another system for measuring the settling of particles, using crossed laser beams. The laser source is split into two beams by a beamsplitter. Lens 1802 focuses those beams in the particle dispersion. An interference pattern is formed at the intersection of the beams. As the particles pass through this pattern, the scattered light, measured by either detector, is modulated, producing a power spectrum as described above. As described previously, the amplitudes of the corresponding peaks (at the same frequency) in power spectra of the detector signals can be used separately, or in ratio, to determine the particle size.

All slit apertures in this disclosure (for example, slit 114 and slit 115 in FIG. 1) can be changed to pinholes or rectangular apertures, whose images at the source beam may be or may not be smaller than the source beam. Unlike slits, the pinholes or rectangular apertures may require alignment in the both of the mutually perpendicular X and Y directions, which are both approximately perpendicular to the optical axis of the detection system.

Figure 19:
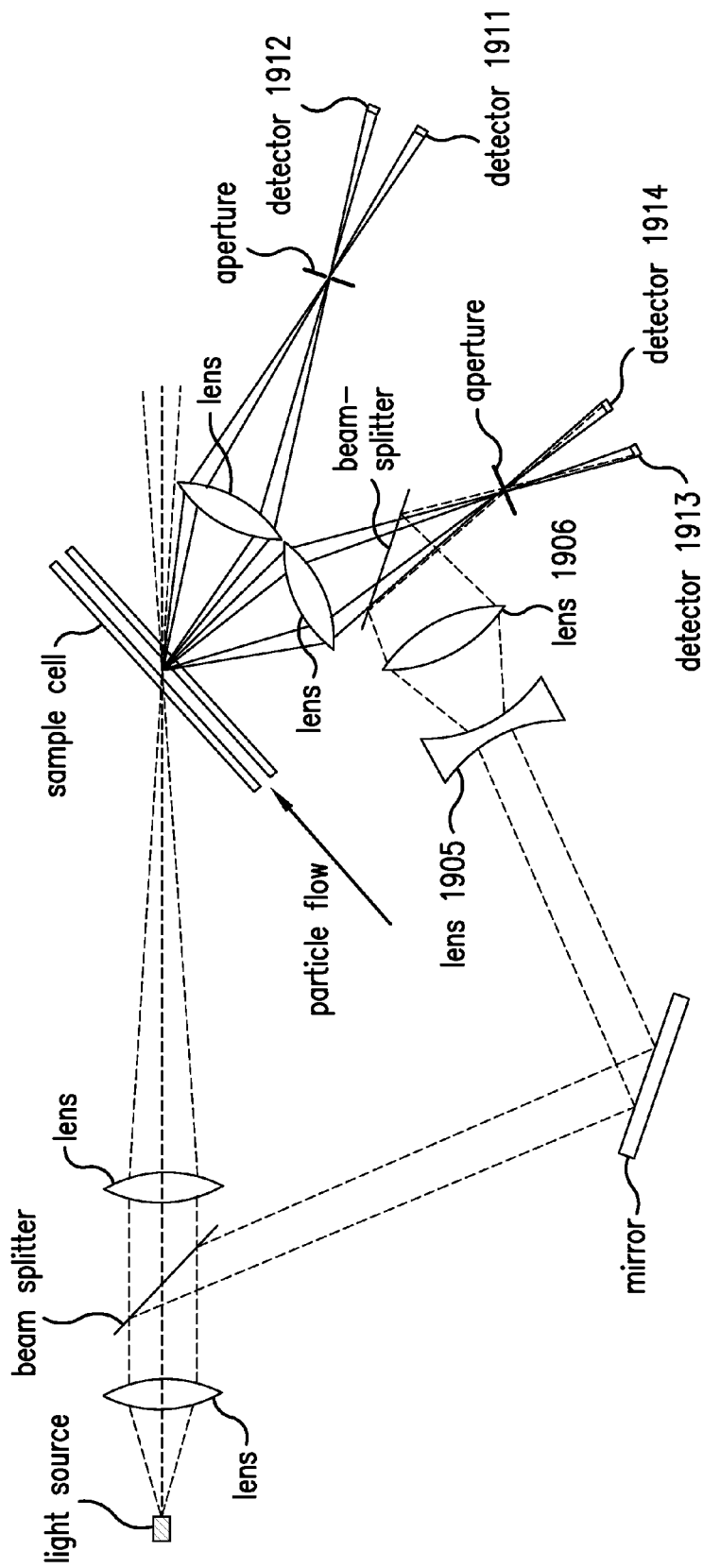
FIG. 19 provides a schematic diagram showing the use of detector size to define the angular range of each detector in FIG. 1.
Figure 20:
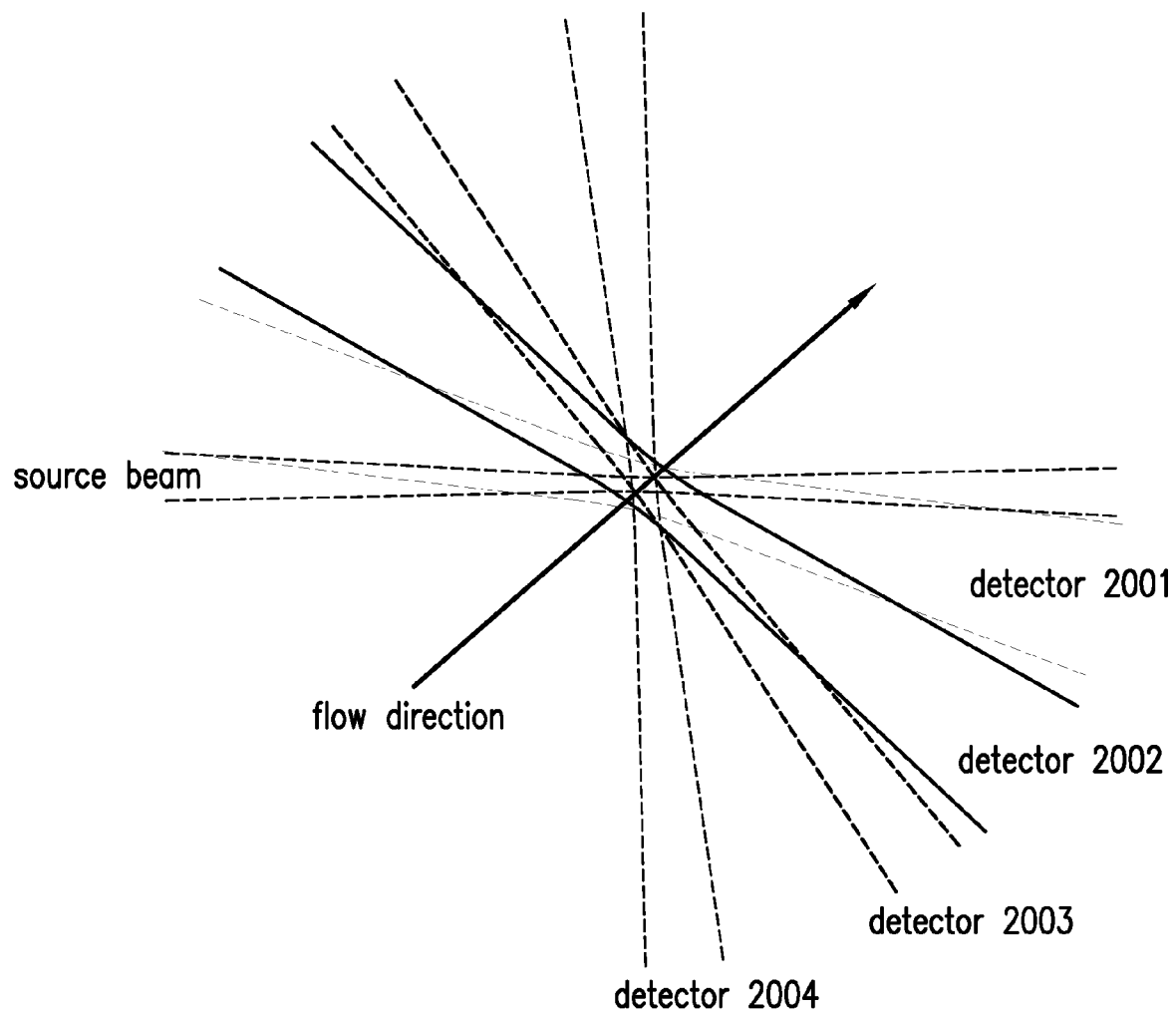

FIG. 19 (or FIG. 106) shows more detail of the actual beam shapes in FIG. 1 for the angular ranges specified for detectors 1911 through 1914. The scattering angle range for each detector is controlled by the detector size or by an aperture on front of a larger detector. FIG. 20 shows the detail of the intersection of the each detector field of view with source beam.

If the signal to noise is sufficient for non-coherent detection with any detector in FIG. 1, or in any other variation of FIG. 1 shown in this document, the local oscillator optics for that detector can be removed and non-coherent detection can be used.

The progression of crossectional size, in the interaction volume, from smallest to largest is: light source, fields of view from detectors 2003 and 2004, and the fields of view from detectors 2001 and 2002, as shown in FIG. 20. The progression could also progress from the smallest to largest as light source, field of views of detector 2004, detector 2003, detector 2002, and detector 2001, respectively. However, this would require different sized apertures for each detector. This would require a separate lens and aperture for each detector, but would insure that any particle passing through the intersection of the source beam and the detector 2004 field of view, will be seen by all of the other detectors during the entire pulse period from detector 2004. Then if all of the detector signal ratios are measured during a period near to the peak of the detector 2004 signal (after the envelope detector), valid scattering ratios will be recorded for all of the detectors.

The particles being measured by system in FIG. 19 are all much smaller than the crossection of the source beam. Therefore particles of different sizes produce the same count-vs.-parameter distribution for the following parameters:

1) scattered light amplitude normalized to the maximum scattered light amplitude measured over all the particles of the same size at that scattering angle.
2) Pulse width at certain fraction of pulse peak level
3) delay between pulses from two different detectors
4) correlation between pulses from two different detectors Any of these parameters can be used to define a threshold for counting particles as shown in FIGS. 10 and 10a, by replacing the S(a2) axis with one of the parameters from above. If the particle count is large, the statistics of the above parameters will be stationary for all particle sizes. Then the strategy outlined for FIG. 10 can be used to properly threshold particles of all sizes in an equivalent manner, by rejecting the same percentage of particles in each size bin in the count-vs.-size distribution. The 3 dimensional surface which corresponds to the one in FIG. 10, can be interpolated or fit to a surface function in order to determine the rejection threshold. Based upon the function or interpolated values, a rejection criteria can be determined which eliminates the particles with poor signal to noise and also removes the same percentage of particles from each size range so as to maintain a true particle size distribution. The rejection threshold is chosen to maintain a sufficiently high signal-to-noise for any particles which are accepted into the total count distribution. In fact, this process will computationally define an interaction volume for the source beam and all detector fields of view, for all particle sizes being detected, where all scattering signals have sufficient signal-to-noise to produce accurate sizes based upon their amplitudes, ratios of amplitudes, or other multi-parameter functions of scattering amplitudes. This selection process is required to reduce the effects of the tails in the intensity distribution of the source and the spatial response tails at the edges of the detector fields of view, where they intersect the source beam. If these tails are sharpened (or cut off) by spatial filtering the source or by using slits, pinholes, or other apertures with low aberration optics for the detectors, the errors due to these tails are further reduced, as shown in FIG. 10a. Also diffractive optics can be used to produce a "flat top" intensity distribution from a Gaussian laser intensity profile. Then the corresponding flat top shape should be used to produce the functions in FIGS. 10 and 10a. This would improve the accuracy of the particle rejection threshold and the resulting particle count distribution. In any event, there is always some parameter which is statistically well described by the millions of particles which are detected. And by eliminating particles from the count based upon this parameter, you can define a group of particles which are sorted by the same criteria at all particle sizes, thereby creating an accurate size distribution, while removing count events which have poor signal to noise.

In the sample cell with flat windows, many of the incident source beams and scattered light rays are at high angles of incidence on the sample cell windows. The interior surface of the window is in contact with a liquid which reduces the Fresnel reflection at that surface. However, the exterior surface is in air which can cause an enormous Fresnel reflection at these high incident angles. This reflection can be reduced by anti-reflection coating the exterior surface, but with high cost. A better solution is to attach prisms (see FIG. 21) to the exterior surface with index matching optical adhesive. The prism surfaces present low angles of incidence for the source beams and the scattered light. Even simple antireflection coatings on the external prism surfaces will reduce the Fresnel reflections to negligible levels. A spherical plano-convex lens, with center of curvature near to the center of the cell could also be used instead of each prism, with plano side attached to the window.

Another configuration for the sample cell is a cylindrical tube. The particle dispersion would flow through the tube and the scattering plane would be nearly perpendicular to the tube axis and flow direction. In this case, the beam focus and detector fields of view would remain coincident in the scattering plane for various dispersant refractive indices and only inexpensive antireflection coatings are needed. However, since the flow is perpendicular to the scattering plane, the heterodyne oscillations cannot be produced by the particle motion. The optical phase modulation mirror in the local oscillator arm (called "mirror") in FIGS. 1 and 19 (and other figures) could be oscillated to provide a heterodyne signal on detectors 112 and 113 as described before. This could also be accomplished with other types of optical phase modulators (electro-optic and acousto-optic) or frequency shifters (acousto-optic).

Any of the measurement techniques described can be used individually or in combination to cover various particle size ranges. Examples of possible combinations are listed below:

For particle diameter 0.05-0.5 microns use FIG. 19 with detectors 1913 and 1914 at 30 and 80 degrees, respectively.

Use heterodyne detection (if needed). Take ratio of the detector signals.

For particle diameter 0.4-1.2 microns use FIG. 19 with detectors 1911 and 1912 at 10 and 20 degrees, respectively.

Use heterodyne detection (if needed). Take ratio of the detector signals.

All 4 signals can also be used together for the range 0.05 to 1.2 microns, using a 4 parameter function or lookup tables.

Many choices for scattering angles will provide high sensitivity to size in certain size ranges. These include the following examples of ratios of signals for various particle size ranges: 75 degree/10 degree for 0.05 to 0.5 micron particles, 10 degree/1 degree for 2 to 15 micron particles, 2 degree/1 degree for 0.5 to 4 micron particles, 10 degree/2 degree for 1 to 5 micron particles, 25 degree/15 degree for 0.4 to 1.4 micron particles, 10 to 20 degrees/5 to 8 degrees for 0.05 to 1.6 micron particles, 25 to 50 degrees/5 to 8 degrees for 0.3 to 0.7 micron particles. Any single angle specification assumes that scattered light is collected in some angular range which is centered on that angle and does not have extensive overlap with the angular range of the other angle in the ratio. These angle pairs could also be used separately to determine particle size, based upon absolute amplitude (instead of ratio) and using look up tables, simultaneous equations, or the 2-dimensional analysis shown later (see FIG. 26 for example).

Use the detector with the smallest interaction volume to trigger data collection.

These angles are only representative of general ranges. Almost any combination of angles will provide sensitivity to size over a certain size range. But some combinations will provide greater size sensitivity and larger size range. For example, instead of 10, 20, 30, 80 degree angles, any group of angles with one widely spaced pair below approximately 30 degrees and another widely spaced pair above approximately 30 degrees would work. Each detector sees an angular range centered about the average angle specified above. But each detector angular range could be somewhat less than the angular spacing between members of a detector pair. In some cases, without optical phase modulation, the angular ranges of each heterodyne detector should be limited to prevent heterodyne spectral broadening as described later (see FIG. 91). The particle size distribution, below 2 microns, from this system is combined with the size distribution above 1 micron as determined from various other systems described in this disclosure, including the following systems:

For particle diameter 1-10 microns use detectors 1113 and 1114, in FIG. 11 or 1420 and 1421 in FIG. 14, at approximately 1 degree and 3 degrees, respectively. Use white light or LED source. Use ratio of detector signals to determine individual particle size.

For particle diameter greater than 1 microns, use the 2 dimensional array in FIG. 11 with a pulsed white light source (such as a pulsed xenon source) to freeze the motion of the flowing particles. The two dimensional array could also be used alone to measure greater than 1 micron, without detectors 1113 and 1114. The system in FIG. 14 could also measure particles greater than 1 micron in diameter, with one (absolute) or both (ratio) detector arrays.

Another configuration is to use the scattering flux ratio of scattering at 4 degrees and 1 degree, in white light, for 0.5 to 3.5 microns. And use absolute flux at 1 degree (white light, same system) for 3 to 15 microns. And use the 2 dimensional array in FIG. 11 or 14 for particles above 10 microns. As noted above, each array in FIG. 14 can separately be used to size particles by measuring the absolute scattered light from each particle, or light lost due to the particle, over one angular range. However, the system size response will be more composition (particle and dispersant refractive indices) dependent using data from a single array than the ratio of the corresponding measurements from both arrays.

In all of these systems, the white light source can be replaced by a laser. However, the particle size response will become more sensitive to particle and dispersant composition. And also the response vs. size may not be monotonic due to interference effects between the particle scattered light and light transmitted by the particle (Mie resonances), producing large size errors. If lasers or LEDs are required for collimation or cost requirements, scattering measurements can be made at more than one wavelength, using multiple sources, to reduce the composition dependence. Particle size of each object would be determined from all of these multi-wavelength measurements by using a multi-parameter function (size=function of multiple parameters), by interpolation in a lookup table as described above, or by a search algorithm. And in all cases the angles are nominal. Many different combinations of average angles, and ranges of angles about those average angles, can be used. Each combination has a different useable particle size range based upon size sensitivity, composition sensitivity, and monotonicity. All of these different possible combinations are claimed in this application. Also note that the ratio of S(a1)/S(a2) in FIG. 10 can be replaced by any parameter or function of parameters which have nearly exclusive sensitivity to particle size, with low sensitivity to incident intensity on the particle. This may include functions of scattering measurements at more than 2 angles.

These cases are only examples of combinations of systems, described in this application, which could be combined to provide a larger particle size range. Many other combinations are possible and claimed by this inventor.

One problem associated with measuring large particles is settling. The system flow should be maintained at a sufficiently high level such that the larger particles remain entrained in the dispersant. This is required so that the scattered light measurements represent the original size distribution of the sample. For dense large particles, impracticable flow speeds may be required. This problem may be avoided by measuring all of the particles in one single pass, so that the total sample is counted even though the larger particles may pass through the light beam as a group (due to their higher settling velocities) before the smaller particles.

Figure 22:
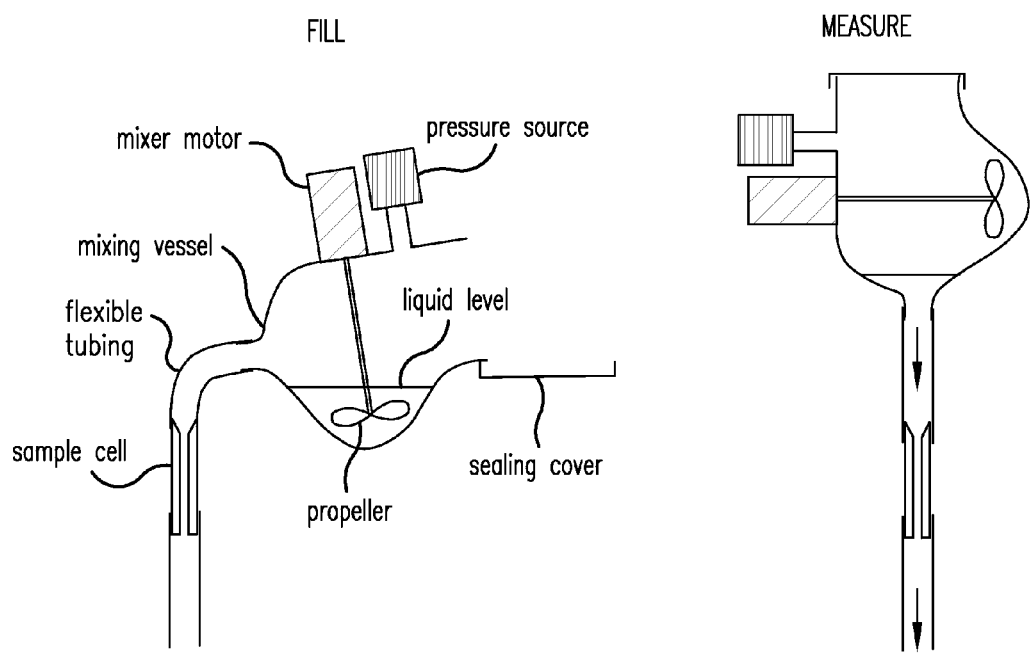
FIG. 22 provides a diagram, partly in schematic form, showing an apparatus for mixing the particle dispersion and passing all of said dispersion through a sample cell in a single pass, according to the present invention.

A small open tank is placed above the sample cell region, connected to the cell through a tube. The tube contains a valve which can be shut during introduction of the particle sample into the tank to prevent the sample from passing through the cell until the appropriate time. The liquid in the tank is continuously stirred during the introduction of sample to maximize the homogeneity in the tank. A light beam may be passed through the mixing vessel via two windows to measure scattered light or extinction to assist in determining the optimum amount of sample to add to obtain the largest counts without a high coincidence count level. The optical detectors are turned on and the valve is opened to allow the particle mixture to pass through the cell with gravitational force. This can also be accomplished by a valve below the sample cell or by tilting the tank up to allow the mixture to flow over a lip and down through the cell, as shown in FIG. 22. The light beam could be wider than the width of the flow stream through the cell so that all of the particles passing through the cell are counted. Single particle counting is assured by only introducing a sufficiently small amount of sample into the tank. Since all of the larger particles are counted in one pass, the count distribution is independent of the sample inhomogeneity. After the entire sample has passed through the cell, the conventional flow system for ensemble scattering measurements is then turned on to circulate the sample through the cell. Ensemble scattering measurements are measurements of scattered light from groups of particles. This flow rate must only be sufficient to suspend the particles which were too small, or too numerous, to be individually counted during the single pass. During this flow period, settling of the larger particles which have been counted does not matter because their count distribution (from the single pass) will be combined with the count-vs.-size distribution of the smaller particles (obtained during flow) to produce a single volume distribution over the entire size range, using the size distribution blending and combination methods described previously.

The system in FIG. 22 could also be used alone to provide significant cost savings by eliminating the pump and associated hardware. FIG. 22 shows the concept for dispersing and measuring the particles in a single pass through the optical system. The particles and dispersant are mixed continuously in a mixing vessel which is connected to the optical system through a flexible tube. The mixing vessel is tilted while being filled, so that no sample enters the optical system. Then once the dispersion is well mixed, the mixing chamber is sealed with a gas tight cover and the mixing vessel is moved into an upright position to allow the dispersion to either fall through the sample cell under gravity (without gas tight cover) or to be pushed through the cell using gas pressure. If gas pressure is not used, the flexible tube could be eliminated and the mixing vessel could pour into a funnel on top of the sample cell.

The systems based upon FIG. 19 and similar systems, where scattered light at multiple-angles are measured from a single particle, will have a lower particle size limit due to the lower scattering intensity of small particles and insensitivity of the scattering ratio to particle size. If the particle refractive index and dispersant refractive index are known, various scattering theories can be used to calculate the scattering signal ratios and absolute scattering signals vs. particle size to provide the look up table or function to calculate the size of each particle from these signals. Since these refractive index values are not always available, the scattering model (the effective refractive indices) may need to be determined empirically from scattering data measured in a region where the scattering ratio is independent of refractive index, but where the absolute scattering amplitudes are dependent upon refractive index. In this region the signal ratio will determine the particle size. And then the absolute scattering signals (relative to the incident source intensity) and this size value can be used to determine the refractive indices by using global search algorithms to search for the refractive indices which give the best fit to the particle size and absolute signal values. This process assumes that the entire particle ensemble is homogeneous in individual particle composition (however, a method is proposed for dealing with inhomogeneous samples in FIG. 27a). This method can be used for any particle, which shows a ratio in the size sensitive region of the response, and this method can be used to determine the effective refractive index of the particle by using the ratio and the absolute values of the scattering signals, because these are unique for particle and dispersant refractive index. The optical model for this effective refractive index could then be used to extend the size response range, of any set of detectors, to a size range outside of the ratio determined size region(where the scattering signal ratio is sensitive to size and the ratio cannot be used). This process can extend the size to both smaller and larger particles by using the absolute scattering intensity in regions where the scattering signal ratio no longer works. Theoretically, very small particles are Rayleigh scatterers, where the shape of the angular scattering distribution is not size dependent. However for very small particles, the peak of the scattering intensity distribution scales as the $6^{th}$ power of the particle diameter and the heterodyne signal scales as the $3^{rd}$ power of the diameter. So as the particle size decreases, the ratio of the intensity at two angles becomes constant, but the actual intensities continue to drop as the particle size decreases. So when the intensity ratio approaches this constant, the particle size algorithm should use absolute scattering intensity to determine the size. The absolute scattered intensity is proportional to a constant (which is a function of scattering angle, particle and dispersant refractive indices, and light wavelength) divided by particle diameter to the $6^{th}$ power ($3^{rd}$ power for the heterodyne signal). This constant is determined from the absolute scattered intensities of particles, in the distribution, whose intensity ratios still provide accurate particle size. Also the functional form for the absolute intensities can be calculated using various scattering theories (Mie theory for example). This process can also be used to extend the useful range to larger particles. As the particle becomes larger, the scattering signal ratio from the detector pair will become more dependent upon the refractive index of the particle. The absolute intensity data from particles, in the region where the ratio is independent of particle composition, can be used to determine the effective composition of the particles and determine which theoretical scattering model to use for absolute scattering intensity from particles outside of that size region. Then the larger particles are measured using this model and the absolute values from each scattering detector, instead of the ratio of scattering signals. Absolute intensity data from particles, in the region where the ratio is independent of particle composition is preferred, but absolute scatter data from multiple scattering angular ranges in any size region can be used to determine the particle and dispersant refractive indices by using the global search algorithms described elsewhere in this application. The scattering values depend more strongly on the ratio of particle refractive index to dispersant refractive index, than their absolute values. So in many cases, only the refractive index ratio must be determined by this search algorithm.

One other remaining problem with absolute scattering intensity measurements is the sensitivity of pulse intensity to the position where the particle passes through the beam. Measuring the distribution of pulse amplitudes from a nearly mono-sized calibration particle dispersion (with a low coefficient of variation for the size distribution) provides the response of the counter for a group of particles of nearly identical size. This count distribution, which is the same for any particle whose size is much smaller than the light beam crossection, provides the impulse response for a deconvolution procedure like the one described previously. The scattering pulses can be selected based upon their pulse length by only choosing pulses with intensity normalized lengths above some threshold or by using the various pulse selection criteria listed below. This selection process will help to narrow the impulse response and improve the accuracy of the deconvolution. This process is also improved by controlling the intensity profile to be nearly "flat top" as described previously.

The scattered signal from any particle is proportional to the intensity of the light incident on the particle. Hence as the particle passes through different portions of the incident light beam, each scattered signal will vary, but the ratio of any two signals (at two different scattering angles) will theoretically be constant as long as the field of view of each detector can see the particle at the same time. This can be insured by eliminating the signals from long intensity tails, of the Gaussian intensity profile of the laser beam, which may not be seen by all detectors. This is accomplished by placing an aperture, which cuts off the tails (which may be Gaussian) of the incident light intensity distribution, in an image plane which is conjugate to the interaction volume. This aperture will produce a tail-less illumination distribution in the interaction volume, providing a narrower size range response to mono-sized particle samples (the impulse response). In the case of an elliptical Gaussian from a laser diode, the aperture size could be chosen to cut the distribution at approximately the 50% points in both the x and y directions (which are perpendicular to the propagation direction). Such an aperture would cause higher angle diffractive lobes in the far field of the interaction volume, which could cause large scatter background for low scattering angle detectors. Since this aperture should only be used for measurements at high scattering angles where the background scatter can be avoided, the low angle detector set and high angle detector set may need to view separate light beams. The apertured beam size should be much larger than the particles which are being measured in that beam. Hence, to cover a large size range, apertured beams of various sizes could be implemented. The particle size distributions from these independent systems (different source beams or different detector groups) could be combined to produce one continuous distribution. These apertures could also have soft edges to apodize the beam, using known methods to flatten the beam intensity profile while controlling the scattering by the aperture. This could also be accomplished by using diffractive optics for producing flat top distributions from Gaussian beam profiles as mentioned earlier. Also apertures can be oriented to only cut into the beam in the appropriate direction such that the diffracted light from that beam obstruction will be in the plane other than the scattering plane of the detectors. This is accomplished by orienting the aperture edges so that they are not perpendicular to the scattering plane. The aperture edges which cut into the beam at higher levels of the intensity profile should be nearly parallel to the scattering plane to avoid high scattering background.

The apertured beams will help to reduce the size width of the system response to a mono-sized particle ensemble, because the intensity variation of the portion of the beam which is passed by the aperture is reduced. Other analysis methods are also effective to reduce the mono-sized response width for absolute scattering and scattering ratio measurements. Methods which accept only scattering signal pulses, or portion of pulses, which meet certain criteria can be very effective in narrowing the size width of the system response to mono-sized particles. Some examples of these acceptance criteria are listed below. Any of these criteria can be used to determine which peaks or which portion of the peaks to be used for either using the scattering signal ratios or absolute values to determine the particle size.

1. Choose only the time portion of both pulses where the pulse from the detector which sees the smaller interaction volume, or has the shorter duration, is above some threshold. The threshold could be chosen to be just above the noise level or at some higher level to eliminate any possibility of measuring one signal while the second signal is not present. Then either take the ratio of the signals (or ratio the peaks of the signals with peak detector) over that time portion or the ratio of the integrals of the signals over that time portion. The absolute integrals or peak values during this time portion could also be used to determine size, as described before.
2. Only accept pulses where the separation (or time delay between peaks or rising edges) between pulses from the multiple detectors is below some limit
3. Only accept pulses where the width of a normalized pulse or width of a pulse at some threshold level is within a certain range as determined by the shortest and longest particle travel paths through the accepted portion of the interaction volume.
4. Only accept the portion of the pulses where the running product S1.*S2 (a vector containing the products of S1 and S2 for every point during the pulses) of the two signals is above some limit. Then either take the ratio of the signals over that portion or the ratio of the integrals of the signals over that portion.
5. Only use the portion of pulses where sum(S1.*S2)/(sum (S1)*sum(S2)) is greater than some limit (sum(x)=summation of the data points in vector x)
6. Use only the portion of the pulses where (S1.*S2)/(S1+ S2) is greater than some limit
7. integrate each pulse and normalize each integral to the pulse length or sample length
8. Use only the portion of the pulses where the value of S1*S2 is be greater than some fraction of the peak value of the running product S1.*S2
9. Integrate both signals S1 and S2 only while the signal from the smaller interaction volume is above a threshold or while any of the above criteria are met.
10. fit a function to the selected portion (based upon various criteria described above) of each pulse. The fitting function form can be measured from the signal of a particle passing through the center of the beam or can be based upon the beam intensity profile
11. When both S1 and S2 have risen above some threshold, start integrating (or sample the integrators from) both signals. If the integrators for S1 and S2 are integrating continually (with resets whenever they approach saturation) then these integrators could be sampled at various times and the differences would be used to determine the integrals in between two sample times. Otherwise the integrators could be started and stopped over the period of interest. These sampled integrals are IT10 and IT20 for S1 and S2 respectively, when each of them rises above the threshold. When the first signal to drop falls back down below the threshold, sample the integrator on each of S1 and S2 (integrals IT1a and IT2a). When the second signal (signal number *) to drop falls below the threshold, sample the integral IT*b for that signal. Use the ratio of the integral differences, (IT1a−IT10)/(IT2a− IT20), during the period when both signals are above the threshold to determine size. Accept and count only pulses where a second ratio (IT*a−IT*0)/(IT*b−IT*0) is above some limit. This second ratio indicates the fraction of the longer pulse which occurs during the shorter pulse. As the particle passes through the light beam further away from the center of the interaction volume, this ratio will decrease. Only particles which pass through the beam close to the center of the interaction volume will be chosen by only accepting pulses where the shorter pulse length is a large fraction of the longer pulse length. These pulse lengths could also be determined by measuring the difference in the length of time between the above trigger points for each pulse. Pulses with a shorter difference in time length are accepted into the count by ratioing their integrals during the period when both of them are above the threshold.

Figure 23A:
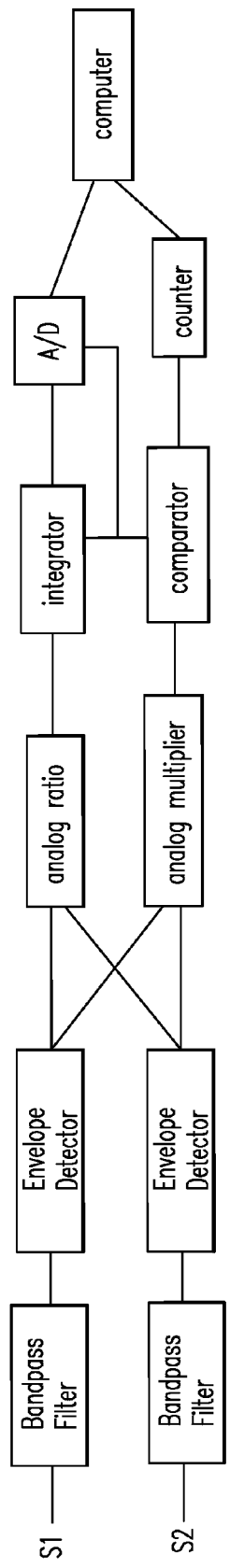
FIG. 23A and FIG. 23B provide block diagrams of systems of analog electronic modules which implement selection criteria used to determine which signal peaks, or portions of the signal peaks, to be utilized in the particle count data, according to the present invention.
Figure 23B:
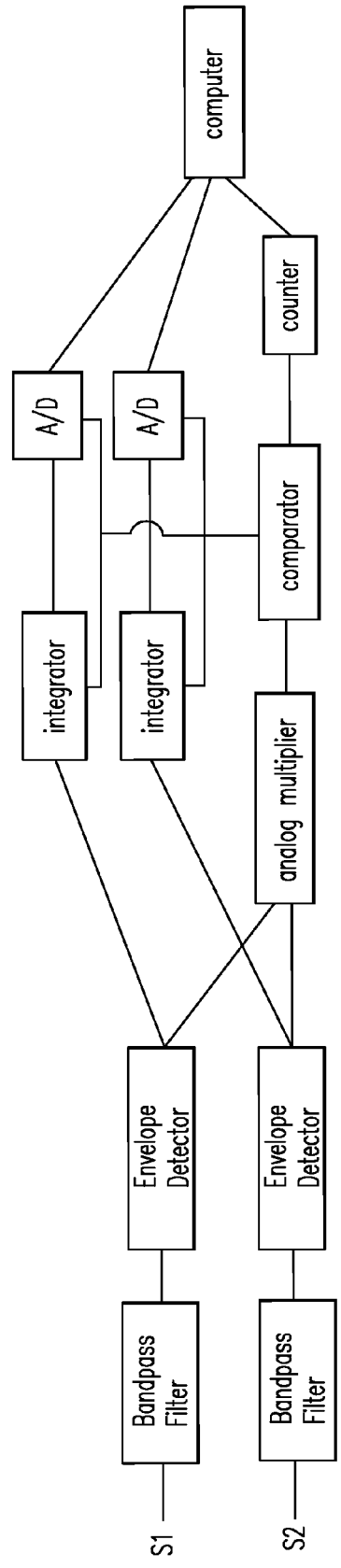

These criteria can be easily implemented by digitizing S1 and S2 and then doing the above comparisons digitally. However, full waveform digitization and digital analysis of 1 million particles may require too much time. FIGS. 23a and 23b show configurations for implementing some of these criteria using analog circuits. The signal digitization and computational load is greatly reduced by using analog equivalents to preprocess data before digitization. This concept is particularly effective when the thresholding or comparative functions, of the criteria described above, are replaced by analog equivalents; but the actual signal analysis used for size determination is done digitally to avoid the poorer linearity and accuracy of the analog equivalents. An example of this is shown in FIG. 23b, where both integrator outputs (one integration per signal pulse) are separately digitized by the A/D converters to do the amplitude or signal ratio calculations digitally instead of using analog ratio circuits; but the criteria related functions, analog multiply and comparator, are done analog to reduce the digitization load. This overall concept of using analog circuitry specifically for only the criteria related functions to reduce the digitization load is claimed by this disclosure, along with applications to other systems.

All of these variations will not be perfect. Many of them rely upon approximations which can lead to variation in calculated size for a particle that passes through different portions of the beam. The important advantage is that the broadening of the mono-sized particle response is the same for all size particles which are much smaller than the source beam. Therefore this broadened response, which is calculated by measuring the count distribution from a mono-sized distribution or by theoretical modeling, can be used as the impulse response to deconvolve the count distribution of any size distribution.

The intensity ratio is sensitive to size and mildly sensitive to particle and dispersant refractive index. Size accuracy is improved by using scattering theory (such as Mie theory for spherical particles), for the actual refractive index values, to calculate the scattering ratio vs. particle diameter function. However, sometimes these refractive indices are not easily determined. Three scattering angles could be measured to generate a function which has reduced sensitivity to refractive index.

$$D = A1*(S2/S1) + A2*(S2/S1)^2 + A3*(S2/S1)^3 + B1*(S3/S1) + B2*(S3/S1)^2 + B3*(S3/S1)^3 + C1$$

D=particle diameter
A1, A2, A3, B1, B2, B3 are constants
S1=scattering signal at the first scattering angle (over the first scattering angle range)
S2=scattering signal at the second scattering angle (over the second scattering angle range)
S3=scattering signal at the third scattering angle (over the third scattering angle range)
Solve the set of equations:

$$Di = A1*(S2/S1)ij + A2*((S2/S1)ij)^2 + A3*((S2/S1)ij)^3 + B1*(S3/S1)ij + B2*((S3/S1)ij)^2 + B3*((S3/S1)ij)^3 + C1$$

where i=diameter index
j=index of refraction index
and
S1$ij$=theoretical scattering signal over scattering angular range #1, for particle diameter D=Di and the jth index of refraction
S2$ij$=theoretical scattering signal over scattering angular range #2, for particle diameter D=Di and the jth index of refraction
(...)ij indicates that all the variables inside the parentheses have index ij.

A set of simultaneous equations are created for various diameters Di using signal ratios calculated from the appropriate scattering theory (Mie theory or non-spherical scattering theory) for various particle and dispersant refractive indices. These equations are then solved for the constants A1, A2, A3, B1, B2, B3, C1 and the scattering angles. Of course this process can be extended to more than 3 angles and for polynomial order greater than 3. These constants and scattering angles are determined using iterative search or optimization methods to repeatedly adjust these parameters to maximize the sensitivity to particle size, while lowering the sensitivity to particle and dispersant refractive indices.

Particles which are two small for single particle counting may be measured by stopping the flow and using the heterodyne signal of the scattered light to measure the size distribution from the Brownian motion of the particles. This Brownian measurement should be done at higher particle concentration, before the particle dispersion is auto-diluted to the lower counting concentration by the system shown in FIG. 13. The particle size distribution is determined by inverting either the power spectrum or the auto-correlation function of the Doppler broadened scattered light from the moving particles, using known methods. The particle size distribution from Brownian motion can also be used to determine the effective particle/dispersant refractive index (scattering model) by measuring the hydrodynamic size of a particle along with the scattering signal amplitudes. The scattering model can be determined from the scattering intensity at each angle, and the true size for a representative single particle or a group of particles. The true size can be determined from the power spectrum or autocorrelation function of the heterodyne signal via Brownian motion, from the ratio of intensities of light scattered at two angles in the size region where the ratio is an accurate indicator of size, or by other size measurement techniques. This scattering model could then be used for computations of particle size in a counting process, which does not use Brownian motion.

Other methods of generating the heterodyne local oscillator are also claimed in this disclosure for systems like in FIG. 19. For example a small reflecting sphere or scattering object could be placed in the interaction volume to scatter or reflect light into the heterodyne detectors along with the light scattered by the moving particle. Since this sphere or object is stationary, the optical phase difference between the scattered light from the moving particle and light scattered (or reflected) from the sphere or object would increase as the particle passed through the beam, creating an oscillating beat scatter signal on the detectors, at high frequencies. Then the local oscillator beam, which passes through lens 1906, could be eliminated.

Figure 24:
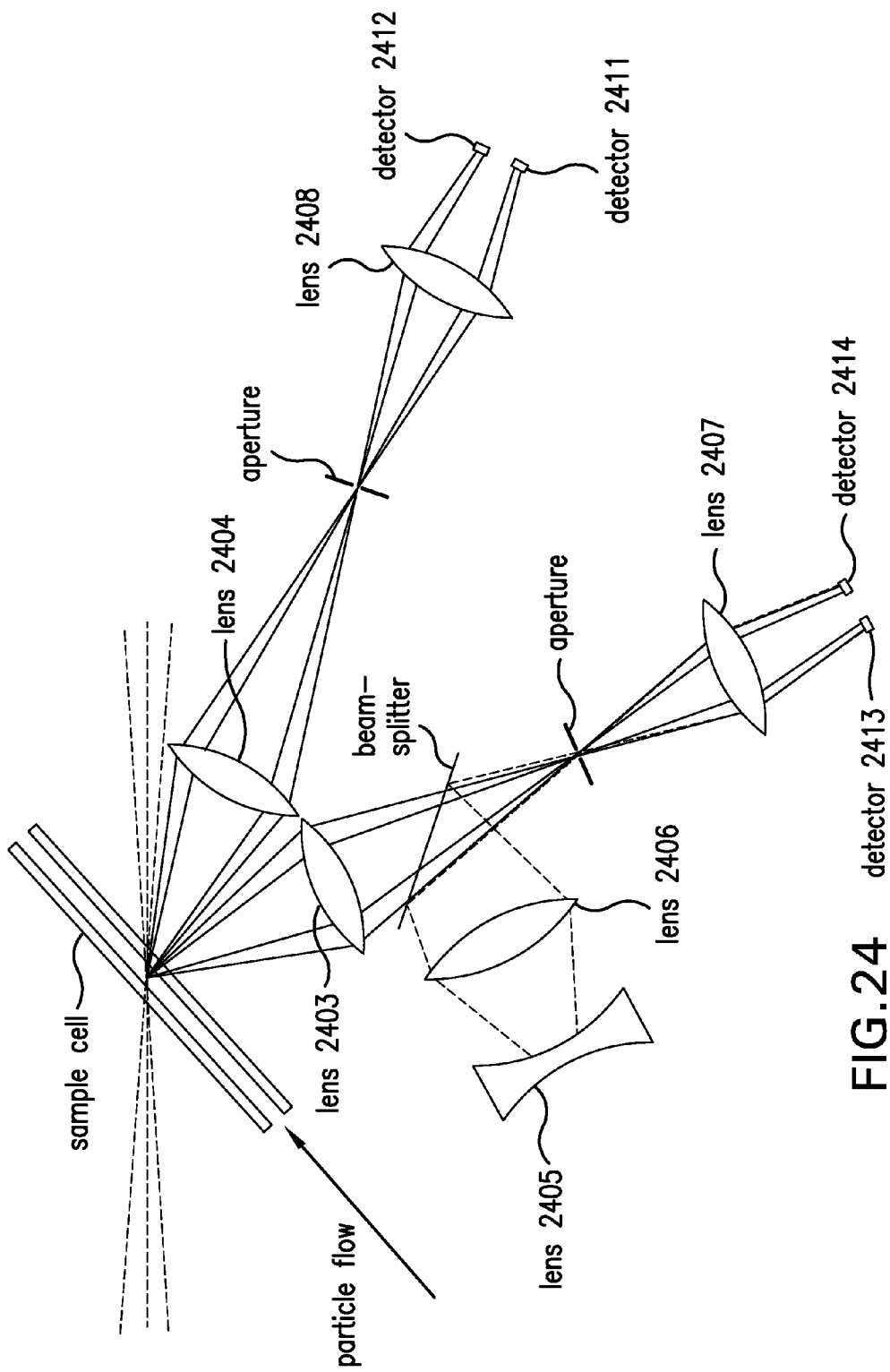
FIG. 24 provides a schematic diagram showing the use of additional lenses to reduce the sensitivity of scattering angle to particle position, according to the present invention.

In FIG. 19, the effective scattering angles seen by each detector can depend upon the position of the particle in the beam. The addition of lenses 2407 and 2408, as shown in FIG. 24 (which only shows the detection portion of FIG. 19), will lower the scatter angle sensitivity to particle position. Each of these lenses place the detectors in a plane which is conjugate to the back focal plane of either lens 2403 or lens 2404. Essentially the back focal plane of lens 2403 is imaged by lens 2407 onto detectors 2413 and 2414; and the back focal plane of lens 2404 is imaged by lens 2408 onto detectors 2411 and 2412. Also the detectors could be placed in the back focal planes of lens 2407 and lens 2408, where each point in the focal plane corresponds to the same scattering angle from any point in the interaction volume. This configuration nearly eliminates dependence of detector scattering angles on the position of particles in the beam. However, in many cases this angular dependence is negligible and the additional lenses are not needed.

By powering the source at various intensity levels, the scattered light from particles which span a large range of scattering intensities can be measured with one analog to digital converter. Even though the dynamic range of the scattered light may be larger than the range of the A/D, particles in different size ranges can be digitized at different source intensity levels. The resulting signals can be normalized to their corresponding source intensity and then used to determine the size of each particle.

In FIG. 11, the 2-Dimensional detector array could also be moved farther away from lens 1104 to the plane which is nearly optically conjugate to the center of the sample cell. This may provide better imaging resolution of the particles on the array.

Also it is recognized that many of the ideas in this disclosure have application outside of particle counting applications. Any other applications for these ideas are also claimed. In particular, the ideas put forth in FIGS. 21 and 22 would also have application in ensemble particle sizing systems.

Many drawings of optical systems in this disclosure show small sources with high divergence which are spatially filtered by a lens and pinhole and then collimated by a second lens. In all cases, a low divergence laser beam could replace this collimated source, as long as the spectral properties of the laser are appropriate for smoothing of Mie resonances if needed.

Another issue is interferometric visibility in the heterodyne signals described before. Misalignment of beamsplitter or lenses 2405 or 2406 in FIG. 24 can lower the visibility of the heterodyne signals. Since this loss may be different on different detectors, the ratio of two signals may not be preserved. However, the ratio of the visibilities for two detectors will be the same for all particles. Therefore a correction for the effects of low visibility, for both absolute signals and signal ratios, can be determined by measuring scattered signals from one or more nearly mono-sized particles of known size and comparing the results with theoretical values to determine the effective visibility for each channel or visibility ratio for pairs of channels. This is most easily accomplished by measuring larger particles with scattering signals of very high signal to noise and looking at the actual heterodyne signals to determine the interferometric visibility for each detector. This could be determined by blocking the local oscillator light and measuring the scattered signal pulse with, and without, the local oscillator to calculate the theoretical heterodyne signal from the measurement of the local oscillator power and the scattered pulse amplitude. Also simply comparing the ratio of two scattering heterodyne signals to the theoretical value for that particle size would also provide a correction factor for the ratio, directly.

Figure 25:
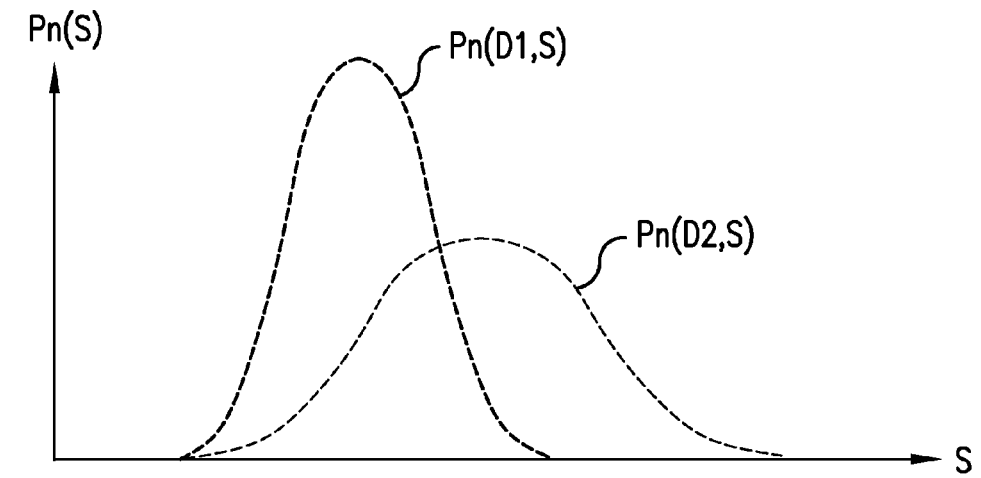
FIG. 25 provides graphs showing the particle count probability functions in linear and logarithmic signal space, the graphs showing the creation of shift invariant functions and a convolution relationship for count distributions as a function of the logarithm of a scattering signal, according to the present invention.
Figure 25:
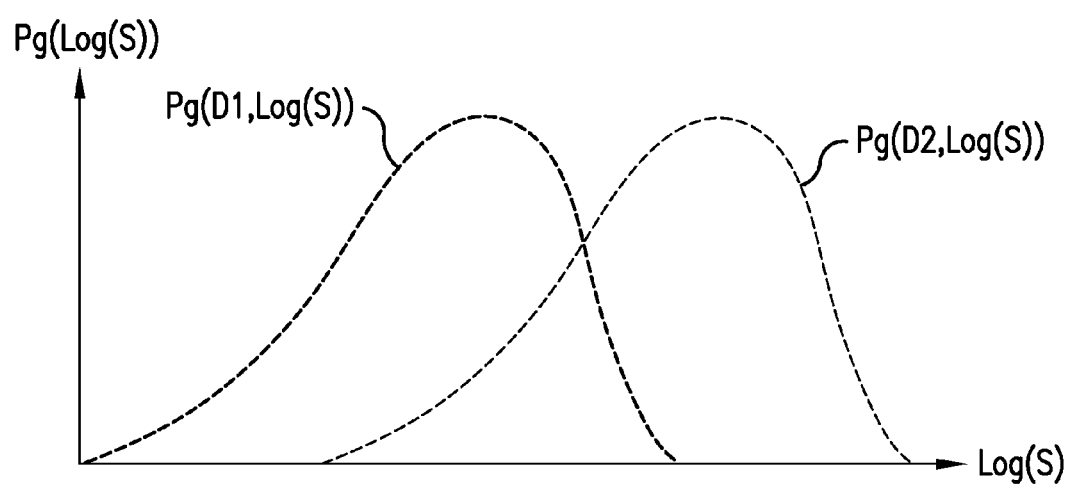

For particles which are much smaller than the size of the laser spot, the scattered signal for particles passing through various portions of the laser spot will be distributed over a range of peak amplitudes. For a group of monosized particles, the probability that a peak amplitude will be between value S−deltaS/2 and S+deltaS/2 is Pn(S)deltaS, where Pn(S) is the probability density function for scattering amplitude in linear S space. "deltaQ" means the difference in Q between the end points of the interval in Q, where Q may be S or Log(S) for example. For a group of monosized particles of a second size (diameter D2 in FIG. 25), the scattering amplitudes, S, for particles that have passed through the same region of laser beam, as particles of the first size diameter D1, are changed by a multiplier R and the probability density amplitude is changed by a multiplier of 1/R, as shown in first graph of FIG. 25 for two particle diameters, D1 and D2 and the following equation:

$Pn(S)\text{delta}S = Pn(RS)\text{delta}S/R$

If we switch to logarithmic space for S, we find that the probability density becomes shift invariant to a change in particle size. (Pg(Log(S)) only shifts along the Log(s) axes as R or particle size changes.

Using $\text{delta}S = R*\text{delta}\text{Log}(S)$ $Pg(\text{Log}(S))\text{delta}\text{Log}(S) = Pg(\text{Log}(R) + \text{Log}(S))\text{delta}\text{Log}(S)$ Where Pg(Log(S)) is the probability density function in Log(S) space. This shift invariance means that the differential count-vs.-Log(S) distribution, Cg, in logarithmic space is a convolution of the probability function Pg shown in FIG. 25, with the number-vs.-size Ng, where all are functions of Log (S).

Cg=Ng⊖Pg in convolution form where Pg is the response (impulse response) from a monosized particle ensemble Cg=Ng*Pgm in matrix form, where each column in matrix Pgm is the probability function for the size corresponding to the element of Ng which multiplies it. This more general equation can also be used for any case, including when Pg is not a convolution form.

These equations can be inverted to solve for Ng, given Cg and Pg, by using deconvolution techniques or matrix equation solutions. Pg is determined theoretically from the laser beam intensity profile or empirically from the Cg measured for one or more monosized particle samples. If the shape of Pg has some sensitivity to particle size, the matrix equation is preferable.

Figure 26:
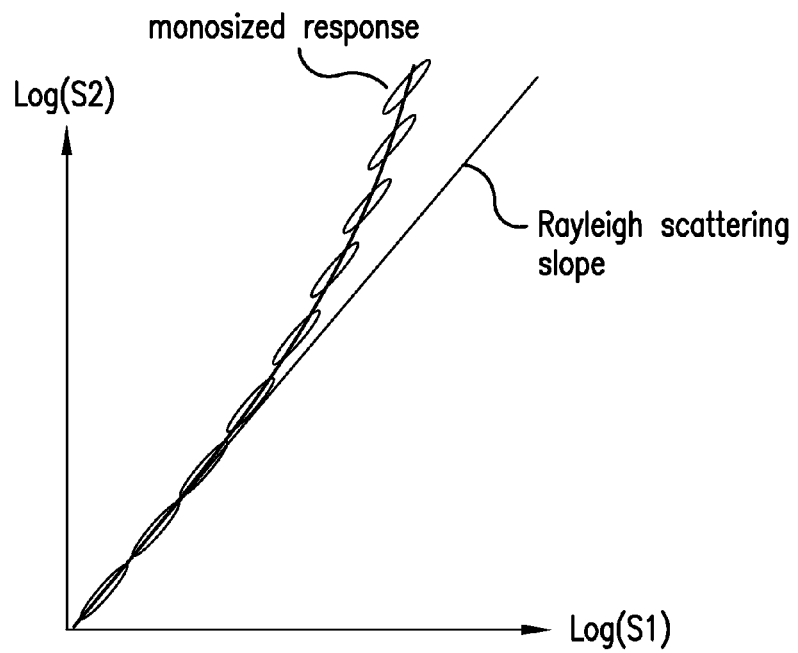
FIG. 26 provides a graph showing an example of scatter signal response in two dimensions, where each dimension is a function of the logarithm of the scatter signal, according to the present invention.

These relationships also hold for the above functions, when they are functions of more than one variable. For example, consider the case where Cg is a function of scattering values S1 and S2 from two scattering detectors at different scattering angles. Then Pg and Cg are 2-dimensional functions because they are functions two variables or dimensions. Then Cg(Log (S1),Log(S2))deltaLog(S1)deltaLog(S2) is the number of events counted with log signals between Log(S1)−delta(Log (S1))/2 and Log(S1)+delta(Log(S1))/2, and between Log (S2)−delta(Log(S2))/2 and Log(S2)+delta(Log(S2))/2. Then Cg(Log(S1),Log(S2)) could be plotted as a surface on the (Log(S1),Log(S2)) plane as shown in FIG. 26. This surface is determined from the event density of the "scatter plot" or "dot plot" of all of the particles on the Log(S1),Log(S2) plane (each particle is represented by its values of Log(S1) on the X axis and Log(S2) on the Y axis on the scatter plot). So an event is the dot or point in Log(S1),Log(S2) space (or S1,S2 space) which represents a counted object. The distribution functions Pg and Cg are calculated from the number of events for each small area in this space. The two dimensional space is divided up into small squares. The number of events or counts are summed inside each square and the value of that sum is placed at the center of that square. These summed values then create the sampled values of Pg or Cg at those locations on the 2-dimensional Log(S1): Log(S2) plane. Then functions of these two variables can be fit (using regression analysis or interpolation) to these sampled values to provide continuous functions of Cg and Pg over the entire 2-dimensional surface. Each square should be of sufficient size to prevent large count errors within the square due to Poisson statistics. Hence the sizes of the squares may vary to accommodate the local count density in each region of the plot. This concept can be extended to any number of scattering parameters and dimensions. For example, for functions of 3-dimensions, the squares would become cubes. A group of monosized particles will theoretically produce a group of points in S1,S2 space which follow the function Log(S2)=Log(S1)+Log(R). Hence the data points will line up along a line of slope=1 and with an offset of Log(R). R is particle size dependent over a certain size range. The distribution of points along the length of the line for the particle group is determined by range of S1 and S2 for that group due to the intensity distribution of the source beam. If particles pass through the beam at random locations, the distribution of data points along the line will follow the intensity distribution along each of the S1 and S2 axes. R, which is the ratio between S2 and S1, changes with particle size. As the particle size decreases below the wavelength of the source, R becomes a constant for all sizes, as determined from Rayleigh scattering theory. However, real measurements do not follow theory exactly due to structural imperfections in the optical system. These imperfections will cause broadening of the line. This broadening is illustrated by an elliptical shape (however the actual shape may not be elliptical) in FIG. 26. Each ellipse represents the approximate perimeter around a group of counted data points on the S1,S2 plane from particles all of one size. The actual shape of this perimeter may not be an ellipse, depending upon the source of broadening. Notice, if the only cause of response broadening is due to the intensity distribution of the source spot, then the ellipses in FIG. 26 will collapse to line segments along the major axes of each ellipse, because both signals from each point will have nearly the same ratio for particles of the same size. If the peak value of the scatter signal is measured, the ellipse perimeter will collapse to a smaller region, because the intensity variations of the source in the flow direction will not effect the broadening of the response. The broadening will be due to the change in peak intensity for different particle paths though the beam.

Figure 27:
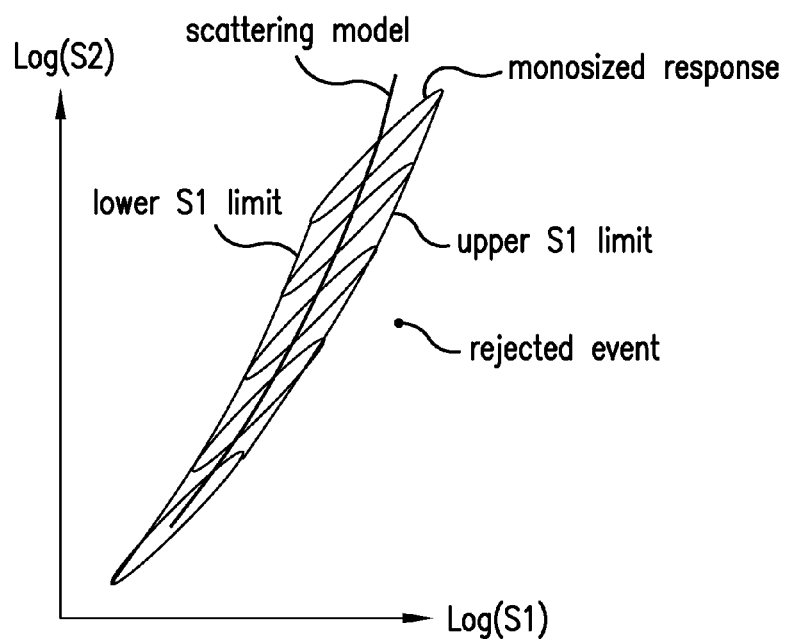
FIG. 27 shows details of the graph of FIG. 26, illustrating limits in the two dimensional space for separation of particles from non-particle events.
Figure 28:
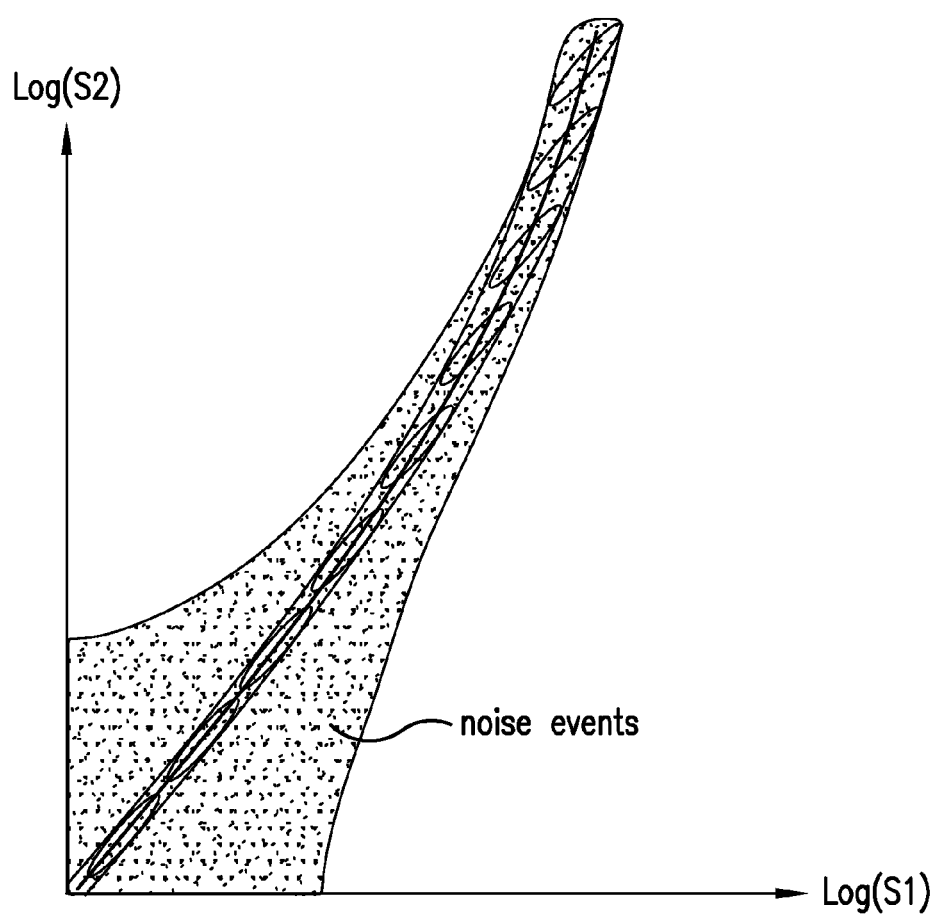
FIG. 28 provides a graph showing noise events which are rejected from the count distribution, according to the present invention.

A group of monosized particles will produce a differential count distribution in S1,S2 or Log(S1),Log(S2) space. In each case, a differential count distribution from a polysized sample will be the sum of the monosized distributions, each weighted by the percentage of particles of that size in the total distribution. Hence the particle number-vs.-size distribution can be determined by inverting this total differential count distribution, as a function of S1 and S2, or Log(S1) and Log(S2), using deconvolution algorithms which may include those already developed for image restoration or image deblurring. Examples of these 2-dimensional deconvolution algorithms are Wiener filter and Lucy-Richardson algorithm. In Log(S1),Log(S2) space the monosized response functions will be similar in shape over a large size range, because the functions are approximately shift invariant to size over the Log(S1),Log(S2) space. In this logarithmic space, deconvolution can be used to invert the count distribution in either one or more dimensions. The signal pulse from each event may pass through an analysis or sorting as described before, to sharpen the monosized response for higher size resolution. These pre-processed pulses are counted vs. a parameter (S1, S2, etc) such as peak value, total area, total correlated signal, etc., using the methods outlined previously. Each counted event is placed into the S1,S2 or Log(S1),Log(S2) space, where S1 and S2 may be the pulse peak value, pulse area, or any of the other size related parameters which can be calculated from the scattering signals. Then this space is broken up into very small regions, and the events in each region are summed to give sampled values of the differential count-vs.-parameter distribution (the 2-dimensional Cg is an example of this distribution) in the 2 dimensional space. The known monosized response (in the 2 dimensional space), which may be size dependent, is used to invert this differential distribution to produce the particle number vs. size distribution. This monosized response may be calculated from scattering theory and the optical design parameters, or it may be measured empirically by recording the differential event count distribution in the space from monosized particle groups of known sizes. The known monosized response defines a region in the space, where scattering from single particles can produce counts as shown in FIG. 27. Events which are outside of this region, can be rejected as non-particle events (i.e. non-single particle events or noise), which may be due to multiple particles in the interaction volume or noise. This is particularly important for small sized particles with low scattering signals, where detection noise can cause many non-particle counted events as shown in FIG. 28. These noise events can also be included into the monosized response functions. For example, when a group of monosized particles are measured to produce an empirical monosized response function, many noise events will be measured. These noise events can be included in the monosized response function so that they are removed as part of the inversion process, when that function is used as one of response set in the inversion algorithm. The complete monosized response function set can be generated from scattering data from only a few well chosen monosized particle groups. The intervening response functions are interpolated from the trend of the theoretical scattering/optical system model. The empirical data from monosized samples may only be needed to locate the theoretical model in the space. The power of this process is that both the absolute signal data, which is needed to size particles in the Rayleigh scattering regime, and the scattering signal ratio information are combined into one space, where non-particle events are easily identified. This process can be applied to data taken in any number of dimensions, from one scattering angle to any number of scattering angles. Also any dimension of this process can be represented by a scattering signal related parameter (peak, integral, etc.) or combination of scattering signals (ratio of S2/S1, correlation between S2 and S1, etc.). Higher number of dimensions provides better discrimination against non-particle events, but with added cost of more detectors and computer processing time. For example, more than two detectors could be placed behind each of slit 114 or slit 115 (aperture 1 or aperture 2), in the previous figures, to provide additional dimensions to the problem. For 3 detectors you could plot each event on the S3/S1, S2/S1 plane. Then the effects of source spot intensity variations would be reduced and the impulse responses (the ellipses shown previously) would become very localized, perhaps eliminating the need for deconvolution. All four detectors from these figures (detectors 110, 111, 112, 113) could also be combined into one four dimensional space as described in this section or into two 2-dimensional spaces, which are first solved separately and then the results are combined into one final size distribution by blending methods described previously.

If all of the particles in a particular sample are in a size region where the signal ratio is not sensitive to particle size, such as the Rayleigh size regime, the scattering model could be determined empirically from dynamic scattering measurements. If the particle flow is stopped, the heterodyning detection system can measure the Doppler spectral broadening due to Brownian motion (dynamic light scattering). The particle size distribution from this measurement may be used directly, or the optical scattering model may be determined from the dynamic scattering size distribution and the static angular scattering to invert the absolute scattering signal amplitudes from the count-vs.-scattering signal distribution. In this way, the low size resolution distribution from dynamic light scattering will provide scattering model selection for the higher size resolution counting method. This technique can be used over the entire size range of the dynamic light scattering to select the scattering model for counting particles inside or outside of the size range of dynamic light scattering. The scattering model may also be determined by inverting the count distribution in S1,S2 or Log(S1),Log(S2) space. This inversion will create a line function in the space. The shape of this line function in the size transition from Rayleigh scattering (where the ratio between S1 and S2 is constant) to larger particles will indicate the scattering model and refractive index of the particles.

Figure 27A:
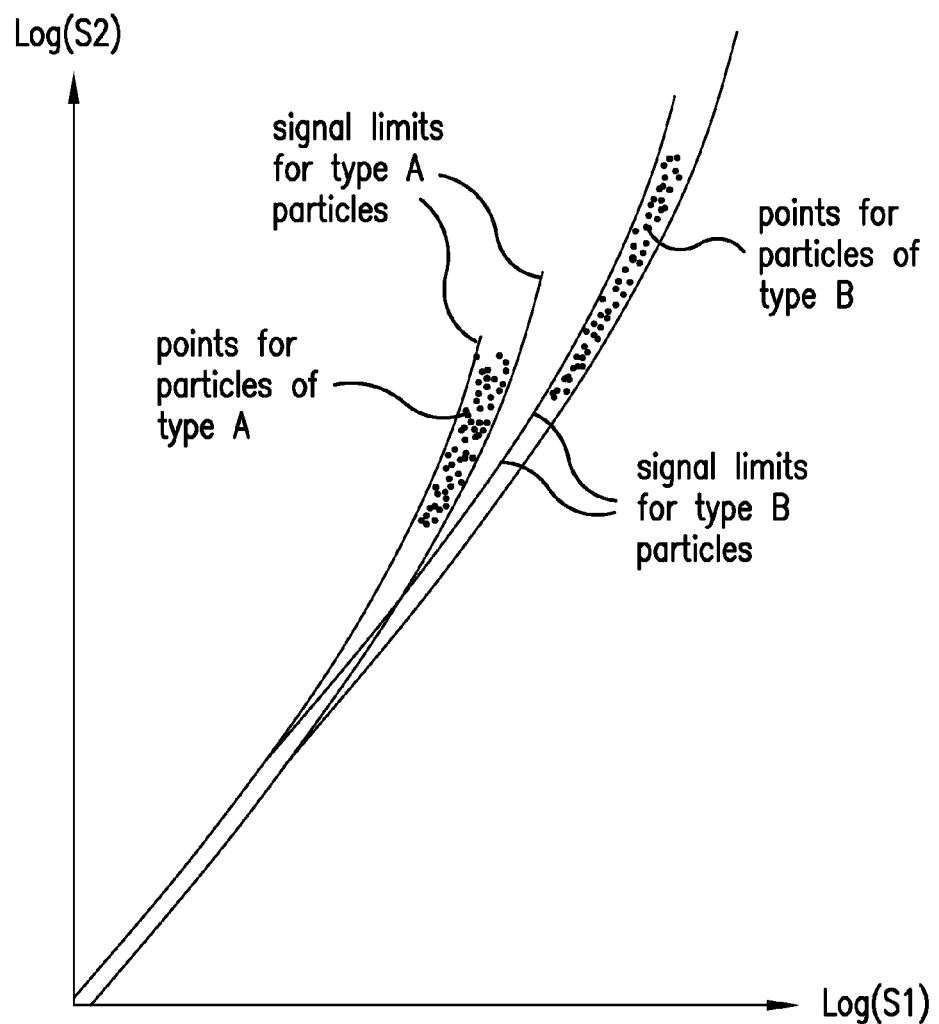
FIG. 27a provides a graph showing the scatter signal responses in two dimensions for particles of two different types, according to the present invention.

This multi-parameter analysis also provides for separation of mixtures of particles of different compositions such as polymer particles mixed with metal particles or polymer particles mixed with air bubbles. Hence, the count of air bubbles could be eliminated from the count distribution. FIG. 27a shows the methodology. Particles of different composition will have different response profiles in the multi-dimensional space. And the count events will be grouped to follow different profiles for each particle composition. So the data points (events) for particles of different composition will occupy different response profiles as shown in FIG. 27a. Individual particle size distributions and particle concentrations, for each particle type, could be determined from analysis of this data using the techniques described in this disclosure, individually for each response profile. Hence, a different particle refractive index and optical scattering model would be determined and used to calculate the size distributions for particles in each composition group, separately. Particle counts due to air bubbles could be eliminated through this process. These techniques could also be extended to larger numbers of dimensions by measuring more signals.

This process could also be used by replacing signals, in these multiple parameter plots, with ratios of signals. Any of these multiple angle configurations may be extended to many more angles simply by adding more scatter detectors which view the same interaction volume. For example, consider 4 such detector signals, S1, S2, S3, S4. Each of these signals could be pulse peak, pulse area, or correlated peak, etc. The ratios S4/S1, S3/S1, and S2/S1 are plotted in 3-dimensional space, one point for each particle counted. These ratios could also be S4/S2, S3/S2, S2/S1, etc. The point here is that the Mie resonances cause the scattering signals at various angles to oscillate together vs. particle size. For any size range, there is always a region of scattering angles where the ratio of scatter from two different ranges of angle are nearly independent of Mie resonances and particle composition. The path of these ratios in 2-dimensional space (e.g. S3/S1,S2/S1) or 3-dimensional space (e.g. S4/S1,S3/S1,S2/S1), are only weakly dependent on particle composition. The strongest particle composition dependence is for spherical particles in the size region of the Mie resonances. When thousands of particles are measured, their points will follow a multi-dimensional curve or line, in this multi-dimensional space, which indicates the sphericity or composition of the particles. This multi-dimensional line is formed by the highest concentration of points in this multidimensional space. Only points which are within a certain distance of this line are accepted as true particles. The outliers represent particles which passed through the edge of the source beam or whose signals are contaminated by noise. Also non-single particle events, such as noise pulses or multiple particles, would also be rejected because their combination of coordinates in this space would not agree with the possible coordinates of a particle. The signal ratios could also be replaced by the signal values to take advantage of absolute signal information, which is particularly advantageous in the Rayleigh region where signal ratios are weakly dependent on particle size, but absolute signal levels are strongly dependent on particle size. For particles of size above the Rayleigh region, the signal ratios may be preferred because the spread of particle events around the multi-dimensional line is very small for signal ratios which remove the dependence upon the particle position in the beam, removing a portion of the monosized response broadening shown in FIGS. 27 and 28. Both of the techniques, described here and in the description of FIGS. 27 and 28, will be needed to cover the entire size range, because the signal ratios are not strongly size dependent in the Rayleigh region (for particles below 0.1 micron in visible light). Another option would be to use a multi-dimensional space where some dimensions were signal ratios and other dimensions where absolute signals (for example see FIG. 39). Then the monosized response would only be strongly broadened in the absolute signal dimensions. For small particles, the absolute signal dimension would be processed with deconvolution and noise event rejection as shown in FIGS. 27 and 28; and for larger particles, signal ratio dimensions would be used to determine size with outlier rejection and minimal deconvolution. The entire path of the line constructed by the particle events determines the optical scattering model. This is particularly important for the Rayleigh region where the particle refractive index must be determined to calculate the dependence of absolute scattering amplitude on particle size. In any case, there will be a line or curve, in multi-dimensional space, which follows the path defined by the highest concentration of counted events. This line will define the optical scattering model and the particle shape or composition, if the user cannot provide that information. Size accuracy may be improved by using any apriori information about the particles to determine the scattering model from theoretical models. For example, the path of the multi-dimensional line could be calculated from scattering theory, given the particle refractive index and shape, but sometimes this information is not well known. If the particle composition or shape is unknown, then this empirically determined line in multidimensional space is compared to the theoretical lines for particles of various compositions and shapes. The theoretical line, which most closely matches the measured line from the unknown particle dispersion, is assumed to represent the composition and shape of the unknown particles.

The accuracy of the process described above improves as more scattering angles are measured. For example, the measured values of the scattered light for each of three scattering angles could be measured for each particle. These data points are then analyzed in a three dimensional scatter or dot plot. A line could be generated in 3 dimensional space by determining the path where the maximum concentration of particles (or dots in the plot) reside. In any one axis, this line may be multi-valued vs. particle diameter, especially in the region of Mie resonances. However, the line will not be multi-valued in 3 dimensional space. The spread of points about this line will be determined by the intensity distribution of the source beam in the interaction region. This group of points could be deconvolved in 3 dimensional space to produce a more sharply defined set of points, with less spread from the line, providing better size resolution along the line. But a better solution is to measure 4 scattering values at 4 different scattering angles for each particle. And then take ratio of each of any 3 values with the fourth value (or any other value) to remove the effect of intensity variation for particles which pass through different portions of the beam. Produce a scatter plot of these 3 ratios in three dimensions, where each point in 3 dimensional space is placed in Xm, Ym, and Zm values corresponding to the three ratios for each particle. Since the intensity distribution broadening is reduced, most of the points will tightly follow a line in three dimensional space. Outliers which are not close to the line passing through the highest concentration of data points may be eliminated as not being real single particles. The remaining data points (Xm,Ym,Zm) are then compared to different theoretical models to determine the composition and/or shape of the particles. The 3 dimensional function which describes the theoretical scattering is Zt where Zt is a function of Xt and Yt:

$$Zt=Zt(Xt,Yt)$$

Let (Xm,Ym,Zm) be the set of data points measured from the counted particles. Where the values in the X, Y, Z coordinates represent the absolute scattering signals S1, S2, S3, the logarithms of these signals, signal ratios S4/S1, S3/S1, S2/S1 (or any other combination of ratios), or any other signals or parameters mentioned in this application. Then define an error function Et for a certain theoretical model as:

$$Et(Xm,Ym)=(Yt(Xm)-Ym)^2 \text{ for } Xm \text{ in the region } Xmy$$
$$\text{where } Yt(Xm) \text{ is single-valued}$$

$$Et(Xm,Zm)=(Zt(Xm)-Zm)^2 \text{ for } Xm \text{ in the region } Zmy$$
$$\text{where } Zt(Xm) \text{ is single-valued}$$

Where Yt(Xm) is the theoretical value of Yt at Xm and Zt(Xm) is the theoretical value of Zt at Xm. Then find the theoretical model which produces the minimum sum of Esum over all values of Xm in the data set.

$$E\text{sum}=\text{SUM}(Et(Xm,Ym))/Ny+\text{SUM}(Et(Xm,Zm))/Nz$$

Where Ny is the number of points in region Xmy and Nz is the number of points in Xmz. And SUM is the sum of Et over its valid region of Xmy or Zmy. Esum is calculated for various theoretical scattering models, for spherical and non-spherical particles, and the model with the lowest Esum is chosen as the model for the sample. The sum of Esum values from multiple particle samples can also be compared for different theoretical models. The model with the lowest sum of Esum values is used to analyze all of those samples of that type. This calculation may be computationally intensive, but it only needs to be done once for each type of sample. Once the optimal theoretical model is determined for each particle sample type, the appropriate stored model can be retrieved whenever that sample type is measured. The chosen theoretical model will provide the particle diameter as a function of Xm, Ym, and Zm for each detected object.

Signal ratios show reduced sensitivity to the position of the particle in the source beam because each scattering signal is proportional to the optical irradiance on the particle. Usually to obtain optimal signal to noise, a laser source will be used to provide high irradiance but with lower irradiance uniformity due to the Gaussian intensity profile. The broadening in the monosized response, as shown in FIGS. 27 and 28 for example, may be reduced by insuring that only particles which pass near to the peak of the beam intensity profile are counted. Many methods have been described above to accomplish this selection process. Other methods could include the use of small capillaries or sheath flow to force all of the particles to go through the center of the source beam. But these methods are sometimes prone to particle clogging. In sheath flow, the particle dispersion is restricted to flow through a narrow jet, which is surrounded by a flow sheath of clean dispersant. If the particle concentration is low, the particles in this narrow stream will pass through the laser in single file and in locations close to the center of the beam. This method could be used with the ideas in this disclosure to restrict the path of the particles through the source beam and provide a single size response with less broadening. But the wide range of particle sizes would require many different sized jets to handle the entire size range with the constant danger of clogging. The methods described in this disclosure can be used within a flow system of much larger dimensions, because the optical system only views and counts particles within a small interaction volume of that much larger volume. Particles which pass through that volume and which are outside of the size range for that measurement system will produce data points in the multidimensional space which are far from the multi-dimensional line of the optical model. They may be rejected based upon this criteria or simply based upon the length of the scattering pulse. The small particles are counted and sized by the higher angle system. The larger particles are sized by the 2-dimensional array or lower angle scattering systems. These independent particle size distributions are then combined to produce one size distribution over the full size range of the instrument.

Figure 29:
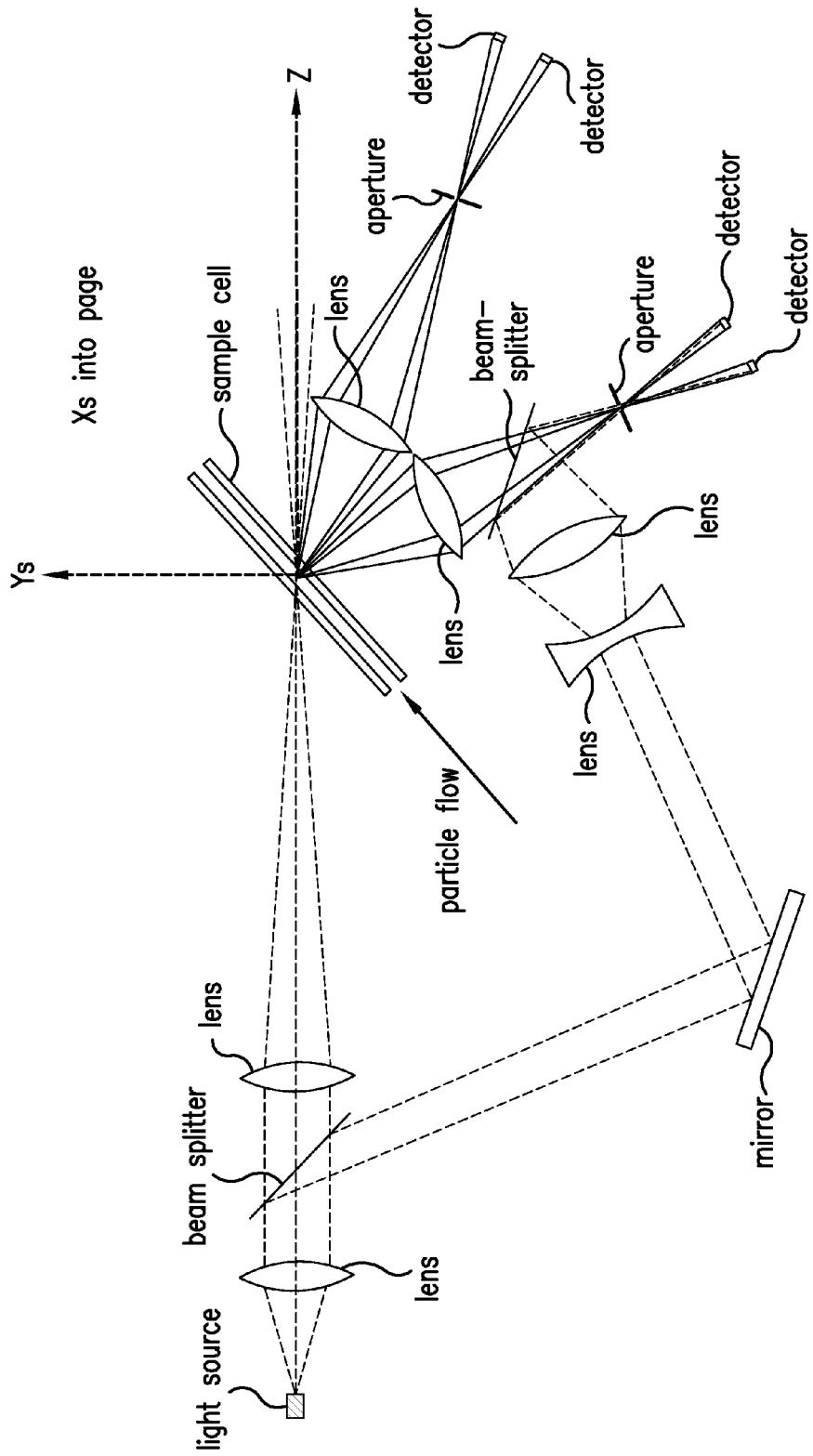
FIG. 29 provides a schematic diagram of an optical system, used in the present invention, the system measuring scattered light in each of two scattering planes, the diagram showing the optics of one scattering plane.
Figure 30:
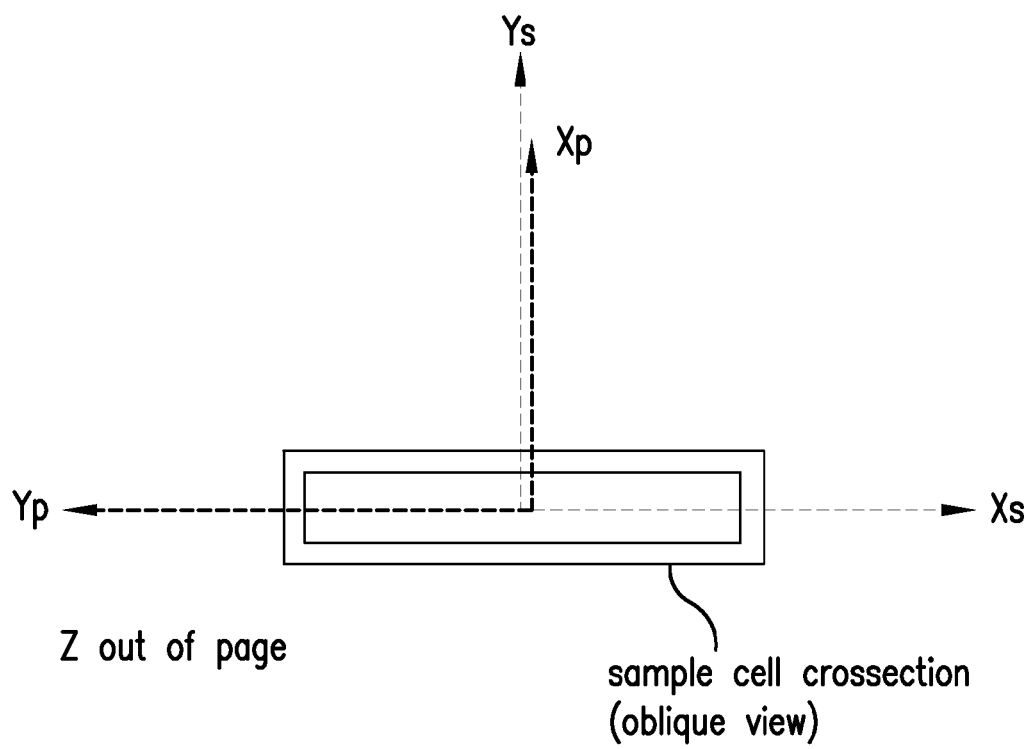
FIG. 30 provides a diagram showing the orientation of the two scattering planes for the system shown in FIG. 29.
Figure 31:
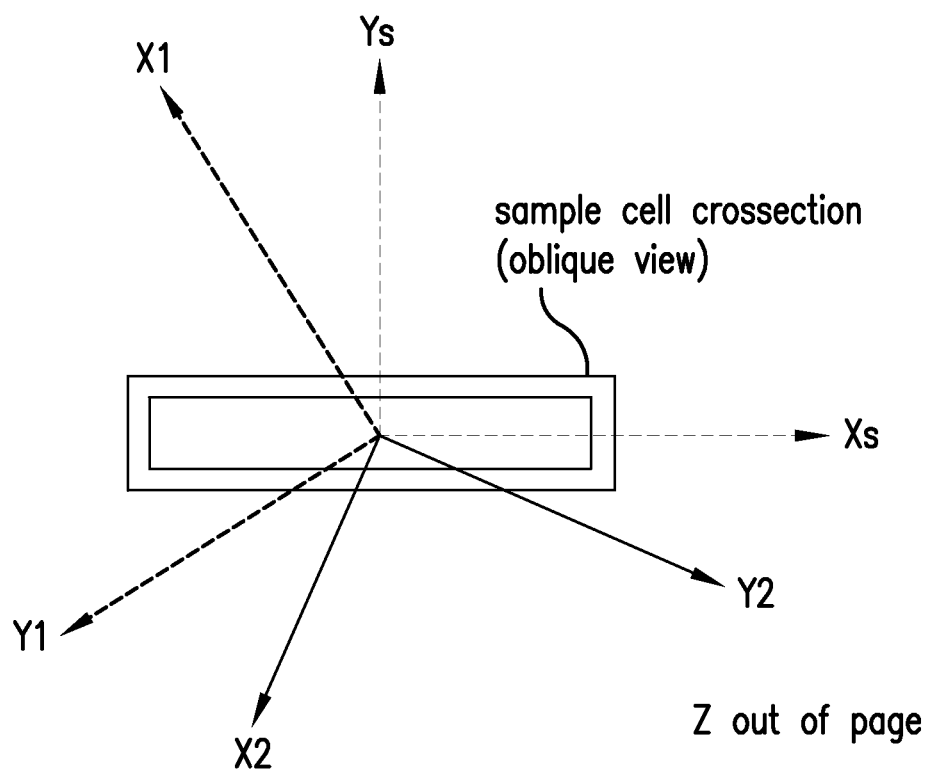
FIG. 31 provides a diagram showing the scattering plane orientations for an optical system, similar to that shown in FIG. 29, with three scattering planes.

The measurement of particle shape has become more important in many processes. Usually the shape can be described by length and width dimensions of the particle. If the length and width of each particle were measured, a scatter plot of the counted particles may be plotted on the length and width space to provide useful information to particle manufacturers and users, and this type scatter plot is claimed in this invention. If the particles are oriented in a flow stream, the angular scattering could be measured in two nearly orthogonal scattering planes, one parallel and one perpendicular to the flow direction. Each of these scatter detection systems would measure the corresponding dimension of the particle in the scattering plane for that detection system. If the flow of particle dispersion flows through a restriction, so as to create an accelerating flow field, elongated particles will orient themselves in the flow direction. FIG. 29 shows one of these scatter detection systems where the scattering plane is parallel to Ys and measures the projected particle dimension in the Ys direction, which is parallel to the projection of the flow direction of the particles in the Ys/Xs plane. A second scattering detection system could be placed in a scattering plane which includes the Z axis and Yp as shown in FIG. 30. This detection system would measure the particle dimension in the plane perpendicular to the flow. Each particle is counted with two dimensions, one parallel to and the other perpendicular to the flow, as measured concurrently by these two detection systems. In some cases, the particles cannot be oriented in the flow and they pass through the beam in random orientations. The detection configuration in FIG. 31 shows three scattering systems. Each system is in a scattering plane which is approximately 120 degrees from the next one. If the particle shapes are assumed to be of a certain type with two dimension parameters such as: rectangular, ellipsoid, etc., three size measurements in various scattering planes can be used to solve for the length, width, (or major and minor axis, etc.) and orientation of each particle. These planes can be separated by any angles, but 120 degrees would be optimal to properly condition the 3 simultaneous equations formed from these three size measurements.

Figure 32:
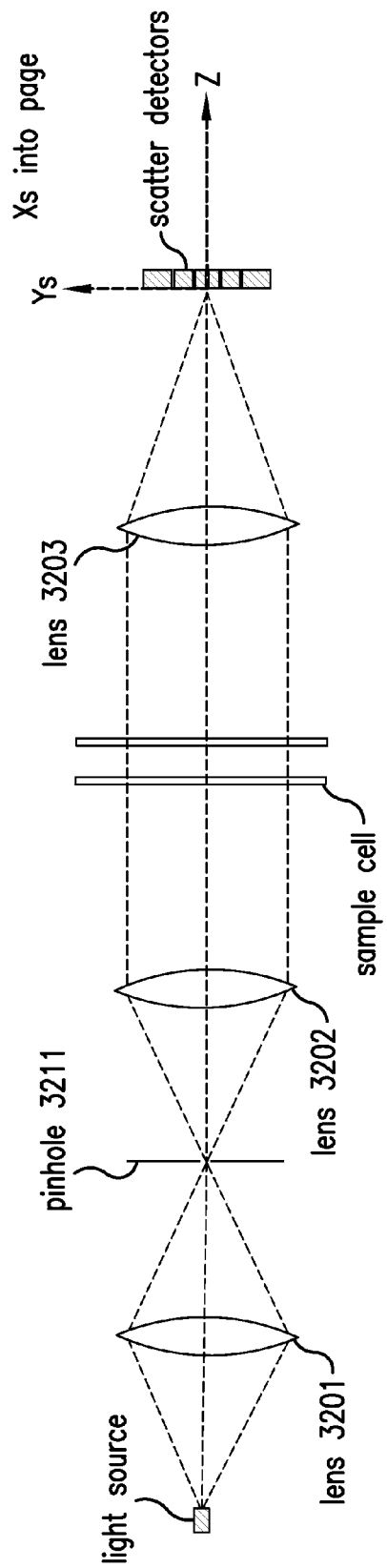
FIG. 32 provides a schematic diagram of an optical system which measures scattered light in multiple scattering planes by utilizing multiple detector elements, according to the present invention.
Figure 33:
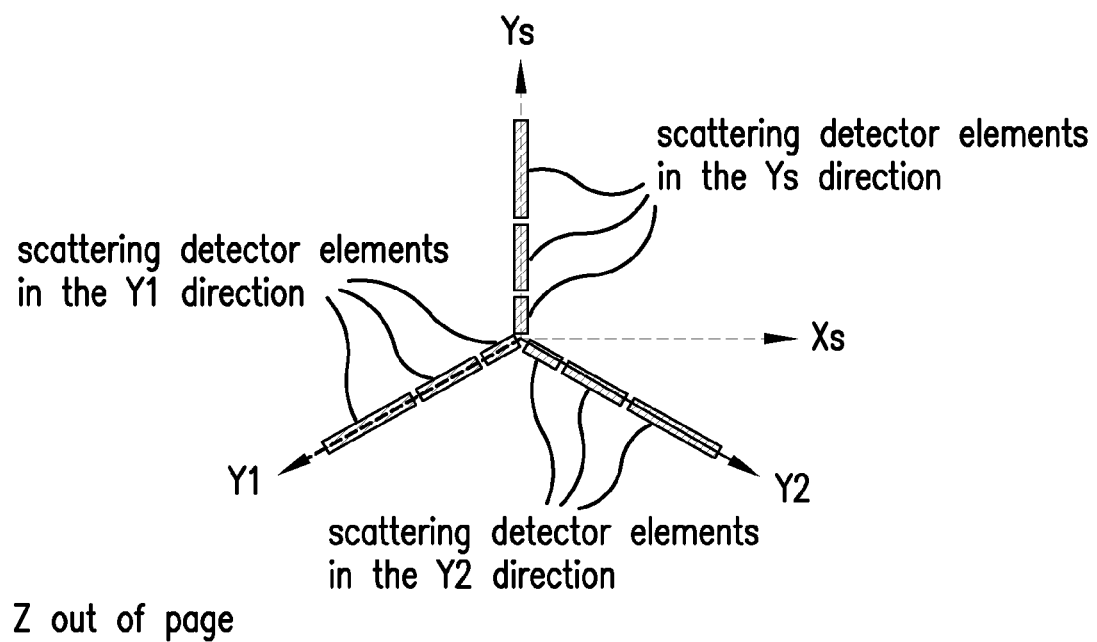
FIG. 33 provides a diagram showing an example of detector element structure for the system of FIG. 32.
Figure 34:
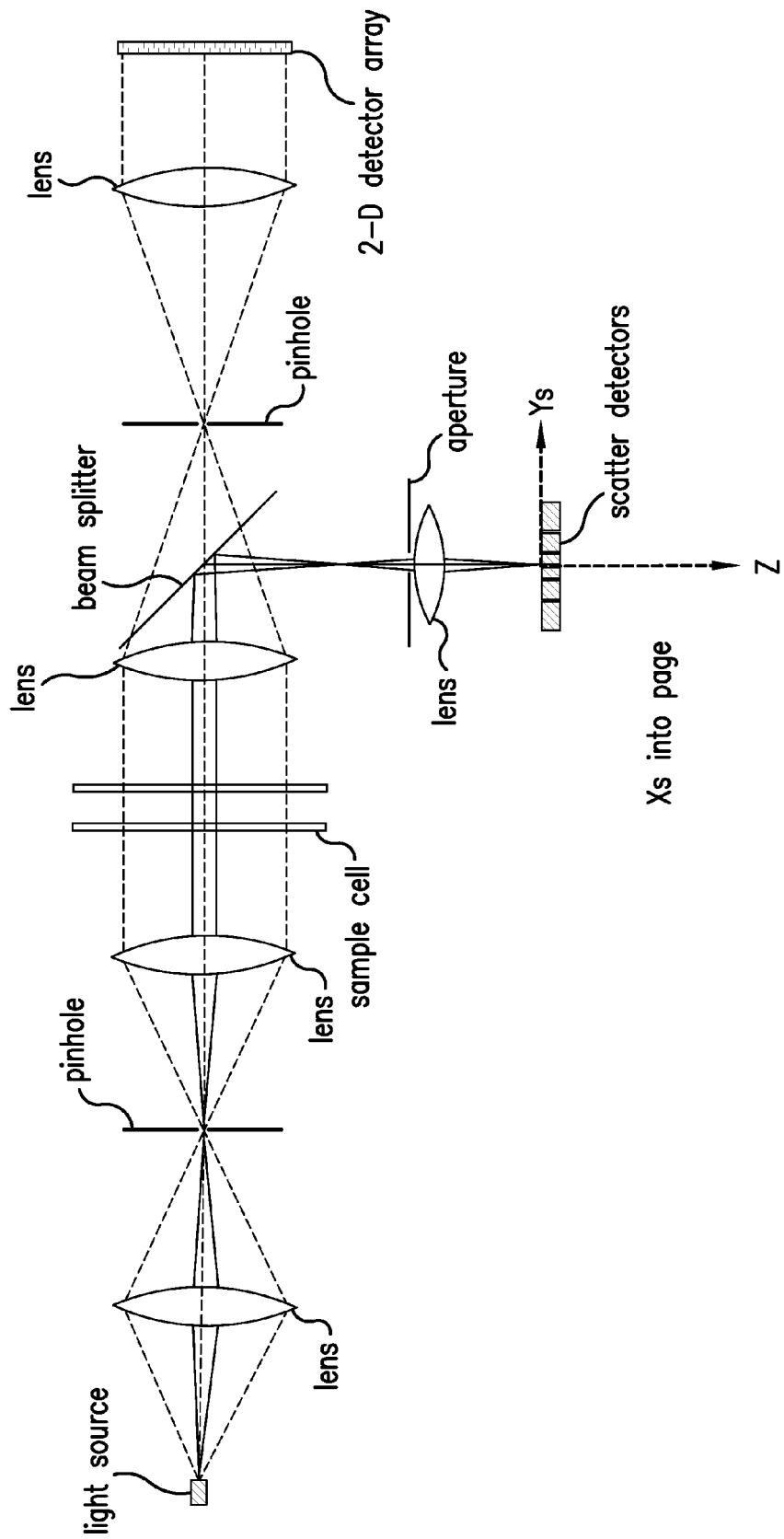
FIG. 34 provides a schematic diagram of a combination of the multiple-element detector systems, such as shown in FIG. 32 or FIG. 33, with the optical system of FIG. 11.

When measuring larger particles, which require smaller scattering angles, the scatter collection lens may be centered on the Z axis, with scattering detectors in the back focal plane of the collection lens, as shown in FIG. 32. As shown before, lens 3201, pinhole 3211, and lens 3202 are not needed if a spatially clean collimated beam, such as a clean laser beam, is incident on the particle dispersion in the sample cell. Lens 3203 collects scattered light from the particles and focuses it onto a group of detectors in the back focal plane. As before, the length and width of each randomly oriented particle is determined by 3 independent size measurements or, in the case where the size measurements are not independent, you must solve a set of simultaneous equations as described below. If the particles are oriented in the flow, only the Ys direction (parallel to the flow) and a set of detectors in the direction perpendicular to Ys are needed. As before, these two directions can be at any angle, but parallel and perpendicular to the flow are optimal. In the random orientation case, each measurement is made by a separate arm of the detector set in the three directions Ys, Y1, and Y2. These directions can be separated by any angles, but 120 degrees (see FIG. 33) would be optimal to properly condition the 3 simultaneous equations formed from these three size measurements. The scatter detector signals in each direction (or scattering plane) are combined by ratio of signals or other algorithms to determine the effective size in that direction. Then three simultaneous equations are formed from these size measurements to solve for the width, length, and orientation of each particle. FIG. 34 shows how this detector configuration is used in the system from FIG. 11. And as indicated above, the scatter in various scattering angular ranges can be measured each scattering plane by a separate optical system, as shown in FIG. 29 for example, in each scattering plane. The scattering plane is the plane which includes the center axis of the source beam and the center axes of the scattered light beams which are captured by the detectors.

The accuracy of the methods outlined above is improved by solving another type of problem. The sizes calculated from angular scattering data in each of two or more directions are not usually independent. In order to accurately determine the shape parameters of a particle, the simultaneous equations must be formed in all of the scattering signals. The form of the equations is shown below:

$$Si = Fi(W, L, O)$$

Where Si is the scattering signal from the ith detector. In the case of three directions (or scattering planes) and three detectors per direction, we have 9 total detectors and i=1, 2, . . . , 9)

W is the "width" parameter and L is the "length" parameter of the particle. In the case of a rectangular shape model, W is width and L is length. In the case of an ellipsoidal model, W is the minor axis and L is the major axis, etc. O is the orientation of the particle which could be the angle of the particle's major axis relative to Ys, for example. The functions Fi are calculated from non-spherical scattering algorithms and the form of Fi changes for different particle shapes (rectangles, ellipsoids, etc.). These equations, Si=Fi, form a set of simultaneous equations which are solved for W, L and O for each particle. If the Fi functions do not have a closed form, iterative methods may be employed where the Jacobian or Hessian are determined by numerical, rather than symbolic, derivatives. Also the closed form functions for Fi could be provided by fitting functions to Fi(W,L,O) calculated from the non-spherical scattering algorithms.

If we had two detection angles per each of three scattering planes, we would have 6 equations with 3 unknowns. With three detectors per scattering plane the size range may be extended and we will have 9 equations with 3 unknowns. For particles with more complicated shapes, such as polygonal, more scattering planes may be required to determine the particle shape parameters. In any case, a shape model is assumed for the particles and the set of equations Si=Fi are created for that model where Fi is a function of the unknown size parameters and Si is the scattered signal on detector i. This method can be applied to any of the shape measuring configurations shown before. This technique can also be applied to ensemble size measuring systems when the particles all have the same orientation as in accelerating flow. This invention claims scattering measurements from any number of angular ranges, in any number of scattering planes.

Figure 35:
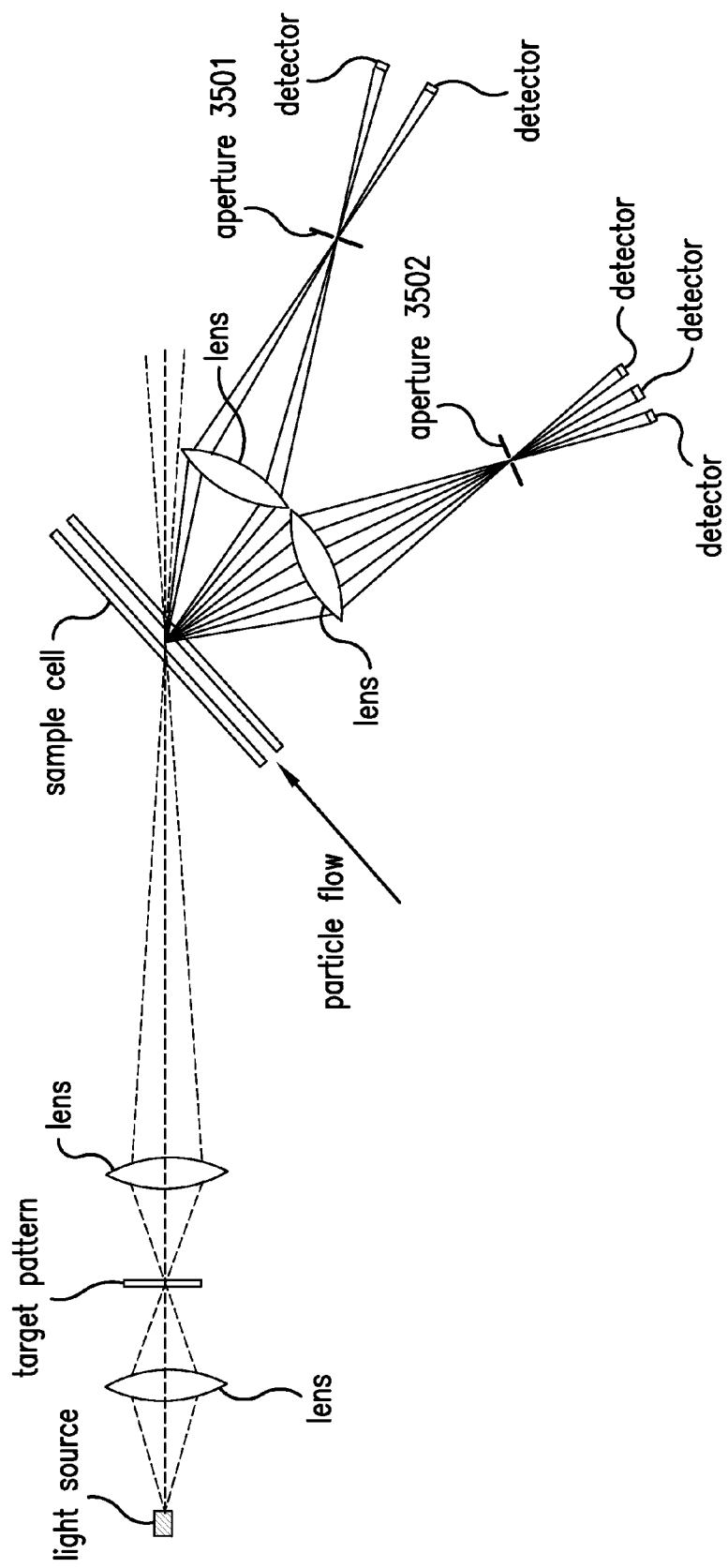
FIG. 35 provides a schematic diagram of a variation of the system shown in FIG. 1, where the signal oscillation is provided by a mask or target pattern, without interferometric mixing of source and scattered light.

Low scattering signals from small particles may be difficult to detect. FIG. 35 shows another variation where the source beam is passed through a patterned target which is conjugate to the interaction volume. The image of the target occurs in the interaction volume which is defined by aperture 3501 or aperture 3502. This target could consist of a sinusoidal transmission pattern or a Barker code pattern. As the particles pass through the image of this pattern, the scattered light is modulated by the modulated source intensity distribution in the interaction volume and so the scattered signal-vs.-time distribution is equivalent to the spatial intensity distribution. For a sinusoidal pattern, a phase sensitive detector with zero degree and quadrature outputs could be used to detect the sinusoidal signal of arbitrary phase. For a given particle velocity, the scattered signal could be filtered by a bandpass filter which is centered on the frequency equal to the particle velocity divided by the spatial wavelength of the sinusoidal intensity distribution in the interaction volume. The phase sensitive detector reference signal would also match this frequency. Better signal to noise may be achieved with other types of patterns. A Barker code target pattern will produce a single peak with very small side lobes when the scattering signal is correlated with a matching Barker code signal using a SAW or CCD correlator. When two scattering signals are multiplied and integrated, the zero delay (tau) value of the correlation function is obtained. This value will have the lowest fluctuation when the two signals have strong correlation as when both signals are from the same particle, instead of uncorrelated noise. The integrated product of the two signals will show less noise than the separated integrated signals. So the product of signals from two different angular ranges or the integral of this product over the particle pulse period will provide a signal parameter which is less sensitive to noise and which can be substituted for Si in any of the analyses described above. FIG. 35 also illustrates an additional scattering detector on aperture 3502 for detection of three scattering angles. This can also be extended to a larger number of detectors.

Figure 36:
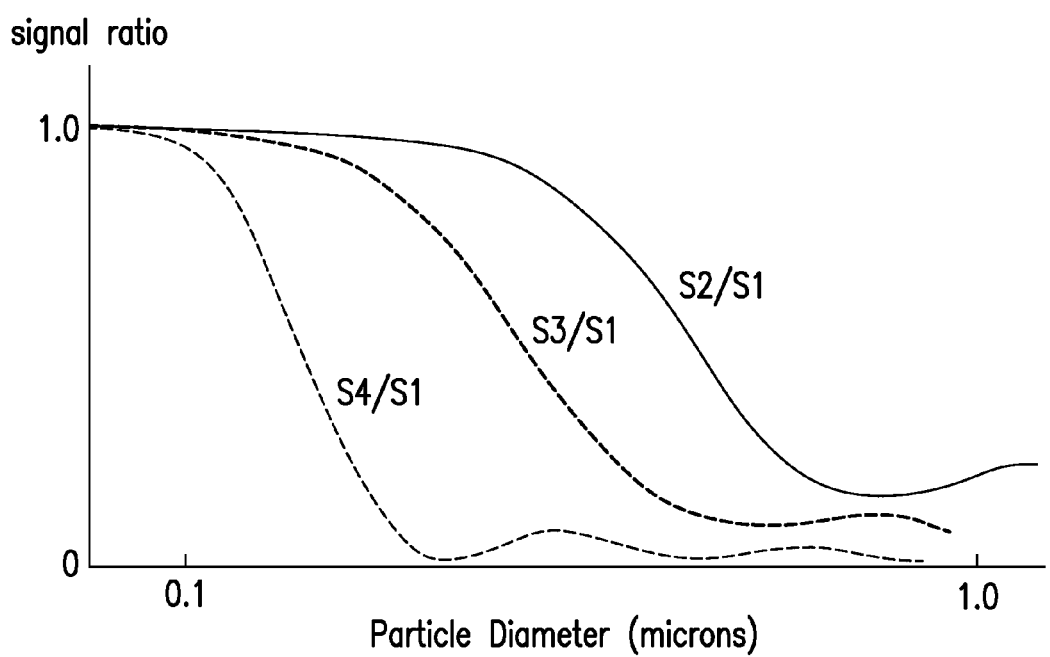
FIG. 36 provides a graph containing plots of examples of three ratios, between four scatter measurements, as a function of particle diameter, according to the present invention.

As shown before, ratios of scattering signals can be analyzed as a multi-dimensional function. Another method is to look at the individual signal ratios vs. particle diameter as shown in FIG. 36 for the case of three signal ratios. Any real particle event should produce a point on each curve which align vertically at the same diameter. Each curve indicates the particle size, but the most accurate size is determined from the curve where its point is in a region of high slope and monotonicity. For any particle, the 3 measured ratios would determine the approximate particle size region and allow selection of the one ratio which is in the region of highest slope vs. particle size and is also not in a multi-valued region (caused by Mie resonances). This selected ratio would then be used to determine the precise particle size for that particle.

Figure 37:
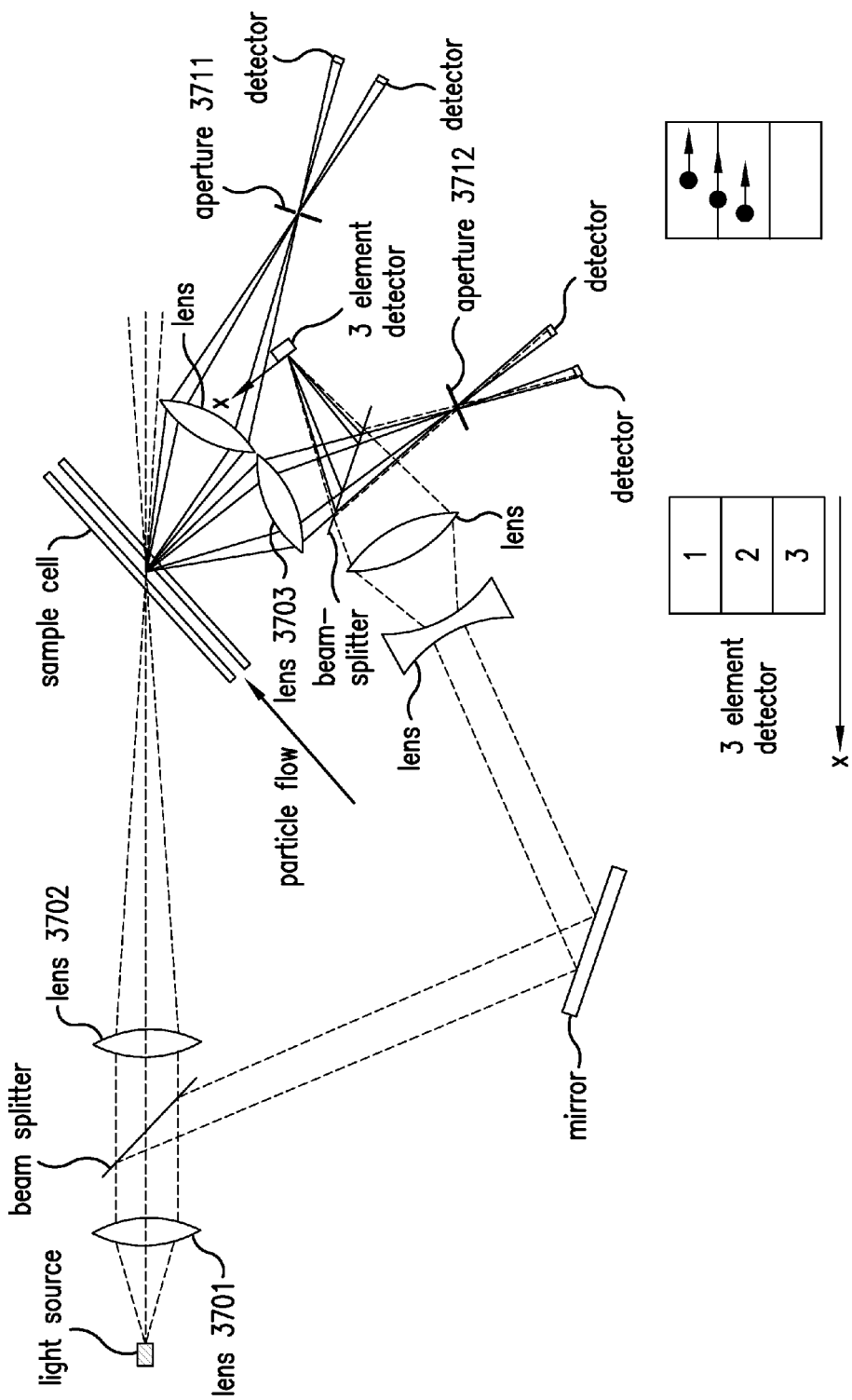
FIG. 37 provides a schematic diagram of an optical system which determines the position where the particle passes through the light beam, according to the present invention.

The ratio of scattering signals from different scattering angles reduces the dependence of the particle size determination on the particle path through the light beam. Particles with signals below some threshold are eliminated from the count to prevent counting objects with low signal to noise. The accuracy of counts in each size bin will depend upon how uniform this elimination criteria is over the entire size range. Many methods have been described in this application for reducing this problem. These methods are improved by having a source beam with a "flat top" intensity distribution and very sharply defined edges. This flat top intensity distribution can be provided by placing an aperture in an optical plane which is conjugate to the interaction volume or by using diffractive optic or absorption mask beam shapers. Another technique which will accurately define an interaction volume is shown in FIG. 37. No selection criteria is required for the direction which is parallel to the particle flow direction, because in this direction each particle passes through a similar intensity distribution and digitized signal values may be analyzed to find maximum or the integral for each particle signal. The primary criteria for eliminating particles from the count is based upon the position of the particle along the axis which is perpendicular to particle flow direction. The position of the particle along the direction perpendicular to the particle flow and the scattering plane (y direction) can be determined by using a 3 element detector which is in an optical plane which is conjugate to the interaction volume as shown in FIG. 37. This figure shows the position and orientation of the 3 element detector in the optical system and an enlarged view of the detector elements showing the path of various particles passing through the interaction volume as seen by the detector elements. The beamsplitter, following lens 3703, splits off some scattered light to the 3 element detector. By measuring the signal ratio between elements 1 and 2 and the ratio between elements 3 and 2, the y position of the each particle is determined and only particles within a certain y distance from the center of the light beam are accepted. If both ratios are equal, the particle is in the center of the 3 detector array. If one ratio is higher than the other, the particle is shifted closer to element whose signal is in the numerator of that higher ratio. This signal ratio criteria is extremely accurate and uniform among all particle sizes so that proper mass balance is maintained over the entire size range. The ratio is also insensitive to how well the particle is optically resolved because the fraction the particle image on each the two detectors spanning the image is not strongly dependent on the size or sharpness of the image, but is strongly dependent on the y position of the particle. FIG. 37 shows the 3 element detector in a heterodyne arrangement, with a portion of the source light being mixed with the scattered light. However, this idea is also applicable to non-heterodyne configurations by just removing the beamsplitter between lens 3701 and lens 3702. And this method can also be applied to any other scatter detection system in this application by placing this three element detector in an image plane of the particles, through a beamsplitter. The orientation of the 3 element array relative to particle motion is shown in FIG. 37.

Figure 38:
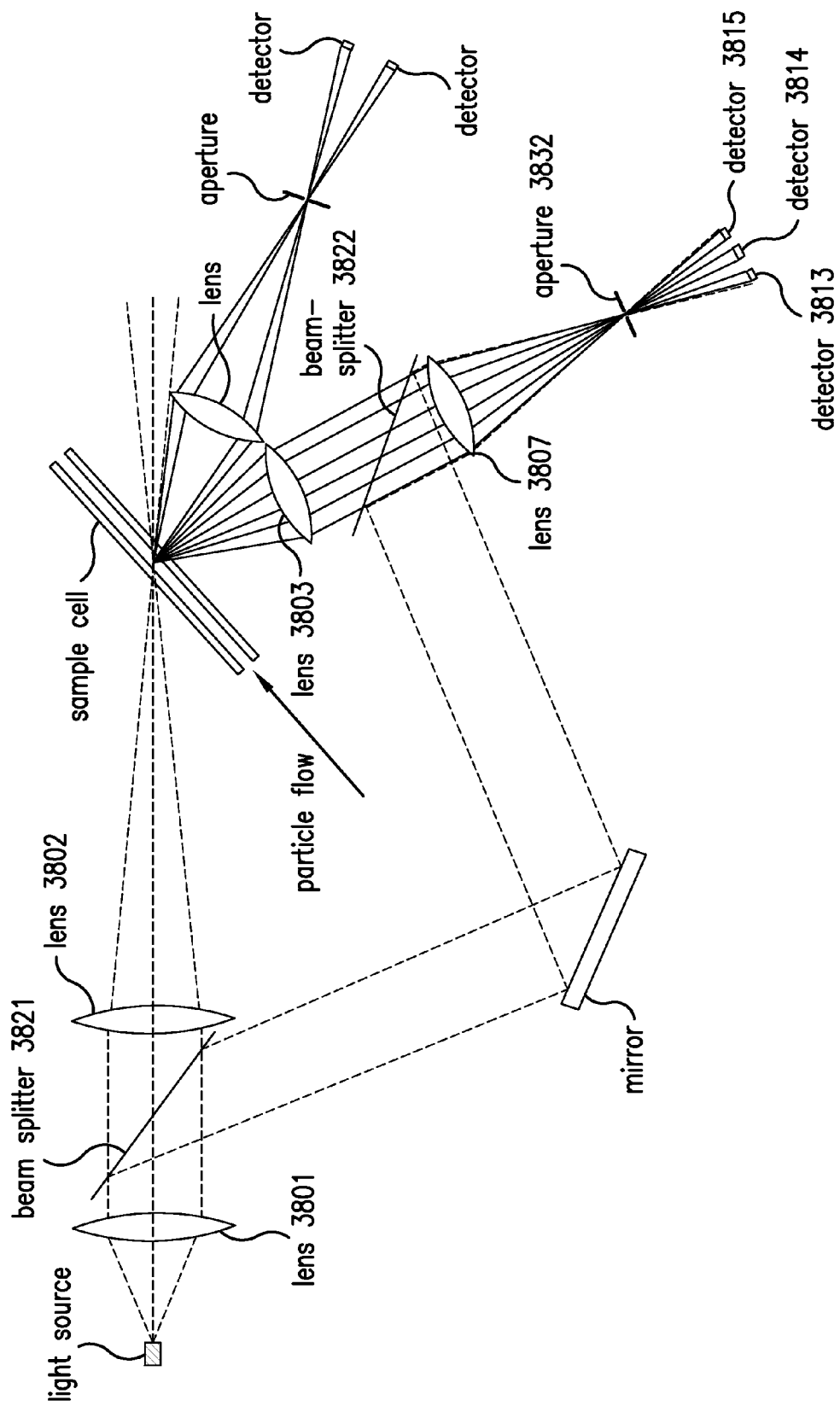
FIG. 38 provides a schematic diagram of an alternative to FIG. 1, where all beams are nearly collimated in the regions of the beamsplitters.

Many figures (FIG. 19 for example) show the heterodyne system with a negative and positive lens pair (lenses 1905 and 1906) which provide a local oscillator beam which matches the wavefront of scattered light from the particles. FIG. 38 shows an alternative design where all beams are nearly collimated in the regions of the beamsplitters. This configuration may be easier to align and focus. Lens 3801 collimates the source light which is sampled by beamsplitter 3821 and directed to beamsplitter 3822 by the mirror. Lens 3803 collimates the light scattered by the particle and this light is combined with the source light by beamsplitter 3822 and focused through aperture 3832 by lens 3807. As before, aperture 3832 is conjugate to the particle interaction volume and defines the interaction volume, in the sample cell, which is viewed by the detectors 3813, 3814 and 3815. Usually, the focal length of lens 3802 is long to provide a source beam of low divergence and the focal length of lens 3803 is short to span a large range of scattering angles. If the light source is a laser diode, without anamorphic optics, the major axis of the intensity distribution ellipse at the interaction volume should be in the plane of the particle flow and scattering plane to provide a long train of heterodyne oscillations for signal detection and to provide the lowest beam divergence in the scattering plane. A circular source beam may require anamorphic optics to create an elliptical beam in the interaction volume to provide the advantages mentioned above. However, the advantages of the ideas described in this disclosure can be applied to a source beam with any intensity distribution.

The matching of light wavefronts between the source beam and scattered light at the heterodyne detectors is important to maintain optimum interferometric visibility and maximum modulation of the heterodyne signal on each detector. Since perfect wavefront matching is not achievable, the interferometric visibility must be determined for each detector to correct the signals for deviation from theoretical heterodyne modulation amplitude. The visibility is determined by measuring particles of known size and comparing the heterodyne signals to the signals expected from theory. To first order, the interferometric visibility should be independent of particle size for particles much smaller than the source beam in the interaction volume. The visibility could be measured for particles of various sizes to measure any second order effects which would create visibility dependence on particle size. If only signal ratios are used for determining size determination, only the ratios of interferometric visibility need to be calibrated by measuring scattering from particles of known size.

The number of cycles in the heterodyne modulated pulse is determined by the length of the trajectory of the particle through the source beam. The frequency of the heterodyne modulation is determined by the velocity of the particle through the beam. In general the power spectrum of the signal will consist of the spectrum of the pulse (which may be 10 KHz wide) centered on the heterodyne frequency (which may be 1 MHz). Both of these frequencies are proportional to the particle velocity. Actually the best frequency region for the signal will be determined by the power spectral density of the detector system noise and/or the gain-bandwidth product of the detector electronics. For this reason, in some cases the particle flow velocity should be lowered to shift the signal spectrum to lower frequencies. The particle concentration is then adjusted to minimize the time required to count a sufficient number of particles to reduce Poisson statistic errors. This is easily accomplished for small particles which usually have higher count per unit volume and require lower noise to maintain high signal to noise.

In cases where optical heterodyne detection is not used, the signal to noise may be improved by phase sensitive detection of the scattered light. Modulation of the optical source may provide for phase sensitive detection of the scattering signal. The source is modulated at a frequency which is much larger than the bandwidth of the signal. For example, consider a source modulated at 1 megahertz with a scattering pulse length of 0.1 millisecond. Then the Fourier spectrum of scattered signal pulse would cover a region of approximately 10 KHz width centered at 1 megahertz. If this signal is multiplied by the source drive signal at 1 megahertz, the product of these two signals will contain a high frequency component at approximately 2 megahertz and a difference frequency component which spans 0 to approximately 10 KHz. In order to eliminate the most noise but preserve the signal, this product signal could be filtered to transmit only the frequencies contained in the scattering pulse, without modulation (perhaps between 5000 and 15000 Hz). This filtered signal product will have higher signal to noise than the raw signal of scattered pulses. This signal product can be provided by an analog multiplier or by digital multiplication after both of these signals (the scattering signal and the source drive signal) are digitized. This product is more easily realized with a photon multiplier tube (PMT) whose gain can be modulated by modulating the anode voltage of the PMT. Since the PMT gain is a nonlinear function of the anode voltage, an arbitrary function generator may be used to create PMT gain modulation which follows the modulation of the source. The voltage amplitude will be a nonlinear function of the source modulation amplitude, such that the gain modulation amplitude is a linear function of the source modulation amplitude. An arbitrary function generator can generate such a nonlinear modulation which is phase locked to the source modulator.

As described at the beginning of this disclosure, multiple sized beams can also be used to control the effects of seeing more than one particle in the viewing volume at one time. The key is to choose the proper scattering configuration to provide a very strong decrease of scattering signal with decreasing particle size. Then the scattering signals from smaller particles do not affect the pulses from larger ones, because the smaller particle signals are much smaller than those from the larger particles. For example, by measuring scattered light at very small scattering angles, the scattered light will drop off as the fourth power of the diameter in the Fraunhofer regime and as the sixth power of diameter in the Rayleigh regime. In addition, for typically uniform particle volume vs. size distributions, there are many more smaller particles than larger ones. The Poisson statistics of the counting process will reduce the signal fluctuations for the smaller particles because individual particles pulses will overlap each other producing a uniform baseline for the larger particles which pass through as individual pulses. This baseline can be subtracted from the larger particle pulse signals to produce accurate large particle pulses. This method can be used in many of the systems in this application, where a large increase in scatter signal level occurs between large and small particles. One example of this method is shown by the optical configuration in FIG. 41.

Figure 41:
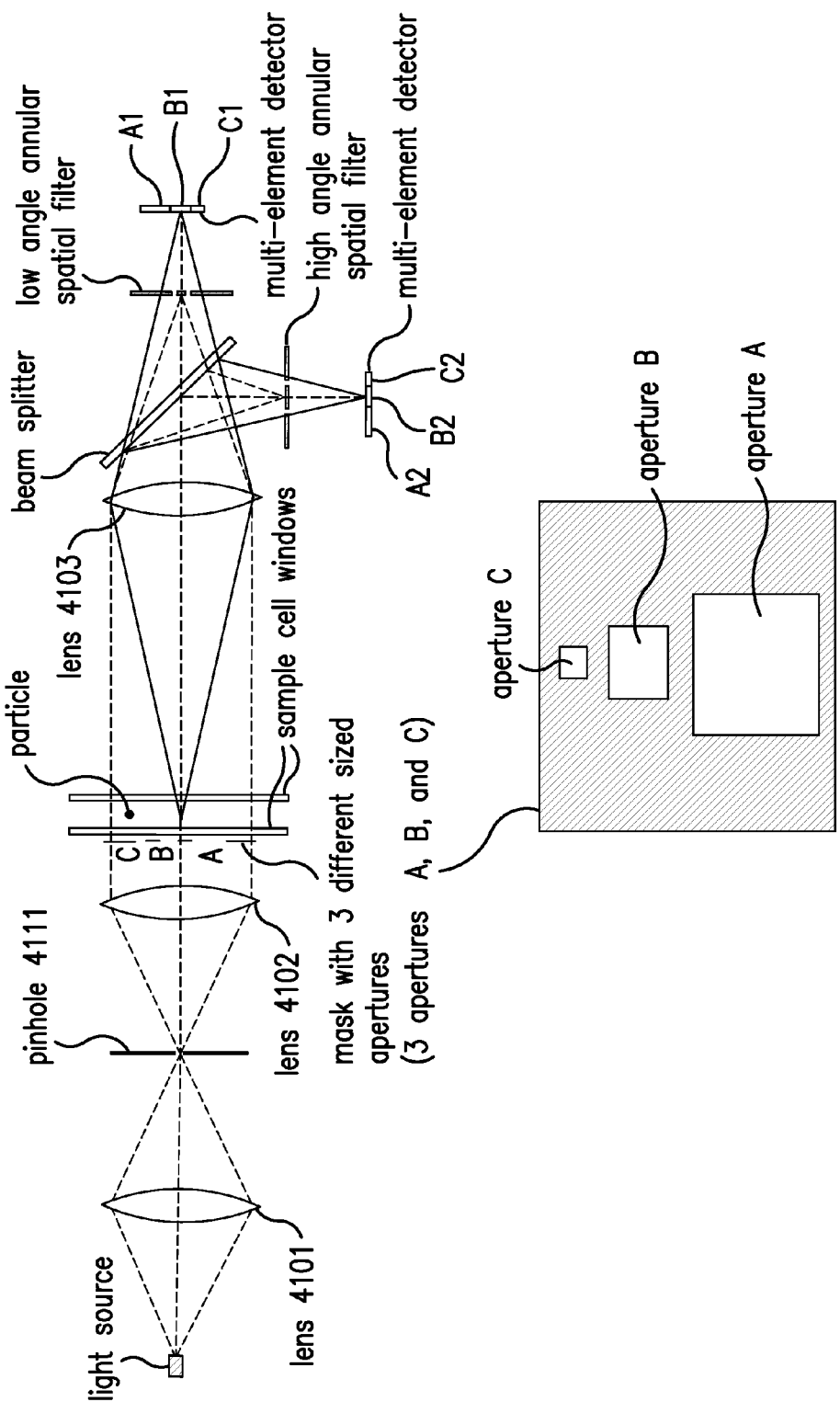
FIG. 41 provides a schematic diagram of an optical system which utilizes mask openings to define interaction volumes of various sizes, according to the present invention.

FIG. 41 shows an optical system where the light source is spatially filtered by lens 4101 and pinhole 4111. Lens 4102 collimates and projects the source beam through the particle sample and an aperture mask, which is imaged onto the detector array by lens 4103. Lens 4102 could also focus the beam into the sample cell to increase light intensity. An annular spatial mask is placed in the back focal plane of lens 4103 to only pass scattered light over a certain range of scatter angle as defined by the inner and outer radii of the annular filter, which is similar to mask 1250 shown in FIG. 12. The very low angle scattering and incident beam are blocked by central stop of the annular aperture in the back focal plane of lens 4103. Hence the detector array 1 sees an image of mask apertures and each detector element measures the scattered light only from particles in it's corresponding mask aperture over the angular range defined by the aperture (or spatial mask) in the back focal plane of lens 4103. Each detector element is equal to or slightly larger than the image of the corresponding mask aperture at the detector plane, but each detector only sees the light from only it's corresponding mask aperture. This configuration creates multiple interaction volumes of differing sizes in a single source beam. The smaller sized apertures will count smaller particles with low coincidence rates and the larger sized apertures count larger particles whose signals are much larger than the signals from smaller particles which are in that larger interaction volume at the same time. FIG. 41 shows 3 apertures (A, B, and C), but many more apertures and corresponding detector elements could be added. A beam splitter splits off a portion of the light to a second annular filter (in the back focal plane of lens 4103) and detector array 2. The angular ranges of the two annular filters are chosen to produce scattered values which are combined by an algorithm which determines the size of each particle. One such algorithm would be a simple ratio of the corresponding pulses from both arrays. And if the total scattered light is sensitive to particle composition, then the ratio of the two scattering signals can be used to determine the particle size more accurately. As with all other systems described in this disclosure, these ideas can be extended to more than two detector arrays or more than two scattering angles, simply by adding more annular spatial masks and detectors by using beamsplitters. And the signals can be processed and analyzed, using the methods described previously.

Figure 71:
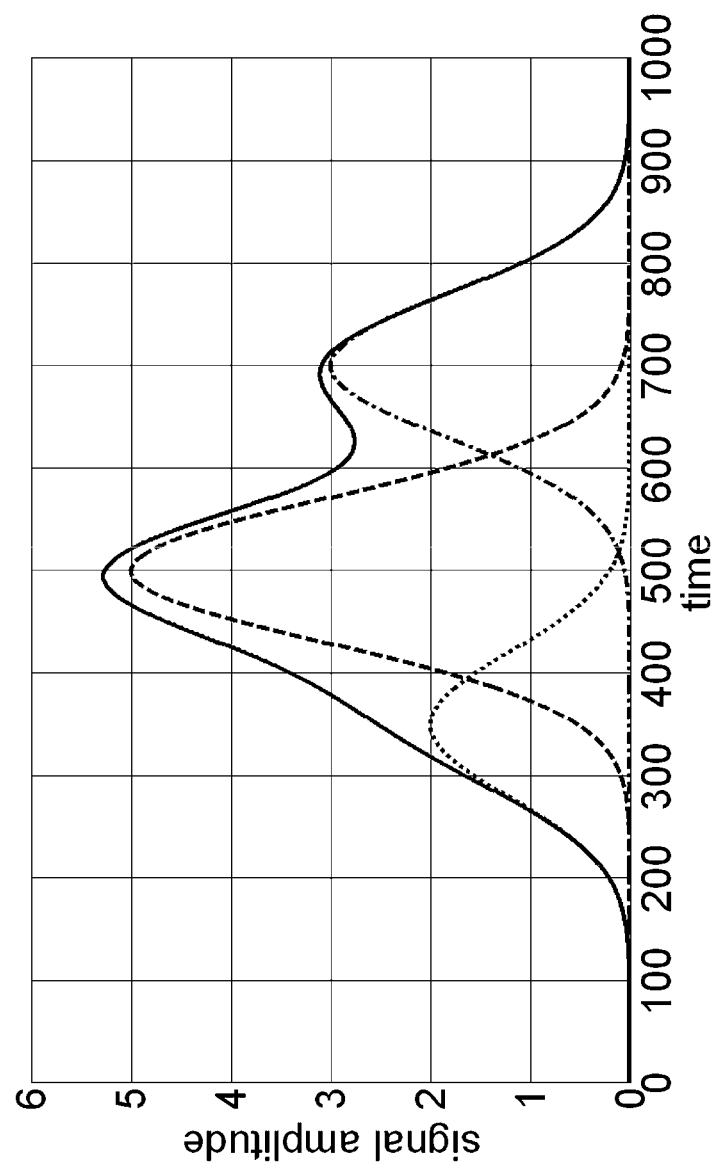
FIG. 71 provides a graph of three overlapping signal pulses and the sum of those three signals as measured by a detector, according to the present invention.
Figure 72:
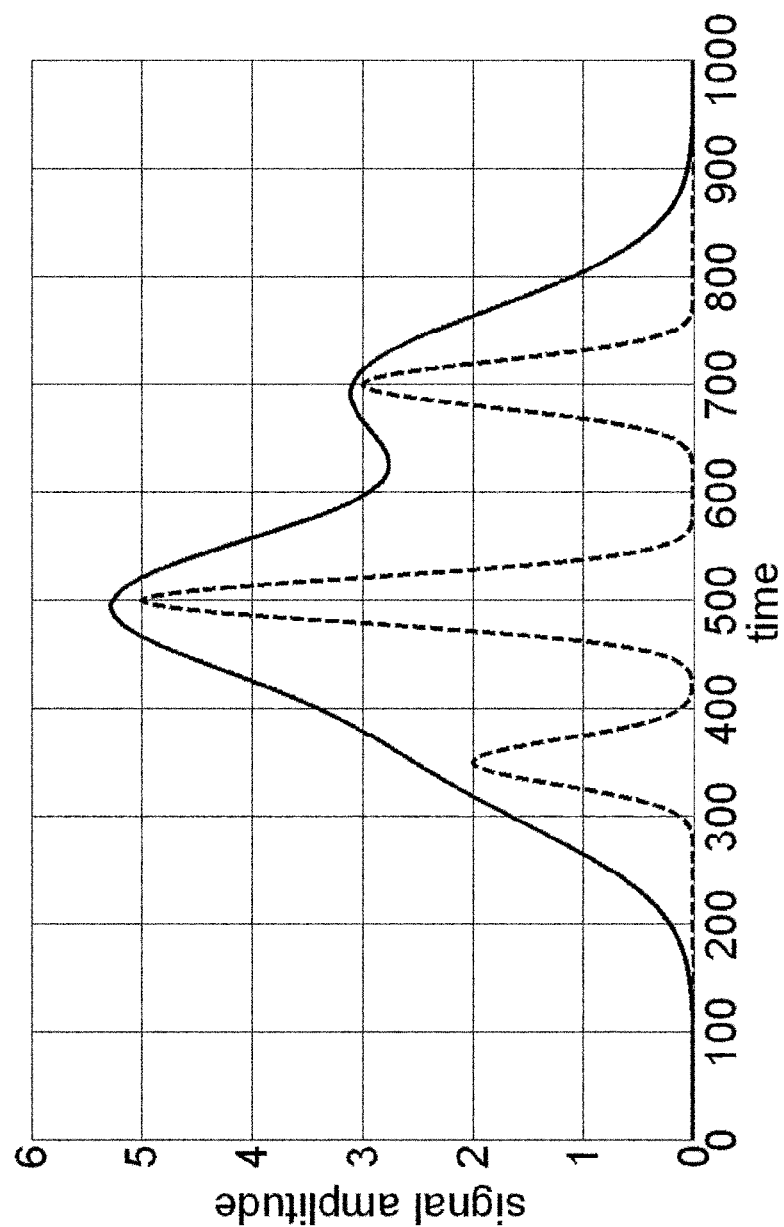
FIG. 72 provides a graph of the sum of those three signals of FIG. 71, and the signal which results from deconvolution of said sum of three signals.
Figure 73:
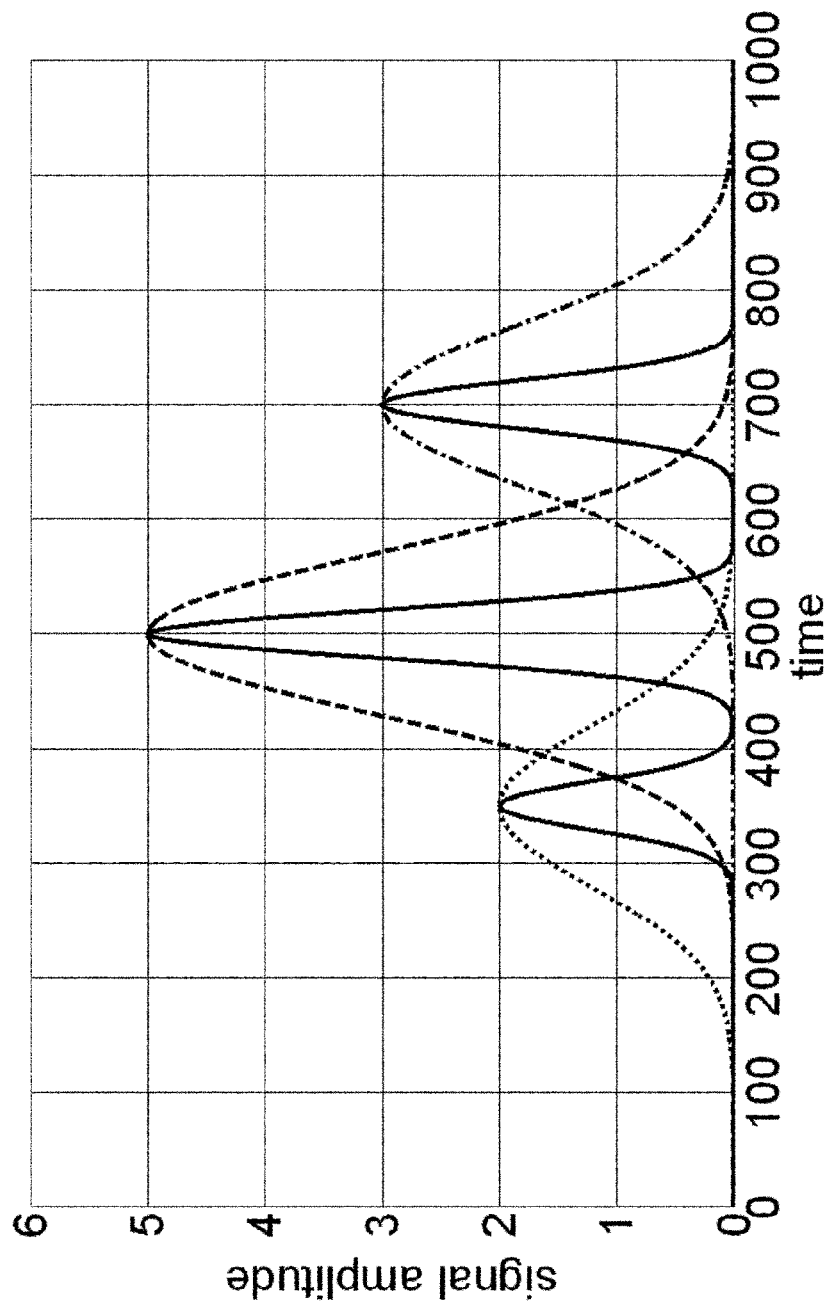
FIG. 73 provides a graph showing the original set of three overlapping signal pulses and the signal, which results from deconvolution of said sum of three signals, according to the present invention.

This configuration allows each detector element to see scatter from only a certain aperture in the mask and over a certain scattering angle range determined by it's spatial mask. If the spatial mask defines a range of low scattering angles, the total scatter for the detectors viewing through that spatial mask will show a strong decrease with decreasing particle size. The signal will decrease at least at a rate of the fourth power of the particle diameter or up to greater than the sixth power of the diameter. Assuming the weakest case of fourth power, we can obtain a drop by a factor of 16 in signal for a factor of 2 change in diameter. This means that you need to control the particle concentration such that no multiple particles are measured for the smallest particle size measured in each aperture. The largest particle size which has significant probability of multiple particles in the aperture at one time should produce scattering signals which are small compared to the scattering from lower size measurement limit set for that aperture. However, this particle concentration constraint is relaxed if multiple pulses are separated by deconvolution within a signal segment, as shown in FIGS. 71, 72 and 73.

One annular filter aperture could also be replaced by a pinhole, which only passes the light from the source (the dashed line rays). Then the signals on each detector element would decrease as a particle passes through it's corresponding aperture at the sample cell. This signal drop pulse amplitude would directly indicate the particle size, or it could be used in conjunction with the other annular signals. No limits on the number of apertures in the sample cell mask or of annular filter/detector sets are assumed. More annular filter/detector sets can be added by using more beamsplitters. Also lens 4102 could focus the source beam into the sample cell to increase intensity and scattering signals. Then the annular apertures must be designed to only pass light outside of the divergence angle of the source beam to prevent large source background on the detectors.

Figure 42:
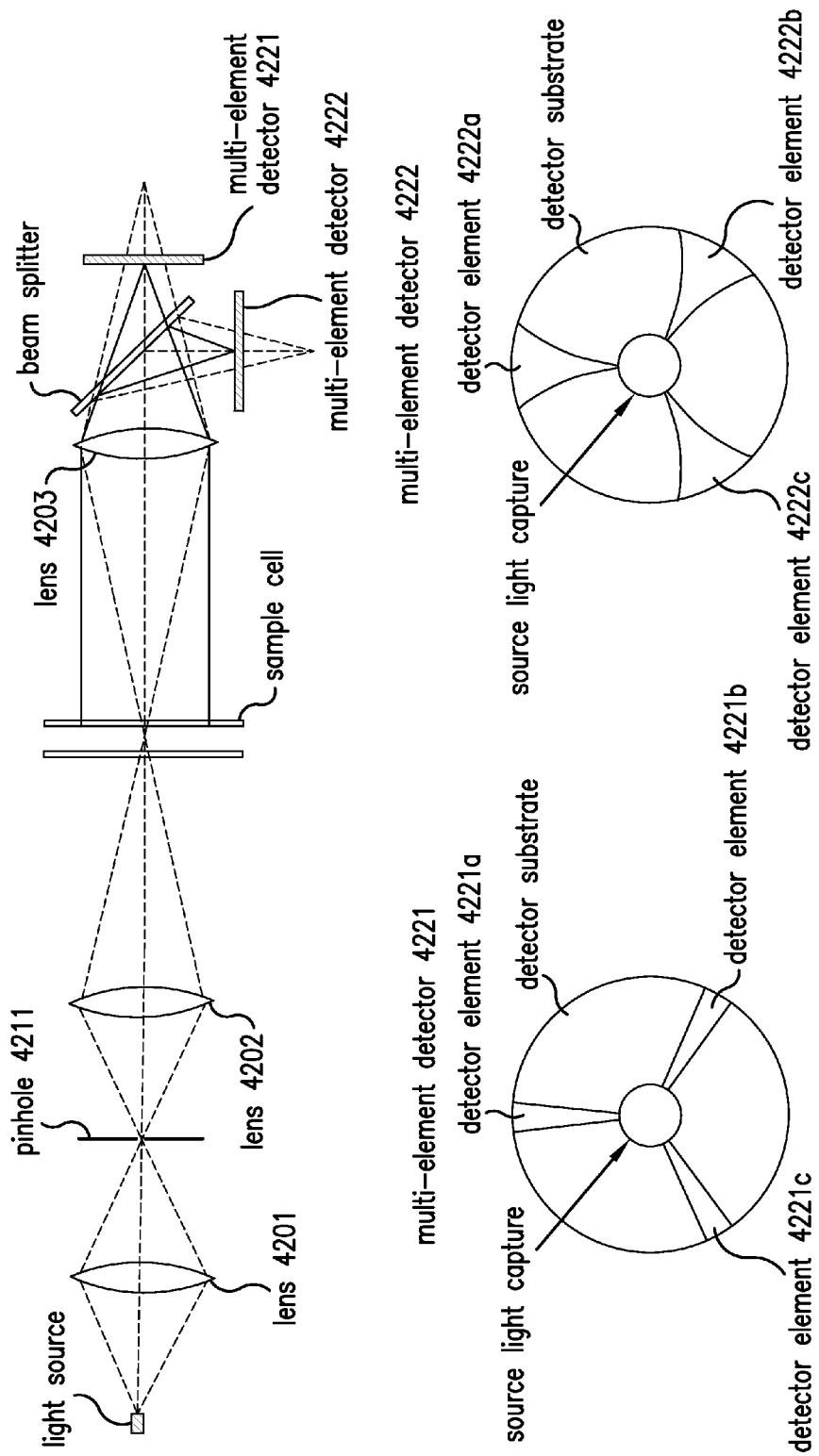
FIG. 42 provides a schematic diagram of an optical system which utilizes detector elements with different angular weighting functions, according to the present invention.

FIG. 42 shows another configuration for determining particle size and shape. The light source light is focused through pinhole 4211 by lens 4201 and then focused into the sample cell by lens 4202. The beam divergence and spot size in the sample cell are determined by the range of scattering angles to be measured and the size range of the particles. Essentially the spot size increases and the divergence decreases for larger particles. The scattered light is collected by lens 4203, which focuses it onto many multi-element detector assemblies, which are in the back focal plane of lens 4203. Each multi-element detector has multiple detector elements which measure a certain range of scattering angles along various scattering planes. FIG. 42 shows an example with three scattering planes separated by approximately 120 degrees between adjacent planes. However, any number of scattering planes with any angular separation is claimed in this application. Each multi-element detector contains a central region which either captures or passes the source light so that it does not contaminate the measurement of the scattered light. The beam divergence will determine the size of the source light capture region on the multi-element detectors.

Each detector element has a shape which determines how much of the scattered light at each scattering angle is collected by the detector element. For example detector 4221 has wedge shaped detectors which weights scattering angles progressively. Detector 4222 has a higher order weighting, the larger scattering angles are gradually weighted more in the total signal for each detector element. These detector element shapes can take on many forms: rectangular, wedged, and higher order. Any shape will work as long as the progression of collection width of the detector is different between the two multi-element assemblies so that when the particle pulse signals from the corresponding detector elements of the two multi-element detectors are ratioed, you obtain a ratio which is particle size dependent. The progression of the weighting function can also be defined by placing a variable absorbing or variable reflecting plate, over each detector element, which varies absorption vs. radius r from the center of the detector assembly. This absorption plate can provide a weighting similar to that obtained by varying the width of the detector element vs. r. And since these size measurements are made in different scattering planes, multiple dimensions of each particle are determined separately. In general each detector element produces a signal Sab, where "a" is the multi-element detector assembly number and "b" is the element number within that assembly. Then we can define Sab as:

$$S_{ab} = \int wa(r) f(r,d) \partial r \text{ for the } bth \text{ element in the } ath \text{ assembly}$$

Here d is the dimension of the particle in the direction of the corresponding scattering plane. The scattered intensity at radius r from the center of the detector assembly (corresponding to zero scattering angle) for dimension of d is f(r,d). And wa(r) is the angular width (or weighting function) of the detector element at radius r in assembly "a", in other words the angle which would be subtended by rotating the r vector from one side of the element to the other side at radius r. For the simple 3 element assemblies shown in FIG. 42, we obtain 6 measured values:

S11, S12, S13 for assembly 1
S21, S22, S23 for assembly 2

The signal on each detector element will consist of pulses as each particle passes through the beam. The Sab values above can be the peak value of the pulse or the integral of the pulse or other signal values mentioned in this disclosure. For example, one possible case would be:

Angular width for assembly 1 $w1(r)=Ar$
Angular width for assembly 1 $w2(r)=Br^*r$ For this case S11/S21, S12/S22, and S13/S23 are almost linear functions of the particle dimension in the direction of the corresponding scattering plane. These ratio values can also be analyzed using methods shown in FIGS. 26 through 28. These 3 dimensions can also be determined from an algorithm which uses all 6 S values by solving simultaneous equations which include the interdependencies of these values on each other, as described previously. In any event, the actual dimensions of the particle can be determined by assumption of a certain particle form such as rectangular, ellipsoidal, hexagonal, etc. More detector elements in each assembly will produce more accurate dimensions for randomly oriented particles. The true power of this technique is that the shape of each particle can be determined over a large size range by measuring only a few signals. Each element of each detector assembly could be broken up into sub-segments along the "r" direction to provide better size information by measuring the angular scattering distribution in each of the scattering planes. However, this may reduce the particle count rate because more digitizations and data analysis may be required per particle.

These S values can also be analyzed using methods shown in FIGS. 26 through 28, by creating two dimensional plots of absolute measurements of S1* vs. S2* (S11 vs. S21, S12 vs. S22, and S13 vs. S23). Also a virtual 6 dimensional plot of all 6 values can be created (but not plotted). Then the same methods can be used to eliminate particles which do not meet criteria for having passed through the central portion of the beam or which are caused by noise pulses (where the absolute S values are not consistent with the size determined from the S ratios)

The actual particle size system may consist of systems, each which is similar to the one shown in FIG. 42. Each system would have a different source beam divergence and spot size in the sample cell to accommodate different size ranges. The count distributions from the systems are then concatenated (or blended as shown previously) into one total distribution over the entire size range of the product. For example, for rectangular or ellipsoidal particles, the width and length dimensions of each particle could be plotted on a "scatter" plot to display the information in a useful format.

For smaller particles, the source beam will be more focused (higher divergence and smaller spot size in the sample cell region) into the sample cell. This will help to define a smaller interaction volume, with higher intensity, for the smaller particles which usually have higher number concentration than the larger particles.

Figure 43:
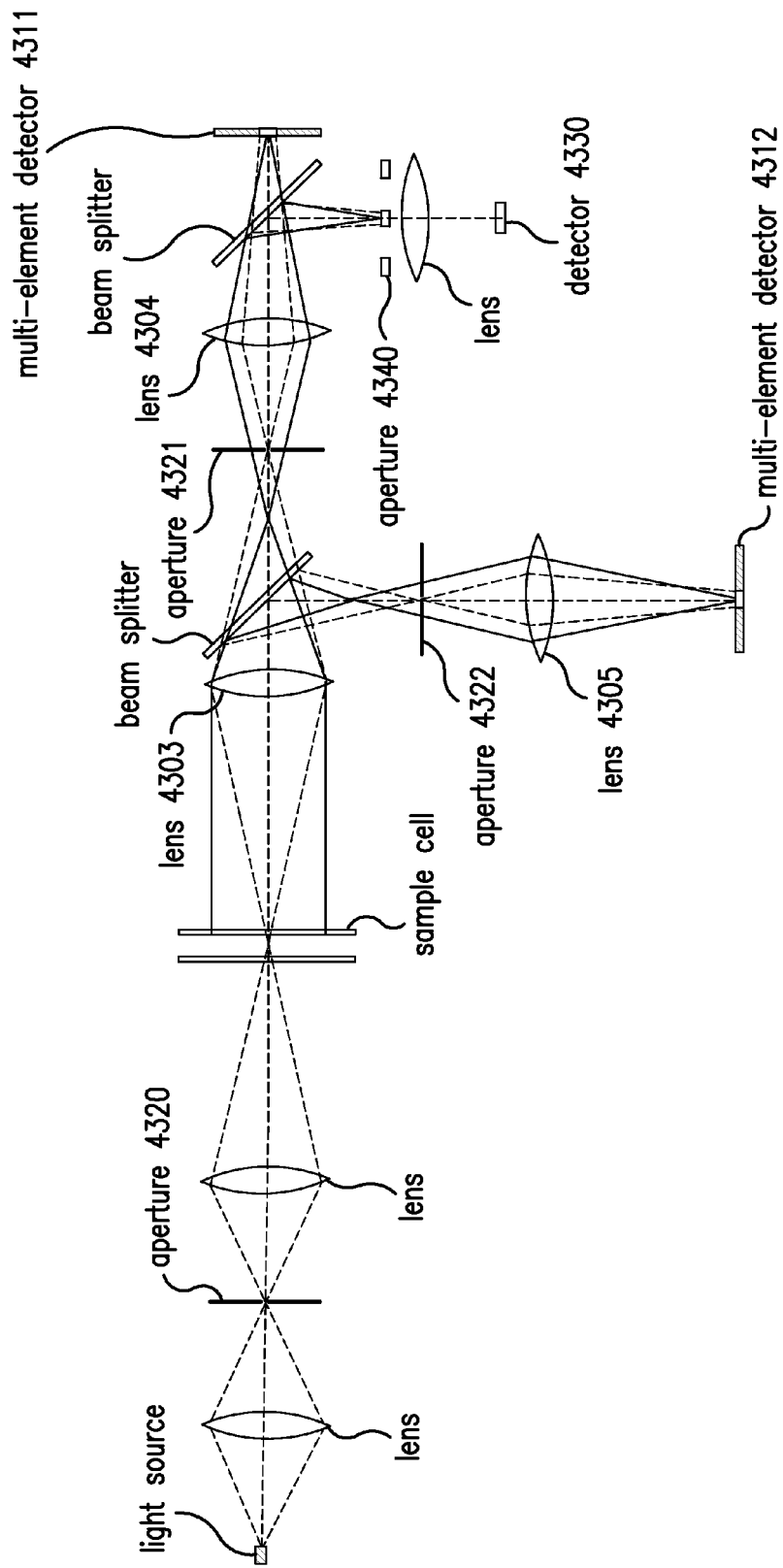
FIG. 43 provides a schematic diagram of an optical system with multi-element detectors which only receive scattered light from a small volume of particle dispersion, according to the present invention.

FIG. 43 shows another version of this concept where the interaction volume for particle scattering is controlled by appropriately positioned apertures and by correlation measurements between signals from different scattering angles. The system is similar to that shown in FIG. 42. But in this case additional apertures and lenses are added in the detection system. Aperture 4321 and aperture 4322 are placed in optical planes which are conjugate to the source focused spot in the sample cell. These apertures are sized and oriented to only allow the image of the focused spot to pass on to the multi-element detector. The source beam in aperture 4320 may have significant intensity variation so as to produce a large variation in scatter signals when particles pass through different portions of the source spot in the sample cell. In this case, the size of apertures 4321 and 4322 may be reduced such that their images, at the sample cell, only pass the uniform portion of the source beam intensity profile in the sample cell. These apertures and lens 4303 limit the volume, in the sample cell, from which scattered light can be detected by the multi-element detectors. Lenses 4304 and 4305 image the back focal plane of lens 4303 on to the multi-element detector so that the detector sees the angular scattering distribution from the particles. The multi-element detectors 4311 and 4312 can also measure scattered light in the back focal plane of lens 4304 and lens 4305, respectively. The multi-element detectors 4311 and 4312 can also measure scattered light directly from apertures 4321 and 4322, without lenses 4304 and 4305, respectively. Detector 4330 collects all of the light that is scattered in a range of scattering angles which are defined by the annular aperture 4340 (similar to the aperture shown in FIG. 12). This detector provides a equivalent diameter based on equivalent spherical particle crossectional area, without shape dependence. In some cases the size as determined by the total scatter thorough aperture 4340 will be more accurate than the particle dimensions from the multi-element detectors. For example, detector 4330 could be used to determine the particle area and the multi-element detectors could determine the aspect ratio of the particle using the ratio of the determined dimensions. Using the area and the aspect ratio, the actual dimensions could be determined. This may be more accurate than simply determining the dimensions separately using the multi-element detectors for particles whose major or minor axis may not line up with a scattering plane and which require the solution of simultaneous equations to determine the particle shape.

Figure 44:
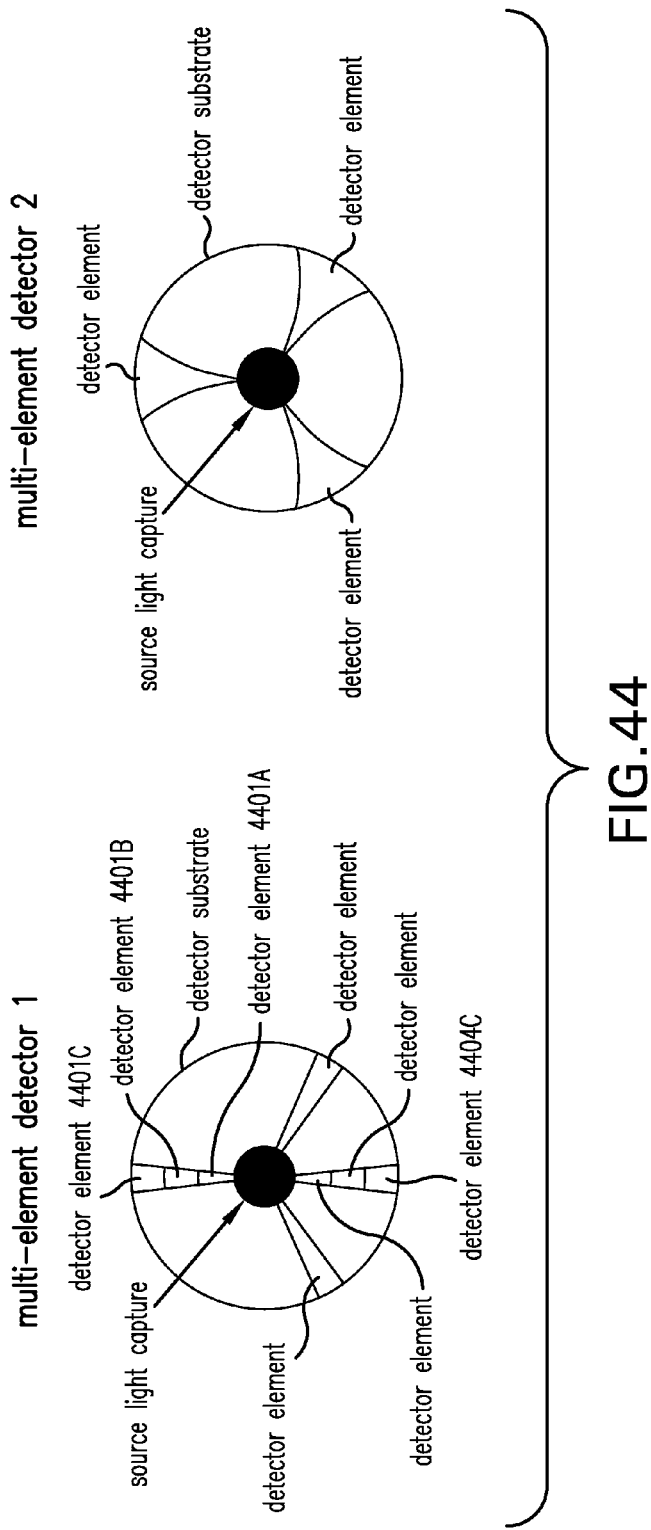
FIG. 44 provides a diagram showing an example of multi-element detectors with different angular weighting functions and additional detector elements for detecting the position of each particle relative to best focus of the light beam, according to the present invention.
Figure 45:
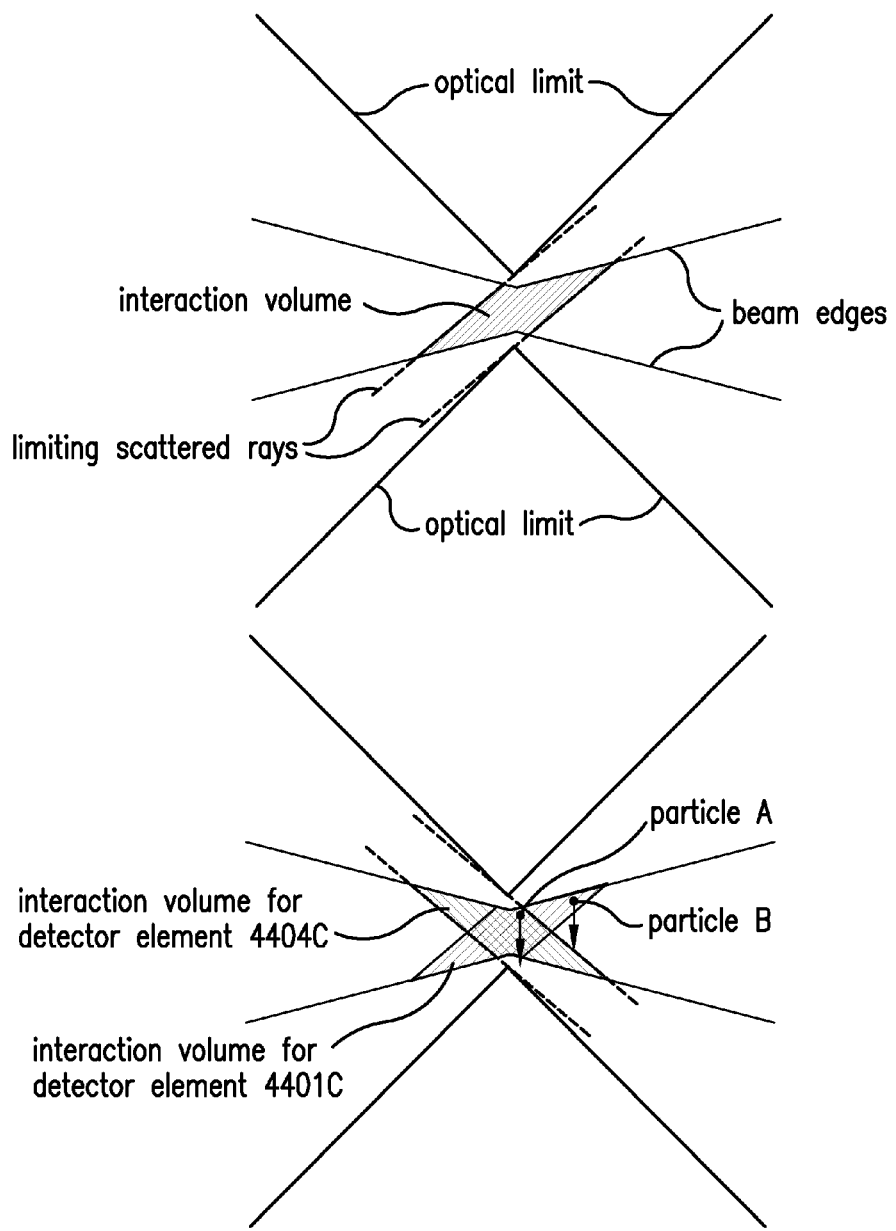
FIG. 45 provides a diagram showing the interaction volume and scattering volumes associated with the concept of FIG. 44.
Figure 46:
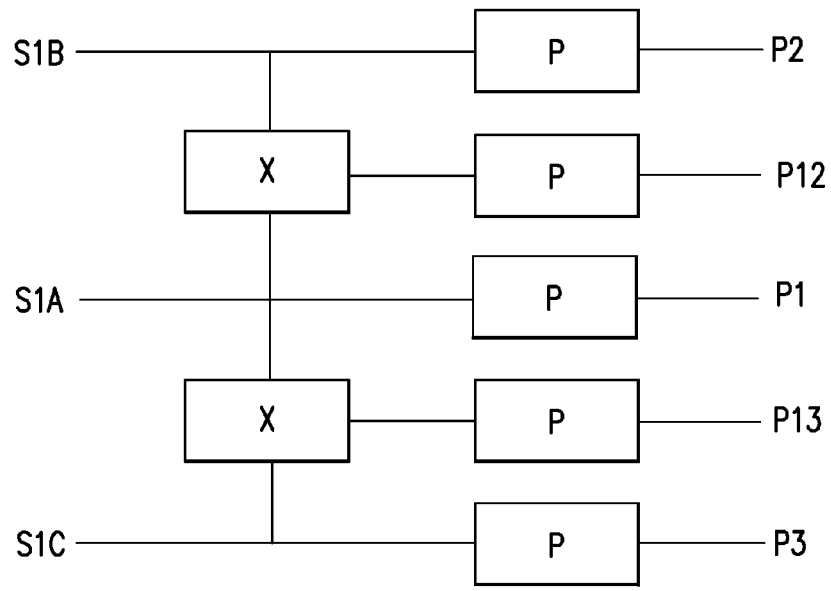
FIG. 46 provides a block diagram showing analog electronics for determining pulse correlation by multiplying scatter signals, used in the present invention.

Another feature of this design is the ability to use correlation or pulse alignment to determine which particle pulses are accurately measured and which pulses may be vignetted in the optical system. FIG. 45 shows a crossection of the source beam focus in the sample cell. The outline of the beam is shown as beam edges and the outline of the optical limits for scattered rays is shown as optical limit. These optical limits are defined by the angular size of the detector elements and the size of aperture 4321 or aperture 4322. Two extreme scattered rays are drawn in dashed lines for scattered light at a particular scattering angle. The intersection (crosshatched area) of volume between those scattered rays and the source beam is the interaction volume in which a detector can detect scattered light at that scattering angle. For example, consider the highest angle detector elements, 4401C and 4404C (see FIG. 44) which are both in a scattering plane which is parallel to flow direction of the particles. The top portion of FIG. 45 shows the interaction volume for detector element 4401C. The bottom portion of FIG. 45 shows an approximation to the interaction volumes for each of the detector elements 4401C and 4404C. Notice that as particle A passes through these interaction volumes, both scattering signals from 4401C and 4404C will be highly correlated, they will rise and fall together with a large amount of overlap in time. However, particle B, which is farther from best focus, will show very poor correlation between these two detectors. In fact the pulses will be completely separated in time. This pulse separation between 4401C and 4404C can be used to determine where the particle has passed through the interaction volume; and particles that are too far from best focus can be eliminated from the particle count. This correlation or pulse separation can be measured between any two detector elements, within a group (i.e. 4401A and 4401C) or between groups (i.e. 4401C and 4404C). Typically the scattering plane for detector groups 1 and 4 would be parallel to the particle flow to obtain maximum delay. The correlation or pulse separation can be determined from the digitized signals using algorithms. However, this may require very high speed analog to digital converters and enormous computational load to obtain a high particle count and size accuracy. Another solution is to use analog electronics to measure the correlation or the pulse separation as shown in FIG. 46, where the P boxes are processing electronics which measure the pulse peak (peak detector) or pulse integral. The X box is an analog multiplier. And S1A, SIB, and S1C are the analog signals from detector elements 4401A, 4401B, and 4401C, respectively. The following equations will provide an estimate to the correlation between the pulses:

$$R12=P12/(P1*P2)$$

$$R13=P13/(P1*P3)$$

When R12 or R13 are small, the pulses have poor correlation and they should be eliminated from the count.

Figure 47:
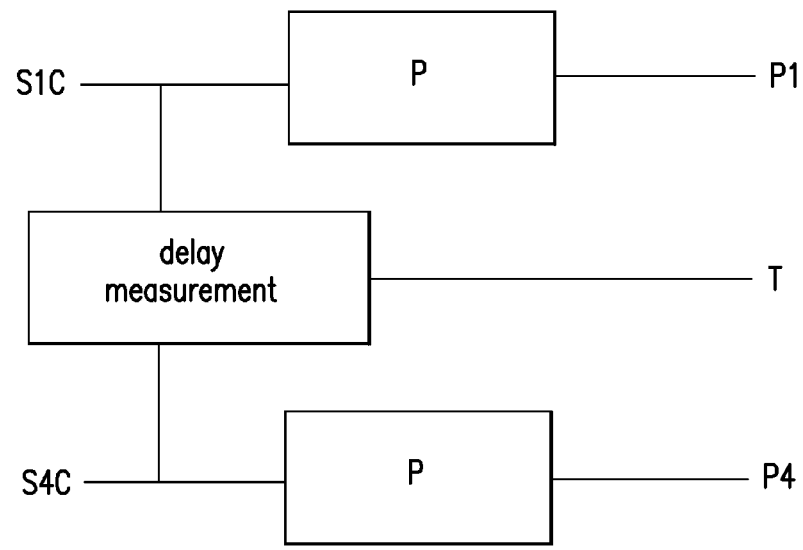
FIG. 47 provides a block diagram of a system for measurement of time delay between two scatter signal pulses, according to the present invention.

The delay between any two pulses from separate detector elements can also be used to select valid pulses for counting. As the particle passes through the beam farther from best focus of the source beam, the delay between the pulses will increase. Some threshold can be defined for the delay. All pulse pairs with delays greater than the threshold are not included in the count. One example is shown in FIG. 47, where the delay between pulses from detector elements 4401C and 4404C (see FIG. 44) is measured to reject particles which pass through the beam too far from the source beam best focus. This delay can be measured by starting a clock when the first pulse (detector 4401C) rises above threshold and stopping the clock when the second pulse (detector 4404C) rises above threshold, assuming that detector 4401C sees the particle first. The delay could also be determined from the digitized profiles of these two signals. These methods can also be used in other systems in this application such as the system showed in FIG. 78, using the detector optics in FIGS. 84 and 85. The same analysis will provide particle rejection criteria using detectors in the scattering plane which is parallel to the flow, such as the corresponding positive and negative scattering angle elements of scattering plane 8405 in FIG. 84.

Another criteria for pulse rejection is pulse width. As shown in FIG. 45, particle B will produce a shorter pulse than particle A, because the detector element will only see scattered light from the particle while it is in the interaction volume (the crosshatched area) for that particular detector element. The pulses could be digitized and the pulse width would then be computed as the width at some percentage of the pulse peak height to avoid errors caused by measuring pulses of different heights. As the particle passage moves away from best source focus, the pulse width will at first increase and then start to decrease (with significant change in pulse shape) as the particle passes through the region of smaller interaction volume. Pulses, with pulse width or pulse shape (pulse symmetry or skewness) outside of an acceptable range, will be eliminated from the particle count. Any of these techniques discussed above can be implemented using digitization of the detector element signals and computation of parameters of interest from that digitized data or using analog modules which directly produce the parameter of interest (pulse delay, pulse width, pulse shape, correlation, etc.). While the analog modules may have poorer accuracy, they can be much faster than digitization and computation, allowing a larger particle count and better count accuracy.

Figure 48:
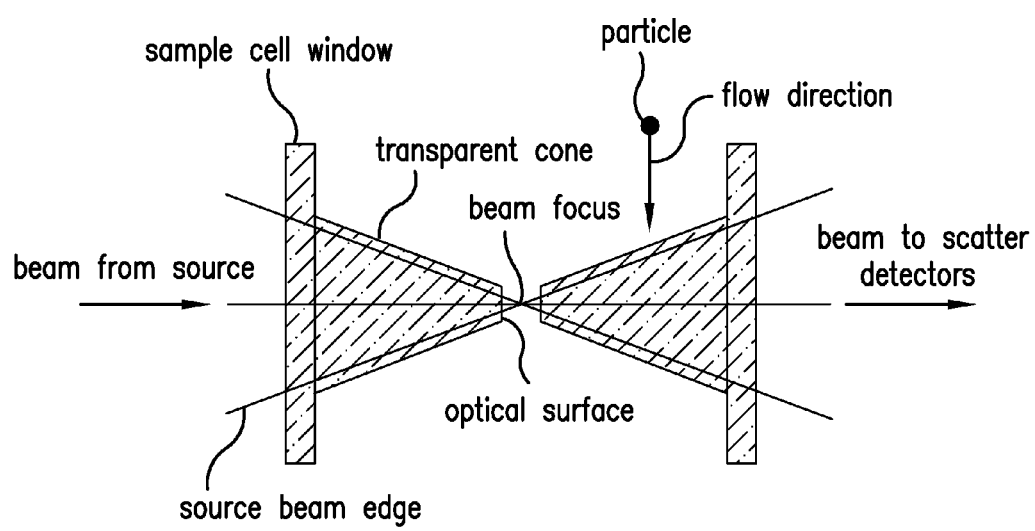
FIG. 48 provides a diagram showing an apparatus for removing particles from regions, of the light beam and scattered light rays, which are far from the interaction volume, according to the present invention.
Figure 104:
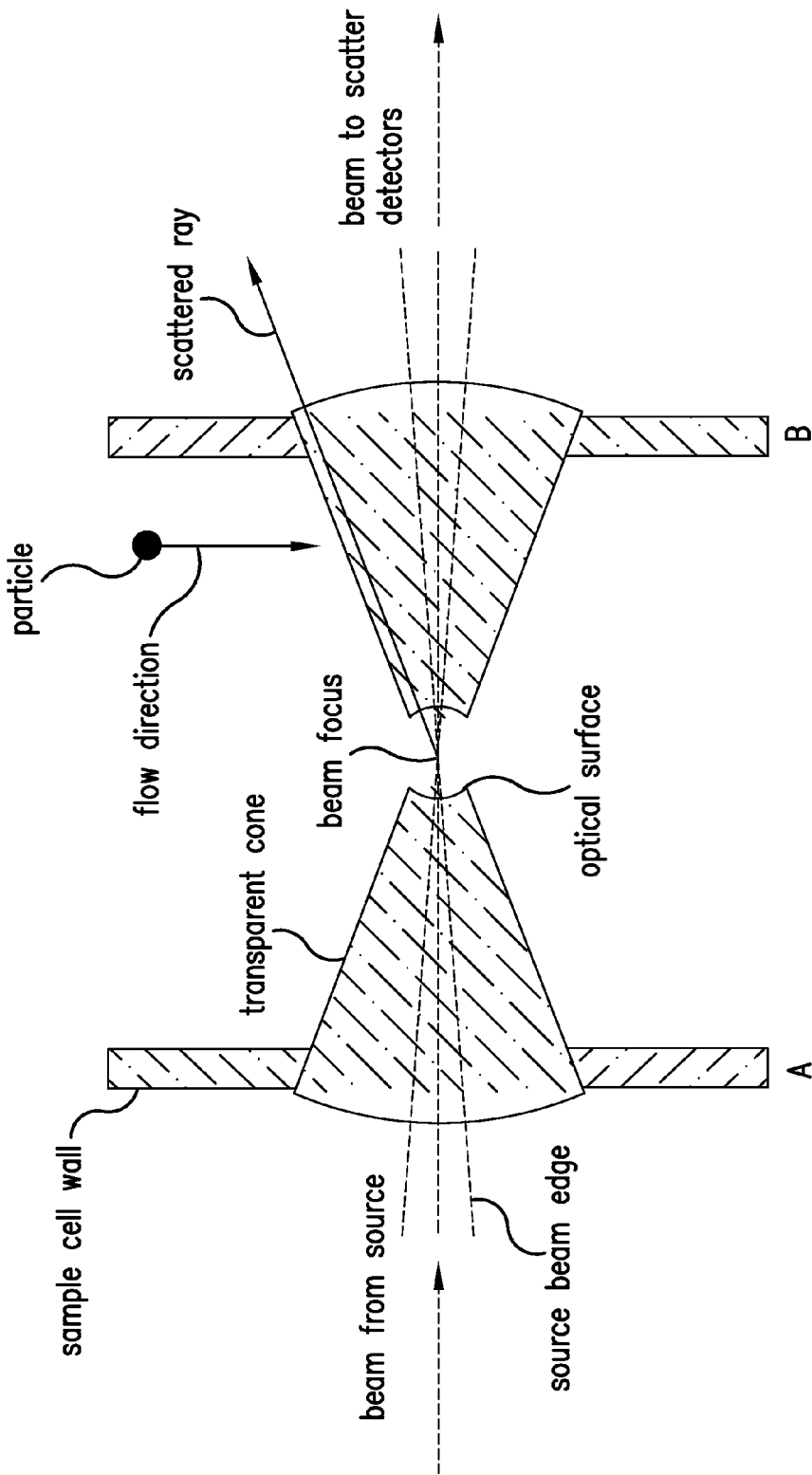
FIG. 104 provides a schematic diagram of a sample cell with transparent cones, which reduce unwanted light scattering from outside of the interaction volume, according to the present invention.

The pulse rejection criteria described above is used to reduce the number of coincidence counts by using apertures to limit the volume which is seen by the detectors. The interaction volume can also be limited by providing a short path where the particles have access to the beam as shown in FIG. 48. Two transparent cones are bonded to the inner walls of the sample cell windows using index matching adhesive. The tips of each cone is cut off and polished to either a flat or a concave optical surface. The optical windows and transparent cones could also be replaced with solid cell walls with holes which are aligned to hollow truncated cones with optical windows on the truncated tip of each cone. In this way the light travels through air or glass, except for a thin layer of particle dispersion between the two windowed cone tips. The gap between the cone tip surfaces provides the only volume where the flowing particles can pass through the source beam and scatter light to the detectors. A dispersion with a large range of particle sizes will not clog this gap because the larger particles will flow around the gap and the particle concentration is very low. The cone tip surfaces can be tilted slightly so that the spacing between them is smaller on the side where the particles enter the gap and larger where they leave the gap. In this way, particles larger than the minimum width of gap, but smaller than the maximum gap width, are prevented from jamming inside the gap. This concept is also shown in FIG. 104 with concave surfaces to reduce reflections.

The beam focus may shift with different dispersant refractive indices due to refraction at the flat surface on the end of each cone. This shift in focus and angular refraction of scattered light at a surface can be corrected for in software by calculating the actual refracted rays which intercept the ends of each detector element to define the scattering angular range of that element for the particular dispersant refractive index in use. This correction is not needed for concave surfaces, on each cone tip, whose centers of curvature are coincident with the best focal plane of the source between the two tips. Then all of the beam rays and scattered rays pass through the concave surface nearly normal to the surface with very little refraction and low sensitivity to dispersant refractive index.

Another problem that can be solved by particle counting is the problem of background drift in ensemble scattering systems which measure large particles at low scattering angles. An ensemble scattering system measures the angular distribution of scattered light from a group of particles instead of a single particle at one time. This angular scattering distribution is inverted by an algorithm to produce the particle size distribution. The optical system measures scattered light in certain angular ranges which are defined by a set of detector elements in the back focal plane of lens 5303 in FIG. 53. Each detector element is usually connected to it's own separate electronic integrator, which is connected to a multiplexing circuit which sequentially samples each of the integrators which may integrate while many particles pass through the beam (see a portion of FIG. 54). So particle pulses cannot be measured in the ensemble system.

The detector elements which measure the low angle scatter usually see a very large scattering background when particles are not in the sample cell. This background is due to debris on optical surfaces or poor laser beam quality. Mechanical drift of the optics can cause this background light to vary with time. Usually the detector array is scanned with only clean dispersant in the sample cell to produce background scatter signals which are then subtracted from the scatter signals from the actual particle dispersion. So first the detector integrators are scanned without any particles in the sample cell and then particles are added to the dispersion and the detector integrators are scanned a second time. The background scan data is subtracted from this second scan for each detector element in the array. However, if the background drifts between the two scans, a true particle scattering distribution will not be produced by the difference between these two scans. A third scan could be made after the second scan to use for interpolation of the background during the second scan, but this would require the sample cell to be flushed out with clean dispersant after the particles are present.

Figure 54:
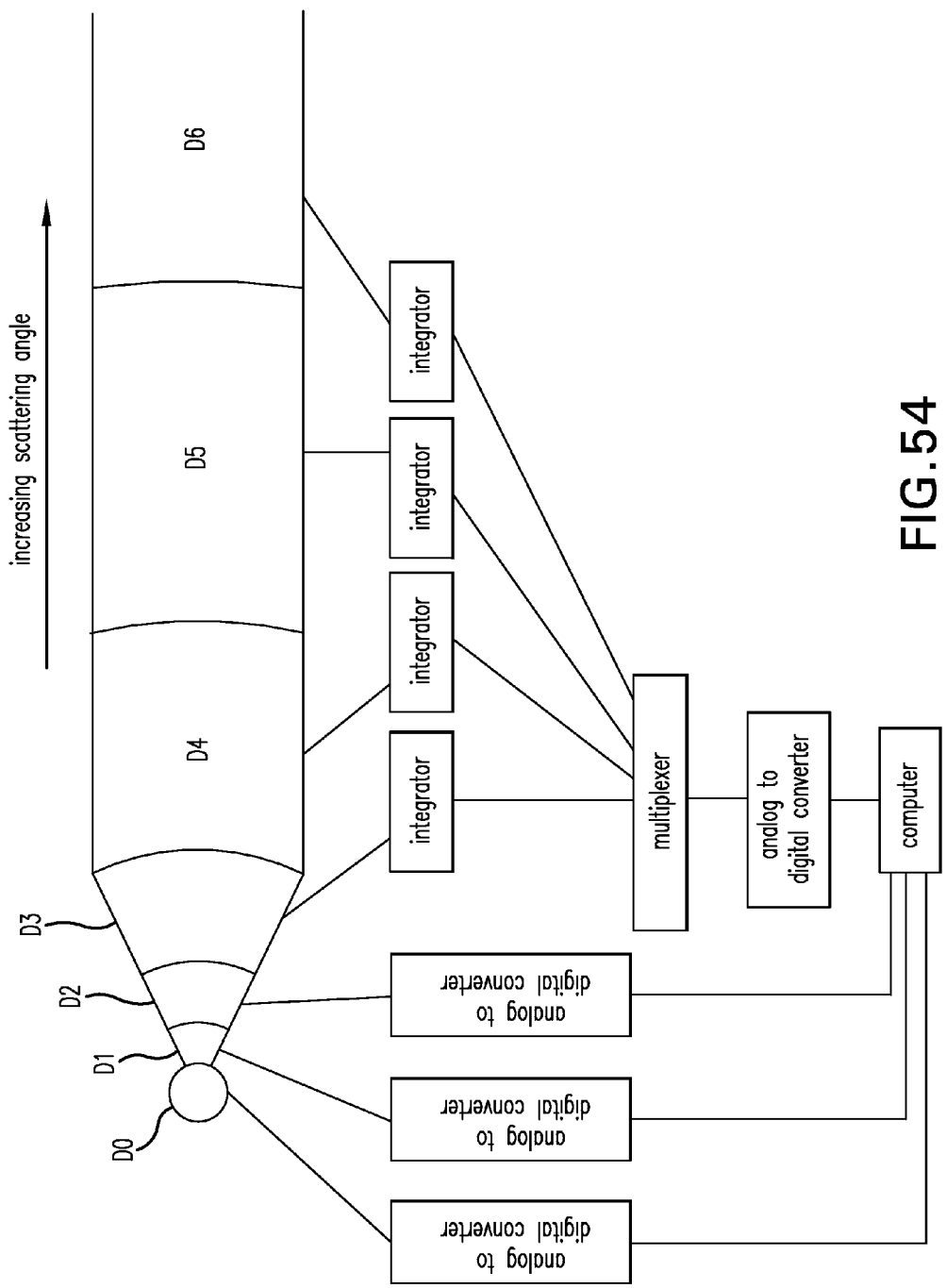
FIG. 54 provides a block diagram showing an example of a detector array and electronics for measuring scatter signals from individual particles and a particle ensemble, according to the present invention.

A much better solution, shown in FIG. 54, is to connect each of the detector elements, for the lowest angles of scatter, to individual analog to digital converters or peak detectors as shown before in this disclosure. Then these signals could be analyzed by many of the counting methods which are described in this disclosure. This would essentially produce an ensemble/counting hybrid instrument which would produce counting distributions for the large particles at low scattering angles and deconvolved particle size distributions from the long time integrated detector elements, in ensemble mode, at higher scattering angles for the smaller particles. These distributions can be converted to a common format (such as particle volume vs. size or particle count vs. size) and combined into one distribution. The advantage is that the frequency range for the particle pulses is so much higher than the frequencies of the background drift. And so these pulses can be measured accurately by subtracting the slowly varying local signal baseline on either side of each pulse. At very low scattering angles, the scattering signal drops off by at least the fourth power of particle diameter. Therefore larger single particle pulses will clearly stand out above the background due to lower overlapping signal pulses from many smaller particles which may be in the beam at any instant of time. Also the number concentration of larger particle will be low and provide for true single particle counting.

Figure 84:
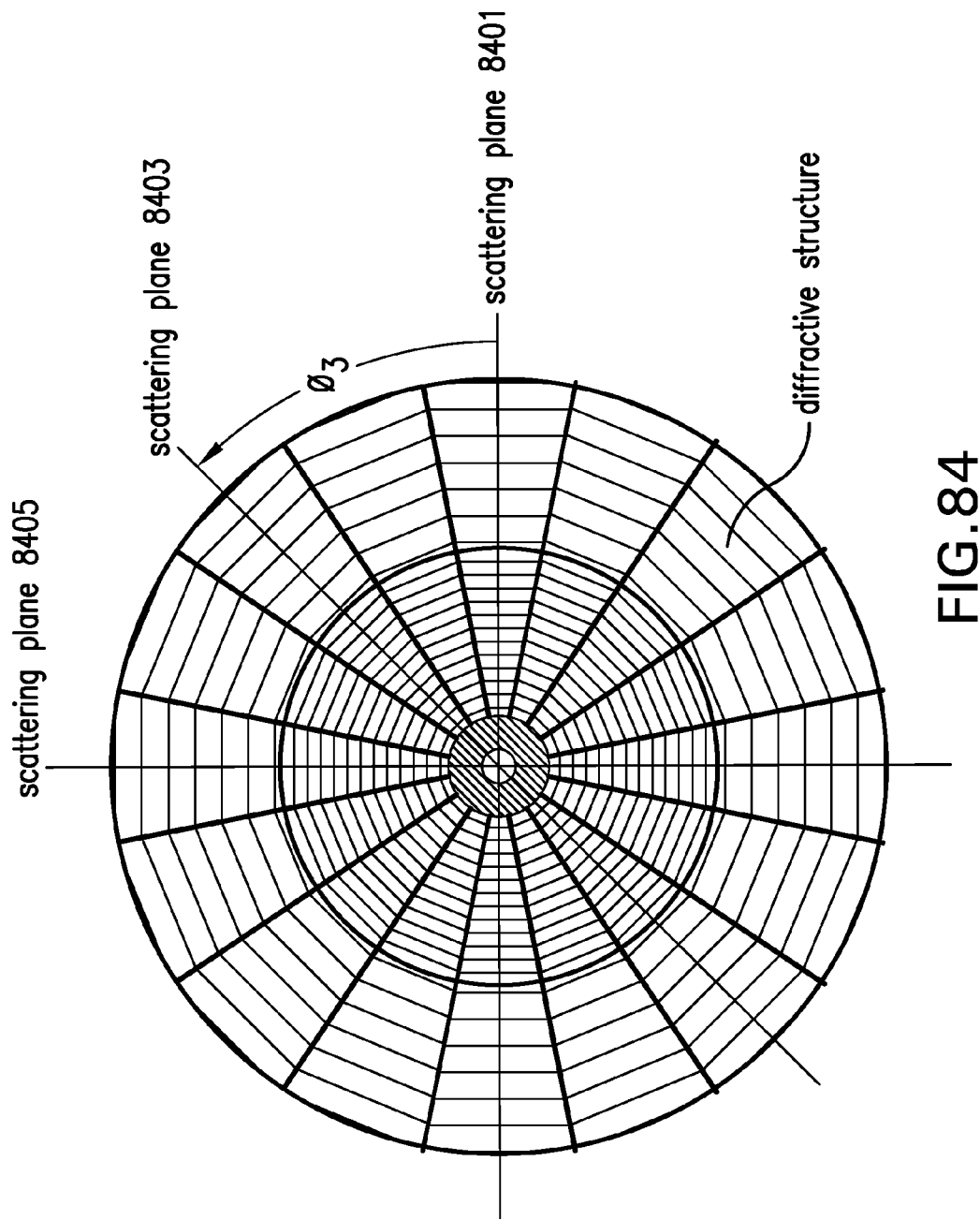
FIG. 84 provides a diagram of a diffractive optic, where different segments consist of linear diffractive gratings, the diagram showing three different center scattering planes, wherein each center scatter plane is the center of a wedge which collects scattered light from a range of scattering planes, according to the present invention.

As mentioned before in this disclosure, the particle shape can be determined by measuring the angular distribution of scattered light in multiple scattering planes, including any number of scattering planes. The particle shape and size is more accurately determined by measuring the angular scattering distribution in a large number of scattering planes, requiring many detector elements in the arrays shown in FIGS. 33 and 44. As the number of detector elements becomes large, the use of less expensive 2-dimensional detector arrays (with rows and columns of detectors on a rectangular grid), such as CCD arrays, becomes more attractive to take advantage of the economies of scale for production of commercial CCD cameras. The 2-dimensional scattering distribution can be converted to optical flux distributions along each of many scattering planes, to use the analysis described for detectors as shown in FIG. 84. Also the flux distribution as a function of x and y coordinates on the array can be analyzed to determine the particle size and shape. However, the use of these 2-dimensional detector arrays presents some problems, which are not associated with custom detector arrays with optimally designed elements as shown previously. These arrays usually have poor dynamic range, poor sensitivity, poor A/D resolution, slow digitization rates, and high levels of crosstalk between pixels (blooming for example). Methods for mitigation of these problems are described below.

The detector array could be scanned at a frame rate, where during the period between successive frame downloads (and digitizations) each pixel will integrate the scattered light flux on its surface during an entire passage of only one particle through the source beam. Each pixel current is electronically integrated for a certain period and then its accumulated charge is digitized and stored; and then this cycle is repeated many times. During each integration period the pixel detector current from scattered light from any particle, which passes through the beam, will be integrated during the particle's total passage through the light source beam. Therefore the angular scattering distribution for that particle will be recorded over a large number of scattering planes by all of the detector elements in the array. This 2-dimensional scattering distribution could be analyzed as described previously, using a large number of simultaneous equations and more shape parameters, by assuming a certain model for the particle shape (ellipsoidal, rectangular, hexagonal, etc.). As shown before, the particle shape and random orientation can be determined from these equations. Also, conventional image processing algorithms for shape and orientation can be used on the digitized scattering pattern to find the orientation (major and minor axes, etc.) and dimensions of the scatter pattern. The particle size and shape can be determined from these dimensions. Also the particle size and shape can be determined from the inverse 2-dimensional Fourier transform of the scattering distribution for particles in the Fraunhofer size range, but with a large computation time for each particle. The inverse Fourier transform of the 2-dimensional scattering distribution, which is measured by the 2 dimensional detector array, will produce an image, of the particle, from which various dimensions can be determined directly, using available image processing algorithms.

For example, consider an absorbing rectangular particle of width and length dimensions A and B, with both dimensions in the Fraunhofer size range and minor and major axes along the X and Y directions. If the particle is not absorbing or is outside of the size range for the Fraunhofer approximation, then the theoretical 2-dimensional scattered intensity distribution is calculated using known methods, such as T-matrix and Discrete Dipole Approximation, (see "Light Scattering by Nonspherical Particles", M. Mishchenko, et al.). In the Fraunhofer approximation, the irradiance in the scattering pattern on the 2-dimensional detector array will be given by:

$$I(a,b) = Io*(SIN\ C(\pi a)*SIN\ C(\pi b))^2$$

Where $SIN\ C(x) = SIN(x)/x$

Io is the irradiance in the forward direction at zero scattering angle relative to the incident light beam direction $$a = A*\sin(anga)/w1$$

$$b = B*\sin(angb)/w1$$

where:
w1=wavelength of the optical source
anga=the scattering angle relative to the incident source beam direction in the scattering plane parallel to the A dimension of the particle
angb=the scattering angle relative to the incident source beam direction in the scattering plane parallel to the B dimension of the particle The corresponding x and y coordinates on the 2 dimensional detector array will be:

$x = F^* \tan(\text{ang}a)$ and $y = F^* \tan(\text{ang}b)$

Figure 49:
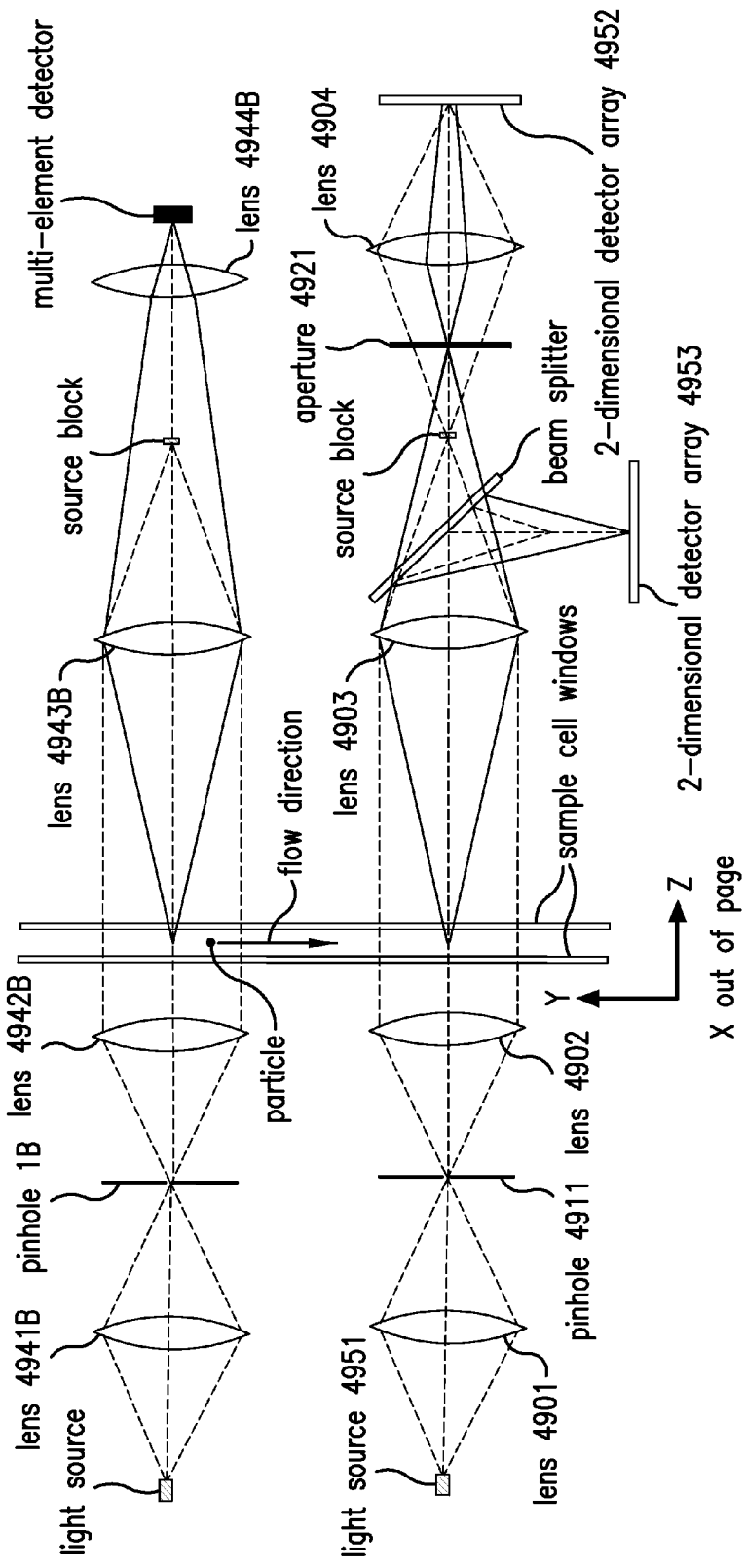
FIG. 49 provides a schematic diagram of an optical system which measures the 2-dimensional scattering distribution and image of each particle, wherein an upstream optical system adjusts this optical system for the characteristics of each particle, according to the present invention.

The scattering pattern crossections in the major and minor axes consist of two SINC functions with first zeros located at:

$$xo = F^* \tan(\arcsin(w1/A))$$

$$yo = F^* \tan(\arcsin(w1/B))$$

where F is the focal length of the lens 3203 in FIG. 32 or F=M*F3 in FIG. 49 where F3 is the focal length of lens 4903 in FIG. 49 and M is the magnification of lens 4904 between the back focal plane of lens 4903 (source block) and the detector array, which is in an image plane of said back focal plane. By inspection of these equations, the dimension of the scattering distribution is inversely proportional to the particle dimension along the direction parallel to direction of the dimension measurement. The 2-dimensional scattering distribution is measured by a 2-dimensional detector array, such as a CCD array. For a rectangular particle, use known image processing methods to determine the major axes, minor axes and orientation (a in FIG. 105) of the scattering pattern and then measure the width and length of the pattern at the first zeros (xo and yo) in the scattering distribution in the directions of the major and minor axes. Then the particle dimensions are given by:

$$A = w1/(\sin(\arctan(xo/F)))$$

$$B = w1/(\sin(\arctan(yo/F)))$$

These equations describe the process for determining particle shape for a randomly oriented rectangular particle where we have assumed that the particle is much smaller than the uniform intensity portion of the source beam. Other equations, which model scatter from non-uniform illumination, must be used when these conditions are not satisfied. Other parameters (such as the point in the scatter distribution which is 50% down from the peak) which describe the width and length of the scattering pattern can be used instead of xo and yo, but with different equations for A and B. In general, the corresponding particle dimensions can be determined from these parameters, using appropriate scattering models which describe the scattering pattern based upon the effects of particle size, shape, particle composition and the fact that the scattering pattern was integrated while the particle passed through a light source spot of varying intensity and phase. This analysis for rectangular particles is one example for rectangular particles. The model for each particle shape (polygon, ellipsoid, cube, etc.) must be computed from scattering theory for nonspherical particles using algorithms such as T-matrix method.

Figure 50:
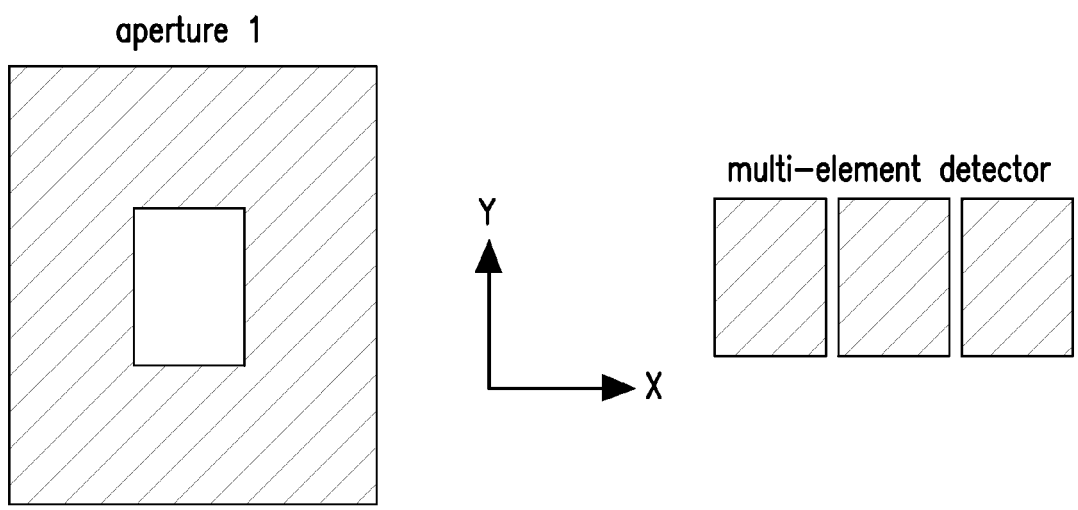
FIG. 50 provides a diagram of a rectangular aperture for defining an interaction volume and a multi-element detector for determining the position where the particle passes through the light beam, according to the present invention.

The hardware concept is shown in FIG. 49. This system is very similar to those shown previously in this disclosure in FIG. 32. Pinhole 4911 removes high angle background from the light source and lens 4902 collimates the source for passage through the sample cell through which the particle dispersion flows. The light source, lenses 4901 and 4902, and pinhole 4911 could be replaced by a nearly collimated light beam such as a laser beam. Two optical systems view the particles. The 2-dimensional array #1 measures the scattering distribution from each particle and 2-dimensional array #2 measures the image of each particle. Array #1 is used to measure the dimensions of a smaller particle and array #2 measures the larger particles where the array pixel size can provide sufficient size resolution as a percentage of particle dimension for accurate dimension measurement. The scattering pattern from the particle is formed in the back focal plane of lens 4903 and this scatter pattern is imaged onto array #1 by lens 4904. A small block is placed in the back focal plane of lens 4903 to block the unscattered focused light from the light source so that it will not reach array #1. The source light would saturate some pixels on that array and these pixels may bloom or crosstalk into adjacent pixels where very low level scattered light is being measured. The source block could also be replaced by an annular spatial mask (as shown previously) to measure scatter only over a certain range of scattering angles. Aperture 4921 (also see FIG. 50) is placed in an image plane of the sample cell to define a restricted region of the beam where particles will be counted. This region is confined to where the intensity profile of the source beam has sufficient uniformity. If this region of confinement is not required and access to the surface of the CCD is available (windowless CCD array) then lens 4904 and aperture 4921 could be removed and the CCD array could be placed in the back focal plane of lens 4903, directly behind the source block. The beam diameter and lens diameters are not drawn to scale. They are drawn to display the details of beam divergence and conjugate planes. Lenses 4942B, 4903 and 4943B might actually be much larger than the beam diameter to collect scatter over a large range of scattering angles.

A second similar optical system (system B which contains lenses 4941B, 4942B, 4943B, 4944B etc.) is placed upstream of the particle flow from the system (the main system which contains lenses 4901, 4902, 4903, 4904, etc.) described above (see FIG. 49). This system B reduces many of the problems associated with CCD arrays which are mentioned above. System B measures the scattered light from each particle before it passes through the main system described above. This scattered light level determines the particle size and predicts the signal levels which will be seen from that particle when it passes though the main system. These predicted levels provide the ability for the system to either adjust the intensity of light source 4951 or the gain of array 4952 to nearly fill the range of the analog to digital converter which digitizes the scattering pattern data from array 4952 and to improve signal to noise. The analog to digital converter and array pixel dynamic signal range is not sufficient to measure scattered light levels from particles over a large range of sizes. For example, the lowest scatter angle signal will change over 8 orders of magnitude for particles between 1 and 100 microns. However, the dynamic range of most CCD arrays is between 200 and 1000. Therefore, by adjusting the source intensity so that the maximum pixel value on array 4952 will be just below saturation for each particle, the optimum signal to noise will be obtained. The time of the pulse from the upper system B will predict when each particle will pass through the main system, using the flow velocity of the dispersion through the cell. So the array only needs to integrate during the particle's passage through the source beam. This minimizes the integration time and shot noise of array 4952. This timing could also be used to pulse the laser when the particle is in the center of the source beam for imaging by array 4953 to freeze the particle motion during the exposure. Also the predicted size from system B could be used to choose only particles in a selected size range for shape measurement. Or some smaller particles could be passed without dimensional measurement to increase the statistical count of larger particles relative to the smaller particles to improve the counting statistics for the larger particles which are usually at lower number concentration than the smaller particles. But the size distribution could then be corrected by the total count distribution from the upper system B, while the particle shape count distribution is determined from the fewer particles counted by the main system. The size of the scattering pattern could also be predicted by system B so that an appropriate sub-array of array 4952 would be digitized and analyzed to save digitization time. The size prediction can also determine which array (4952, 4953 or both) will be digitized to determine the particle dimensions. The upstream system B particle counts could also be used to determine coincidence counting while the particle concentration is being adjusted. Many of these techniques are used to reduce the digitization load on the analog to digital converter, if required.

Lens 4944B acts as a field lens to collect scattered light and place the scatter detector in the image plane of the sample cell. This detector could be a single element detector which simply measures the all of the scattered light over a large range of scattering angles. However, this single detector measurement could be complicated by the variation of light intensity across the source beam. The use of a three detector multi-element detector (see FIG. 50) could be used in this image plane of the sample cell. Then only particles which produce signal primarily on the center detector (of the three detector set) would be accepted for counting. This particle selection could be based upon the ratios between the signal from the center detector element with the corresponding signal from either of the outer elements, as described previously in FIG. 37. The particle will be counted only if these two ratios are both above some threshold. If a large single detector is used instead of the multi-element detector, lens 4944B could be removed and the detector could be placed directly behind the source block if it is large enough to collect all of the scattered flux. Otherwise a lens should be used to collect the scattered light and focus it onto the detector.

If the upstream system B is not used, the CCD array scans of each scatter pattern should be made over multiple long periods (many individual particles counted per period with one array scan per particle) where the light source intensity or detector pixel gain is chosen to be different during each period. In this way particles in different size and scattering efficiency ranges will be counted at the appropriate source irradiance or detector pixel gain to provide optimal signal to noise. So during each period, some particles may saturate the detectors and other particles may not be measured due to low scattering signals. Only particles whose scattering efficiency can produce signals within the dynamic range of the array for that chosen light source level or gain will be measured during that period. So by using a different source level or gain during each period, different size ranges are measured separately, but with optimal signal to noise for each size range. The counting distributions from each period are then combined to create the entire size and shape distribution. This method will require longer total measurement time to accumulate sufficient particle counts to obtain good accuracy because some particles will be passed without counting. The use of system B to predict the optimal light source level or pixel gain provides the optimum result and highest counts per second. These methods can also be used to mitigate detector array dynamic range problems in any other system in this application.

The main system counting capability, as shown in FIG. 49, could be added to any diffraction ensemble system by using the scatter collection lens (lens 5303 in FIG. 53) in the ensemble system to act as lens 4903 in the counting system in FIG. 49. The light path after the ensemble system scatter collection lens (the lens forming the scatter pattern) would be partially diverted, by a beamsplitter, to a detection system as shown in FIG. 49 after lens 4903. This detection system could be any appropriate variation of the detection system (with or without array 4953 and its beamsplitter as shown in FIG. 49 for example). Also if source region confinement (as discussed above) is not required and access to the surface of the CCD is available (windowless CCD array) then lens 4904 and aperture 4921 could be removed and the CCD array could be placed in the back focal plane of lens 4903, behind the source block. System B could also be added to the ensemble scattering system, but with significant added expense.

Figure 51:
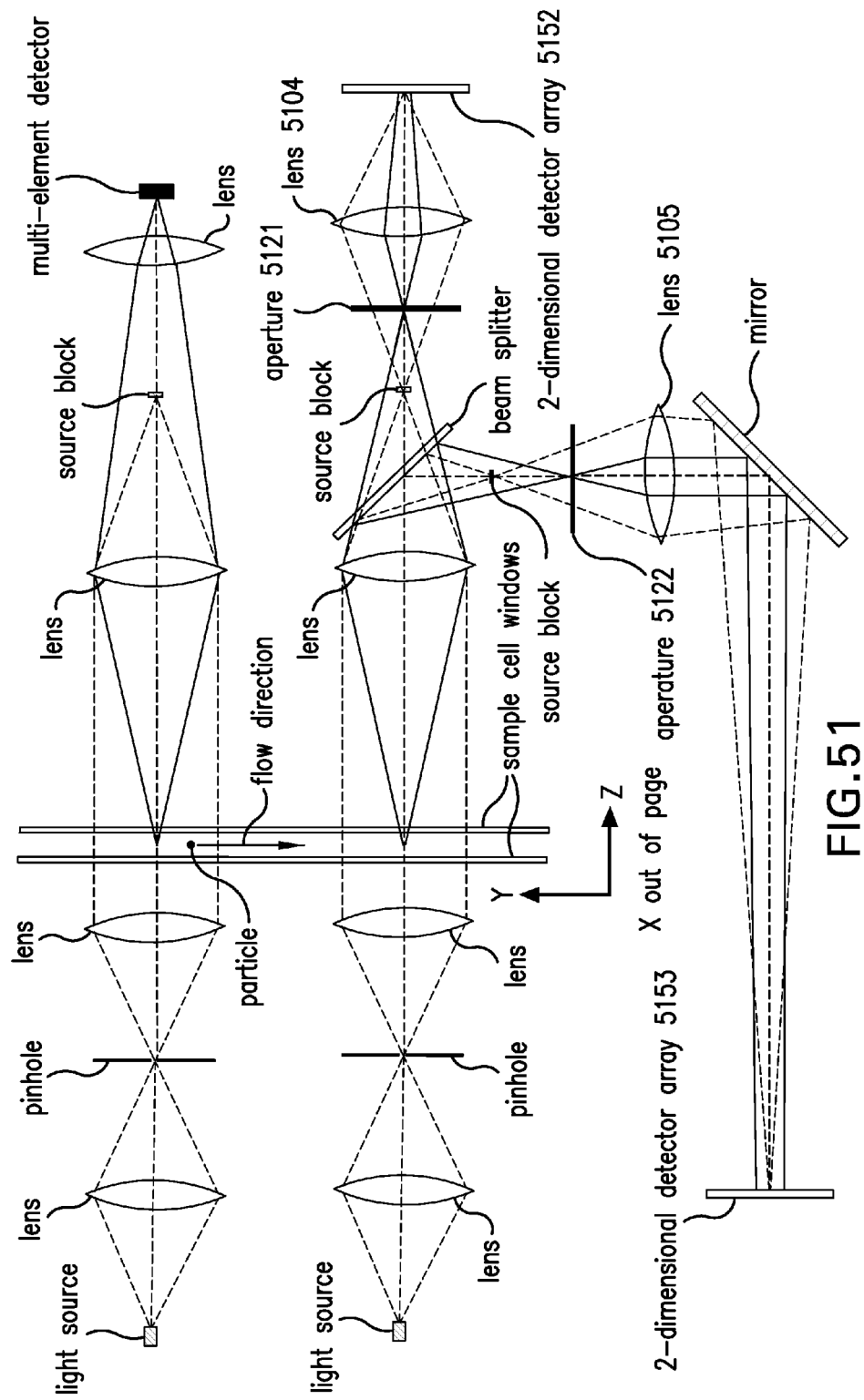
FIG. 51 provides a schematic diagram of an optical system which uses multiple detector arrays, with different scattering angle scales, to extend the particle size range, according to the present invention.

Linear CCD arrays do not have sufficient dynamic spatial range to accurately measure scatter pattern profiles from particles over a large range of particle size. For example, for a million pixel array, the dimensions are 1000 by 1000 pixels. If at least 10 pixel values are needed to be measured across the scatter profile to determine the dimension in each direction, then 1000 pixels will only cover 2 orders of magnitude in size. This size range can be increased to 4 orders of magnitude by using two arrays with different angular scales. FIG. 51 shows a system similar to that shown in FIG. 49, but with an additional scatter detection array (2-dimensional array 5153). Arrays 5152 and 5153 are in the back focal planes of lens 5104 and lens 5105, respectively. Lens 5105 has a much longer focal length than lens 5104, so that each pixel in array 5152 covers a proportionately larger scattering angle interval. As each particle passes through system B, the particle size is estimated to determine which array (5152 of 5153) should be scanned and digitized. Array 5152 should be used for small particles which scatter over large angles and Array 5153 should be used for larger particles. The use of two arrays with different angular scales provides much higher particle count rates. For example, for 2 orders of size magnitude with a single array, 1 million pixels must be digitized (1000 by 1000 with minimum of 10 pixels for the largest particle). However, if two smaller 100 by 100 pixel arrays were used for array 5152 and array 5153 and the focal length for lens 5105 was 10 times longer than the focal length of lens 5104. Then these two 10,000 pixel arrays could cover 2 orders of magnitude in size, equivalent to that of the single 1 million pixel array; but only a maximum of 10,000 pixels must be digitized for each particle by using the size estimate from system B to determine which array to digitize. This design provides a factor of 100 increase in the particle count rate. This rate could be further increased by only digitizing the minimum subarray needed to measure each particle, based upon the size prediction provided by system B. Also, FIG. 51 shows the use of separate apertures (aperture 5121 and aperture 5122) which have different size openings. A smaller opening is used for the smaller particle detector array to reduce the scatter volume and reduce the probability of coincidence counting. Also detector arrays 5152 and 5153 could both be digitized for each particle, without any array selection based upon signals from system B. The scattering data from both arrays would be combined to determine the size of each particle.

Figure 49A:
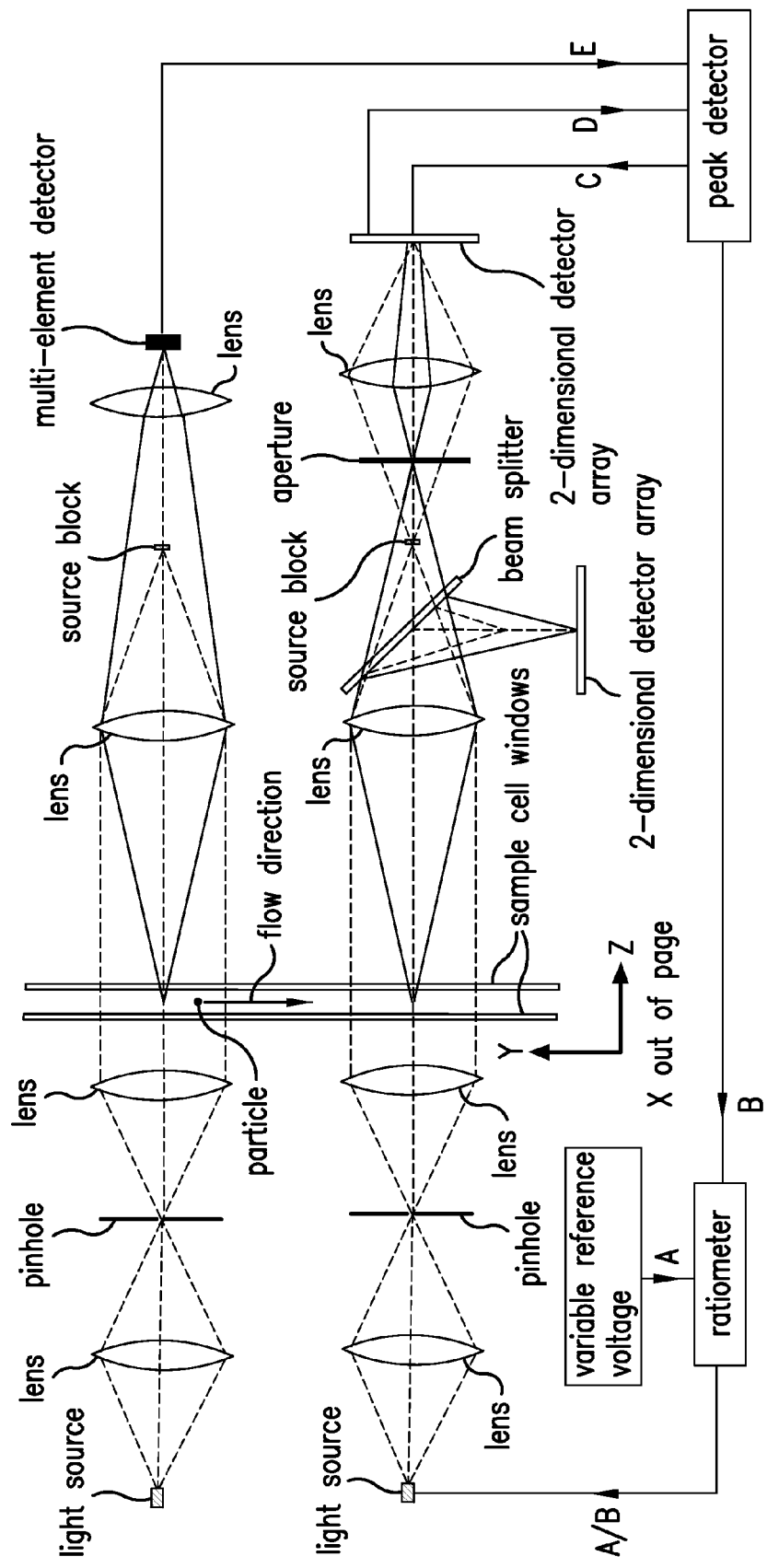
FIG. 49a provides a schematic diagram of an optical system which measures the 2-dimensional scattering distribution and image of each particle, with an analog version of laser power control by an upstream optical system, according to the present invention.

FIG. 49*a* shows an analog version of the laser power control by system B. The peak detector receives the total signal, through port E, from the detector elements of the multi-element detector behind lens B. This detector could also be a single element detector if particle position detection is not used to define a small interaction volume, as described previously. When the peak detector breaks a threshold, it starts (by port C) the integration of the detector arrays in the main system after an appropriate delay, accounting for the distance between the systems and the flow velocity. When the integration is finished, the array (through port D) resets the peak detector to start to look for the next particle. The peak value held by the peak detector is input (input B) to an analog ratiometer with an adjustable reference voltage input A, which can be set to adjust the laser power, and hence the scatter signal, to nearly fill the analog to digital converter of the detector array in the main system. In this way, the light source intensity is rapidly changed to always nearly fill the range of the A/D converter for particles over a large range of size and scattered light signal. The value A/B could also be used to set the gain on the detector arrays, but this will probably not have sufficient speed. This entire process could also be replaced by its digital equivalents, but with much slower response and lower count rate.

One note must be made about diagrams in this application. The size of the scatter collection lens, (i.e. lens 4903 in FIGS. 49 and 50) is not shown in proper size relationship to the source beam in order to show more detail of the source beam and different focal planes in the design. This is true for all scatter collection lenses shown in this disclosure. In all cases we assume that the scatter collection lens is of sufficient diameter to collect scattered light from the particles over all of the scattering angles being measured. In some cases this may require the lens diameter to be much larger than the diameter of the source beam.

This application also describes concepts for combining three different particle size measurement modalities: particle counting, ensemble scattering measurements, and dynamic light scattering. In this case, particle counting is used for the largest particles (>100 microns) which have the largest scattering signals and lowest particle concentration and least coincidence counts. The angular scatter distribution from a particle ensemble is used to determine particle size in the mid-sized range (0.5 to 100 microns). And dynamic light scattering is used to measure particles below 0.5 micron diameter. These defined size range break points, 0.5 and 100 microns, are approximate. These methods will work over a large range of particle size break points because the useful size ranges of these three techniques have substantial overlap:

| | |
|---|---|
| Single beam large particle counting (depends on the source beam size) | 10 to 3000 microns |
| Particle ensemble | 0.1 to 1000 microns |
| Dynamic light scattering | 0.001 to 2 microns |

Figure 53:
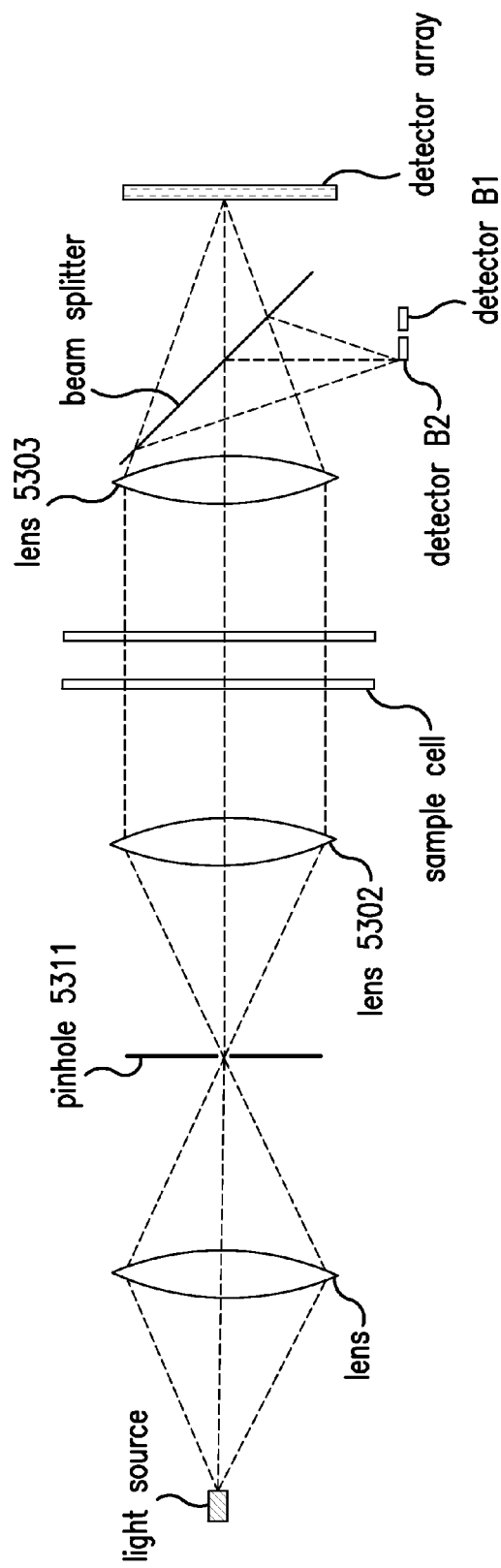
FIG. 53 provides a schematic diagram of an optical system which measures the angular distribution of scattered light with detector arrays in the back focal plane of the scatter light collection lens, according to the present invention.

One problem that can be solved by particle counting is the problem of background drift in ensemble scattering systems which measure large particles at low scattering angles. An ensemble scattering system measures the angular distribution of scattered light from a group of particles instead of a single particle at one time. FIG. 53 shows an ensemble scattering system (except for detectors B1 and B2 which illustrate additional detectors) which illuminates the particles with a nearly collimated light beam and collects light scattered from many particles in the dispersion which flow through the sample cell. The light source is focused through pinhole 5311, which removes high angle defects in the beam intensity profile. Lens 5302 collimates the beam through the sample cell. Lens 5303 collects scattered light from the particles in the sample cell and focuses that light onto a detector array in the back focal plane of lens 5303. An example of the detector array design is shown in FIG. 54. The optical system measures scattered light in certain angular ranges which are defined by the set of detector elements. The elements can have different shapes, but in general the scattering angle range for each element is determined by the radius from the optical axis in the back focal plane of lens 5303. In some cases, the detector array will have a central detector, D0, which captures the light from the source beam. Detectors D1, D2, etc. collect various angular ranges of scattered light. Each detector element is connected to its own separate electronic integrator, which is connected to a multiplexing circuit and analog to digital converter (ADC) as shown in FIG. 54 for detectors D3, D4, D5, and D6. This multiplexer sequentially samples each of the integrators which may integrate while many particles pass through the beam. So particle pulses cannot be measured in the ensemble system. All detector elements are connected to the multiplexer through integrators in a particle ensemble measuring system. FIG. 54 shows the modification, for detector elements D0, D1 and D2, proposed by this invention.

The detector elements which measure the low angle scatter (for example D1 and D2) usually see a very large scattering background without particles in the sample cell. This background is due to debris on optical surfaces or poor laser beam quality. Mechanical drift of the optics can cause this background light to vary with time. Usually the detector array is scanned with only clean dispersant in the sample cell to produce background scatter readings which are then subtracted from the subsequent readings of the actual particle dispersion. So first the detector integrators are integrated and scanned without any particles in the sample cell and then particles are added to the dispersion and the detector integrators are integrated and scanned a second time. The first background scan data is subtracted from this second scan for each detector element in the array. However, if the actual background drifts between the two scans, a true particle scattering distribution will not be produced by the difference between these two scans.

A much better solution is to connect each of the detector elements, for the lowest angle scatter, to individual analog to digital converters, or peak detectors as disclosed before by this inventor. Then these signals could be analyzed by many of the counting methods which were disclosed by this inventor. This would essentially produce an ensemble/counting hybrid instrument which would produce counting distributions for the large particles at low scattering angles and deconvolved particle size distributions from the long time integrated detector elements (ensemble measurement) at higher scattering angles for the smaller particles. These distributions can be converted to a common format (such as particle volume vs. size or particle count vs. size) and combined into one distribution. The advantage is that the frequency range for the particle pulses is much higher than the frequencies of the background drift. And so these pulses can be measured accurately by subtracting the local signal baseline (under the pulse), determined from interpolation of the signals on the leading and trailing edge of each pulse, using the digitized signal samples. At very low scattering angles, the scattering signal drops off by at least the fourth power of particle diameter. Therefore larger particle pulses will stand out from the signals from many smaller particles which may be in the beam at any instant of time. Also the number concentration of larger particle will be low and provide for true single particle counting.

Figure 55:
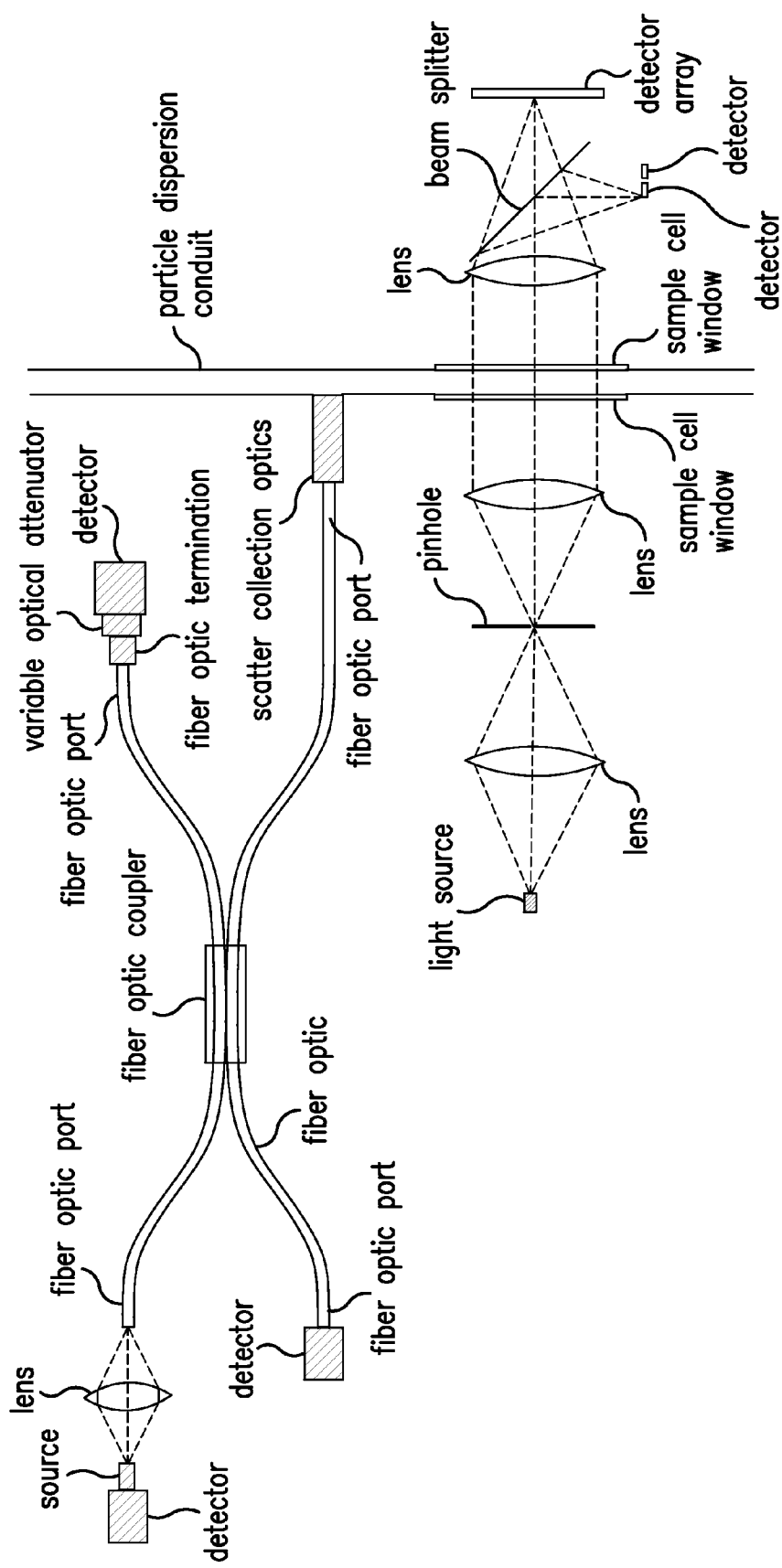
FIG. 55 provides a schematic diagram of an optical system which combines dynamic light scattering and angular light scattering measurements, according to the present invention.

The smallest particles are measured using dynamic light scattering as shown in FIG. 55. A fiber optic dynamic light scattering system, as described previously by the inventor, is inserted into the tubing through which the particle dispersion flows. This fiber optic interferometer measures the Doppler optical spectral broadening of the scattered light caused by Brownian motion of the particles. The size range is determined from this spectral broadening by techniques described previously by this inventor. The counting and ensemble scattering measurements are made with dispersion flowing through the system. This flow would be turned off during the collection of dynamic light scattering signals to avoid Doppler shifts in the scattering spectrum due to particle motion. The particle size distributions determined from each of the three systems: counting, ensemble, and dynamic light scattering are combined into one particle size distribution which covers a very large size range.

Figure 52:
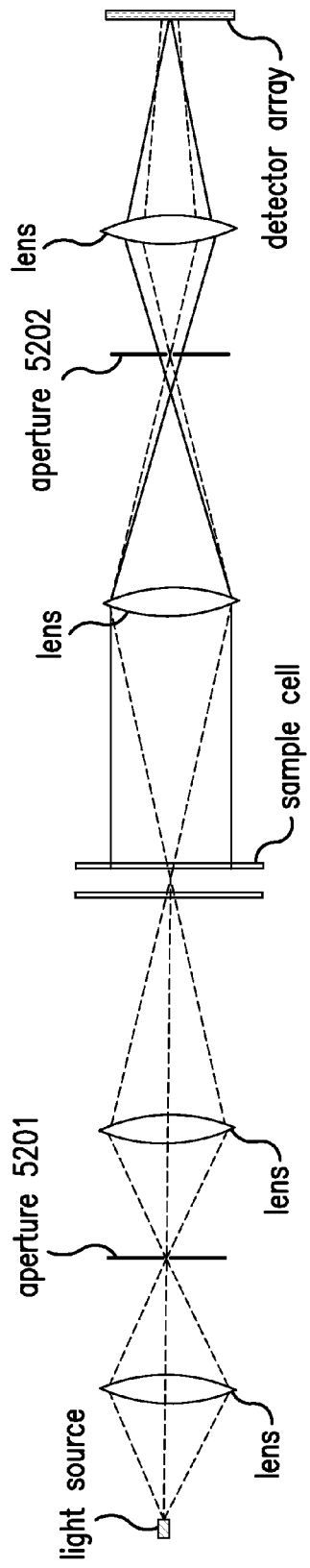
FIG. 52 provides a schematic diagram showing multiple planes, in an optical system, where an aperture would eliminate scattered light from particles passing through portions of the light beam with poor intensity uniformity, according to the present invention.
Figure 56:
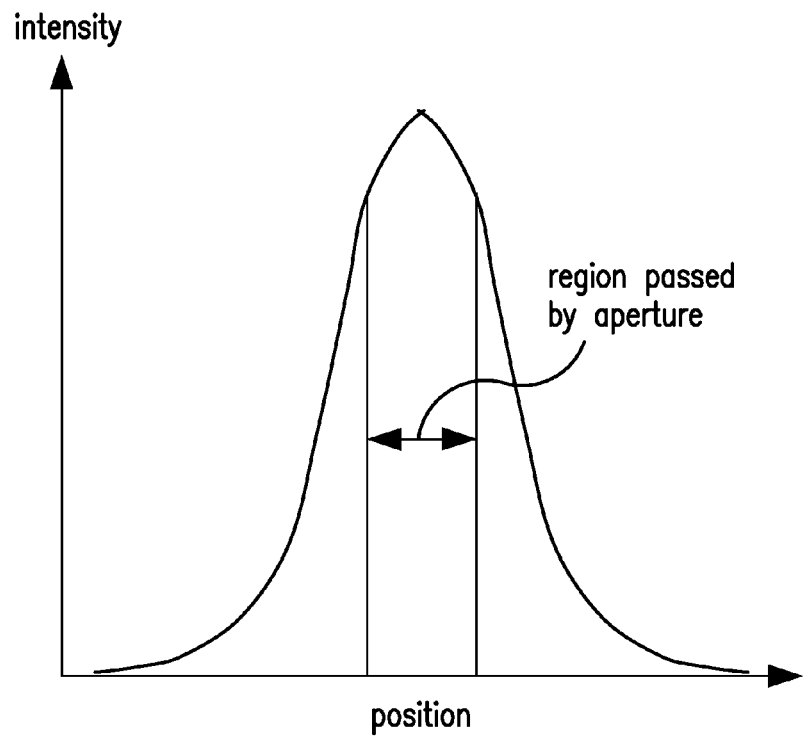
FIG. 56 provides a graph showing the intensity distribution across the width of an optical beam and the portion of the beam which is passed by an aperture, according to the present invention.
Figure 57:
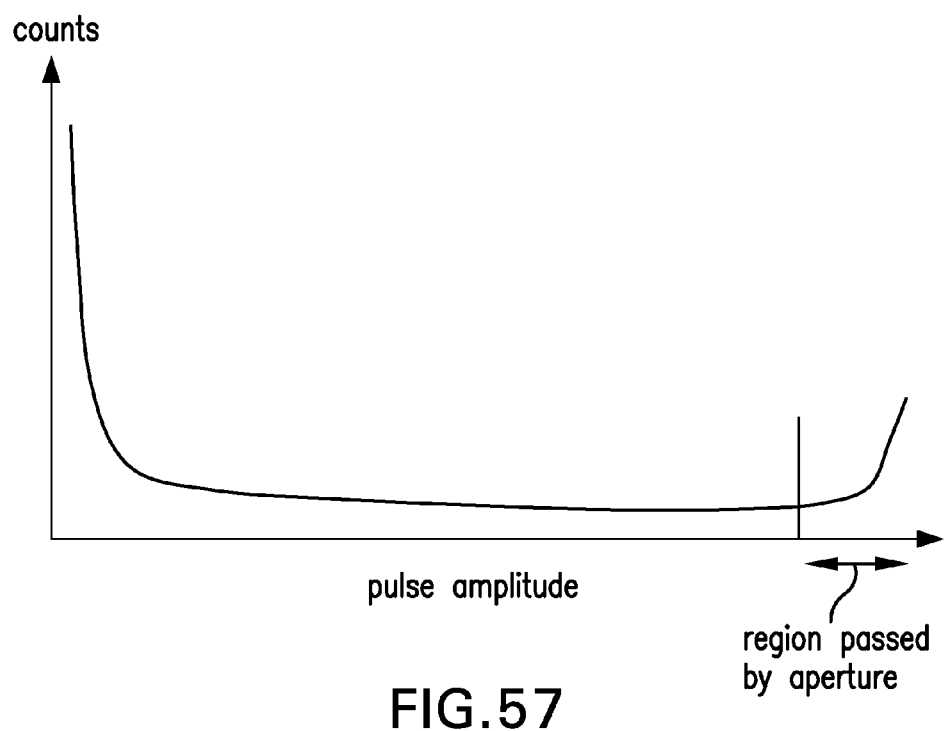
FIG. 57 provides a graph showing a count distribution, indicating the portion of the count distribution which is removed by an aperture, according to the present invention.

The particle counting uses the lowest angle zones (D1, D2, etc.) and the beam measuring zone (D0) of the detector array (an example of a detector array is shown in FIG. 54). Each of these detector elements are connected to a separate ADC to measure the scattering pulse in D1, D2, etc. and the signal drop on detector D0 as each particle passes through the interaction volume where the beam illuminates and from which the scattering detectors can receive scattered light from the particles. One problem is that the amount of scattered light is nearly proportional to the illumination intensity of the source on the particle. Therefore as particles pass through different regions in the beam they may produce different pulse heights. FIG. 56 shows a Gaussian intensity distribution which might be characteristic of the cross-section of a laser beam. Since the probability of particle passing through this beam at any position is approximately the same, we can generate the count vs. pulse amplitude distribution in FIG. 57, which shows the count distribution for large number of identical particles (also shown in FIGS. 10 and 10a). Notice that most of the particles pass through the low intensity portions of the intensity distribution and many particles also pass through the uniform intensity region which is close to the peak of the intensity distribution, with a region of lower count level in between. This broad count response to a group of mono-sized particles will prevent accurate determination of complicated particle size distributions, because the pulse heights may be ambiguous for various sized particles. For example, a large particle passing through the lower intensity region can produce a pulse which is very similar to that from a smaller particle passing through the higher intensity region. The region of the intensity distribution which can produce scattered light into the detectors must be truncated by apertures in the source optics (aperture 5201 in FIG. 52) or in the detection optics (aperture 5202 in FIG. 52). Either of these apertures can create a "region passed by aperture" as indicated in FIGS. 56 and 57. By using either or both apertures, only the upper region of the count vs. pulse amplitude distribution will be seen for many particles of a single particle size. This truncation by aperture can be used in any of the systems described in this document to reduce the broadening of the particle count peaks due to intensity variations of the source. Any residual broadening is then removed by algorithms such as deconvolution.

Figure 58A:
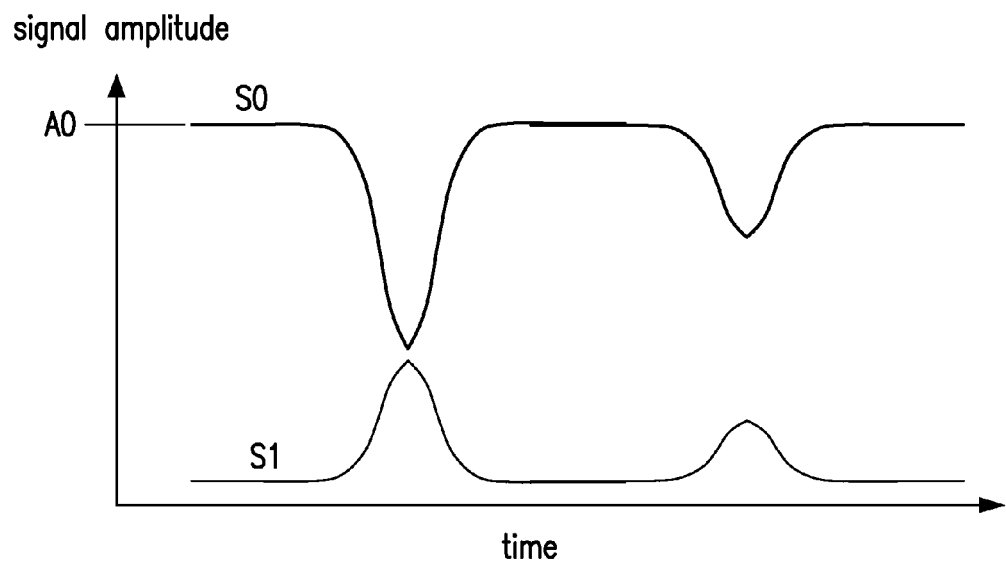
FIG. 58A provides a graph showing two scatter signals, the first signal (S0) showing attenuation of the light beam due to particle scatter, and the second signal (S1) showing a signal from a detector receiving scattered light from a particle, according to the present invention.
Figure 58B:
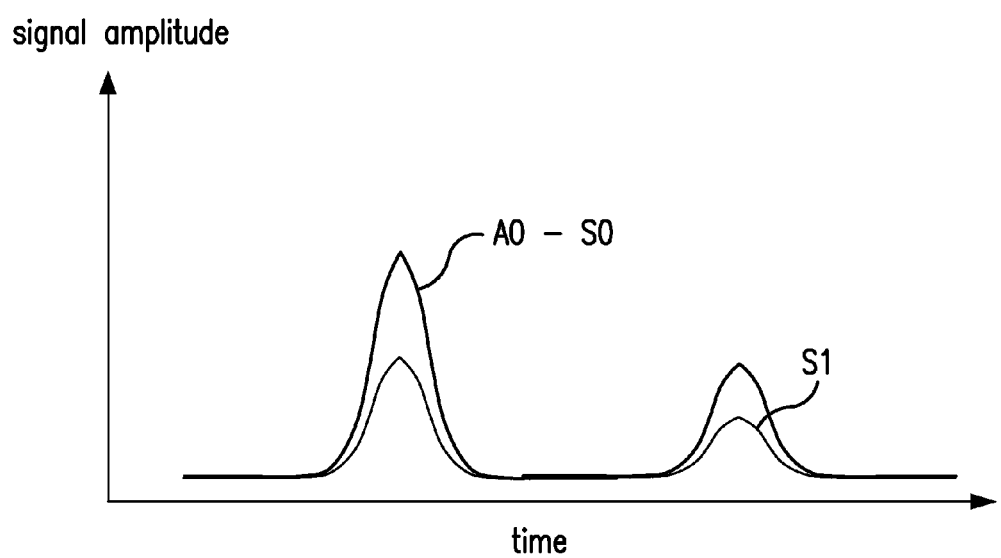
FIG. 58B provides a graph showing two signals produced after the first signal in FIG. 58A is modified to produce a signal which increases with the scattered light.
Figure 59:
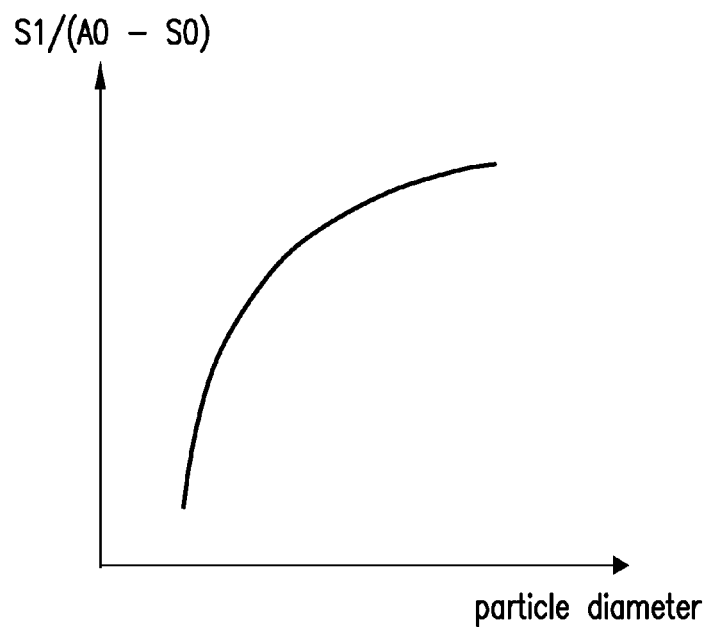
FIG. 59 provides a graph showing the ratio of values from FIG. 58B as a function of particle diameter.

Another method for eliminating this intensity distribution effect is to use ratios of detector signals. This works particularly well when many of the detectors have scatter signals. However, for very large particles, only scattering detector D1 will see a high scatter signal with high signal to noise. So for very large particles, the apertures described previously may be required to use the absolute scatter from D1. Another solution is to use the ratio of the drop in D0 (signal S0) and the increase in D1 (signal S1) due to scatter as shown in FIG. 58A. As a particle passes through the beam D0 will decrease by approximately the total scattered light and D1 will increase by only the amount of light scattered into the angular range defined by that detector. The drop in D0 can be determined by subtracting the minimum of drop in S0 from the baseline A0 to produce a positive pulse A0-S0 as shown in FIG. 58B. As shown in FIG. 59, the ratio of either the integral or the peak value of the corresponding pulses from these two signals can be used to determine the size of the counted particle for the largest size particles which have insufficient scatter signal in D2 to produce a ratio between S1 and S2. As long as D2 has sufficient scatter signal and D2 captures a portion of the primary lobe of the angular scatter distribution, the ratio between S1 and S2 will produce more accurate indication of size, than a ratio between S0 and S1. The primary lobe of the scattering distribution is the portion of the distribution from zero scattering angle up to the scattering angle where the size information becomes more ambiguous and particle composition dependent. Usually this happens when the scatter function first drops below 20% of the zero angle (maximum) value of the function. For a certain range of smaller particles, the ratio between S1 and S3 (if D3 were connected to an A/D as D2) may have higher sensitivity to particle size than the ratio of S1 to S2. For smaller particle diameters, ratios to larger angle scatter signals will provide better sensitivity. A0-S0, S1, etc. could be also be analyzed using the other methods described in this document.

Figure 60:
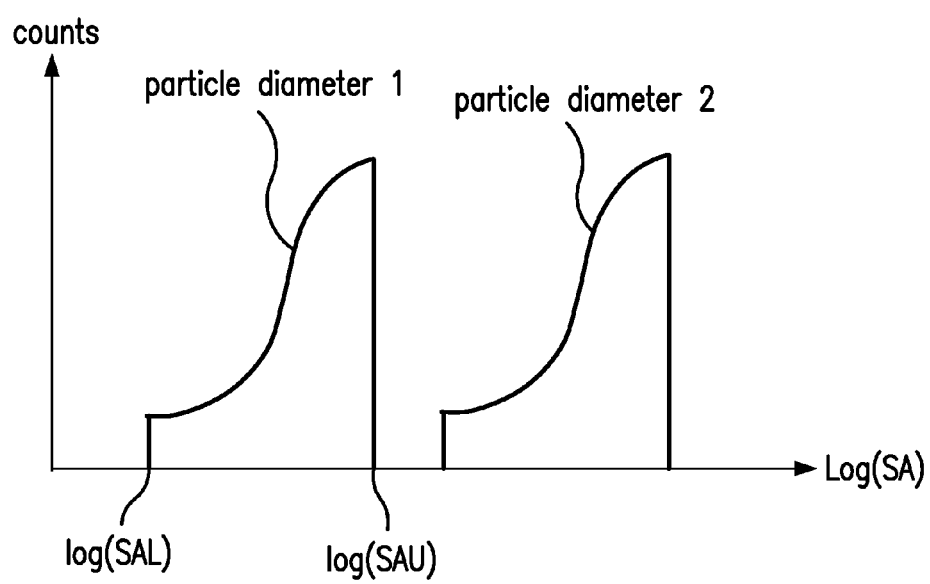
FIG. 60 provides a graph showing count distribution as a function of a logarithm of scatter signal, or scatter parameter, for two different particle sizes, the functional shapes demonstrating the shift-invariant impulse response, according to the present invention.
Figure 61:
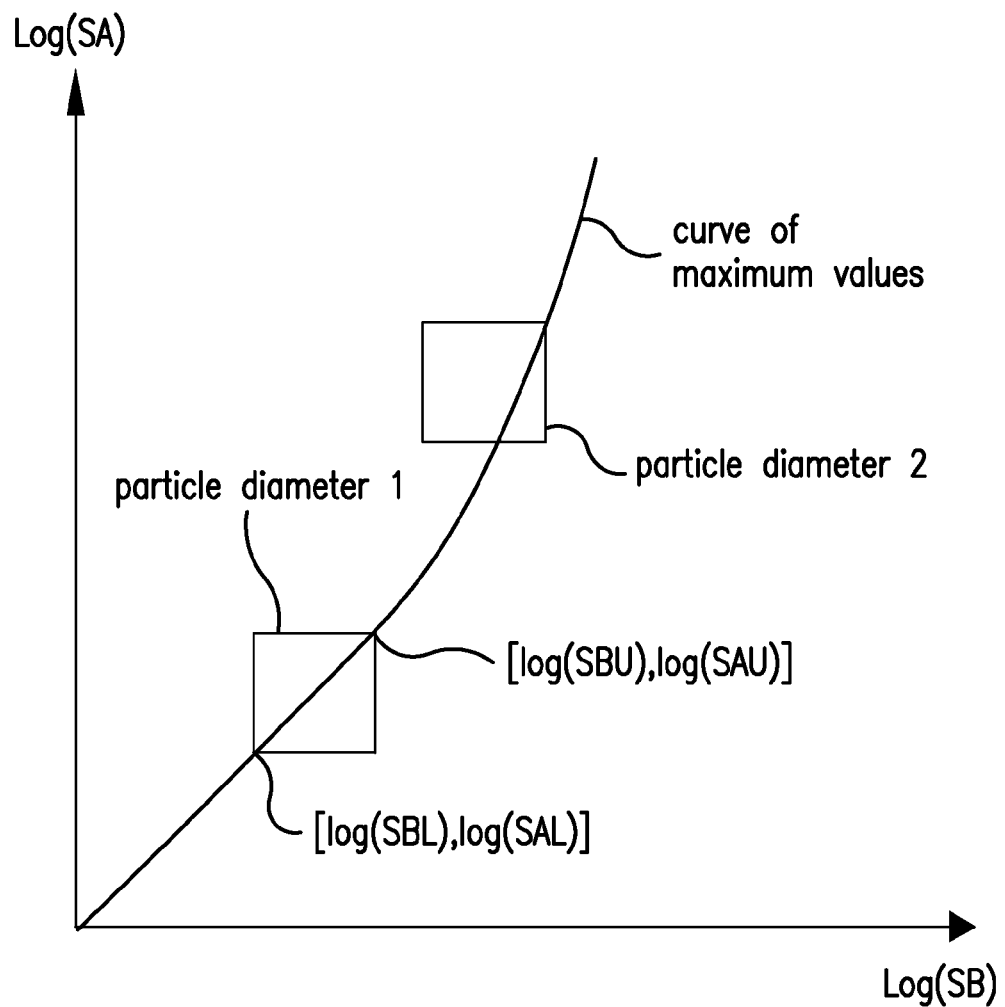
FIG. 61 provides a graph showing the response region limits for a two-dimensional scatter plot, of counted events, as a function of the logarithms of two scattering signal values, wherein the functional shapes demonstrate the two-dimensional shift-invariant impulse response for particles of two different diameters, according to the present invention.

The signal ratio technique is needed when the "region passed by aperture" in FIGS. 56 and 57 is too large such that mono-sized particles produce pulse peaks over a large amplitude range. For example, if no aperture were used, then mono-sized particles will produce the entire count distribution shown in FIG. 57, with ambiguity between small particles passing through the center of the Gaussian intensity distribution and large particles passing through the tail of the distribution. In cases where the "region passed by aperture" is too large, the use of signal ratios (as described previously) is required to reduce the effect of the intensity variation (because the intensity variation drops out of the ratio, approximately). If the source intensity distribution can be made more uniform by use of an aperture (aperture 5201 of FIG. 52) or by use of a non-coherent source, or if the viewing aperture (aperture 5202 in FIG. 52) of the detector only views a restricted region where the source intensity is more uniform, then scattering amplitude can be used directly to determine size as shown in FIGS. 60 and 61, using the methods described for FIGS. 26, 27, 27a, and 28. This may have some advantages when only one detector has sufficient signal and two signals are not available to create a ratio. Also the absolute signal amplitude information, which is lost in the ratio calculation, can be useful in determining the particle composition and in eliminating pulses which are due to noise, as will be described in FIG. 61. FIG. 57 shows a count vs. pulse amplitude response with a "region passed by aperture". This count distribution in the "region passed by aperture" is plotted on a logarithmic scale of S (or pulse peak or integral) for two different particle sizes, in FIG. 60. Each function has an upper and lower limit in log(S). Notice that, in logarithmic S space, the two functions are shift invariant to particle diameter. The upper limit is due to particles which pass through the peak of the source intensity distribution and the lower limit is from the edge of the truncated source intensity profile. So that the count per unit log(S) interval vs. log(S), Ns(log(S)), distribution from particles of the count vs. particle diameter distribution Nd(d) is the convolution between the shift invariant function in FIG. 60, H(log(S)), and the count vs. particle size distribution, Nd(d) as described previously for FIGS. 26, 27, 27a and 28:

$$Ns(\log(S)) = Nd(d) \ominus H(\log(S))$$

This equation is easily inverted by using iterative deconvolution to determine Nd(d) by using H(log(S)) to deconvolve Ns(log(S)). In some cases, for example when S=A0–S0, the form of this equation may not be a convolution and a more generalized matrix equation must be solved.

$$Ns(\log(S)) = H(\log(S)) * Nd(d)$$

Where H is the matrix and Nd(d) is a vector of the actual counts per unit size interval. Each column of matrix H is the measured count per unit log(S) interval vs. log(S) response to a particle of size corresponding to the element in Nd(d) which multiplies times it in the matrix multiply '*'. This matrix equation can be solved for Nd(d), given Ns(log(S)) and H(log (S)). This equation will also hold for the case where the functions of log(S) are replaced by other functions of S.

Figure 39:
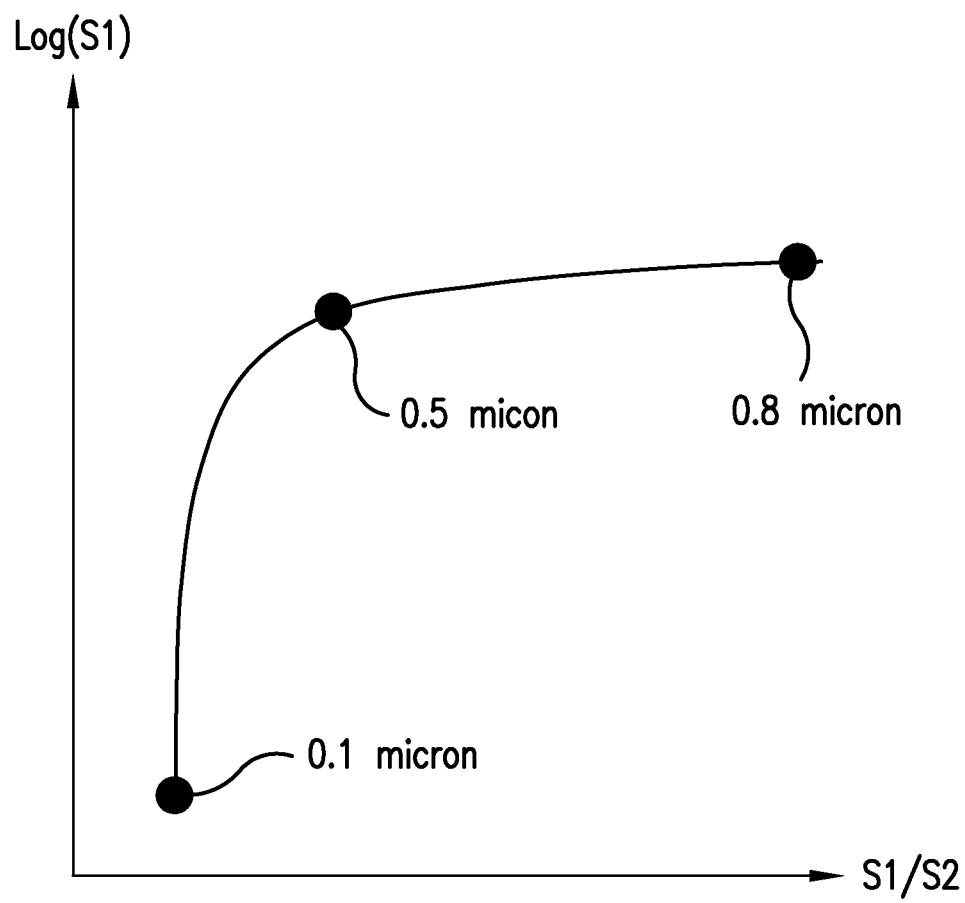
FIG. 39 provides a graph showing a functional relationship between the logarithm of a scattering signal value and the ratio of signal values, measured in two ranges of scattering angle, for various particle diameters, according to the present invention.
Figure 62:
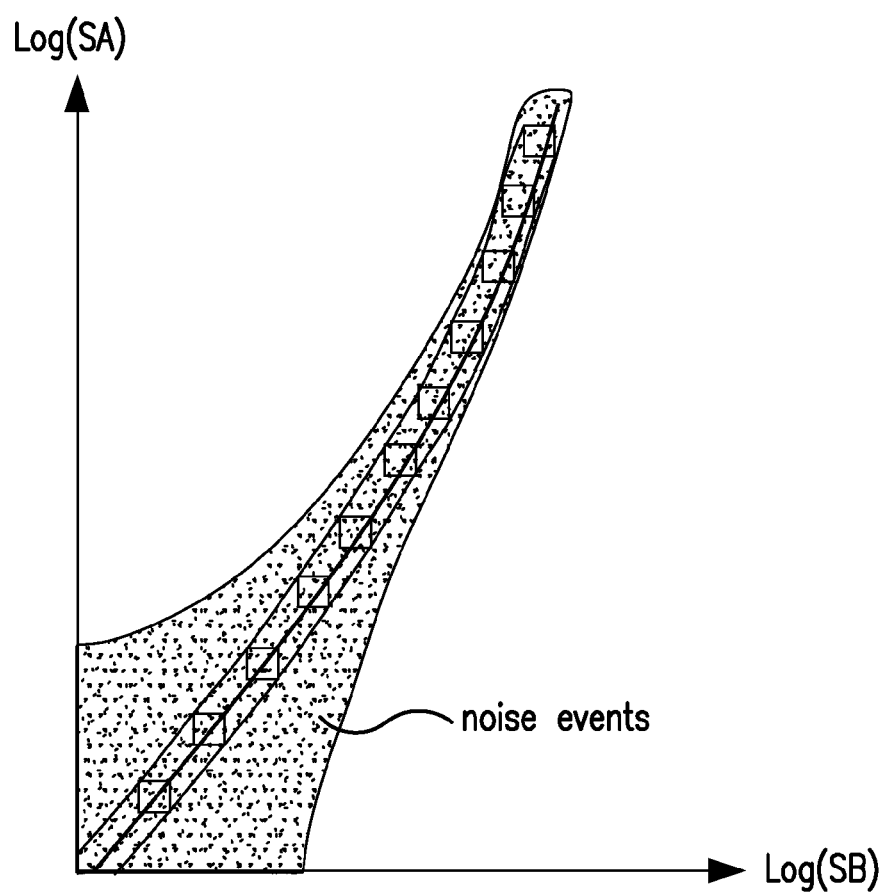
FIG. 62 provides a graph showing a scatter plot of signal events, as described in FIG. 61, wherein particle scatter impulse response region limits and noise events are indicated.

FIG. 61 shows a scatter plot of the counted data points in the two dimensional space, where the two dimensions are the logarithm of pulse amplitude or pulse integral for two different signals A or B. For example SA and SB could be S1 and S2, or A0-S0 and S1. Two squares are shown which encompass the approximate region where counts from particles could occur for each of two particle diameters. SAU and SAL refer to the upper and lower limits of the signal, respectively, as shown in FIG. 60. The lower limit, SAL, is determined by the cutoff of the aperture on the source intensity profile. The upper limit, SAU, is the maximum signal value when the particle passes through the peak of the source intensity profile. In the two dimensional space, shown in FIG. 61, points are shown where the particle passes through the intensity peak, [log(SBU),log(SAU)], and where the particle passes through the edge of the intensity profile, [log(SBL),log (SAL)], where the intensity is lowest. As particle size changes, this square region will move along a curve which describes the scatter for particles of a certain composition, as shown in FIG. 62. The moving square will define a region, between the two lines which pass through the edges of the square. Real particles can only produce points within this region. Points outside this region can be rejected as noise points or artifact signals. This two dimensional count profile can be deconvolved using 2-dimensional image deconvolution techniques (as described previously), because each square defines the outline of the two dimensional impulse response in Log(S) space. The two dimensional count profile is the concentration (counted points per unit area of log(SA) and log(SB) plot 2-dimensional space) of counted points at each coordinate in the log(SA) and log(SB) space. This count concentration could be plotted as the Z dimension of a 3-dimensional plot where the X and Y dimensions are log(SA) and log(SB), respectively. The two dimensional impulse function plotted in the Z dimension of this 3-dimensional space is determined from the product of functions as shown in FIG. 60, one along each of the log(SA) and log(SB) axes of FIGS. 61 and 62. If absolute signal values are used instead of signal ratios, the single size response will be broader in the multi-dimensional space and the deconvolution (or general inversion if not a convolution) problem will be more ill-conditioned. However, this can be the best choice for very small particles where the absolute signals will have much greater particle size sensitivity than the signal ratios. FIG. 39 shows a hybrid 2-dimensional plot of Log(S1) vs. S1/S2 which combines these two methods. Three data points for 0.1, 0.5, and 0.8 micron diameter particles are shown to illustrate size dependence. The S1/S2 axis shows more sensitivity to larger particles and the Log(S1) axis shows more sensitivity to smaller particles. This hybrid plot is a good compromise over a large size range. All of the techniques for multi-dimensional analysis, described previously, apply to this case. In this case, the 2 dimensional space would be deconvolved primarily in the Log(S1) direction only, where the function broadening due to source intensity variation occurs. Very little broadening will occur in the S1/S2 function dimension due to the ratio correction, but the single particle response should include any broadening in the S1/S2 direction also. If deconvolution is too slow, another technique may be used to eliminate broadening in the Log(S1) direction. After the outlier events are eliminated and the Cg function is created from the raw count points on the Log(S1): S1/S2 plane, as described for FIG. 26, slices of that Cg function can be made parallel to the Log(S1) axis at various values of S1/S2. Each slice will provide a function of Log(S1) with the broadening due to Log(S1) at that value of S1/S2. Each slice function will look like one of the functions shown in FIG. 60. Since this function is the known function from theoretical or empirical measurements of single sized particles, a fitting algorithm can very quickly determine the position of this function on the Log(S1) axis. Each function in each slice is then replaced by a single point at a consistent location (center or upper edge SAU in FIG. 60, etc.) of the function in each slice, with a value equal to the total particles counted in that slice. Then the broad distribution of points in Cg becomes a single line in Log(S1): (S1/S2) space, as in the deconvolution case. In either case, the count distribution function along this single line has one to one correspondence to particle size. Therefore, the counts at each point along this line represent the number of particles with a size corresponding to that point. This line data can also be analyzed by methods described elsewhere in this application to produce the particle count vs. size distribution. These multi-dimensional views and the previously described methods apply to all combinations of signals (S1, S2, etc.), Log(signals) (Log(S1), Log(S2), etc), Ratios of signals (S2/S1, S3/S1, etc), and/or any combinations of these (S1/S2 and Log(S1), etc.). Where the signals S1, S2, etc. are functions of the measured scatter signal (such as peak value, integral, value at a certain time during the pulse, product of two scatter signals, etc.)

FIGS. 10*a*, 26, 27, 27*a*, 28, 60, 61, 62 all describe different aspects of correction for broadening of the count distribution vs. signal response for a single sized particle. FIG. 10*a* describes the particle count distribution vs. scattering signal from single sized particles in a source spot with a Gaussian intensity profile. This figure shows the effects of spatial truncation (FIG. 1A for example) of the beam, before the sample cell area, using an aperture in a plane conjugate to the plane of the particles. More particles will be counted in the regions of low slope in the intensity distribution, explaining the rise at each end of the count distribution in FIG. 10*a*. FIGS. 26 through 28 show the general form of the 2-dimensional count distribution, showing that the count distribution from a group of single sized particles would be concentrated in region with shape similar to an ellipse. Ideally this ellipse impulse response would collapse to a line segment which is equivalent to the major axis of each ellipse in these figures, if the only source of count distribution broadening is the intensity profile of the source. The projection of the count distribution along this line, onto the Log(S2) and Log(S1) axes will look like the function in FIG. 10*a*. In this case, we obtain FIGS. 60, 61, and 62. FIG. 60 shows the same response as FIG. 10*a*, with truncation of the source beam at a very high intensity level to eliminate the long intensity tails. The distributions in FIG. 60 (for Log(S)) are for ideal truncation, the actual functions will look more like the "with aperture (aberrated)" case in FIG. 10*a* (but for the Log(S) instead of S case). FIGS. 61 and 62 show rectangles indicating the axes of these projections and the extent of the functions in FIG. 60, in 2-dimensions. This 2-dimensional response to a single particle is the impulse response for the deconvolution of the 2-dimensional count distribution. Each of the 1-dimensional distributions of count per unit Log(S1) vs. Log(S1) and count per unit Log(S2) vs. Log(S2) could each be deconvolved separately using the impulse response similar to that shown in FIG. 10*a* or FIG. 60. Then the results from these two deconvolved functions would be combined between corresponding data points to create a 2-dimensional plot without broadening. Also a single 1-dimensional distribution (signal vs. particle size) could also be deconvolved to use only absolute scattering signal as the particle size indicator. However, the 2-dimensional deconvolution, using existing image deconvolution algorithms, should produce better results but with longer computation time. Since this deconvolution is only done once, after all of the particles are counted, the long computation time may not be an issue. The 2-dimensional response function can be determined by measuring the 2-dimensional count distribution from a large number of single sized particles, which will randomly pass through paths covering the entire source spot. If the signal threshold in FIG. 10a is set too high, the bottom portion of the response from the smallest particle may be cut off, requiring a matrix model and inversion instead of a convolution model and deconvolution. The best solution is to insure that the signal detection threshold is lower than lowest end of the count response from the smallest particle. If binary optic of other methods are used to create a flat top intensity distribution for the source spot, then the line segment will collapse close to a small spot in 2-dimensional space and the deconvolution will be very well conditioned. A longer line segment or width of the "ellipse" of the single size response will create an ill-conditioned inversion problem, producing larger errors in the resulting size distribution. The 1-dimensional or 2-dimensional particle count per unit log(S) distribution, after deconvolution, will have a one to one correspondence to size, because each particle diameter will have a corresponding location in S1,S2 space or Log(S1),Log(S2) space. The counts per unit S1 and S2 interval can be converted to counts per particle size interval based upon this one to one correspondence. Also each signal could be separately analyzed as signal vs. size parameter to produce a size distribution for each signal in the size range where that signal has the best size sensitivity or monotonicity. Then these multiple size distributions are combined by concatenation with overlap regions as shown previously.

These multi-dimensional views and the previously described methods apply to all combinations of signals (S1, S2, etc.), Log(signals) (Log(S1), Log(S2), etc), Ratios of signals (S2/S1, S3/S1, etc), and/or any combinations of these (S1/S2 and Log(S1), etc.). Where the signals S1, S2, etc. are functions of the measured scatter signal (such as peak value, integral, value at a certain time during the pulse, product of two scatter signals, etc.) These signals can include: individual scatter signal peak heights (the individual peak of each signal without simultaneous detection), signals values measured simultaneously at the time when a chosen detector is at peak value, scatter signal pulse widths (time), pulse shape, time delay between pulses from different detectors, pulse frequency spectrum parameters (pulse structure such as heterodyne oscillation frequency), integrals of pulses, product of two signals from two different detectors (correlation relationship), integral of the product of two signal pulses from different detectors, ratio of any two of the parameters in this list, logarithm of any parameter in this list. The logarithm scale for the count distribution is particularly useful to remove broadening from spatial variations of beam intensity with deconvolution techniques, because then the count response is shift invariant to signal level. Also peak detection (simultaneous or individual) will also remove some broadening from the single size response to improve inversion or deconvolution results. The above parameters will create single particle size response functions which can be used to remove broadening of those parameters in the multi-dimensional space, through deconvolution or solution of simultaneous equations. These parameters can also be used to create rules for rejection of signal events which are not particles or do not have sufficient signal to noise.

Figure 63:
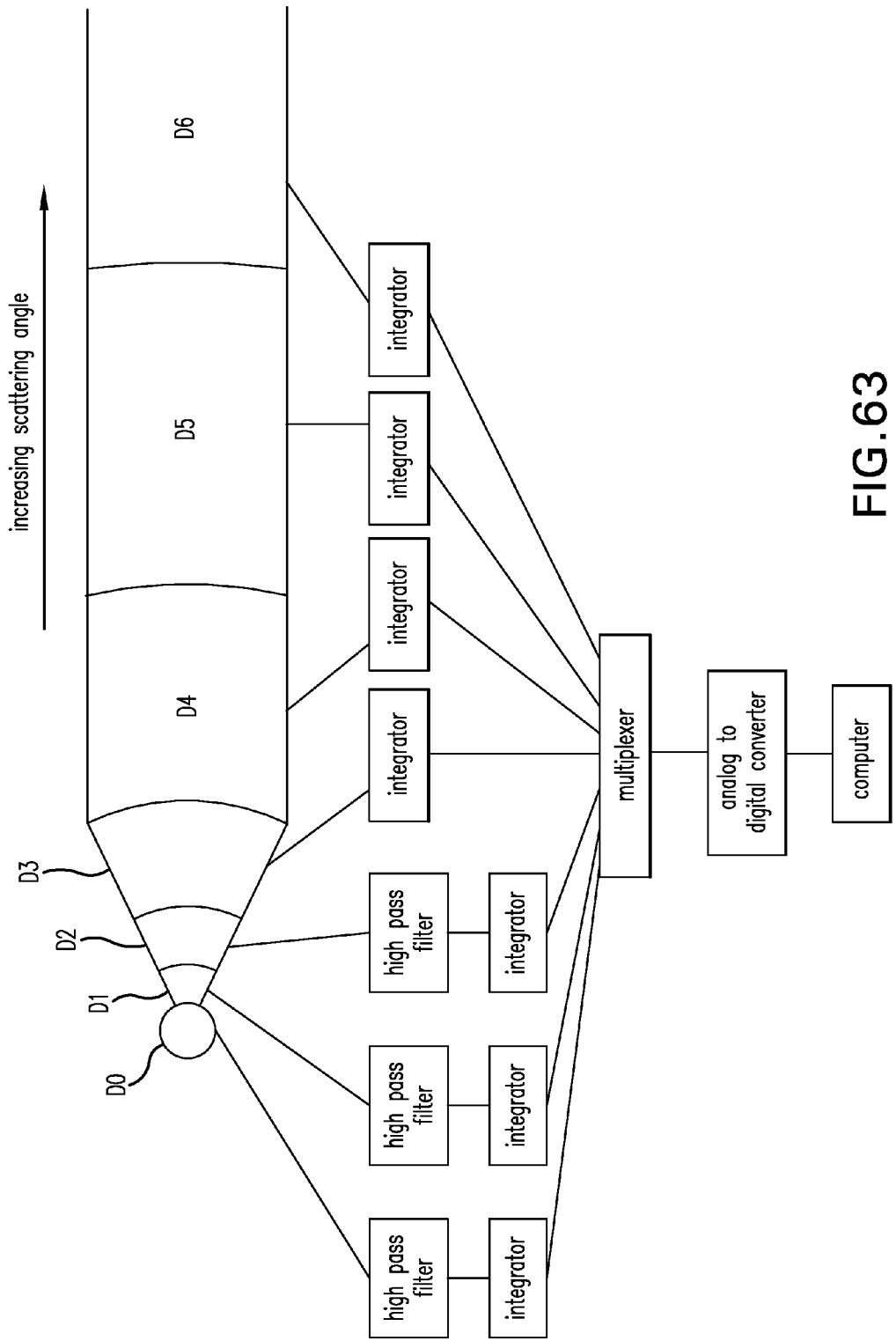
FIG. 63 provides a block diagram of a detector array and electronics for measuring scatter signals from individual particles and a particle ensemble, by utilizing high pass filters, according to the present invention.

The previous concept for ensemble particle systems uses particle counting to eliminate the particle size errors caused by background drift in the angular scattering signals, because the frequency content of the counted pulses is much higher than the background drift, and so the pulses can be detected by methods described previously by this inventor, without being effected by background drift. The local baseline is easily subtracted from each pulse because the background drift is negligible during the period of the pulse. However, this advantage can also be used with the integrators as shown in FIG. 63. The slowly varying baseline can be removed by high pass analog electronic filters with a cutoff frequency between the lowest frequency of the particle scatter pulse spectrum and the highest frequency of the background drift spectrum. The input to each of the integrators which follow each high pass filter are the particle scatter pulses, without background which is attenuated by the filter. These pulses can be integrated and multiplexed into the same analog to digital converter as the higher scattering angle signals, which do not need the highpass filtering to remove the baseline drift. These integrators integrate over an extended period where many particles pass through the beam. In the case of smaller particles, there may be many particles in the beam at any instant in time. However, since the scatter signal from larger particles is much larger than that for smaller particles and with many smaller particles in the beam, these smaller particle signals will have very low fluctuations relative to the discrete pulses from the larger particles. So this high pass filtering will select the larger particles where the scatter signal fluctuations are large. This measurement could also be made with an RMS (root mean squared) module which only detects the higher frequency portion of the scatter signal for the lower angle detectors. All of these integrated signals, from low and high angle scatter detectors, are then inverted by techniques such as deconvolution. The detector signals could also be digitized directly; and the filtering and integration steps could be done digitally. However, the optical scatter model for the deconvolution must include the loss of the small particle contribution to these filtered signals, because as the number of particles in the beam increases, the higher frequency components will be attenuated due to overlap of pulses. Given this attenuation process and the fact that signals at the lowest scattering angles scale as the fourth power of particle diameter, the smaller particle signals should not be significant in these filtered low angle signals. The correction to the model is very minor; essentially the small particle contribution to these filtered detector signals can be assumed to be small in the scattering model.

These methods do not assume any particular number of lower angle zones. For example, D0, D1, D2, and D3 could be handled with the techniques above. Essentially, any detectors with background drift problems should be handled with these methods.

Normally all of the ADC scans of the multiplexer output are summed together and this sum is then inverted to produce the particle size distribution. But due to the large difference in scattering efficiency between large and small particles, smaller particles can be lost in the scatter signal of larger ones in this sum. This problem can be mitigated by shortening the integration time for each multiplexer scan and ADC cycle to be shorter than the period between pulses from the large particles. Then each multiplexer scan and subsequent digitization can be stored in memory and compared to each other for scattering angle distribution. ADC scans of similar scattering angular distribution shape are summed together and inverted separately to produce multiple particle size distributions. Then these resulting particle size distributions are summed together, each weighted by the amount of total integration time of its summed ADC scans. In this way, scans which contain larger particles will be summed together and inverted to produce the large particle size portion of the size distribution and scans which contain only smaller particles will be summed together and inverted to produce the small particle size portion of the size distribution, without errors caused by the presence of higher angle scatter from larger particles.

Another method to measure larger particles is to place a sinusoidal target in an image plane of the sample cell on front of a scatter detector as described previously by this inventor. The dispersant flow could be turned off and then the particle settling velocity could be measured by the modulation frequency of the scatter signal from individual particles settling through the source beam. The hydrodynamic diameter of each particle can then be determined from the particle density, and dispersant density and viscosity.

Finally the three size distributions from dynamic light scattering, ensemble scattering and counting are combined to produce one single distribution over entire size range of the instrument by scaling each size distribution to the adjacent distribution, using overlapping portions of the distribution. Then segments of each distribution can be concatenated together to produce the complete size distribution, with blending between adjacent distributions in a portion of each overlap region. This method works well but it does not make most effective use of the information contained in the data from the three sizing methods. Each inversion process for each of the three techniques would benefit from size information produced by other techniques which produce size information in its size range. This problem may be better solved by inverting all three data sets together so that each of the three methods can benefit from information generated by the others at each step during the iterative inversion process. For example, the logarithmic power spectrum (dynamic light scattering), logarithmic angular scattering distribution and logarithmic count distribution could be concatenated into a single data vector and deconvolved using an impulse response of likewise concatenated theoretical data. However, in order to produce a single shift invariant function, the scale of the counting data must be changed to produce a scale which is linear with particle size. For example, the pulse heights on an angular detector array will scale nearly as a power function of particle size, but the power spectrum and ensemble angular scattering distributions shift along the log frequency and log angle axes linearly with particle size. So a function of the pulse heights must be used from the count data to provide a count function which shifts by the same amount (linear with particle size) as the dynamic light scattering and ensemble distributions. This function may vary depending upon the particle size range, but for low scattering angles the pulse height would scale as the fourth power of the particle diameter, so that the log of the quarter power of the pulse heights should be concatenated into the data vector. This technique will work even though the concatenated vectors are measured verses different parameters (logarithm of frequency for dynamic light scattering, logarithm of scattering angle for ensemble scattering, and logarithm of pulse height or integral for counting), simply because each function will shift by the same amount, in its own space, with change in particle diameter. And so the concatenation of the three vectors will produce a single shift invariant function which can be inverted by powerful deconvolution techniques to determine the particle size distribution. This technique can also be used with any two of the measurement methods (for example: ensemble scattering and dynamic light scattering) to provide particle size over smaller size ranges than the three measurement process. In the concatenated problem where this convolution form is not realized, the problem can also be formulated as a matrix equation, where the function variables can be Log(x) or x (where x is the variable frequency (dynamic light scattering), scattering angle (ensemble angular scattering) or S (the counting parameter)). Again these functions can be concatenated into vectors and a matrix of theoretical concatenated vectors. And this single matrix equation, which contains the dynamic light scatter, the ensemble scatter and the count data, can be solved for the differential particle volume vs. size distribution, Vd, without being restricted to convolution relationships or the need for matching function shifts with particle size.

$$Fm = Ht*Vd$$

Where Fm is the vector of measured values which consist of three concatenated data sets (dynamic, angular, and counting). Ht is the theoretical matrix, whose columns are the theoretical vectors which each represent the theoretical Fm of the size corresponding to the value Vd which multiplies that column. This matrix equation can be solved for Vd, given Fm and Ht.

If the convolution form holds, then the equation becomes:

$$Fm = Him \Theta Vd$$

Where Him is the Fm response at a single particle size and $\Theta$ is the convolution operator. This equation can be solved for Vd, given Fm and Him.

Another way to accomplish this is to constrain the inversion process for each technique (dynamic light scattering, ensemble scattering and counting), to agree with size distribution results from the other two techniques in size regions where those other techniques are more accurate. This can be accomplished by concatenating the constrained portion of the distribution, Vc, onto the portion (Vk) which is being solved for by the inversion process during each iteration of the inversion. The concatenated portion is scaled relative to the solved portion (AVc), at each iteration, by a parameter A which is also solved for in the inversion process during the previous iteration. This can be done with different types of inversion methods (global search, Newton's method, Levenburg-Marquart, etc.) where the scaling parameter A is solved for as one additional unknown, along with the unknown values of the particle size distribution. This technique will work for any processes where data is inverted and multiple techniques are combined to produce a single result.

$$Fn = Hnm*Vn \text{(matrix equation describing the scattering model)}$$

$$Vn = Vk|AVc \text{(concatenation of vectors } Vk \text{ and } AVc, n \text{ number of total values in } Vn\text{)}$$

Solve for k values of Vk and constant A $$Vn = Fn/Hnm \text{(solution of the matrix equation by iterative techniques (not a literal division))}$$

$$k \leq n+1$$

Figure 65:
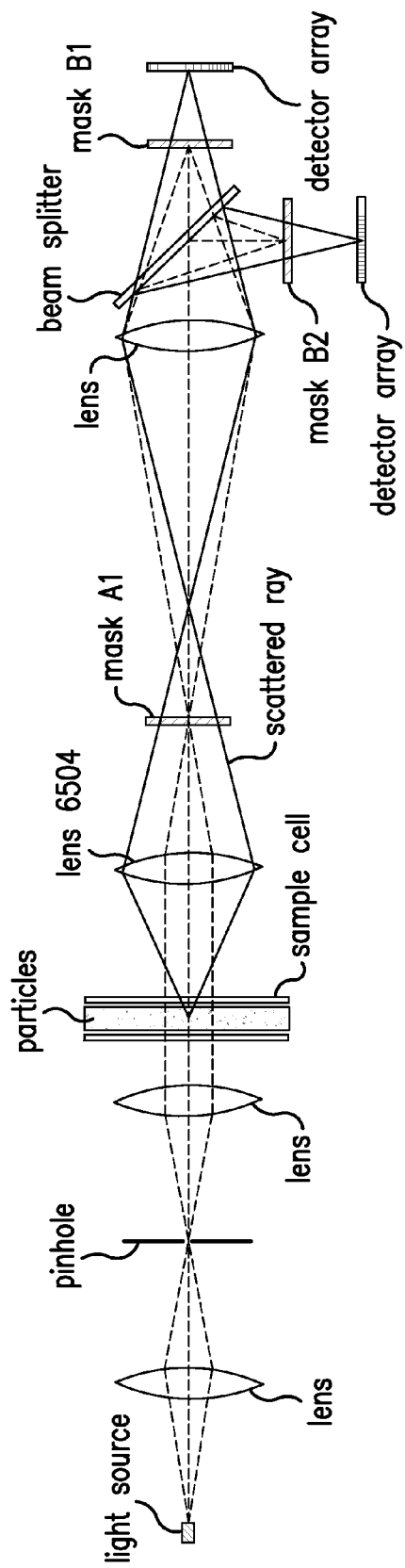
FIG. 65 provides a schematic diagram of a modification of FIG. 14, which provides measurement of scatter from various scatter planes by utilizing at least one rotating scattering plane mask.
Figure 66:
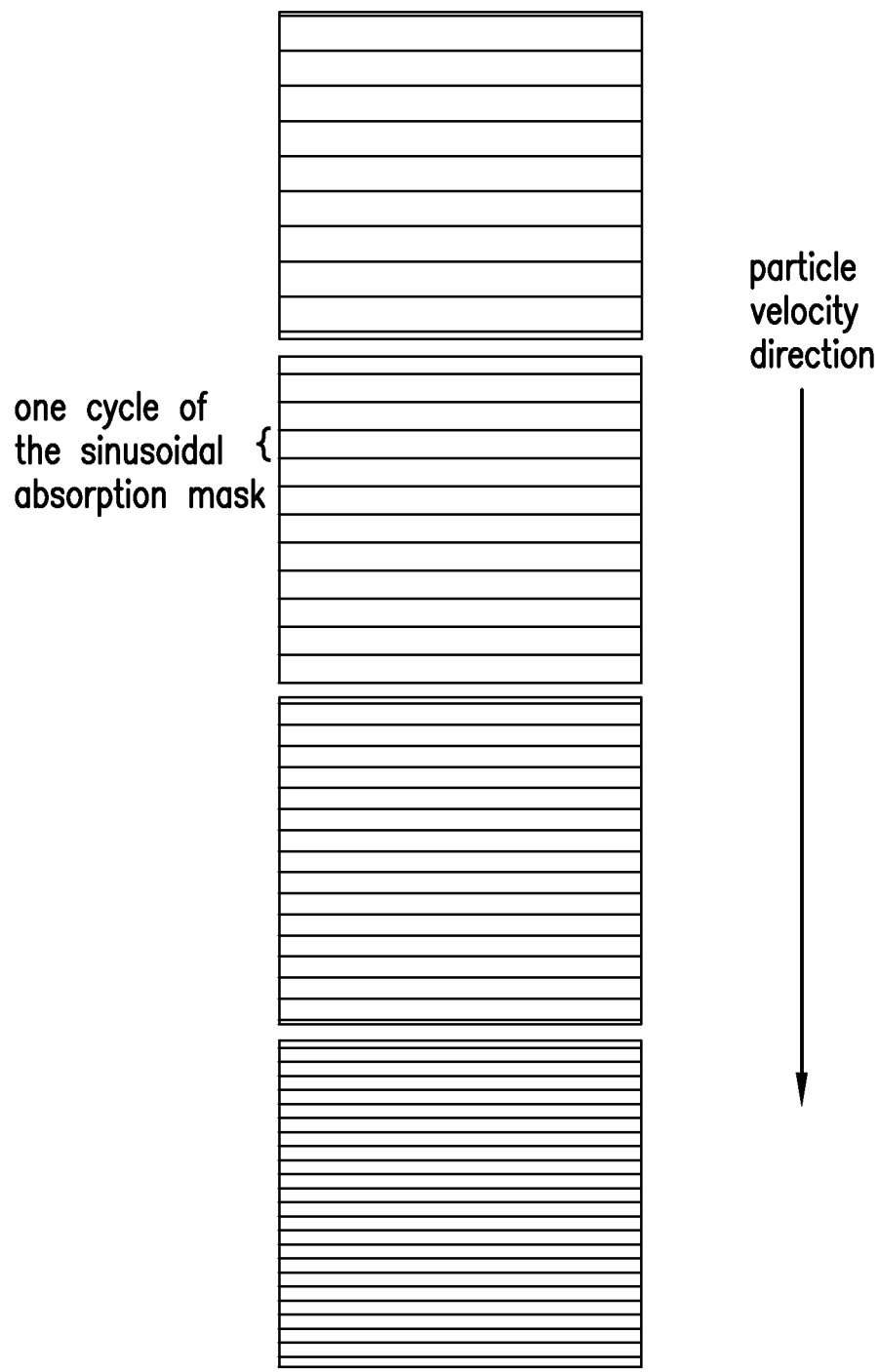
FIG. 66 provides a diagram of a periodic mask for producing an oscillating scatter signal, according to the present invention.

Another hybrid combination is particle settling, ensemble scattering, and dynamic light scattering as shown in FIG. 64. As before, dynamic light scattering probes a portion of the particle dispersion flow stream, with the flow turned off. The ensemble scattering system uses a detector array to measure the angular scattering distribution from groups of particles in the sample cell as the dispersion flows through the cell. A particle settling measurement is used for the largest particles which have the highest settling velocities. The settling is measured by sensing the power spectrum of the scattered light as viewed through a set of sinusoidal or periodic masks, which are also referred to as a multi-frequency modulation transfer target. Some examples of these masks are shown in FIGS. 16, 65 and 66. The mask can be placed between lens 6402 and lens 6403 or on front of a group of detectors as shown in FIG. 64. The detector is placed in the back focal plane of lens 6403, as shown previously by the inventor, to collect scattered light in separate ranges of scattering angle. A portion of the scattered light is split off by a beam splitter to an aperture in the focal plane of lens 6403. This aperture can be an annular opening, which passes a certain range of scattering angles (signal rises as particle passes through a bright fringe), or a pinhole centered to pass only the focused spot of the source (signal drops as particle passes through a bright fringe) in the back focal plane of lens 6403. Where the fringe is defined in the sample cell plane as an image of each highly transmitting line in the multi-frequency target. The light passing through the aperture, also passes through a periodic mask, as described previously, which is in a plane conjugate to the sample cell. This mask contains multiple regions, each with a different spatial frequency for the periodic absorption or reflection pattern. Behind each region in the mask is a separate detector which collects the light which only passes through that region, as also shown in FIGS. 15 and 15*a* for a different mask location. As particles pass through a region, the scattered light (for the annular aperture) or the attenuation (for the pinhole passing the source) of the beam are modulated by the motion of the particle's image across the absorption cycles of the mask. The particle dispersion flow pump is turned off and the particles are allowed to settle through the sample cell. The frequency of signal modulation for any particle is proportional to its settling velocity, which indicates the hydrodynamic size of the particle, given the particle and dispersant densities and the dispersant viscosity. The signal can be digitized and analyzed on an individual particle basis to count and size individual particles by measuring the settling velocity of each particle. In this case zero crossing measurement or Fourier transform of the signal segments for each particle could be used. In the case where many particles are in the beam at each instant, the power spectrum of the signal could be measured over an extended time. This power spectrum would then be inverted to produce the particle size distribution using a matrix model as described previously. As identical particles pass though different focal planes (planes perpendicular to the optic axis) in the sample cell, the power spectrum will change because the sharpness of the image of the mask will be reduced as the particle moves farther from the image plane. Also if the source beam is focused into the sample cell, as shown previously, then the source intensity and the scatter signal will drop as the particle passes farther from the best focus plane of the source. These effects can be included in the counting system model which is inverted to produce the particle size. The H function (or H matrix) described previously will contain columns which describe the count vs. signal frequency from a group of identical particles, of the size corresponding to that matrix column, passing through every point in the sample cell. For the ensemble scattering system model, the H function (or H matrix) will contain columns which describe the integrated scatter signal vs. angle from a group of identical particles, of the size corresponding to that matrix column, passing through every point in the sample cell.

The following list describes the various options for using scattered light to measure size. In each case, the following matrix equation must be solved to determine V from measurement of F:

$$F=H*V$$

This equation can be solved by many different methods. However, because this equation is usually ill-conditioned, the use of constraints on the values of V is recommended, using apriori knowledge. For example, constraining the particle count or particle volume vs. size distributions to be positive is very effective. In some cases, as shown previously by this inventor, changing the abscissa scale (for example from linear to logarithmic) of F can produce a convolution relationship between F and V, which can be inverted by very powerful deconvolution techniques.

$$F=H\Theta V$$

Particle Counting

1) Angular scatter or attenuation due to scatter:
    V=particle count per size interval vs. size
    F=count per signal amplitude interval vs. signal amplitude where signal amplitude is either pulse peak value, integral of the pulse, or other function of these values
    H=matrix where each column is the F function for the particle size corresponding to that column
    Response broadening mechanisms in the H matrix:
    A) source intensity variation in x and y directions where particles can pass
    (broadening reduced by aperturing of the intensity distribution at an image plane of the sample cell or using diffractive or absorptive optic beam shapers and apodizers to provide a "flat top" intensity distribution in the interaction volume)
    B) source intensity variation in z direction
    (broadening reduced by double pulse sensing and correlation, and detector aperture at image plane of sample cell)
    C) Residual broadening of signal amplitudes and ratios of signals due to differences in interaction volumes between different detectors.
    D) Passage of the particles through various portions of each detector field of view
    (broadening reduced by only counting particles which are detected by the detector with the smallest interaction volume, which is totally included in all of the other detector interaction volumes)
    E) Random orientation of non-spherical particles
    (broadening reduced by using annular detector elements which collect scattered light equally from all scattering planes.)
    F) Variation of signal due to presence of more than one particle in the interaction volume at one time.
    (This broadening is reduced by measuring at low scattering angles so that scatter is proportional to at least the fourth power of particle diameter or by reducing the particle concentration to avoid particle coincidences)
    Advantages: high resolution and aerosol capability
    Disadvantages: counting statistic errors for low count
2) Settling (hydrodynamic size)
    V=particle count per size interval vs. size
    F=count per signal frequency interval vs. signal frequency where signal frequency is the frequency of the scatter signal segment for the counted particle
    H=matrix where each column is the F function for the particle size corresponding to that column
    Response broadening mechanisms in the H matrix:
    Finite length of modulated signal segment from each particle
    Brownian motion
    Variation of signal frequency along z direction
    Advantages: high size resolution, excellent detection of small particles mixed with large particles, excellent measurement of low tails in the size distribution Disadvantages: counting statistic errors for low count; and possible difficulty measuring large particles in aerosols due to very high settling velocities Ensemble Scattering 1) Angular Scatter or Attenuation Due to Scatter V=particle volume per size interval vs. size F=scattered light flux per scattering angle interval vs. scattering angle H=matrix where each column is the F function for the particle size corresponding to that column Response broadening mechanisms in the H matrix:

The broad angular range of scatter from a single particle described by scattering theory Advantages: excellent size reproducibility Disadvantages: low size resolution, poor detection of small particles mixed with large particles, poor measurement of low tails in the size distribution.

2) Settling (Hydrodynamic Particle Size)

V=particle volume per size interval vs. size

F=scattered light detector current power per frequency interval vs. frequency

H=matrix where each column is the F function for the particle size corresponding to that column Response broadening mechanisms in the H matrix:

Finite length of modulated signal segment from each particle

Brownian motion

Variation of signal frequency along z direction

Advantages: high size resolution, excellent detection of small particles mixed with large particles, excellent measurement of low tails in the size distribution Disadvantages: difficulty measuring large particles in aerosols due to very high settling velocities In some cases, the matrix equation must be replaced by a set of non-linear equations which are solved to determine the particle size distribution from a count distribution which contains broadening due to a mechanism listed above. A more generalized form for this equation is to use operator notation Q=O[W], where O is an operator which operates on W to produce Q. For example in the case of counting:

$$Nm(S)=O[Nt(S)]$$

Depending upon the type of broadening mechanism, O may include operations such as matrix operation, set of non-linear equations, or convolution operator. The count distribution N(S) is the number of events with signal characteristic S between S-deltaS and S+deltaS as a function of S. S can be any of the signal characteristics (such as scatter signal peak or integral) or functions (such as logarithm) of these signal characteristics. Let Nm(S) be the measured count distribution which contains the broadening. And let Nt(S) be the count distribution without broadening. In each case, the operator describes the contribution to Nm(S) from an event of signal characteristic S. This operator is produced by calculating the broadened N(s) response to a large group of particles, with identical size and shape characteristics. This response is calculated for many values of particle characteristics to produce a set of equations. The response can also be determined empirically by measurement of a large number of particles with a narrow size distribution. Multiple narrow sized samples are measured at various mean sizes to produce the count response functions Nm(S) for those sizes. Then the response functions at other sizes are produced by interpolation between these measured cases, using theoretical behavior to solve for the interpolated values. The operator O is created by fitting functions to these measured results or by the closed form equations from theory.

Figure 67:
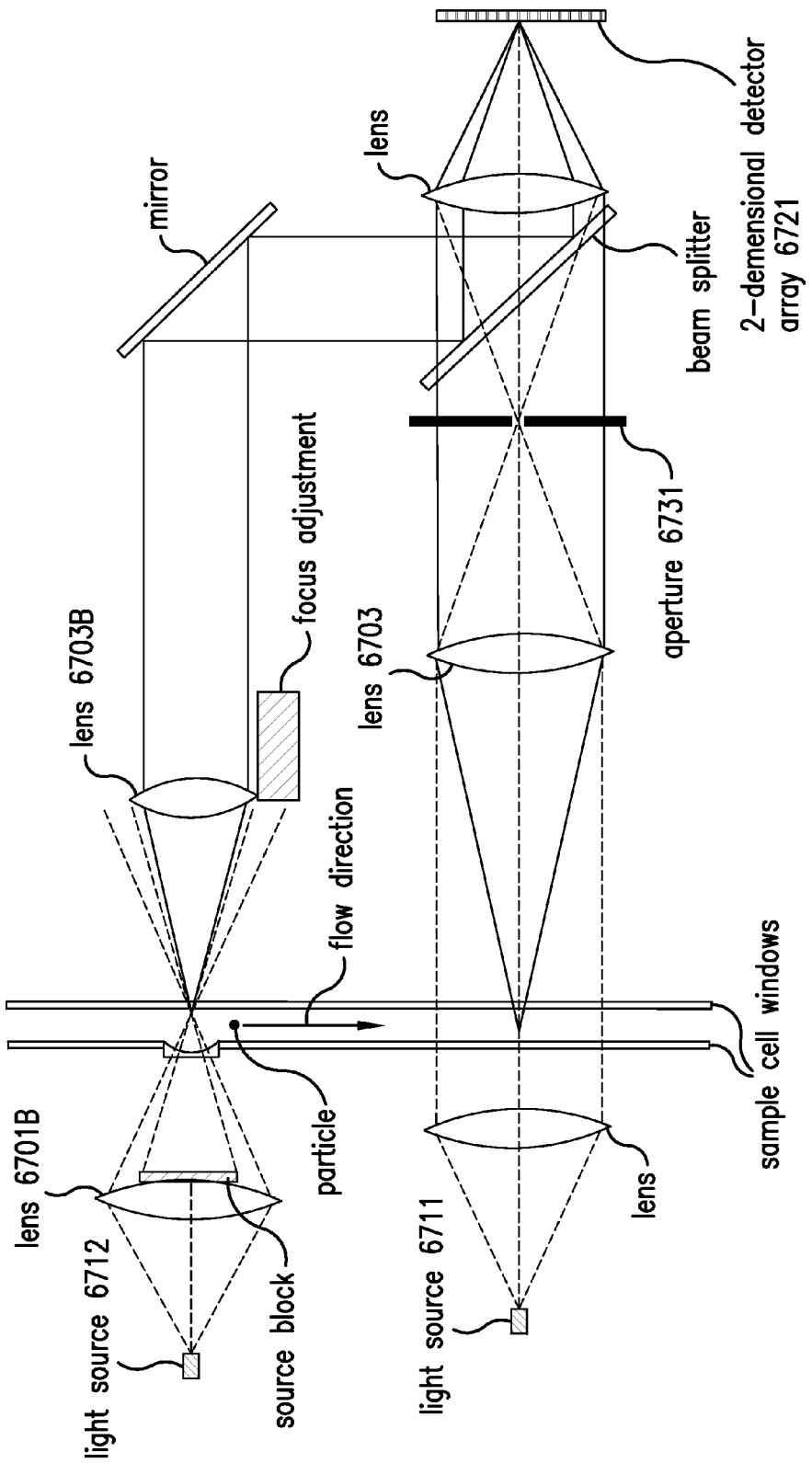
FIG. 67 provides a schematic diagram of an optical system which multiplexes a detector array between two light sources, where one source is utilized for measuring the light beam attenuation due to light scattered by particles, according to the present invention.

Another system for counting and sizing particles, using imaging, is shown in FIG. 67. There are two optical systems, using light source 6711 and light source 6712. The source 6711 system measures larger particles by direct imaging of the particles, flowing through the sample cell, onto 2-dimensional detector array 6721. The source 6712 system produces a cone shaped illuminating beam, using the source block on lens 6701B, which defines an illuminated focus volume in the particle dispersion. This focal volume is imaged by lens 6703B though the mirror and beamsplitter onto the same 2-dimensional detector array 6721. The focal volume is placed close to the sample cell window which is closest to the 2-dimensional array. Before and after the focal point of the source 6712 in the cell, the illumination beam is a hollow cone, which provides an un-illuminated volume through which lens 6703B can view the focal point of source 6712 in the sample cell. The 2-dimensional array is multiplexed between the two systems by sequentially turning on either source 6711 or source 6712. Each source is pulsed so as to only illuminate the flowing particles during a travel distance which is less than the required imaging resolution. Alternately, the flow can be stopped during the exposure to eliminate any smearing of the image.

Figure 68:
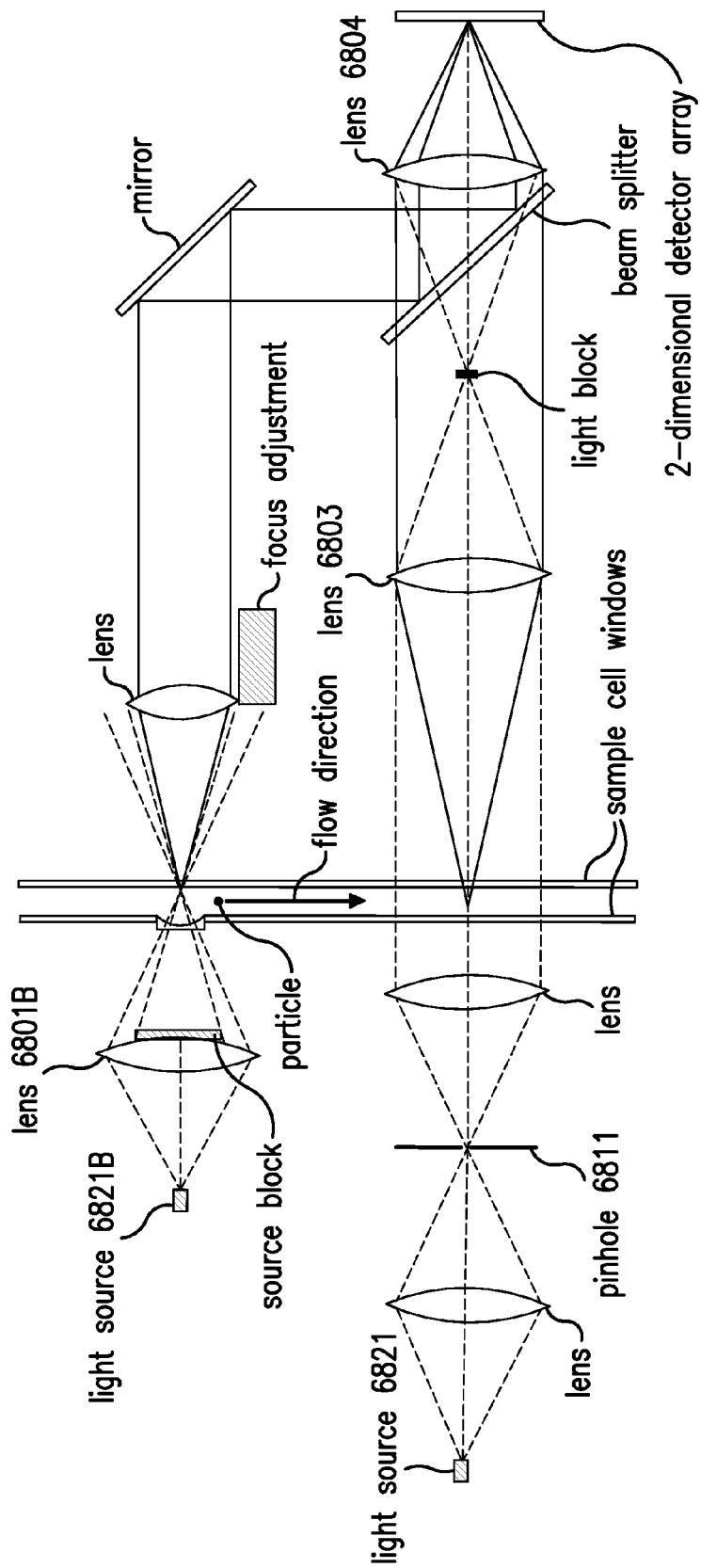
FIG. 68 provides a schematic diagram of an optical system which multiplexes a detector array between two light sources, where one source is utilized for measuring the light scattered by particles, according to the present invention.

The source 6711 system can take many forms. In FIG. 67, aperture 6731 (in the back focal plane of lens 6703) blocks the scattered light and passes the un-scattered light (approximately) so that particles will appear as dark on a bright background. In FIG. 68, aperture 6731 is replaced by a light block which blocks the un-scattered light and passes the scattered light (approximately) so that particles will appear as bright on a dark background. In FIG. 68, pinhole 6811 is used to remove any higher angle components of light source 6821 which could create background light which can pass around the light block. In either case, contiguous detector array pixel values, which are above some threshold in FIG. 68 or below some threshold in FIG. 67, can be combined to determine the total light extinction of the particle (in FIG. 67) or the light scattered in the acceptance angle of lens 6803 in FIG. 68. These values can be used to determine the size of particles throughout the size range, even for a particle whose image size is less than the size of single pixel, as described previously in this document for FIGS. 11 and 14. However, for very small particles, many particle coincidence counts may occur in the source 6821 system and the signal to noise may drop below acceptable levels. So the smaller particles are measured by the source 6821B system, which focuses the source to a higher irradiance in the sample cell and defines a much smaller interaction volume than the other system. The source block on lens 6801B creates a hollow cone of light, which is focused close to inner sample cell window wall which is closest to the detector array. This is shown in more detail in FIG. 69. Lens 6903B collects scattered light from the particles, with a field of view which falls inside of the hollow cone of light. Therefore, only particles in the source focal volume will contribute to the scattered light and the image formed on the detector array. Since the focus is close to the inner wall, few particles will block or rescatter light which is scattered by particles in the focal volume. However, this method will produce good results for any location of the lens 6901B focus, as long as lens 6903B is focused to the same location. Also particles in the extended illuminated portions of the hollow cone cannot contribute scatter to lens 6903B due to the limited acceptance cone of this lens. The optical magnification is chosen such that the 2-dimensional array only sees the focal volume, without seeing any light from the hollow light cones on the input or exit of the focal volume. The scattered light, accepted by lens 6903B, is reflected by a mirror and a beamsplitter, through lens 6804, to the detector array. The lenses 6803, 6903B, and 6804 are designed to work at infinite conjugates, however lens 6804 could be removed and lens 6803 and lens 6903B could be adjusted to create images of the particles directly onto the detector array at finite conjugates. In both Figures, the size of very large particles can be measured directly by the size of digitized image to avoid errors in the magnitude of the scattered light from these large objects which only scatter at very small scattering angles, where the background light is high.

Figure 69:
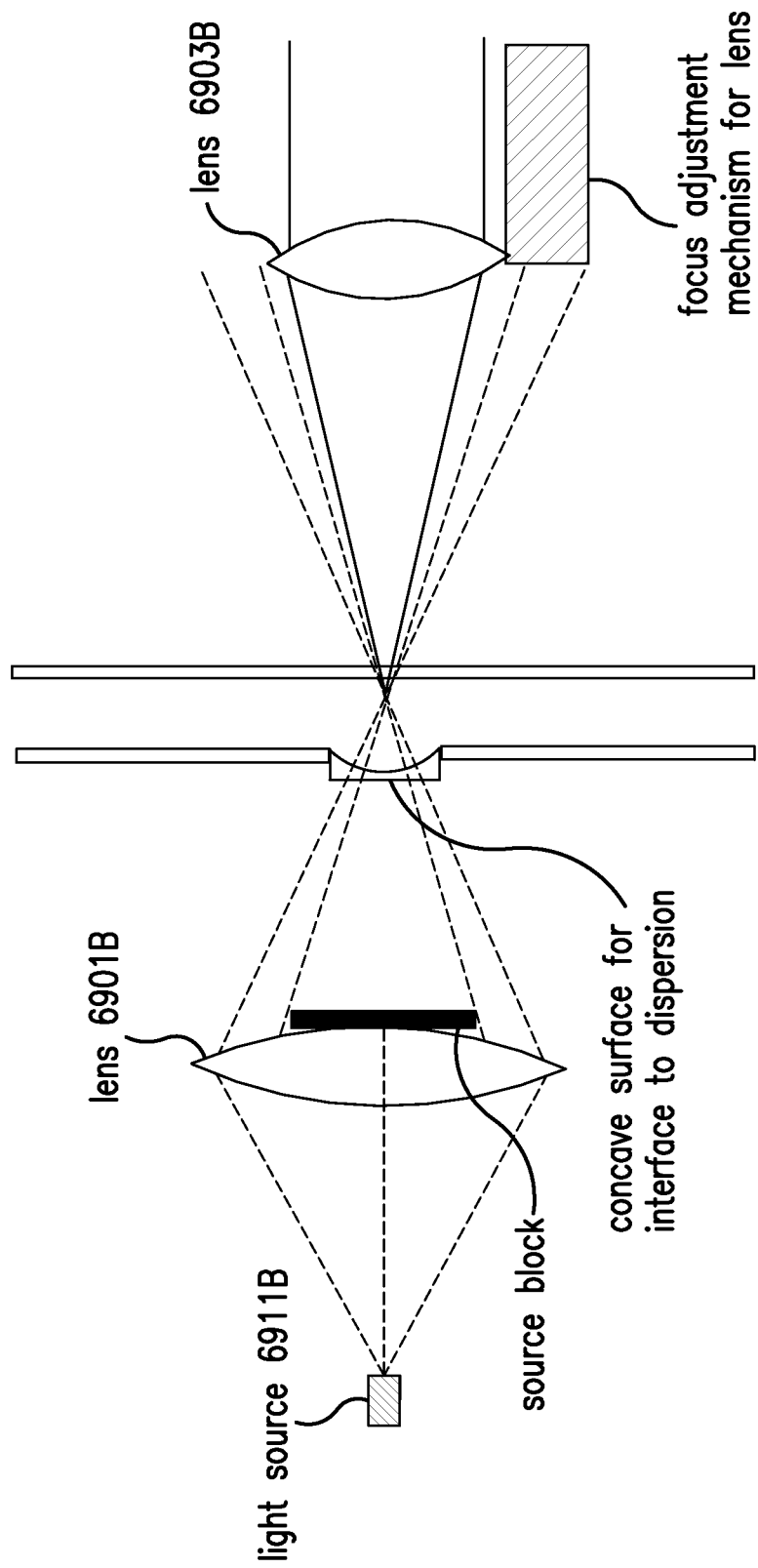
FIG. 69 provides a schematic diagram of an optical system schematic diagram, which shows more details of FIG. 67 and FIG. 68.

As shown in FIG. 69, the Source 6911B system also uses a concave inner surface whose center of curvature is approximately coincident with the focal volume. This design produces a focal volume which does not shift with change in the refractive index of the dispersing fluid in the sample cell. A concave surface could also be used on the opposing window to control the focal shift of lens 6903B due to refractive index change of the dispersant, to maintain sharp focus of the scattered light in the particle image on the detector array. Again, the center of curvature would be coincident with the focal volume. However, FIG. 69 shows another alternative which may be more flexible and provide better focus precision. Lens 6903B is attached to a focus mechanism which can move the lens to various focal positions. This mechanism could be any appropriate mechanical means, including motor or piezoelectric drivers. The position of lens 6903B, along the optical axis, is changed under computer control to maximize particle edge sharpness in the image on the detector array. This sharpness could be determined by many image sharpness criteria which include the spatial derivative of the image. In the case where the depth of field of lens 6903B is shorter than the depth of the focal volume of lens 6901B, this focus adjustment can be used to only select particles which are in sharp focus, by measuring the edge sharpness of each particle in the field of view, at three different focal positions. Only particles, whose edge sharpness is maximum in the middle focal position, are sized and counted. In this way, only particles which are accurately sized are counted. The maximum edge sharpness for each particle may vary among different particles which may have soft edges. So by measuring the edge sharpness in three different planes, the particles which are located in the middle plane can be selected by choosing only the ones whose sharpness is maximum in that plane. The edge sharpness could be determined by the spatial derivative of the intensity profile at the edge of each particle. This could also be calculated from the maximum of the spatial derivative of the entire particle, because this usually occurs at the particle's edge. The derivative could also be calculated from a smoothed version of the image, if image noise is a problem. This comparison can be done while the particles are stationary or by using 3 successive source pulses with a detector array scan during each pulse.

Figure 70:
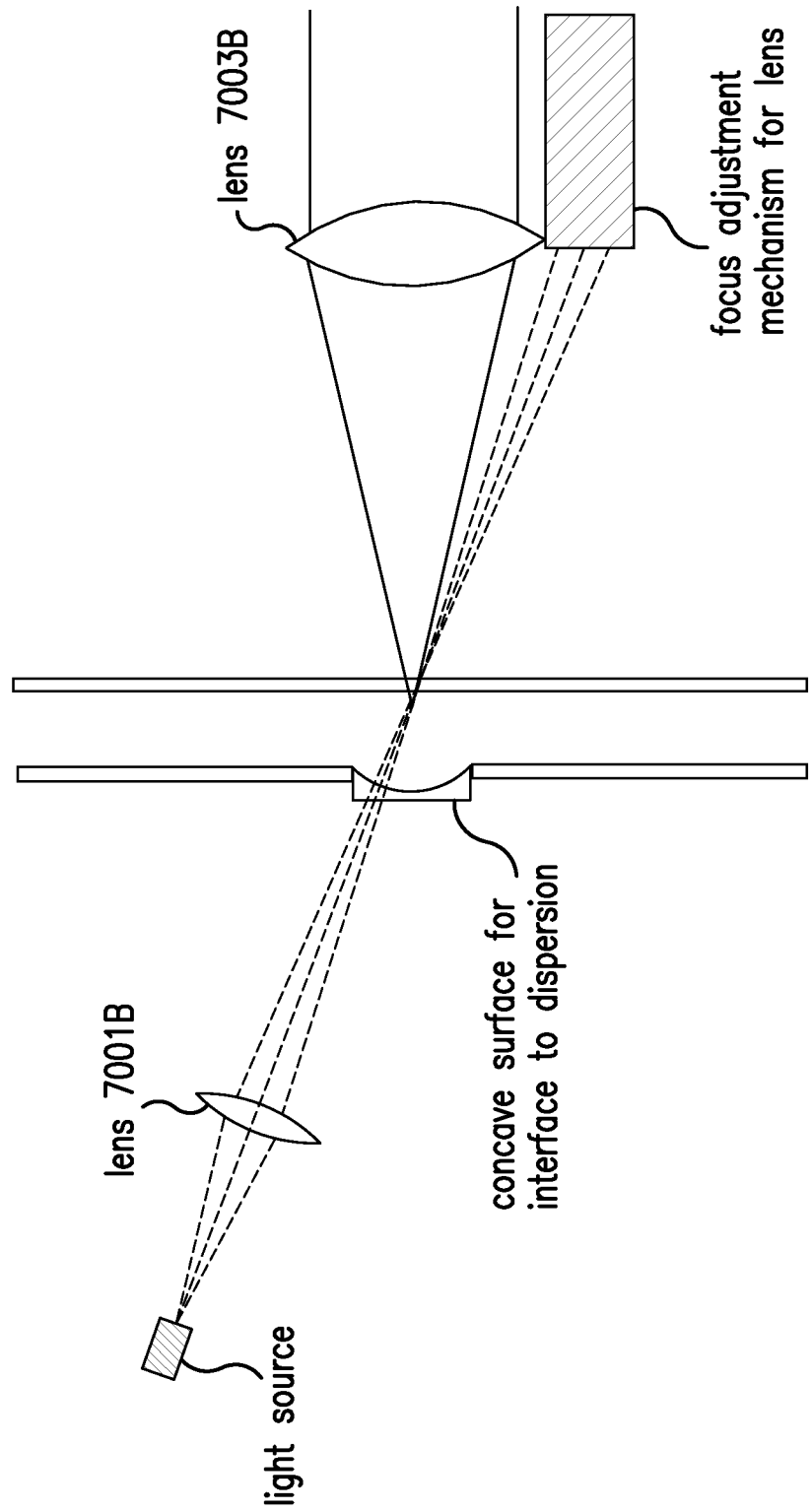
FIG. 70 provides a schematic diagram of an optical system schematic diagram, depicting a variation of the optical system in FIG. 69.

Also, the hollow cone source in FIG. 69 could be replaced by a single focused light beam, which is focused through the focal volume and projected at an angle to the optical axis of lens 6903B, such that it is not captured by lens 6903B, as shown in FIG. 70. The scattering interaction volume is the intersection of the viewing focus of lens 7003B and the source focus of lens 7001B. The 2-dimensional detector array sees the image of the particles at the focus of lens 7001B, using only light scattered from the particles. In this way, the 2-dimensional array only sees particles in a very small interaction volume. All of the other focusing mechanisms and options mentioned previously for FIG. 69, also apply for FIG. 70.

Another problem associated with counting techniques is the coincidence counting error. In some cases, pulses from individual particles will overlap as shown in FIG. 71, which shows three pulses and the signal which represents the sum of those three pulses. In most cases, these pulses all have the same shape, but with different pulse amplitudes. For example, any particle passing through a Gaussian laser beam will produce a pulse with a Gaussian shape. The only difference between different pulses from different particles is the amplitude of the pulse and the position of the pulse in time. Therefore, the sum of the pulses is simply the convolution of a single pulse with three delta functions, each delta function centered at one of the different pulse positions. The general equation for this sum of pulses is:

$$S(t) = H(t) \Theta \Sigma (A_i * \partial(t - t_i))$$

Where:
$\Sigma$ = sum over variable i
t = time
S(t) = the total signal from the overlapping pulses
$\partial(t)$ = the delta function
ti = the time at the center of the ith pulse
Ai = the amplitude of the ith pulse
$\Theta$ is the convolution operator
H(t) = the function describing a single particle pulse shape So the original pulses can be recovered from S(t) by inverting the above equation, using H(t) as the impulse response in a Fourier transform deconvolution or in iterative deconvolution algorithms. As shown by FIG. 71, the individual pulse heights and areas cannot be determined from the sum of the pulses S(t). However, through deconvolution the pulses can be separated as shown in FIG. 72, which shows S(t) and the total deconvolved signal resulting after some degree of deconvolution of S(t). Due to signal noise in S(t), S(t) cannot be deconvolved down to separate delta functions, the deconvolution will usually stop at some point before artifacts are created, leaving separated pulses of finite width. However, these pulse heights will be proportional to the actual heights of the original separated pulses. So that by using a single scale factor on the deconvolved signal, all of the individual pulse heights will agree with those of the original separated pulses. FIG. 73 shows this scaled deconvolved result along with the original separated pulses to show that the separated pulse heights are recovered by the decovolution process. This technique can be applied to any time signals which have overlapping pulses of the same shape, such as found in particle counting. For most laser beams, H(t) will be a Gaussian. However, in some cases, where the laser beam has been apodized or truncated to reduce the large intensity variation, H(t) will take on the functional form describing the signal vs. time profile of a single particle passing through that beam, which may be flat-topped Gaussian, rectangular, etc.

Figure 74:
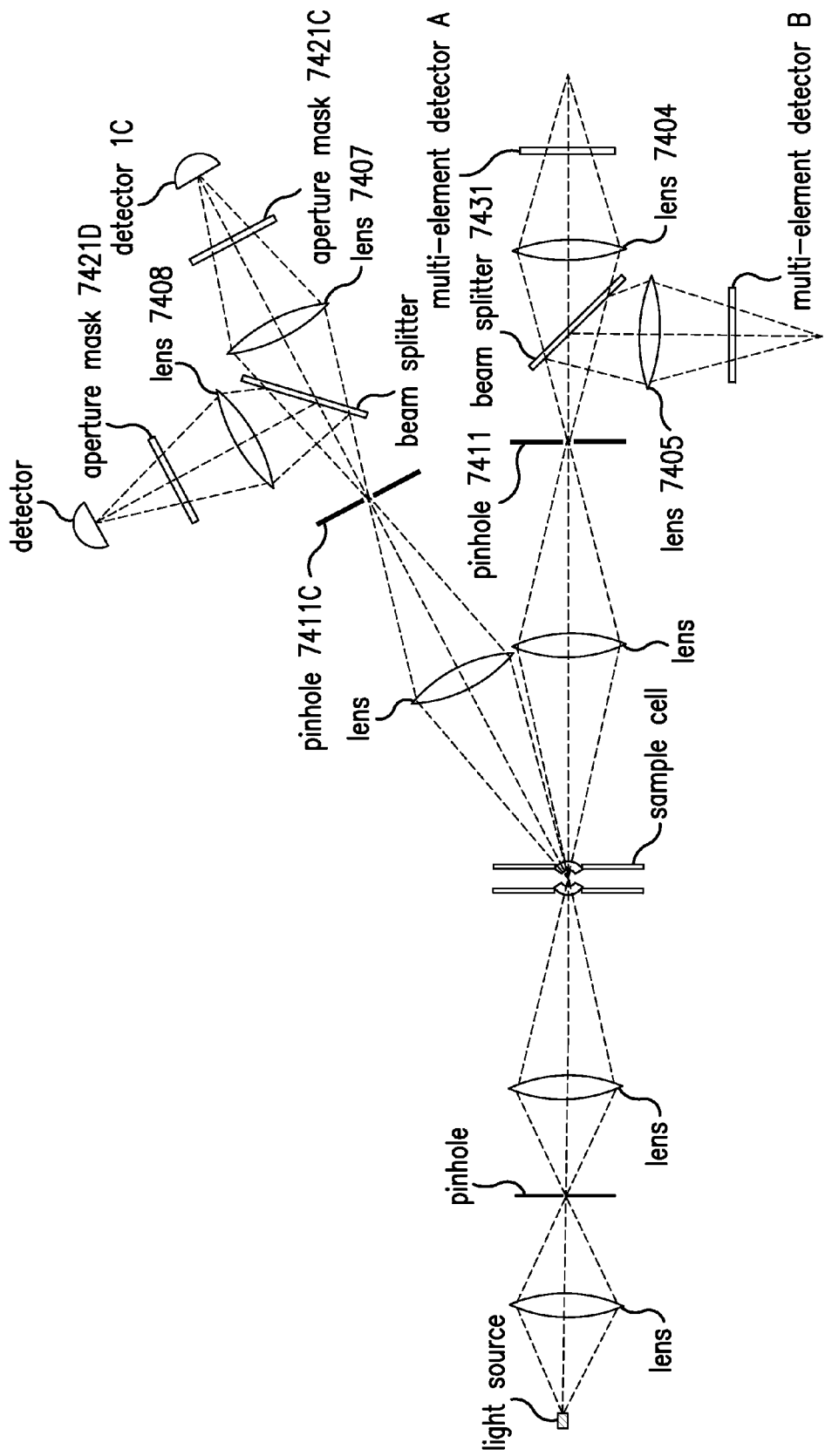
FIG. 74 provides a schematic diagram of a scatter plane of an optical system, which is repeated in multiple scattering planes to determine the shape of a particle, according to the present invention.
Figure 75:
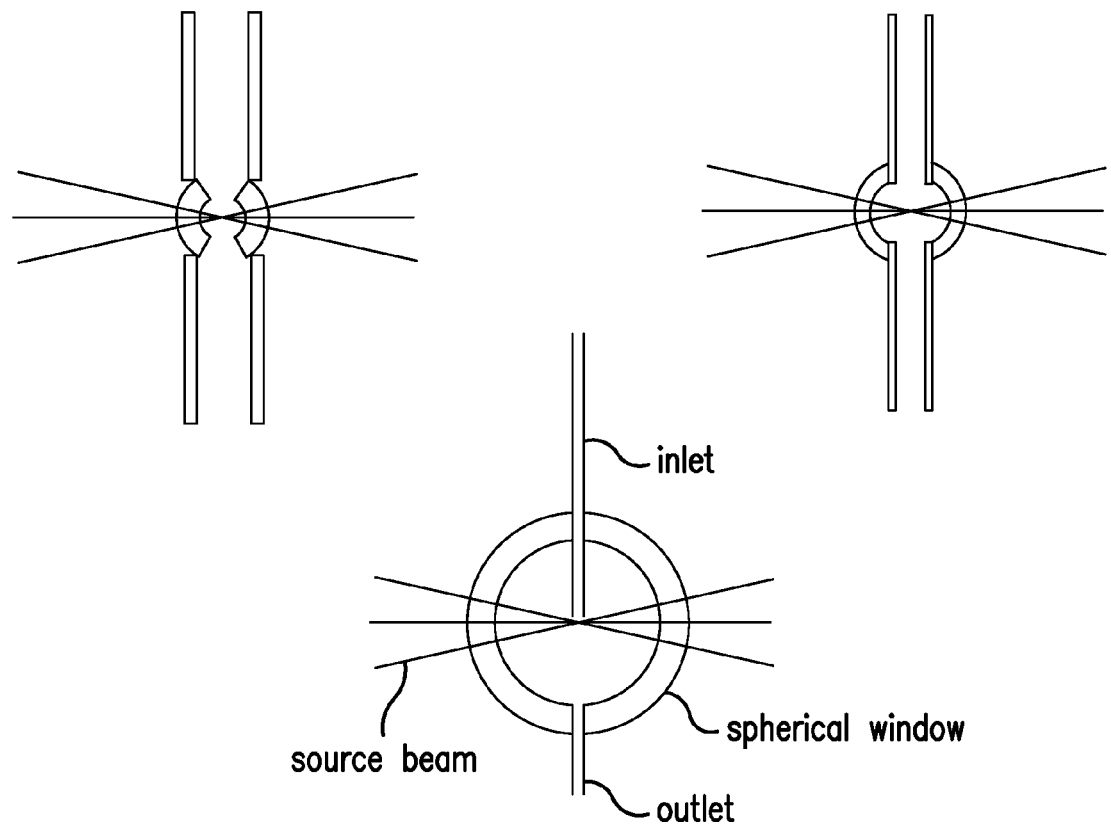
FIG. 75 provides diagrams of three variations of particle sample cells.
Figure 76:
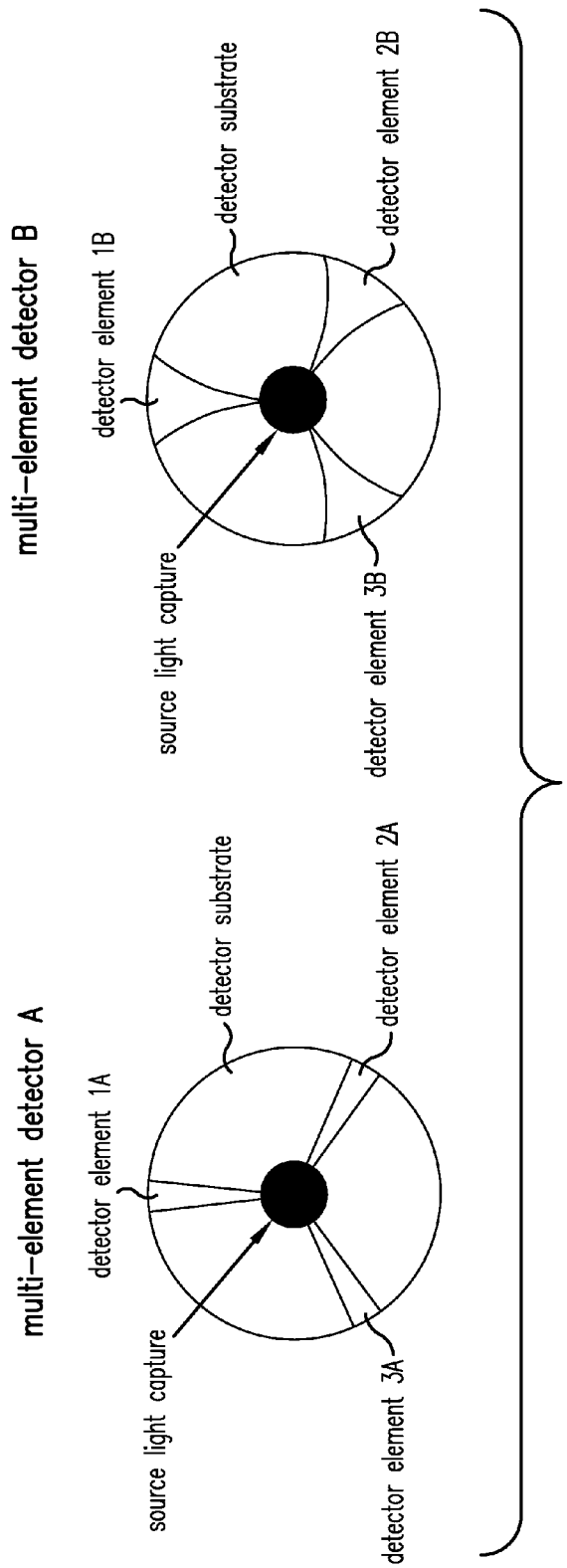
FIG. 76 provides a diagram showing detector elements for measuring the shape of a particle, according to the present invention.
Figure 77:
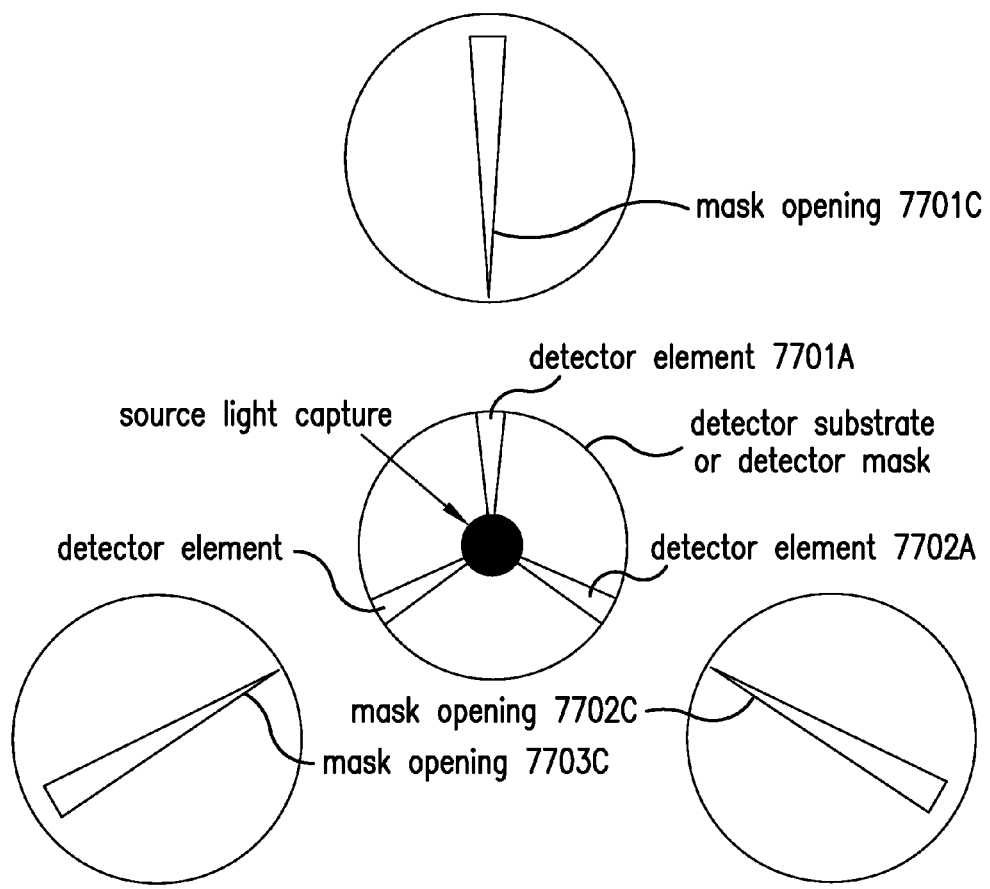
FIG. 77 provides a diagram showing the orientation of detector elements for the optical system of FIG. 74, when measuring scattered light in three ranges of optical scattering planes.

FIGS. 74 through 77 show particle shape measuring systems which combine the concepts of FIGS. 29 through 31, and FIGS. 42 through 45. FIG. 74 shows one system in the first scattering plane of multiple scattering planes. A three scattering plane system is shown, but as mentioned before, any number of scattering planes may be needed to describe the shape of more complicated particles. The lens 7404 and lens 7405 systems use multiple detector elements to measure scatter in each of the scattering planes on one detector array/lens assembly, which is preferably in the focal plane of each lens. The lens 7407 and lens 7408 systems are repeated in each of the scattering planes to measure the high angle scattered light. Pinhole 7411C and pinhole 7411 can be replaced by apertures which are appropriate to the shape of the source beam spot crossection, such as elliptical or rectangular for laser diodes These detection systems are aligned as shown in FIG. 77, so that each scattering plane element on multi-element detector A and multi-element detector B measures in the same scattering plane as the corresponding lens 7407/lens 7408 aperture openings. For example mask openings 7421C and 7421D, measure scatter in the same scatter plane as detector element 7701A; and mask openings 7702C and 2D, measure scatter in the same scatter plane as detector element 7702A. Some possible configurations of the multi-element detectors are shown in FIG. 76. This concept combines the two concepts described earlier in FIGS. 29-31 and FIGS. 42-45. There is one lens 7404/lens 7405 system with both lens 7404 and lens 7405 (through beamsplitter 7431) centered on the optical axis of the source to measure low angle scatter. Each detector element, shown in FIG. 76, is aligned to view the same scattering plane as the corresponding element on the other multi-element detector, but all three scattering planes are measured by the same multi-element detector, through either lens 7404 or lens 7405. The three Lens 7407/lens 7408 systems, which measure the higher angle scatter, each have at least one aperture (instead of 3 elements for each of lens 7404 or lens 7405) for each lens with shapes like those in FIG. 76 (7701C, 7702C, 7703C apertures have the same (or similar) shape as the detector elements in multi-element detector A and 7421D, 2D, 3D have shapes similar to those in multi-element detector B). As before, the ratios of the corresponding detectors C to D and the ratio of each element on the multi-element detector A to the corresponding element on multi-element detector B, provide the particle dimension parameter for the corresponding scattering plane. These parameters are then combined using a lookup table, search algorithm, or regression algorithm to solve for the particle shape. As before, to solve for the dimensions of a rectangular particle with arbitrary orientation, parameters in at least 3 scattering planes must be measured. The optimal separation of these planes in the plane of FIG. 77 is approximately 120 degrees, with one of the planes being parallel to the flow direction (because many particles will align with the flow direction). The search algorithm will take an initial guess at the width, length, and orientation angle, and then calculate the three parameters for that guess and then compare those parameters to the measured ones to generate a change in the width, length, and orientation for the next guess and then go through the same loop again. As this loop is repeated, the change in the width, length, and orientation diminishes as the algorithm approaches the true width, length, and orientation of the particle. Optimization algorithms such as Newton's method, global optimization, or Levenburg Marquardt could be used. The three dimension parameters could also be replaced by the full set of 12 detector signal values (6 for detectors A and B and 6 for detector sets C and D) for input to these search or optimization algorithms. This would be the case for 3 scattering planes. For particles with more complicated shapes, measurements in more scattering planes would be needed to solve for the shape parameters and the arbitrary orientation, but the same methods would be used to search for the solution. The corresponding elements in detector C and D and in detector A and B could also be detector segments which view different ranges of scattering angle instead of different angular weightings (as shown in FIG. 76) of the same range of scattering angles. Any of the detector or mask designs described in this application could be used, including multiple scattering angular ranges on each mask in each scattering plane or detector/mask designs using radial weighting functions Wijs (as described later). For example, mask 7421C could have a different weighting function Wijs than 7421D, so that the ratio of these two signals is indicative of size. The use of the use of different angular weightings may provide larger size range because when the particles become very large, very little light may fall on the higher angle detectors and the ratio of high to low angle signals will become multi-valued. The ratio of 2 detectors with different angular weightings (FIG. 76) will have a smooth monotonic size dependence over a large size range.

FIG. 75 shows the use of spherical window shape on the sample cell to avoid focal shift of the focused source spot and of the focal viewing spot of the collection optics as the refractive index of the dispersing fluid is changed. The center of curvature for each surface on each spherical window is at the beam focal position in the sample cell. The bottom portion of FIG. 75 shows a spherical cell with an inlet tube, which ends just above the focal spot of the source beam. This cell is placed into a flow loop as shown in FIG. 13, where the pump pulls the dispersion from the outlet and returns dispersion to the inlet. In this way, homogeneous dispersion passes through the source beam directly from the inlet. Regions far from the inlet, in the spherical cell, may have inhomogeneous particle dispersion, which may not be representative of the entire particle sample. Also when the flow loop is drained, this orientation of the spherical cell will drain completely without leaving residual particles to contaminate the next particle sample.

Figure 78:
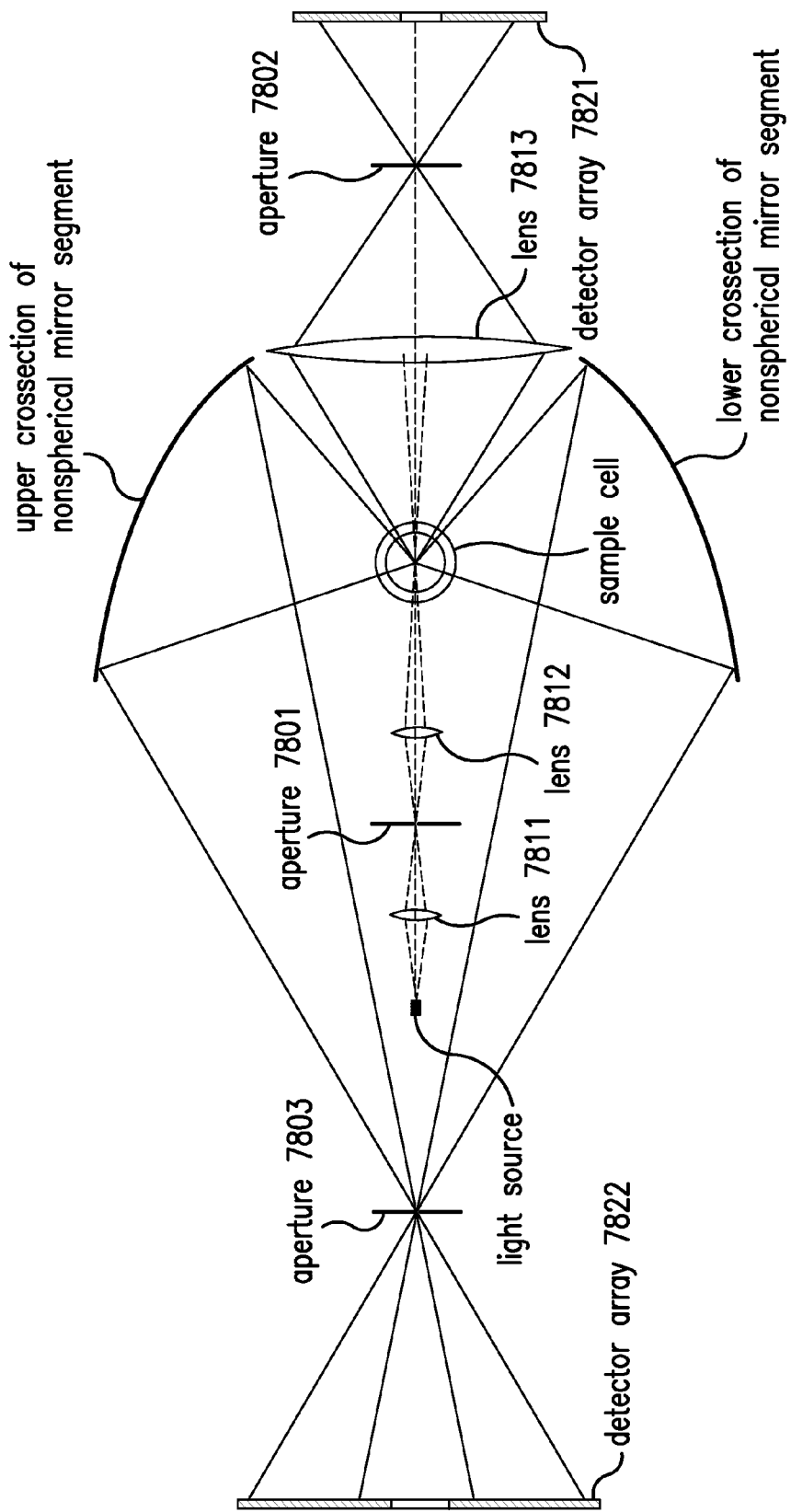
FIG. 78 provides a schematic diagram of an optical system, which measures low angle scatter with a lens, and high angle scattering with a perforated concave mirror, according to the present invention.
Figure 79:
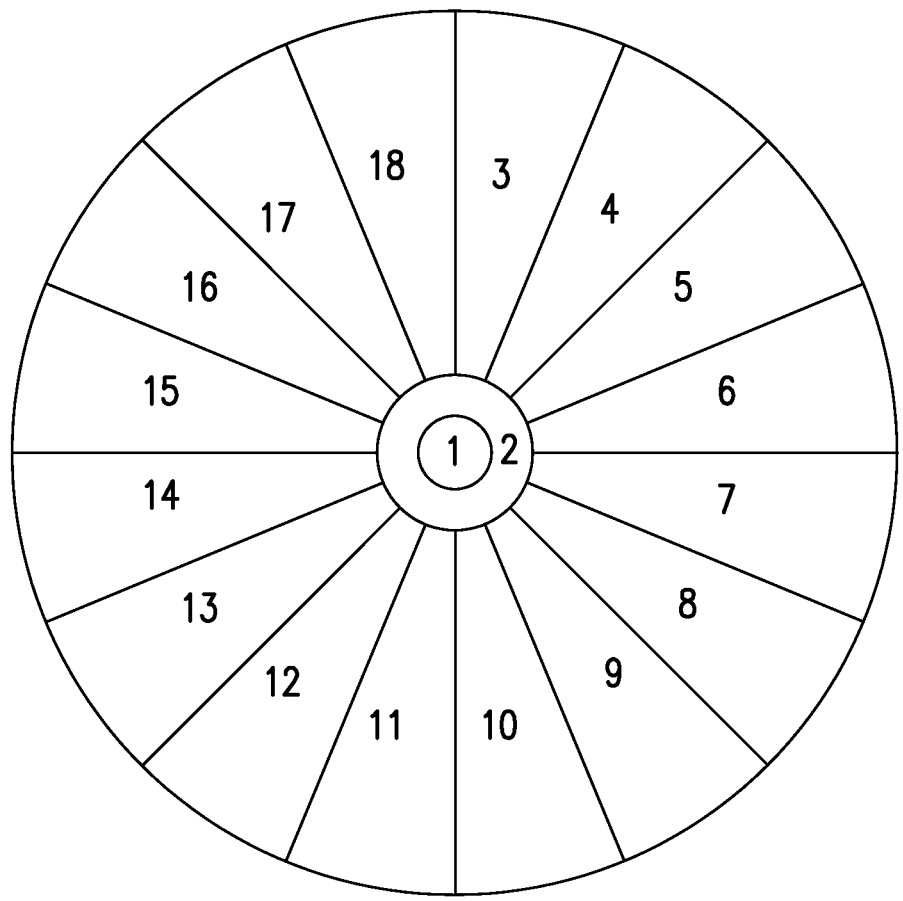
FIG. 79 provides a diagram showing an array of detector elements or optical elements which measure scattered light in multiple ranges of scatter planes and scattering angles, according to the present invention.

Another concept for measuring the shape and size of small particles is shown in FIG. 78. This system consists of two scatter collection subsystems: the first subsystem using lens 7813 and detector array 7821 and the second subsystem using a segment of a nonspherical mirror and detector array 7822. Detector array 7821 measures scattered light at low scattering angles and detector 7822 measures light scattered at high scattering angles. The light source is spatially filtered by aperture 7801 and lens 7811. The spatially filtered beam is then focused, by lens 7812, into a spherical sample cell (see FIG. 75) which contains the flowing particle dispersion. FIG. 78 does not show the inlet and outlet portions of the cell which are shown in FIG. 75. If the source beam already has appropriately attenuated components at higher divergence angles, then Lens 7811 and aperture 7801 can be eliminated and lens 7812 can focus the source directly into the sample cell. The sample cell should have spherical shaped windows (also see FIG. 75) to minimize the focal shift of the light beam focal spot, due to changes in the refractive index of the dispersant and to reduce Fresnel reflections. If this focal shift or Fresnel reflections are not a problem, planar windows can be used on the sample cell as shown previously. The scattered light from the particles is focused through aperture 7802 by lens 7813. Aperture 7802 is in the image plane of the focal spot of the source inside of the sample cell. As shown previously in FIGS. 43 and 45, aperture 7802 will restrict the size of the scattering interaction volume which can be seen by detector array 7821 so that the probability of detecting more than one particle in the scattering interaction volume is small. The light passing through aperture 7802 is detected by a detector array, as shown in FIG. 79, for example. The unscattered source light beam is either blocked at lens 7813 or passes onto a central detector element on detector array 7821 to monitor source beam intensity drift. The beam may also pass through a hole in the center of detector array 7821. The detector array contains 18 separate detector elements (numbered 1 through 18 in FIG. 79). Element 1 measures the approximate optical flux of the unscattered light. Element 2 measures the low angle scatter for all scattering planes. Elements 3 through 18 measure the scattered light in 8 different scattering planes (2 detection sides per scattering plane for a total of 16 detectors). For example, detector element 4 and detector element 12 measure the positive and negative scattering angular ranges for a single scattering plane. Actually, each scattering plane is the sum of scattering over a small range of scattering planes, around the center scattering plane for that wedge segment. Sometimes the positive and negative angular ranges will be the same, if the intensity is uniform across the particle and if the crossection of the particle in the scattering plane has rotational symmetry about an axis perpendicular to the scattering plane. Then only detectors 3 through 10 (half of the detector array) would be needed to cover all of the scattering planes. This source uniformity could be insured by using an appropriate attenuation profile across the beam at aperture 1 or diffractive beam shaper as discussed previously. If the intensity uniformity of the source focused spot or particle crossectional symmetry cannot be insured, the positive and negative sides of each scattering plane should be measured separately as shown in FIG. 79. The scattering angle range for detector 1 is limited by the size of lens 7813. Typically, a single lens can measure up to scattering angles of approximately 60 degrees. The nonspherical mirror segment collects light scattered at higher angles and focuses this light through aperture 7803, which is also in an image plane of the source focal spot in the sample cell. The shape of the nonspherical mirror is designed to minimize the aberrations between the source focal plane in the sample cell and aperture 7803. For example, the nonspherical mirror could be a segment of an ellipsoid of revolution, where the source focus in the sample cell and aperture 7803 are each located at different foci of the ellipsoid. This aperture 7803 defines a restricted scattering volume as shown previously in FIGS. 43 and 45. The light passing through the aperture is projected onto a second detector array, which is similar to that shown in FIG. 79. However, elements 1 and 2 will not be needed for detector array 7822 because they are only effective at low scattering angles, where the scattered intensity does not change significantly for various scattering planes. Detector arrays 7821 and 7822 are oriented so that the bisector of element 3 is parallel to the particle flow direction. Then each element on detector array 7822 will provide the scattered light signal at higher scattering angles for the same scattering plane of the corresponding detector element in detector array 7821. For each scattering plane, the signals from elements 1 and 2, the 2 elements (for example elements 4 and 12) in that scattering plane from detector array 7821, and the 2 corresponding elements in that scattering plane from detector array 7822 will determine the "effective dimension" in that plane for that particle. Since these calculated "effective dimensions" are not totally independent of each other, they must be calculated from a set of simultaneous equations, one equation from each scattering plane. However, the advantage using many scattering planes is that the directions of the minimum and maximum dimension can be found quickly by comparing the ratio of the high and low angle scattering for each scattering plane. Fewer scattering planes would require much more computation time to solve for the dimensions of a randomly oriented particle, using iterative inversion of the equations. However, when many scattering planes are measured, the major and minor axes, and orientation, of the randomly oriented particle can be found quickly by inspection of flux ratios (see later in FIGS. 89, 102, and 103). One of the scattering planes should be parallel to the flow of the particles, because the major or minor axis of each particle is more likely to be parallel to the flow direction, particularly in accelerating flow which may occur from a crossectional area change in the sample cell. This crossectional area change may be designed into the flow path to provide the flow acceleration and particle orientation parallel to one of the measured scattering planes. The techniques shown in FIGS. 74 and 76 could also be used in the FIG. 78 system by replacing the system of aperture 7802 and detector array 7821 or aperture 7803 and detector array 7822 (all from FIG. 78), with pinhole 7411, beamsplitter 7431, lenses 7404 and 7405, and multi-element detectors A and B (all from FIG. 74).

Figure 80:
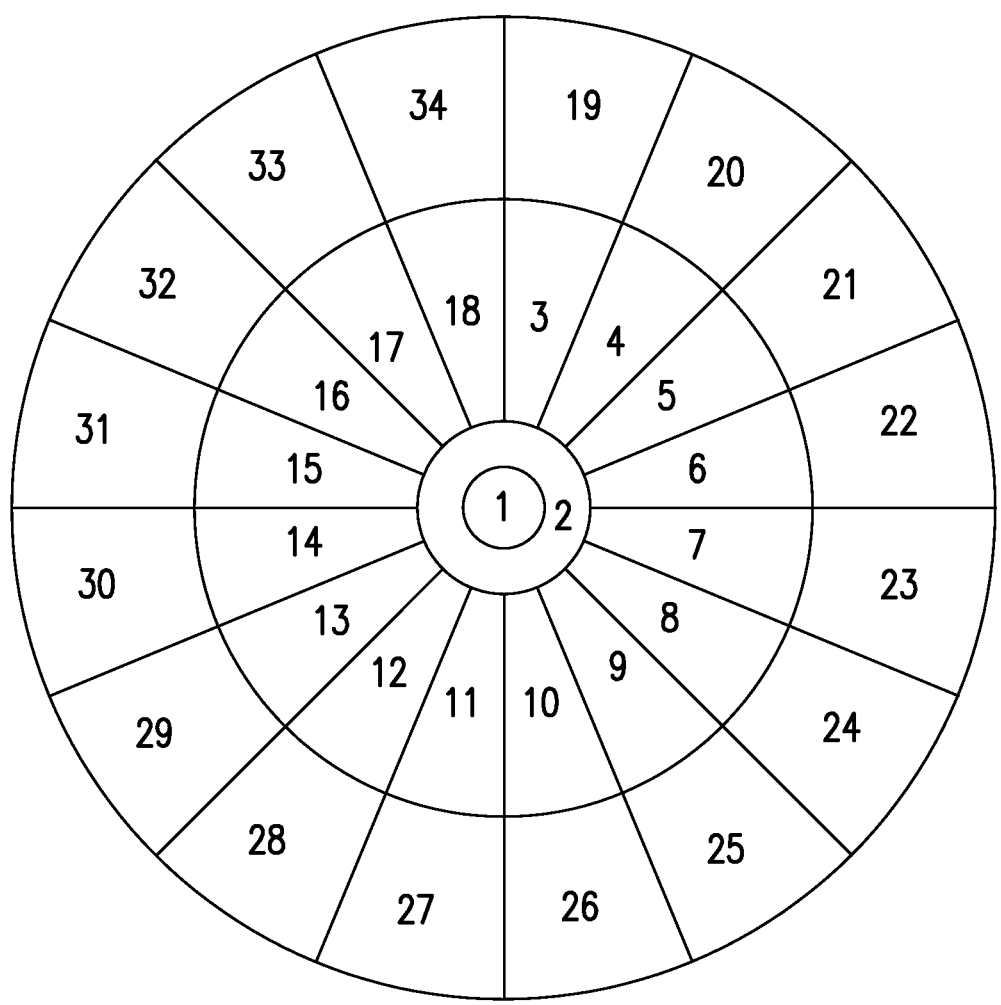
FIG. 80 provides a diagram showing an array of detector elements or optical elements which measure scattered light in multiple ranges of scatter planes and scattering angles, where each group of scattering planes is further divided into ranges of scattering angle, according to the present invention.

In order to increase the range of dimensions which can be measured, more scattering angular ranges must be measured. For example, FIG. 80 shows a detector array which measures two scattering angle ranges for each of the positive and negative scattering sides of each scattering plane. For example, elements 4 and 20 are low and high angle ranges for the positive scattering side and elements 12 and 28 are low and high angle ranges for the negative scattering side of the same scattering plane. These types of detector arrays are easily fabricated in custom silicon photodetector arrays. When very small particles are measured, silicon photodetector arrays may not have sufficient signal to noise to detect the very small scattering intensities. In this case, photomultipliers or avalanche photodiodes may be used, but at much greater expense for manufacture of custom arrays. One solution to this problem is to replace the custom detector array with an array of diffractive, Fresnel, or binary lenses and rout the light from each element of the diffractive optic array to a separate element of a commercially available (inexpensive) linear or 2-dimensional detector array, which could be made of PMT (photomultiplier) elements. However, it is claimed that any diffractive optic array could be replaced by a detector array with elements of the same shape, if that option is affordable. Arrays of conventional curved surface lenses, diffractive lenses, Fresnel lenses, or binary lenses are all included in the terms optic array or diffractive optic array used in this application. The diffractive optic array would consist of a separate diffractive lens structure covering the aperture of each detector element shape in FIG. 79 or 80. Each diffractive lens would have a separate optical axis. Therefore, each diffractive lens element (or segment) would focus the scattered light, which is captured by the aperture shape of that lens element, to a separate point behind the lens array. FIGS. 81*a* and 81*b* show a lens array, where each detection element section contains a lens with a different optical axis. This idea will work for any types of lens arrays: spherical, nonspherical, diffractive, binary, and Fresnel lenses. FIG. 81*a* shows a front view of the diffractive or binary lens array, where the curved lines inside each detection element segment represent each diffractive optic structure, whose center is the optical axis of that lens element. The optical axis, of the element corresponding to detector element 1 in FIG. 80, is approximately in the center of that element. The optical axis, of the element corresponding to detector element 2 in FIG. 80, is located off of center of the array to shift the optical axis away from that of element 1.

Figure 82:
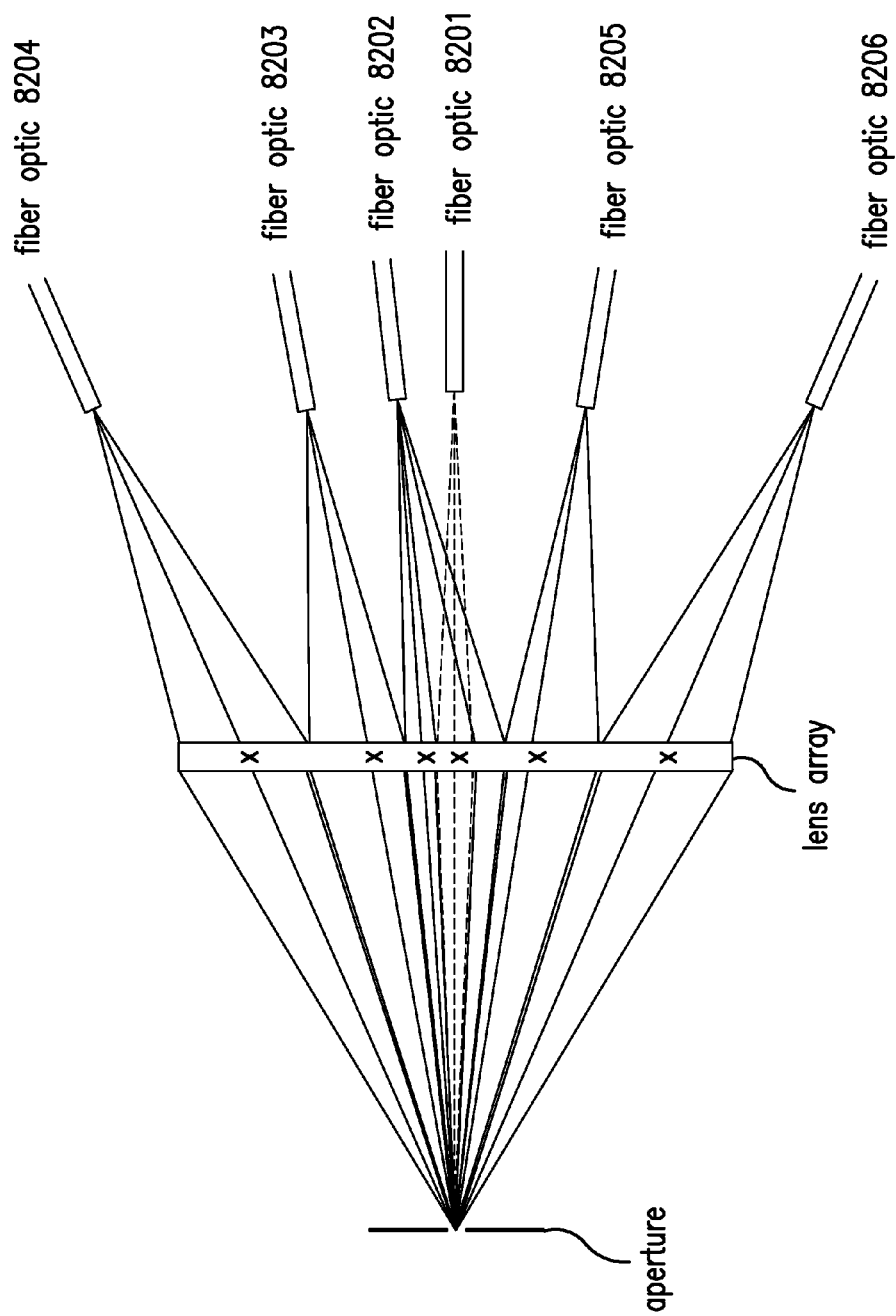
FIG. 82 provides an optical schematic diagram of the diffractive optic of FIGS. 81*a* and 81*b*, as used to separate and distribute scattered light among a group of fiber optics.

To demonstrate this concept, consider the elements with optical axes marked with "x", in the front view (FIGS. 81*a* and 81*b*) and side view (FIG. 82) of FIG. 81, and the corresponding element numbers in FIG. 80. FIG. 82 shows the paths for light rays which pass through aperture 7802 in FIG. 78. The aperture in FIG. 82 could be aperture 7802 or aperture 7803 in FIG. 78. The lens element for detection element 1 collects the light from the unscattered light beam and focuses that light into fiber optic 8201, as shown in FIG. 82. The annular lens element for detection element 2 collects the scattered light at the lower scattering angles and focuses that light into fiber optic 8202, as shown in FIG. 82. All of the light from the annular segment of element 2 is focused to one fiber optic, because that annular section is an annular section of one lens element with an optical axis which is shifted from the center of the lens array. FIG. 82 also shows the scattered light focused by other lens elements in the same scattering plane into fiber optics 8203, 8204, 8205, and 8206. Each lens element has a separate optical axis so that light passing through aperture 7802 (FIG. 78) will be focused into a separate fiber optic for each lens array element, which are shaped to collect the scattered light over the appropriate range of scattering angles for each scattering plane. Each lens element focuses the light from that element into a separate fiber optic, which carries that light to a separate element of a detector array, which may be any type of detector array, including 2 dimensional array or linear arrays. Each fiber optic might also carry light to separate detectors, which are not in an array. Therefore, the detector array does not need to have the shapes of the lens elements so that commercially available (non-custom) detector arrays can be used. And also the detector elements can be much smaller than the lens elements, providing much lower noise and lower cost. The cost of fabricating the custom lens array is much less than the cost of fabricating a custom photomultiplier detector array or silicon detector array. Spherical lens arrays can be molded into plastic or glass. And diffractive lens arrays can be molded or patterned (lithography) into nearly planar plastic or glass plates. The choice of positions for the optical axis for each element should be optimized to reduce optical aberrations. In some cases, the optical axis may lie outside of the lens element. Also, the optical axes could be arranged so that the focused array of spots conforms to the configuration of a 2 dimensional detector array so that the spots can be focused directly onto the detector array, eliminating the fiber optics. This could also be done with linear arrays by creating a linear array of optical axes in the lens array. In each case, fiber optic or detector, the aperture 7802 or 7803 in FIG. 78 will be the limiting aperture. Each fiber optic core (or detector element which replaces each fiber optic) is underfilled by the scattered light image of aperture 7802 or 7803.

The same technique can be used for aperture 7803 by replacing detector array 7822 (see FIG. 78) with a lens array whose elements are coupled to a separate detector array through fiber optics (or directly coupled to the detector array, without fiber optics, as described above). In this case, elements 1 and 2 may not be needed, because the scattered light distribution from the non-spherical mirror segment has a hole in the center where low scattered light is not captured. The high angle scattering should be separated into different scattering planes due to the high degree of asymmetry in the scattering pattern at higher scattering angles, so the scattered light in annular segments of elements 1 and 2 would not be as useful. However for large particles, elements 1 and 2 could be broken up into multiple scattering plane detectors to determine particle shape.

This lens array idea is most effective for large numbers of detection elements. For smaller numbers of elements, each element could have a separate wedge prism behind it to divert the light to a lens which would focus it onto a particular fiber optic or detector element. But still the point is to eliminate the need for a custom detector array, to reduce the detector element size to reduce noise, and to allow use of highly sensitive detectors such as photomultipliers, which have limited customization.

Figure 83:
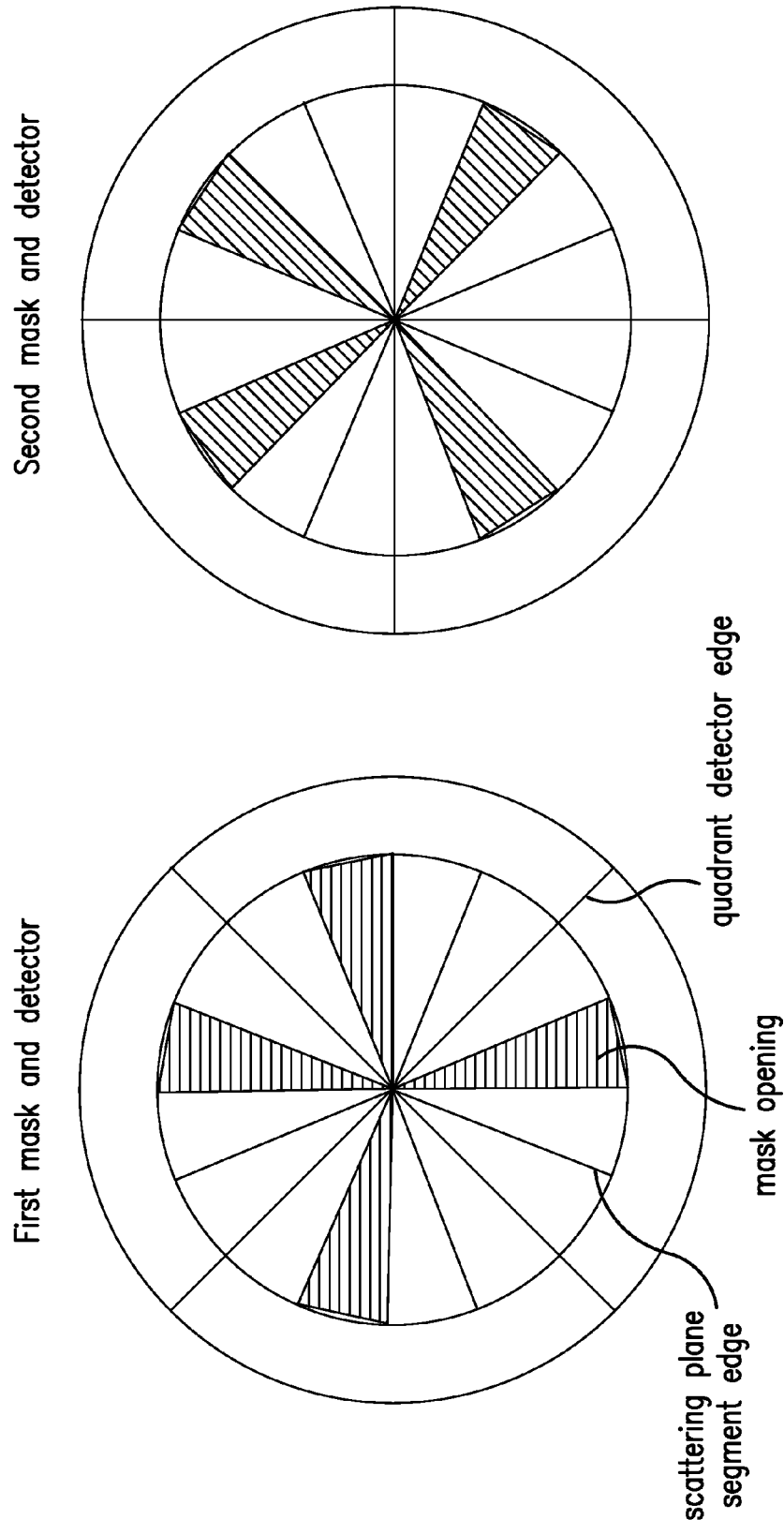
FIG. 83 provides diagrams showing the use of two quadrant detectors and masks to separately measure scattered light in eight different ranges of scattering planes, according to the present invention.

Quadrant detectors are commercially available for most detector types, including silicon photodiodes and photomultipliers. FIG. 83 shows a method to use two quadrant detectors to measure scattered light from 8 adjacent scattering planes by using a mask which is positioned on top of the quadrant detector. Each scattering plane actually covers a range of scattering plane angles, as defined by the angle Ø in FIG. 84. The first quadrant detector replaces each of the detector arrays in FIG. 78. The second quadrant detector captures scattered light at the same distance from the aperture 7803 (or aperture 7802) as the first quadrant detector by diverting a portion of the beam with a beam splitter placed on front of the first quadrant detector. Each mask is designed and each quadrant detector is oriented as shown in FIG. 83, so that all 8 scattering planes are measured by the two quadrant detectors. In this way, two inexpensive quadrant detectors can measure the equivalent scattering planes measured by one expensive custom 8 element custom detector array. Typically, the central portion of the mask is designed to block the unscattered light from the source beam and to define a minimum scattering angle for each detector element. The detection concepts described in FIGS. 79, 80, 81, 82, and 83 can also be used in the other particle shape measuring optical systems, which were described previously in this disclosure.

Figure 85:
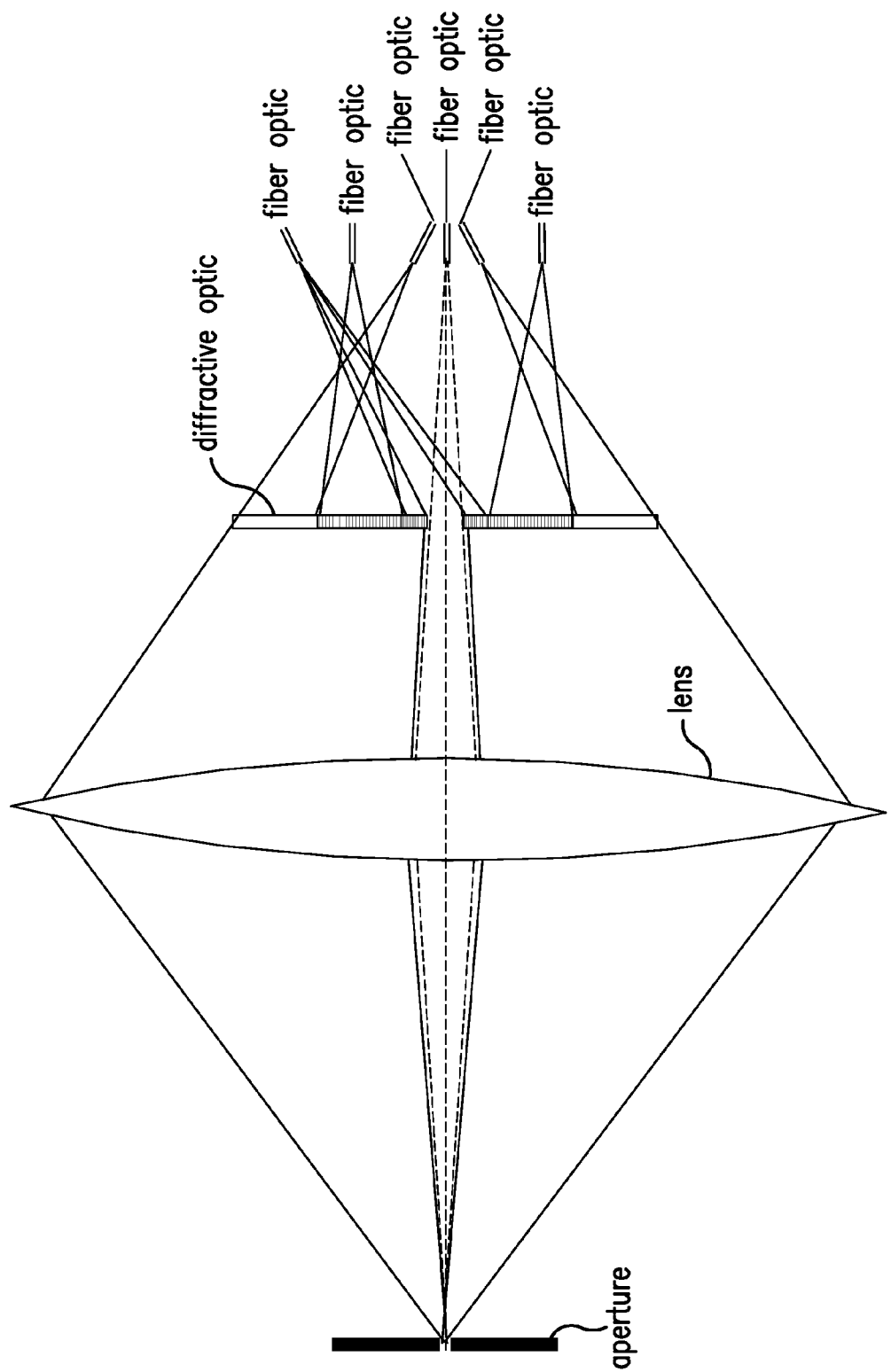
FIG. 85 provides an optical schematic diagram of a hybrid diffractive/conventional lens system, which utilizes diffractive optics as shown in FIG. 84.

FIG. 84 shows a diffractive optic, where different segments consist of linear diffractive gratings which are designed to diffract nearly all of the light into one diffraction order. This diffractive optic is used in a hybrid diffractive/conventional lens system as shown in FIG. 85. The diffractive optic is normal to the optical axis of the optical system. The aperture in FIG. 85 is the same as aperture 7802 in FIG. 78. And this design can also be used with aperture 7803 in FIG. 78, without the need for the central hole and annular ring segment, because aperture 7803 passes only high angle scatter. Consider the case with aperture 7802 in FIG. 78. The scattered light is collected by the lens in FIG. 85. The diffractive optic (as shown in FIG. 84) in the back focal plane of the lens, diffracts the light incident on each segment of the diffractive optic into various directions. Each direction is perpendicular to the grating lines (see FIG. 84) in each segment. When the aperture hole is small and only single particles are measured, the diffractive optic does not need to be placed in the back focal plane of the lens, but the diffractive lens array must be scaled to match the marginal rays (the ray of highest scattering angle) of the lens in the plane in which it resides. The light from each segment is nominally focused to the image plane of the aperture. However, the light from each segment is focused to a different position on that plane, because the linear grating structure in each segment is oriented in a different direction, or has a different grating period, from the grating structures in other segments. Each wedge segment of the diffractive optic is split into 2 sections, each with a different grating line spacing and diffraction angle. These 2 wedge shaped segments collect scattered light in 2 different angular ranges in each of various scattering planes. For example, scattering planes 8401, 8403, and 8405 are shown in FIG. 84. In addition, there is a central hole and a surrounding annular region. The central hole passes the unscattered light beam and the surrounding annular region collects scattered light at very low scattering angles in all scattering planes. At low scattering angles, the scattered light is not strongly dependent upon scattering plane and this annular segment provides a measure of very low angle scattering (which contains less shape information) to be used as with the scattering data from each of the scattering planes to determine the particle dimension in that plane. FIG. 85 shows the light rays in one of the scattering planes. FIGS. 84 and 85 show the case where the spatial frequency of the lower scattering angle segments is higher than the spatial frequency of the higher scattering angle segments. Hence the separated beams cross each other after the diffractive optic, because the diffraction angle of the lower scattering angle segments is higher than that for the higher scattering angle segments. This could also be reversed, where the spatial frequencies are higher for the higher scattering angle segments. In this second case, the focused beams would still be separated at the plane of the fiber optics, but the beams may not cross each other.

The shape of detector array or optic array elements is not limited to wedge shape. Other shapes such as linear shapes shown in FIG. 33 could be used. Also each grating structure of a certain spatial frequency and orientation could be replaced by a prism of a certain wedge angle and orientation so as to deflect the light in the same direction as the grating structure.

Figure 86:
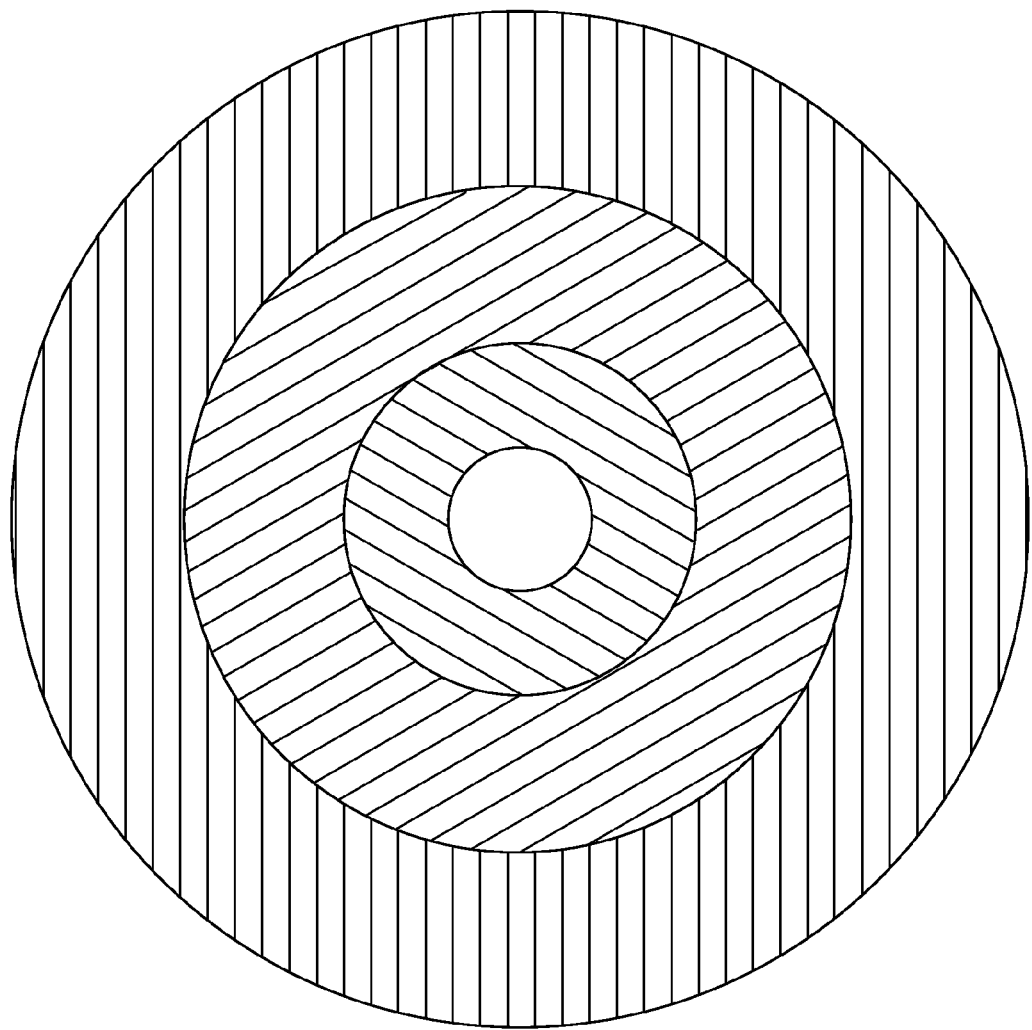
FIG. 86 provides a diagram of an optical element which includes multiple annular regions, each with a different diffractive grating, according to the present invention.

This method can also be used to measure "equivalent particle diameter" without any shape determination. In this case, a diffractive optic as shown in FIG. 86 could be used in FIG. 85. This diffractive optic consists of annual rings which define multiple scattering angle ranges. The signals from these annual rings are independent of particle orientation and will only provide "equivalent particle diameter". The orientation (or grating line spacing) of the grating structure in each annular ring is different from the orientation (or grating line spacing) of any other annular ring to separate the focused scattered light of each annular ring into different detectors as shown in FIG. 85.

Any of the masks or detector structures, including those in FIGS. 76, 77, 79, 80, 81, 82, 84, 85, 86, and 87, may be replaced by custom holographic or binary optic elements which are designed to optimize the shape of the signal vs. particle dimension of each detector element. For example, some higher scattering angle signals and ratios of scattering signals will show multivalued functionality, where the same value of the function occurs at two different particle sizes due to minima in the function. Also the function may have a very nonlinear dependence upon particle dimension, with regions of low sensitivity to dimension value. In these cases, custom holographic or binary optics can be designed with angular transform properties which will reduce these signal distortions. These type of optics can provide a wide range of transform functionality, which describes how the direction of an incident ray at each incident angle is changed by the optical element at each position on the element. These optics are usually computer generated as surface structures, on a substrate, which can be replicated inexpensively by molding from a computer generated master or by electron beam etching of the surface. The characteristics of these structures can be optimized by using the scattering program to produce the scattering vs. angle in all scattering planes, a propagation program to calculate how this scattered light is redirected by the holographic or binary optic element, and an algorithm describing how this transformed light is collected by each detector element. An optimization program uses these three programs to produce the detector signal response as a function of holographic or binary optic parameters. The optimization program iteratively adjusts these optic parameters until the optimal form of the detector vs. particle dimension is obtained.

When using a photomultiplier (PMT), one must prevent the detector from producing large current levels which will damage the detector. This damage could be avoided by using a feedback loop which reduces the anode voltage of the PMT when the anode current reaches damaging levels. In order to avoid non-linear behavior over the useful range of the detector, the change of anode voltage should be relatively sharp at the current damage threshold level, with very little change below that level. The response time of the feedback loop should be sufficiently short to prevent damage. The feedback signal could also be provided by a premeasuring system as shown in FIGS. 49, 49B, and 51.

Another important point is that any of the scattering techniques described in this disclosure can be applied to particles which are prepared on a microscope slide (or other particle container), which is scanned through the interaction volume instead of flowing a particle dispersion through the interaction volume. This provides some advantages: the particles are confined to a thin layer reducing the number of coincidence counts and the detection system could integrate scattered light signal for a longer time from smaller particles, to improve signal to noise, by stopping the scan stage or reducing the scan speed when smaller particles are detected (this can also be accomplished by slowing the flow rate in the dispersion case). However, preparing a slide of the particles for analysis, greatly increases the sample preparation time and the potential for sample inhomogeneity. When a cover slip is placed onto the dispersion, the smaller particles are forced farther from their original positions, distorting the homogeneity of the sample. This method can also be used in dynamic scattering cases (heterodyne detection with flow) by moving the microscope slide with a known velocity through the source beam.

The scattering signal currents from elements on these detector arrays are digitized to produce scattered signal vs. time for each detector element. All detectors could be digitally sampled simultaneously (using a sample and hold or fast analog to digital converter) or each detector could be integrated over the same time period, so that signal ratios represent ratios of signals at the same point in time or over the same period of time and same portion of the source beam intensity profile. The data from each detector element is analyzed to produce a single value from that element per particle. This analysis may involve determining the time of maximum peak of the detection element with largest scatter signal and then using the same time sample for all of the other detection elements. Also the peak can be integrated for all detection elements to produce a single value for each element. Also the methods described previously for pulse analysis can be employed, including the methods (FIG. 28) for eliminating events which are not particles. The final single value for each detector element represents the scattered light flux collected by that element. In the following analysis, the following definitions will be used:

The integral of F(x) between x=x1 and x=x2 is given by:

$$INT(F(x),x1,x2)$$

The sum of terms of Fi(x) over index i from i=n to i=m is given by:

$$SUM(Fi(x),i=n,i=m)$$

Where Fi(x) is the ith term

Each scattering angle corresponds to a radius, measured from the center of the source beam, in the detection plane. For the case shown in FIG. 78, z is the distance between aperture 7802 and detector 7821 (or between aperture 7803 and detector array 7822). Then the relationship between scattering angle θ and the radius r on the detector is given by:

$$r=z*\tan(M\theta)$$

where M is the angular magnification of the optical system (angular magnification of lens 7813 for detector array 7821 and the nonspherical mirror segment for detector array 7822). In the case of aperture 7803 and detector array 7822, the θ in the above equation is related to the actual scattering angle through a simple equation which describes the angular transformation of the nonspherical mirror segment. This angular transformation can also be nonlinear for certain types of optics, but in any case there is a one to one correspondence between scattering angle and position r on the detector, mask, or diffractive optic plane. And r is measured from the center of the scattering pattern or the center of the source beam on that plane.

Figure 105:
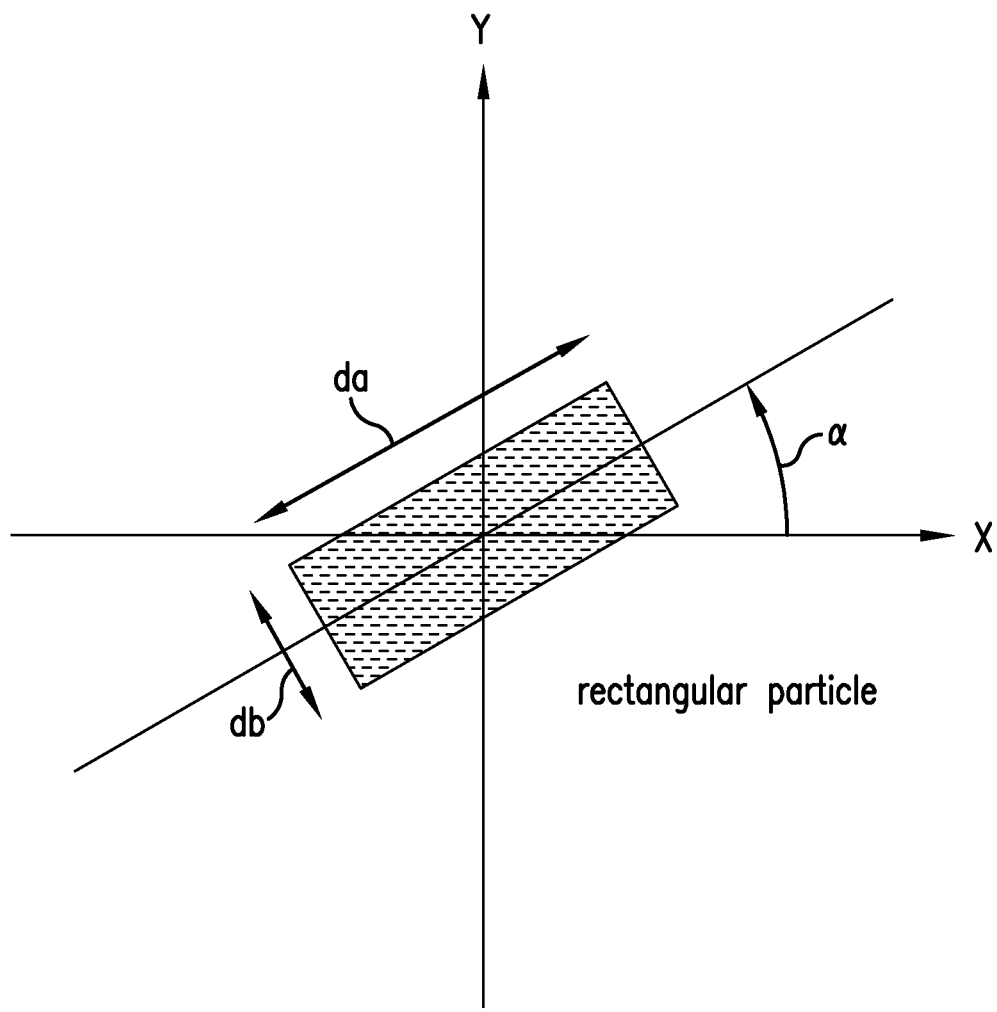
FIG. 105 provides a diagram showing the dimensions and orientation of a rectangular particle, as used in the present invention.

Consider the case of rectangular particles, with dimensions da and db and rotational orientation α, as shown in FIG. 105. Then the scattered flux (flux integrated over the pulse, peak flux value of pulse, etc.) collected by the ith detector element can be described by:

$$Fij=INT(I(da,db,\alpha,\emptyset i,r)*Wij(r),r1ij,r2ij)$$

I is the scattered intensity. Øi is the bisecting angle of the intersection of the ith scattering plane with the detector plane in the detector plane, as illustrated in FIG. 84 for scattering plane 8403. The scattering plane (which contains the scattered ray and the incident light beam) is perpendicular to the detector plane (which is the plane of FIGS. 79, 80, and 83 for example). Wij(r) is the weighting function of scattered light as a function of r for the jth detector aperture, with limits between r1$ij$ and r2$ij$, of the detector for the ith scattering plane. Notice that Ø and α are corresponding angles; Ø is in the detector plane and α is in the particle plane (FIG. 105 for example). If the scattering distribution changes significantly with Ø, within a single scattering plane detector, then the scattered intensity must be integrated over that detector in both Ø and r:

$$Fij=INT(I(da,db,\alpha,\emptyset i,\emptyset,r)*Wij(\emptyset,r),r1ij,r2ij,\emptyset 1ij,\emptyset 2ij)$$

where INT is now a 2-dimensional integral over Ø and r.

$$Fij=INT(I(da,db,\alpha,x,y)*Wij(x,y),x1ij,x2ij,y1ij,y2ij)$$ for a conventional detector array (such as a CCD array) with pixels on a rectangular coordinate system in x and y, where INT is a 2-dimensional integral in x and y space. In this case the r and Ø (or Øi) coordinates are replaced by x and y using the conversion relationships:

$$x=r\cos(\emptyset) \text{ and } y=r\sin(\emptyset)$$

Let F1 be the flux measured on detector element 1 in FIG. 80 and let F2 be the flux measured on detector element 2 in FIG. 80. Then the following sets of simultaneous equations can be formed to solve for the dimensions da, db, and random orientation, α, of the particle, where Ri is a ratio of two fluxes.

| | |
|---|---|
| Fi = Fij | equation set: [Fij]m = [Fij]t |
| Ri = Fij/Fik | equation set: [Fij/Fik]m = [Fij/Fik]t |
| Rijk = Fik/Fij | equation set: [Fik/Fij]m = [Fik/Fij]t |
| Ri = Fij/F2 | equation set: [Fij/F2]m = [Fij/F2]t |
| Ri = Fij/F1 | equation set: [Fij/F1]m = [Fij/F1]t |
| Ri = Fij/Fkj | equation set: [Fij/Fkj]m = [Fij/Fkj]t |
| Ri = Fij/Fkn | equation set: [Fij/Fkn]m = [Fij/Fkn]t |
| Ri = FijA/FijB | equation set: [FijA/FijB]m = [FijA/FijB]t |
| Ri = FijA/FknB | equation set: [FijA/FknB]m = [FijA/FknB]t |

[X]m is the measured value of X (derived from signals measured by the optical system detectors) and [X]t is the theoretical function which describes X as a function of the particle characteristics. Some of these particle characteristics are unknowns (da, db, and a for example) to be solved from the equation set. Recognize that i indicates the ith scattering plane and ij indicates the jth detector in the ith scattering plane. FijA and FijB are the corresponding detector elements from two different detector arrays (A and B), each with a different Wij(r), as shown in detector pairs A and B in FIG. 74, and diffractive optics 8701 and 8702 in FIG. 87. This equation also holds for more than two detectors (Ri=FijC/FijB, etc.). Also, for all other Ri equations, Wij can be the same or different for the numerator F and the denominator F in the ratio. The above simultaneous equations can be formed from the Fij values measured from each particle. Any groups of the above equations, for any values of i, j, k, n, A, and B, can be solved for da, db, and α (or other particle characteristics) by using various search, optimization, and regression methods.

In most cases, the equations will be non-linear functions of these unknowns, requiring iterative methods for solution. The computation of theoretical values for scattered intensity I(da, db, α, Øi, r), of nonspherical particles, requires long computer time. This is particularly problematic as this computation must be accomplished for each counted particle. Also numerical integration of these functions to produce Fij values during the iterative optimization process requires far too much computer time. This computer time can be reduced by fitting a series of explicitly integratible functions to each of the theoretical I(da, db, α, Øi, r) functions. For example consider the following power series form for the I(da, db, α, Øi, r) and Wij(r) functions:

$$Wij=\text{SUM}(Qp(j)*(r\hat{p}),p=0,p=pmax)$$

$$Ii=\text{SUM}(Cm(da,db,\alpha,\emptyset i)*(r\hat{m}),m=0,m=mmax)$$

Where x^p=x to the pth power and x*y=product of x and y.

$$Fij=INT(I(da,db,\alpha,\emptyset i,r)*Wij(r),r1ij,r2ij)$$

$$Fij=INT(\text{SUM}(Cm(da,db,\alpha,\emptyset i)*(r\hat{m}),m=0,m=mmax)$$
$$*\text{SUM}(Qp(j)*(r\hat{p}),p=0,p=pmax),r1ij,r2ij)$$

$$Fij=\text{SUM}(Bq(da,db,\alpha,\emptyset i)*(r2^{ij}(q+1))/(q+1)),q=0,$$
$$q=pmax+mmax)-\text{SUM}(Bq(da,db,\alpha,\emptyset i)*(r1ij\hat{}$$
$$(q+1))/(q+1)),q=0,q=pmax+mmax)$$

Then the previously listed sets of simultaneous equations can be formed from these equations for Fij. Where Bq are coefficients which are products of values of Cm and Qp, which are all known functions of da, db, α, and Øi. This concept can easily be extended to other particle types (just assume da and db to be the major and minor axes for an elliptical particle) and particles with more dimensions, such as pentagons, etc. In each case, the model must expand to account for the added dimensions dc, dd, de, etc.

$$Fij=INT(I(da,db,dc,dd,de,\ldots,\emptyset i,r)*Wij(r),r1ij,r2ij)$$

Figure 89:
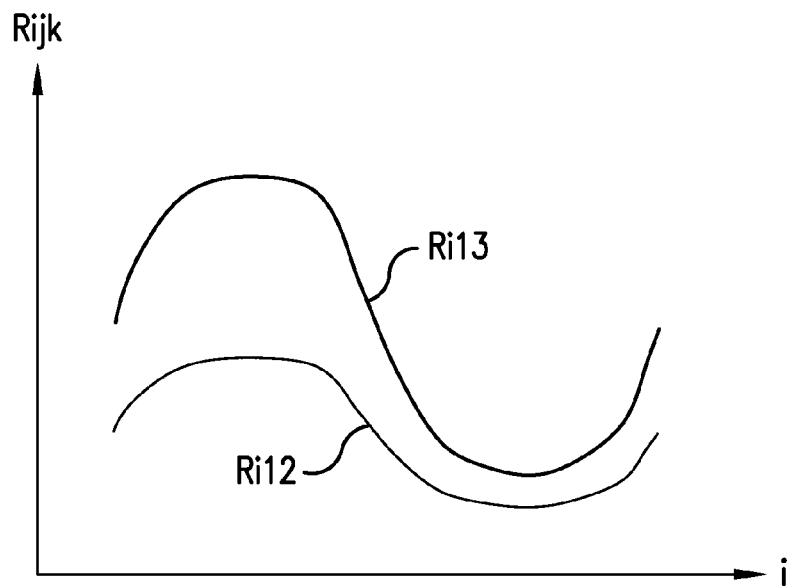
FIG. 89 provides a graph which plots ratios of scatter parameters as a function of center scattering plane orientation, according to the present invention.
Figure 90:
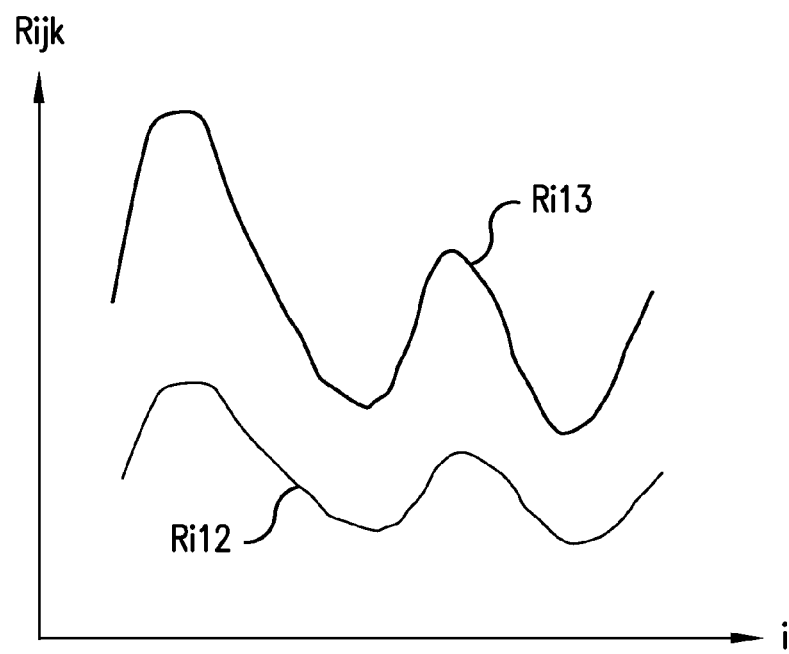
FIG. 90 provides a graph showing plots of ratios of scatter parameters as a function of center scattering plane orientation for a particle with more than two dimensions, according to the present invention.
Figure 102:
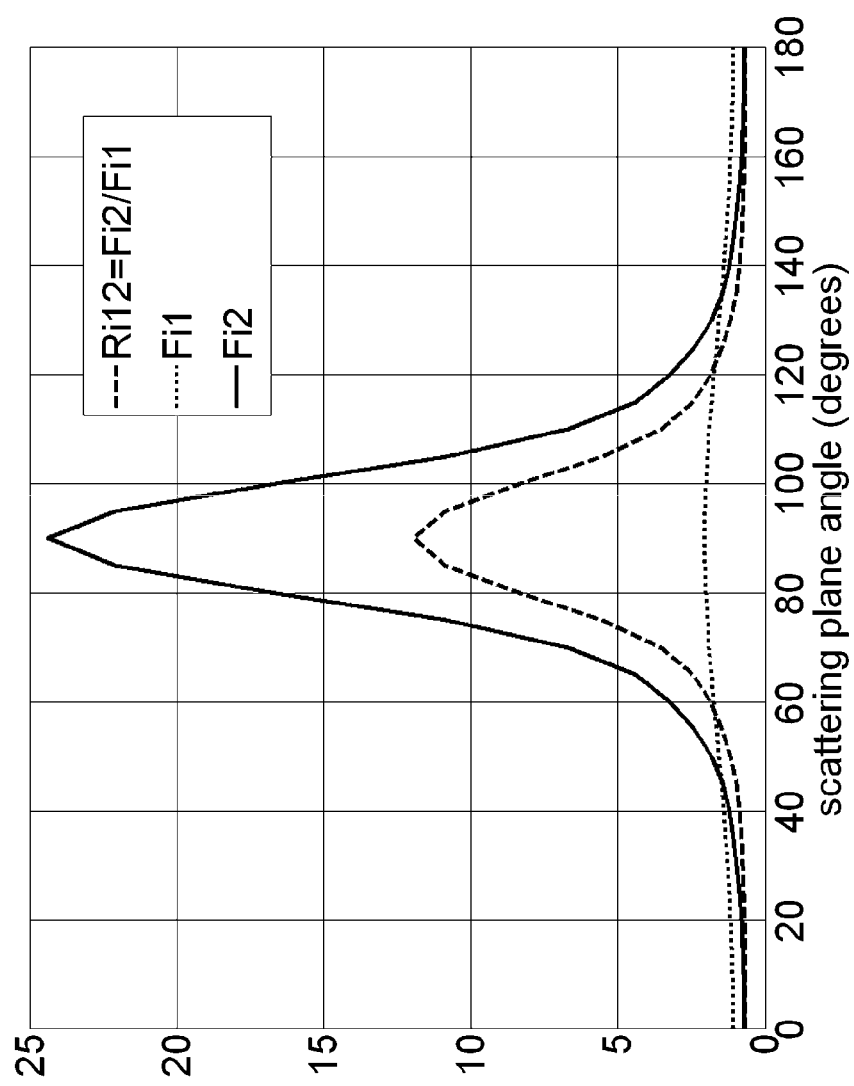
FIG. 102 provides a graph showing plots of low angle scatter, high angle scatter, and the ratio of these values as a function of the scattering plane angle, for a rectangular shaped particle, according to the present invention.
Figure 103:
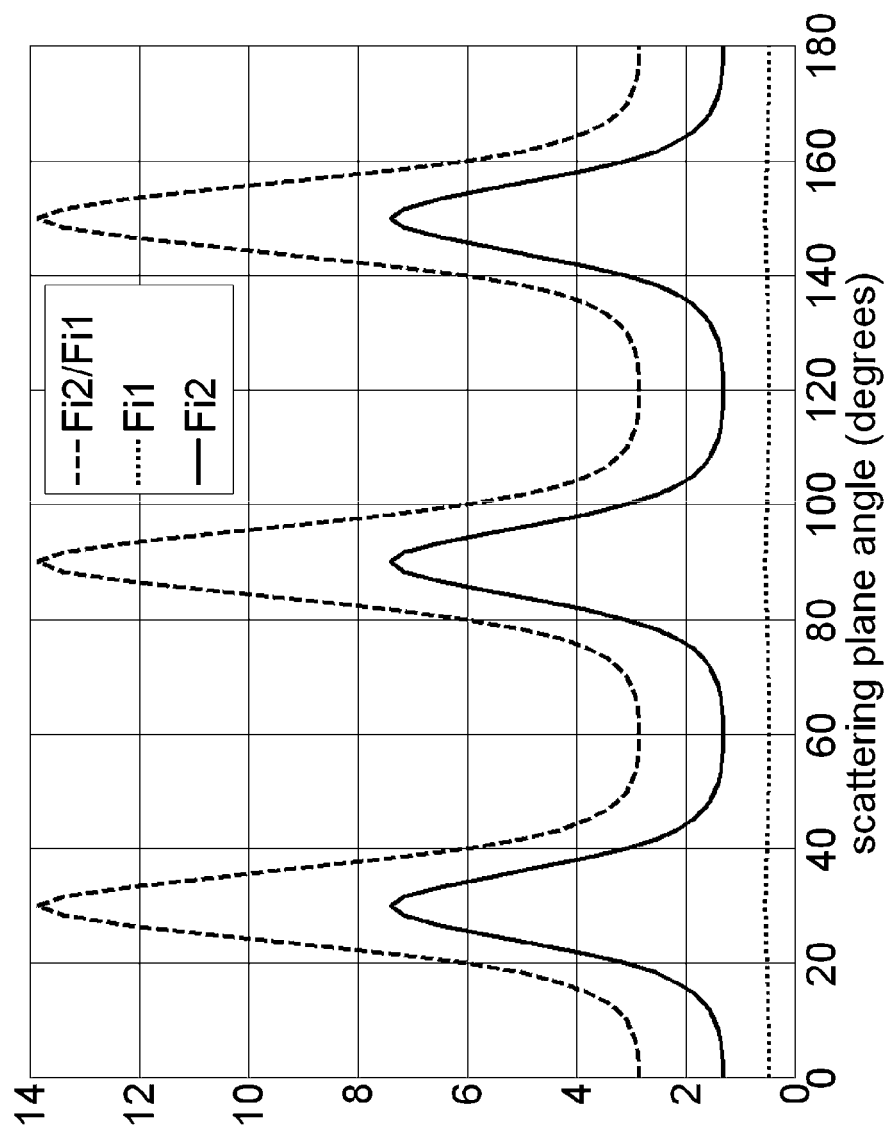
FIG. 103 provides a graph showing plots of low angle scatter, high angle scatter, and the ratio of these values as a function of the scattering plane angle, for a triangle shaped particle, according to the present invention.

In order to solve for particle types with larger number of dimensions (i.e. octagons, etc.), sufficient scattering planes and detectors must be used to provide a fully determined set of simultaneous equations. In other words, the number of equations should be greater than or equal to the number of unknowns, which include the dimensions, da, db, dc, ... etc. and the particle orientation, α. However, as indicated before, the solution of these equations can be computationally time consuming. The measurement of scattered light in many scattering planes can reduce the computational time, because the extrema of the dimension function can be found quickly. For example, take the case of the rectangular particle, where da, db, and α could be solved for with only measurements in 3 scattering planes. The solution of these 3 equations may require iterative search and much computer time per particle. However, if scattering is measured in many more scattering planes, the major and minor axes of the rectangle can be determined immediately, eliminating the requirement for determining the particle orientation a or reducing the range of a for the search solution. For example, if we interpolate a plot of Ri vs. Øi (or Rijk vs. i), we will obtain a function (or functions) with a maximum at Ømax and a minimum at Ømin, as shown in FIGS. 89, 102, and 103. If Ri is the ratio of the high angle flux divided by the low angle flux in the ith scattering plane, then the direction Ømin will provide major axis and the direction Ømax will provide minor axis of the particle; and the R values for those directions will provide the particle dimensions in those directions. An example of the rectangular case is shown in FIG. 102 for a rectangle with 1:5 aspect ratio. The scattered flux in the higher scattering angle detector element (Fi2) is divided by that of a lower scattering angle element (Fi1) to produce a ratio Ri12 for each scattering plane angle Øi. Øi equals 90 degrees at the maximum of Fi2 and Ri12, indicating the direction parallel to the smallest dimension of the rectangle. In this way the orientation and shorter dimension of the rectangle can be determined immediately from the direction Øimax=90 and values of Fi1, Fi2, Ri12 for that scattering plane. And the longer dimension is determined from the values of Fi1, Fi2, Ri12 for the scattering plane which is perpendicular to the plane at 90 degrees, Øi=0 degrees, assuming a rectangle. For example the equation for I(a,b) could be used to calculate the flux values Fi1 and Fi2 for the major and minor axis scattering planes, as a function of dimensions A and B of the rectangle. Then these functions are inverted to provide dimensions as a function of Fi1, Fi2, and Ri12 for the major and minor axis scattering planes. This could also be accomplished with a search routine. This process is simple in this case because in the directions of the major and minor axes Fij are approximately only a function of the dimension in that plane. Hence the two dimensions can be determined independently. This technique can be extended to particles with more dimensions, as shown in FIG. 90, where multiple extrema indicate the Ø direction and effective particle dimension in that direction. The case for a triangle shaped particle is shown in FIG. 103, where a maximum in Fi2 and Ri12 is shown in each scattering plane which is perpendicular to each side of the triangle. The peak locations provide the particle orientation and fast determination of dimensions using the simultaneous equation sets above. For the case where the particle shape is not assumed, the relative Øi orientation of the peaks in the Fi2 or Ri12 function indicate the shape and orientation of the particle, and the values of Fi2 or Ri12 indicate the dimensions. In some cases these dimensions may not be completely independent, requiring iterative minimization of the RMS error between Fij(measured) and Fij(theoretical) using various search, optimization, and regression methods (such as Newton's method, Levenburg-Marquardt method, etc.). These methods use a first guess to the unknowns (all the dimensions and α) from which the Fij(theoretical) is calculated. Then the difference between Fij(measured) and Fij(theoretical) is used to refine the next guess for the unknowns from which the next Fij (theoretical) is calculated. The change to the particle parameters (unknowns) to calculate the next Fij (theoretical) or Rijk(theoretical) is determined by the type of optimization algorithm (Newton's method, Marquardt Levenburg, etc.). This iteration loop is repeated until the fit between all Fij(measured)'s and Fij(theoretical)'s is sufficient, where i=scattering plane index and j=detection array element or lens array element index in a certain scattering plane. This iterative loop is run many times until one (or the sum of both) of the following RMS errors are minimized.

$$\text{Error}=\text{SUM}((Fij(\text{measured})-Fij(\text{theoretical}))^2)$$
summed over all $ij$ $$\text{Error}=\text{SUM}((Rijk(\text{measured})-Rijk(\text{theoretical}))^2)$$
summed over all $ijk$ Many applications will require only particle characteristics which correlate to some quality of the manufactured product. Examples of these characteristics include: 1) equivalent spherical diameter and aspect ratio, 2) maximum and minimum equivalent dimensions as determined from the scattering planes with minimum and maximum Rijk, respectively, 3) dimension in the minimum Rijk scattering plane and the dimension in the plane perpendicular to that plane, 4) dimension in the maximum Rijk scattering plane and the dimension in the plane perpendicular to that plane. The equivalent dimension is the dimension calculated for that plane as though the plane were a major or minor axis plane using the scattering theory for a rectangle. All of the detector, mask, and diffractive optic configurations shown in this disclosure are only examples. This disclosure claims the measurement of any number of scattering angular ranges in each of any number of scattering planes, as required to determine the shape and size of each particle.

All segmented detector arrays or lens arrays could be replaced by 2-dimensional detector arrays. In this case the inverse 2-dimensional Fourier Transform of the spatial distribution of detector element flux values would produce a direct 2-dimensional function of the particle shape, in the Fraunhofer approximation. The dimensions of the contour plot (perhaps by choosing the 50% contour of the peak contour) of this 2-dimensional inverse Fourier Transform function will provide the outline of the particle directly, for particles which are modeled by the Fraunhofer approximation. However, the size range of this type of array (per number of detector elements) is not as efficient as the wedge shaped scattering plane arrays described previously, because the detector elements in the commercially available 2-dimensional arrays are all the same size. When the particles become large enough to produce scattered light in only the lowest scattering angle detector element, the size determination becomes difficult, because two reliable scattering values are not available to determine the size in that scatter plane and absolute scatter signals must be used without signal ratios. This problem could be solved by using a custom array, where low scattering angle elements are smaller than larger scattering angle elements. This progression of element size with increasing scattering angle can also be accomplished with a equal pixel 2-D array which follows a lens, holographic optic, binary optic, or diffractive optic with non-linear distortion. The lens or diffractive optic distorts the scattering pattern so that the pattern is spread out near the center and compressed more at higher radii (larger scattering angles) in the pattern. In this way, detector elements closer to the center of the pattern will subtend a smaller scattering angular width than elements farther from the center. This would increase the size range of the detector array and still allow use of standard CCD type linear arrays. However, due to the limited dynamic range of most CCD arrays, a single PMT or other large dynamic range pre-sensor, placed upstream of the CCD array, could provide some indication of scattering signal level before the particle arrives in the view of the CCD array, similar to the systems shown in FIGS. 49, 49B, 50, 51, 67, and 68. Then the source power level or CCD electronic gain could be adjusted during the CCD data collection to optimize the signal to noise and fully utilize the range of the analog to digital converter on the CCD. Any optical system in this application can be used as a pre-sensor for any other optical system (the primary system) in this application, by placing that pre-sensor system upstream of the primary system to quickly measure the scattering properties and adjust the source power level or detection electronic gain of the primary system to optimize the detection system performance of the primary system, using the same concepts as described for FIGS. 49, 49B, 50, 51, 67, and 68.

Figure 87:
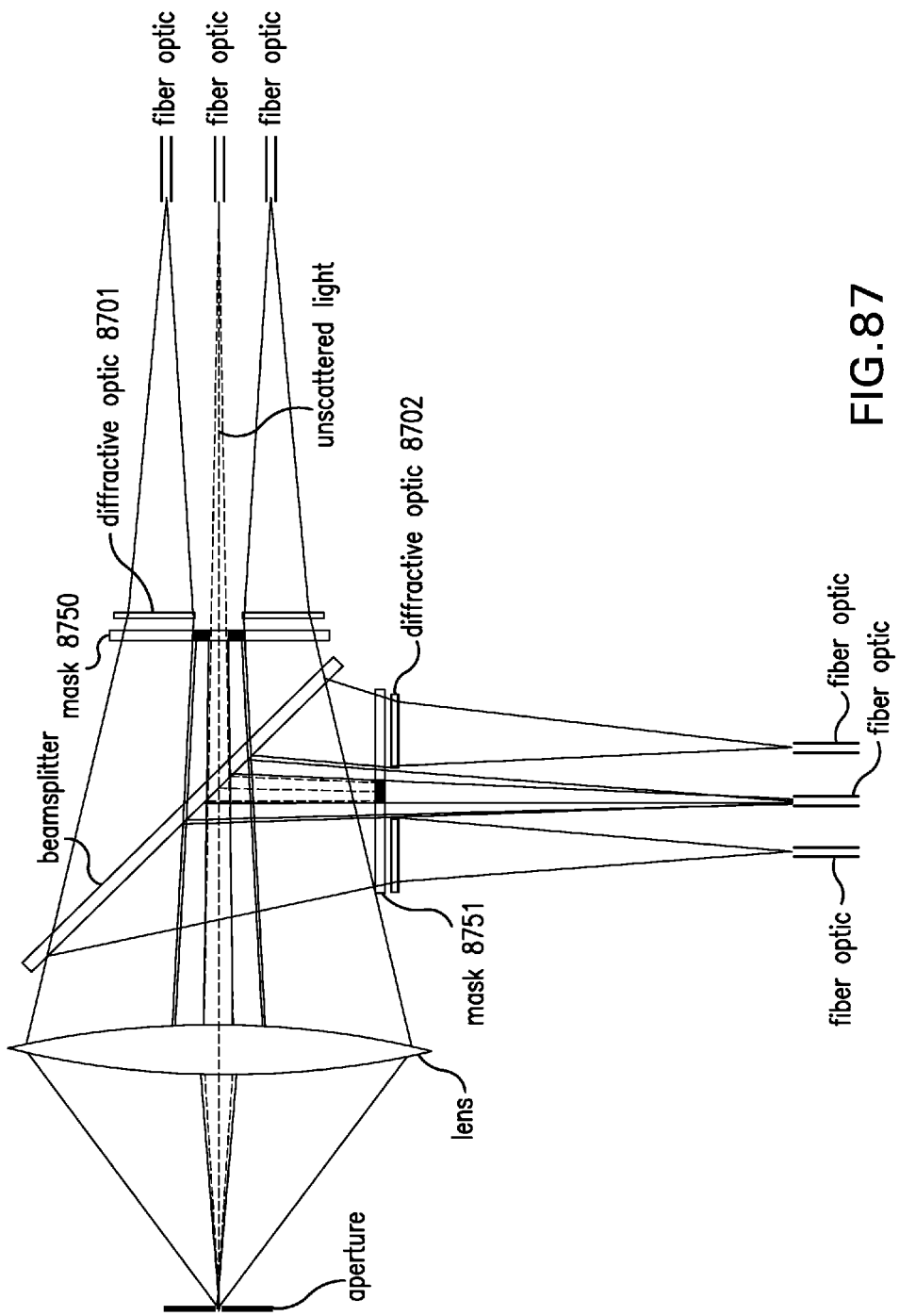
FIG. 87 provides a schematic diagram of an optical system, which utilizes two masks and two optical arrays, or diffractive optics, according to the present invention.
Figure 88:
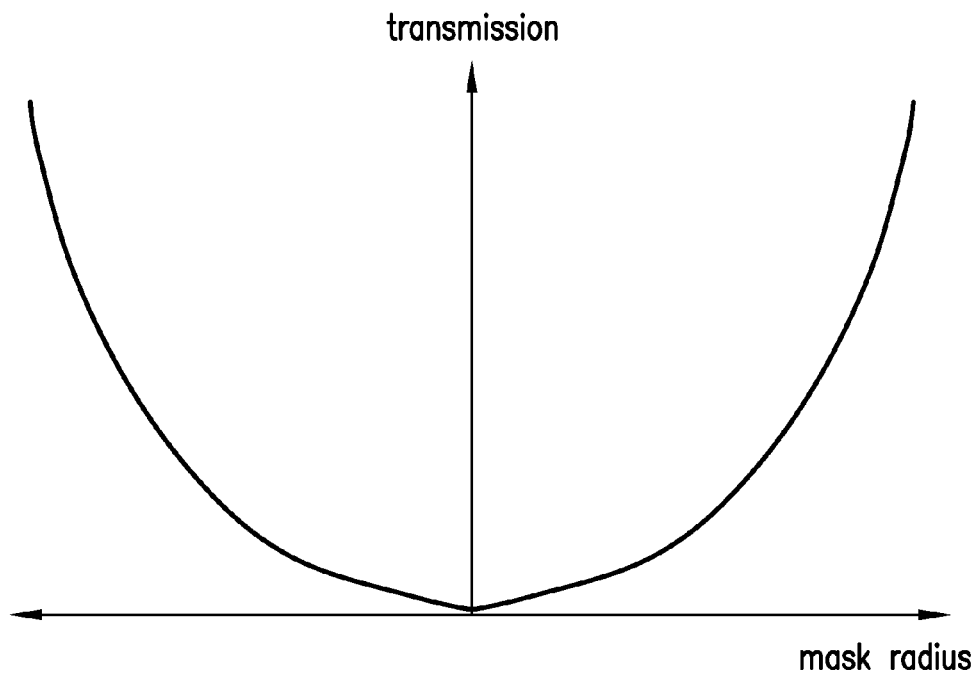
FIG. 88 provides a graph showing an example of a radial transmission function for an optical mask, according to the present invention.

This wider size range can also be obtained by using different weighting functions (Wij) for two different detector elements which view the same range of scattering angle (or different ranges of scattering angle) in the same scattering plane, as described previously. As long as the Wij functions are different for the two measurements, the ratio of those scattered flux values will be size dependent over a large range of particle size and will be relatively insensitive to position of the particle in the beam. The Wij function can be implemented in the detector element shape, as shown in FIG. 76, and/or by placing an attenuation mask, which has varying attenuation along the direction of changing scattering angle, over the detector elements of one the arrays or with different Wij functions on each of two or more arrays which see the same scattering angle ranges and scattering planes. This idea can be implemented in the system shown in FIG. 78, using the detection module shown in FIG. 87. The aperture in FIG. 87 could be either aperture 7802 or aperture 7803 in FIG. 78. In this case, the scattered light (and incident beam when used with aperture 7802) is focused by a lens, through a beamsplitter, onto two optical arrays, which are diffractive arrays using conventional lens/diffractive array hybrid as in FIG. 85 (or conventional molded or diffractive optics if no single conventional lens is used). The lens arrays (examples are shown in FIGS. 79, 80, 84, 86) are used to divert the scattered light from different array elements to different positions in the image plane of the beam focus in the cell so that the flux from each element can be collected separately by fiber optics or detectors. The lens array in FIG. 87 is similar to that in FIG. 79, just for illustration, but any of the previous lens arrays could be used in this design. There is a mask on front of each lens array which provides selection of center hole (element 1 in FIG. 78) or the annular ring (element 2 in FIG. 78). This mask also provides light attenuation which varies along the radius (or scattering angle) of the mask, as shown by the transmission function, for example only, in FIG. 88. This transmission function can take many forms, but as long as the radial transmission function of mask 8750 is different from the radial transmission function of mask 8751, the ratio of flux from corresponding lens elements in diffractive optic 8701 and diffractive optic 8702 (as captured by the fiber optics or detector elements) will provide dimensional information for the particle in the scattering plane of that element. For example transmission functions for mask 8750, T1$ij$, and for mask 8751, T2$ij$, could have many cases including:

Case 1: T1$ij$=1 (constant transmission), T2$ij$=r
Case 2: T1$ij$=r, T2$ij$=r^2 where r is the radius in the scattering plane from the center of the lens array. Each value of r corresponds to a different scattering angle.

Then the effective weighting functions are the product of the transmission functions and the weighting function, Wij s, of the segment or element shape in the detector array or optic array. For wedge shaped segments the shape weighting function is:

$$Wijs=r$$

Hence the effective weighting functions are:

$$W1ij=W1ijs.*T1ij$$

$$W2ij=W2ijs.*T2ij$$

$$R12ij=F1ij/F2ij$$

Where F1$ij$=flux from the jth detector aperture in the ith scattering plane of detector array 1 or optic array 1

Where F2$ij$=flux from the jth detector aperture in the ith scattering plane of detector array 2 or optic array 2

In some cases, wedge shaped detector elements are easily implemented because they include the same group of scattering planes throughout the range of scattering angle. When the same wedged shaped elements are used in both arrays, the transmission functions could provide the difference in Wij. For example one combination could consist of these functions:

| T1ij = r^0.5 | W1ijs = r | W1ij = r^1.5 |
| T2ij = r^−2.5 | W2ijs = r | W2ij = r^−1.5 |

Many combinations of transmission functions will work. This invention disclosure claims the use of any two different W1$ij$ and W2$ij$ functions (using transmission and/or shape weighting functions) and using flux from corresponding array elements, one with W1$ij$ and the other with W2$ij$. Diffractive optic array 8701 and diffractive optic array 8702 are identical and they are rotated so that each array segment collects scattered light from the same scattering plane as the corresponding element in the other diffractive optic. Then ratio (R12$ij$) of light flux values from these two elements is used to determine the "effective dimension" of the particle in that scattering plane. However, as described previous, these dimensions are not independent and the full set of simultaneous R12$ij$ equations must be used to solve for the actual dimensions.

The radial weighting function Wij can also be used with a single position sensitive detector, which uses multiple electrodes to determine the position of the centroid of the pattern on the detector. As the particle size deceases, the centroid, as measured through the Wij mask, will move towards larger radial value r, indicating the particle size.

In general, we have two cases for measuring 2 dimensional scattering distributions. The detector array can be a set of radial extensions in various scattering planes (as in FIG. 84) or a 2-dimensional array. In first case, we define the array as a function of radius, r, and angle Ø in the detector array or optic array plane, as shown in FIG. 84. In the second case the array is a standard 2-dimensional array (i.e. CCD array) with elements arranged in columns and rows which are defined as a function of x and y. The choice between these cases will be determined from the available computer speed, shape constraints, and particle size range. In order to measure particle shape statistics of a particle sample, an enormous number of particles must be characterized. For example, consider the following case. We are to count particles and characterize them into 25 different dimensional classes. Each class could vary by size or shape. If we want to measure the content of each class to within 5% we need to measure 400 particles per class, if the counting process is Poisson. Therefore we need to measure and characterize 10000 particles. If we want the entire analysis process to take 5 minutes, then we have 30 milliseconds per particle to measure and digitize the scattered light, and solve equations for the shape and dimensions. We could do a full global search for the particle orientation and dimensions using the equations given above. All of the parameters of those equations can be solved from the 2-dimensional scattered intensity distribution in the plane of the detector array or optic array. The theoretical 2-dimensional scattered intensity distribution is calculated using known methods, such as T-matrix and Discrete Dipole Approximation, (see "Light Scattering by Nonspherical Particles", M. Mishchenko, et al.). Then this theoretical intensity distribution is integrated over the areas of each element of detector array or optic array. These values for Fij are calculated for various particle orientations, α, and various particle dimensions. A global search routine would search among these theoretical Fij sets to find the one which best fits to the measured set of Fij. Then the dimensions of that set would be accepted for that particle. While this process might take far longer than 30 milliseconds per particle, it would produce the most accurate determination of particle dimensions and shape. This full search method is claimed by this invention because in some cases, users will be willing to collect data on the optical system computer and then transfer the raw data off-line to a set of parallel processors which continuously crunch data sets 24 hours per day. And also future computers will be capable of doing these computations in the required time. However, for the users, who want their results in real-time (i.e. within 5 minutes) with present personal computers, some of the shortcuts, as described previously, must be employed. In the case of process control, users need results quickly in order to adjust the process parameters in nearly real-time. And also, many times the determined shape and size does not need to be precise because these results only need to correlate to the quality of their product. In general a particle with multiple flat edges will produce a scattering pattern with a radial projection for each edge into a scattering plane which is perpendicular to that edge. So when the ratio data, Rijk, is plotted vs. Øi (or vs. scattering plane) as shown in FIGS. 90 and 103, one will obtain a maximum in Rijk for each side of a multi-sided particle. So evaluation of Rijk vs. Øi will very quickly determine the orientation of the particle's sides and the values of Rijk are then used in a more limited global search routine, which does not have to search over all possible orientations of the particle and over all possible number of particle sides. This will dramatically reduce the search time. Also, the "dimension" of the particle in the direction perpendicular to each side can be determined approximately from Rijk values in the scattering plane which is perpendicular to that side. These values could be used directly to determine "approximate dimensions" of the multisided particle, without a search algorithm, because the approximate dimension can be calculated directly from a theoretical function of Rijk. As the particle model becomes simpler (i.e. rectangle) the orientation and dimensions are calculated immediately by finding the Ømax and Ømin in the Rijk vs. Øi, and then using the Rijk values in those two scattering planes to calculate the dimensions in those scattering planes. If only a few scattering planes are measured, the Rijk function could be interpolated or fit to a theoretical function for the rectangle case, to calculate a more exact orientation, which may be between two adjacent scattering planes.

Figure 91:
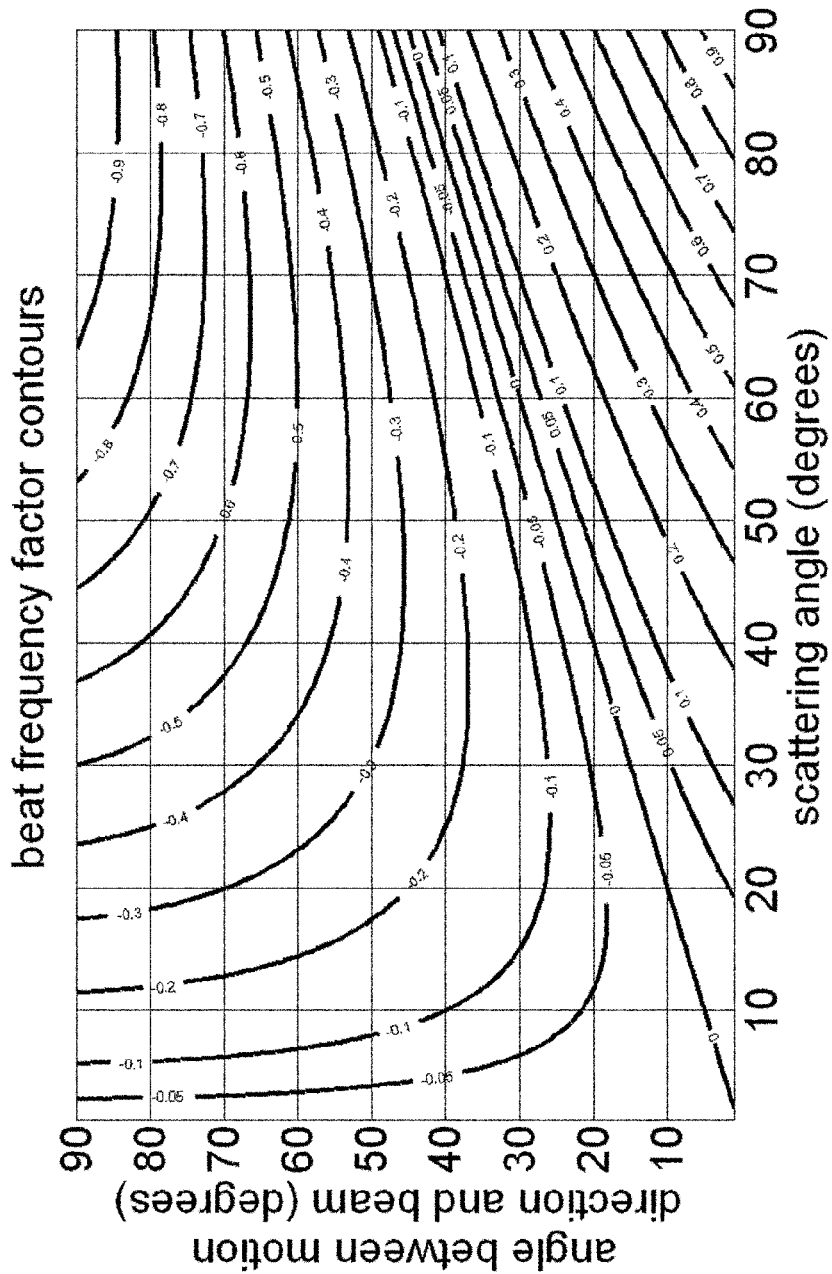
FIG. 91 provides a graph which plots beat frequency factor contours as a function of scattering angle, and the angle between the motion direction and the light beam, according to the present invention.
Figure 94:
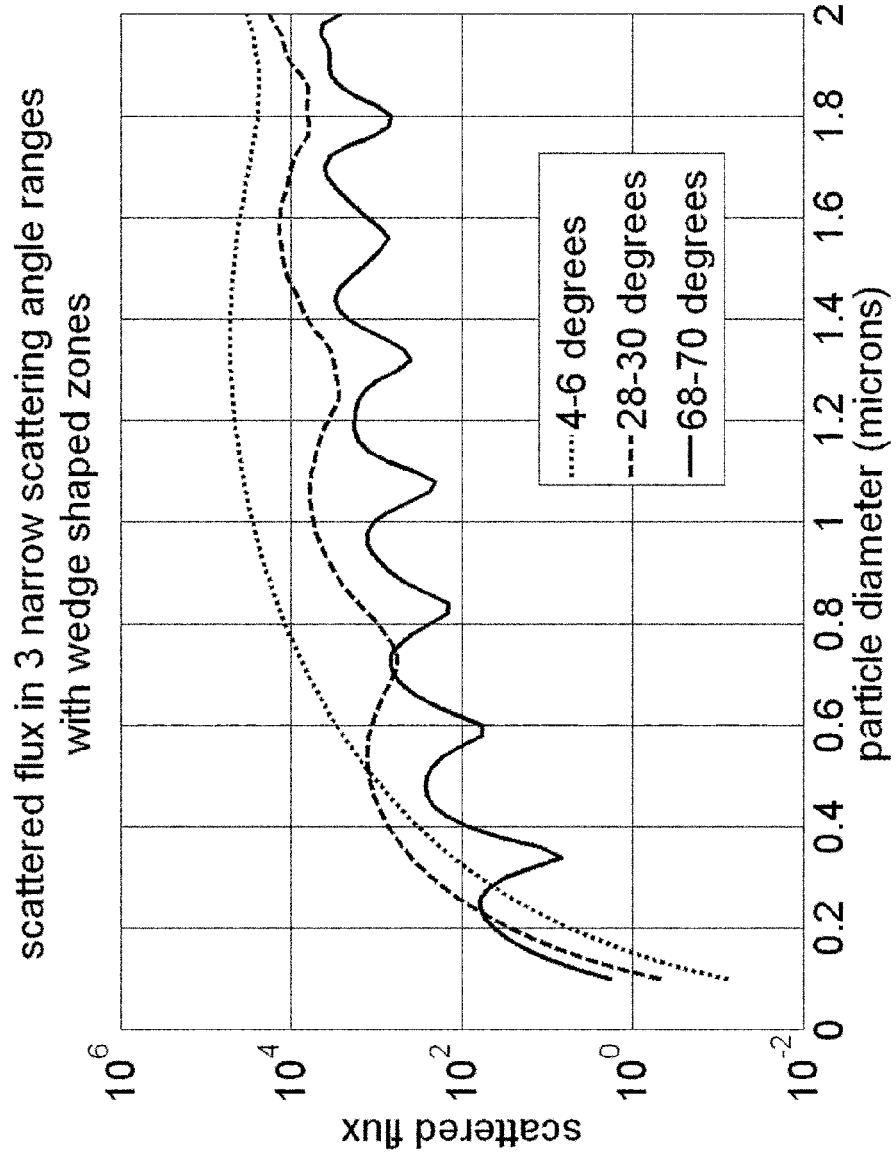
FIG. 94 provides a graph showing plots of scattered flux in 3 narrow scattering angle ranges, with wedge shaped zones or segments, according to the present invention.
Figure 95:
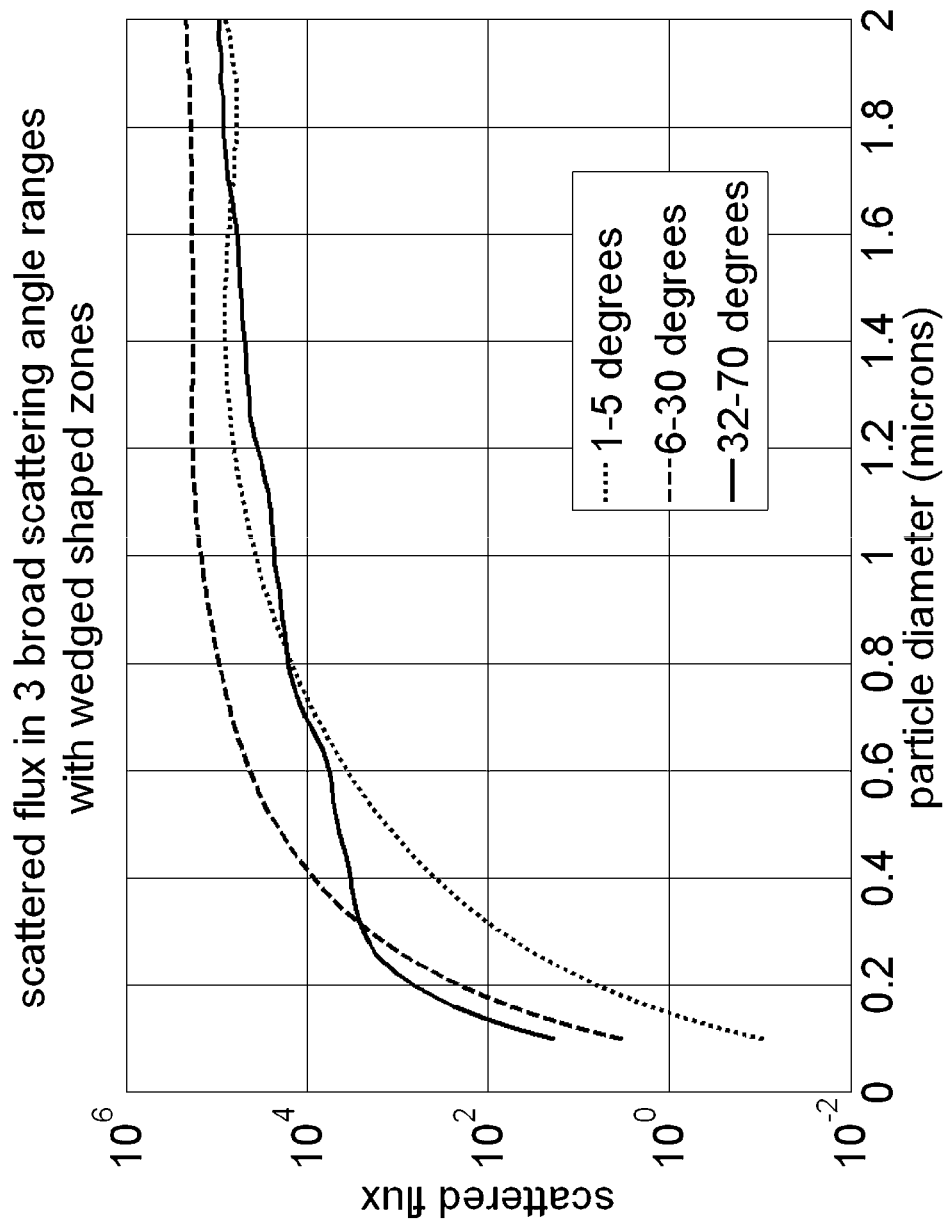
FIG. 95 provides a graph showing plots of scattered flux in 3 broad scattering angle ranges, with wedge shaped zones or segments, according to the present invention.

In general, the values Fij values as a function of size may be multi-valued in some size regions. Consider the simple case of 3 flux measurements, in each of 3 different scattering angle ranges. The first case, shown in FIG. 94, shows integrated flux for wedge shaped elements over narrow scattering angular ranges 4-6, 28-30, and 68-70 degrees. Notice that the higher angle flux has many oscillations vs. size and is multi-valued (i.e. for the 68-70 degree flux measurement one absolute level can indicate multiple sizes). However, particles at each diameter are uniquely determined by the 3 flux measurements. These oscillations and multi-valued behavior can be reduced by increasing the width of the angular ranges as shown in FIG. 95 for scattering angular ranges of 1-5, 6-30, and 32-70 degrees. However, the width of angular ranges may be limited in heterodyne systems due to loss of interferometric visibility as shown by FIG. 91.

These concepts can be combined with imaging systems to record the image of selected particles after they have passed through the interaction volume. An imaging system could be placed downstream of the interaction volume, with a pulsed light source which is triggered to fire at the correct delay, relative to the scatter pulse time, so that the particle has flowed into the center of the imaging beam during image capture. The pulsed light source has a very short pulse period so that the moving particle has very little motion during the illumination and image capture on a CCD array. The particle is imaged onto the CCD array at high magnification with a lens (microscope objective would be a good choice). In this way, particles which meet certain criteria, can be imaged to determine their morphology.

The alignment of aperture 7802 and aperture 7803 in FIG. 78, and other related figures, could be accomplished by running a medium concentration sample of sub-micron particles through the sample cell. The concentration is chosen so that a large number of particles are in the interaction volume at the same time so that a constant large scatter signal is seen on the detectors. Then the x, y, and z position of each aperture is adjusted to maximize the scatter signal on the detectors. This adjustment could include the methods described for FIGS. 5 and 6.

Most of the concepts in this application can accommodate aerosol particle samples, by removing the sample cell and by flowing the aerosol through the interaction volume of the incident beam. The effective scattering angles may change due to the change in refractive index of the dispersant.

Figure 92:
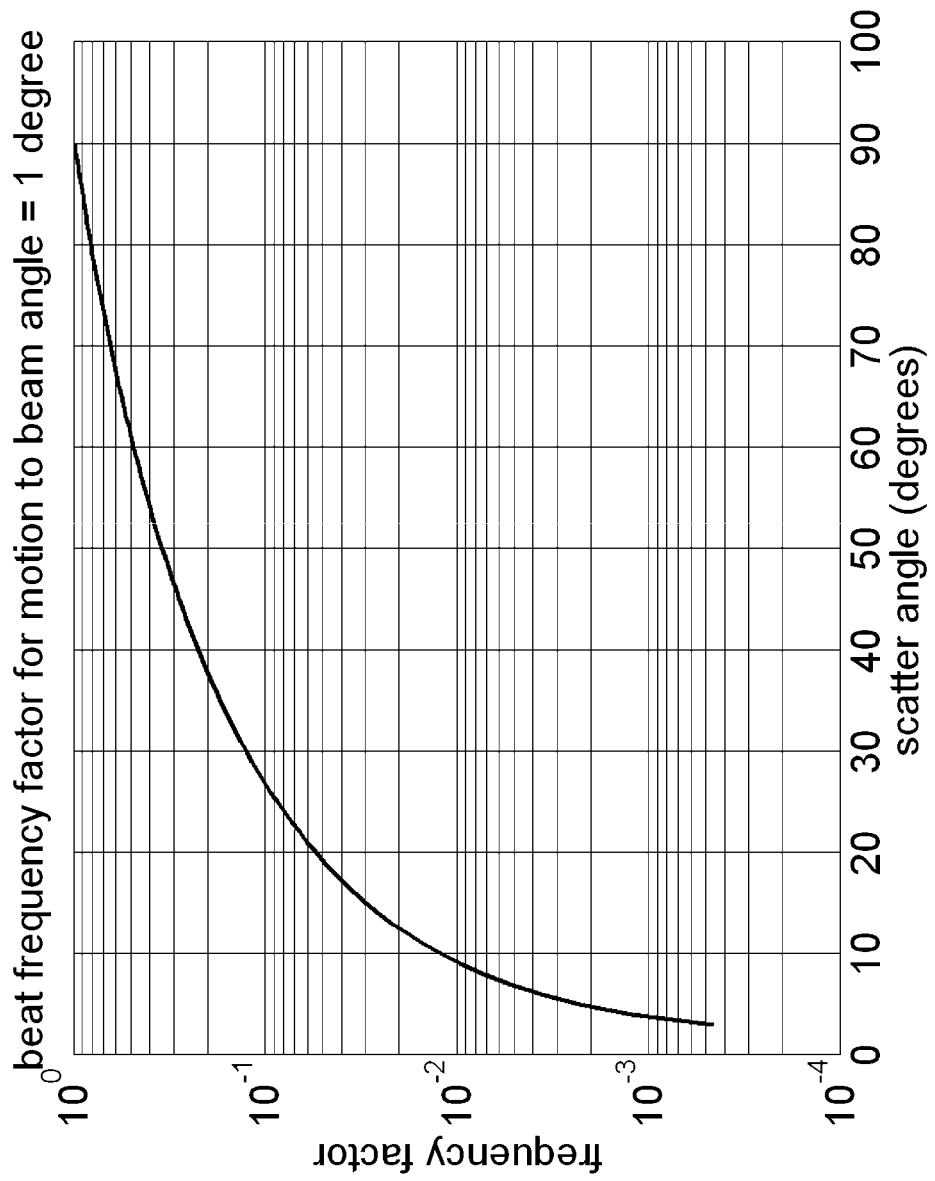
FIG. 92 provides a graph which plots beat frequency factor as a function of scattering angle for an angle of 1 degree between the motion direction and the light beam, according to the present invention.

Many methods in this application have used the heterodyne detection of scattered light to detect a particle. This is particularly useful for silicon detectors, which have lower sensitivity than PMTs. The beat frequency, Fb, depends upon the angle, θm, between the direction of motion and the direction of the incident light beam, and upon the scattering angle, θs.

$$Fb = v(\cos(\theta m) - \cos(\theta s - \theta m))/w1$$

Where v is the particle velocity and w1 is the light wavelength in the dispersant. FIG. 91 shows the contours of this function (normalized) vs. θs and θm. Notice that the beat frequency has very strong dependence upon these two angles. Consider the case where θm is 1 degree and the particle flow is nearly parallel to the incident beam. Then we obtain the dependence shown in FIG. 92. If all of the scattered light, over the scattering angular range of interest, from this moving particle were collected onto one detector in heterodyne mode, the scattered signal would contain a broad range of beat frequencies and the signal amplitude at each frequency would indicate the scattering amplitude at the corresponding scattering angle. Hence, the Fourier Transform of the signal vs. time from a single heterodyne detector could provide the entire angular scattering distribution from that particle, by using the Fourier Transform and the scattering angle to frequency correspondence curve, as shown in FIG. 92. Using the above equation, scattering angle to frequency correspondence curves could be computed for other values of θm that might be used.

Figure 93:
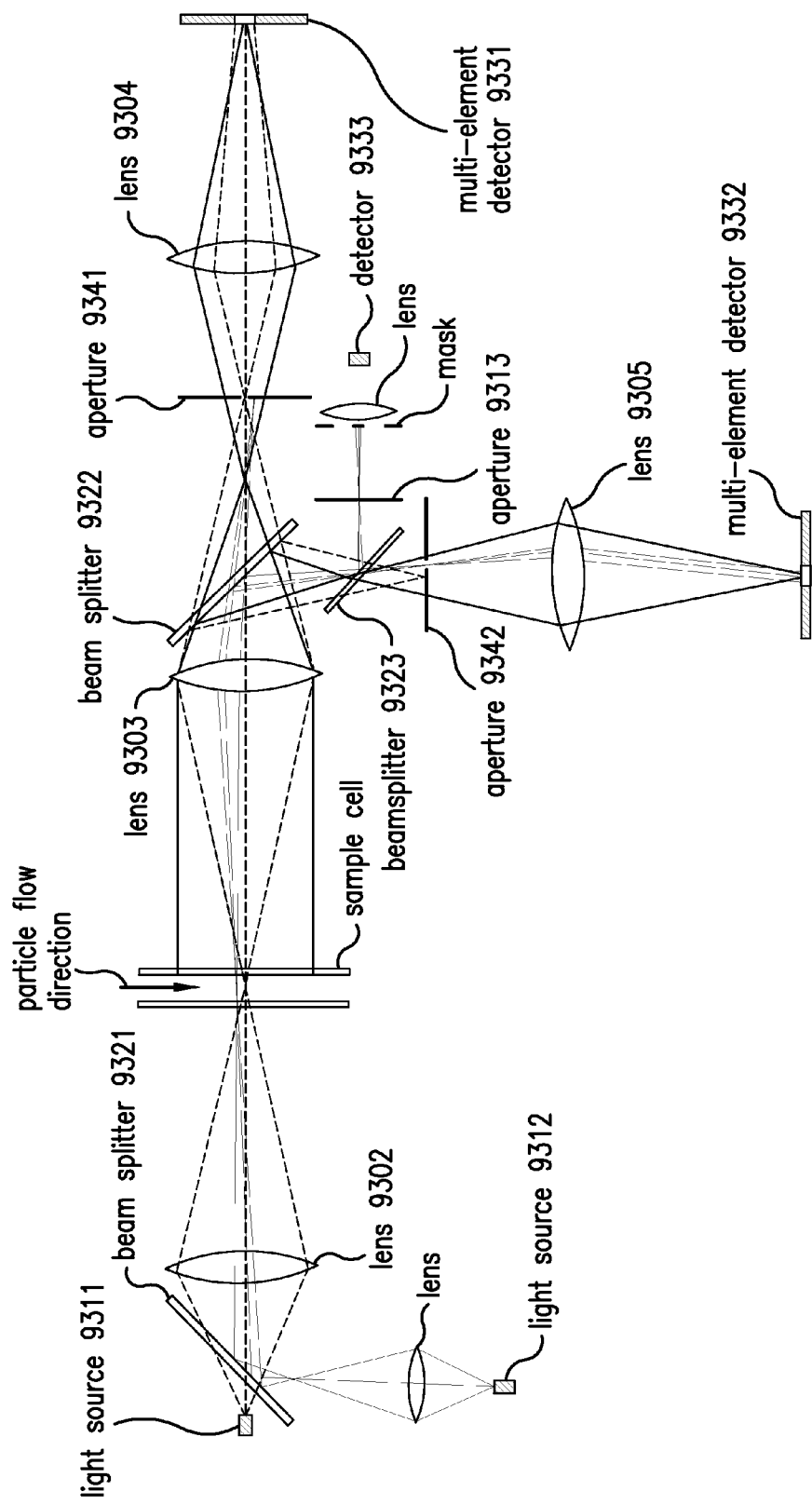
FIG. 93 provides a schematic diagram of an optical system, which provides an upstream scatter detection system to determine the expected scatter signal level for the primary scatter system for each particle, according to the present invention.

In some cases, the dynamic range of detectors will not be sufficient to cover the entire range of scatter signals from the particles. In particular, particles in the Rayleigh scattering range will produce scatter signals proportional to the $6^{th}$ power of the particle diameter. Photomultipliers can also be damaged by large levels of light. FIG. 93 shows an optical system which uses upstream scatter measurement to control the laser power or detection gain (or anode voltage) for a system down stream in particle flow to protect photomultipliers, to maximize the signal to noise, or to avoid detector saturation. Two light sources, light source 9311 and light source 9312, are combined by beamsplitter 9321 and focused into the center of the sample cell to two different locations along the particle flow path. Light source 9312 could be magnified to produce a larger spot size in the sample cell for detecting larger particles than the spot from light source 9311. However, the other purpose of light source 9312 is to detect an oncoming particle before it reaches the focused spot from light source 9311. The spot from light source 9312 is upstream from the light source 9311 spot. The light from both sources and the light scattered from both sources pass through lens 9303, which images both light spots to the planes of three apertures, 9341, 9342 and 9313. Apertures 9342 and 9313, which receive light reflected from beamsplitter 9322, block light from the interaction volume of light source 9311 but pass light from the interaction volume of light source 9312. Likewise, aperture 9341, which receives light transmitted by beamsplitter 9321, blocks light from the interaction volume of light source 9312 but passes light from the interaction volume of light source 9311. Therefore multi-element detector 9331 sees only light scattered from light source 9311; and multi-element detector 9332 and detector 9333 see only light scattered from light source 9312. These multi-element detectors can also be replaced by the optic array systems described previously. Multi-element detector 9332 is operated at much lower sensitivity than Multi-element detector 9331, which is operated at maximum sensitivity to detect the smallest particles. Whenever a particle, which would saturate and/or damage Multi-element detector 9331, passes through light source 9312 spot, detector(s) from Multi-element detector 9332 or detector 9333 will measure the larger amount of scattered light and trigger a circuit to lower the power level of light source 9311 or lower the gain (or anode voltage) of Multi-element detector 9331 so that Multi-element detector 9331 will not be saturated and/or damaged when that same particle passes through the interaction volume for light source 9311. This pre-sensor signal can also be used to optimize the signal to noise or dynamic range of the downstream sensors, as described previously for FIGS. 49, 49B, 50, 51, 67, and 68. The level of adjustment can be variable depending upon the light level measured by Multi-element detector 9332 or detector 9333. Light source 9311 is normally run at maximum power to detect the smallest particles. Light source 9311 power is only reduced after a calculated delay time after Multi-element detector 9332 detects a potentially damaging or saturating particle scatter signal. After that particle passes through the light source 9311 spot, the source 9311 power (or gains, anode voltages etc) is reset to maximum. The time delay is calculated from the spacing between the two source spots in the sample cell and the particle flow velocity. The multi-element detector arrays are in the focal plane of lens 9304 or lens 9305. Notice that the dark solid light rays indicate that multi-element detector arrays 9331 and 9332 are effectively, at infinity, in the back focal planes of lenses 9304 and 9305. These lenses place the detectors at infinity so that the effects of finite pinhole size in apertures 9341 and 9342 do not cause smearing in the scatter pattern. Typically the pinhole sizes are small enough so that lens 9304 and lens 9305 are not needed. The advantage of using lens 9302 for both sources is not only the cost of manufacture. This design allows the two source spots in the sample cell to be very close to each other, insuring that all particles which flow through the light source 9311 spot will have also previously flowed through the light source 9312 spot and been detected by multi-element detector 9332, even in the event of any flow anomalies (such as non-laminar flow) in the cell. To provide a large size dynamic range, the sample cell spot size for light source 9312 may be much larger than the spot size for light source 9311, in order to measure much larger particles. Then many particles which pass through source 9311 spot will flow around source 9312 spot. In this case, a third system is added using beamsplitter 9323 and aperture 9313. The pinhole of aperture 9313 is smaller than aperture 9342 to only pass scatter from the portion of Source 9312 spot which is directly above the Source 9311 spot. In this way, detector 9333 will only see the particles which will eventually pass through the source 9311 spot. So detector 9333 is used to set the source 9311 power level or detector 9331 gain (or anode voltage) using the time delay described above. Multi-element detector 9332 measures the size of larger particles from a much larger interaction volume as defined by aperture 9342. For example, the spot sizes in the sample cell could be 20 microns for light source 9311 and 500 microns for light source 9312, but aperture 9313 would only allow detector 9333 to see scatter from a 30 micron portion, of the Source 9312 spot, which is directly above the 20 micron spot of Source 9311. The 30 micron portion could be slightly larger than the 20 micron spot to accommodate slight flow direction misalignment, because the larger size will only trigger the source 9311 power drop more times than needed, but it will guarantee that no particle scatter will saturate and/or damage multi-element detector 9331.

Figure 96:
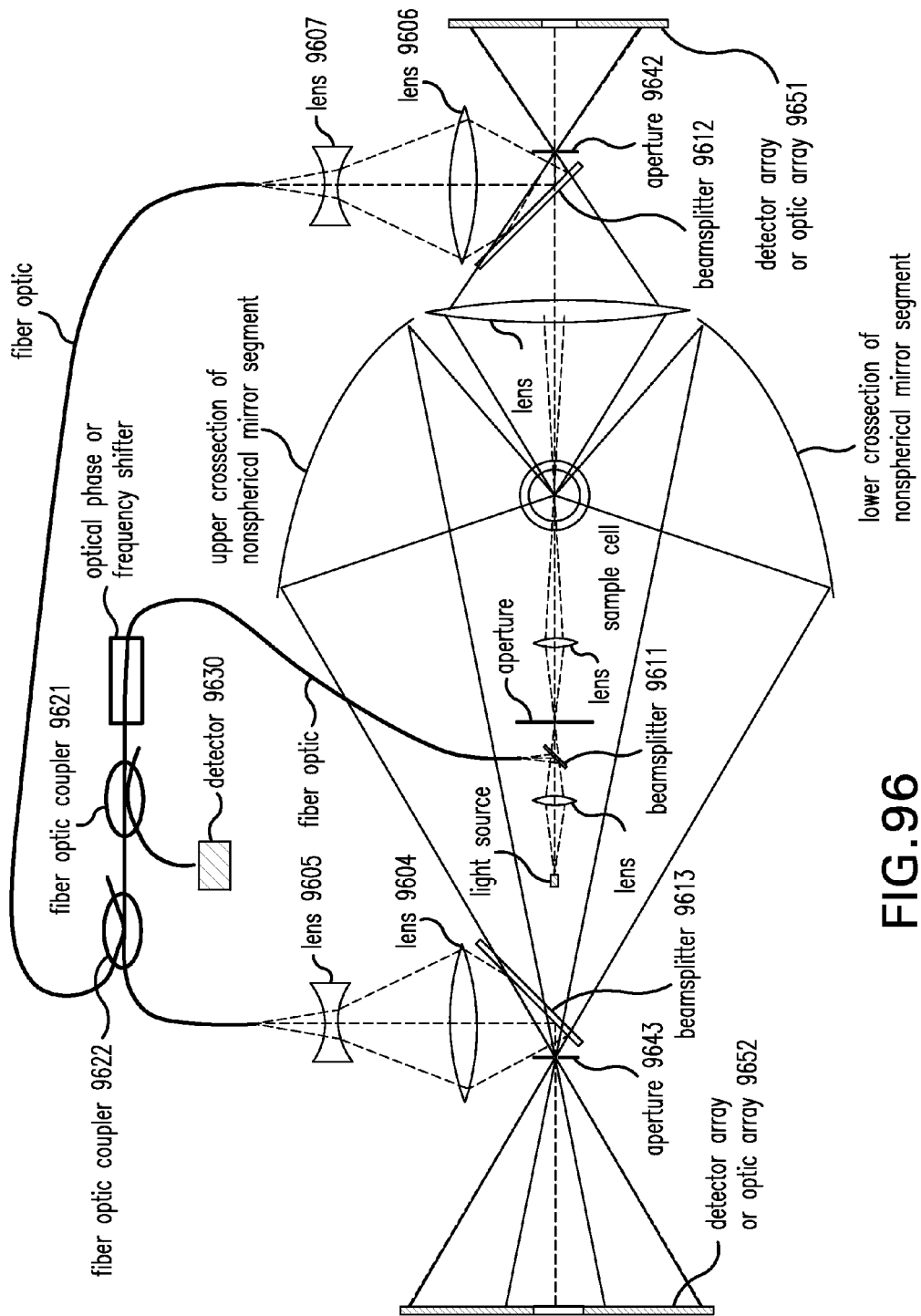
FIG. 96 provides a schematic diagram of a variation of the optical system shown in FIG. 78, which provides heterodyne detection and measures scattered light over multiple scattering angle ranges and in multiple scattering planes.

FIG. 96 shows a variation of the optical system shown in FIG. 78, which provides heterodyne detection and measures scattered light over multiple scattering angle ranges and in multiple scattering planes. Heterodyne detection, with the source noise correction methods describe earlier, may provide better detection of small particles. Some light is split off from the source light by beamsplitter 9611 and focused into a fiber optic. This fiber optic passes through an optional optical phase or frequency shifter to provide an optical frequency shifted local oscillator for the detection of scattered light. This shifter could be an acousto-optic device or moving diffraction grating. The frequency shift can also be provided by a scanned optical phase shifter (moving mirror or piezoelectric fiber stretcher) whose optical phase is ramped by a sawtooth function to produce an effective optical frequency shift during each period of phase ramp. Fiber optic coupler 9621 splits off a portion of the light after the phase shifter and passes this light to detector 9630 which monitors the fluctuations in the light intensity (12 in the previous description of source noise correction) which may be due to laser noise or amplitude modulation from the optical frequency or phase shifter. Then the source light is finally split into two fibers by fiber optic coupler 9622 to provide local oscillators for both detection systems. The light exiting the one fiber from fiber optic coupler 9622 is expanded by negative lens 9607 and then focused by lens 9606 through aperture 9642 (via beamsplitter 9612) to be mixed with the scattered light on detector array 9651 (or optic array 9651). Likewise light, from the other output fiber of fiber optic coupler 9622, is expanded by negative lens 9605 and then focused by lens 9604 through aperture 9643 (via beamsplitter 9613) to be mixed with the scattered light on detector array 9652 (or optic array 9652). In this way, heterodyne detection is accomplished with laser noise reduction using the equation and method described previously:

$$Idiff = I1nb - (R/K)*I2nb = \sqrt{R*(1-R)*S}*Ioc*\cos(F*t+A)$$

Idiff only contains the heterodyne signal. The common mode noise in the local oscillator and the heterodyne signal is removed by this differential measurement (see the previous description of the method). Heterodyne detection provides very high signal to noise, if the laser noise is removed by this equation and method. However, if the heterodyne frequency is only due to Doppler shift of the scattered light from particle motion, then the frequency of the heterodyne beat frequency will depend upon scattering angle and scattering plane (for example, the scattering plane, which is perpendicular to the particle flow, will show zero Doppler frequency shift of the scattered light). The addition of the optical phase or frequency shifter provides a much higher heterodyne frequency which is nearly equal for all scattering angles and scattering planes, allowing heterodyne detection of particle size and shape. The only problem presented by the frequency shifter is that all light that hits the detector, by scatter or reflection, will be frequency shifted. Without the frequency shifter, only scatter from moving particles will contribute to the heterodyne signal at the beat frequency, so background light can be distinguished from particle scatter based upon signal frequency. So when the frequency shifter is used, a background scatter heterodyne signal should be recorded without particles and this background signal should be subtracted from the scatter heterodyne signal with particles present. Addition of an optical frequency shifter also provides a higher beat frequency and phase sensitive detection capability. The signals due to the particle motion and the Doppler effect have random phase for each particle. So the other advantage of the frequency shifter is that the heterodyne signal will have a known phase (same as the frequency shifter), which could allow for phase sensitive detection (lock in amplifier). As shown before, the signals from this system will consist of a sinusoidal signal with an envelope function from a particle's passage through the intensity profile of the source beam. So all of the techniques described previously for processing these signals can be applied to this case.

Figure 98:
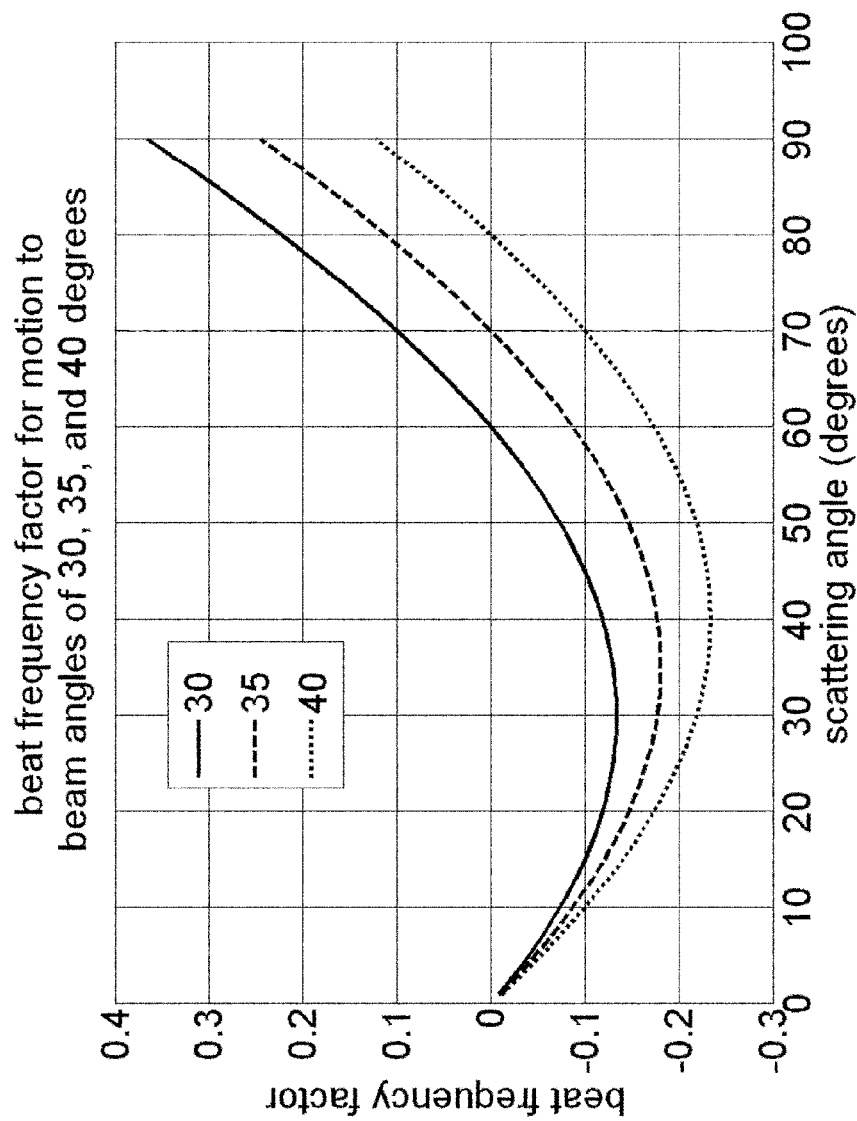
FIG. 98 provides a graph showing plots of beat frequency factor as a function of scattering angle for angles of 30, 35, and 40 degrees between the motion direction and the light beam, according to the present invention.
Figure 99:
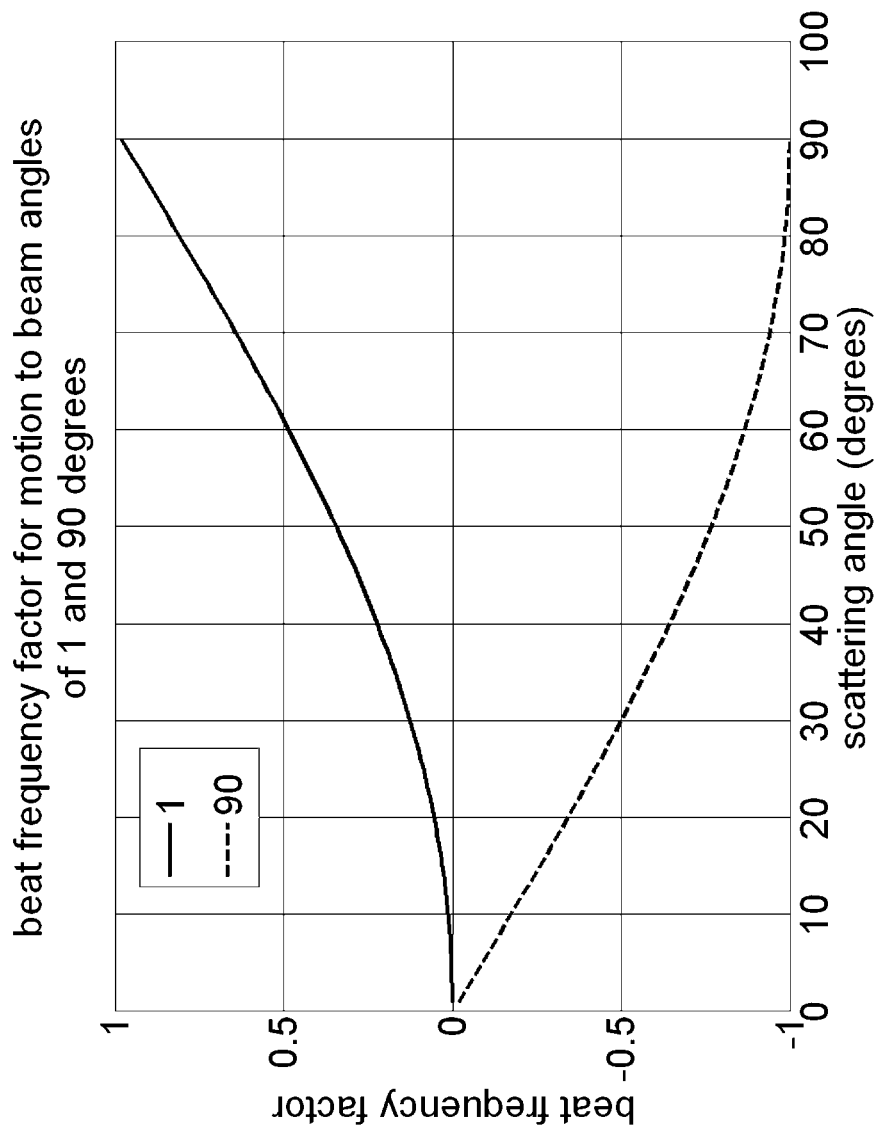
FIG. 99 provides a graph showing plots of beat frequency factor as a function of scattering angle for angles of 1 and 90 degrees between the motion direction and the light beam, according to the present invention.

For the heterodyne systems, as shown in FIG. 96, FIG. 91 shows the factor between the actual distance moved by the particle along the motion direction and the effective distance representing the optical phase shift at the detector. Hence this factor is the ratio between the Doppler frequency as computed from the particle motion along the direction of that motion and the Doppler frequency measured on a detector which measures scattered light from that moving particle at a certain scattering angle. This factor is also the ratio between the optical phase shift as computed from the particle motion along the direction of that motion and the optical phase shift as measured on a detector which measures scattered light from that moving particle at a certain scattering angle. In most cases, in order to maintain high interferometric visibility in the heterodyne signal, the angular range of any single detector element (or optic array element) should be limited so that the phase change across the element during the particles passage is less than approximately 2 pi. For example, if the particle passes through a distance of 10 light wavelengths during passage through the beam, then the factor shown in FIG. 91 cannot change by more than ⅒ across the detector element. The dependence in the regions with greatest phase shift (motion to beam angles of 1 degree or 90 degrees) is plotted in FIG. 99. For this case, most detector elements should be limited to cover less than 5 degrees scattering angle range and the beat frequencies will change on different elements, which may require a separate band pass filter for each element. Also the beat frequency will be different for each scattering plane. One method to eliminate this dependence is to design the system to have minimal particle motion induced phase shift by choosing angles, between the particle motion direction and the beam, of approximately 30 to 40 degrees as shown in FIG. 98, and using the optical frequency or phase shifter (FIG. 96) to provide the phase modulation at a high frequency, instead of the phase shift due to particle motion. Then all detector heterodyne signals will have almost the same frequency and phase, with the high signal to noise provided by heterodyne detection. Also the phase modulation signal could be used with phase sensitive detection (lock in amplifier) to detect the heterodyne signal. However, two disadvantages of this system are light reflections and amplitude modulation due to the phase modulator. Without the phase modulator, only scattered light from moving particles will create a heterodyne beat signal. However, with the phase modulator and angles between the particle motion direction and the beam, of approximately 30 to 40 degrees, all light reaching the detector from scattering or reflections will be at the beat frequency and will be passed by the band pass filter. Also the phase or frequency modulator will produce some small amount of amplitude modulation in the beam, which may completely overwhelm the particle scattering signal, even after it is removed using detector 9630 (FIG. 96) and the differential detection described previously. The severity of these problems will be determined by the characteristics of the phase or frequency modulator and the level of light reflections in the optical system.

The system in FIG. 96 could also be designed without fiber optics. Each fiber optic coupler would be replaced by a beamsplitter and the light beams could be routed to lens 9605 and lens 9607 using mirrors and lenses to create a beam focus at aperture 9642 and aperture 9643 through beamsplitter 9612 and beamsplitter 9613, respectively. The negative lenses 9605 and 9607 may be needed to expand the beam to fill the angular range of light on each detector array or optic array.

Figure 97:
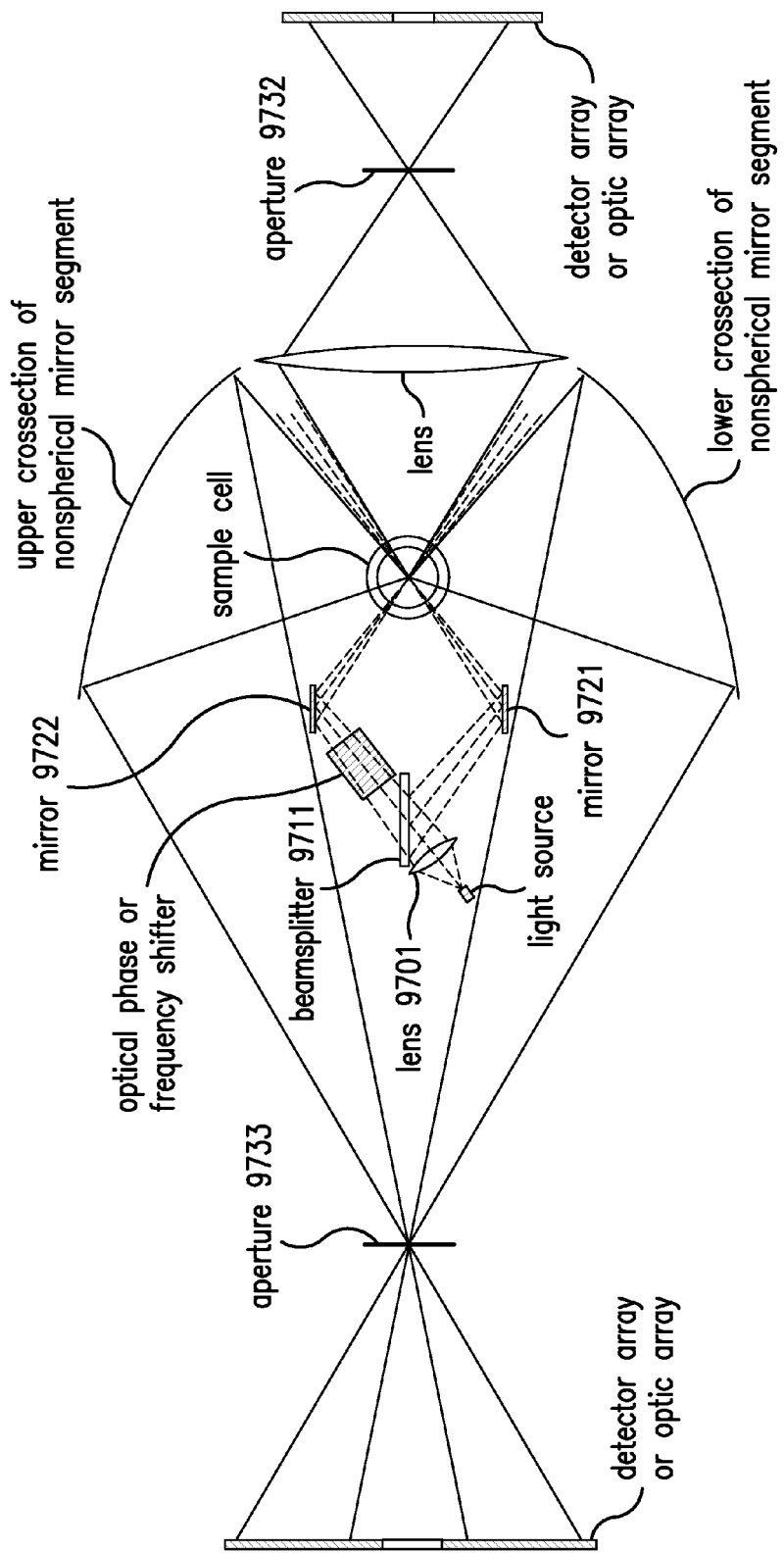
FIG. 97 provides a schematic drawing of a variation of the optical system shown in FIG. 78, which provides an oscillating scatter signal by producing an interference pattern in the interaction volume.

FIG. 97 shows another variation of the optical system shown in FIG. 78. The source beam is split into two beams which cross each other in the interaction volume in the sample cell. The two beams will create a fringe pattern at their intersection, which will modulate the scattered intensity as a particle passes through the intersection, as shown previously in FIG. 18. Lens 9701 focuses the source light into the center of the sample cell. However, the light beam is split into two beams by beamsplitter 9711. These two beams are reflected by mirror 9721 and minor 9722 to cross in the center of the sample cell. One of the beams may pass through an optical frequency shifter to provide a beat signal of known phase and/or higher frequency. The advantage of this method is that only particles passing through the fringe pattern at the intersection of these dual beams will produce signals at the beat frequency. This intersection, and aperture 9732 or aperture 9733, define a small interaction volume which reduces coincidence particle counts. Addition of an optical frequency shifter provides a higher beat frequency and phase sensitive detection capability. The signals due to the periodicity of the fringe pattern have random phase for each particle. So the other advantage of the frequency shifter is that the heterodyne signal will have a known phase (same as the frequency shifter), which could allow for phase sensitive detection (lock in amplifier). As shown before, the signals from this system will consist of a sinusoidal signal with an envelope function from a particle's passage through the intensity profile of the fringe pattern. So all of the techniques described previously for processing these signals can be applied to this case. In this case, the scattered signal, at each position on the detector array, is the square root of the product of the scattered intensities from each of the crossed light beams. Hence the scattered light intensities, from a particular position on the detector array, in the simultaneous equations shown previously, must be replaced with the square root of the product of the scattered intensities from each of the crossed light beams at the scattering angle from each beam for that same detector array position.

The method shown in FIG. 97 could also be implemented using the optical system in FIG. 78, by placing a periodic mask in the plane of aperture 7801 in FIG. 78. The image of this mask in the sample cell would provide a periodic intensity profile which would modulate the scatter signal from a particle passing through the intensity profile. The mask could have a sinusoidal or square wave transmission profile as shown in a single section of the mask in FIG. 66 (for example). The mask could also be fabricated with a Barker code or other code which has a very sharp autocorrelation function to use correlation between detector signals (also see below). However, in this case the scattering signals are not the square root of the product of scattering signals from two different scattering angles. The signal is only from the actual scattering angles relative to the incident beam as defined before for detector array 7821 or detector array 7822.

In both FIGS. 96 and 97, the system can be designed to provide beat signals on all detector elements with nearly the same phase and frequency. Hence high level signals can be multiplied times lower level signals to retrieve the lower level signals from noise. This method can also be used with the system shown in FIG. 78, where each particle produces a single pulse. The integral of the product of the largest scatter signal with a smaller signal, which needs to be recovered from the noise, will improve the signal to noise of the integral over the pulse for that smaller signal. This could also be accomplished by only integrating the lower signal while the larger signal is above some threshold, as described previously. This method will also work for signals which are not modulated. The integral of the product of single pulses will also improve the signal to noise of lower level signals when multiplied by higher level signals which have the same pulse shape. This could be accomplished with the following equation which calculates a more accurate estimate to the integral of S2 by using correlation with a higher level signal of the same functional shape (single pulse, amplitude modulated heterodyne signal, etc.):

$$S2I = INT(S1.*S2, t1, t2)/INT(S1, t1, t2)$$

Where S1 is the high level signal and S2 is the low level signal which has high correlation to S1. And t1 and t2 are the start and stop times of the particle scatter pulse. The value of INT(S1.*S2, t1,t2) could be used directly, without normalization, in simultaneous equations, lookup tables, or search models as long as the theoretical model is calculated for INT(S1.*S2, t1,t2).

In both FIGS. 96 and 97, the detector arrays can be replaced by optic arrays as shown in FIGS. 79, 80, 81, 83, 84, and 86, for example. These optic arrays can be configured in a detection system as shown in FIGS. 82, 85, and 87, for example.

Consider two optical systems, AA and BB. Any detector system in system AA using an aperture, which is in the image plane of the particle, can be used in any other system BB by placing that aperture at an appropriate image plane of the particles in system BB, along with the detection system from system AA. For example, the detector subsystem of pinhole 7411, lens 7404, lens 7405, beam splitter 7431, multi-element detector array A and B in FIG. 74 could replace aperture 7802 and detector array 7821 in FIG. 78. Other examples are replacing the aperture 9341 and aperture 9342 systems in FIG. 93, or the aperture 5202 system in FIG. 52, or the pinhole 7411 system in FIG. 74, with any of the systems shown in FIG. 82, 85, or 87. Also any methods used by system AA, which defines interaction volumes by using apertures and which measures scattered light in multiple angular ranges, can be used in any other system BB, which also defines interaction volumes by using apertures and which measures scattered light in multiple angular ranges. For example, the methods used for FIGS. 1, 2, 2a, and 37 can be applied to the system in FIG. 78, whose apertures 7802 and 7803 behave in a similar fashion to slits 114 and 115 in FIG. 1 or apertures 3711 and 3712 in FIG. 37.

In many cases, the light intensity, illuminating the particles, must be increased by focusing the source light beam to provide sufficient scatter signals. In all scattering systems with a collimated light source, the collimated light beam may be replaced by a focused light beam. However, the scatter detectors must not receive light from this focused beam in order to avoid large background signals which must be subtracted from the detector signals to produce the scatter portion of the signal. The source light beam should be blocked between the particle sample and the scatter detector. The most effective location for this light block is in the back focal plane of the lens which collects the scattered light. Examples of this plane are the planes of annular spatial filters in FIGS. 14, 15 and 41, the source blocks in FIGS. 49, 49B, 51, and the light block in FIG. 68. The central light block at these planes must be of proper size to block the direct source light from the beam, but also pass the scattered light at scattering angles which are higher than the highest angle of the diverging source light beam rays, after the beam focus.

All drawings of optical systems in this disclosure are for illustrative purposes and do not necessarily describe the actual size of lens apertures, lens surface shapes, lens designs, lens numerical apertures, and beam divergences. All lens and mirror designs should be optimized for their optical conjugates and design requirements of that optical system using known lens and minor design methods. Any single lens can be replaced by an equivalent multi-lens system which may provide lower aberrations. The drawings are designed to describe the concept; and so some beam divergences are exaggerated in order to clearly show beam focal planes and image planes within the optical system. If these drawings were made to scale, certain aspects of the invention could not be illustrated. And in particular, the source beam divergence half angle must be smaller than the lowest scattering angle which will be measured from particles in that beam. For low scattering angles (larger particles) the source beam would have a very small divergence angle, which could not be seen on the drawing.

Also in this disclosure, where ever an aperture is used to pass scattered light and that aperture is in an image plane of the scattering particle, a lens can be placed between the detector(s) (or optic array) and that aperture to reduce smearing of the scattering pattern due to the finite size of the aperture. The detectors could be placed in the back focal plane of said lens, where each point in the focal plane corresponds to the same scattering angle from any point in the interaction volume. The detector(s) (or optic array) would be placed in the back focal plane of said lens to effectively place the detector at infinity, where the angular smearing is negligible, as shown and discussed in FIG. 24. Conversely, in some single particle counting cases and cases with a very small interaction volume, where the detector is placed in the back focal plane of a lens, that lens can be removed to allow the detector to see the scatter directly from the interaction volume or from the aperture which is in the image plane of the interaction volume, because the single scatterer is essentially a point source. However, in these cases the angular scale of the scatter pattern at the plane of the detector may change; and the angular scale must be determined to theoretically model the scattering signals. In most cases, the angular scale is given by:

$$\text{Scattering angle} = \arctan(r/L)$$

Where r is the radius on the scattering detector or optic array and L is the distance between the array and the aperture which is conjugate to the particle. When the detector is in the back focal plane of a lens, then L is the lens focal length.

Also in this document, any use of the term "scattering angle" will refer to a range of scattering angles about some mean scattering angle. The angular range is chosen to optimize the performance of the measurement in each case. For example the use of the terms "low scattering angle" or "high scattering angle" refer to two different ranges of scattering angles, because each detector measures scattered light over a certain range of scattering angles Note that all optic arrays described in this disclosure can be constructed from segments of conventional spherical and aspherical lenses, diffractive optics, binary optics, and Fresnel lenses.

Also the local signal baseline (local or close to the pulse in time) should be subtracted from most of the signals described in this application because very small amounts of background scattered light will be detected from multiple scattering of particles outside of the interaction volume. This background light will usually change over a time period which is longer than the pulse length from a particle passing through the interaction volume, due to larger particles, which pass outside of the interaction volume. As these larger particles pass through any portion of the beam they create primary scatter which is rescattered from particles in the field of view of the detectors, but which are outside of the interaction volume. Since large numbers of particles may be involved, their scatter into the detectors may be equal to or larger than the scatter from the single particle in the interaction volume. Therefore, both fluctuating and static background scatter should be removed from the single particle scatter signal by baseline subtraction. This subtraction could be accomplished by fitting a curve to the scattering signal, using only points before and after the single particle pulse. The values of this fitted curve in the region of the pulse would be subtracted from the signal to correct the pulse signal for the added background. In most cases a linear fit will be sufficient. Particle scatter signal pulses with large baseline levels or large changes in baseline across the pulse, can be eliminated from the particle count due to inaccurate baseline correction. This problem of multiple scattering is also mitigated by the concept, shown in FIG. 48 and FIG. 104, which eliminates most of the scattered light from particles outside of the interaction volume, reducing the secondary scatter from these particles and other particles in the detector's field of view. Both of these figures show the crossection of optical elements (transparent cones) which are symmetrical about the optical axis of the light source. In FIG. 104, the inner and outer surfaces of each cone are concave spherical surfaces, with centers of curvature at the beam focus or interaction volume, to reduce reflection at high scattering angles and to prevent shift of beam focus and viewing volume due to any change in the refractive index of the dispersant. In FIG. 104, both the incident beam and scattered light pass through the cones, in both the forward or backward directions. However, the cone angle could also be reduced to only contain the source light beam, leaving the scattered light to pass through the particle dispersion and exit the cell through transparent cell walls or spherical transparent cell walls with center of curvature at the interaction volume. The flowing particle dispersion fills the entire volume (except for the cones) between the sample cell wall A and wall B. The cones displace the dispersant to create particle-free volume between wall A and wall B. As shown before in FIG. 48, the larger particles pass around the cones, while the smaller particles, of interest to the cone scattering detectors, can pass through the gap between the cones. This design will provide substantial reduction of background scatter from other particles and provide stable baselines for detection of low level pulses from small particles. The cones could also be constructed from hollow cones with spherical windows on each end, but this would probably be more expensive than a solid cone which can be molded as one piece in glass or plastic. This idea could also be designed for use in one scattering plane without the symmetry about the optical axis of the light source and particle flow into the page on FIG. 104. In this case each truncated cone would become a truncated wedge.

Ensemble particle size measuring systems gather data from a large group of particles and then invert the scattering information from the large particle group to determine the particle size distribution. This scatter data usually consists of a scatter signal vs. time (dynamic scattering) or scatter signal vs. scattering angle (static scattering). The data is collected in data sets, which are then combined into a single larger data record for processing and inversion to produce the particle size distribution. Inversion techniques such as deconvolution and search routines have been used. The data set for dynamic light scattering consists of a digital record of the detector signal over a certain time, perhaps 1 second. The power spectra or autocorrelation functions of the data sets are usually combined to produce the combined input to the inversion algorithm for dynamic light scattering to invert the power spectrum or autocorrelation function into a particle size distribution. Also the data sets can be combined by concatenation, or by windowing and concatenation, to produce longer data sets prior to power spectrum estimation or autocorrelation. Then these power spectra or autocorrelation functions are averaged (the values at each frequency or delay are averaged over the data sets) to produce a single function for inversion to particle size. Likewise for angular scattering, the angular scatter signals from multiple detectors are integrated over a short interval. These angular scattering data sets are combined by simply averaging data values at each scattering angle over multiple data sets.

Since the inverse problem for these systems is usually ill-conditioned, detecting small amounts of large particles mixed in a sample of smaller particles may be difficult because all of the particle signals from the particle sample are inverted as one signal set. If the signals, from only a few larger particles, is mixed with the signals from all of the other smaller particles, the total large particle scatter signal may be less than 0.01 percent of the total and be lost in the inversion process. However, in the single short data set which contained the larger particle's scattered light, the larger particle scatter may make up 50% to 90% of the total signal. The larger particle will easily be detected during inversion of these individual data sets.

Users of these systems usually want to detect small numbers of large particles in a much larger number of smaller particles, because these larger particles cause problems in the use of the particle sample. For example, in lens polishing slurries, only a few larger particles can damage the optical surface during the polishing process. In most cases these larger particles represent a very small fraction of the sample on a number basis. Therefore, if many signal sets (a digitized signal vs. time for dynamic scattering or digitized signal vs. scattering angle for static scattering) are collected, only a few sets will include any scattered signals from larger particles. An algorithm could sort out all of the data sets which contain signals from larger particles and invert them separately, in groups, to produce multiple size distributions, which are then weighted by their total signal time and then combined to form the total particle size distribution. The data sets may also be sorted into groups of similar characteristics, and then each group is inverted separately to produce multiple size distributions, which are then weighted by their total signal time and then summed over each size channel to form the total particle size distribution. In this way, the larger particles are found easily and the smaller particle data sets are not distorted by scatter signals from the larger particles. Even if all of the signals for large particles over the full data collection time is less than 1% of the total signal, including large and small particles, this small amount would be inverted separately and the resulting distribution would be added to the rest of the size distribution with the proper relative particle volume percentage.

This technique works better when many short pieces of data are analyzed separately, because then the best discrimination and detection of particles is obtained. However, this also requires much pre-inversion analysis of a large number of data sets. The key is that these data sets can be categorized with very little analysis. In the case of angular light scattering, comparison of signal values from a few scattering angles from each signal set is sufficient to determine which signal sets include signals from larger particles or have specific characteristics. In the case of dynamic light scattering, the spectral power in certain frequency bands, as measured by fast Fourier transform of the data set or by analog electronic bandpass filters could be used to categorize data sets. Consider a dynamic scattering system where the scattering signal from the detector (in heterodyne or homodyne mode) is digitized by an analog to digital converter for presentation to a computer inversion algorithm. In addition, the signal is connected to multiple analog filters and RMS circuits, which are sequentially sampled by the analog to digital converter to append each digitized data set with values of total power in certain appropriate frequency bands which provide optimal discrimination for larger particles. The use of analog filters may shorten the characterization process when compared to the computation of the Fourier transform. These frequency band power values are then used to sort the data sets into groups of similar characteristics. Since larger particles will usually produce a large signal pulse, both signal amplitude and/or frequency characteristics can be used to sort the data sets. The total data from each formed group is then processed and inverted separately from each of the other groups to produce an individual particle size distribution. These particle size distributions are summed together after each distribution is weighted by the total time of the data collected for the corresponding group.

The use of analog filters is only critical when the computer speed is not sufficient to calculate the power spectrum of each data set. Otherwise the power spectra could be calculated from each data set first, and then the power values in appropriate frequency bands, as determined from the computed power spectrum, could be used to sort the spectra into groups before the total data from each group is then processed and inverted separately to produce an individual particle size distribution. For example the ratio of the power in two different frequency bands can indicate the presence of large particles. The resulting particle size distributions are summed together after each distribution is weighted by the total time of the data collected for the corresponding group. This process could also be accomplished using the autocorrelation function instead of the power spectrum of the scatter signal. Then the frequency would be replaced by time delay of the autocorrelation function and different bands of time delay would be analyzed to sort the data sets before creating data groups.

In angular scattering, a group of detectors measure scattered light from the particles over a different angular range for each detector. These detector signals are integrated over a certain measurement interval and then the integrals are sampled by multiplexer and an analog to digital converter. In this case, the angular scattering values at appropriate angles, which show optimal discrimination for larger particles, could be used to sort the angular scattering data sets into groups before the total data from each group is then processed and inverted separately to produce an individual particle size distribution for that group. These resulting particle size distributions are summed together after each distribution is weighted by the total time of the data collected for the corresponding group.

These sorting techniques can also be used to eliminate certain data sets from any data set group which is inverted to produce the particle size distribution. For example, in dynamic scattering, very large particles may occasionally pass through the interaction volume of the optical system and produce a large signal with non-Brownian characteristics which would distort the results for the data set group to which this defective data set would be added. Large particles, which are outside of the instrument size range, may also cause errors in the inverted size distribution for smaller particles when their data sets are combined. Also vibration or external noise sources may be present only during small portions of the data collection. These contaminated data sets could be identified and discarded, before being combined with the rest of the data. Therefore, such defective data sets should be rejected and not added to any group. This method would also be useful in conventional dynamic light scattering systems, where multiple groups are not used, to remove bad data sets from the final grouped data which is inverted. By breaking the entire data record into small segments and sorting each segment, the bad data segments can be found and discarded prior to combination of the data into power spectra or autocorrelation functions and final data inversion. This method would also be useful in static angular scattering to eliminate data sets from particles which are outside of the instrument size range.

In some cases, a large number of categories for sorted groups are appropriate to obtain optimal separation and characterization of the particle sample. The number of categories is only limited by the cumulated inversion time for all of the sorted groups. The total inversion time may become too long for a large number of groups, because a separate inversion must be done for each group. However, after the information is sorted, abbreviated inversion techniques may be used because the high accuracy of size distribution tails would not be required to obtain high accuracy in the final combined particle size distribution. In many cases, only two groups are necessary to separate out the largest particles or to eliminate defective data sets.

This disclosure claims sorting of data sets for any characteristics of interest (not only large particles) and for any applications where large data sets can be broken up into smaller segments and sorted prior to individual analysis or inversion of each individual set. Then the resulting distributions are combined to create the final result. This includes applications outside of particle size measurement.

Another application is Zeta potential measurement. Low scattering angles are desirable in measurement of mobility of particles to reduce the Doppler broadening due to Brownian motion. However, large particles scatter much more at small angles than small particles do; and so the scatter from any debris in the sample will swamp the Doppler signal from the motion of the smaller charged particles in the electric field. This inventor has disclosed methods of measuring Dynamic light scattering from small interaction volumes created by restricting the size of the illuminating beam and the effective viewing volume. When only scattered light from a very small sample volume is measured, the scatter from large dust particles will be very intermittent, due to their small count per unit volume. So the techniques outlined above can be used to eliminate the portions of the signal vs. time record which contain large signal bursts due to passage of a large particle. In this way, Zeta potential measurements can be made at low scattering angles without the scattering interference from dust contaminants.

In optical systems which need to count very small particles, light sources with shorter wavelengths may be preferred due to the higher scattering efficiencies (or scattering crossections) at shorter wavelengths.

Figure 100:
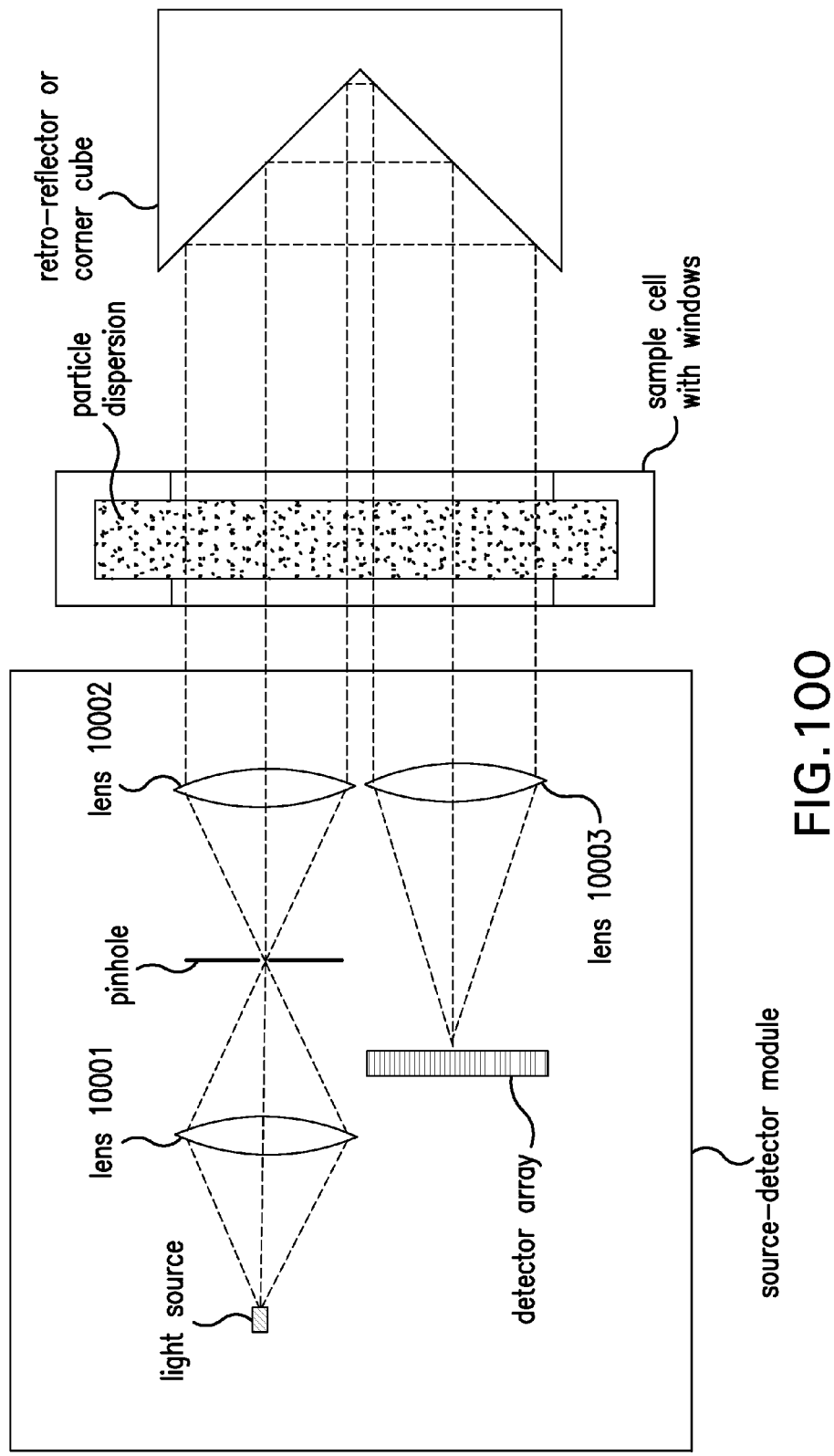
FIG. 100 provides a schematic diagram of an optical system which measures angular scattering distribution from a particle dispersion in a sample cell, wherein optical alignment is maintained by a retro-reflector, according to the present invention.

The alignment of angular scattering systems can drift due to drift of the source beam position or changes in the wedge between the sample cell windows. FIG. 100 shows an optical system which measures angular scattering distribution from a particle dispersion in a sample cell. The angular scattering distribution is used to determine the size distribution of the particles. If the optical wedge between the sample cell windows changes or if the dispersant refractive index is changed, the system will go out of alignment due to refraction in the optical wedge. The laser focus spot will move to another position on the detector array, saturating detector elements which should be measuring scattered light only. This invention uses a retroreflector and a source-detector module to provide stable alignment against the drift sources described above. Lens 10001, pinhole, and lens 10002 form a spatial filter. The light beam from this spatial filter passes through the sample cell and dispersion. The beam and scattered light are then retroreflected back through the same sample cell, where more scatter occurs on the second pass. All of the scattered light is collected by lens 10003, which focuses it onto a detector array in the back focal plane of lens 10003. As long as the components are rigidly mounted to a common base in the source-detector module, the system will maintain alignment after initial alignment at the factory. After initial alignment, this system will maintain alignment over a large range of beam alignment drift, dispersant refractive index change, or sample cell wedge drift. If the sample cell drift or dispersant refractive index drift are not problems, the optics can be arranged so that the beam between lens 10002 and the retroreflector does not pass through the sample cell, while the beam does pass through the sample cell between the retroreflector and lens 10003.

In most of the optical systems described in this application, certain ranges of angular scattered light are measured separately. Usually two angular ranges will only provide high particle dimension sensitivity over a limited size range. The following methods can be used to extend the size range of the detection systems:

1) many detectors in each scattering plane
2) many lens/multi-detector systems, with different scattering angle ranges, multiplexed into a single optical system using beam splitters.
3) One lens in the scatter path has adjustable focal length (such as a zoom lens) to measure the scattering pattern at various angular scale factors (scattering angle vs. radius on the detector array)
4) With no lens between the particle image plane aperture and the detector array (for example aperture 7802 and detector array 7821 in FIG. 78) the angular scale factor of the detector array or optic array is adjusted by changing the distance between the aperture and the detector array. The angular extent of the detector array is inversely proportional to that distance.
5) Case 3 or 4 with the focal length or distance adjustment based upon: size range known by user or the counted size distribution from the first group of particles counted. The user or computer controller could also choose different scattering angular scale factors (by changing the lens focal length or the moving the detector) for each of a group of sequential counting sessions on the same particle sample and then invert each of these data sets separately, using the proper angular scale factor for each set. Then the resulting size distributions are combined into one size distribution.

In cases where a 2-dimensional detector array is in the image plane of the particles, that 2-dimensional array can be replaced by a 1-dimensional array which repeatedly scans across the interaction volume as the particles flow through that volume in a direction perpendicular to the long dimension of that array (the direction between adjacent pixels). Essentially the same information as obtained with the 2-dimensional array can be obtained sequentially on the 1-dimensional array because the other perpendicular dimension is provided by the particle motion. The two dimensional "virtual pixel" distribution of scattered signals is reconstructed by combining these sequential 1-dimensional scans, based upon the flow velocity. And as before, contiguous particle pixels (virtual pixels with signals indicative of a particle) are combined to produce scattering signals for each particle, as described previously for FIGS. 11, 12, and 14.

In all cases shown in this application, all possible polarizations and wavelengths of the source and all polarization and wavelength selections of the detection system can be employed. Each Fij in the previous analysis can have a specific light polarization and wavelength which optimizes the accuracy of the particle characterization. Any combination will provide size and shape information. However, the theoretical scattering model must accurately describe the wavelength and polarization state of the source and the polarization and wavelength selection of the detector. Polarization and wavelength effects can be used to determine particle size and shape using the search or optimization methods described previously. Below is a list of the best configurations for detection of size and shape using polarization effects in the optical systems described in this application:

Any source can be polarized in a particular direction. Any detection system can select any polarization, including the polarizations parallel and perpendicular to that source polarization direction. For example two orthogonal polarizations can be selected by a polarizing beamsplitter which splits the scattered light into two separated scattering detection systems. Each of these detectors can consist of any detection system described previously in this application. Also each scattering plane segment in a detection array, such as shown in FIG. 84, could be covered by a polarizing material with polarization orientation parallel or perpendicular to the scattering plane to provide multiple polarizations for each particle count. The scattered flux passing through each segment will have a theoretical dependence upon the size and shape of the particle. As before, simultaneous equations can be formed as functions of these flux values to solve for unknown size and shape parameters. To save computation time per particle, each of these equations should be a parameterized into a simple function which is fit to the actual computed flux values which are obtained from Fraunhofer theory (without polarization information) or known polarization methods, such as T-matrix and Discrete Dipole Approximation, (see "Light Scattering by Nonspherical Particles", M. Mishchenko, et al.). These methods are usually very computationally demanding. However, the theoretical results from these demanding methods can be fit to simple functions (such as polynomial or power series) of the particle size and shape, using regression analysis of computed data. And when closed form solutions are available, the simultaneous equations can be formed directly from the closed form solutions or from less computationally demanding closed form approximations (using said function fitting methods) of the full closed form solution. The only requirement is that the theory be capable of describing the scatter from particles of the sizes and shapes of interest and with the source polarization and polarization selection of the detection system. Once the simplified simultaneous equations are formed, the optimal inversion technique can be chosen from among the various search, regression, and optimization algorithms available. In many cases, the simultaneous equations can be posed as a functional minimization problem which is amenable to many of the minimization algorithms. The RMS error between the theoretical flux output of the simultaneous equations for a given set of particle parameters (for example, particle dimensions) and the actual measured signal values can create a function to be minimized by various minimization algorithms as described previously.

$$[S, f(S), R] = M(P, O)$$

The set of signal values S (flux signal peak, integral, etc.), other functions of S (f(S)), and ratios, R, of signal values are a function M of the particle parameters, P, (dimensions, size, shape, etc.). M is also a function of the descriptors, O, of the optical system such as scattering plane orientations, scattering angles, polarization states and wavelengths of the sources, and polarization selections of the detectors. M may include a set of simultaneous equations (linear or nonlinear), an integral equation such as a convolution, or a single equation. M is determined from known scattering theory based upon the optical system O and the range of parameters P. M should be simplified by the methods described above to reduce computation time. In some cases, M can be directly inverted to Minv to produce P as a function of S, f(S), and R.

$$P = Minv(O, S, f(S), R)$$

In other cases, where explicit inversion of M is not possible, search, function minimization, or optimization methods should be employed to minimize an error function, such as E:

$$E = SQRT(SUMi((Smeasi-Sti)^2) + SUMi((Rmeasi-Rti)^2) + SUMi((f(S)measi-f(S)ti)^2))$$

These may include iterative methods. Where Smeasi is the value measured for the ith signal and Sti is the theoretical value for the ith signal based on the estimate for P; and where Rmeasi is the signal ratio value measured for the ith signal ratio and Rti is the theoretical ratio value for the ith signal ratio based on the estimate for P; and where f(S)measi is the signal function value measured for the ith signal function and f(S)ti is the theoretical signal function value for the ith signal function based on the estimate for P. The algorithms are designed to refine this P estimate using iterative procedures to find the estimated P values which minimize the error E. These algorithms include Newton's method, Levenburg Marquardt method, Davidon-Fletcher-Powell, constrained and unconstrained optimization methods, global search algorithms, etc. All of these methods will minimize E, by using M to calculate Sti, f(S)ti, and Rti for each new estimate of P. This minimization is performed individually for each particle to determine the size and shape parameters for that particle. In some cases, this inversion process will use a certain conceptual form for the properties of M, such as the 2-dimensional structure in FIG. 27, which provides both elimination of counted signal events, which do not meet the requirements to be particles, and a means for deconvolution or inversion of the remaining counted signal events.

In general we can define a Sv vector which consists of all of the measured quantities and a Pv vector which consists of all of the particle characteristics, which are to be determined from Sv:

$$Sv = [S1, S2, S3, \ldots, R1, R2, R3, \ldots, f1(S1, S2, S3 \ldots), f2(S1, S2, S3 \ldots), f3(S1, S2, S3 \ldots)]$$

$$Pv = [P1, P2, P3, \ldots]$$

Where Si are scatter signals (flux signal peak, integral, etc.), Ri are ratios of different Si values, and fi are other functions of the Si values. The Pv vector consists of particle characteristic values, such as particle major axis length, particle aspect ratio, and particle orientation, for example. Then the optical model M is the transform operator between these two vectors:

$$Sv = M(Pv)$$

M is a function of the optical configuration descriptor, O, which includes the scattering plane orientations, scattering angles, polarization states and wavelengths of the sources, and polarization selections of the detectors. The M function is determined from theoretical scattering calculations such as Mie theory or T-matrix and Discrete Dipole Approximation, (see "Light Scattering by Nonspherical Particles", M. Mishchenko, et al.). This M function can be approximated by regression analysis of the scattering value results from these scattering calculations. An example of this regression is shown below for 2 Pv parameters for polynomial regression:

$$Svj = SUMi[Aij(Oj, P2) * (P1^{Ai})]$$

$$Aij = SUMk[Bijk(Oj) * (P2^i)]$$

Where Oj is the optical system descriptor for signal Svj and ^ is the power operator. The regression analysis of scattering results from the theoretical scattering calculations produces the coefficients, Aij and Bijk. This technique can be extended to more than 2 elements in Pv, by providing more layers of coefficients. These equations, or the more general solution equations for M(Pv) shown above, are solved iteratively by finding the values in Pv which minimize the error Err:

$$Err = SUMj((Svej-Svmj)^2)$$

Where Svmj are the measured values of Svj; and Svej are the calculated values, in vector Sve, for the current iteration estimate for Pve (Sve=M(Pve)). The optimization methods, described above, are used to iteratively change the values in Pve to lower and minimize Err. Then the best Pv is equal to Pve, when Err(Pve) is minimum. This iterative process may consume excessive time, when required for each counted particle. Depending upon the available computer resources, direct inversion of M may be preferred. In some cases, the operator M can be inverted directly. For example, the regression analysis could switch the variables in the regression approximation equations to solve for Pv:

$$Pj = SUMi[Cij(Oj, S2) * (Sv1^{Ai})]$$

$$Aij = SUMk[Dijk(Oj) * (Sv2^i)]$$

The regression analysis of scattering results from the theoretical scattering calculations produces the coefficients, Cij and Dijk and creates the inverse operator Minv. Then Pv is directly calculated from Sv:

$$Pv = Minv(Sv)$$

The use of polynomial regression is just one example of reducing scatter results from very computationally intensive algorithms (such as Mie, T-matrix, or Discrete Dipole Approximation) to simple equations which can be computed in a fraction of a second instead of minutes. In general, other types of regression functions, such as Bessel functions, may be more appropriate.

The optical system, O, must be designed to produce Sv which has large sensitivity to Pv. The scattering plane orientations, scattering angles, polarization states and wavelengths of the sources, and polarization selections of the detectors must be chosen to maximize this sensitivity to avoid ill-conditioning of the equation set Pv=Minv(Sv).

Also in some cases, the discrete values in the data sets (Svd and Pvd) from the theoretical scattering calculations can be used to create a discrete multi-dimensional function set which can be searched in multi-dimensional space:

$Svd=M(Pvd)$

Find the discrete values Pvd, by search and interpolation of the multi-dimensional data set, which produce Svd values which agree with Svm values to minimize Errd.

$Errd=\text{SUM}j((Svdj-Svmj)^2)$

The same analysis, as described for polarization properties, can be used for different source or detection wavelengths, which also determine the system response to particle characteristics. Optical filters in the detection system and various source wavelengths are used. And appropriate scattering models are used to describe the effects of wavelength on the scattering pattern. In many cases, the angular scale of the scattering distribution scales approximately inversely with wavelength. Any point in the angular scattering distribution moves toward higher scattering angle as the wavelength is decreased. Therefore, use of different wavelengths for Fij, can provide additional information for particle characteristics. For example, the Mie resonances respond to wavelength changes differently than the non-resonating portion of the scattering distribution, providing a means for better correction of Mie resonance induced errors.

Also in any system described previously, the flow velocity could be lowered for smaller particles to increase their residence time in the interaction volume, providing longer signal period and better signal to noise. Also most of these techniques do not require the dispersant to be a liquid. These techniques are also claimed for measuring the size and shape of particles dispersed in a gas or aerosol. The same flowing conditions can be produced by pumping the gas aerosol in a closed loop through the optical system, or by pumping or settling the aerosol in a single pass through the optical system.

If absolute signal values are used instead of signal ratios, the single size response will be broader in the multi-dimensional space and the deconvolution problem will be more ill-conditioned. However, this can be the best choice for very small particles where the absolute signals will have much higher particle size sensitivity than the signal ratios.

This application claims any combination of the apparatus and methods described in this application to extend the size range of the total system. These methods may also be combined with conventional direct imaging systems to size larger particles.

When more than one particle is present in the interaction volume, particle size errors can occur. Many of the systems and methods described in this application reduce the probability of counting coincident particles by providing interaction volumes of various sizes, such as shown in FIG. 41, where a set of apertures define various sized interaction volumes in the sample cell. The concept shown in FIG. 93 could also be used to define multiple interaction volumes, where each interaction volume has a separate light source. This may have some advantages over the system in FIG. 41 in producing source focal spots with maximum intensity in the sample cell. FIG. 14 uses a 2-dimensional detector array to define multiple interaction volumes. Multiple sized source spots could also be used to define multiple interaction volumes in FIG. 78, by using the source beamsplitter system in FIG. 93 in FIG. 78. These interaction volumes (source spots) could be coincident in the sample cell and each one could be selected by sequentially turning each source on and collecting scatter from that source, while many particles pass through the beam. The particle concentration is reduced (perhaps in steps) by a system as shown in FIG. 13 to reduce the counting of coincident particles to an acceptable level. However, for broad size distributions, single particle counting is difficult to achieve in the larger interaction volumes where many small particles may be present with each large particle. In this case, very low angle scattering can be measured. Since low angle scattering scales approximately proportionately to the fourth power of the particle diameter and the smaller particle pulses will overlap, their scatter signal can be removed from the larger particle pulses by baseline subtraction and/or peak detection. This problem is also mitigated using the methods, shown in FIGS. 71, 72, and 73, which allow overlapping pulses to be measured separately.

Figure 88A:
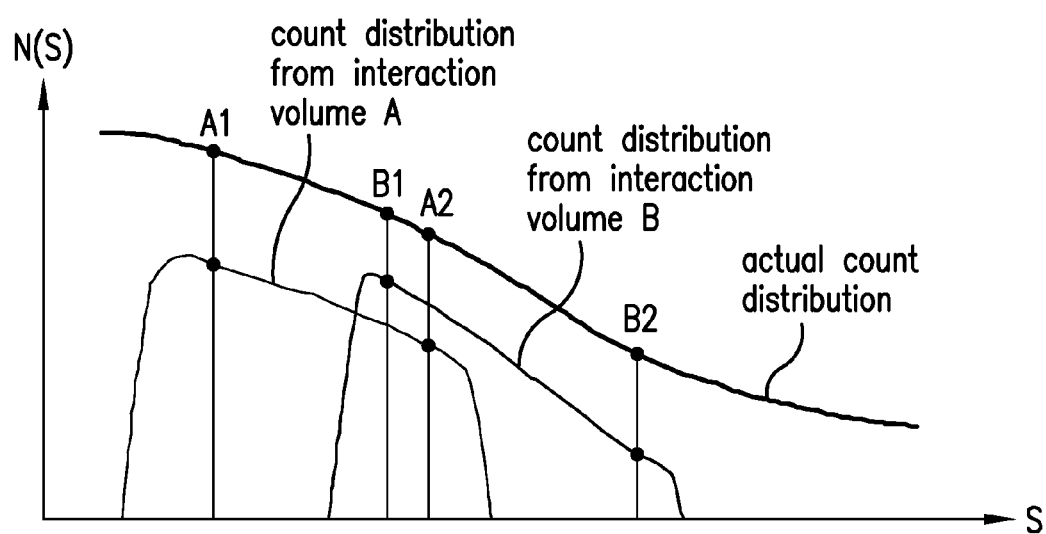
FIG. 88a provides a graph which plots the total count distribution and the measured count distributions from two different sized interaction volumes, according to the present invention.

FIG. 88*a* shows the actual total count distribution and the measured count distributions from two different sized interaction volumes, A and B. Interaction volume A, which detects smaller particles, is smaller than interaction volume B. Therefore, interaction volume A can measure particles at higher particle concentrations than interaction volume B. The count distribution will usually increase as the particle size, and S, decrease because usually there are many more smaller particles than larger particles. For both volumes A and B, the count distributions will be limited to a certain range in S. The low signal detection limit affects the lower S limit. And the upper limit is determined by the largest particles which will produce a pulse, from which particle size can be determined for the size of the interaction volume. Particles which are larger than the interaction volume will not produce accurate pulses. Accurate single particle detection is maintained over the regions between A1 and A2 for interaction volume A, and between B1 and B2 for interaction volume B. These two regions should be contiguous or have overlap to provide a continuous measured count distribution, when the count distributions from volumes A and B are combined to produce a single count distribution. In the interaction region with the smallest particles, the coincidence counts should be reduced by adjustment of particle concentration. The count distribution from that interaction volume, A, can be used to correct the counts from the adjacent interaction volume B, using the equations shown below. Then the A distribution and corrected B distribution can be used to correct the distribution from the next larger interaction volume C (not shown) and so on, until all of the count distributions are corrected for coincidence counts. The techniques shown below can also be used to correct a single count distribution which covers the entire range of S.

In many cases described above, coincidence counts cannot be avoided and the measured count distribution must be corrected for coincidence counts. The count distribution N(S) is the number of events with signal characteristic S between S-deltaS and S+deltaS as a function of S. As before, S can be any of the signal characteristics (such as scatter signal peak or integral) or some functions of these signal characteristics. Let Nm(S) be the measured count distribution which contains count errors due to coincidence counts. And let Nt be the true count distribution without coincidence count errors. Then the following relationship can be formed:

$Nm(Si)=\text{SUM}((\text{SUM}(Nt(Si+kSj)*Pk(Sj)),j=1,j=nns),k=1,k=nnk)$ for $i=1$ to $Nsi$ Where Pk(S) is the probability that k particles, with characteristic S, will be present coincidentally in the interaction volume used to measure characteristic S. This probability is derived from the Poisson probability distribution using the average number (Na) of particles of signal characteristic S present in the interaction volume during a single data collection or at the point of data sampling (signal peak or integral measurement for example).

$$Pk(S)=EXP(-Na)*((Na)^k)/k!=EXP(-Nt(S))*((Nt(S))^k)/k!$$

where EXP is the exponential function and * is multiply operation

The equations for Nm(Si) form a set of Nsi simultaneous equations which can be solved for Nt(Si), given Nm(Si) and Pk(Si). The value nns is the total number of counting channels, each with a different center Sj value. The value nnk is the maximum number of coincident particles in the interaction volume for a particle which produces signal Sj. The value of nnk depends upon the particle concentration for each value of Sj. The value nnk may be limited to the point where Pk(S) (for k=nnk) becomes negligible or to the point where baseline correction effectively removes the signal due to the coincident particles of signal Sj. These equations are solved by many different types of algorithms including iterative processes such as function minimization or optimization algorithms (global search, Newton's method, Levenburg-Marquardt method, etc.). The values of Nt can be constrained to be positive, using constrained optimization methods to improve accuracy. The iterative process could start with an estimate for Nt(S), called Nte(S). Then, using iterative optimization methods, the values in Nte(S) are changed, during each iteration, to produce a new estimated Nm(S) function, called Nme(S), (calculated from the equation below) which fits better to the actual measured values of Nm(S). This iterative process is continued until the error, Em, is minimized. The values of Nte(S) at minimum Em are the final values for the count distribution without coincidence counts. Nm(S) are the actual measured values.

$$Nme(Si)=SUM((SUM(Nte(Si+kSj)*Pk(Sj)),j=1,j=nns),k=1,k=nnk) \text{ for } i=1 \text{ to } Nsi$$

$$Em=SQRT(SUMi((Nm(Si)-Nme(Si))^2))$$

In general, the coincidence counts are best removed from the count data using the methods described for FIGS. 26, 27, 28, 61, and 62, which show the 2-dimensional case of a multi-dimensional concept. The multi-dimensional analysis creates a function of multiple variables of S (or functions of S). Typically each variable is measured from a different scattering angle range, different scattering plane, different light polarization, different light wavelength or a function of these different variables. In any case, the function for a system, without any broadening mechanisms, will be a nonlinear line (or path) which traverses the multi-dimensional space. Each point along this line (or path) corresponds to a different value of the particle characteristic or size. When broadening mechanisms are added, a probability distribution for existence of a particle is created around this line in multi-dimensional space. Detected events, which are too far from this ideal line or in the regions of low probability, are rejected and not added to the count. The distance of a count event location from this ideal line, and corresponding probability of event acceptance, is determined by an algorithm using analytical geometry relationships for the multi-dimensional space. Any single particle will have a certain nominal combination of S values or S function values (one for each dimension of the space). If a second particle is coincident with that single particle, the S values or S function values from that particle pair will usually not be within the acceptable region of the space and can be rejected. This rejection process is improved by reducing the broadening mechanisms, which create a wider region of acceptance in the multi-dimensional space. For example, use of an apodized or truncated beam, to provide better intensity uniformity of the source in the interaction volume, will reduce this broadening source and reduce the region of acceptance around the ideal line in multi-dimensional space. Then the coincidence count rejection will be much more effective. The acceptance region in the multi-dimensional space can also be determined from the region which is most populated by events, if the particle concentration is low so that coincidences are rare. In this case, outliers of the multi-dimensional distribution are rejected.

Application PCT/US2005/007308 (Application 1) is a basis document for this application. The term Application 1 also includes updates made to PCT/US2005/007308, which are included in this application. The particle counting optical systems, including those described previously by this inventor, can measure and count particles on microscope slides or other substrates (windows for example), without flowing particles through the interaction volume. The interaction volume is the volume of particle dispersion from which scatter detectors can receive scattered light from the particles. The interaction volume is the intersection of the particle dispersion volume, the incident light beam, and viewing volume of the detector system. These substrates can include particles dispersed on microscope slides (with and without cover slips) or a particle dispersion sandwiched in a thin layer between two optical windows. Using this method, the thickness of the sample volume is reduced, reducing the background scatter from other particles, in the sample, which are illuminated by the source beam or scattered light from other particles. The counting process is accomplished by moving the substrate, upon which the particles are dispersed, so that the optical system can view various spots or interaction volumes on that substrate and measure any particles that are present at each location. Essentially the moving substrate provides the particle motion which is provided by the dispersion flow in the flowing systems described previously by this inventor. This motion can also provide the Doppler shift required for some of the heterodyne detection systems described previously by this inventor. Either the optical system or the substrate (or both) can be moved so that the interaction volume of the optical system is scanned across the substrate to sample continuous scatter signals during the motion or to interrogate individual sites for particles. This scan can consist of any profile (zig-zag, serpentine, spiral etc.) which will efficiently interrogate a large portion of the substrate surface. The scan could also be stopped at various locations to collect scattering signal over a longer period with improved signal to noise.

The flow system shown in FIG. 107, uses two flow loops: flow loop 10702 at high particle concentration and flow loop 10701 at the adjustable particle concentration, as controlled by dispersion injections through the valve. The particle sample is introduced into the open sample vessel 10712 in loop 10702 to be mixed with dispersant in flow loop 10702. The flow velocity in either flow loop is sufficient to prevent settling losses of large particles and maintain a homogeneous dispersion. The sample vessels provide access to the particle dispersion for introducing particles to the loop; and they provide a means for removal of air bubbles, from the dispersion in the flow loop, which pass into the atmosphere. The arrows indicate the direction of the dispersion flow into the top of each sample vessel. The injection of dispersion through the valve could also be injected directly into sample vessel 10711 instead of the loop tubing. Also, the flow tube in each sample vessel could end above the liquid level in the sample vessel, so that the dispersant falls through air before entering the fluid in the vessel.

In order to optimize the counting efficiency, the particle concentration should be increased to the maximum level, which will still allow a high probability of single particle counting, without coincidences. In this way, the largest number of particles will be counted in a given time period, with very few coincidence counts. This is difficult to accomplish on a substrate, such as a microscope slide, without using trial and error. Microscope slides and other substrates are difficult to populate with particles in a repeatable manner, with predictable particle concentration per unit area. The system, in FIG. 108, uses a flowing system, as shown in FIG. 107, to adjust the particle concentration in a sample cell, with adjustable window separation. The system consists of a sample cell housing, which consists of two cell halves: sample cell housing 10801 and sample cell housing 10802. These cell housing halves can be moved relative to each other to provide various cell window spacings. Each housing half contains a cell window to pass the incident light beam and any scattered light from the particles, as required by the optical system which measures scattered light from the particles in the sample cell. The sample cell in FIG. 108 can be placed in the location of sample cell 10721 in FIG. 107. The conduit on the inlet and outlet of the sample cell is flexible and the two sample cell halves are connected by flexible material, so that the sample cell halves can be moved relative to each other to change the spacing, between the windows, where the particles reside. The flexible conduit, flexible connecting material, and two sample cell housing halves provide a sealed chamber with window access for light, and inlet and outlet access for flowing dispersion, while allowing for adjustment of window spacing. This spacing is controlled by actuator(s) which move one or both of the sample cell halves. The housing parts could be designed with O-ring seals, so that the windows can be removed from the housing for cleaning. The windows could also reside in O-ring seals, which allow the window to slide though the O-ring seal to provide window spacing adjustment, while providing a sealed chamber for the particle dispersion.

The flowing system in FIG. 107 adjusts the concentration by monitoring the particle count rate and injecting the proper amount of concentrated dispersion from flow loop 10702 into flow loop 10701, with the cell housing in Position A, in FIG. 108. Position A provides a longer optical path through the particles than position B. Repeated injection and measuring steps may be needed to obtain an accurate concentration level. After the proper particle concentration is attained, the flow is turned off and the window spacing is reduced to trap a thin layer of particle dispersion between the windows, as shown by Position B in FIG. 108. The window spacing should be reduced slowly so that particles are not segregated by particle size during the movement of dispersion from the cell. As dispersion is squeezed out of the gap between the windows, the ability of particles to move with the dispersion may be particle size dependent. If the dispersion moves slowly, particles of all sizes can follow the dispersion as it is pushed out from between the windows, maintaining the original (Position A) particle size distribution between the windows, when they are in Position B. The flow path of the cell and internal window surfaces should be parallel to the gravitational force, so that larger particles do not settle onto the windows as the window spacing is changed. During the window spacing changes, the particles should settle into the top of the cell and out of the bottom of cell, maintaining the size distribution. Once the final window spacing is reached (Position B), the cell housing could be tilted to orient the inner window surfaces to be perpendicular to the gravitational force to reduce settling motion of the particles during the scan. In position B, the optical system scans in a pattern (zig-zag, serpentine, spiral etc.) over that thin layer (in a plane parallel to the windows) to count the particles in that layer. The interaction volume of the optical system should be maintained in the thin layer of dispersion, during the scan, by real time control of optical system focus or position of the optical system along the optical axis, if needed. The window area should be sufficient to hold the large number of particles needed to obtain accurate count statistics and distributions. Otherwise, repeated steps, of Position A with flow, and then Position B with a counting session, may be needed to accumulate sufficient counts, by filling (Position A) the cell with a new sample of dispersion between each counting (Position B) session. The windows are maintained at a larger separation (Position A) while the concentration is being adjusted by injections of particle dispersion from flow loop 10702 into flow loop 10701 through the computer controlled valve, with both loops flowing. The number of particles per unit volume and the largest particle size are measured, by the optical system counting particles with flow on, during this concentration adjustment process. The concentration adjustment is complete (in position A) when the volume concentration is such that the predicted particle number per unit area in the predicted thin layer (Position B) will be optimal (the largest number per area which will still avoid significant levels of coincidence counts). This is determined from the measured number of particles per unit volume (determined from the particle count rate, the interaction volume size and the flow velocity) and the predicted thickness, of the thin layer, which can be determined to be some factor larger than the size of the largest particle counted during the flow period. The thickness of this layer could be controlled to be a certain percentage larger than the diameter of the largest counted particle to prevent crushing the largest particles in position B. If the particle concentration is low, the optimal thickness may be much larger than this minimum particle crush distance in order to obtain sufficient particles per area for high particle count rates. Also, a force sensor (as shown in FIG. 109) can be placed between the actuator and the sample cell housing to determine when particles are being compressed, in order to stop the actuator from reducing the window spacing further and crushing the largest particles. This force sensor feedback system can also stop the actuator when the two windows are in contact to prevent damage to the windows or the actuator. The window position adjustment also could be accomplished by a single piece sample cell housing with an actuator movable window which slides through an O-ring seal to adjust the window spacing. However, this option may require higher cost and maintenance. Also the flexible conduit can take the form of a flexible diaphragm as shown in FIG. 109. As before, sample cell housing 10902 is moved by the actuator. Cell housing 10902 is connected to the stationary sample cell housing 10902B by a flexible diaphragm, which allows the sample cell housing 10902 and window 10912 to move relative to window 10911 to adjust the spacing between window 10912 and window 10911. The flexible diaphragm and two sample cell housing halves provide a sealed chamber with window access for light, and inlet and outlet access for flowing dispersion, while allowing for adjustment of window spacing. The diaphragm and cell housing 10902 are mounted on the face (see FIG. 110) of the sealed cell chamber which consists of cell housing 10901 and cell housing 10902B. FIG. 110 shows a frontal view (light source axis is perpendicular to the page) of the cell and a top view A-A' which shows the sides of the chamber which connect cell housing 10902B to cell housing 10901.

This adjustable sample cell concept can be used in any particle counter (including those described previously by this inventor) by replacing the sample cell in said system with this adjustable sample cell and providing the hardware and software which will generate the information from which the cell window spacing adjustment will be determined. Since, during the particle counting scan, movement of either the optical system or sample cell (or both) may be provided by motor driven stages, the weight of these systems should be limited to avoid heavy acceleration loads on the stages. The optical system weight could be lowered by using laser diode or LED sources. Also the sample cell could be connected to the flow system through long flexible tubes to allow motion of only the light weight cell. If the velocity of the motor driven stage is too low to obtain high particle count rates, the effective speed of the source spot in the thin particle layer can be increased by mounting the optics (or sample cell) on piezoelectric actuators and using linear motion of the stage. The piezoelectric actuators would quickly scan the source spot and collection optics in a short oscillating pattern perpendicular to the linear motion of the stage to produce a serpentine pattern across the window with very high surface velocity. A single serpentine sweep across the window covers a rectangular region with length equal to the total linear motion and width equal to the perpendicular oscillating pattern motion. After each full single serpentine sweep, the stage is moved so that the rectangular region of the next sweep is placed adjacent to the prior sweep region, by jumping over one sweep rectangular width in the direction perpendicular to the linear motion. The stage would travel back and forth across the entire window (stepping forward with each cycle) to move the fast oscillating source spot across the entire area of window. The flow system in FIG. 107 is usually used when particle concentration adjustment is required. Otherwise, lightweight substrates, such as microscope slides, can be used.

This concept can also be used in other types of scattering systems. For example, in ensemble angular scattering instruments (measuring scattered light from a group of particles), low particle concentration is required to avoid multiple scattering. But some users prefer to measure the particle size of dispersions at higher particle concentration when the particle size distribution is dependent upon the particle concentration. Multiple scattering occurs when the scattered light from a particle is scattered again by other particles, before being received by the detector. Since the optical scatter model usually assumes only primary scattered light, inversion of this multiple scattered light angular distribution will produce errors in the calculated particle size distribution. Multiple scattering depends upon the total number of particles in the beam. Therefore, by reducing the pathlength of the incident light beam in the particle dispersion, multiple scattering can be reduced to optimal levels, even at very high particle concentration. This pathlength adjustment could be accomplished under computer control using the sample cell shown in FIGS. 108 and 109. The light beam attenuation due to scatter, at the initial pathlength of measurement (Position A), could be used to calculate the appropriate pathlength adjustment (Position B) to avoid significant multiple scattering. Then the sample cell window spacing is adjusted by the actuator(s) to provide this optimal window spacing (position B) and pathlength, before the final optical scatter measurement, which is inverted to produce the particle size distribution. If the particle concentration is low, the window spacing at position B could be larger than the spacing at position A to provide sufficient scattered intensity. The optimum spacing could also be determined by monitoring the angular scattering distribution or particle size distribution at various optical pathlengths (window spacings) in the cell. Multiple scattering causes the higher angle scatter to increase relative to the low angle scatter. Starting in position A, the scattering distribution (Distribution 1) is measured. Then the window spacing is reduced and the angular scattering distribution (Distribution 2) is measured again and compared to the distribution (Distribution 1) measured at the prior spacing. If the change (see DIFF below for example) in the shape of the distribution (for example the change in the ratio of low angle scatter to high angle scatter) is less than a certain threshold, then the multiple scattering is negligible and Distribution 2 can be inverted to generate the particle size distribution. If the change is larger than the threshold, then the multiple scattering was reduced by the spacing change and the spacing is reduced again to produce a new measurement of scattering distribution, Distribution 3. The shape of Distribution 3 is compared to the shape of Distribution 2. If the difference (see DIFF below for example) between the two shapes is less than the threshold, Distribution 3 is inverted to create the particle size distribution. If the shape difference is greater than that threshold, the window spacing is reduced again to generate Distribution 4. This cycle is repeated until the difference in shape between the scattering distributions measured at two successive window spacings is less than the threshold. At this point, the multiple scattering is negligible because changes in dispersion pathlength have little effect on the shape of the angular scattering distribution. Then the distribution from this final spacing is inverted to produce the particle size distribution. This process could also be accomplished by comparing the particle size distributions calculated from the angular scattering distributions measured at successive window spacings. Again the change in distribution shape a (ratio of large particle volume to small particle volume or DIFF function for example) is used to stop the process and accept the last size distribution. The advantage of using the particle size distribution is that the size distribution error due to multiple scattering is determined directly from the difference between two successive distributions. However, this process will take more computation time than comparing the scattering distributions, because an inversion of the scattering distribution must be completed at each window spacing. The threshold for the difference between scattering distribution shapes measured at two successive window spacings is determined from the particle size distribution error caused by that threshold difference. In either case, the shape difference between distributions F1 and F2 can also be determined by normalizing F1 and F2 at the same angle or normalizing them by their sums (as shown in DIFF). Then the mean square (sum of the squares of the differences at each scattering angle) difference between these normalized functions will provide the difference in shape between the distributions.

$$DIFF=SUM(((F1i/SUM(F1i))-(F2i/SUM(F2i)))^2)$$

Where SUM=sum over the index i and F1$i$ and F2$i$ are either scattered intensities at the ith scattering angle (scattering distribution) or particle volumes (or numbers) at the ith particle diameter (particle size distribution). In the case of dynamic scattering, F1 and F2 could also be the power spectrum or autocorrelation function of the scattered light detector current. The source beam attenuation due to scatter is also a direct indicator of multiple scattering. However, the attenuation threshold is particle size dependent. The first scattering distribution at position A could be inverted to obtain a rough estimate of the particle size distribution. Then that particle size distribution, the window spacing and the beam attenuation at position A could be used to calculate the new window spacing (position B) which would reduce the multiple scattering to reasonable levels.

In any system, particle counting or ensemble scattering, the concentration can also be adjusted by adding clean dispersant to the flow loop 10701 in FIG. 107. Then flow loop 10702 could be eliminated and the computer would only control the injection of clean dispersant into flow loop 10701. As described before, this clean dispersant would be added under computer control until the count rate or source beam attenuation due to scatter is appropriate to avoid coincidence counts or multiple scattering. This method may require large amounts of dispersant to reduce the concentration to appropriate levels. This may present problems for cost and disposal of expensive or dangerous dispersants.

Also the distribution shape difference method could also be used between successive particle concentration changes (by sample injection in FIG. 107 or dilution) to optimize the particle concentration, without adjusting the cell dispersion pathlength (changing between Position A to Position B).

The design in FIGS. 108 and 109 can be also used to measure dispersions with high viscosity dispersants (such as pastes) which cannot flow through the sample cell. In these cases one of the windows can be removed from the housing to introduce the sample into the cell, by placing the sample (smearing the paste onto the window surface) on the opposite window. The window is then replaced and the window spacing adjusted to compress the dispersion between the windows. Again the same window spacing adjustment methods, as described above, could be used to obtain the proper number of particles in the beam to avoid multiple scattering for ensemble angular scattering and to avoid coincidences for particle counting.

In either case, counting or ensemble measurement, the dispersion flow must be stopped if the window spacing becomes too small to allow flow in the small gap between the windows. Otherwise, the particles could be counted as they flow through the cell in position B, without the serpentine scan if the particles can flow at sufficient velocity to provide a high count rate for a fixed detector system. Ensemble scattering measurements could also be made during dispersion flow through the cell in Position B. The windows could also extend into the sample cell volume, with regions for passage of particles around both sides of the windows. Then when the windows are close together, the dispersion flow can continue around the windows, while the flow between the windows is restricted. FIG. 111 shows an extension of this idea, where two optical cones are attached to the windows with optical adhesive. Only the particles between the tips of the cones, whose spacing is adjusted with the window spacing, will contribute to the scatter signal. The other particles can continue to flow around the cones. And the scattered light from the particles between the cones will not be rescattered by other particles which are displaced from the paths of the scattered rays by the cones. FIG. 104 shows a version of FIG. 111 with spherical surfaces.

FIG. 112 shows another system which was described previously by this inventor in the filed Application 1 (FIG. 14 of Application 1). FIG. 112 shows an optical system where the light source is spatially filtered by lens 11201 and pinhole 11211. Lens 11202 collimates and projects the source beam through the particle sample, which is imaged onto the 2-dimensional detector arrays by lens 11203. A spatial mask is placed in the back focal plane of lens 11203 to only pass scattered light over a certain range of scatter angle as defined by the inner and outer radii, R1 and R2, of the annular spatial mask, as shown by mask B. The very low angle scattering and incident beam are blocked by central stop of the annular aperture in the back focal plane of lens 11203. If the light beam passing through the sample cell is not collimated or is focused into the cell to increase beam intensity, R1 must be increased to be greater than or equal to the radius of the beam on the mask to block the unscattered light. Application 1 describes many spatial masks which can be placed in the back focal plane of lens 11203, such as those shown in FIGS. 42, 44, 76, 79, 80, 81, 83, 84, 86, and 88 of Application 1. FIG. 112 shows two such annular mask (mask 11221 and mask 11222) systems which are accessed through a beamsplitter. The 2-dimensional detector arrays (such as a CCD array for example) are in the image plane of the particles. Hence the detector array 11231 sees an image of the particles, and the sum of the light flux on contiguous pixels associated with each particle's image is equal to the scattered light from that particle over the angular range defined by the aperture of mask 11221 in the back focal plane of lens 11203. A beam splitter splits off a portion of the light to a second annular spatial mask (in the back focal plane of lens 11203) and detector array 11232, whose angular range is defined by mask 11222. The angular ranges of the two annular spatial filters are chosen to produce scattered values which are combined by an algorithm to determine the size of each particle. Radii R1 and R2 can be different for mask 11221 and mask 11222. Also either or both masks may be covered by an absorbing filter with a radial transmission function (see FIG. 88 of Application 1 for example), which is different for mask 11221 and mask 11222. These concepts have been described in more detail by this inventor in this application and previous disclosures and filed applications. In any case, the sum of signals from contiguous detector array pixels, which view the same particle, are analyzed to produce the particle size of that particle. One such algorithm would be a ratio of the corresponding sums (the sum of contiguous pixel signals from the image of each particle) from the same particle detected by both arrays, detector array 11231 and detector array 11232. The key advantage is that when the particle size is too small to size accurately by dimensional measurements on the image (resolution is limited by pixel size) then the total scattered light, through each mask, from each particle may be used to determine the size, by summing contiguous pixel values for that particle. And if the total scattered light is sensitive to particle composition, then the ratio of the two scattering signals (each signal from different scattering angle ranges, for example) can be used to determine the particle size more accurately. Said two scattering signals would consist a first signal which is the sum of contiguous pixels from detector array 11231 for a certain particle, and a second signal which is the sum of contiguous pixels from detector array 11232 for the same particle. If the particle image size on a detector array is below the size of one pixel, the signal may result from only the value measured from the single pixel excited by scattered light from that particle. In FIG. 112, ideally scattered light is only present when a particle is present. Each particle image creates an increase in light from a dark background level. If the particle is smaller than a single pixel, then the amount of scattered light measured by that pixel will indicate the total light scattered from that particle in the angular range defined by the focal plane aperture, providing that particle's size. If more than one pixel is associated with a particle, those pixel values are summed together to obtain the scattered signal from that particle. The increase in pixel signals, relative to the background signal measured without particles, are summed to produce the total light scattered from that particle in the angular range of the annular aperture in FIG. 112. These ideas can be extended to more than two detector arrays or more than two scattering angles, simply by adding more spatial masks and detectors by using additional beamsplitters. In this way, each pixel in the detector array creates a small independent interaction volume, providing individual detection of a very small particle contained in that interaction volume, with low coincidence probability. But yet contiguous pixels can be combined to measure particles of sizes approaching the dimensions of the entire detector array's image in the sample cell. The size dynamic range is enormous. FIG. 112 could also be used with a source beam which is focused into the sample cell to reduce the interaction volume and increase the beam intensity and scattered signal. In this case the center portion of the mask must be increased in size to block the diverging light from the source so that each detector array only sees scattered light. The optical source used FIG. 112 could be a pulsed broad band source such as a xenon flash lamp which produces broadband light to wash out the Mie resonances, and which produces a short light pulse to freeze the motion of particles flowing through the cell. However, this technique can also be used with the methods described for FIGS. 107 through 111, without the need for serpentine scanning Repeated cycles of Position A, to exchange dispersion, and Position B, with stopped flow, would be used. During the stopped flow in Position B, the optical system in FIG. 112 would collect an image on each array, without the need for a pulsed source. This process may be much slower than the continuous flow case due to the time required to stop flow and change to position B. The change to Position B is only needed when the coincidence count level is significant due to pixels which see scattered light from more than one particle during each measurement. Then the reduced dispersion pathlength in Position B would reduce the level of coincidence counts.

This inventor has also disclosed and filed applications which describe methods and apparatus which can determine the shape of particles by measuring scattered light in various scattering planes, as described in FIGS. 79, 80, 81, 83, 84, 86, and 88 of Application 1, for example. Mask A in FIG. 112 shows an aperture which measures scatter from only a small range of scattering planes. A scattering plane is the plane which contains the incident light beam and the scattered ray. Mask A can be placed in the positions of mask 11221 and/or mask 11222. As mask A rotates, the mask aperture will capture light from different scattering planes, sequentially. The total light from contiguous pixels of each particle image will represent the scattered light for the angular range and range of scattering planes defined by the inner and outer radii of the aperture and the rotation position of that aperture during the time when the detector array pixel currents are integrated. If the detector array pixel currents are integrated and sampled at various rotation positions of Mask A, the scattering values, for each pixel in each detector array, will be sampled for various scattering planes sequentially. The total integrated currents from the contiguous pixels representing the image of each single particle are measured and summed when both mask 11221 and mask 11222 are seeing the same angular position of the scattering plane. The digitized detector array images provide the same information for each particle in the detector array images as the binary optic arrays and masks (see FIGS. 79, 80, 81, 82, 83, 84, 85, 86, 87, and 88 in Application 1, for example), described previously by this inventor, provided for a single particle in a single interaction volume. Therefore, all of the analysis techniques, described previously by this inventor, can be used to determine particle size and shape for each particle in these detector array images, by using the total signal from each particle in each image. Essentially, the system in FIG. 112 measures the scattered light from many interaction volumes in parallel and measures the scattered light from each scattering plane sequentially for all interaction volumes, as the mask rotates to each position. The systems in Application 1 (FIG. 78 for example) measure all of the scattering planes in parallel and measures each particle sequentially as it passes through a single interaction volume. Each range of scattering angle or radial (angular) weighting function is measured by a separate mask and detector array system, in FIG. 112. All such systems view the same particles through beamsplitters and each of such systems measures each scattering plane sequentially as the mask for that system rotates. Two or more masks can have different weighting functions (Wij in Application 1) and/or different range of scattering angles. Additional mask/detector systems can be added by placing additional beamsplitters in the optical paths after Lens 11203. So that the contiguous pixel sum for each particle can be measured for all of the scattering angles, weighting functions, and scattering planes required to determine the size and/or shape of each particle using the methods described in Application 1 (see pages 101 to 109 in Application 1 for example).

FIG. 65 shows another version of FIG. 112, where the functions of Mask A and Mask B are separated into Mask A1 (like the rotating Mask A of FIG. 112), and Mask B1 and Mask B2 (both like the Mask B of FIG. 112). Mask A1 selects different scattering planes as it rotates; and the light passing through Mask A1 is split by the beam splitter to two stationary masks, Mask B1 and Mask B2 which have different weighting functions (Wij in Application 1) and/or different range of scattering angles (as defined by R1 and R2 in FIG. 112 for example). All masks are in planes which are conjugate to the back focal plane of Lens 6504 and all detector arrays are in planes which are conjugate to the particles. All of the features of FIG. 112 apply to FIG. 65, including the use of a converging source beam instead of a collimated beam. However, FIG. 65 has the advantage of only needing one rotating mask for all of the detector arrays. Again, by using more beam splitters, more type B masks and accompanying detector arrays may be added to extend the size range of the instrument by measuring at other weighting functions (Wij in Application 1) and/or other ranges of scattering angles (as defined by R1 and R2 in FIG. 112 for example).

This rotating mask method can also be used in any system which measures a single interaction volume (FIG. 78 in Application 1 for example). The rotating mask, lens, and a single detector would replace the detector array in FIG. 78. The lens would collect light which passes through the mask and focus that light onto the single detector. The mask must rotate very quickly to capture all of the scattering plane measurements on a single detector sequentially, as each particle passes through the interaction volume. Also this system can be used with the methods described above in FIGS. 107, 108, 109 and 111 to scan a sample between two windows or on a microscope slide. The scan could stop at each position on the sample to allow full rotation of the mask on a single particle, without particle motion. By using beamsplitters and multiple mask/lens/detector systems, the scatter signals for each particle can be measured for all of the scattering angles, weighting functions, and scattering planes required to determine the size and/or shape of each particle using the methods described in Application 1 (see pages 101 to 109 in Application 1 for example).

Also notice that most counting systems, including these counting systems and other systems described in Application 1, can be combined with an ensemble scattering system by using a beam splitter to split off a portion of the scattered light from the ensemble system to the counting system (or visa versa).

Figure 21:
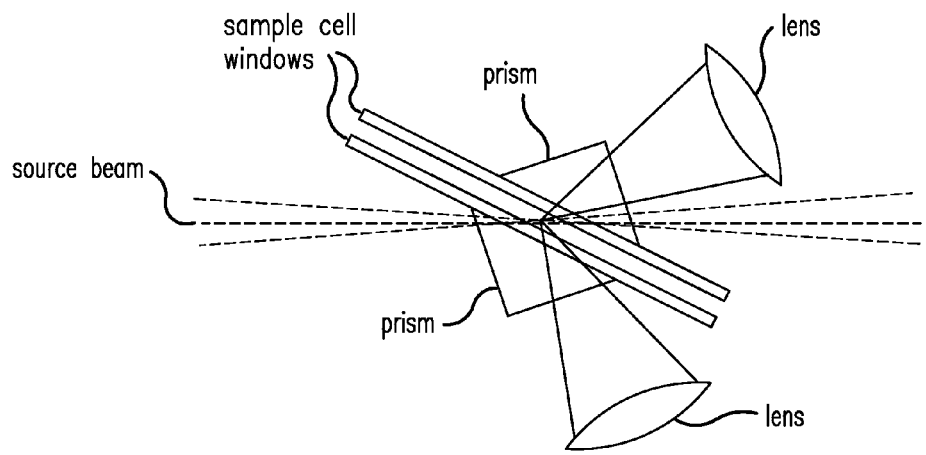
FIG. 21 provides a diagram of a particle dispersion sample cell, which utilizes prisms to reduce light reflections at sample cell window surfaces, according to the present invention.
Figure 40:
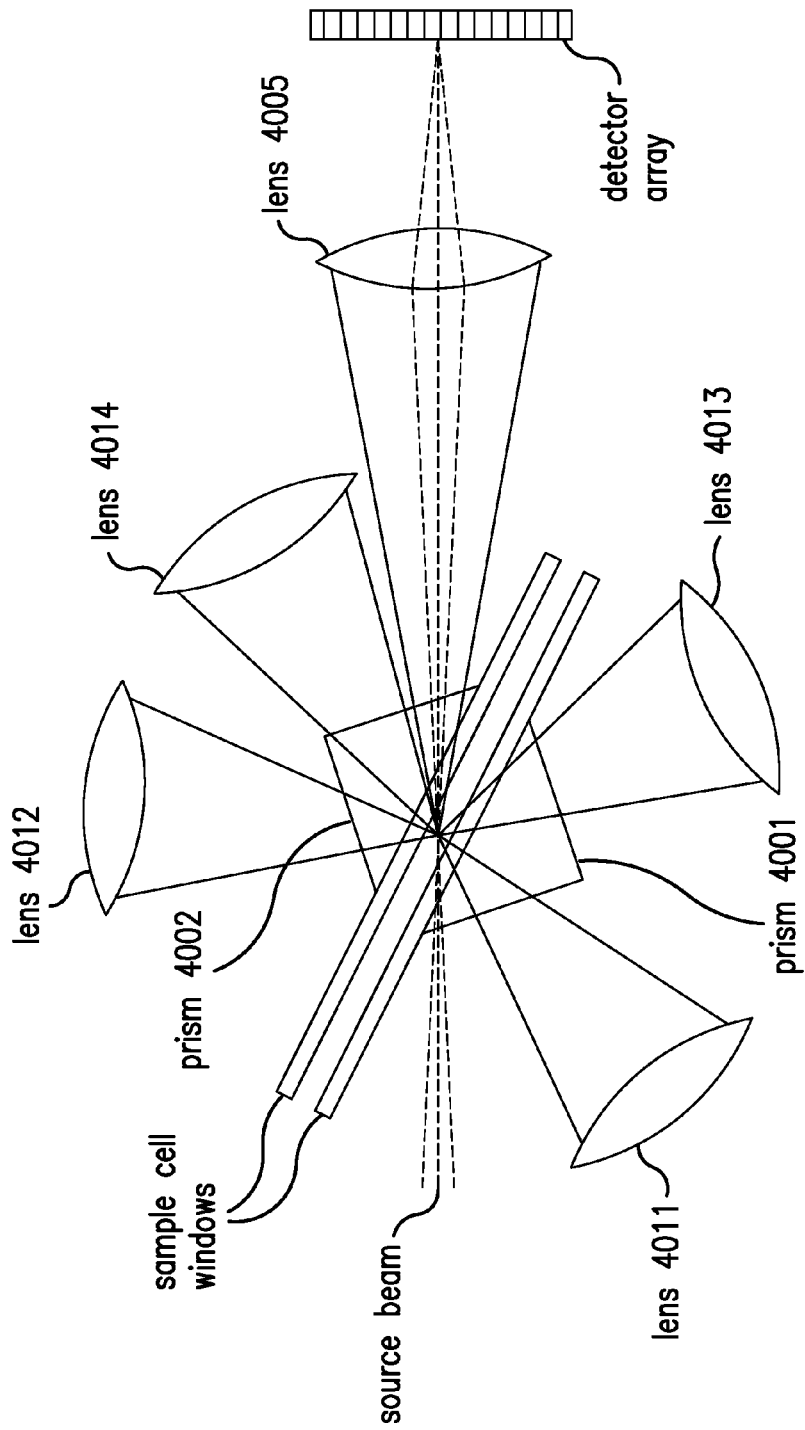
FIG. 40 provides a schematic diagram of an optical system which reduces reflection losses at the window surfaces of a particle dispersion sample cell, according to the present invention.

In some cases, where scattered light at very high scattering angles must be measured to determine the size of very small particles, the sample cell can be modified as shown in FIG. 40 to reduce Fresnel reflections at the air/glass interfaces (also described in FIG. 21 of Application 1). The particle dispersion fills the volume between the two sample cell windows. Prism 4001 is attached to the entrance of the sample cell and Prism 4002 is attached to the exit of the sample cell, using refractive index matching adhesive. Prism 4001 and Prism 4002 could also directly replace the windows by using appropriate seals to interface the prisms to an enclosed cavity though which the dispersion flows. The scattered light in lowest scatter angle range is captured by Lens 4005, which focuses the light onto a detector array. This array could be placed in the back focal plane of Lens 4005. The light from the light source is collected by a central element of the detector array to monitor scatter attenuation of the light beam. Alternatively, that focused source light can pass through a hole in the detector array. Lens 4011, Lens 4012, Lens 4013, and Lens 4014 collect scattered light from higher ranges of scattering angle. The detectors are not shown for these lenses, but they can consist of single or multiple detectors, or detector arrays, placed in the back focal plane of each lens. Each detector or detector element, measures scattered light from a different range of scattering angles. The air/glass prism surfaces are at much lower incidence angles for scattered light rays than would be the case for the simple plano glass windows. Hence the Fresnel reflection losses are much lower. The prism surfaces can also be anti-reflection coated to further reduce these reflections. The interaction volume in FIG. 40 can be the interaction volume of any scattering system including a dynamic scattering system or static angular scattering system.

FIG. 113 shows a crossection of a portion of an optical system, which illuminates particles in a sample cell and collects scattered light from the illuminated particles. This system could be utilized in the system shown in FIG. 78, for example. Light source 11315 is focused by lens 11311 through an aperture 11301, which removes unwanted stray light from the light source. The size of aperture 11301 could be chosen to only select a portion of the source beam intensity distribution, where the intensity is sufficiently uniform, as shown in FIG. 56. Since the scattered light, from each particle, is proportional to the illuminating intensity at that particle, any monosized particle dispersion will produce a count distribution, which is spread over a range of scatter intensity values, as shown in FIG. 57. This due to the fact that the particle motion paths, in the flowing dispersion, will be distributed across the illuminating beam, so that different particles will each pass though a region of different intensity in the beam. A monosized particle dispersion is a group of particles, wherein all the particles have generally the same particle size. Aperture 11301 could be designed to only allow a restricted range of scattering signal amplitudes for any monosized dispersion, as shown in FIG. 57 and FIG. 60, by restricting the intensity variation of the portion, of the source light beam, which illuminates the particles. Also the size of aperture 11302 could also be chosen to only accept scattered light from a restricted region of the illuminating beam, where the intensity is sufficiently uniform. Either or both apertures 11301 and 11302 could be designed to provide the restriction shown in FIG. 56. The width of the region passed by the aperture in FIG. 56 only illustrates the concept. The width of the region passed by the aperture must be chosen to provide sufficient intensity uniformity among all allowed particle paths. However, if aperture 11301 cuts into the high intensity portion of the beam, diffraction will create large scatter background in the scatter detectors. So the actual aperture size and width of the region passed by the aperture will depend upon the application.

The light from aperture 11301 is focused into the sample cell 11316 by lens 11312, creating a focal spot of proper size for the size range of the particles. For example, the size of the light source focused spot, generally at the center of sample cell 11316, should be generally at least 5 times the size of the largest particle of interest for that detection system. The light passing through the sample cell is blocked by beam block 11317 to prevent unscattered light from entering the detection system, though aperture 11302. The scatter collection lens 11313 focuses the scattered light through aperture 11302. Aperture 11301, the focused spot in sample cell 11316, and aperture 11302 are generally in conjugate planes. Hence aperture 11302 determines the interaction volume, from where scattered light is detected by scatter detector(s), as shown for aperture 11402 and detectors 11606 and 11607 in FIG. 118. Aperture 11314 removes stray light, in the source beam, which would propagate into the angular range, of scattered light, which is accepted by the scatter detection system. Hence a light ray passing through the edge of the opening of aperture 11314 should exit the sample cell at an angle less than the lowest measured scattering angle. A beam block, of equivalent function to 11317, should be utilized in any optical system (including those in this specification) where source light is intercepted by a scatter detector.

FIG. 114 shows a variation of the system in FIG. 113, where low angle and high angle scattered light are measured by two detection systems. The complete optical system is shown in FIG. 118. In FIG. 114, items 11401, 11402, 11411, 11412, 11413, 11414, 11415, 11416, and 11417 have the same function as previously described items 11301, 11302, 11311, 11312, 11313, 11314, 11315, 11316, and 11317, respectively. Mirror 11418 is added to fold the illuminating optical system, so that a second scatter detection system can be easily added, using lens 11419. Lens 11419 and aperture 11420 have similar functions to lens 11313 and aperture 11302, respectively. However, 11419 collects high angle scattered light. Aperture 11420 is generally conjugate to (or an image plane of) the focused light spot in sample cell 11416. Hence aperture 11420 defines the interaction volume for the high angle scattering detectors (11806 and 11807) in FIG. 118. FIG. 115 shows a magnified view of FIG. 114, showing the folding function of minor 11418.

FIG. 116 shows addition of an optical detection system to the systems in FIG. 113 or FIG. 114. FIG. 116 is a crossectional view of the optical system. This detection system is similar to that shown in FIG. 12. The scattered light through aperture 11302 is generally collimated by lens 11601. Beamsplitter 11602 reflects a portion of this scattered light to low angle scatter detector 11607. Beamsplitter 11602 also transmits a portion of this scattered light to higher angle scatter detector 11606. The range of scattering angles received by detector 11606 and detector 11607 are defined by aperture 11609 and aperture 11610, respectively. Each aperture has a generally annular shape, as shown by mask 1250, for example, in FIG. 12. The scattered light is focused on detector 11606 and detector 11607 by lens 11603 and lens 11604, respectively. A third scatter detector could be added, by adding a second beamsplitter between beamsplitter 11602 and aperture 11609. This second beamsplitter would reflect scattered light to a third detection system with components of similar function to aperture 11610, lens 11604, and detector 11607. However, the aperture would pass a third range of scattering angles, using appropriate inner and outer radii for the annular mask opening. Any number of additional detection systems could be added to measure scattering over more ranges of scattering angles, by extending the space between beamsplitter 11602 and aperture 11609 to accommodate the added beam splitters, each which would reflect a portion of scattered light to an annular aperture, lens, and scatter detector, with the functions similar to those of 11610, 11604, and 11607, respectively. Each annular aperture would pass a different range of scattering angles, as defined by appropriate inner and outer radii for each annular mask opening.

In FIG. 116, beamsplitter 11605 reflects a portion of the scattered light to multi-element detector 11608. This multi-element detector provides the same function as the multi-element detector shown in FIG. 37, FIG. 49, FIG. 50, FIG. 119, and FIG. 120. Notice that the flow direction in FIG. 37, FIG. 49, FIG. 50, FIG. 119, and FIG. 120 is X, Y, Y, Y, Y, respectively. Multi-element detector 11608 is generally in the image plane of the interaction volume and aperture 11302. The Y direction in FIG. 37 and the X direction in FIGS. 49, 50, 119, and 120 are generally perpendicular to the plane of the page of FIG. 116. Multi-element detector 11608 determines the position of each particle path through the illumination spot in the sample cell. Particles which pass far from the center of the spot, where the illumination intensity is too low to maintain a narrow monosized count distribution (as shown in FIG. 60) can be rejected and not used in the particle characteristic analysis. This rejection process could be used in addition to, or in place of, the illumination intensity range restrictions described previously using aperture 11301 and/or aperture 11302.

FIG. 117 shows a variation of the systems shown in FIG. 12 and FIG. 116. In FIG. 117, beamsplitter 11602 is replaced by mirror 11702. Aperture 11703 and mirror 11702 serve similar functions to beamsplitter 11602, aperture 11609, and aperture 11610. The outer radius of minor 11702 and the inner radius of the opening of aperture 11703 can define the highest scattering angle and lowest scattering angle, respectively, for detector 11607. The outer radius of minor 11702 and the outer radius of the opening of aperture 11703 can define the lowest scattering angle and highest scattering angle, respectively, for detector 11606. Aperture 11609 and/or aperture 11610 could also be utilized in the system shown in FIG. 117 to more accurately define the range of scattering angles for detector 11606 and detector 11607, respectively, eliminating the need for aperture 11703. As described for expansion of the system in FIG. 116, additional mirrors of similar function to minor 11702 can be added between minor 11702 and lens 11603, to accommodate additional detection systems, each with components of function similar to lens 11604 and detector 11607. However, in this case the diameter of each added minor should be larger than the preceding mirror, such that higher angle scatter which is not reflected by a mirror is passed on to the next mirror to be reflected to the next lens and detector. For example, the diameter, of a second mirror between mirror 11702 and lens 11603, would be between the outer diameter of mirror 11702 and the outer diameter of the opening in aperture 11703. This second mirror would reflect an angular range between the angular ranges of detector 11606 and detector 11607. Any number of additional detection systems could be added to measure scattering over more ranges of scattering angles, by extending the space between mirror 11702 and lens 11603 to accommodate the added mirrors with progressing larger diameters (left to right in FIG. 117). Annular apertures 11609 and 11610 could also be utilized with the mirror 11702, to define the ranges of scattering angle for each detector. The use of these apertures, 11609 and 11610, in FIG. 117 may be preferred because the dimensions of apertures may be more accurate than the dimensions of mirrors.

The function of lens 1403 and lens 1503, in FIGS. 14 and 15, can be provided by lens 11601 in FIGS. 116 and 117. Lens 11603 and lens 11604 could be eliminated, in FIGS. 116 and 117, by choosing the focal length of lens 11601 for finite conjugates (1:1 magnification, for example). Then lens 11601 would also provide the additional functions of lens 11603 and lens 11604, by focusing the scattered light directly onto detector 11606 and onto detector 11607, through beamsplitter 11602 or mirror 11702. Beam splitter, in FIGS. 14 and 15, provides similar function to beamsplitter 11602 in FIG. 116. The same function for apertures 11609, 11610, 11703, and the outer radius of mirror 11702 can be performed in a converging scattered light beam, as demonstrated by the functions of low angle annular spatial filter and high angle annular spatial filter, in FIGS. 14 and 15. The size of apertures 11609, 11610, 11703, and the outer radius of mirror 11702, must be scaled to intercept the light rays for the same scattering angles in the converging scattered light beam, as in the generally collimated scatter beam of FIGS. 116 and 117. However, additional scatter detection systems are more easily added to the generally collimated systems of FIGS. 116 and 117, because the distance between lens 11601 and 11603 can be easily expanded.

If only one detector is used in the type of system shown in FIG. 116, aperture 11609 can be placed anywhere in the optical system after the sample cell. At any position, the size of the inner and outer radii, of the annular aperture 11609, must be scaled to intercept the lowest and highest scattering angle, respectively, of the angular range for that detector. If the scaled version of aperture 11602 is placed between the sample cell 11316 and aperture 11302, detector 11606 could be placed directly behind aperture 11302 to capture the light passing through aperture 11302, eliminating 11601, 11602, 11603, 11610, 11604, and 11607. Multielement detector 11608 and beamsplitter 11605 could be placed in the converging scatter light beam between lens 11313 and aperture 11302. Detector 11606 could also be replaced by multielement detector 11608, in an image plane of the interaction volume. Then the ratios of individual signals from each detector element would be used for position detection and the sum of the individual signals would produce the scatter signal for particle characterization.

FIG. 118 shows an example of a complete optical system for measuring light scattered over 4 different ranges of scattering angle. Items 11801, 11802, 11803, 11804, 11805, 11806, and 11807 perform similar functions to 11601, 11702, 11703, 11604, 11605, 11606, and 11607, respectively. However, detector 11806 and detector 11807 measure scattered light at much larger scattering angles than detector 11606 and detector 11607. Multi-element detector 11808 could be eliminated, if multi-element detector 11608 is sufficient to reject unwanted particles from the analysis. The first detection module (items 116and 117**) and the second detection module (items 118**), in FIG. 118, could each be replaced by a beamsplitter detection module, as shown in FIG. 116 or by a diffractive optic detection module as shown in FIG. 121. In either case, FIG. 116 or FIG. 121, aperture 11302 would serve the same function as apertures 11402 and 11420 in FIG. 118**.

FIG. 119 shows the scattered light intensity distributions from a particle at 4 different positions in the illuminating light beam, for the multielement detector 11608 and 3 element detector shown in FIG. 37. This figure shows a crossection of the detector in FIG. 50, along the X axis, with the particle flow direction along the Y direction, which is generally perpendicular to the page of FIG. 119. The image of the light beam is shown by the dashed line, beam intensity 11905. Since this light beam image is blocked by beam block 11317, the detectors only receive the scattered light intensity distribution, as exemplified by the intensity distributions 11901, 11902, 11903, and 11904. The signal on each detector will generally be equal to the area under the scattering intensity distribution on that particular detector. The ratio of signals from detector 11906 and detector 11907 and the ratio of signals from detector 11908 and detector 11907 will indicate the position of the particle in the illuminating beam. For example, when signal of detector 11907 divided by signal of detector 11906, or when signal of detector 11907 divided by signal of detector 11908, is generally greater than one, then the particle is passing through the beam over the space defined by the image of detector 11907 in the interaction volume. Hence, the width of detector 11907 and the magnification of lenses 11604 and 11601, determine the region through which particles can pass and be accepted for particle characteristic analysis. This 3 detector configuration is optimal for most cases where the width of the particle scatter intensity distribution (11901 for example) is much smaller than the width of the beam intensity distribution 11905. In most cases, the width of the scatter intensity distribution will be determined by the aberrations of the optical sub-system consisting of lens 11601, beamsplitter 11602, lens 11604, and beamsplitter 11605. If this sub-system is diffraction limited, then the width of the particle scatter intensity distribution (11901 for example) will be determined by the physical optical properties of the sub-system, such as numerical aperture. For example, the beam spot in the interaction volume could have a Gaussian beam waist radius of 20 microns, while measuring particles up to 1 micron diameter. These intensity distributions are always compared in the same optical plane. The beam intensity (virtual distribution) and particle scatter intensity distributions can be projected to the plane of the detectors, as shown in FIG. 119.

In the case, where the particle scatter intensity distribution and beam intensity distributions are of comparable width, a 2 detector system can be utilized, as shown in FIG. 120. In this case, a reasonable amount of scattered light remains on both detectors for particle positions over the acceptable region of the beam intensity. Hence the ratio of signals from detector 12006 and detector 12007 will determine the position of particle passage through the beam, for particles between positions 12001 and 12004. Particles passing through positions 12002 and 12003 are accepted for further analysis. Particles passing through positions 12001 and 12004 are rejected. The illuminating intensity for the particle can be calculated from this determined position. Then the scatter signal, for each particle, can be divided by the actual illumination intensity for that particular particle to remove the effects of illumination variation across the intensity profile of the illumination spot. This illumination intensity correction can also be utilized in the 3 detector system of FIG. 119, because the signal ratios, from the 3 detectors will also provide particle position in the illuminating beam.

The number of detector elements in a multielement detector, with equivalent function to the multielement detector 11608 and the detectors in FIG. 119 and FIG. 120, can be greater than three, to obtain more position resolution for the path of the particle. However, three detectors provide the optimal position information per detector, since the width of detector 11907 and the magnification of lenses 11604 and 11601, can define the optimum region through which particles can pass and be accepted for particle characteristic analysis.

FIG. 121 shows a variation of FIG. 85, where generally collimated scattered light passes though the diffractive optic. FIG. 121 shows a crossectional view of the optical system and the diffractive optic 12102, which is similar to that shown in FIG. 84. FIG. 84 shows the view of a diffractive optic of similar function to 12102. However, the view of FIG. 84 is perpendicular to the view of FIG. 121. The diffractive optic in FIG. 84 measures two different ranges of scattering angle for each range of scattering planes. Diffractive optic 12102 measures three different ranges of scattering angle for each range of scattering planes. After passing through an aperture (such as aperture 11302), which defines the interaction volume, the scattered light is generally collimated by lens 12101. This generally collimated light passes through diffractive optic 12102, which contains different regions corresponding to different ranges of scattering planes and/or different ranges of scattering angles, with a similar structure to the optic shown in FIG. 84. The crossectional views of FIGS. 85 and 121 show diffracting regions of differing scattering angle ranges, all for generally one range of scattering planes. Each region or segment is covered by a diffractive structure with an orientation and/or spatial frequency which is specific to that region. Examples of region definition are shown in FIG. 79 and FIG. 80. Examples of diffractive optics are shown in FIG. 84 and FIG. 86. The plane of the page in FIGS. 79, 80, 84, and 86, is generally perpendicular to the zero angle scatter direction, or the unscattered light beam. Hence the view of diffractive optic 12102 is crossectional, as also shown in FIG. 85. FIG. 85 and FIG. 121 only show detectors or fiber optics along one diameter of the diffractive optic. A detector or fiber optic exists for each segment or region of the diffractive optic in three dimensional space, as exemplified by the multiple segments in FIG. 84. Each region in diffractive optic 12102, diverts the generally collimated light, passing though that region, into a direction which is specific to that region. Lens 12103 focuses the light passing through each region to a separate spot, generally in the back focal plane of lens 12103. Detectors 12104, 12105, 12106, 12107, 12108, 12109, and 12110 separately receive each light spot from each region of diffractive optic 12102, for the scattering plane range, whose center plane is generally in the plane of the page of FIG. 121. In a three dimensional view of FIG. 121, a set of similar detectors exist for each scattering plane range of the diffractive optic. Some scatter plane ranges are identified in FIG. 84, by the angle, ø, of the center scatter plane of each scatter plane range. The angle ø is defined in the plane, of the diffractive optic, in FIG. 84, which is generally perpendicular to the direction of the incident light beam. So measuring scattered light from a range of scattering planes is equivalent to measuring scattered light over a range of angle ø, which is defined in a plane which is generally perpendicular to the direction of the incident light beam. Likewise, a set of similar fiber optics exist for each scattering plane range of the diffractive optic in a three dimensional view of FIG. 85. Detectors or fiber optics, transferring scattered light to detectors, can be utilized in FIG. 85 and FIG. 121. In FIG. 121, the spatial frequency, and angle of diffraction, is larger for regions at larger radii on the diffractive optic. The region, which passes light to detector 12107, has no diffractive structure, passing the generally collimated light to lens 12103, with diversion. An optional beam block is placed in the center of diffractive optic 12102 to block unscattered source beam light from entering the detectors. This detection module could replace the detection modules of FIG. 118. Aperture 11402 and the optics to the right of that aperture, in FIG. 118, would be replaced by aperture 11302 and the optical system of FIG. 121. Likewise, Aperture 11420 and the optics to the left of that aperture, in FIG. 118, would be replaced by aperture 11302 and the optical system of FIG. 121, reversed left to right. This design would provide scattered light measurements over various ranges of scattering planes and/or various ranges of scattering angles, as desired for measuring particle characteristics, including particle size and shape. The diffractive optic in FIG. 85 and FIG. 121 could be replaced by an optic with the same segment shapes, but where each segment contains a prism element, wherein the prisms in different segments differ by at least one of prism apex angle and orientation. This multi-prism segmented optic could be molded as one piece.

In some cases, only equivalent particle size or diameter, independent of particle orientation, is the desired particle characteristic. Then a diffractive optic, similar to that shown in FIG. 86, could replace the 12102 diffractive optic, in the optical system shown in FIG. 121, and the diffractive optic in the optical system shown in FIG. 85. The annular shape of the diffraction regions send all scattered light in each range of scattering angles to a different detector, for all scattering planes. This detection module could replace the detection modules shown in FIG. 116 and FIG. 117, for measuring scatter through an annular section of the 2-dimensional scattering distribution to remove particle shape and orientation effects from the particle count vs. particle equivalent size distribution. In some cases, the particle equivalent size is the diameter of a sphere of volume equivalent to that of the arbitrarily shaped particle being measured. In all of the diffractive optics, the shape of each diffractive line could be optimized to send most of the diffracted light into one diffractive order to increase optical efficiency and reduce stray light spots in the detection module.

The optical systems, shown in FIGS. 116, 117, and 121, are detection modules, which include the means for distributing scattered light to scatter detectors. Each detector detects light scattered over a different range of scattering angles and/or a different range of scattering planes and/or with different weighting as a function of scattering angle.

FIGS. 122 through 128 show Mie theory scatter signal data for an optical system which measures scattered light over 3 different ranges of scattering angle, using annular apertures as exemplified by mask 1250 in FIG. 12. The 3 signals are: Si=light scattered in the angular range between 2 to 8 degrees, S2=light scattered in the angular range between 10 to 40 degrees, and S3=light scattered in the angular range between 120 to 160 degrees. Scatter signals S1, S2, and S3 represent values of signal characteristics, including peak value of a scatter detector signal pulse, integral of a scatter detector signal pulse, and integral of a scatter detector signal pulse above some percentage of the peak value, after subtraction of scatter detector signal background. This detector signal background could comprise electronic noise, electronic offsets, light scattered from the optical system, and/or light scattered from other particles. Usually these other particles would comprise a large number of smaller particles in the interaction volume, present with the larger particles of interest. The larger particles of interest would be counted with a low level of coincidences, due to the low count rate of larger particles through the interaction volume. The large number of smaller particles would not create coincidence counts due to the large number of low signal pulses, which overlap to create a generally constant background scatter signal. Since the background scatter from these many smaller particles would be generally constant during the signal pulse from a larger particle, the background during the pulse could be estimated by interpolation of the signal levels before and after the pulse to produce the background signal during the large particle pulse. For an optical sub-system measuring particles at the lower limit of the size range, the background from other particles is generally very low, because the particle concentration is adjusted to provide generally single particle counting for the smallest particles in the dispersion.

The plots, in FIGS. 122 through 128, represent actual theoretical calculations of data represented in FIGS. 26, 27, 27a, 28, 39, 60, 61, and 62. The coordinates of any point on a curve in FIGS. 122 through 128 corresponds to the signal values from a particle of a different size. These three signals, S1, S2, and S3, could be measured by the optical system shown in FIG. 118, for example. Every Figure shows data for spherical particles of three different refractive indices: 1.59-0.0i, 1.80-0.0i, and 1.80-1.0i, all dispersed in water. The plots in these figures, represent the signal scattered by a particle passing through some nominal point in the light beam, such as where the intensity is maximized. The three signals (such as peak pulse scatter detector signal amplitude) can be plotted on these Figures as a point for any particle. Multiple plotted points from a monosized group of particles, passing through various locations in the light beam, will show a spread over a certain region, due to intensity variation across the beam, as described previously in FIGS. 26, 27, 28, 61, and 62. FIG. 60 and FIG. 61 describe this region for plots of FIG. 122 and FIG. 125. The scattered light signals, S1 and S2, from any two angular ranges will generally be proportional to the light intensity on the particle.

$$S1 = E1 * Io$$

$$S2 = E2 * Io$$

$$S1/S2 = E1/E2$$

E1 and E2 are the scattering efficiencies for angular ranges 1 and 2, respectively. Io is the incident light intensity on the particle. Therefore, the ratio, S1/S2, of scattered light over any two angular ranges will be generally independent of light intensity on the particle and generally independent of the position in the light beam through which the particle has passed. Additionally, the ratio S1/S2=E1/E2 is dependent upon particle size. However even the signal ratio (S1/S2 or S1/S3 for example) may have some dependence on particle position. For example, particles passing through a Gaussian intensity beam off center will produce a slightly different angular scattering distribution from those passing through the center of the Gaussian distribution. Hence, in general, the region covered by a group of data points from a group of monosized particles will show minor broadening parallel to the axis of a ratio parameter (S1/S2 or S1/S3) and major broadening parallel to an axis of amplitude (S1, S2, or S3). Hence the monosized region will have a minor axis and a major axis. FIG. 122 shows S2 plotted vs. S1 for particle sizes between 50 and 1000 nanometers (nm). Markers indicate points at particle diameter increments of 50 nm, starting at particle diameter of 50 nm on the left bottom corner and ending at 1000 nm on the upper right hand corner of FIG. 122. The scatter coordinates of particles from a monosized group of particles would cover a region, the multi-dimensional monosized response, with a major and minor axis. In FIGS. 122 and 125, the major axis of the monosized response distribution would be at generally 45 degrees for count density functions depending upon logarithmic signal values, because the ratio of S1/S2 is generally constant for all of the particles, as also shown previously in FIG. 26 and FIG. 27. A three dimensional plot of particle coordinates in all three coordinates, S1, S2, and S3 could be created. The local density of points (probability or occurrence density) could be plotted in these 3 dimensions to create a three dimensional monosized response, which could be used to invert the three dimensional distribution from a group of particles with unknown size distribution to determine the particle size distribution. If the count density function is created with logarithmic signal dependence, as described previously for Cg, then the inversion process could utilize 3 dimensional deconvolution methods, using the 3 dimensional response as the impulse response for that deconvolution. The inversion process is the process of calculating the particle size distribution from the scatter data. Likewise, 2 dimensional deconvolution methods could be used for count density functions, with logarithmic signal dependence, in the 2 dimensional spaces of FIG. 122 and FIG. 125. In each case, the projection of the monosized response distribution, with a logarithmic progression, onto a log(S) axis (log(S1), log(S2), or log(S3), for example) will have a functional form similar to those shown in FIG. 10*a* and FIG. 60. The ratio (SAU/SAL in FIG. 60, for example) of the two S values at the edges of that functional form will be generally equal to the ratio of the maximum source intensity value to the minimum source intensity value, passed by aperture 11301 or 11302. In many cases that ratio could be in the range of 1.2 to 1.5. The projection of the monosized response onto a signal ratio axis (S1/S2 for example) will be a narrow function in S ratio space, with typically a ratio of maximum signal ratio to minimum signal ratio of less than 1.02 across the monosized response. Hence the ratio of major to minor axis of the monosized response could be in the range of 10 to 100, for the 2 dimensional space of S1 and S1/S2, for example.

The count density function from any monosized particle dispersion, of particle diameter Dj, will be the monosized response, R(P, Dj), located at the corresponding theoretical point, for that particle size, in the multidimensional space, P, where each dimension is a function (S1, log(S1), or S1/S2, for example) of scatter signals. Then the total count density function in that multidimensional space from a particle dispersion of arbitrary particle size distribution, Nj, is:

$$Ct(P)=\text{SUM}j[Nj*R(P,Dj)]$$

Where SUMj[Zj] is the sum of Zj over index j. R(P, Dj) is the multidimensional count density function for a monosized dispersion of particles of size Dj, in space P. R(P, Dj) includes the effects of response broadening, due to illumination intensity variation in the interaction volume, for example. And Nj is the number of particles of diameter Dj in the dispersion of arbitrary size distribution. Nj is the number of particles, with diameter D within the jth diameter interval, between values of Dj−Da to Dj+Db. These diameter intervals could follow a linear or logarithmic progression, for example, as described below. The product of Nj and R(P, Dj) is summed over j, to produce the multidimensional count density function, Ct(P), for the arbitrary size distribution, in space P. P describes the space over which the count density is defined. P=[log(S1), log(S2)] for FIG. 122 and P=[log(S1), S1/S2] for FIG. 124, for example. This is the generalized problem, solving for Nj, by measuring Ct(P) and inverting the equation for Ct(P) by utilizing knowledge of R(P, Dj). The data set Nj vs. Dj describes the particle size distribution of particle number vs. particle diameter. This equation can also be solved for functions of any other particle parameter Qj, by using the mono-response function Rq(P, Qj), where Nj vs. Qj is the number distribution of parameter Qj. Rq(P, Qj) is the multidimensional count density function for a dispersion of particles of parameter Qj.

$$Ct(P)=\text{SUM}j[Nj*Rq(P,Qj)]$$

This generalized equation for Ct can be solved by many methods, including iterative error minimization techniques. However, in the case of broadening due to illumination intensity variation, logarithmic progressions (P=[log(S1), log(S2)] for FIG. 122 and P=[log(S1), S1/S2] for FIG. 124, for example) may be preferred.

As described previously, Cg, the count distribution on a logarithmic progression, contains data points which represent the total counts in equal intervals of log(S). This term "count distribution on a logarithmic progression" is equivalent to previously described terms such as "the probability density function in Log(S) space" and "count distribution in Log(S1), Log(S2) space". Cgi, the counts in the ith logarithmic channel, is the sum of all counts, C(X), with Log(S) values between Xa and Xb as described by the following equations:

$$Cgi=\text{SUM}(Xa:Xb)C(X)$$

Where C(X) is the number of counts with signal value S=EXP(X), EXP is the exponential function.

$$Xa=\log(Si)-\log(B)/2$$

$$Xb=\log(Si)+\log(B)/2$$

$$Xb-Xa=\log(B)$$

$$Sbi=B*Sai$$

Hence the particle counts in the ith channel of the logarithmic count progression is produced by summing particle counts with signal values between Sai and Sbi. For contiguous channels, Saj=Sbi, for j=i+1 and Saj=B*Sai. So the interval edges of the set of summation intervals are such that the S value of each edge is B times the S value of the preceding edge. The value of B will determine how many data points are in the vector of Cgi values. The scatter signal resolution of count channels and the resulting particle size resolution are improved by decreasing B. As shown previously in this document, this logarithmic progression produces a convolution relationship between the measured count distribution, Cg, and the number vs. size distribution, Ng, using the impulse response (or monosized response) Pg.

$$Cg=Ng\Theta Pg$$

In this equation, the relationship between scatter signal and particle size, as described in FIGS. 122 through 128, is included in the impulse response Pg, which also describes the count distribution broadening due to source beam intensity variations. The measured Cg distribution is deconvolved, using the impulse response Pg, to produce the count vs. size distribution Ng. This convolution equation is equivalent to a matrix equation, when the sampled values of the functions are utilized. This inversion process can more easily be understood by considering the equivalent matrix equation where Cg and Ng are column vectors and Pm is a matrix of generally monosized responses.

$$Cg=Pm*Ng$$

Each column in Pm is the count distribution measured from a narrow sized dispersion of particles with particle sizes which span the corresponding size channel, of Ng, which multiplies that column in the matrix equation. Hence, the count function described in each column of Pm is counts vs. Log(S) in the logarithmic progression described above. The position of the function, along the Log(S) axis, in each column of Pm is determined from the theoretical scatter efficiency of particles which span the corresponding size channel, of Ng, which multiplies that column. Hence, the maximum of each column in Pm is not necessarily close to the diagonal of matrix Pm, due to the nonlinear dependence of particle scatter signal vs. particle size, as shown in FIG. 128.

The inversion of the matrix equation, where the maximum of each column in Pm is not close to the diagonal of matrix Pm, is difficult. The following 2 step procedure is preferred for inversion of this equation. First create the matrix equation describing the convolution relationship with a new matrix Hm, which contains column vectors with maximum values close to the diagonal of the matrix Hm. This equation can be solved for a corrected count distribution Cc.

$Cg = Hm * Cc$ matrix form $Cg = Cc \ominus Hg$ convolution form

In this case, the position of each column is not determined by scatter efficiency. Each successive column in Hm is the generally monosized response, shifted by one channel from the succeeding column in the matrix, to maintain the maximum of each column vector close to the diagonal of matrix Hm. Cc is the corrected count distribution, without the distribution broadening due to intensity variations of the light source intensity. Hm is the set of count distributions from groups of monosized particles including the effects of distribution broadening due to intensity variations of the light source intensity. However, Hm does not include the relationship between scatter signal and particle size. The Cg distribution is deconvolved, using the impulse response Hg in matrix Hm, to produce the count distribution Cc. The particle size of each point in Cc is determined by the coordinates of that point in the signal, S, space as determined from theoretical model plots, as shown in FIGS. 122 through 128, for example. The number of counted particles at that S coordinate is the number of particles with the theoretical particle size, corresponding to that S coordinate, as determined from a scattering model (as shown in FIG. 128, for example). The size axis of Cc will have a nonlinear progression, which does not match any accepted standard progressions for particle number vs. particle size. The resulting count vs. particle size distribution can be summed over particle size intervals which match the desired standard particle size progressions. Hence the particle number, as a function of particle size, can be created, generally without the distribution broadening present in Cg, using a matrix Hm which is generally maximized on the matrix diagonal. This matrix formulation provides much more accurate inversion of the matrix equation to determine Cc from the measured values Cg.

These matrix equations could also be created using functions with linear progressions. Then Sbi=Sai+Bo. This linear progression matrix equation and equivalent integral equation can also be solved for Ng. However, the inversion of the matrix or integral equation is more easily accomplished using logarithmic progressions for S (Log(S)) and deconvolution.

FIG. 123 shows the ratio S1/S2 plotted vs. particle diameter, showing the slight dependence on refractive index. The dependence of signal ratio on particle refractive index and/or dispersant refractive index is lower than the dependence of signal amplitude. FIG. 124 shows a plot of the ratio, S1/S2 vs. S1, again with markers every 50 nm, as in FIG. 122. In this plot the major axis of any monosized response region will be along the S1 axis, with the minor axis along the S1/S2 axis. As before, the particle point density could be plotted as a function of these two dimensions, S1/S2 and S1. For a monosized sample (all particles of same size but passing through various paths in the beam), this point density distribution will create the two dimensional monosized response, which can be used as the 2 dimensional impulse response to deconvolve, in 2 dimensions, the point density distribution from a particle group of unknown size distribution. As the particle size increases, the monosized responses will become more separated along the S1/S2 direction, as the curves progress from left to right (increasing particle size left to right) due to the increasing slope of the curve. The curve at the small particle region (lower left) has almost zero slope, so that the major axes of the monosized responses could overlap. However, in this region the derivative of S1 with respect to particle diameter is large, and the monosized responses are separated along the S1 dimension. Therefore, the 2 dimensional deconvolution of count density as a function of the two dimensions, S1/S2 and S1, will produce excellent results over the entire size range of S1 and S2, because the impulse responses for various particle sizes are well separated in the space of S1/S2 and S1. This impulse response separation will occur for any space with dimensions of signal ratio and signal amplitude, including S1/S2 and S1, S2/S1 and S1, S1/S3 and S1, and S1/S2 and S2, for example.

FIGS. 125, 126, 127 show curves for S1 and S3, corresponding to curves for S1 and S2 shown in FIGS. 122, 123, 124, respectively. Comparing FIG. 123 and FIG. 126 shows how these 3 measurements could be used to cover the size range from 50 nm to 1000 nm. The S1/S3 ratio provides good size sensitivity from 10 nm to 150 nm (0.15 microns) and the S1/S2 ratio provides good size sensitivity from 150 nm to 1000 nm (1 micron). Outside of these size regions, the particle refractive index dependence is large. Particle points in these plots, in the areas where the scatter response has high sensitivity to particle and dispersant refractive index, can be used to determine the particle and dispersant refractive index, to be used for analyzing particles counted in regions where the refractive index sensitivity is lower. In the areas with large refractive index sensitivity, a search or optimization algorithm can be utilized to find the refractive index, which produces a scatter function, which best fits to the count density function in the multidimensional space.

An event occurs when the measured scatter signals and/or scatter parameters indicate potential origin from a particle. Each event is stored in a bin which stores other events with similar scatter signals and/or scatter parameters. Further analysis is required to confirm that the scatter signals and/or scatter parameters from each event meets acceptance criteria, such as acceptable signal level, signal shape, and signal ratio, for example. Many of these acceptance criteria have been described previously in this document. For example, the methods, described in FIG. 10 and FIG. 10a, can be utilized to reject unwanted counted events, in FIGS. 124 and 127. This rejection method can be employed for count density functions depending upon linear or logarithmic (Cg for example) signal values. All events with similar values of signal ratio (S1/S2 for example), should only span a certain absolute scatter signal (S1 for example) range as defined by the truncation of the illuminating beam intensity profile and the scattering efficiency of a particle with size corresponding to that signal ratio. The effect of truncation on the counted scatter signal range is demonstrated in FIGS. 56, 57 and 60, for example. Events, with coordinates positioned outside of this certain range, should be rejected as either non-particle events, counts of coincident particles, or particle events with insufficient scatter signal, as described previously in FIGS. 10 and 10a. These rejection criteria should be used to eliminate unwanted events from the accepted counted events before creating the particle count density function for subsequent inversion or deconvolution. Also, since the functional form of the count density function along a scatter signal axis (S1 or log(S1) for example) is known (see FIG. 60 for log(S), for example), the count data can be fit to that known function, at points along that scatter signal axis, to improve accuracy for creating the particle count density function. For example, in FIG. 124, the known functions (from FIG. 60, for example) could be fit to particle count data, as a function of S1, at each level of ratio S1/S2. So the fitting process would break the 2-dimensional set of counted points into horizontal sections, in FIG. 124. The data in each section would be fit to the appropriate known function of log(S1) to produce the count density distribution in that horizontal section of generally constant ratio S1/S2. This process is repeated for each horizontal section, for each value of S1/S2.

Notice that the functions in FIG. 60 show the monosized response, without the effects of optical system aberrations or diffraction. These effects are included in the function labeled "with aperture (aberrated)" in FIG. 10a. The lower edge, labeled log(SAL) in FIG. 60, will be rounded by the effects of optical system aberrations and diffraction broadening on the image of aperture 11302 in the interaction volume or on the image of the particle at aperture 11302, as shown by the particle intensity profiles in FIG. 119 or 120. The plane of the detector in FIGS. 119 and 120 are generally conjugate to aperture 11302.

Multi-dimensional deconvolution of a count distribution as a function of multiple scatter parameters, is a particularly power method. For example, consider the case where the first parameter is a scatter signal (S1 for example), with logarithmic progression, and the second parameter is ratio between two scatter signals (S1/S2 for example). The scatter plots of these counted events at coordinates in the Log(S1)–S1/S2 plane provides the mechanism for eliminating unwanted events, as described previously. Additionally, the separation of each monosized response region from the monosized response region of another particle size, is greater in this multi-dimensional space, than in a single dimensional space, as described previously for the coordinates of S1 and S1/S2.

As described previously, the scatter parameters include any scatter signal dependent parameter such as signal amplitude (S1, S2, or S3, for example) and signal ratio (S1/S2 of S1/S3, for example). Each counted event is plotted in the space with a dimension (or plot axis) for each scatter parameter. Counted events, which do not meet the criteria for scattered light from a particle of interest, are rejected from the counted points in the space. A count density function is created from the remaining counted events, which describes the density of counts per unit volume of the space, for 3 dimensions or density of counts per unit area of the space, for 2 dimensions. This process can be extended to any number of dimensions, including one dimension. The count density function is inverted, by utilizing a model which describes the expected response including the broadening effects, which may include intensity variation across the interaction volume. Logarithmic progressions of signal amplitude allow the use of powerful deconvolution inversion techniques. Count density distributions as a function of scatter signal parameters, which do not have logarithmic progression, may be inverted by other known methods, such as those used for solving matrix equations. After the broadening effects are removed by inversion, the resulting broadening corrected count density function, is converted to a particle count (or number) vs. size distribution by integrating the density distribution over the desired particle size intervals of the particle count (or number) vs. size distribution. The particle size corresponding to any particular point in the space is determined by the point on the theoretical curve, which has shortest distance from the particular point, as described previously by minimization of the function $(S1-S1T)^2+(S2-S2T)^2+(S3-S3T)^2+(S4-S4T)^2$, which was described for a 4 dimensional space.

The truncation of the beam intensity profile, as described previously in FIG. 56 and FIG. 57, can be provided by apertures such as aperture 11301 or aperture 11302. Aperture 11302 may be preferable in cases where aperture 11301 scatters source beam light into a scatter detector.

The scatter signal amplitude is proportional to the detection responsivity (volts of signal per optical power of light on detector) of the detector electronics and the optical intensity of the portion, of source light, intercepted by the particle. In any optical system, which requires absolute scatter amplitude measurement, the measured scattered light amplitudes should be divided by the product of the total responsivity, of the detection system (which includes the electronic gain) and optical intensity of the source, during each measurement. This is particularly important when absolute signal amplitudes, such as S1, S2 or S3 are used to determine particle size, where the particle size is determined from the light scattered per unit incident light intensity. This is also important when two different scatter signals, which each originate from a different responsivity detection system (including different electronic gain) and/or different illumination intensity, are compared or used together to determine a particle characteristic.

In general, high illumination intensity is required for smaller particles, due to the low scattering efficiency (scattered light per unit incident illumination intensity (or irradiance)) of small particles, as shown in FIGS. 122 through 128. This high intensity is generally provided by focusing a laser beam to a small spot size in the interaction volume. Diffractive optics can convert the typical Gaussian intensity distributions of most lasers to a relatively uniform intensity distribution, sometimes referred to as a flat top distribution. These beam conversion optics are sometimes called beam shapers or flat top generators. A flat top distribution will produce very narrow monosized count distributions (as a function of scatter signal S), and so Pg and Hg would be narrow functions. If the width, in signal space, of these monosized response functions is sufficiently low, such that the raw count distributions, Cg, have sufficient size resolution, the deconvolution step can be eliminated and the size distribution could be generated directly from Cg and the information in FIGS. 122 through 128. As described previously, the information in FIGS. 122 through 128 describes the one-to-one correspondence between scatter parameters and particle size. However, the performance of present flat top diffractive optics may not produce sufficient intensity uniformity. Also the flat top convertors may produce low, but significant, light intensity outside of the main light spot. So in general the aperture techniques (such as provided by 11301 and 11302), described in this document may be needed to optimize a flat top converted laser beam for scatter measurements, to choose particle scatter from the most uniform portion of the beam and avoid scatter from particles passing though the tails of the flat top distribution. In general, the source beam divergence increases as the spot size decreases. The half angle of the beam divergence should be sufficiently lower than the minimum scattering angle to avoid large background scatter signal levels when a particle is not present in the interaction volume. The scattering angle ranges, utilized in FIGS. 122 through 128, will generally provide determination of the particle size below generally 1 micron. In general, scattering angles below 2 degrees could be used to measure particles larger than 1 micron, using lower light beam divergence in the interaction volume to accommodate the lower scattering angles. For very large particles, a large diameter, low divergence, uniform intensity beam can be utilized in the interaction volume, with measurement of low angle scatter. The scattering efficiency of large particles is sufficiently large such that a, lower intensity, uniform light source, such as a white light source, could be utilized. For small particles, the light source is focused to a small spot, of high intensity, in the interaction volume to provide adequate scatter signal for small particles. In many cases, this focusing process creates non-uniform intensity in the interaction volume, requiring the use of apertures 11301 and/or 11302. So in general, multiple optical systems with different light sources and/or scatter detection systems are utilized to cover an entire size range, which may span from nanometers to millimeters. Many of the methods and optical systems, described in this specification, can be combined to extend the size range of the system.

As described previously, for the larger interaction volumes, required for larger particle measurement, the low concentration requirements to attain single particle counting, without coincidence counts, may not be practical, except for narrow particle size distributions. Broader particle size distributions could have particle counts, from small particles, which are orders of magnitude larger than the particle counts for large particles. Therefore, if the particle concentration is reduced to avoid coincidence counts, millions of small particles may need to be counted for each large particle, resulting in a very long measurement time. In general, multiple optical sub-systems, each with a different particle size range or sub-range, are desirable to lower the total measurement time. A complete instrument comprises multiple optical sub-systems. The particle characterizations measured from each of the sub-systems, in each sub-range, are combined to produce the final particle characterization function (particle count vs. particle size, for example) over the entire particle size range of the instrument. The sub-systems would generally have inter-action volumes of different sizes to accommodate the particle size sub-range for each subsystem. For sub-systems, measuring larger particles, absolute single particle counting over the entire instrument particle size range will require enormous measurement times in order to obtain accurate count statistics, as described above. Therefore, in most cases, the particle concentration, in the large particle subsystems, will be adjusted to provide reasonable measurement times, while correcting for the presence of many smaller particles in the interaction volume with the larger particles of interest. The particle of interest in a subsystem is a particle in the size range of that subsystem. Therefore, each of the larger particle optical subsystems will measure larger particle scatter pulses with a background of many smaller particles. Hence the size range of each optical subsystem must be limited to the size range which provides single particle counting for the particles of interest, after subtraction of smaller particle background and utilization of signal deconvolution as described in FIGS. 71 through 73.

In general, the laser sources, without diffractive optic beam shaping, will have an intensity distribution which is generally a circularly symmetrical Gaussian or elliptical Gaussian. The shape of apertures, with the optical function of aperture 11301 or 11302, could follow a certain contour level of the 2-dimensional intensity distribution of the beam. Square and rectangular apertures could also be utilized to accommodate the aspect ratio of the source intensity distribution. Sources, with symmetrical Gaussian intensity distributions, and circular apertures (with the function of 11301 and 11302) would generally be preferred for use in systems using annular detection apertures (with the function of 11609 and 11610) in the scatter detection system.

As described previously, most of the figures of optical systems, in this specification, provide crossectional views of the optical system. Any lens represents the appropriate optic, providing the required function in that optical system. This required function may be performed by any appropriate optic, including conventional spherical lenses, aspheric lenses, gradient index lenses, diffractive optics, or binary optics. Also most systems, in this specification, can be used without a sample cell to count particles dispersed in an aerosol, which flows though the interaction volume.

In most instances in this specification, the term "image plane" does not assume a specific direction of light propagation. Any plane has image planes, elsewhere in the optical system, which are defined by the optical properties of the intervening optics. These image planes, which can be on either side of an object plane, are determined as though light is traveling from the object plane to the image plane. For example, aperture 11302 has an image plane which is generally in the interaction volume, as defined by the optical properties of the intervening optic 11313, even though the primary direction of light propagation, in use, is not from aperture 11302 (object plane) to the interaction volume (image plane).

As described before, the signal S includes scatter signal pulse amplitude related measurements, such as peak value and integral of the pulse. The intensity distribution, of the source, in the interaction volume is known either theoretically or by direct measurement with a detector array. Therefore, the functional dependence of each signal pulse, as a function of time, is known. A function, with that known functional dependence, can be fit to the digitized values of the measured scatter signal pulse. Then any parameter (peak value or integral for example) of that pulse can be derived from the fitting parameters of that function. For example, if the source beam has a Gaussian intensity distribution, each pulse can be fit to a Gaussian function, where the amplitude and position of the unknown Gaussian function are the solvable parameters. Curve fitting, optimization, and search methods, including those mentioned previously in this specification, could be used to determine those 2 parameters from the set of digitized scatter signal values, which were recorded at different times as a particle passed through the source light beam. Because more signal information is utilized, this fitting method will produce pulse amplitude related measurements with much higher accuracy than direct measurement of the peak, for example. And this fit method will also improve the accuracy of ratios of pulse parameters from two different ranges of scattering angle.

The apertures and beam blocks of these optical systems perform many functions including the following:

1) reduction of scatter signal background (11314, 11317, and 11302, for example)
2) eliminating scatter signal from particles which are in a portion of the light beam with unacceptable light intensity (11301 and 11302, for example). This type of aperture provides the function described in FIG. 56, FIG. 57, and FIG. 60, for example. The region passed by aperture in FIG. 56 is defined generally by the image of the aperture in the interaction volume.
3) defining the range of scatter angle and/or range of scattering planes for a scatter detector (11609 and 11610 for example)
4) reducing the probability of detecting scatter signal from more than one particle of interest simultaneously (11302 for example)
5) blocking the source light from reaching the scatter detectors, from zero scattering angle to scattering angle A1 (11317 for example)
6) blocking the source light from reaching the scatter detectors, from scattering angle A2 to scattering angle A3 (11314 for example)
7) removing unwanted source light from the light beam (11301 for example)

Scatter signal background is the scatter signal present without a particle of interest in the interaction volume.

An aperture with the function of aperture 11301 is placed in a plane which is generally conjugate to the interaction volume, between the light source and the sample cell. In cases where the smallest interaction volume is desired, the interaction volume is usually generally conjugate to the beam waist of the light source, in order to minimize the illumination spot size in the interaction volume. If the edges of aperture 11301 intercept the light beam at sufficiently high intensity level, diffraction artifacts, which may be created at higher angles, could be removed by aperture 11314. An aperture with the function of aperture 11314 is placed in any plane between the light source and the sample cell, far from the planes which are conjugate to the source. The edge of the opening in aperture 11314 is chosen to intercept the source beam ray which has an angle A2 between the sample cell and a lens with equivalent function to lens 11313. Angle A2 is usually chosen to be slightly less than the minimum scatter angle detected by the detection module. Angle A3 is usually chosen to be greater than the maximum scatter angle detected by the detection module. If the edges of aperture 11314 intercept the light beam at sufficiently high intensity level, diffraction artifacts may be created. These diffraction artifacts could be removed by aperture 11302. An aperture with the function of aperture 11302 is placed in a plane, which is generally conjugate to the interaction volume, between the sample cell and the scatter detectors. Generally, the function, of eliminating scatter signal from particles which are in a portion of the light beam with unacceptable light intensity, is most easily performed by an aperture with the function of aperture 11302. An aperture with the function of aperture 11610 can be placed at any plane between the sample cell and a scatter detector. The dimensions of the openings in the 11610 type aperture must be scaled to intercept the appropriate scattered rays (rays with appropriate scatter angles or scattering planes) at the plane where the aperture is placed. A 11610 type aperture must not be in a plane where unacceptable variation of scattering angles for different particle positions in the interaction volume is observed. Beam blocks with the function of beam block 11317, can be placed in any plane between the sample cell and the detectors. At any chosen plane, the size of the beam block should be scaled to block light from the angular range of zero scattering angle to the appropriate scattering angle A1, which is slightly less than the minimum scattering angle which is detected by the detection module. In many cases, placement of the beam block between the sample cell and a lens, with equivalent function to lens 11313, is preferred to avoid reflections and scatter of source light inside of the scatter detection module. These are preferred design rules for use of apertures and beam blocks, with these functions, in all optical systems in this specification.

Other examples of apertures, which comprise a function similar to that of aperture 11302, are: slits 114 and 115 in FIG. 1, pinhole in FIG. 12, apertures 3501 and 3502 in FIG. 35, apertures 4321 and 4322 in FIG. 43, apertures 7802 and 7803 in FIG. 78, aperture in FIG. 82, aperture in FIG. 85, aperture 9341 in FIG. 93, and apertures 9642 and 9643 in FIG. 96.

As described previously, the pulse length of a signal pulse can be used to reduce the broadening of a monosized response due to the source intensity variation across the interaction volume. The pulse length may indicate the position of particle passage through the light beam, when the length of the illumination spot, generally along the direction of particle motion, changes as a function of position generally along the direction perpendicular to the particle motion. This length vs. position dependence can also be provided by an aperture with the function of 11302. The design would include an 11302 type aperture where the length of the opening, of the aperture, generally along the direction of particle motion, changed as a function of position generally along the direction perpendicular to the particle motion. Then each different particle path through the interaction volume would produce a scatter pulse of different length in time, providing the particle position and illumination intensity for each particle. This information could be utilized to reject particles, with undesired illumination, and/or correct for the illumination intensity variation of accepted particles, by dividing the pulse amplitude of each scatter signal pulse by the corresponding local source intensity for the path, through the source spot, of the particle producing that scatter signal pulse.

In many figures, of this specification, some drawn light rays appear to pass through blocking surfaces of apertures or other objects. These rays are usually drawn to indicate the general conjugate plane locations for certain types of light rays. Any light ray passing through a surface, with generally zero light transmission, is drawn for the purpose of generally defining characteristics of certain light rays. No light rays in these optical systems actually pass though surfaces with generally zero light transmission.

Many figures in this document contain optical rays which are drawn only to define object planes, image planes, and focal planes. The numerical apertures, scattered ray angles, beam diameters, and lens diameters are not necessarily drawn to scale.

As described previously, most of the figures of optical systems, in this specification, provide crossectional views of the optical system. Unless indicated otherwise, most lenses are optically symmetrical about the optical axis. Any lens represents the appropriate optic, providing the required function in that optical system. This required function may be performed by any appropriate optic, including conventional spherical lenses, aspheric lenses, multiple lens systems, gradient index lenses, diffractive optics, or binary optics. Also most systems, in this specification, can be used without a sample cell to count particles dispersed in an aerosol, which flows though, or resides in, the interaction volume.

Some equations, which are written in this application and which exist in the literature, may contain errors as written in this application. While the inventor has attempted to avoid such errors, some may still exist. In any of these cases, the correct equation is assumed. These equation errors do not detract from the functionality of the method or apparatus which use them, because that same functionality is maintained when using the correct equation. The invention may be modified in ways which will be apparent to the reader skilled in the art. Such modifications should be considered within the spirit and scope of the following claims.

What is claimed is:

1. A method for analyzing particles, comprising:
   a) providing a sample space for particles, the sample space having a volume,
   b) illuminating at least one of the particles,
   c) detecting selected scattered light, which is scattered only from particles located within a region of the sample space, said region having a volume which is smaller than the volume of the sample space,
   i) wherein the detecting step includes passing said scattered light through an aperture means which allows selected scattered light, which is scattered generally only from particles located within said region to be received by at least one detecting means, ii) wherein the aperture means is located in a plane which is optically conjugate to a plane in said region of the sample space by transfer of light through an optical means, iii) wherein said aperture means and said optical means are designed for providing at least one of the group consisting of 1) selecting scattered light from generally one particle of interest which resides within a plurality of particles and rejecting scattered light from generally other particles of interest which are concurrently in said sample space, 2) lower coincidence counts of particles of interest, and 3) acceptable coincidence counts of particles of interest at higher particle concentration, and d) analyzing the scattered light detected in step (c) to derive information about the particles.

2. The method of claim 1, wherein said aperture means comprises an aperture and wherein the detecting step includes passing said light through said aperture which allows light scattered only from particles located generally within said region to be received by a plurality of detecting means, wherein each detecting means detects light scattered with a different property set from a property set of scattered light detected by another detecting means, and wherein said different property set comprises at least one of the group consisting of a different range of scattering angles, over a different range of scattering planes, and with a different weighting as a function of scattering angle.

3. The method of claim 1, wherein step (c) is performed a plurality of performances simultaneously, wherein each performance of step (c) detects light scattered with a different property set from a property set of scattered light detected by another performance, and wherein said different property set comprises at least one of the group consisting of a different range of scattering angles, over a different range of scattering planes, and with a different weighting as a function of scattering angle, and wherein each performance utilizes a different aperture means, and wherein all aperture means of said plurality of performances pass light scattered only from particles located generally within the same region.

4. The method of claim 1, further comprising:

a) measuring at least one characteristic of light scattered from a particle, the measuring being performed for a plurality of performances, wherein each performance detects light scattered with a different property set from a property set of scattered light detected by another performance, and wherein said different property set comprises at least one of the group consisting of a different range of scattering angles, over a different range of scattering planes, and with a different weighting as a function of scattering angle, and b) determining a ratio of characteristics of said scattered light measured from at least two of said performances, and using said ratio to determine particle characteristics.

5. The method of claim 1, wherein illumination light intensity is not uniform in the illuminated portion of said sample space, wherein said region consists of a selected portion of said sample space, wherein particles having the same particle characteristics, passing through generally all different paths through said illuminated portion of said sample space, produce scatter signal characteristics which cover a range of scatter signal characteristic, and wherein particles having the same particle characteristics, passing through generally all different paths within said selected portion, produce scatter signal characteristics which are limited to within a generally smaller range of scatter signal characteristic, providing a scatter signal response with less broadening.

6. The method of claim 1, further comprising the steps of:

a) adjusting an intensity of a light source directed towards at least one of the particles, and adjusting a gain level of a detecting means positioned to detect light scattered from the particles, b) counting events during a first time period, each event comprising detecting a scatter signal with characteristics of light which could be scattered from a particle of interest, the counting step including measuring characteristics of a scatter signal, c) determining a first count distribution as a function of scatter signal parameter from the scatter signal characteristics, d) repeating steps (a) adjusting through (c) determining for different combinations of levels of light source intensity and/or gain of detecting means, during sequential time periods, so as to produce a new particle count distribution for each pair of values of light source intensity and detector gain, and e) combining particle count distributions, each distribution corrected for a corresponding combination of levels of light source intensity and gain of detecting means, into a single particle count distribution.

7. The method of claim 1, wherein step (c) is performed a plurality of performances, wherein each performance of step (c) detects scattered light from a region of different size and wherein the probability of multiple particles of interest for each region, occupying each said region simultaneously, is sufficiently low to provide an acceptable number of coincidence counts of particles of interest for that particular region, and wherein a particle count distribution is determined from each of said performances.

8. The method of claim 1, further comprising the steps of:

a) passing a stream of particles through a first detection system, the first detection system including a light source having an intensity and a detecting means having a gain, the detecting means being capable of producing a signal in response to detected light, b) directing the stream of particles leaving said first detection system into a second detection system, the second detection system including a light source having an intensity and a detecting means having a gain, the detecting means being capable of producing a signal in response to detected light, c) monitoring parameters comprising at least one of the intensity of the light source of said first detection system, the gain of the detecting means of said first detection system, and the signal of said first detection system, and d) adjusting at least one of the intensity of the light source of said second detection system and the gain of the detecting means of said second detection system, in response to said parameters monitored in monitoring step (c), wherein the second detection system maintains a scatter signal amplitude within an optimum range.

9. The method of claim 1, wherein detected particles are selected for analysis of step (d) by a method comprising:

a) detecting scattered light from a particle, in a plane which is generally optically conjugate to said particle, b) determining a position of the spatial distribution of said detected scattered light, in said generally conjugate plane, along a direction which is generally perpendicular to the flow direction of the particles, and c) selecting, for further analysis in step (d), only particles with said positions indicative of particles which have passed through a portion of said region where the illuminating light intensity characteristics are inside of a certain range, wherein all selected particles having the same particle characteristics, passing through generally all different paths through said portion, produce scatter signal characteristics which are limited to generally within a certain range of scatter signal characteristic for reducing scatter signal response broadening.

10. The method of claim 9, wherein step (a) is performed by a plurality of detectors and step (b) comprises using at least one ratio between signals from different detectors to determine said position.

11. The method of claim 5 further comprising a method to reduce the effects of broadening of scatter signal response utilizing the reduced broadening of said scatter signal characteristics which are limited to within a generally smaller range of scatter signal characteristic, the method comprising the steps of:
 e) counting a plurality of events, each event comprising detecting a scatter signal which is generally characteristic of light scattered from a particle of interest, and sorting said events according to values of a first parameter S, and creating a vector of values $C_i$ where each value $C_i$ represents a number of counted events having first parameter S in an interval of S between $S_i$ and $S_{i+1}$, wherein the first parameter is a scattering signal or a function of at least one scattering signal, and wherein $S_{i+1}=B*S_i$ for all values of i with constant B,
 f) creating an impulse response vector H, with values $H_i$, wherein $H_{i-j}$ represents the value of $C_i$ summed from a representative group of particles, which have second parameter D between $D_j$ and $D_{j+1}$, and wherein said representative group of particles have scatter signals which are representative of generally all particle paths through said region, and wherein said impulse response vector H is determined by methods comprising theoretical and/or empirical determinations,
 g) solving for vector of values $N_j$ the convolution equation, C equals the convolution of H and N $$C_i = \sum_j (H_{i-j} * N_j)$$

where each value $N_j$ comprises a number of counted events having second parameter D between $D_j$ and $D_{j+1}$ and wherein second parameter D is particle size, wherein the values $N_j$ are a corrected vector and wherein a scatter signal range, of events in vector C and vector H, is limited by said generally smaller range of scattering signal characteristic to improve the accuracy of solving for at least one value of $N_j$.

12. The method of claim 1, further comprising performing a plurality of performances of step (c), all such performances being with regard to generally a same range of scattering angles and generally a same range of scattering planes,
 wherein the multiple performances of step (c) measure scattered light from multiple regions, generally simultaneously,
 wherein said plurality of performances comprises using a plurality of detectors, and wherein each detector receives light from generally a different region,
 wherein the aperture means for each detector is the boundary of the light sensitive area of said detector, and
 wherein each detector is generally optically conjugate to a corresponding region.

13. The method of claim 1, further comprising a method for enhancing the accuracy of a count of particles by rejecting detected events, which do not have scatter signal parameters consistent with scatter from a single-particle of interest, wherein each detected event comprises detecting a scatter signal with characteristics which could possibly originate from a particle of interest, the method comprising:
 e) creating a multidimensional space in which each dimension comprises a scatter signal parameter, such that any particle with specific values of scatter signal parameters can be identified by a point in said space, and wherein each scatter signal parameter is a function of at least one scatter signal,
 f) determining a path through said multidimensional space according to expected and/or measured values of scatter signal parameters for various values of particle parameters,
 g) rejecting counted events where said events have scatter signal parameters such that said events, when represented in said multidimensional space, are not consistent with scatter from a particle of interest and/or are located beyond a predetermined distance from said path, and
 h) selecting counted events which have not been rejected in rejecting step (g) for further analysis.

14. The method of claim 13, further comprising determining a particle parameter for each event selected in step (h) from a position, along said path, which is closest to said event, and creating a count distribution, as a function of particle parameter, using said determined particle parameters from said selected events.

15. The method of claim 1 further comprising a method for determining particle size and/or shape particle parameters from scatter signal parameters of a counted event, each event comprising detecting a scatter signal which is generally characteristic of light scattered from a particle of interest, comprising the steps of:
 e) creating a set of theoretical simultaneous equations relating each scatter signal parameter to a function of particle parameters, and
 f) solving said set of equations for the particle parameters, using measured scatter signal parameters.

16. The method of claim 1, further comprising a method for determining particle size and/or shape, comprising the steps of:
 e) measuring a two-dimensional scatter distribution of light scattered by a particle,
 f) calculating a two-dimensional inverse Fourier transform of said two-dimensional scatter distribution to produce a second two-dimensional distribution, and
 g) determining size and shape of said particle from a size and shape of said second two-dimensional distribution.

17. The method of claim 1, further comprising the steps of:
 e) counting a plurality of events, each event comprising detecting a scatter signal which is generally characteristic of light scattered from a particle of interest, and sorting said events according to values of a first parameter, and creating a vector of values $A_i$ where each value $A_i$ represents a number of counted events having first parameter S, within an interval of S which is centered at $S_i$, and wherein the first parameter is a function of at least one scattering signal,
 f) creating a vector of values $B_i$ where each value $B_i$ represents a scattering parameter from at least one scattering signal measurement over an interval of scattering abscissa parameter X, centered at scattering abscissa parameter $X_i$, and wherein the scattering parameter is a function of at least one scattering signal, g) performing step (f) for at least one type of scattering signal measurement, wherein said types of scatter signal measurement comprise at least one of the group consisting of ensemble static angular light scattering measurement and ensemble dynamic light scattering measurement, and wherein all said measurements are performed on generally identical particle dispersions, and wherein scattering abscissa parameter $X_i$ comprises a function of at least one of the group consisting of scattering angle, signal frequency, and time, h) concatenating the vectors from step (e) of creating the vector of values $A_i$ and performances of step (f) of creating the vector of values $B_i$ into one vector of values $G_i$, i) creating a matrix of values $H_{ij}$, wherein the jth column of the matrix of values $H_{ij}$ comprises a vector of values $G_i$ relating to second parameter $D_j$, wherein the second parameter is particle size, f) solving for vector of values $N_j$ the matrix equation $$G_i = \sum_j (H_{ij} N_j)$$

wherein each value $N_j$ comprises a particle parameter having second parameter D within a interval of D which is centered at $D_j$, and wherein the values $N_j$ comprise one of the group consisting of particle number, particle area, and particle volume.

18. The method of claim 1, further comprising:

e) creating a multidimensional space in which each dimension comprises a scatter signal parameter, such that any particle with specific values of scatter signal parameters can be identified by a point in said space, and wherein each scatter signal parameter is a function of at least one scatter signal, f) determining a path through said multidimensional space according to expected and/or measured values of scatter signal parameters for various values of particle parameters, g) using step (d) to determine a number of events at each of various points in said multidimensional space, wherein each detected event comprises detecting a scatter signal with characteristics which could possibly originate from a particle of interest, h) rejecting counted events where said events have scatter signal parameters such that said events are not consistent with scatter from a particle of interest and/or are located beyond a predetermined distance from said path, and i) selecting counted events which have not been rejected in rejecting step (h), to create a first count distribution function in said multidimensional space, j) producing a second count distribution by applying multidimensional deconvolution to said first multidimensional count distribution function, utilizing a multidimensional impulse response in said multidimensional space, wherein said multidimensional impulse response represents the total broadened response from a group of generally identical particles, wherein said multidimensional impulse response is determined by methods comprising theoretical and/or empirical determinations, wherein said group of generally identical particles produce scatter signals which are representative of generally all particle paths through said region, wherein said multidimensional deconvolution comprises image deblurring methods in the case of two dimensional space, and k) determining a particle parameter for each point in said second count distribution function based upon said path and creating a count distribution, as a function of particle parameter, using said determined particle parameters from said points.

19. The method of claim 1, further comprising the steps of:

mixing some of the light which illuminates the particles in step (b) with some of the scattered light detected in step (c), so as to create an optical interference signal on said detecting means, and accepting only a portion of said interference signal, with a certain range of frequency and/or phase, for input to the analysis of step (d).

20. The method of claim 1, further comprising a method for enhancing the accuracy of a count of particles by rejecting detected events, which do not have scatter signal time characteristics consistent with scatter from a single-particle of interest, wherein said scatter signal time characteristics comprise at least one member of the group consisting of correlation between signals, product of signals, and time delay between signals, and wherein each detected event comprises detecting a scatter signal with characteristics which could possibly originate from a particle of interest, the method comprising:

e) calculating the scatter signal time characteristics between scatter signals from at least two detecting means, f) accepting counted events where said events have said scatter signal time characteristics, which are consistent with scatter from a particle of interest, and g) selecting counted events which have been accepted in accepting step (f) for further analysis.

21. The method of claim 1, wherein scatter signals from detected particles are corrected for illumination intensity for analysis of step (d) by a method comprising:

e) detecting scattered light from a particle, in a plane which is generally optically conjugate to said particle, f) determining a position of the spatial distribution of said detected scattered light, in said generally optically conjugate plane, along a direction which is generally perpendicular to the flow direction of the particles, g) determining an illumination intensity characteristic at said determined position from known characteristics of said illuminating, and h) correcting a scatter signal amplitude with said determined illumination intensity characteristic.

22. The method of claim 21, wherein step (e) is performed by a plurality of detectors and step (f) comprises using at least one ratio between signals from different detectors to determine said position.

23. The method of claim 18, further comprising:

l) measuring at least one characteristic of light scattered from a particle, the measuring being performed for a plurality of performances, wherein each performance detects light scattered with a different property set from a property set of scattered light detected by another performance, and wherein said different property set comprises at least one of the group consisting of a different range of scattering angles, over a different range of scattering planes, and with a different weighting as a function of scattering angle, and m) determining a ratio of characteristics of said scattered light measured from at least two of said performances, n) performing step (e), wherein at least one signal parameter is a ratio, determined by the method of step (m), and o) performing steps (f) through (k).

24. A method for analyzing particles, comprising:
a) providing a sample space for particles, the sample space having a volume,
b) illuminating at least one of the particles,
c) detecting selected scattered light, which is scattered only from particles located within a region of the sample space, said region having a volume which is smaller than the volume of the sample space,
  i) wherein the detecting step includes passing said scattered light through an aperture which allows selected scattered light, which is scattered generally only from particles located within said region to be received by at least one detecting means,
  ii) wherein the aperture is located in a plane which is optically conjugate to a plane in said region of the sample space by transfer of light through an optical means,
  iii) wherein said aperture and said optical means are designed for providing at least one of the group consisting of 1) selecting scattered light from generally one particle of interest which resides within a plurality of particles and rejecting scattered light from generally other particles of interest which are concurrently in said sample space, 2) lower coincidence counts of particles of interest, and 3) acceptable coincidence counts of particles of interest at higher particle concentration, and
d) analyzing the scattered light detected in step (c) to derive information about the particles.

25. Apparatus for analyzing particles, comprising:
a) a sample space for particles, the sample space having a volume,
b) means for illuminating at least one of the particles,
c) means for selectively detecting selected scattered light, which is scattered only from particles located within a region of the sample space, said region having a volume which is smaller than the volume of the sample space,
  i) wherein the selectively detecting means includes means for passing said scattered light through an aperture means which allows selected scattered light, which is scattered generally only from particles located within said region, to be received by at least one detecting means,
  ii) wherein the aperture means is located in a plane which is optically conjugate to a plane in said region of the sample space by transfer of light through an optical means,
  iii) wherein said aperture means and said optical means are designed for providing at least one of the group consisting of 1) selection of scattered light from generally one particle of interest which resides within a plurality of particles and rejection of scattered light from generally other particles of interest which are concurrently in said sample space, 2) lower coincidence counts of particles of interest, and 3) acceptable coincidence counts of particles of interest at higher particle concentration, and
d) means for analyzing the scattered light detected by the detecting means, to derive information about the particles.

26. The apparatus of claim 25, wherein said aperture means comprises an aperture and wherein the selectively detecting means includes means for passing said light through said aperture which allows light scattered only from particles located generally within said region to be received by a plurality of detecting means, each detecting means adapted to receive light scattered with a different property set from a property set of scattered light received by another detecting means, and wherein said different property set comprises at least one of the group consisting of a different range of scattering angles, over a different range of scattering planes, and with a different weighting as a function of scattering angle.

27. The apparatus of claim 25, wherein there are multiple selectively detecting means, each selectively detecting means adapted to receive light scattered with a different property set from a property set of scattered light received by another detecting means, and wherein said different property set comprises at least one of the group consisting of a different range of scattering angles, over a different range of scattering planes, and with a different weighting as a function of scattering angle and wherein each selectively detecting means detects scattered light from generally the same region of the sample space.

28. The apparatus of claim 25, wherein illumination light intensity is not uniform in the illuminated portion of said sample space,
  wherein said region consists of a selected portion of the sample space, wherein particles having the same particle characteristics, passing through generally all different paths through said illuminated portion of said sample space, produce scatter signal characteristics which cover a range of scatter signal characteristic, and wherein particles having the same particle characteristics, passing through generally all different paths within said selected portion, produce scatter signal characteristics which are limited to within a generally smaller range of scatter signal characteristic, providing a scatter signal response with less broadening.

29. The apparatus of claim 25, the apparatus including a sample cell into which particles to be analyzed are directed, the sample cell being bounded by walls, the walls including optical paths for allowing light to enter the sample cell and to leave the sample cell, the sample cell also defining a volume within which particles pass through the sample cell, wherein the sample cell includes at least one shaped object, the shaped object being positioned outside of a desired portion of said volume so as to prevent particles from passing through a volume occupied by said object and wherein said occupied volume comprises generally the portion of illuminated volume in the particle dispersion outside of the desired portion of said volume, and wherein said object is shaped such that particles, which are too large to pass through the desired portion of said volume, pass around said object in the particle dispersion flow, and wherein said object has acceptable optical transmission at the optical wavelength of said scattered light.

30. The apparatus of claim 25, the apparatus including a sample cell into which particles to be analyzed are directed, the sample cell including windows for allowing light to enter the sample cell and to leave the sample cell,
  wherein at least one window includes at least one curved surface, the curved surface having a center of curvature, the curved surface being shaped such that its center of curvature is located generally at said region.

31. The apparatus of claim 25, further comprising an optical element for use in directing light scattered from particles to a plurality of detectors, the optical element comprising:
a) a plurality of segments,
b) each segment comprising means for capturing light, each segment adapted to receive light scattered with a different property set from a property set of scattered light received by another segment, and wherein said different property set comprises at least one of the group consisting of a different range of scattering angles, over a different range of scattering planes, and with a different weighting as a function of scattering angle, and c) each segment comprising means for redirecting, or redirecting and focusing, light captured by said segment onto a different light detector.

32. The apparatus of claim 25, further comprising an optical element for use in directing light scattered from particles to a plurality of detectors, the optical element comprising:

a) a plurality of segments, b) each segment comprising means for capturing light, each segment adapted to receive light scattered with a different property set from a property set of scattered light received by another segment, and wherein said different property set comprises at least one of the group consisting of a different range of scattering angles, over a different range of scattering planes, and with a different weighting as a function of scattering angle, and c) each segment comprising means for redirecting, or redirecting and focusing, light captured by said segment onto a different light detector, and wherein each segment includes a plurality of diffractive structures, wherein the diffractive structures in different segments differ in at least one of orientation, shape, and spatial frequency.

33. The apparatus of claim 29, wherein the shape of said shaped object is generally of the form of a truncated converging shape, comprising generally the shape of a truncated cone, and wherein the truncation at the small end of said converging shape comprises a generally flat surface or a curved surface, the curved surface having a center of curvature, the curved surface being shaped such that its center of curvature is located generally at said region.

34. The apparatus of claim 25, wherein there are multiple selectively detecting means, and wherein each selectively detecting means measures scattered light having generally a same range of scattering angles and a same range of scattering planes, and wherein each selectively detecting means detects light scattered from a different region of the sample space, wherein said multiple selectively detecting means comprise a plurality of generally contiguous detectors, wherein each detector is generally optically conjugate to a corresponding region, and wherein the aperture means for each detector is the boundary of the light sensitive area of said detector.

35. The apparatus of claim 25, further comprising a plurality of illumination means, each illumination means illuminating a different portion of the sample space and a plurality of selectively detecting means wherein each selectively detecting means detects scattered light only from one specific illumination means of said plurality of illumination means.

36. The apparatus of claim 25, wherein the detecting means includes a mirror having an opening, and a lens, wherein the lens is positioned to detect light scattered at relatively low scattering angles, and the mirror is positioned to detect light scattered at relatively high scattering angles, and wherein said light, scattered at relatively low scattering angles, passes through said opening.

37. The apparatus of claim 25, further comprising means for modulating the scatter signal by using an optical element having spatially modulated transmission, the optical element being positioned at a location which is generally optically conjugate to said region and means for accepting only a portion of said scatter signal, with characteristics of said modulation, for input to the means for analyzing the scattered light.

38. The apparatus of claim 25, further comprising:

a) means for measuring at least one characteristic of light scattered from a particle, the measuring being performed for a plurality performances wherein each performance detects light scattered with a different property set from a property set of scattered light detected by another performance, and wherein said different property set comprises at least one of the group consisting of a different range of scattering angles, over a different range of scattering planes, and with a different weighting as a function of scattering angle, and b) means for determining a ratio of characteristics of said scattered light measured from at least two of said performances, and using said ratio to determine particle characteristics.

* * * * *